US008084240B2

(12) United States Patent
Cuevas et al.

(10) Patent No.: US 8,084,240 B2
(45) Date of Patent: Dec. 27, 2011

(54) GEOBACILLUS STEAROTHERMOPHILUS α-AMYLASE (AMYS) VARIANTS WITH IMPROVED PROPERTIES

(75) Inventors: William A Cuevas, San Francisco, CA (US); Sang-Kyu Lee, Palo Alto, CA (US); Sandra W Ramer, Sunnyvale, CA (US); Andrew Shaw, San Francisco, CA (US); Amr R Toppozada, San Francisco, CA (US); David E Estell, San Francisco, CA (US); Sura H Hadi, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 267 days.

(21) Appl. No.: 12/477,028

(22) Filed: Jun. 2, 2009

(65) Prior Publication Data

US 2009/0314286 A1   Dec. 24, 2009

Related U.S. Application Data

(60) Provisional application No. 61/059,423, filed on Jun. 6, 2008.

(51) Int. Cl.
*C12N 9/28* (2006.01)
*C07K 14/00* (2006.01)
*C12P 21/00* (2006.01)
*C12Q 1/40* (2006.01)

(52) U.S. Cl. .......... 435/202; 435/69.1; 435/22; 530/350
(58) Field of Classification Search .................. 435/22, 435/202, 69.1; 530/350
See application file for complete search history.

(56) References Cited

U.S. PATENT DOCUMENTS

| | | | |
|---|---|---|---|
| 3,912,590 A | 10/1975 | Slott et al. | |
| 4,106,991 A | 8/1978 | Markussen et al. | |
| 4,316,956 A | 2/1982 | Lützen | |
| 4,335,208 A | 6/1982 | Norman | |
| 4,435,307 A | 3/1984 | Barbesgaard et al. | |
| 4,643,736 A | 2/1987 | Cholley | |
| 4,661,452 A | 4/1987 | Markussen et al. | |
| 4,683,202 A | 7/1987 | Mullis | |
| 4,689,297 A | 8/1987 | Good et al. | |
| 5,231,017 A | 7/1993 | Lantero et al. | |
| 5,324,649 A | 6/1994 | Arnold et al. | |
| 5,648,263 A | 7/1997 | Schülein et al. | |
| 5,691,178 A | 11/1997 | Schülein et al. | |
| 5,776,757 A | 7/1998 | Schülein et al. | |
| 5,814,501 A | 9/1998 | Becker et al. | |
| 5,989,169 A | 11/1999 | Svendsen et al. | |
| 6,187,576 B1 | 2/2001 | Svendsen et al. | |
| 6,297,038 B1 | 10/2001 | Bisgård-Frantzen et al. | |
| 6,475,762 B1 | 11/2002 | Stafford et al. | |
| 6,562,612 B2 | 5/2003 | Jones et al. | |
| 6,867,031 B2 | 3/2005 | Bisgård-Frantzen et al. | |
| 7,498,158 B2 * | 3/2009 | Svendsen et al. ............. 435/202 |
| 2004/0096952 A1 * | 5/2004 | Svendsen et al. ............. 435/202 |
| 2008/0220498 A1 | 9/2008 | Cervin et al. | |
| 2009/0143270 A1 | 6/2009 | Svendsen et al. | |
| 2010/0144575 A1 | 6/2010 | Svendsen et al. | |

FOREIGN PATENT DOCUMENTS

| | | |
|---|---|---|
| EP | 0 063 909 A1 | 11/1982 |
| EP | 0.119 920 A2 | 9/1984 |
| EP | 0 218 272 A1 | 4/1987 |
| EP | 0 252 666 A2 | 1/1988 |
| EP | 0 252 730 A2 | 1/1988 |
| EP | 0 258 068 A2 | 3/1988 |
| EP | 0 260 105 A2 | 3/1988 |
| EP | 0 305 216 A1 | 3/1989 |
| EP | 0407 225 A1 | 1/1991 |
| GB | 1 296 839 | 11/1972 |
| GB | 1 372 034 | 10/1974 |
| JP | 64-074992 | 3/1989 |
| WO | WO 89/06270 | 7/1989 |
| WO | WO 89/06279 | 7/1989 |
| WO | WO 89/09259 | 10/1989 |
| WO | WO 91/00353 | 1/1991 |
| WO | WO 91/16422 | 10/1991 |
| WO | WO 91/17243 | 11/1991 |
| WO | WO 92/05249 | 4/1992 |
| WO | WO 92/06165 | 4/1992 |
| WO | WO 92/06221 | 4/1992 |
| WO | WO 92/19708 | 11/1992 |
| WO | WO 92/19709 | 11/1992 |
| WO | WO 92/19729 | 11/1992 |
| WO | WO 93/24618 | 12/1993 |
| WO | WO 94/01541 | 1/1994 |
| WO | WO 94/02597 | 2/1994 |
| WO | WO 94/18314 | 8/1994 |
| WO | WO 94/25578 | 11/1994 |

(Continued)

OTHER PUBLICATIONS

Altschul, S.F. et al. "Gapped BLAST and PSI—BLAST: a new generation of protein database search programs." *Nucleic Acids Res.* 25:3389-3402, 1997.

Beaucage, S.L. et al. "Deoxynucleoside phosphoramidites—a new class of key intermediates for deoxypolynucleotide synthesis." *Tetrahedron Lett.* 22(20):1859-1862, 1981.

Boel, E., I. Hjort, et al. "Glucoamylases G1 and G2 from *Aspergillus niger* are synthesized from two different but closely related mRNAs." *The EMBO Journal* 3(5):1097-1102, 1984.

(Continued)

*Primary Examiner* — Delia Ramirez

(57) ABSTRACT

Described are variants of a parent α-amylase that exhibits an alteration in at least one of the following properties relative to said parent α-amylase: specific activity, substrate specificity, substrate binding, substrate cleavage, thermal stability, pH-dependent activity, pH-dependent stability, oxidative stability, Ca2+ dependency, pI, and wash performance. The variants are suitable for starch conversion, ethanol production, laundry washing, dish washing, hard surface cleaning, textile desizing, and/or sweetener production.

1 Claim, 38 Drawing Sheets

FOREIGN PATENT DOCUMENTS

| | | |
|---|---|---|
| WO | WO 94/25583 | 11/1994 |
| WO | WO 95/06720 | 3/1995 |
| WO | WO 95/10602 | 4/1995 |
| WO | WO 95/14807 | 6/1995 |
| WO | WO 95/21247 | 8/1995 |
| WO | WO 95/22615 | 8/1995 |
| WO | WO 95/22625 | 8/1995 |
| WO | WO 95/26397 | 10/1995 |
| WO | WO 95/30744 | 11/1995 |
| WO | WO 95/35381 | 12/1995 |
| WO | WO 96/00292 | 1/1996 |
| WO | WO 96/12012 | 4/1996 |
| WO | WO 96/13580 | 5/1996 |
| WO | WO 96/23873 | 8/1996 |
| WO | WO 96/27002 | 9/1996 |
| WO | WO 96/28567 | 9/1996 |
| WO | WO 96/39528 | 12/1996 |
| WO | WO 97/00324 | 1/1997 |
| WO | WO 97/04079 | 2/1997 |
| WO | WO 97/07202 | 2/1997 |
| WO | WO 97/43424 | 11/1997 |
| WO | WO 98/15257 | 4/1998 |
| WO | WO 98/20115 | 5/1998 |
| WO | WO 98/20116 | 5/1998 |
| WO | WO 98/23732 | 6/1998 |
| WO | WO 98/34946 | 8/1998 |
| WO | WO 99/19467 | 4/1999 |
| WO | WO 99/20770 | 4/1999 |
| WO | WO 99/28448 | 6/1999 |
| WO | WO 99/49740 | 10/1999 |
| WO | WO 00/04136 | 1/2000 |
| WO | WO 01/04273 | 1/2001 |
| WO | WO 02/14490 | 2/2002 |
| WO | WO 2006/002643 | 1/2006 |
| WO | WO 2006/043178 | 4/2006 |
| WO | WO 2006/060062 | 6/2006 |
| WO | WO 2008/002472 | 1/2008 |
| WO | WO 2008/153925 A2 | 12/2008 |
| WO | WO 2008/153925 A9 | 12/2008 |
| WO | WO 2009/061379 | 5/2009 |
| WO | WO 2009/061381 | 5/2009 |

OTHER PUBLICATIONS

Cha, J. et al. "Lowering the pH optimum of D-xylose isomerase: the effect of mutations of the negatively charged residues." *Molecules and Cells* 8(4):374-382, 1998.

Cohen, N. et al. "In vitro enzyme evolution: the screening challenge of isolating the one in a million." *Trends in Biotechnology* 19(12):507-510, 2001.

Hahn, J. et al. "Regulatory inputs for the synthesis of ComK, the competence transcription factor of *Bacillus subtilis*." *Molecular Microbiology* 21(4):763-775, 1996.

Huber, T. et al. "Protein fold recognition without Boltzmann statistics or explicit physical basis." *Protein Science* 7(1):142-149, 1998.

Dartois, V. et al. "Cloning, nucleotide sequence and expression in *Escherichia coli* of a lipase gene from *Bacillus subtilis* 168." *Biochimica et Biophysica Acta* 1131(3):253-260, 1992.

Engelen, A.J. et al. "Simple and rapid determination of phytase activity." *Journal of AOAC International* 77(3):760-764, 1994.

Freire, E. "Differential Scanning Calorimetry." In *Protein Stability and Folding: Theory and Practice*, Methods in Molecular Biology, No. 40, ed. B.A. Shirley. New York: Humana Press, pp. 191-218, 1995.

Gaboriaud, C. et al. "Hydrophobic cluster analysis: an efficient new way to compare and analyse amino acid sequences." *FEBS Letters* 224(1):149-55, 1987.

Holm, L. et al. "Random mutagenesis used to probe the structure and function of *Bacillus stearothermophilus* alpha-amylase." *Protein Engineering* 3(3):181-191, 1990.

Matthes, H.W.D. et al. "Simultaneous rapid chemical synthesis of over one hundred oligonucleotides on a microscale." EMBO J. 3(4):801-805, 1984.

McKenzie, T. et al. "The nucleotide sequence of pUB110: some salient features in relation to replication and its regulation." *Plasmid* 15(2):93-103, 1986.

Needleman, S.B. et al. "A general method applicable to the search for similarities in the amino acid sequence of two proteins." *J. Mol. Biol* 48(3):443-53, 1970.

Neidhardt, F.C. et al. "Culture Medium for Enterobacteria." *J. Bacteriol.* 119(3):736-747, 1974.

Pearson, W.R. et al. "Improved Tools for Biological Sequence Comparison." *Proc. Natl. Acad. Sci. USA* 85(8):2444-2448, 1988.

Vogtentanz, G. et al. "A *Bacillus subtilis* fusion protein system to produce soybean Bowman-Birk protease inhibitor." *Protein Expression and Purification* 55(1):40-52, 2007.

Russell, A.J., P G Thomas, et al. "Electrostatic effects on modification of charged groups in the active site cleft of subtilisin by protein engineering." *Journal of Molecular Biology* 193(4):803-813, 1987.

Sambrook, J. et al. *Molecular Cloning: A Laboratory Manual*. 2nd ed. New York: Cold Spring Harbor Press. 1989.

Smirnova, N. A. et al. "Mutation in α-Amylase Gene of *Bacillus amyloliquefaciens* Leading to Reduction in Termperature of Protein Inactivation," *Molecular Biology Journal*, 22(5):921-1036, 1988.

Tsukamoto, A. et al. "Nucleotide sequence of the maltohexaose-producing amylase gene from an alkalophilic *Bacillus* sp. #707 and structural similarity to liquefying type alpha-amylases." *Biochemical and Biophysical Research Communications* 151(1):25-31, 1988.

\* cited by examiner

```
                    1                                                  50
SEQID No  1   (1)  -AAPFNGTMMQYFEWYLPDDGTLWTKVANEANNLSSLGITALWLPPAYKG
SEQID No  2   (1)  -AAPFNGTMMQYFEWYLPDDGTLWTKVANEANNLSSLGITALWLPPAYKG
SEQID No  3   (1)  -AAPFNGTMMQYFEWYLPDDGTLWTKVANEANNLSSLGITALWLPPAYKG
SEQID No  4   (1)  -AAPFNGTMMQYFEWYLPDDGTLWTKVANEANNLSSLGITALWLPPAYKG
SEQID No  5   (1)  -AAPFNGTMMQYFEWYLPDDGTLWTKVANEANNLSSLGITALWLPPAYKG
SEQID No  6   (1)  HHNGTNGTMMQYFEWYLPNDGNHWNRLNSDASNLKSKGITAVWIPPAWKG
SEQID No  7   (1)  --ANLNGTLMQYFEWYMPNDGQHWKRLQNDSAYLAEHGITAVWIPPAYKG
SEQID No  8   (1)  --ANLNGTLMQYFEWYMPNDGQHWRRLQNDSAYLAEHGITAVWIPPAYKG
SEQID No  9   (1)  ----VNGTLMQYFEWYTPNDGQHWKRLQNDAEHLSDIGITAVWIPPAYKG
SEQID No 10   (1)  HHNGTNGTMMQYFEWYLPNDGNHWNRLRSDASNLKDKGISAVWIPPAWKG
SEQID No 11   (1)  HHNGTNGTMMQYFEWHLPNDGNHWNRLRDDASNLRNRGITAIWIPPAWKG
SEQID No 12   (1)  HHNGTNGTMMQYFEWHLPNDGNHWNRLRDDAANLKSKGITAVWIPPAWKG
SEQID No 13   (1)  --DGLNGTMMQYYEWHLENDGQHWNRLHDDAAALSDAGITAIWIPPAYKG
SEQID No 14   (1)  --DGLNGTMMQYYEWHLENDGQHWNRLHDDAEALSNAGITAIWIPPAYKG
SEQID No 15   (1)  -AAPFNGTMMQYFEWYLPDDGTLWTKVANEANNLSSLGITALWLPPAYKG
Consensus     (1)      A  NGTMMQYFEWYLPNDGQHW RL NDA NLSS GITALWIPPAYKG
                    51                                                100
SEQID No  1  (50)  TSRSDVGYGVYDLYDLGEFNQKGTVRTKYGTKAQYLQAIQAAHAAGMQVY
SEQID No  2  (50)  TSRSDVGYGVYDLYDLGEFNQKGTVRTKYGTKAQYLQAIQAAHAAGMQVY
SEQID No  3  (50)  TSRSDVGYGVYDLYDLGEFNQKGTVRTKYGTKAQYLQAIQAAHAAGMQVY
SEQID No  4  (50)  TSRSDVGYGVYDLYDLGEFNQKGTVRTKYGTKAQYLQAIQAAHAAGMQVY
SEQID No  5  (50)  TSRSDVGYGVYDLYDLGEFNQKGTVRTKYGTKAQYLQAIQAAHAAGMQVY
SEQID No  6  (51)  ASQNDVGYGAYDLYDLGEFNQKGTVRTKYGTRSQLAAVTSLKNNGIQVY
SEQID No  7  (49)  TSQADVGYGAYDLYDLGEFHQKGTVRTKYGTKGELQSAIKSLHSRDINVY
SEQID No  8  (49)  TSQADVGYGAYDLYDLGEFHQKGTVRTKYGTKGELQSAIKSLHSRDINVY
SEQID No  9  (47)  LSQSDNGYGPYDLYDLGEFQQKGTVRTKYGTKSELQDAIGSLHSRNVQVY
SEQID No 10  (51)  ASQNDVGYGAYDLYDLGEFNQKGTIRTKYGTRNQLAAVNALKSNGIQVY
SEQID No 11  (51)  TSQNDVGYGAYDLYDLGEFNQKGTVRTKYGTRSQLESAIHALKNNGVQVY
SEQID No 12  (51)  TSQNDVGYGAYDLYDLGEFNQKGTVRTKYGTRSQLQGAVTSLKNNGIQVY
SEQID No 13  (49)  NSQADVGYGAYDLYDLGEFNQKGTVRTKYGTKAQLERAIGSLKSNDINVY
SEQID No 14  (49)  NSQADVGYGAYDLYDLGEFNQKGTVRTKYGTKAQLERAIGSLKSNDINVY
SEQID No 15  (50)  TSRSDVGYGVYDLYDLGEFNQKGTVRTKYGTKAQYLQAIQAAHAAGMQVY
Consensus    (51)  TSQSDVGYGAYDLYDLGEFNQKGTVRTKYGTKAQL  AI ALHA GIQVY
                    101                                               150
SEQID No  1 (100)  ADVVFDHKGGADGTEWVDAVEVNPSDRNQEISGTYQIQAWTKFDFPGRGN
SEQID No  2 (100)  ADVVFDHKGGADGTEWVDAVEVNPSDRNQEISGTYQIQAWTKFDFPGRGN
SEQID No  3 (100)  ADVVFDHKGGADGTEWVDAVEVNPSDRNQEISGTYQIQAWTKFDFPGRGN
SEQID No  4 (100)  ADVVFDHKGGADGTEWVDAVEVNPSDRNQEISGTYQIQAWTKFDFPGRGN
SEQID No  5 (100)  ADVVFDHKGGADGTEWVDAVEVNPSDRNQEISGTYQIQAWTKFDFPGRGN
SEQID No  6 (101)  GDVVMNHKGGADATEMVRAVEVNPNNRNQEVTGEYTIEAWTRFDFPGRGN
SEQID No  7  (99)  GDVVINHKGGADATEDVTAVEVDPADRNRVISGEHLIKAWTHFHFPGRGS
SEQID No  8  (99)  GDVVINHKGGADATEDVTAVEVDPADRNRVISGEHLIKAWTHFHFPGRGS
SEQID No  9  (97)  GDVVLNHKAGADATEDVTAVEVNPANRNQETSEEYQIKAWTDFRFPGRGN
SEQID No 10 (101)  GDVVMNHKGGADATEMVRAVEVNPNNRNQEVSGEYTIEAWTKFDFPGRGN
SEQID No 11 (101)  GDVVMNHKGGADATENVLAVEVNPNNRNQEISGDYTIEAWTKFDFPGRGN
SEQID No 12 (101)  GDVVMNHKGGADGTEMVNAVEVNRSNRNQEISGEYTIEAWTKFDFPGRGN
SEQID No 13  (99)  GDVVMNHKMGADFTEAVQAVQVNPTNRWQDISGAYTIDAWTGFDFSGRNN
SEQID No 14  (99)  GDVVMNHKLGADFTEAVQAVQVNPSNRWQDISGVYTIDAWTGFDFPGRNN
SEQID No 15 (100)  ADVVFDHKGGADGTEWVDAVEVNPSDRNQEISGTYQIQAWTKFDFPGRGN
Consensus   (101)  GDVVMNHKGGADGTE V AVEVNPSDRNQEISG Y I  AWTKFDFPGRGN
```

Figure 1

```
                   151                                              200
SEQID No  1  (150) TYSSFKWRWYHFDGVDWDESRKLS-RIYKFRGIGKAWDWEVDTENGNYDY
SEQID No  2  (150) TYSSFKWRWYHFDGVDWDESRKLS-RIYKFRGIGKAWDWEVDTENGNYDY
SEQID No  3  (150) TYSSFKWRWYHFDGVDWDESRKLS-RIYKFRGIGKAWDWEVDTENGNYDY
SEQID No  4  (150) TYSSFKWRWYHFDGVDWDESRKLS-RIYKFRGIGKAWDWEVDTENGNYDY
SEQID No  5  (150) TYSSFKWRWYHFDGVDWDESRKLS-RIYKFRGIGKAWDWEVDTENGNYDY
SEQID No  6  (151) THSSFKWRWYHFDGVDWDQSRRLNNRIYKFRGHGKAWDWEVDTENGNYDY
SEQID No  7  (149) TYSDFKWHWYHFDGTDWDESRKLN-RIYKFQG--KAWDWEVSNENGNYDY
SEQID No  8  (149) TYSDFKWHWYHFDGTDWDESRKLN-RIYKFQG--KAWDWEVSNENGNYDY
SEQID No  9  (147) TYSDFKWHWYHFDGADWDESRKIS-RIFKFRGEGKAWDWEVSSENGNYDY
SEQID No 10  (151) THSNFKWRWYHFDGVDWDQSRKLNNRIYKFRGDGKGWDWEVDTENGNYDY
SEQID No 11  (151) TYSDFKWRWYHFDGVDWDQSRQFQNRIYKFRGDGKAWDWEVDSENGNYDY
SEQID No 12  (151) THSNFKWRWYHFDGTDWDQSRQLQNKIYKFRGTGKAWDWEVDIENGNYDY
SEQID No 13  (149) AYSDFKWRWFHFNGVDWDQRYQEN-HIFRFAN--TNWNWRVDEENGNYDY
SEQID No 14  (149) AYSDFKWRWFHFNGVDWDQRYQEN-HLFRFAN--TNWNWRVDEENGNYDY
SEQID No 15  (150) TYSSFKWRWYHFDGVDWDESRKLS-RIYKFRG--KAWDWEVDTEFGNYDY
Consensus    (151) TYS FKWRWYHFDGVDWDESRKLN RIYKFRG GKAWDWEVDTENGNYDY
                   201                                              250
SEQID No  1  (199) LMYADLDMDHPEVVTELKNWGKWYVNTTNIDGFRLDAVKHIKFSFFPDWL
SEQID No  2  (199) LMYADLDMDHPEVVTELKNWGKWYVNTTNIDGFRLDAVKHIKFSFFPDWL
SEQID No  3  (199) LMYADLDMDHPEVVTELKNWGKWYVNTTNIDGFRLDAVKHIKFAFFPDWL
SEQID No  4  (199) LMYADLDMDHPEVVTELKNWGKWYVNTTNIDGFRLDAVKHIKFQFFPDWL
SEQID No  5  (199) LMYADLDMDHPEVVTELKNWGKWYVNTTNIDGFRLDAVKHIKFEFFPDWL
SEQID No  6  (201) LMYADIDMDHPEVVNELRNWGVWYTNTLGLDGFRIDAVKHIKYSFTRDWI
SEQID No  7  (196) LMYADIDYDHPDVAAEIKRWGTWYANELQLDGFRLDAVKHIKFSFLRDWV
SEQID No  8  (196) LMYADIDYDHPDVAAEIKRWGTWYANELQLDGFRLDAVKHIKFSFLRDWV
SEQID No  9  (196) LMYADVDYDHPDVVAETKKWGIWYANELSLDGFRIDAAKHIKFSFLRDWV
SEQID No 10  (201) LMYADIDMDHPEVVNELRNWGVWYTNTLGLDGFRIDAVKHIKYSFTRDWI
SEQID No 11  (201) LMYADVDMDHPEVVNELRRWGEWYTNTLNLDGFRIDAVKHIKYSFTRDWL
SEQID No 12  (201) LMYADIDMDHPEVINELRNWGVWYTNTLNLDGFRIDAVKHIKYSYTRDWL
SEQID No 13  (196) LLGSNIDFSHPEVQDELKDWGSWFTDELDLDGYRLDAIKHIPFWYTSDWV
SEQID No 14  (196) LLGSNIDFSHPEVQEELKDWGSWFTDELDLDGYRLDAIKHIPFWYTSDWV
SEQID No 15  (197) LMYADLDMDHPEVVTELKNWGKWYVNTTNIDGFRLDAVKHIKFSFFPDWL
Consensus    (201) LMYADIDMDHPEVV ELKNWG WY NTLNLDGFRLDAVKHIKFSF  DWL
                   251                                              300
SEQID No  1  (249) SYVRSQTGKPLFTVGEYWSYDINKLHNYITKTNGTMSLFDAPLHNKFYTA
SEQID No  2  (249) SYVRSQTGKPLFTVGEYWSYDINKLHNYITKTNGTMSLFDAPLHNKFYTA
SEQID No  3  (249) SYVRSQTGKPLFTVGEYWSYDINKLHNYITKTNGTMSLFDAPLHNKFYTA
SEQID No  4  (249) SYVRSQTGKPLFTVGEYWSYDINKLHNYITKTNGTMSLFDAPLHNKFYTA
SEQID No  5  (249) SYVRSQTGKPLFTVGEYWSYDINKLHNYITKTNGTMSLFDAPLHNKFYTA
SEQID No  6  (251) NHVRSATGKNMFAVAEFWKNDLGAIENYLQKTNWNHSVFDVPLHYNLYNA
SEQID No  7  (246) NHVREKTGKEMFTVAEYWQNDLGALENYLNKTNFNHSVFDVPLHYQFHAA
SEQID No  8  (246) NHVREKTGKEMFTVAEYWQNDLGALENYLNKTNFNHSVFDVPLHYQFHAA
SEQID No  9  (246) QAVRQATGKEMFTVAEYWQNNAGKLENYLNKTSFNQSVFDVPLHFNLQAA
SEQID No 10  (251) NHVRSATGKNMFAVAEFWKNDLGAIENYLNKTNWNHSVFDVPLHYNLYNA
SEQID No 11  (251) THVRNATGKEMFAVAEFWKNDLGALENYLNKTNWNHSVFDVPLHYNLYNA
SEQID No 12  (251) THVRNTTGKPMFAVAEFWKNDLAAIENYLNKTSWNHSVFDVPLHYNLYNA
SEQID No 13  (246) RHQRNEADQDLFVVGEYWKDDVGALEFYLDEMNWEMSLFDVPLNYNFYRA
SEQID No 14  (246) RHQRSEADQDLFVVGEYWKDDVGALEFYLDEMNWEMSLFDVPLNYNFYRA
SEQID No 15  (247) SYVRSQTGKPLFTVGEYWSYDINKLHNYITKTNGTMSLFDAPLHNKFYTA
Consensus    (251) SHVRS TGK LFTVGEYW  DIGALENYL KTNW MSLFDVPLHYNFY A
```

Figure 1 (cont.)

```
                   301                                               350
SEQID No  1  (299) SKSGGAFDMRTLMTNTLMKDQPTLAVTFVDNHDTEPGQALQSWVDPWFKP
SEQID No  2  (299) SKSGGAFDMRTLMTNTLMKDQPTLAVTFVDNHDTEPGQALQSWVDPWFKP
SEQID No  3  (299) SKSGGAFDMRTLMTNTLMKDQPTLAVTFVDNHDTEPGQALQSWVDPWFKP
SEQID No  4  (299) SKSGGAFDMRTLMTNTLMKDQPTLAVTFVDNHDTEPGQALQSWVDPWFKP
SEQID No  5  (299) SKSGGAFDMRTLMTNTLMKDQPTLAVTFVDNHDTEPGQALQSWVDPWFKP
SEQID No  6  (301) SKSGGNYDMRNIFNGTVVQRHPSHAVTFVDNHDSQPEEALESFVEEWFKP
SEQID No  7  (296) STQGGGYDMRKLLNGTVVSKHPLKSVTFVDNHDTQPGQSLESTVQTWFKP
SEQID No  8  (296) STQGGGYDMRKLLNGTVVSKHPLKSVTFVDNHDTQPGQSLESTVQTWFKP
SEQID No  9  (296) SSQGGGYDMRRLLDGTVVSRHPEKAVTFVENHDTQPGQSLESTVQTWFKP
SEQID No 10  (301) SKSGGNYDMRQIFNGTVVQRHPMHAVTFVDNHDSQPEEALESFVEEWFKP
SEQID No 11  (301) SNSGGNYDMAKLLNGTVVQKHPMHAVTFVDNHDSQPGESLESFVQEWFKP
SEQID No 12  (301) SNSGGYFDMRNILNGSVVQKHPIHAVTFVDNHDSQPGEALESFVQSWFKP
SEQID No 13  (296) SQQGGSYDMRNILRGSLVEAHPMHAVTFVDNHDTQPGESLESWVADWFKP
SEQID No 14  (296) SKQGGSYDMRNILRGSLVEAHPIHAVTFVDNHDTQPGESLESWVADWFKP
SEQID No 15  (297) SKSGGAFDMRTLMTNTLMKDQPTLAVTFVDNHDTEPGQALQSWVDPWFKP
   Consensus (301) SKSGGAYDMR LL GTLV  HP  AVTFVDNHDTQPGQALESWVD WFKP
                   351                                               400
SEQID No  1  (349) LAYAFILTRQEGYPCVFYGDYYGIPQYN---IPSLKSKIDPLLIARRDYA
SEQID No  2  (349) LAYAFILTRQEGYPCVFYGDYYGIPQYN---IPSLKSKIDPLLIARRDYA
SEQID No  3  (349) LAYAFILTRQEGYPCVFYGDYYGIPQYN---IPSLKSKIDPLLIARRDYA
SEQID No  4  (349) LAYAFILTRQEGYPCVFYGDYYGIPQYN---IPSLKSKIDPLLIARRDYA
SEQID No  5  (349) LAYAFILTRQEGYPCVFYGDYYGIPQYN---IPSLKSKIDPLLIARRDYA
SEQID No  6  (351) LAYALTLTREQGYPSVFYGDYYGIPTHG---VPAMRSKIDPILEARQKYA
SEQID No  7  (346) LAYAFILTRESGYPQVFYGDMYGTKGDSQREIPALKHKIEPILKARKQYA
SEQID No  8  (346) LAYAFILTRESGYPQVFYGDMYGTKGDSQREIPALKHKIEPILKARKQYA
SEQID No  9  (346) LAYAFILTRESGYPQVFYGDMYGTKGTSPKEIPSLKDNIEPILKARKEYA
SEQID No 10  (351) LAYALTLTREQGYPSVFYGDYYGIPTHG---VPAMKSKIDPILEARQKYA
SEQID No 11  (351) LAYALILTREQGYPSVFYGDYYGIPTHS---VPAMKAKIDPILEARQNFA
SEQID No 12  (351) LAYALILTREQGYPSVFYGDYYGIPTHG---VPSMKSKIDPLLQARQTYA
SEQID No 13  (346) LAYATILTREGGYPNVFYGDYYGIPNDN---ISAKKDMIDELLDARQNYA
SEQID No 14  (346) LAYATILTREGGYPNVFYGDYYGIPNDN---ISAKKDMIDELLDARQNYA
SEQID No 15  (347) LAYAFILTRQEGYPCVFYGDYYGIPQYN---IPSLKSKIDPLLIARRDYA
   Consensus (351) LAYAFILTRE GYP VFYGDYYGIPQYN   IPSLKSKIDPLL ARR YA
                   401                                               450
SEQID No  1  (396) YGTQHDYLDHSDIIGWTREGVTEKPGSGLAALITDGPGGSKWMYVGKQHA
SEQID No  2  (396) YGTQHDYLDHSDIIGWTREGVTEKPGSGLAALITDGPGGSKWMYVGKQHA
SEQID No  3  (396) YGTQHDYLDHSDIIGWTREGVTEKPGSGLAALITDGPGGSKWMYVGKQHA
SEQID No  4  (396) YGTQHDYLDHSDIIGWTREGVTEKPGSGLAALITDGPGGSKWMYVGKQHA
SEQID No  5  (396) YGTQHDYLDHSDIIGWTREGVTEKPGSGLAALITDGPGGSKWMYVGKQHA
SEQID No  6  (398) YGKQNDYLDHHNIIGWTREGNTAHPNSGLATIMSDGAGGSKWMFVGRNKA
SEQID No  7  (396) YGAQHDYFDHHDIVGWTREGDSSVANSGLAALITDGPGGAKRMYVGRQNA
SEQID No  8  (396) YGAQHDYFDHHDIVGWTREGDSSVANSGLAALITDGPGGAKRMYVGRQNA
SEQID No  9  (396) YGPQHDYIDHPDVIGWTREGDSSAAKSGLAALITDGPGGSKRMYAGLKNA
SEQID No 10  (398) YGRQNDYLDHHNIIGWTREGNTAHPNSGLATIMSDGAGGNKWMFVGRNKA
SEQID No 11  (398) YGTQHDYFDHHNIIGWTREGNTTHPNSGLATIMSDGPGGEKWMYVGQNKA
SEQID No 12  (398) YGTQHDYFDHHDIIGWTREGDSSHPNSGLATIMSDGPGGNKWMYVGKHKA
SEQID No 13  (393) YGTQHDYFDHWDVVGWTREGSSSRPNSGLATIMSNGPGGSKWMYVGRQNA
SEQID No 14  (393) YGTQHDYFDHWDIVGWTREGTSSRPNSGLATIMSNGPGGSKWMYVGQQHA
SEQID No 15  (394) YGTQHDYLDHSDIIGWTREGGTEKPGSGLAALITDGPGGSKWMYVGKQHA
   Consensus (401) YGTQHDYLDH DIIGWTREG TSKPNSGLAALITDGPGGSKWMYVGKQ A
```

Figure 1 (cont.)

```
                451                                                    500
SEQID No  1 (446) GKVFYDLTGNRSDTVTINSDGWGEFKVNGGSVSVWVPRKTTVSTIARPIT
SEQID No  2 (446) GKVFYDLTGNRSDTVTINSDGWGEFKVNGGSVSVWVPRKTT---------
SEQID No  3 (446) GKVFYDLTGNRSDTVTINSDGWGEFKVNGGSVSVWVPRKTTVSTIARPIT
SEQID No  4 (446) GKVFYDLTGNRSDTVTINSDGWGEFKVNGGSVSVWVPRKTTVSTIARPIT
SEQID No  5 (446) GKVFYDLTGNRSDTVTINSDGWGEFKVNGGSVSVWVPRKTTVSTIARPIT
SEQID No  6 (448) GQVWSDITGNRTGTVTINADGWGNFSVNGGSVSIWVNK------------
SEQID No  7 (446) GETWHDITGNRSEPVVINSEGWGEFHVNGGSVSIYVQR------------
SEQID No  8 (446) GETWHDITGNRSEPVVINSEGWGEFHVNGGSVSIYVQR------------
SEQID No  9 (446) GETWYDITGNRSDTVKIGSDGWGEFHVNDGSVSIYVQK------------
SEQID No 10 (448) GQVWTDITGNRAGTVTINADGWGNFSVNGGSVSIWVNK------------
SEQID No 11 (448) GQVWHDITGNKPGTVTINADGWANFSVNGGSVSIWVKR------------
SEQID No 12 (448) GQVWRDITGNRSGTVTINADGWGNFTVNGGAVSVWVKQ------------
SEQID No 13 (443) GQTWTDLTGNNGASVTINGDGWGEFFTNGGSVSVYVNQ------------
SEQID No 14 (443) GQTWTDLTGNHAASVTINGDGWGEFFTNGGSVSVYVNQ------------
SEQID No 15 (444) GKVFYDLTGNRSDTVTINSDGWGEFKVNGGSVSVWVPRKTTVS-------
Consensus   (451) G VWYDLTGNRSDTVTINSDGWGEF VNGGSVSVWV R
                501         520
SEQID No  1 (496) TRPWTGEFVRWTEPRLVAWP
SEQID No  2 (487) --------------------
SEQID No  3 (496) TRPWTGEFVRWTEPRLVAWP
SEQID No  4 (496) TRPWTGEFVRWTEPRLVAWP
SEQID No  5 (496) TRPWTGEFVRWTEPRLVAWP
SEQID No  6 (486) --------------------
SEQID No  7 (484) --------------------
SEQID No  8 (484) --------------------
SEQID No  9 (484) --------------------
SEQID No 10 (486) --------------------
SEQID No 11 (486) --------------------
SEQID No 12 (486) --------------------
SEQID No 13 (481) --------------------
SEQID No 14 (481) --------------------
SEQID No 15 (487) --------------------
Consensus   (501)
```

Figure 1 (cont.)

```
                        1                                                50
SEQID No 1     (1)   -AAPFNGTMMQYFEWYLPDDGTLWTKVANEANNLSSLGITALWLPPAYKG
SEQID No 6     (1)   HHNGTNGTMMQYFEWYLPNDGNHWNRLNSDASNLKSKGITAVWIPPAWKG
Consensus      (1)         NGTMMQYFEWYLP DG  W KL   DA NL S GITALWIPPAWKG
                       51                                               100
SEQID No 1     (50)  TSRSDVGYGVYDLYDLGEFNQKGTVRTKYGTKAQYLQAIQAAHAAGMQVY
SEQID No 6     (51)  ASQNDVGYGAYDLYDLGEFNQKGTVRTKYGTRSQLQAAVTSLKNNGIQVY
Consensus      (51)   S  DVGYG YDLYDLGEFNQKGTVRTKYGTKAQ    AI A    GIQVY
                      101                                               150
SEQID No 1    (100)  ADVVFDHKGGADGTEWVDAVEVNPSDRNQEISGTYQIQAWTKFDFPGRGN
SEQID No 6    (101)  GDVVMNHKGGADATEMVRAVEVNPNNRNQEVTGEYTIEAWTRFDFPGRGN
Consensus     (101)  ADVV  HKGGADATE V AVEVNP  RNQEISG Y I AWTKFDFPGRGN
                      151                                               200
SEQID No 1    (150)  TYSSFKWRWYHFDGVDWDESRKLS-RIYKFRGIGKAWDWEVDTENGNYDY
SEQID No 6    (151)  THSSFKWRWYHFDGVDWDQSRRLNNRIYKFRGHGKAWDWEVDTENGNYDY
Consensus     (151)  THSSFKWRWYHFDGVDWD SRKL  RIYKFRG GKAWDWEVDTENGNYDY
                      201                                               250
SEQID No 1    (199)  LMYADLDMDHPEVVTELKNWGKWYVNTTNIDGFRLDAVKHIKFSFFPDWL
SEQID No 6    (201)  LMYADIDMDHPEVVNELRNWGVWYTNTLGLDGFRIDAVKHIKYSFTRDWI
Consensus     (201)  LMYADIDMDHPEVV ELKNWG WY NT  IDGFRIDAVKHIKFSF  DWI
                      251                                               300
SEQID No 1    (249)  SYVRSQTGKPLFTVGEYWSYDINKLHNYITKTNGTMSLFDAPLHNKFYTA
SEQID No 6    (251)  NHVRSATGKNMFAVAEFWKNDLGAIENYLQKTNWNHSVFDVPLHYNLYNA
Consensus     (251)   HVRS TGK LF VAEFW  DI I NYI KTN   SLFD PLH  Y A
                      301                                               350
SEQID No 1    (299)  SKSGGAFDMRTLMTNTLMKDQPTLAVTFVDNHDTEPGQALQSWVDPWFKP
SEQID No 6    (301)  SKSGGNYDMRNIFNGTVVQRHPSHAVTFVDNHDSQPEEALESFVEEWFKP
Consensus     (301)  SKSGG FDMR I   TLM   PS AVTFVDNHDS P  AL SFVD WFKP
                      351                                               400
SEQID No 1    (349)  LAYAFILTRQEGYPCVFYGDYYGIPQYNIPSLKSKIDPLLIARRDYAYGT
SEQID No 6    (351)  LAYALTLTREQGYPSVFYGDYYGIPTHGVPAMRSKIDPILEARQKYAYGK
Consensus     (351)  LAYA  LTR  GYP VFYGDYYGIP H  IPALKSKIDPIL AR  YAYG
                      401                                               450
SEQID No 1    (399)  QHDYLDHSDIIGWTREGVTEKPGSGLAALITDGPGGSKWMYVGKQHAGKV
SEQID No 6    (401)  QNDYLDHHNIIGWTREGNTAHPNSGLATIMSDGAGGSKWMFVGRNKAGQV
Consensus     (401)  Q DYLDH  IIGWTREG T  P SGLA IISDG GGSKWMFVGKN AG V
                      451                                               500
SEQID No 1    (449)  FYDLTGNRSDTVTINSDGWGEFKVNGGSVSVWVPRKTTVSTIARPITTRP
SEQID No 6    (451)  WSDITGNRTGTVTINADGWGNFSVNGGSVSIWVNK---------------
Consensus     (451)  F DITGNRS TVTINADGWG F VNGGSVSIWV K
                      501            517
SEQID No 1    (499)  WTGEFVRWTEPRLVAWP
SEQID No 6    (486)  -----------------
Consensus     (501)
```

Figure 4A

```
                         1                                                  50
SEQID No 1     (1)  AAPFNGTMMQYFEWYLPDDGTLWTKVANEANNLSSLGITALWLPPAYKGT
SEQID No 8     (1)  -ANLNGTLMQYFEWYMPNDGQHWRRLQNDSAYLAEHGITAVWIPPAYKGT
Consensus      (1)   A  NGTLMQYFEWYLP DG W  KL NDA   LA  GITALWIPPAYKGT
                         51                                                 100
SEQID No 1    (51)  SRSDVGYGVYDLYDLGEFNQKGTVRTKYGTKAQYLQAIQAAHAAGMQVYA
SEQID No 8    (50)  SQADVGYGAYDLYDLGEFHQKGTVRTKYGTKGELQSAIKSLHSRDINVYG
Consensus     (51)  S  ADVGYG YDLYDLGEF QKGTVRTKYGTKA      AI A HA   INVYA
                         101                                                150
SEQID No 1   (101)  DVVFDHKGGADGTEWVDAVEVNPSDRNQEISGTYQIQAWTKFDFPGRGNT
SEQID No 8   (100)  DVVINHKGGADATEDVTAVEVDPADRNRVISGEHLIKAWTHFHFPGRGST
Consensus    (101)  DVV  HKGGADATE V AVEV PADRN  ISG H I AWT F FPGRG T
                         151                                                200
SEQID No 1   (151)  YSSFKWRWYHFDGVDWDESRKLSRIYKFRGIGKAWDWEVDTENGNYDYLM
SEQID No 8   (150)  YSDFKWHWYHFDGTDWDESRKLNRIYKFQ--GKAWDWEVSNENGNYDYLM
Consensus    (151)  YS FKW WYHFDG DWDESRKL RIYKF    GKAWDWEV  ENGNYDYLM
                         201                                                250
SEQID No 1   (201)  YADLDMDHPEVVTELKNWGKWYVNTTNIDGFRLDAVKHIKFSFFPDWLSY
SEQID No 8   (198)  YADIDYDHPDVAAEIKRWGTWYANELQLDGFRLDAVKHIKFSFLRDWVNH
Consensus    (201)  YADID DHPDV   EIK WG WY N   IDGFRLDAVKHIKFSF DWL H
                         251                                                300
SEQID No 1   (251)  VRSQTGKPLFTVGEYWSYDINKLHNYITKTNGTMSLFDAPLHNKFYTASK
SEQID No 8   (248)  VREKTGKEMFTVAEYWQNDLGALENYLNKTNFNHSVFDVPLHYQFHAAST
Consensus    (251)  VR  TGK  LFTVAEYW  DI L NYI KTN    SLFD PLH  FH AS
                         301                                                350
SEQID No 1   (301)  SGGAFDMRTLMTNTLMKDQPTLAVTFVDNHDTEPGQALQSWVDPWFKPLA
SEQID No 8   (298)  QGGGYDMRKLLNGTVVSKHPLKSVTFVDNHDTQPGQSLESTVQTWFKPLA
Consensus    (301)   GGAFDMR LL  TLM   P  AVTFVDNHDT PGQAL S V   WFKPLA
                         351                                                400
SEQID No 1   (351)  YAFILTRQEGYPCVFYGDYYGIP---QYNIPSLKSKIDPLLIARRDYAYG
SEQID No 8   (348)  YAFILTRESGYPQVFYGDMYGTKGDSQREIPALKHKIEPILKARKQYAYG
Consensus    (351)  YAFILTR  GYP VFYGD YG      Q  IPALK KIDPIL ARK YAYG
                         401                                                450
SEQID No 1   (398)  TQHDYLDHSDIIGWTREGVTEKPGSGLAALITDGPGGSKWMYVGKQHAGK
SEQID No 8   (398)  AQHDYFDHHDIVGWTREGDSSVANSGLAALITDGPGGAKRMYVGRQNAGE
Consensus    (401)   QHDY DH DIIGWTREG S      SGLAALITDGPGGAK MYVGKQ AG
                         451                                                500
SEQID No 1   (448)  VFYDLTGNRSDTVTINSDGWGEFKVNGGSVSVWVPRKTTVSTIARPITTR
SEQID No 8   (448)  TWHDITGNRSEPVVINSEGWGEFHVNGGSVSIYVQR--------------
Consensus    (451)    FHDITGNRSD V INSDGWGEF VNGGSVSIWV R
                         501      518
SEQID No 1   (498)  PWTGEFVRWTEPRLVAWP
SEQID No 8   (484)  ------------------
Consensus    (501)
```

Figure 4B

|  |  | 1 | 50 |
|---|---|---|---|
| SEQID No 1 | (1) | AAPFNGTMMQYFEWYLPDDGTLWTKVANEANNLSSLGITALWLPPAYKGT | |
| SEQID No 9 | (1) | ---VNGTLMQYFEWYTPNDGQHWKRLQNDAEHLSDIGITAVWIPPAYKGL | |
| Consensus | (1) | NGTLMQYFEWY P DG W KL NDA LS IGITALWIPPAYKG | |
|  |  | 51 | 100 |
| SEQID No 1 | (51) | SRSDVGYGVYDLYDLGEFNQKGTVRTKYGTKAQYLQAIQAAHAAGMQVYA | |
| SEQID No 9 | (48) | SQSDNGYGPYDLYDLGEFQQKGTVRTKYGTKSELQDAIGSLHSRNVQVYG | |
| Consensus | (51) | S SD GYG YDLYDLGEFNQKGTVRTKYGTKA AI A HA MQVYA | |
|  |  | 101 | 150 |
| SEQID No 1 | (101) | DVVFDHKGGADGTEWVDAVEVNPSDRNQEISGTYQIQAWTKFDFPGRGNT | |
| SEQID No 9 | (98) | DVVLNHKAGADATEDVTAVEVNPANRNQETSEEYQIKAWTDFRFPGRGNT | |
| Consensus | (101) | DVV HKAGADATE V AVEVNPA RNQE S YQI AWT F FPGRGNT | |
|  |  | 151 | 200 |
| SEQID No 1 | (151) | YSSFKWRWYHFDGVDWDESRKLSRIYKFRGIGKAWDWEVDTENGNYDYLM | |
| SEQID No 9 | (148) | YSDFKWHWYHFDGADWDESRKISRIFKFRGEGKAWDWEVSSENGNYDYLM | |
| Consensus | (151) | YS FKW WYHFDG DWDESRKISRIFKFRG GKAWDWEV SENGNYDYLM | |
|  |  | 201 | 250 |
| SEQID No 1 | (201) | YADLDMDHPEVVTELKNWGKWYVNTTNIDGFRLDAVKHIKFSFFPDWLSY | |
| SEQID No 9 | (198) | YADVDYDHPDVVAETKKWGIWYANELSLDGFRIDAAKHIKFSFLRDWVQA | |
| Consensus | (201) | YADLD DHPDVV E K WG WY N IDGFRIDA KHIKFSF DWL | |
|  |  | 251 | 300 |
| SEQID No 1 | (251) | VRSQTGKPLFTVGEYWSYDINKLHNYITKTNGTMSLFDAPLHNKFYTASK | |
| SEQID No 9 | (248) | VRQATGKEMFTVAEYWQNNAGKLENYLNKTSFNQSVFDVPLHFNLQAASS | |
| Consensus | (251) | VR TGK LFTVAEYW KL NYI KT SLFD PLH AS | |
|  |  | 301 | 350 |
| SEQID No 1 | (301) | SGGAFDMRTLMTNTLMKDQPTLAVTFVDNHDTEPGQALQSWVDPWFKPLA | |
| SEQID No 9 | (298) | QGGGYDMRRLLDGTVVSRHPEKAVTFVENHDTQPGQSLESTVQTWFKPLA | |
| Consensus | (301) | GGAFDMR LL TLM P AVTFVDNHDT PGQAL S V WFKPLA | |
|  |  | 351 | 400 |
| SEQID No 1 | (351) | YAFILTRQEGYPCVFYGDYYGIPQYN---IPSLKSKIDPLLIARRDYAYG | |
| SEQID No 9 | (348) | YAFILTRESGYPQVFYGDMYGTKGTSPKEIPSLKDNIEPILKARKEYAYG | |
| Consensus | (351) | YAFILTR GYP VFYGD YG IPSLK IDPIL ARKDYAYG | |
|  |  | 401 | 450 |
| SEQID No 1 | (398) | TQHDYLDHSDIIGWTREGVTEKPGSGLAALITDGPGGSKWMYVGKQHAGK | |
| SEQID No 9 | (398) | PQHDYIDHPDVIGWTREGDSSAAKSGLAALITDGPGGSKRMYAGLKNAGE | |
| Consensus | (401) | QHDYIDH DIIGWTREG S SGLAALITDGPGGSK MY G AG | |
|  |  | 451 | 500 |
| SEQID No 1 | (448) | VFYDLTGNRSDTVTINSDGWGEFKVNGGSVSVWVPRKTTVSTIARPITTR | |
| SEQID No 9 | (448) | TWYDITGNRSDTVKIGSDGWGEFHVNDGSVSIYVQK-------------- | |
| Consensus | (451) | FYDITGNRSDTV I SDGWGEF VN GSVSIWV K | |
|  |  | 501 | 518 |
| SEQID No 1 | (498) | PWTGEFVRWTEPRLVAWP | |
| SEQID No 9 | (484) | ------------------ | |
| Consensus | (501) |  | |

Figure 4C

```
                         1                                                50
SEQID No 1       (1)  -AAPFNGTMMQYFEWYLPDDGTLWTKVANEANNLSSLGITALWLPPAYKG
SEQID No 10      (1)  HHNGTNGTMMQYFEWYLPNDGNHWNRLRSDASNLKDKGISAVWIPPAWKG
Consensus        (1)         NGTMMQYFEWYLP DG   W KL  DA NL   GISALWIPPAWKG
                         51                                               100
SEQID No 1      (50)  TSRSDVGYGVYDLYDLGEFNQKGTVRTKYGTKAQYLQAIQAAHAAGMQVY
SEQID No 10     (51)  ASQNDVGYGAYDLYDLGEFNQKGTIRTKYGTRNQLQAAVNALKSNGIQVY
Consensus       (51)   S  DVGYG YDLYDLGEFNQKGTIRTKYGTK Q    AINA   A GIQVY
                         101                                              150
SEQID No 1     (100)  ADVVFDHKGGADGTEWVDAVEVNPSDRNQEISGTYQIQAWTKFDFPGRGN
SEQID No 10    (101)  GDVVMNHKGGADATEMVRAVEVNPNNRNQEVSGEYTIEAWTKFDFPGRGN
Consensus      (101)   ADVV  HKGGADATE V AVEVNP  RNQEISG Y I  AWTKFDFPGRGN
                         151                                              200
SEQID No 1     (150)  TYSSFKWRWYHFDGVDWDESRKLS-RIYKFRGIGKAWDWEVDTENGNYDY
SEQID No 10    (151)  THSNFKWRWYHFDGVDWDQSRKLNNRIYKFRGDGKGWDWEVDTENGNYDY
Consensus      (151)  THS FKWRWYHFDGVDWD SRKL  RIYKFRG GKAWDWEVDTENGNYDY
                         201                                              250
SEQID No 1     (199)  LMYADLDMDHPEVVTELKNWGKWYVNTTNIDGFRLDAVKHIKFSFFPDWL
SEQID No 10    (201)  LMYADIDMDHPEVVNELRNWGVWYTNTLGLDGFRIDAVKHIKYSFTRDWI
Consensus      (201)  LMYADIDMDHPEVV ELKNWG WY NT   IDGFRIDAVKHIKFSF  DWI
                         251                                              300
SEQID No 1     (249)  SYVRSQTGKPLFTVGEYWSYDINKLHNYITKTNGTMSLFDAPLHNKFYTA
SEQID No 10    (251)  NHVRSATGKNMFAVAEFWKNDLGAIENYLNKTNWNHSVFDVPLHYNLYNA
Consensus      (251)    HVRS TGK LF VAEFW  DI I NYI KTN    SLFD PLH Y A
                         301                                              350
SEQID No 1     (299)  SKSGGAFDMRTLMTNTLMKDQPTLAVTFVDNHDTEPGQALQSWVDPWFKP
SEQID No 10    (301)  SKSGGNYDMRQIFNGTVVQRHPMHAVTFVDNHDSQPEEALESFVEEWFKP
Consensus      (301)  SKSGG FDMR I    TLM  P  AVTFVDNHDS P  AL SFVD WFKP
                         351                                              400
SEQID No 1     (349)  LAYAFILTRQEGYPCVFYGDYYGIPQYNIPSLKSKIDPLLIARRDYAYGT
SEQID No 10    (351)  LAYALTLTREQGYPSVFYGDYYGIPTHGVPAMKSKIDPILEARQKYAYGR
Consensus      (351)  LAYA  LTR  GYP VFYGDYYGIP H   IPALKSKIDPIL AR  YAYG
                         401                                              450
SEQID No 1     (399)  QHDYLDHSDIIGWTREGVTEKPGSGLAALITDGPGGSKWMYVGKQHAGKV
SEQID No 10    (401)  QNDYLDHHNIIGWTREGNTAHPNSGLATIMSDGAGGNKWMFVGRNKAGQV
Consensus      (401)  Q DYLDH   IIGWTREG T   P SGLA IISDG GG KWMFVGKN AG V
                         451                                              500
SEQID No 1     (449)  FYDLTGNRSDTVTINSDWGEFKVNGGSVSVWVPRKTTVSTIARPITTRP
SEQID No 10    (451)  WTDITGNRAGTVTINADGWGNFSVNGGSVSIWVNK---------------
Consensus      (451)  F DITGNRA TVTINADGWG F VNGGSVSIWV K
                         501          517
SEQID No 1     (499)  WTGEFVRWTEPRLVAWP
SEQID No 10    (486)  -----------------
Consensus      (501)
```

Figure 4D

```
              1                                                  50
SEQID No 1   (1)  -AAPFNGTMMQYFEWYLPDDGTLWTKVANEANNLSSLGITALWLPPAYKG
SEQID No 11  (1)  HHNGTNGTMMQYFEWHLPNDGNHWNRLRDDASNLRNRGITAIWIPPAWKG
Consensus    (1)       NGTMMQYFEWHLP DG  W KL  DA NL   GITAIWIPPAWKG
             51                                                 100
SEQID No 1   (50)  TSRSDVGYGVYDLYDLGEFNQKGTVRTKYGTKAQYLQAIQAAHAAGMQVY
SEQID No 11  (51)  TSQNDVGYGAYDLYDLGEFNQKGTVRTKYGTRSQLESAIHALKNNGVQVY
Consensus    (51)  TS  DVGYG YDLYDLGEFNQKGTVRTKYGTKAQ    AI A   GMQVY
             101                                                150
SEQID No 1   (100) ADVVFDHKGGADGTEWVDAVEVNPSDRNQEISGTYQIQAWTKFDFPGRGN
SEQID No 11  (101) GDVVMNHKGGADATENVLAVEVNPNNRNQEISGDYTIEAWTKFDFPGRGN
Consensus    (101) ADVV  HKGGADATE V AVEVNP  RNQEISG Y I AWTKFDFPGRGN
             151                                                200
SEQID No 1   (150) TYSSFKWRWYHFDGVDWDESR-KLSRIYKFRGIGKAWDWEVDTENGNYDY
SEQID No 11  (151) TYSDFKWRWYHFDGVDWDQSRQFQNRIYKFRGDGKAWDWEVDSENGNYDY
Consensus    (151) TYS FKWRWYHFDGVDWD SR    RIYKFRG GKAWDWEVDSENGNYDY
             201                                                250
SEQID No 1   (199) LMYADLDMDHPEVVTELKNWGKWYVNTTNIDGFRLDAVKHIKFSFPPDWL
SEQID No 11  (201) LMYADVDMDHPEVVNELRRWGEWYTNTLNLDGFRIDAVKHIKYSFTRDWL
Consensus    (201) LMYADLDMDHPEVV ELK WG WY NT NIDGFRIDAVKHIKFSF  DWL
             251                                                300
SEQID No 1   (249) SYVRSQTGKPLFTVGEYWSYDINKLHNYITKTNGTMSLFDAPLHNKFYTA
SEQID No 11  (251) THVRNATGKEMFAVAEFWKNDLGALENYLNKTNWNHSVFDVPLHYNLYNA
Consensus    (251) SHVR  TGK LF VAEFW  DI L NYI KTN    SLFD PLH   Y A
             301                                                350
SEQID No 1   (299) SKSGGAFDMRTLMTNTLMKDQPTLAVTFVDNHDTEPGQALQSWVDPWFKP
SEQID No 11  (301) SNSGGNYDMAKLLNGTVVQKHPMHAVTFVDNHDSQPGESLESFVQEWFKP
Consensus    (301) S SGG  FDM  LL  T LM   P  AVTFVDNHDS PG AL SFV  WFKP
             351                                                400
SEQID No 1   (349) LAYAFILTRQEGYPCVFYGDYYGIPQYNIPSLKSKIDPLLIARRDYAYGT
SEQID No 11  (351) LAYALILTREQGYPSVFYGDYYGIPTHSVPAMKAKIDPILEARQNFAYGT
Consensus    (351) LAYA ILTR  GYP VFYGDYYGIP H IPALKAKIDPIL AR  FAYGT
             401                                                450
SEQID No 1   (399) QHDYLDHSDIIGWTREGVTEKPGSGLAALITDGPGGSKWMYVGKQHAGKV
SEQID No 11  (401) QHDYFDHHNIIGWTREGNTTHPNSGLATIMSDGPGGEKWMYVGQNKAGQV
Consensus    (401) QHDY DH  IIGWTREG T P  SGLA IISDGPGG KWMYVG N AG V
             451                                                500
SEQID No 1   (449) FYDLTGNRSDTVTINSDGWGEFKVNGGSVSWVPRKTTVSTIARPITTRP
SEQID No 11  (451) WHDITGNKPGTVTINADGWANFSVNGGSVSIWVKR---------------
Consensus    (451) FHDITGNK   TVTINADGWA F VNGGSVSIWV R
             501         517
SEQID No 1   (499) WTGEFVRWTEPRLVAWP
SEQID No 11  (486) -----------------
Consensus    (501)
```

Figure 4E

```
                         1                                                  50
SEQID No 1     (1)  -AAPFNGTMMQYFEWYLPDDGTLWTKVANEANNLSSLGITALWLPPAYKG
SEQID No 12    (1)  HHNGTNGTMMQYFEWHLPNDGNHWNRLRDDAANLKSKGITAVWIPPAWKG
Consensus      (1)        NGTMMQYFEWHLP DG  W KL  DA NL S GITALWIPPAWKG
                         51                                                100
SEQID No 1    (50)  TSRSDVGYGVYDLYDLGEFNQKGTVRTKYGTKAQYLQAIQAAHAAGMQVY
SEQID No 12   (51)  TSQNDVGYGAYDLYDLGEFNQKGTVRTKYGTRSQLQGAVTSLKNNGIQVY
Consensus     (51)  TS  DVGYG YDLYDLGEFNQKGTVRTKYGTKAQ    AI A    GIQVY
                        101                                                150
SEQID No 1   (100)  ADVVFDHKGGADGTEWVDAVEVNPSDRNQEISGTYQIQAWTKFDFPGRGN
SEQID No 12  (101)  GDVVMNHKGGADGTEMVNAVEVNRSNRNQEISGEYTIEAWTKFDFPGRGN
Consensus    (101)  ADVV  HKGGADGTE V AVEVN S RNQEISG Y I AWTKFDFPGRGN
                        151                                                200
SEQID No 1   (150)  TYSSFKWRWYHFDGVDWDESR-KLSRIYKFRGIGKAWDWEVDTENGNYDY
SEQID No 12  (151)  THSNFKWRWYHFDGTDWDQSRQLQNKIYKFRGTGKAWDWEVDIENGNYDY
Consensus    (151)  THS FKWRWYHFDG DWD SR    KIYKFRG GKAWDWEVD ENGNYDY
                        201                                                250
SEQID No 1   (199)  LMYADLDMDHPEVVTELKNWGKWYVNTTNIDGFRLDAVKHIKFSFFPDWL
SEQID No 12  (201)  LMYADIDMDHPEVINELRNWGVWYTNTLNLDGFRIDAVKHIKYSYTRDWL
Consensus    (201)  LMYADIDMDHPEVI ELKNWG WY NT NIDGFRIDAVKHIKFSF  DWL
                        251                                                300
SEQID No 1   (249)  SYVRSQTGKPLFTVGEYWSYDINKLHNYITKTNGTMSLFDAPLHNKFYTA
SEQID No 12  (251)  THVRNTTGKPMFAVAEFWKNDLAAIENYLNKTSWNHSVFDVPLHYNLYNA
Consensus    (251)  SHVR  TGKPLF VAEFW  DI  I NYI KT    SLFD PLH  Y A
                        301                                                350
SEQID No 1   (299)  SKSGGAFDMRTLMTNTLMKDQPTLAVTFVDNHDTEPGQALQSWVDPWFKP
SEQID No 12  (301)  SNSGGYFDMRNILNGSVVQKHPIHAVTFVDNHDSQPGEALESFVQSWFKP
Consensus    (301)  S SGG FDMR IL   SLM    P  AVTFVDNHDS PG AL SFV  WFKP
                        351                                                400
SEQID No 1   (349)  LAYAFILTRQEGYPCVFYGDYYGIPQYNIPSLKSKIDPLLIARRDYAYGT
SEQID No 12  (351)  LAYALILTREQGYPSVFYGDYYGIPTHGVPSMKSKIDPLLQARQTYAYGT
Consensus    (351)  LAYA ILTR  GYP VFYGDYYGIP H  IPSLKSKIDPLL AR   YAYGT
                        401                                                450
SEQID No 1   (399)  QHDYLDHSDIIGWTREGVTEKPGSGLAALITDGPGGSKWMYVGKQHAGKV
SEQID No 12  (401)  QHDYFDHHDIIGWTREGDSSHPNSGLATIMSDGPGGNKWMYVGKHKAGQV
Consensus    (401)  QHDY DH DIIGWTREG S  P SGLA IISDGPGG KWMYVGK  AG V
                        451                                                500
SEQID No 1   (449)  FYDLTGNRSDTVTINSDGWGEFKVNGGSVSVWVPRKTTVSTIARPITTRP
SEQID No 12  (451)  WRDITGNRSGTVTINADGWGNFTVNGGAVSVWVKQ---------------
Consensus    (451)  F DITGNRS TVTINADGWG F VNGGAVSVWV
                        501        517
SEQID No 1   (499)  WTGEFVRWTEPRLVAWP
SEQID No 12  (486)  -----------------
Consensus    (501)
```

Figure 4F

```
                      1                                                50
SEQID No 1      (1)   AAPFNGTMMQYFEWYLPDDGTLWTKVANEANNLSSLGITALWLPPAYKGT
SEQID No 13     (1)   -DGLNGTMMQYYEWHLENDGQHWNRLHDDAAALSDAGITAIWIPPAYKGN
Consensus       (1)        NGTMMQYFEWHL  DG  W KL  DA  LS   GITAIWIPPAYKG
                      51                                               100
SEQID No 1      (51)  SRSDVGYGVYDLYDLGEFNQKGTVRTKYGTKAQYLQAIQAAHAAGMQVYA
SEQID No 13     (50)  SQADVGYGAYDLYDLGEFNQKGTVRTKYGTKAQLERAIGSLKSNDINVYG
Consensus       (51)  S  ADVGYG YDLYDLGEFNQKGTVRTKYGTKAQ     AI A A  INVYA
                      101                                              150
SEQID No 1      (101) DVVFDHKGGADGTEWVDAVEVNPSDRNQEISGTYQIQAWTKFDFPGRGNT
SEQID No 13     (100) DVVMNHKMGADFTEAVQAVQVNPTNRWQDISGAYTIDAWTGFDFSGRNNA
Consensus       (101) DVV  HK GAD TE V AV VNPS R QDISG Y I  AWT FDF GR N
                      151                                              200
SEQID No 1      (151) YSSFKWRWYHFDGVDWDESRKLSRIYKFRGIGKAWDWEVDTENGNYDYLM
SEQID No 13     (150) YSDFKWRWFHFNGVDWDQRYQENHIFRFANTN--WNWRVDEENGNYDYLL
Consensus       (151) YS FKWRWFHF GVDWD         IFKF       W W VD ENGNYDYLL
                      201                                              250
SEQID No 1      (201) YADLDMDHPEVVTELKNWGKWYVNTTNIDGFRLDAVKHIKFSFFPDWLSY
SEQID No 13     (198) GSNIDFSHPEVQDELKDWGSWFTDELDLDGYRLDAIKHIPFWYTSDWVRH
Consensus       (201)  A  ID  HPEV  ELK WG WF        IDGFRLDAIKHI F F  DWL H
                      251                                              300
SEQID No 1      (251) VRSQTGKPLFTVGEYWSYDINKLHNYITKTNGTMSLFDAPLHNKFYTASK
SEQID No 13     (248) QRNEADQDLFVVGEYWKDDVGALEFYLDEMNWEMSLFDVPLNYNFYRASQ
Consensus       (251)  R       LF VGEYW  DI   L    YI  N  MSLFD PL  FY AS
                      301                                              350
SEQID No 1      (301) SGGAFDMRTLMTNTLMKDQPTLAVTFVDNHDTEPGQALQSWVDPWFKPLA
SEQID No 13     (298) QGGSYDMRNILRGSLVEAHPMHAVTFVDNHDTQPGESLESWVADWFKPLA
Consensus       (301)  GGA FDMR IL   SLM    P  AVTFVDNHDT PG AL SWV  WFKPLA
                      351                                              400
SEQID No 1      (351) YAFILTRQEGYPCVFYGDYYGIPQYNIPSLKSKIDPLLIARRDYAYGTQH
SEQID No 13     (348) YATILTREGGYPNVFYGDYYGIPNDNISAKKDMIDELLDARQNYAYGTQH
Consensus       (351) YA ILTR  GYP VFYGDYYGIPN NI A K   ID LL AR  YAYGTQH
                      401                                              450
SEQID No 1      (401) DYLDHSDIIGWTREGVTEKPGSGLAALITDGPGGSKWMYVGKQHAGKVFY
SEQID No 13     (398) DYFDHWDVVGWTREGSSSRPNSGLATIMSNGPGGSKWMYVGRQNAGQTWT
Consensus       (401) DY DH D IIGWTREG S  KP SGLA IIS GPGGSKWMYVGKQ AG  F
                      451                                              500
SEQID No 1      (451) DLTGNRSDTVTINSDGWGEFKVNGGSVSVWVPRKTTVSTIARPITTRPWT
SEQID No 13     (448) DLTGNNGASVTINGDGWGEFFTNGGSVSVYVNQ-----------------
Consensus       (451) DLTGN     SVTIN DGWGEF  NGGSVSVWV
                      501       515
SEQID No 1      (501) GEFVRWTEPRLVAWP
SEQID No 13     (481) ---------------
Consensus       (501)
```

Figure 4G

```
                         1                                                  50
SEQID No 1      (1)   AAPFNGTMMQYFEWYLPDDGTLWTKVANEANNLSSLGITALWLPPAYKGT
SEQID No 14     (1)   -DGLNGTMMQYYEWHLENDGQHWNRLHDDAEALSNAGITAIWIPPAYKGN
Consensus       (1)       NGTMMQYFEWHL  DG   W KL  DA  LS  GITAIWIPPAYKG
                         51                                                100
SEQID No 1      (51)  SRSDVGYGVYDLYDLGEFNQKGTVRTKYGTKAQYLQAIQAAHAAGMQVYA
SEQID No 14     (50)  SQADVGYGAYDLYDLGEFNQKGTVRTKYGTKAQLERAIGSLKSNDINVYG
Consensus       (51)  S ADVGYG YDLYDLGEFNQKGTVRTKYGTKAQ    AI A  A   INVYA
                         101                                               150
SEQID No 1     (101)  DVVFDHKGGADGTEWVDAVEVNPSDRNQEISGTYQIQAWTKFDFPGRGNT
SEQID No 14    (100)  DVVMNHKLGADFTEAVQAVQVNPSNRWQDISGVYTIDAWTGFDFPGRNNA
Consensus      (101)  DVV   HK GAD TE V AV VNPS R QDISG Y I AWT FDFPGR N
                         151                                               200
SEQID No 1     (151)  YSSFKWRWYHFDGVDWDESRKLSRIYKFRGIGKAWDWEVDTENGNYDYLM
SEQID No 14    (150)  YSDFKWRWFHFNGVDWDQRYQENHLFRFANTN--WNWRVDEENGNYDYLL
Consensus      (151)  YS FKWRWFHF GVDWD        IFKF        W W VD ENGNYDYLL
                         201                                               250
SEQID No 1     (201)  YADLDMDHPEVVTELKNWGKWYVNTTNIDGFRLDAVKHIKFSFFPDWLSY
SEQID No 14    (198)  GSNIDFSHPEVQEELKDWGSWFTDELDLDGYRLDAIKHIPFWYTSDWVRH
Consensus      (201)   A ID HPEV  ELK WG WF      IDGFRLDAIKHI F F  DWL H
                         251                                               300
SEQID No 1     (251)  VRSQTGKPLFTVGEYWSYDINKLHNYITKTNGTMSLFDAPLHNKFYTASK
SEQID No 14    (248)  QRSEADQDLFVVGEYWKDDVGALEFYLDEMNWEMSLFDVPLNYNFYRASK
Consensus      (251)   RS      LF VGEYW  DI   L  YI  N  MSLFD PL  FY ASK
                         301                                               350
SEQID No 1     (301)  SGGAFDMRTLMTNTLMKDQPTLAVTFVDNHDTEPGQALQSWVDPWFKPLA
SEQID No 14    (298)  QGGSYDMRNILRGSLVEAHPIHAVTFVDNHDTQPGESLESWVADWFKPLA
Consensus      (301)    GGAFDMR IL   SLM    P  AVTFVDNHDT PG AL SWV  WFKPLA
                         351                                               400
SEQID No 1     (351)  YAFILTRQEGYPCVFYGDYYGIPQYNIPSLKSKIDPLLIARRDYAYGTQH
SEQID No 14    (348)  YATILTREGGYPNVFYGDYYGIPNDNISAKKDMIDELLDARQNYAYGTQH
Consensus      (351)  YA ILTR  GYP VFYGDYYGIPN NI A K  ID LL AR  YAYGTQH
                         401                                               450
SEQID No 1     (401)  DYLDHSDIIGWTREGVTEKPGSGLAALITDGPGGSKWMYVGKQHAGKVFY
SEQID No 14    (398)  DYFDHWDIVGWTREGTSSRPNSGLATIMSNGPGGSKWMYVGQQHAGQTWT
Consensus      (401)  DY DH DIIGWTREG  S KP SGLA IIS GPGGSKWMYVG QHAG  F
                         451                                               500
SEQID No 1     (451)  DLTGNRSDTVTINSDGWGEFKVNGGSVSVWVPRKTTVSTIARPITTRPWT
SEQID No 14    (448)  DLTGNHAASVTINGDGWGEFFTNGGSVSVYVNQ-----------------
Consensus      (451)  DLTGN A SVTIN DGWGEF  NGGSVSVWV
                         501           515
SEQID No 1     (501)  GEFVRWTEPRLVAWP
SEQID No 14    (481)  ---------------
Consensus      (501)
```

Figure 4H

|  |  | 1 | 50 |
|---|---|---|---|
| SEQID No 1 | (1) | AAPFNGTMMQYFEWYLPDDGTLWTKVANEANNLSSLGITALWLPPAYKGT | |
| SEQID No 15 | (1) | AAPFNGTMMQYFEWYLPDDGTLWTKVANEANNLSSLGITALWLPPAYKGT | |
| Consensus | (1) | AAPFNGTMMQYFEWYLPDDGTLWTKVANEANNLSSLGITALWLPPAYKGT | |
|  |  | 51 | 100 |
| SEQID No 1 | (51) | SRSDVGYGVYDLYDLGEFNQKGTVRTKYGTKAQYLQAIQAAHAAGMQVYA | |
| SEQID No 15 | (51) | SRSDVGYGVYDLYDLGEFNQKGTVRTKYGTKAQYLQAIQAAHAAGMQVYA | |
| Consensus | (51) | SRSDVGYGVYDLYDLGEFNQKGTVRTKYGTKAQYLQAIQAAHAAGMQVYA | |
|  |  | 101 | 150 |
| SEQID No 1 | (101) | DVVFDHKGGADGTEWVDAVEVNPSDRNQEISGTYQIQAWTKFDFPGRGNT | |
| SEQID No 15 | (101) | DVVFDHKGGADGTEWVDAVEVNPSDRNQEISGTYQIQAWTKFDFPGRGNT | |
| Consensus | (101) | DVVFDHKGGADGTEWVDAVEVNPSDRNQEISGTYQIQAWTKFDFPGRGNT | |
|  |  | 151 | 200 |
| SEQID No 1 | (151) | YSSFKWRWYHFDGVDWDESRKLSRIYKFRGIGKAWDWEVDTENGNYDYLM | |
| SEQID No 15 | (151) | YSSFKWRWYHFDGVDWDESRKLSRIYKFR--GKAWDWEVDTEFGNYDYLM | |
| Consensus | (151) | YSSFKWRWYHFDGVDWDESRKLSRIYKFR  GKAWDWEVDTE GNYDYLM | |
|  |  | 201 | 250 |
| SEQID No 1 | (201) | YADLDMDHPEVVTELKNWGKWYVNTTNIDGFRLDAVKHIKFSFFPDWLSY | |
| SEQID No 15 | (199) | YADLDMDHPEVVTELKNWGKWYVNTTNIDGFRLDAVKHIKFSFFPDWLSY | |
| Consensus | (201) | YADLDMDHPEVVTELKNWGKWYVNTTNIDGFRLDAVKHIKFSFFPDWLSY | |
|  |  | 251 | 300 |
| SEQID No 1 | (251) | VRSQTGKPLFTVGEYWSYDINKLHNYITKTNGTMSLFDAPLHNKFYTASK | |
| SEQID No 15 | (249) | VRSQTGKPLFTVGEYWSYDINKLHNYITKTNGTMSLFDAPLHNKFYTASK | |
| Consensus | (251) | VRSQTGKPLFTVGEYWSYDINKLHNYITKTNGTMSLFDAPLHNKFYTASK | |
|  |  | 301 | 350 |
| SEQID No 1 | (301) | SGGAFDMRTLMTNTLMKDQPTLAVTFVDNHDTEPGQALQSWVDPWFKPLA | |
| SEQID No 15 | (299) | SGGAFDMRTLMTNTLMKDQPTLAVTFVDNHDTEPGQALQSWVDPWFKPLA | |
| Consensus | (301) | SGGAFDMRTLMTNTLMKDQPTLAVTFVDNHDTEPGQALQSWVDPWFKPLA | |
|  |  | 351 | 400 |
| SEQID No 1 | (351) | YAFILTRQEGYPCVFYGDYYGIPQYNIPSLKSKIDPLLIARRDYAYGTQH | |
| SEQID No 15 | (349) | YAFILTRQEGYPCVFYGDYYGIPQYNIPSLKSKIDPLLIARRDYAYGTQH | |
| Consensus | (351) | YAFILTRQEGYPCVFYGDYYGIPQYNIPSLKSKIDPLLIARRDYAYGTQH | |
|  |  | 401 | 450 |
| SEQID No 1 | (401) | DYLDHSDIIGWTREGVTEKPGSGLAALITDGPGGSKWMYVGKQHAGKVFY | |
| SEQID No 15 | (399) | DYLDHSDIIGWTREGGTEKPGSGLAALITDGPGGSKWMYVGKQHAGKVFY | |
| Consensus | (401) | DYLDHSDIIGWTREG TEKPGSGLAALITDGPGGSKWMYVGKQHAGKVFY | |
|  |  | 451 | 500 |
| SEQID No 1 | (451) | DLTGNRSDTVTINSDGWGEFKVNGGSVSVWVPRKTTVSTIARPITTRPWT | |
| SEQID No 15 | (449) | DLTGNRSDTVTINSDGWGEFKVNGGSVSVWVPRKTTVS------------ | |
| Consensus | (451) | DLTGNRSDTVTINSDGWGEFKVNGGSVSVWVPRKTTVS | |
|  |  | 501 | 515 |
| SEQID No 1 | (501) | GEFVRWTEPRLVAWP | |
| SEQID No 15 | (487) | --------------- | |
| Consensus | (501) |  | |

Figure 4I

| Liquefaction conditions | Alcohol yield Gallon/Bushel | DDGS, % ds | | | |
|---|---|---|---|---|---|
| | | starch | Phytic acid | % IP 6 | Free Phosphate | Sulphate |
| Conventional Process-pH 5.8 (Liquefact A) | 2.70 | 7.25 | 0.6 | 100 | 1.20 | 1.92 mg/gds |
| No pH adjustment-Process, pH 5.2 3+1 AAU (Split dose), 4 FTU BP-17, with jet cooking, 225°F (Liquefact B) | 2.69 | 9.28 | 0.2 | 0 | 1.33 | 0.23mg/gds |

Figure 20

B
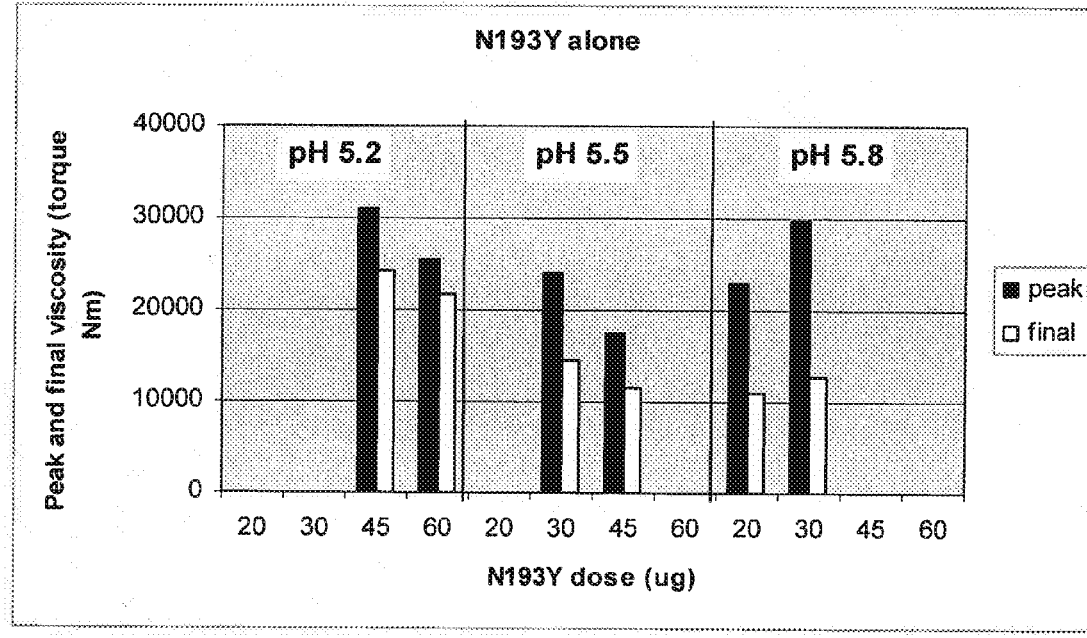
C
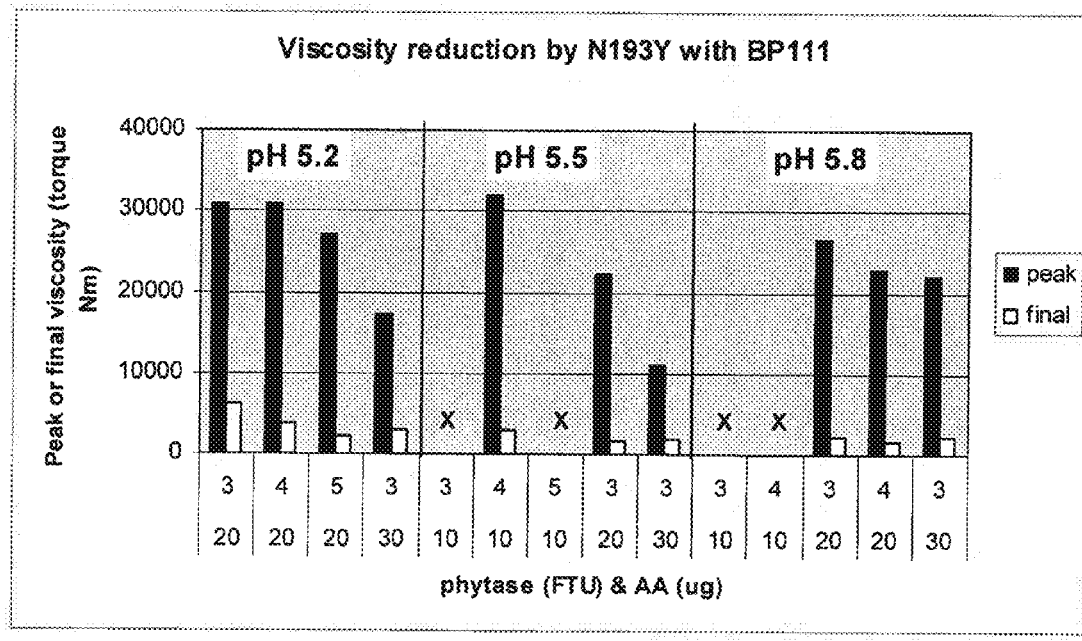
Figure 32 (cont.)

SEQUENCE LISTING

<160> NUMBER OF SEQ ID NOS: 35

<210> SEQ ID NO 1
<211> LENGTH: 515
<212> TYPE: PRT
<213> ORGANISM: Geobacillus stearothermophilus
<220> FEATURE:
<221> NAME/KEY: misc_feature
<223> OTHER INFORMATION: full-length, wild-type AmyS

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

```
Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
 65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
            130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
            210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
            290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
```

```
                   450                 455                 460
Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 2
<211> LENGTH: 486
<212> TYPE: PRT
<213> ORGANISM: G. stearothermophilus
<220> FEATURE:
<221> NAME/KEY: misc_feature
<223> OTHER INFORMATION: truncated, wild-type AmyS; SPEZYME Xtra

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
```

```
                 290                 295                 300
Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
                355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
                435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr
                485

<210> SEQ ID NO 3
<211> LENGTH: 515
<212> TYPE: PRT
<213> ORGANISM: Artificial Sequence
<220> FEATURE:
<223> OTHER INFORMATION: Synthetic full-length, S242A AmyS

<400> SEQUENCE: 3

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175
```

```
Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ala Phe Phe Pro Asp Trp Leu Ser Tyr Val Arg Ser Gln Thr Gly
            245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
            290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
            325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
            405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
            450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
            485                 490                 495

Arg Pro Trp Thr Gly Glu Phe Val Arg Trp Thr Glu Pro Arg Leu Val
            500                 505                 510

Ala Trp Pro
        515

<210> SEQ ID NO 4
<211> LENGTH: 515
<212> TYPE: PRT
<213> ORGANISM: Artificial Sequence
<220> FEATURE:
<223> OTHER INFORMATION: Synthetic full-length, S242Q AmyS

<400> SEQUENCE: 4

Ala Ala Pro Phe Asn Gly Thr Met Met Gln Tyr Phe Glu Trp Tyr Leu
1               5                   10                  15
```

-continued

```
Pro Asp Asp Gly Thr Leu Trp Thr Lys Val Ala Asn Glu Ala Asn Asn
         20                  25                  30

Leu Ser Ser Leu Gly Ile Thr Ala Leu Trp Leu Pro Pro Ala Tyr Lys
         35                  40                  45

Gly Thr Ser Arg Ser Asp Val Gly Tyr Gly Val Tyr Asp Leu Tyr Asp
 50                  55                  60

Leu Gly Glu Phe Asn Gln Lys Gly Thr Val Arg Thr Lys Tyr Gly Thr
 65                  70                  75                  80

Lys Ala Gln Tyr Leu Gln Ala Ile Gln Ala Ala His Ala Ala Gly Met
                 85                  90                  95

Gln Val Tyr Ala Asp Val Val Phe Asp His Lys Gly Ala Asp Gly
                100                 105                 110

Thr Glu Trp Val Asp Ala Val Glu Val Asn Pro Ser Asp Arg Asn Gln
         115                 120                 125

Glu Ile Ser Gly Thr Tyr Gln Ile Gln Ala Trp Thr Lys Phe Asp Phe
         130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                 165                 170                 175

Lys Phe Arg Gly Ile Gly Lys Ala Trp Asp Trp Glu Val Asp Thr Glu
                 180                 185                 190

Asn Gly Asn Tyr Asp Tyr Leu Met Tyr Ala Asp Leu Asp Met Asp His
         195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Gln Phe Phe Pro Asp Trp Leu Ser Tyr Val Arg Ser Gln Thr Gly
                 245                 250                 255

Lys Pro Leu Phe Thr Val Gly Glu Tyr Trp Ser Tyr Asp Ile Asn Lys
                 260                 265                 270

Leu His Asn Tyr Ile Thr Lys Thr Asn Gly Thr Met Ser Leu Phe Asp
         275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                 325                 330                 335

Ala Leu Gln Ser Trp Val Asp Pro Trp Phe Lys Pro Leu Ala Tyr Ala
         340                 345                 350

Phe Ile Leu Thr Arg Gln Glu Gly Tyr Pro Cys Val Phe Tyr Gly Asp
         355                 360                 365

Tyr Tyr Gly Ile Pro Gln Tyr Asn Ile Pro Ser Leu Lys Ser Lys Ile
 370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                 405                 410                 415

Thr Glu Lys Pro Gly Ser Gly Leu Ala Ala Leu Ile Thr Asp Gly Pro
         420                 425                 430

Gly Gly Ser Lys Trp Met Tyr Val Gly Lys Gln His Ala Gly Lys Val
         435                 440                 445
```

```
Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 5
<211> LENGTH: 515
<212> TYPE: PRT
<213> ORGANISM: Artificial Sequence
<220> FEATURE:
<223> OTHER INFORMATION: Synthetic full-length, S242E AmyS

<400> SEQUENCE: 5

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Glu Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285
```

```
Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 6
<211> LENGTH: 485
<212> TYPE: PRT
<213> ORGANISM: Bacillus sp.
<220> FEATURE:
<221> NAME/KEY: misc_feature
<223> OTHER INFORMATION: Yamane 707

<400> SEQUENCE: 6

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125
```

```
Gln Glu Val Thr Gly Glu Tyr Thr Ile Glu Ala Trp Thr Arg Phe Asp
            130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
        260                 265                 270

Gly Ala Ile Glu Asn Tyr Leu Gln Lys Thr Asn Trp Asn His Ser Val
    275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
            305                 310                 315                 320

His Pro Ser His Ala Val Thr Phe Val Asp Asn His Asp Ser Gln Pro
            325                 330                 335

Glu Glu Ala Leu Glu Ser Phe Val Glu Glu Trp Phe Lys Pro Leu Ala
        340                 345                 350

Tyr Ala Leu Thr Leu Thr Arg Glu Gln Gly Tyr Pro Ser Val Phe Tyr
    355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
        420                 425                 430

Gly Ala Gly Gly Ser Lys Trp Met Phe Val Gly Arg Asn Lys Ala Gly
    435                 440                 445

Gln Val Trp Ser Asp Ile Thr Gly Asn Arg Thr Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
            485
```

<210> SEQ ID NO 7
<211> LENGTH: 483
<212> TYPE: PRT
<213> ORGANISM: B. licheniformis
<220> FEATURE:
<221> NAME/KEY: misc_feature
<223> OTHER INFORMATION: wild-type AmyL; LAT

<400> SEQUENCE: 7

-continued

```
Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65              70                  75                  80

Gly Glu Leu Gln Ser Ala Ile Lys Ser Leu His Ser Arg Asp Ile Asn
            85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130             135                 140

Gly Arg Gly Ser Thr Tyr Ser Asp Phe Lys Trp His Trp Tyr His Phe
145             150                 155                 160

Asp Gly Thr Asp Trp Asp Glu Ser Arg Lys Leu Asn Arg Ile Tyr Lys
            165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
            195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225             230                 235                 240

Leu Arg Asp Trp Val Asn His Val Arg Glu Lys Thr Gly Lys Glu Met
            245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
    275                 280                 285

His Tyr Gln Phe His Ala Ala Ser Thr Gln Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
        340                 345                 350

Thr Arg Glu Ser Gly Tyr Pro Gln Val Phe Tyr Gly Asp Met Tyr Gly
    355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
            405                 410                 415

Ser Ser Val Ala Asn Ser Gly Leu Ala Ala Leu Ile Thr Asp Gly Pro
            420                 425                 430
```

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
            450                 455                 460

Glu Gly Trp Gly Glu Phe His Val Asn Gly Gly Ser Val Ser Ile Tyr
465                 470                 475                 480

Val Gln Arg

<210> SEQ ID NO 8
<211> LENGTH: 483
<212> TYPE: PRT
<213> ORGANISM: Unknown
<220> FEATURE:
<223> OTHER INFORMATION: wild-type AmyL; Termamyl

<400> SEQUENCE: 8

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser

```
                    305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
        450                 455                 460

Glu Gly Trp Gly Glu Phe His Val Asn Gly Gly Ser Val Ser Ile Tyr
465                 470                 475                 480

Val Gln Arg

<210> SEQ ID NO 9
<211> LENGTH: 483
<212> TYPE: PRT
<213> ORGANISM: B. amyloliquefaciens
<220> FEATURE:
<221> NAME/KEY: misc_feature
<223> OTHER INFORMATION: B. amyloliquefaciens amylase

<400> SEQUENCE: 9

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190
```

```
Tyr Asp Tyr Leu Met Tyr Ala Asp Val Asp Tyr Asp His Pro Asp Val
            195                 200                 205

Val Ala Glu Thr Lys Lys Trp Gly Ile Trp Tyr Ala Asn Glu Leu Ser
            210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
                260                 265                 270

Tyr Leu Asn Lys Thr Ser Phe Asn Gln Ser Val Phe Asp Val Pro Leu
            275                 280                 285

His Phe Asn Leu Gln Ala Ala Ser Ser Gln Gly Gly Tyr Asp Met
            290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Thr Ser Pro Lys Glu Ile Pro Ser Leu Lys Asp Asn Ile
            370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
            450                 455                 460

Asp Gly Trp Gly Glu Phe His Val Asn Asp Gly Ser Val Ser Ile Tyr
465                 470                 475                 480

Val Gln Lys

<210> SEQ ID NO 10
<211> LENGTH: 485
<212> TYPE: PRT
<213> ORGANISM: Unknown
<220> FEATURE:
<223> OTHER INFORMATION: STAINZYMETM

<400> SEQUENCE: 10

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Ile Arg Thr Lys Tyr Gly
```

```
                65                  70                  75                  80
Thr Arg Asn Gln Leu Gln Ala Ala Val Asn Ala Leu Lys Ser Asn Gly
                    85                  90                  95
Ile Gln Val Tyr Gly Asp Val Val Met Asn His Lys Gly Gly Ala Asp
                    100                 105                 110
Ala Thr Glu Met Val Arg Ala Val Glu Val Asn Pro Asn Asn Arg Asn
                    115                 120                 125
Gln Glu Val Ser Gly Glu Tyr Thr Ile Glu Ala Trp Thr Lys Phe Asp
            130                 135                 140
Phe Pro Gly Arg Gly Asn Thr His Ser Asn Phe Lys Trp Arg Trp Tyr
145                 150                 155                 160
His Phe Asp Gly Val Asp Trp Asp Gln Ser Arg Lys Leu Asn Asn Arg
                165                 170                 175
Ile Tyr Lys Phe Arg Gly Asp Gly Lys Gly Trp Asp Trp Glu Val Asp
                180                 185                 190
Thr Glu Asn Gly Asn Tyr Asp Tyr Leu Met Tyr Ala Asp Ile Asp Met
                195                 200                 205
Asp His Pro Glu Val Val Asn Glu Leu Arg Asn Trp Gly Val Trp Tyr
210                 215                 220
Thr Asn Thr Leu Gly Leu Asp Gly Phe Arg Ile Asp Ala Val Lys His
225                 230                 235                 240
Ile Lys Tyr Ser Phe Thr Arg Asp Trp Ile His Val Arg Ser Ala
                245                 250                 255
Thr Gly Lys Asn Met Phe Ala Val Ala Glu Phe Trp Lys Asn Asp Leu
                260                 265                 270
Gly Ala Ile Glu Asn Tyr Leu Asn Lys Thr Asn Trp Asn His Ser Val
                275                 280                 285
Phe Asp Val Pro Leu His Tyr Asn Leu Tyr Asn Ala Ser Lys Ser Gly
            290                 295                 300
Gly Asn Tyr Asp Met Arg Gln Ile Phe Asn Gly Thr Val Val Gln Arg
305                 310                 315                 320
His Pro Met His Ala Val Thr Phe Val Asp Asn His Asp Ser Gln Pro
                325                 330                 335
Glu Glu Ala Leu Glu Ser Phe Val Glu Glu Trp Phe Lys Pro Leu Ala
                340                 345                 350
Tyr Ala Leu Thr Leu Thr Arg Glu Gln Gly Tyr Pro Ser Val Phe Tyr
                355                 360                 365
Gly Asp Tyr Tyr Gly Ile Pro Thr His Gly Val Pro Ala Met Lys Ser
370                 375                 380
Lys Ile Asp Pro Ile Leu Glu Ala Arg Gln Lys Tyr Ala Tyr Gly Arg
385                 390                 395                 400
Gln Asn Asp Tyr Leu Asp His His Asn Ile Ile Gly Trp Thr Arg Glu
                405                 410                 415
Gly Asn Thr Ala His Pro Asn Ser Gly Leu Ala Thr Ile Met Ser Asp
                420                 425                 430
Gly Ala Gly Gly Asn Lys Trp Met Phe Val Gly Arg Asn Lys Ala Gly
                435                 440                 445
Gln Val Trp Thr Asp Ile Thr Gly Asn Arg Ala Gly Thr Val Thr Ile
            450                 455                 460
Asn Ala Asp Gly Trp Gly Asn Phe Ser Val Asn Gly Gly Ser Val Ser
465                 470                 475                 480
Ile Trp Val Asn Lys
                485
```

<210> SEQ ID NO 11
<211> LENGTH: 485
<212> TYPE: PRT
<213> ORGANISM: Unknown
<220> FEATURE:
<223> OTHER INFORMATION: NATALASE

<400> SEQUENCE: 11

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala

```
                     370                 375                 380
Lys Ile Asp Pro Ile Leu Glu Ala Arg Gln Asn Phe Ala Tyr Gly Thr
385                 390                 395                 400

Gln His Asp Tyr Phe Asp His Asn Ile Ile Gly Trp Thr Arg Glu
                405                 410                 415

Gly Asn Thr Thr His Pro Asn Ser Gly Leu Ala Thr Ile Met Ser Asp
                420                 425                 430

Gly Pro Gly Gly Glu Lys Trp Met Tyr Val Gly Gln Asn Lys Ala Gly
                435                 440                 445

Gln Val Trp His Asp Ile Thr Gly Asn Lys Pro Gly Thr Val Thr Ile
                450                 455                 460

Asn Ala Asp Gly Trp Ala Asn Phe Ser Val Asn Gly Ser Val Ser
465                 470                 475                 480

Ile Trp Val Lys Arg
                485

<210> SEQ ID NO 12
<211> LENGTH: 485
<212> TYPE: PRT
<213> ORGANISM: Uknown
<220> FEATURE:
<223> OTHER INFORMATION: KAO KSM 1378

<400> SEQUENCE: 12

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
                35                  40                  45

Lys Gly Thr Ser Gln Asn Asp Val Gly Tyr Gly Ala Tyr Asp Leu Tyr
                50                  55                  60

Asp Leu Gly Glu Phe Asn Gln Lys Gly Thr Val Arg Thr Lys Tyr Gly
65              70                  75                  80

Thr Arg Ser Gln Leu Gln Gly Ala Val Thr Ser Leu Lys Asn Asn Gly
                85                  90                  95

Ile Gln Val Tyr Gly Asp Val Val Met Asn His Lys Gly Gly Ala Asp
                100                 105                 110

Gly Thr Glu Met Val Asn Ala Val Glu Val Asn Arg Ser Asn Arg Asn
                115                 120                 125

Gln Glu Ile Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
                180                 185                 190

Ile Glu Asn Gly Asn Tyr Asp Tyr Leu Met Tyr Ala Asp Ile Asp Met
                195                 200                 205

Asp His Pro Glu Val Ile Asn Glu Leu Arg Asn Trp Gly Val Trp Tyr
                210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
                245                 250                 255
```

```
Thr Gly Lys Pro Met Phe Ala Val Ala Glu Phe Trp Lys Asn Asp Leu
            260                 265                 270

Ala Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Phe Asp Met Arg Asn Ile Leu Asn Gly Ser Val Val Gln Lys
305                 310                 315                 320

His Pro Ile His Ala Val Thr Phe Val Asp Asn His Asp Ser Gln Pro
                325                 330                 335

Gly Glu Ala Leu Glu Ser Phe Val Gln Ser Trp Phe Lys Pro Leu Ala
                340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Gly Val Pro Ser Met Lys Ser
370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu
                405                 410                 415

Gly Asp Ser Ser His Pro Asn Ser Gly Leu Ala Thr Ile Met Ser Asp
                420                 425                 430

Gly Pro Gly Gly Asn Lys Trp Met Tyr Val Gly Lys His Lys Ala Gly
                435                 440                 445

Gln Val Trp Arg Asp Ile Thr Gly Asn Arg Ser Gly Thr Val Thr Ile
    450                 455                 460

Asn Ala Asp Gly Trp Gly Asn Phe Thr Val Asn Gly Gly Ala Val Ser
465                 470                 475                 480

Val Trp Val Lys Gln
                485

<210> SEQ ID NO 13
<211> LENGTH: 480
<212> TYPE: PRT
<213> ORGANISM: Unknown
<220> FEATURE:
<223> OTHER INFORMATION: KAO KSM K38

<400> SEQUENCE: 13

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Ala Ala Leu
                20                  25                  30

Ser Asp Ala Gly Ile Thr Ala Ile Trp Ile Pro Pro Ala Tyr Lys Gly
            35                  40                  45

Asn Ser Gln Ala Asp Val Gly Tyr Gly Ala Tyr Asp Leu Tyr Asp Leu
        50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
                100                 105                 110

Glu Ala Val Gln Ala Val Gln Val Asn Pro Thr Asn Arg Trp Gln Asp
            115                 120                 125
```

```
Ile Ser Gly Ala Tyr Thr Ile Asp Ala Trp Thr Gly Phe Asp Phe Ser
        130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
    290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
    370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
        435                 440                 445

Leu Thr Gly Asn Asn Gly Ala Ser Val Thr Ile Asn Gly Asp Gly Trp
    450                 455                 460

Gly Glu Phe Phe Thr Asn Gly Gly Ser Val Ser Val Tyr Val Asn Gln
465                 470                 475                 480

<210> SEQ ID NO 14
<211> LENGTH: 480
<212> TYPE: PRT
<213> ORGANISM: Unknown
<220> FEATURE:
<223> OTHER INFORMATION: KAO KSM K36

<400> SEQUENCE: 14

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Glu Ala Leu
```

-continued

```
                    20                  25                  30
Ser Asn Ala Gly Ile Thr Ala Ile Trp Ile Pro Pro Ala Tyr Lys Gly
                35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Leu Gly Ala Asp Phe Thr
            100                 105                 110

Glu Ala Val Gln Ala Val Gln Val Asn Pro Ser Asn Arg Trp Gln Asp
        115                 120                 125

Ile Ser Gly Val Tyr Thr Ile Asp Ala Trp Thr Gly Phe Asp Phe Pro
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Leu Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Glu Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Ser Glu Ala Asp Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Lys Gln Gly Gly Ser Tyr Asp Met
    290                 295                 300

Arg Asn Ile Leu Arg Gly Ser Leu Val Glu Ala His Pro Ile His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
    370                 375                 380

Leu Asp Ala Arg Gln Asn Tyr Ala Tyr Gly Thr Gln His Asp Tyr Phe
385                 390                 395                 400

Asp His Trp Asp Ile Val Gly Trp Thr Arg Glu Gly Thr Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Gln Gln His Ala Gly Gln Thr Trp Thr Asp
        435                 440                 445
```

```
<210> SEQ ID NO 15
<211> LENGTH: 486
<212> TYPE: PRT
<213> ORGANISM: Unknown
<220> FEATURE:
<223> OTHER INFORMATION: LIQUIZYME SC

<400> SEQUENCE: 15
```

| | | | | | | | | | | | | | | | |
|---|---|---|---|---|---|---|---|---|---|---|---|---|---|---|---|
| Leu | Thr | Gly | Asn | His | Ala | Ala | Ser | Val | Thr | Ile | Asn | Gly | Asp | Gly | Trp |
| | | | | 450 | | | | | 455 | | | | | 460 | |
| Gly | Glu | Phe | Phe | Thr | Asn | Gly | Gly | Ser | Val | Ser | Val | Tyr | Val | Asn | Gln |
| 465 | | | | | 470 | | | | | 475 | | | | | 480 |
| Ala | Ala | Pro | Phe | Asn | Gly | Thr | Met | Met | Gln | Tyr | Phe | Glu | Trp | Tyr | Leu |
| 1 | | | | 5 | | | | | 10 | | | | | 15 | |
| Pro | Asp | Asp | Gly | Thr | Leu | Trp | Thr | Lys | Val | Ala | Asn | Glu | Ala | Asn | Asn |
| | | | 20 | | | | | 25 | | | | | 30 | | |
| Leu | Ser | Ser | Leu | Gly | Ile | Thr | Ala | Leu | Trp | Leu | Pro | Pro | Ala | Tyr | Lys |
| | | 35 | | | | | 40 | | | | | 45 | | | |
| Gly | Thr | Ser | Arg | Ser | Asp | Val | Gly | Tyr | Gly | Val | Tyr | Asp | Leu | Tyr | Asp |
| | 50 | | | | | 55 | | | | | 60 | | | | |
| Leu | Gly | Glu | Phe | Asn | Gln | Lys | Gly | Thr | Val | Arg | Thr | Lys | Tyr | Gly | Thr |
| 65 | | | | | 70 | | | | | 75 | | | | | 80 |
| Lys | Ala | Gln | Tyr | Leu | Gln | Ala | Ile | Gln | Ala | Ala | His | Ala | Ala | Gly | Met |
| | | | | 85 | | | | | 90 | | | | | 95 | |
| Gln | Val | Tyr | Ala | Asp | Val | Val | Phe | Asp | His | Lys | Gly | Gly | Ala | Asp | Gly |
| | | | 100 | | | | | 105 | | | | | 110 | | |
| Thr | Glu | Trp | Val | Asp | Ala | Val | Glu | Val | Asn | Pro | Ser | Asp | Arg | Asn | Gln |
| | | 115 | | | | | 120 | | | | | 125 | | | |
| Glu | Ile | Ser | Gly | Thr | Tyr | Gln | Ile | Gln | Ala | Trp | Thr | Lys | Phe | Asp | Phe |
| | 130 | | | | | 135 | | | | | 140 | | | | |
| Pro | Gly | Arg | Gly | Asn | Thr | Tyr | Ser | Ser | Phe | Lys | Trp | Arg | Trp | Tyr | His |
| 145 | | | | | 150 | | | | | 155 | | | | | 160 |
| Phe | Asp | Gly | Val | Asp | Trp | Asp | Glu | Ser | Arg | Lys | Leu | Ser | Arg | Ile | Tyr |
| | | | | 165 | | | | | 170 | | | | | 175 | |
| Lys | Phe | Arg | Gly | Lys | Ala | Trp | Asp | Trp | Glu | Val | Asp | Thr | Glu | Phe | Gly |
| | | | 180 | | | | | 185 | | | | | 190 | | |
| Asn | Tyr | Asp | Tyr | Leu | Met | Tyr | Ala | Asp | Leu | Asp | Met | Asp | His | Pro | Glu |
| | | 195 | | | | | 200 | | | | | 205 | | | |
| Val | Val | Thr | Glu | Leu | Lys | Asn | Trp | Gly | Lys | Trp | Tyr | Val | Asn | Thr | Thr |
| | 210 | | | | | 215 | | | | | 220 | | | | |
| Asn | Ile | Asp | Gly | Phe | Arg | Leu | Asp | Ala | Val | Lys | His | Ile | Lys | Phe | Ser |
| 225 | | | | | 230 | | | | | 235 | | | | | 240 |
| Phe | Phe | Pro | Asp | Trp | Leu | Ser | Tyr | Val | Arg | Ser | Gln | Thr | Gly | Lys | Pro |
| | | | | 245 | | | | | 250 | | | | | 255 | |
| Leu | Phe | Thr | Val | Gly | Glu | Tyr | Trp | Ser | Tyr | Asp | Ile | Asn | Lys | Leu | His |
| | | | 260 | | | | | 265 | | | | | 270 | | |
| Asn | Tyr | Ile | Thr | Lys | Thr | Asn | Gly | Thr | Met | Ser | Leu | Phe | Asp | Ala | Pro |
| | | 275 | | | | | 280 | | | | | 285 | | | |
| Leu | His | Asn | Lys | Phe | Tyr | Thr | Ala | Ser | Lys | Ser | Gly | Gly | Ala | Phe | Asp |
| | 290 | | | | | 295 | | | | | 300 | | | | |
| Met | Arg | Thr | Leu | Met | Thr | Asn | Thr | Leu | Met | Lys | Asp | Gln | Pro | Thr | Leu |
| 305 | | | | | 310 | | | | | 315 | | | | | 320 |
| Ala | Val | Thr | Phe | Val | Asp | Asn | His | Asp | Thr | Glu | Pro | Gly | Gln | Ala | Leu |
| | | | | 325 | | | | | 330 | | | | | 335 | |
| Gln | Ser | Trp | Val | Asp | Pro | Trp | Phe | Lys | Pro | Leu | Ala | Tyr | Ala | Phe | Ile |

-continued

```
                340                 345                 350
Leu Thr Arg Gln Glu Gly Tyr Pro Cys Val Phe Tyr Gly Asp Tyr Tyr
            355                 360                 365
Gly Ile Pro Gln Tyr Asn Ile Pro Ser Leu Lys Ser Lys Ile Asp Pro
        370                 375                 380
Leu Leu Ile Ala Arg Arg Asp Tyr Ala Tyr Gly Thr Gln His Asp Tyr
385                 390                 395                 400
Leu Asp His Ser Asp Ile Ile Gly Trp Thr Arg Glu Gly Gly Thr Glu
                405                 410                 415
Lys Pro Gly Ser Gly Leu Ala Ala Leu Ile Thr Asp Gly Pro Gly Gly
            420                 425                 430
Ser Lys Trp Met Tyr Val Gly Lys Gln His Ala Gly Lys Val Phe Tyr
        435                 440                 445
Asp Leu Thr Gly Asn Arg Ser Asp Thr Val Thr Ile Asn Ser Asp Gly
    450                 455                 460
Trp Gly Glu Phe Lys Val Asn Gly Gly Ser Val Ser Val Trp Val Pro
465                 470                 475                 480
Arg Lys Thr Thr Val Ser
                485

<210> SEQ ID NO 16
<211> LENGTH: 484
<212> TYPE: PRT
<213> ORGANISM: Unknown
<220> FEATURE:
<223> OTHER INFORMATION: SPEZYME Ethyl

<400> SEQUENCE: 16

Ala Ala Pro Phe Asn Gly Thr Met Met Gln Tyr Phe Glu Trp Tyr Leu
1               5                   10                  15
Pro Asp Asp Gly Thr Leu Trp Thr Lys Val Ala Asn Glu Ala Asn Asn
                20                  25                  30
Leu Ser Ser Leu Gly Ile Thr Ala Leu Trp Leu Pro Pro Ala Tyr Lys
            35                  40                  45
Gly Thr Ser Arg Ser Asp Val Gly Tyr Gly Val Tyr Asp Leu Tyr Asp
        50                  55                  60
Leu Gly Glu Phe Asn Gln Lys Gly Thr Val Arg Thr Lys Tyr Gly Thr
65                  70                  75                  80
Lys Ala Gln Tyr Leu Gln Ala Ile Gln Ala Ala His Ala Ala Gly Met
                85                  90                  95
Gln Val Tyr Ala Asp Val Val Phe Asp His Lys Gly Gly Ala Asp Gly
                100                 105                 110
Thr Glu Trp Val Asp Ala Val Glu Val Asn Pro Ser Asp Arg Asn Gln
            115                 120                 125
Glu Ile Ser Gly Thr Tyr Gln Ile Gln Ala Trp Thr Lys Phe Asp Phe
        130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Ile Gly Lys Ala Trp Asp Trp Glu Val Asp Thr Glu Asn Gly
                180                 185                 190
Asn Tyr Asp Tyr Leu Met Tyr Ala Asp Leu Asp Met Asp His Pro Glu
            195                 200                 205
Val Val Thr Glu Leu Lys Asn Trp Gly Lys Trp Tyr Val Asn Thr Thr
        210                 215                 220
```

```
Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Gln Thr Gly Lys Pro
            245                 250                 255

Leu Phe Thr Val Gly Glu Tyr Trp Ser Tyr Asp Ile Asn Lys Leu His
        260                 265                 270

Asn Tyr Ile Thr Lys Thr Asn Gly Thr Met Ser Leu Phe Asp Ala Pro
    275                 280                 285

Leu His Asn Lys Phe Tyr Thr Ala Ser Lys Ser Gly Gly Ala Phe Asp
290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
            325                 330                 335

Gln Ser Trp Val Asp Pro Trp Phe Lys Pro Leu Ala Tyr Ala Phe Ile
        340                 345                 350

Leu Thr Arg Gln Glu Gly Tyr Pro Cys Val Phe Tyr Gly Asp Tyr Tyr
    355                 360                 365

Gly Ile Pro Gln Tyr Asn Ile Pro Ser Leu Lys Ser Lys Ile Asp Pro
370                 375                 380

Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Val Thr Glu
            405                 410                 415

Lys Pro Gly Ser Gly Leu Ala Ala Leu Ile Thr Asp Gly Pro Gly Gly
        420                 425                 430

Ser Lys Trp Met Tyr Val Gly Lys Gln His Ala Gly Lys Val Phe Tyr
    435                 440                 445

Asp Leu Thr Gly Asn Arg Ser Asp Thr Val Thr Ile Asn Ser Asp Gly
450                 455                 460

Trp Gly Glu Phe Lys Val Asn Gly Gly Ser Val Ser Val Trp Val Pro
465                 470                 475                 480

Arg Lys Thr Thr

<210> SEQ ID NO 17
<211> LENGTH: 39
<212> TYPE: DNA
<213> ORGANISM: Artificial Sequence
<220> FEATURE:
<223> OTHER INFORMATION: Synthetic primer S242 F
<220> FEATURE:
<221> NAME/KEY: misc_feature
<222> LOCATION: (19)..(20)
<223> OTHER INFORMATION: n is a, c, g, or t

<400> SEQUENCE: 17
gtcaagcata ttaagttcnn sttttttcct gattggttg                          39

<210> SEQ ID NO 18
<211> LENGTH: 39
<212> TYPE: DNA
<213> ORGANISM: Artificial Sequence
<220> FEATURE:
<223> OTHER INFORMATION: Synthetic primer S242 R
<220> FEATURE:
<221> NAME/KEY: misc_feature
<222> LOCATION: (20)..(21)
<223> OTHER INFORMATION: n is a, c, g, or t

<400> SEQUENCE: 18
```

```
caaccaatca ggaaaaaasn ngaacttaat atgcttgac                                39
```

<210> SEQ ID NO 19
<211> LENGTH: 413
<212> TYPE: PRT
<213> ORGANISM: Artificial Sequence
<220> FEATURE:
<223> OTHER INFORMATION: Synthetic BP-17 variant of Buttiauxiella phytase

<400> SEQUENCE: 19

```
Asn Asp Thr Pro Ala Ser Gly Tyr Gln Val Glu Lys Val Ile Leu
1               5                  10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
                35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
                100                 105                 110

Thr Ile His His Gln Gln Asn Leu Glu Lys Ala Asp Pro Leu Phe His
            115                 120                 125

Pro Val Lys Ala Gly Thr Cys Ser Met Asp Lys Thr Gln Val Gln Gln
        130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
                180                 185                 190

Leu Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
        210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
                260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
        290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
                340                 345                 350
```

```
Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 20
<211> LENGTH: 87
<212> TYPE: DNA
<213> ORGANISM: B. licheniformis
<220> FEATURE:
<221> NAME/KEY: misc_feature
<223> OTHER INFORMATION: coding sequence for the LAT signal peptide

<400> SEQUENCE: 20
atgaaacaac aaaaacggct ttacgcccga ttgctgacgc tgttatttgc gctcatcttc      60
ttgctgcctc attctgcagc ttcagca                                         87

<210> SEQ ID NO 21
<211> LENGTH: 29
<212> TYPE: PRT
<213> ORGANISM: B. licheniformis
<220> FEATURE:
<221> NAME/KEY: misc_feature
<223> OTHER INFORMATION: LAT signal peptide

<400> SEQUENCE: 21

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala
            20                  25

<210> SEQ ID NO 22
<211> LENGTH: 486
<212> TYPE: PRT
<213> ORGANISM: Artificial Sequence
<220> FEATURE:
<223> OTHER INFORMATION: Synthetic truncated S242Q AmyS

<400> SEQUENCE: 22

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140
```

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Gln Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr
            485

<210> SEQ ID NO 23
<211> LENGTH: 1545
<212> TYPE: DNA
<213> ORGANISM: Geobacillus stearothermophilus
<220> FEATURE:
<221> NAME/KEY: misc_feature
<223> OTHER INFORMATION: coding sequence for mature AmyS

<400> SEQUENCE: 23
gccgcaccgt taacggtac catgatgcag tattttgaat ggtacttgcc ggatgatggc      60

| | |
|---|---|
| acgttatgga ccaaagtggc caatgaagcc aacaacttat ccagccttgg catcaccgct | 120 |
| ctttggctgc cgcccgctta caaaggaaca agccgcagcg acgtagggta cggagtatac | 180 |
| gacttgtatg acctcggcga attcaatcaa aaagggaccg tccgcacaaa atatggaaca | 240 |
| aaagctcaat atcttcaagc cattcaagcc gcccacgccg ctggaatgca agtgtacgcc | 300 |
| gatgtcgtgt cgaccataa aggcggcgct gacggcacgg aatgggtgga cgccgtcgaa | 360 |
| gtcaatccgt ccgaccgcaa ccaagaaatc tcgggcacct atcaaatcca agcatggacg | 420 |
| aaatttgatt ttcccgggcg gggcaacacc tactccagct ttaagtggcg ctggtaccat | 480 |
| tttgacggcg ttgactggga cgaaagccga aaattaagcc gcatttacaa attccgcggc | 540 |
| atcggcaaag cgtgggattg ggaagtagac acggaaaacg gaaactatga ctacttaatg | 600 |
| tatgccgacc ttgatatgga tcatcccgaa gtcgtgaccg agctgaaaaa ctgggggaaa | 660 |
| tggtatgtca acacaacgaa cattgatggg ttccggcttg atgccgtcaa gcatattaag | 720 |
| ttcagttttt ttcctgattg gttgtcgtat gtgcgttctc agactggcaa gccgctattt | 780 |
| accgtcgggg aatattggag ctatgacatc aacaagttgc acaattacat tacgaaaaca | 840 |
| aacggaacga tgtctttgtt tgatgccccg ttacacaaca aattttatac cgcttccaaa | 900 |
| tcagggggcg catttgatat gcgcacgtta atgaccaata ctctcatgaa agatcaaccg | 960 |
| acattggccc tcaccttcgt tgataatcat gacaccgaac ccggccaagc gctgcagtca | 1020 |
| tgggtcgacc catggttcaa accgttggct tacgccttta ttctaactcg gcaggaagga | 1080 |
| tacccgtgcg tcttttatgg tgactattat ggcattccac aatataacat tccttcgctg | 1140 |
| aaaagcaaaa tcgatccgct cctcatcgcg cgcagggatt atgcttacgg aacgcaacat | 1200 |
| gattatcttg atcactccga catcatcggg tggacaaggg aagggtcac tgaaaaacca | 1260 |
| ggatccgggc tggccgcact gatcaccgat gggccgggag gaagcaaatg gatgtacgtt | 1320 |
| ggcaaacaac acgctggaaa agtgttctat gaccttaccg gcaaccggag tgacaccgtc | 1380 |
| accatcaaca gtgatggatg ggggaattc aaagtcaatg gcggttcggt ttcggttgg | 1440 |
| gttcctagaa aaacgaccgt ttctaccatc gctcggccga tcacaacccg accgtggact | 1500 |
| ggtgaattcg tccgttggac cgaaccacgg ttggtggcat ggcct | 1545 |

<210> SEQ ID NO 24
<211> LENGTH: 32
<212> TYPE: DNA
<213> ORGANISM: Artificial Sequence
<220> FEATURE:
<223> OTHER INFORMATION: Synthetic primer Satori F

<400> SEQUENCE: 24

| | |
|---|---|
| ctcatcttct tgctgcctca ttctgcagct tc | 32 |

<210> SEQ ID NO 25
<211> LENGTH: 24
<212> TYPE: DNA
<213> ORGANISM: Artificial Sequence
<220> FEATURE:
<223> OTHER INFORMATION: Synthetic primer Satori R

<400> SEQUENCE: 25

| | |
|---|---|
| ttatcctta ccttgtctcc aagc | 24 |

<210> SEQ ID NO 26
<211> LENGTH: 436
<212> TYPE: PRT
<213> ORGANISM: Unknown
<220> FEATURE:

<223> OTHER INFORMATION: consensus sequence: Figure 1

<400> SEQUENCE: 26

```
Ala Asn Gly Thr Met Met Gln Tyr Phe Glu Trp Tyr Leu Pro Asn Asp
1               5                   10                  15

Gly Gln His Trp Arg Leu Asn Asp Ala Asn Leu Ser Ser Gly Ile Thr
            20                  25                  30

Ala Leu Trp Ile Pro Pro Ala Tyr Lys Gly Thr Ser Gln Ser Asp Val
        35                  40                  45

Gly Tyr Gly Ala Tyr Asp Leu Tyr Asp Leu Gly Glu Phe Asn Gln Lys
    50                  55                  60

Gly Thr Val Arg Thr Lys Tyr Gly Thr Lys Ala Gln Leu Ala Ile Ala
65                  70                  75                  80

Leu His Ala Gly Ile Gln Val Tyr Gly Asp Val Val Met Asn His Lys
                85                  90                  95

Gly Gly Ala Asp Gly Thr Glu Val Ala Val Glu Val Asn Pro Ser Asp
            100                 105                 110

Arg Asn Gln Glu Ile Ser Gly Tyr Ile Ala Trp Thr Lys Phe Asp Phe
        115                 120                 125

Pro Gly Arg Gly Asn Thr Tyr Ser Phe Lys Trp Arg Trp Tyr His Phe
    130                 135                 140

Asp Gly Val Asp Trp Asp Glu Ser Arg Lys Leu Asn Arg Ile Tyr Lys
145                 150                 155                 160

Phe Arg Gly Gly Lys Ala Trp Asp Trp Glu Val Asp Thr Glu Asn Gly
                165                 170                 175

Asn Tyr Asp Tyr Leu Met Tyr Ala Asp Ile Asp Met Asp His Pro Glu
            180                 185                 190

Val Val Glu Leu Lys Asn Trp Gly Trp Tyr Asn Thr Leu Asn Leu Asp
        195                 200                 205

Gly Phe Arg Leu Asp Ala Val Lys His Ile Lys Phe Ser Phe Asp Trp
    210                 215                 220

Leu Ser His Val Arg Ser Thr Gly Lys Leu Phe Thr Val Gly Glu Tyr
225                 230                 235                 240

Trp Asp Ile Gly Ala Leu Glu Asn Tyr Leu Lys Thr Asn Trp Met Ser
                245                 250                 255

Leu Phe Asp Val Pro Leu His Tyr Asn Phe Tyr Ala Ser Lys Ser Gly
            260                 265                 270

Gly Ala Tyr Asp Met Arg Leu Leu Gly Thr Leu Val His Pro Ala Val
        275                 280                 285

Thr Phe Val Asp Asn His Asp Thr Gln Pro Gly Gln Ala Leu Glu Ser
    290                 295                 300

Trp Val Asp Trp Phe Lys Pro Leu Ala Tyr Ala Phe Ile Leu Thr Arg
305                 310                 315                 320

Glu Gly Tyr Pro Val Phe Tyr Gly Asp Tyr Tyr Gly Ile Pro Gln Tyr
                325                 330                 335

Asn Ile Pro Ser Leu Lys Ser Lys Ile Asp Pro Leu Leu Ala Arg Arg
            340                 345                 350

Tyr Ala Tyr Gly Thr Gln His Asp Tyr Leu Asp His Asp Ile Ile Gly
        355                 360                 365

Trp Thr Arg Glu Gly Thr Ser Lys Pro Asn Ser Gly Leu Ala Ala Leu
    370                 375                 380

Ile Thr Asp Gly Pro Gly Gly Ser Lys Trp Met Tyr Val Gly Lys Gln
385                 390                 395                 400

Ala Gly Val Trp Tyr Asp Leu Thr Gly Asn Arg Ser Asp Thr Val Thr
```

```
                     405                 410                 415
Ile Asn Ser Asp Gly Trp Gly Glu Phe Val Asn Gly Gly Ser Val Ser
                 420                 425                 430

Val Trp Val Arg
        435

<210> SEQ ID NO 27
<211> LENGTH: 380
<212> TYPE: PRT
<213> ORGANISM: Unknown
<220> FEATURE:
<223> OTHER INFORMATION: consensus sequence: Figure 4A

<400> SEQUENCE: 27

Asn Gly Thr Met Met Gln Tyr Phe Glu Trp Tyr Leu Pro Asp Gly Trp
1               5                   10                  15

Lys Leu Asp Ala Asn Leu Ser Gly Ile Thr Ala Leu Trp Ile Pro Pro
            20                  25                  30

Ala Trp Lys Gly Ser Asp Val Gly Tyr Gly Tyr Asp Leu Tyr Asp Leu
        35                  40                  45

Gly Glu Phe Asn Gln Lys Gly Thr Val Arg Thr Lys Tyr Gly Thr Lys
    50                  55                  60

Ala Gln Ala Ile Ala Gly Ile Gln Val Tyr Ala Asp Val Val His Lys
65                  70                  75                  80

Gly Gly Ala Asp Ala Thr Glu Val Ala Val Glu Val Asn Pro Arg Asn
                85                  90                  95

Gln Glu Ile Ser Gly Tyr Ile Ala Trp Thr Lys Phe Asp Phe Pro Gly
            100                 105                 110

Arg Gly Asn Thr His Ser Ser Phe Lys Trp Arg Trp Tyr His Phe Asp
        115                 120                 125

Gly Val Asp Trp Asp Ser Arg Lys Leu Arg Ile Tyr Lys Phe Arg Gly
    130                 135                 140

Gly Lys Ala Trp Asp Trp Glu Val Asp Thr Glu Asn Gly Asn Tyr Asp
145                 150                 155                 160

Tyr Leu Met Tyr Ala Asp Ile Asp Met Asp His Pro Glu Val Val Glu
                165                 170                 175

Leu Lys Asn Trp Gly Trp Tyr Asn Thr Ile Asp Gly Phe Arg Ile Asp
            180                 185                 190

Ala Val Lys His Ile Lys Phe Ser Phe Asp Trp Ile His Val Arg Ser
        195                 200                 205

Thr Gly Lys Leu Phe Val Ala Glu Phe Trp Asp Ile Ile Asn Tyr Ile
    210                 215                 220

Lys Thr Asn Ser Leu Phe Asp Pro Leu His Tyr Ala Ser Lys Ser Gly
225                 230                 235                 240

Gly Phe Asp Met Arg Ile Thr Leu Met Pro Ser Ala Val Thr Phe Val
                245                 250                 255

Asp Asn His Asp Ser Pro Ala Leu Ser Phe Val Asp Trp Phe Lys Pro
            260                 265                 270

Leu Ala Tyr Ala Leu Thr Arg Gly Tyr Pro Val Phe Tyr Gly Asp Tyr
        275                 280                 285

Tyr Gly Ile Pro His Ile Pro Ala Leu Lys Ser Lys Ile Asp Pro Ile
    290                 295                 300

Leu Ala Arg Tyr Ala Tyr Gly Gln Asp Tyr Leu Asp His Ile Ile Gly
305                 310                 315                 320

Trp Thr Arg Glu Gly Thr Pro Ser Gly Leu Ala Ile Ile Ser Asp Gly
                325                 330                 335
```

Gly Gly Ser Lys Trp Met Phe Val Lys Asn Ala Gly Val Phe Asp
            340                 345                 350

Ile Thr Gly Asn Arg Ser Thr Val Thr Ile Asn Ala Asp Gly Trp Gly
        355                 360                 365

Phe Val Asn Gly Gly Ser Val Ser Ile Trp Val Lys
    370                 375                 380

<210> SEQ ID NO 28
<211> LENGTH: 369
<212> TYPE: PRT
<213> ORGANISM: Unknown
<220> FEATURE:
<223> OTHER INFORMATION: consensus sequence: Figure 4B

<400> SEQUENCE: 28

Ala Asn Gly Thr Leu Met Gln Tyr Phe Glu Trp Tyr Leu Pro Asp Gly
1               5                   10                  15

Trp Lys Leu Asn Asp Ala Leu Ala Gly Ile Thr Ala Leu Trp Ile Pro
            20                  25                  30

Pro Ala Tyr Lys Gly Thr Ser Ala Asp Val Gly Tyr Gly Tyr Asp Leu
        35                  40                  45

Tyr Asp Leu Gly Glu Phe Gln Lys Gly Thr Val Arg Thr Lys Tyr Gly
    50                  55                  60

Thr Lys Ala Ala Ile Ala His Ala Ile Asn Val Tyr Ala Asp Val Val
65                  70                  75                  80

His Lys Gly Gly Ala Asp Ala Thr Glu Val Ala Val Glu Val Pro Ala
                85                  90                  95

Asp Arg Asn Ile Ser Gly His Ile Ala Trp Thr Phe Phe Pro Gly Arg
            100                 105                 110

Gly Thr Tyr Ser Phe Lys Trp Trp Tyr His Phe Asp Gly Asp Trp Asp
        115                 120                 125

Glu Ser Arg Lys Leu Arg Ile Tyr Lys Phe Gly Lys Ala Trp Asp Trp
    130                 135                 140

Glu Val Glu Asn Gly Asn Tyr Asp Tyr Leu Met Tyr Ala Asp Ile Asp
145                 150                 155                 160

Asp His Pro Asp Val Glu Ile Lys Trp Gly Trp Tyr Asn Asn Ile Asp
                165                 170                 175

Gly Phe Arg Leu Asp Ala Val Lys His Ile Lys Phe Ser Phe Asp Trp
            180                 185                 190

Leu His Val Arg Thr Gly Lys Leu Phe Thr Val Ala Glu Tyr Trp Asp
        195                 200                 205

Ile Leu Asn Tyr Ile Lys Thr Asn Ser Leu Phe Asp Pro Leu His Phe
    210                 215                 220

His Ala Ser Gly Gly Ala Phe Asp Met Arg Leu Leu Thr Leu Met Pro
225                 230                 235                 240

Ala Val Thr Phe Val Asp Asn His Asp Thr Pro Gly Gln Ala Leu Ser
                245                 250                 255

Val Trp Phe Lys Pro Leu Ala Tyr Ala Phe Ile Leu Thr Arg Gly Tyr
            260                 265                 270

Pro Val Phe Tyr Gly Asp Tyr Gly Gln Ile Pro Ala Leu Lys Lys Ile
        275                 280                 285

Asp Pro Ile Leu Ala Arg Lys Tyr Ala Tyr Gly Gln His Asp Tyr Asp
    290                 295                 300

His Asp Ile Ile Gly Trp Thr Arg Glu Gly Ser Ser Gly Leu Ala Ala
305                 310                 315                 320

```
Leu Ile Thr Asp Gly Pro Gly Ala Lys Met Tyr Val Gly Lys Gln
        325                 330                 335

Ala Gly Phe His Asp Ile Thr Gly Asn Arg Ser Asp Val Ile Asn Ser
            340                 345                 350

Asp Gly Trp Gly Glu Phe Val Asn Gly Gly Ser Val Ser Ile Trp Val
            355                 360                 365

Arg

<210> SEQ ID NO 29
<211> LENGTH: 362
<212> TYPE: PRT
<213> ORGANISM: Unknown
<220> FEATURE:
<223> OTHER INFORMATION: consensus sequence: Figure 4C

<400> SEQUENCE: 29

Asn Gly Thr Leu Met Gln Tyr Phe Glu Trp Tyr Pro Asp Gly Trp Lys
1               5                   10                  15

Leu Asn Asp Ala Leu Ser Ile Gly Ile Thr Ala Leu Trp Ile Pro Pro
            20                  25                  30

Ala Tyr Lys Gly Ser Ser Asp Gly Tyr Gly Tyr Asp Leu Tyr Asp Leu
        35                  40                  45

Gly Glu Phe Asn Gln Lys Gly Thr Val Arg Thr Lys Tyr Gly Thr Lys
    50                  55                  60

Ala Ala Ile Ala His Ala Met Gln Val Tyr Ala Asp Val His Lys
65                  70                  75                  80

Ala Gly Ala Asp Ala Thr Glu Val Ala Val Glu Val Asn Pro Ala Arg
                85                  90                  95

Asn Gln Glu Ser Tyr Gln Ile Ala Trp Thr Phe Phe Pro Gly Arg Gly
            100                 105                 110

Asn Thr Tyr Ser Phe Lys Trp Trp Tyr His Phe Asp Gly Asp Trp Asp
        115                 120                 125

Glu Ser Arg Lys Ile Ser Arg Ile Phe Lys Phe Arg Gly Gly Lys Ala
    130                 135                 140

Trp Asp Trp Glu Val Ser Glu Asn Gly Asn Tyr Asp Tyr Leu Met Tyr
145                 150                 155                 160

Ala Asp Leu Asp Asp His Pro Asp Val Val Glu Lys Trp Gly Trp Tyr
                165                 170                 175

Asn Ile Asp Gly Phe Arg Ile Asp Ala Lys His Ile Lys Phe Ser Phe
            180                 185                 190

Asp Trp Leu Val Arg Thr Gly Lys Leu Phe Thr Val Ala Glu Tyr Trp
        195                 200                 205

Lys Leu Asn Tyr Ile Lys Thr Ser Leu Phe Asp Pro Leu His Ala Ser
    210                 215                 220

Gly Gly Ala Phe Asp Met Arg Leu Leu Thr Leu Met Pro Ala Val Thr
225                 230                 235                 240

Phe Val Asp Asn His Asp Thr Pro Gly Gln Ala Leu Ser Val Trp Phe
                245                 250                 255

Lys Pro Leu Ala Tyr Ala Phe Ile Leu Thr Arg Gly Tyr Pro Val Phe
            260                 265                 270

Tyr Gly Asp Tyr Gly Ile Pro Ser Leu Lys Ile Asp Pro Ile Leu Ala
        275                 280                 285

Arg Lys Asp Tyr Ala Tyr Gly Gln His Asp Tyr Ile Asp His Asp Ile
    290                 295                 300

Ile Gly Trp Thr Arg Glu Gly Ser Ser Gly Leu Ala Ala Leu Ile Thr
305                 310                 315                 320
```

Asp Gly Pro Gly Gly Ser Lys Met Tyr Gly Ala Gly Phe Tyr Asp Ile
            325                 330                 335

Thr Gly Asn Arg Ser Asp Thr Val Ile Ser Asp Gly Trp Gly Glu Phe
            340                 345                 350

Val Asn Gly Ser Val Ser Ile Trp Val Lys
            355                 360

<210> SEQ ID NO 30
<211> LENGTH: 377
<212> TYPE: PRT
<213> ORGANISM: Unknown
<220> FEATURE:
<223> OTHER INFORMATION: consensus sequence: Figure 4D

<400> SEQUENCE: 30

Asn Gly Thr Met Met Gln Tyr Phe Glu Trp Tyr Leu Pro Asp Gly Trp
1               5                   10                  15

Lys Leu Asp Ala Asn Leu Gly Ile Ser Ala Leu Trp Ile Pro Pro Ala
            20                  25                  30

Trp Lys Gly Ser Asp Val Gly Tyr Gly Tyr Asp Leu Tyr Asp Leu Gly
        35                  40                  45

Glu Phe Asn Gln Lys Gly Thr Ile Arg Thr Lys Tyr Gly Thr Lys Gln
50                  55                  60

Ala Ile Asn Ala Ala Gly Ile Gln Val Tyr Ala Asp Val Val His Lys
65                  70                  75                  80

Gly Gly Ala Asp Ala Thr Glu Val Ala Val Glu Val Asn Pro Arg Asn
            85                  90                  95

Gln Glu Ile Ser Gly Tyr Ile Ala Trp Thr Lys Phe Asp Phe Pro Gly
            100                 105                 110

Arg Gly Asn Thr His Ser Phe Lys Trp Arg Trp Tyr His Phe Asp Gly
            115                 120                 125

Val Asp Trp Asp Ser Arg Lys Leu Arg Ile Tyr Lys Phe Arg Gly Gly
        130                 135                 140

Lys Ala Trp Asp Trp Glu Val Asp Thr Glu Asn Gly Asn Tyr Asp Tyr
145                 150                 155                 160

Leu Met Tyr Ala Asp Ile Asp Met Asp His Pro Glu Val Val Glu Leu
            165                 170                 175

Lys Asn Trp Gly Trp Tyr Asn Thr Ile Asp Gly Phe Arg Ile Asp Ala
            180                 185                 190

Val Lys His Ile Lys Phe Ser Phe Asp Trp Ile His Val Arg Ser Thr
        195                 200                 205

Gly Lys Leu Phe Val Ala Glu Phe Trp Asp Ile Asn Tyr Ile Lys
210                 215                 220

Thr Asn Ser Leu Phe Asp Pro Leu His Tyr Ala Ser Lys Ser Gly Gly
225                 230                 235                 240

Phe Asp Met Arg Ile Thr Leu Met Pro Ala Val Thr Phe Val Asp Asn
            245                 250                 255

His Asp Ser Pro Ala Leu Ser Phe Val Asp Trp Phe Lys Pro Leu Ala
            260                 265                 270

Tyr Ala Leu Thr Arg Gly Tyr Pro Val Phe Tyr Gly Asp Tyr Tyr Gly
        275                 280                 285

Ile Pro His Ile Pro Ala Leu Lys Ser Lys Ile Asp Pro Ile Leu Ala
    290                 295                 300

Arg Tyr Ala Tyr Gly Gln Asp Tyr Leu Asp His Ile Ile Gly Trp Thr
305                 310                 315                 320

```
Arg Glu Gly Thr Pro Ser Gly Leu Ala Ile Ile Ser Asp Gly Gly
                325                 330                 335

Lys Trp Met Phe Val Gly Lys Asn Ala Gly Val Phe Asp Ile Thr Gly
            340                 345                 350

Asn Arg Ala Thr Val Thr Ile Asn Ala Asp Gly Trp Gly Phe Val Asn
        355                 360                 365

Gly Gly Ser Val Ser Ile Trp Val Lys
        370                 375

<210> SEQ ID NO 31
<211> LENGTH: 376
<212> TYPE: PRT
<213> ORGANISM: Unknown
<220> FEATURE:
<223> OTHER INFORMATION: consensus sequence: Figure 4E

<400> SEQUENCE: 31

Asn Gly Thr Met Met Gln Tyr Phe Glu Trp His Leu Pro Asp Gly Trp
1               5                   10                  15

Lys Leu Asp Ala Asn Leu Gly Ile Thr Ala Ile Trp Ile Pro Pro Ala
            20                  25                  30

Trp Lys Gly Thr Ser Asp Val Gly Tyr Gly Tyr Asp Leu Tyr Asp Leu
        35                  40                  45

Gly Glu Phe Asn Gln Lys Gly Thr Val Arg Thr Lys Tyr Gly Thr Lys
    50                  55                  60

Ala Gln Ala Ile Ala Gly Met Gln Val Tyr Ala Asp Val Val His Lys
65                  70                  75                  80

Gly Gly Ala Asp Ala Thr Glu Val Ala Val Glu Val Asn Pro Arg Asn
                85                  90                  95

Gln Glu Ile Ser Gly Tyr Ile Ala Trp Thr Lys Phe Asp Phe Pro Gly
            100                 105                 110

Arg Gly Asn Thr Tyr Ser Phe Lys Trp Arg Trp Tyr His Phe Asp Gly
        115                 120                 125

Val Asp Trp Asp Ser Arg Arg Ile Tyr Lys Phe Arg Gly Gly Lys Ala
    130                 135                 140

Trp Asp Trp Glu Val Asp Ser Glu Asn Gly Asn Tyr Asp Tyr Leu Met
145                 150                 155                 160

Tyr Ala Asp Leu Asp Met Asp His Pro Glu Val Val Glu Leu Lys Trp
                165                 170                 175

Gly Trp Tyr Asn Thr Asn Ile Asp Gly Phe Arg Ile Asp Ala Val Lys
            180                 185                 190

His Ile Lys Phe Ser Phe Asp Trp Leu Ser His Val Arg Thr Gly Lys
        195                 200                 205

Leu Phe Val Ala Glu Phe Trp Asp Ile Leu Asn Tyr Ile Lys Thr Asn
    210                 215                 220

Ser Leu Phe Asp Pro Leu His Tyr Ala Ser Ser Gly Gly Phe Asp Met
225                 230                 235                 240

Leu Leu Thr Leu Met Pro Ala Val Thr Phe Val Asp Asn His Asp Ser
                245                 250                 255

Pro Gly Ala Leu Ser Phe Val Trp Phe Lys Pro Leu Ala Tyr Ala Ile
            260                 265                 270

Leu Thr Arg Gly Tyr Pro Val Phe Tyr Gly Asp Tyr Tyr Gly Ile Pro
        275                 280                 285

His Ile Pro Ala Leu Lys Ala Lys Ile Asp Pro Ile Leu Ala Arg Phe
    290                 295                 300

Ala Tyr Gly Thr Gln His Asp Tyr Asp His Ile Ile Gly Trp Thr Arg
```

```
              305                 310                 315                 320
Glu Gly Thr Pro Ser Gly Leu Ala Ile Ile Ser Asp Gly Pro Gly Gly
                325                 330                 335

Lys Trp Met Tyr Val Gly Asn Ala Gly Val Phe His Asp Ile Thr Gly
                340                 345                 350

Asn Lys Thr Val Thr Ile Asn Ala Asp Gly Trp Ala Phe Val Asn Gly
                355                 360                 365

Gly Ser Val Ser Ile Trp Val Arg
                370                 375

<210> SEQ ID NO 32
<211> LENGTH: 377
<212> TYPE: PRT
<213> ORGANISM: Unknown
<220> FEATURE:
<223> OTHER INFORMATION: consensus sequence: Figure 4F

<400> SEQUENCE: 32

Asn Gly Thr Met Met Gln Tyr Phe Glu Trp His Leu Pro Asp Gly Trp
1               5                   10                  15

Lys Leu Asp Ala Asn Leu Ser Gly Ile Thr Ala Leu Trp Ile Pro Pro
            20                  25                  30

Ala Trp Lys Gly Thr Ser Asp Val Gly Tyr Gly Tyr Asp Leu Tyr Asp
        35                  40                  45

Leu Gly Glu Phe Asn Gln Lys Gly Thr Val Arg Thr Lys Tyr Gly Thr
50                  55                  60

Lys Ala Gln Ala Ile Ala Gly Ile Gln Val Tyr Ala Asp Val Val His
65                  70                  75                  80

Lys Gly Gly Ala Asp Gly Thr Glu Val Ala Val Glu Val Asn Ser Arg
                85                  90                  95

Asn Gln Glu Ile Ser Gly Tyr Ile Ala Trp Thr Lys Phe Asp Phe Pro
            100                 105                 110

Gly Arg Gly Asn Thr His Ser Phe Lys Trp Arg Trp Tyr His Phe Asp
        115                 120                 125

Gly Asp Trp Asp Ser Arg Lys Leu Tyr Lys Phe Arg Gly Gly Lys Ala
    130                 135                 140

Trp Asp Trp Glu Val Asp Glu Asn Gly Asn Tyr Asp Tyr Leu Met Tyr
145                 150                 155                 160

Ala Asp Ile Asp Met Asp His Pro Glu Val Ile Glu Leu Lys Asn Trp
                165                 170                 175

Gly Trp Tyr Asn Thr Asn Ile Asp Gly Phe Arg Ile Asp Ala Val Lys
            180                 185                 190

His Ile Lys Phe Ser Phe Asp Trp Leu Ser His Val Arg Thr Gly Lys
        195                 200                 205

Pro Leu Phe Val Ala Glu Phe Trp Asp Ile Ile Asn Tyr Ile Lys Thr
    210                 215                 220

Ser Leu Phe Asp Pro Leu His Tyr Ala Ser Ser Gly Gly Phe Asp Met
225                 230                 235                 240

Arg Ile Leu Ser Leu Met Pro Ala Val Thr Phe Val Asp Asn His Asp
                245                 250                 255

Ser Pro Gly Ala Leu Ser Phe Val Trp Phe Lys Pro Leu Ala Tyr Ala
            260                 265                 270

Ile Leu Thr Arg Gly Tyr Pro Val Phe Tyr Gly Asp Tyr Tyr Gly Ile
        275                 280                 285

Pro His Ile Pro Ser Leu Lys Ser Lys Ile Asp Pro Leu Leu Ala Arg
    290                 295                 300
```

```
Tyr Ala Tyr Gly Thr Gln His Asp Tyr Asp His Asp Ile Ile Gly Trp
305                 310                 315                 320

Thr Arg Glu Gly Ser Pro Ser Gly Leu Ala Ile Ile Ser Asp Gly Pro
                325                 330                 335

Gly Gly Lys Trp Met Tyr Val Gly Lys Ala Gly Val Phe Asp Ile Thr
            340                 345                 350

Gly Asn Arg Ser Thr Val Thr Ile Asn Ala Asp Gly Trp Gly Phe Val
        355                 360                 365

Asn Gly Gly Ala Val Ser Val Trp Val
    370                 375
```

<210> SEQ ID NO 33
<211> LENGTH: 334
<212> TYPE: PRT
<213> ORGANISM: Unknown
<220> FEATURE:
<223> OTHER INFORMATION: consensus sequence: Figure4G

<400> SEQUENCE: 33

```
Asn Gly Thr Met Met Gln Tyr Phe Glu Trp His Leu Asp Gly Trp Lys
1               5                   10                  15

Leu Asp Ala Leu Ser Gly Ile Thr Ala Ile Trp Ile Pro Pro Ala Tyr
            20                  25                  30

Lys Gly Ser Ala Asp Val Gly Tyr Gly Tyr Asp Leu Tyr Asp Leu Gly
        35                  40                  45

Glu Phe Asn Gln Lys Gly Thr Val Arg Thr Lys Tyr Gly Thr Lys Ala
    50                  55                  60

Gln Ala Ile Ala Ala Ile Asn Val Tyr Ala Asp Val Val His Lys Gly
65                  70                  75                  80

Ala Asp Thr Glu Val Ala Val Val Asn Pro Ser Arg Gln Asp Ile Ser
                85                  90                  95

Gly Tyr Ile Ala Trp Thr Phe Asp Phe Gly Arg Asn Tyr Ser Phe Lys
            100                 105                 110

Trp Arg Trp Phe His Phe Gly Val Asp Trp Asp Ile Phe Lys Phe Trp
        115                 120                 125

Trp Val Asp Glu Asn Gly Asn Tyr Asp Tyr Leu Leu Ala Ile Asp His
130                 135                 140

Pro Glu Val Glu Leu Lys Trp Gly Trp Phe Ile Asp Gly Phe Arg Leu
145                 150                 155                 160

Asp Ala Ile Lys His Ile Phe Phe Asp Trp Leu His Arg Leu Phe Val
                165                 170                 175

Gly Glu Tyr Trp Asp Ile Leu Tyr Ile Asn Met Ser Leu Phe Asp Pro
            180                 185                 190

Leu Phe Tyr Ala Ser Gly Gly Ala Phe Asp Met Arg Ile Leu Ser Leu
        195                 200                 205

Met Pro Ala Val Thr Phe Val Asp Asn His Asp Thr Pro Gly Ala Leu
210                 215                 220

Ser Trp Val Trp Phe Lys Pro Leu Ala Tyr Ala Ile Leu Thr Arg Gly
225                 230                 235                 240

Tyr Pro Val Phe Tyr Gly Asp Tyr Tyr Gly Ile Pro Asn Asn Ile Ala
                245                 250                 255

Lys Ile Asp Leu Leu Ala Arg Tyr Ala Tyr Gly Thr Gln His Asp Tyr
            260                 265                 270

Asp His Asp Ile Ile Gly Trp Thr Arg Glu Gly Ser Lys Pro Ser Gly
        275                 280                 285
```

```
Leu Ala Leu Ile Ser Gly Pro Gly Gly Ser Lys Trp Met Tyr Val Gly
            290                 295                 300

Lys Gln Ala Gly Phe Asp Leu Thr Gly Asn Ser Val Thr Ile Asn Asp
305                 310                 315                 320

Gly Trp Gly Glu Phe Asn Gly Gly Ser Val Ser Val Trp Val
                325                 330

<210> SEQ ID NO 34
<211> LENGTH: 338
<212> TYPE: PRT
<213> ORGANISM: Unknown
<220> FEATURE:
<223> OTHER INFORMATION: consensus sequence: Figure4H

<400> SEQUENCE: 34

Asn Gly Thr Met Met Gln Tyr Phe Glu Trp His Leu Asp Gly Trp Lys
1               5                   10                  15

Leu Asp Ala Leu Ser Gly Ile Thr Ala Ile Trp Ile Pro Pro Ala Tyr
                20                  25                  30

Lys Gly Ser Ala Asp Val Gly Tyr Gly Tyr Asp Leu Tyr Asp Leu Gly
            35                  40                  45

Glu Phe Asn Gln Lys Gly Thr Val Arg Thr Lys Tyr Gly Thr Lys Ala
50                  55                  60

Gln Ala Ile Ala Ala Ile Asn Val Tyr Ala Asp Val Val His Lys Gly
65                  70                  75                  80

Ala Asp Thr Glu Val Ala Val Val Asn Pro Ser Arg Gln Asp Ile Ser
                85                  90                  95

Gly Tyr Ile Ala Trp Thr Phe Asp Phe Pro Gly Arg Asn Tyr Ser Phe
            100                 105                 110

Lys Trp Arg Trp Phe His Phe Gly Val Asp Trp Asp Ile Phe Lys Phe
        115                 120                 125

Trp Trp Val Asp Glu Asn Gly Asn Tyr Asp Tyr Leu Leu Ala Ile Asp
    130                 135                 140

His Pro Glu Val Glu Leu Lys Trp Gly Trp Phe Ile Asp Gly Phe Arg
145                 150                 155                 160

Leu Asp Ala Ile Lys His Ile Phe Phe Asp Trp Leu His Arg Ser Leu
                165                 170                 175

Phe Val Gly Glu Tyr Trp Asp Ile Leu Tyr Ile Asn Met Ser Leu Phe
            180                 185                 190

Asp Pro Leu Phe Tyr Ala Ser Lys Gly Gly Ala Phe Asp Met Arg Ile
        195                 200                 205

Leu Ser Leu Met Pro Ala Val Thr Phe Val Asp Asn His Asp Thr Pro
    210                 215                 220

Gly Ala Leu Ser Trp Val Trp Phe Lys Pro Leu Ala Tyr Ala Ile Leu
225                 230                 235                 240

Thr Arg Gly Tyr Pro Val Phe Tyr Gly Asp Tyr Tyr Gly Ile Pro Asn
                245                 250                 255

Asn Ile Ala Lys Ile Asp Leu Leu Ala Arg Tyr Ala Tyr Gly Thr Gln
            260                 265                 270

His Asp Tyr Asp His Asp Ile Ile Gly Trp Thr Arg Glu Gly Ser Lys
        275                 280                 285

Pro Ser Gly Leu Ala Ile Ile Ser Gly Pro Gly Gly Ser Lys Trp Met
    290                 295                 300

Tyr Val Gly Gln His Ala Gly Phe Asp Leu Thr Gly Asn Ala Ser Val
305                 310                 315                 320

Thr Ile Asn Asp Gly Trp Gly Glu Phe Asn Gly Gly Ser Val Ser Val
```

Trp Val

<210> SEQ ID NO 35
<211> LENGTH: 484
<212> TYPE: PRT
<213> ORGANISM: Unknown
<220> FEATURE:
<223> OTHER INFORMATION: consensus sequence: Figure 4I

<400> SEQUENCE: 35

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Lys Ala Trp Asp Trp Glu Val Asp Thr Glu Gly Asn
            180                 185                 190

Tyr Asp Tyr Leu Met Tyr Ala Asp Leu Asp Met Asp His Pro Glu Val
        195                 200                 205

Val Thr Glu Leu Lys Asn Trp Gly Lys Trp Tyr Val Asn Thr Thr Asn
    210                 215                 220

Ile Asp Gly Phe Arg Leu Asp Ala Val Lys His Ile Lys Phe Ser Phe
225                 230                 235                 240

Phe Pro Asp Trp Leu Ser Tyr Val Arg Ser Gln Thr Gly Lys Pro Leu
                245                 250                 255

Phe Thr Val Gly Glu Tyr Trp Ser Tyr Asp Ile Asn Lys Leu His Asn
            260                 265                 270

Tyr Ile Thr Lys Thr Asn Gly Thr Met Ser Leu Phe Asp Ala Pro Leu
        275                 280                 285

His Asn Lys Phe Tyr Thr Ala Ser Lys Ser Gly Gly Ala Phe Asp Met
    290                 295                 300

Arg Thr Leu Met Thr Asn Thr Leu Met Lys Asp Gln Pro Thr Leu Ala
305                 310                 315                 320

Val Thr Phe Val Asp Asn His Asp Thr Glu Pro Gly Gln Ala Leu Gln
                325                 330                 335

Ser Trp Val Asp Pro Trp Phe Lys Pro Leu Ala Tyr Ala Phe Ile Leu
            340                 345                 350
```

-continued

```
Thr Arg Gln Glu Gly Tyr Pro Cys Val Phe Tyr Gly Asp Tyr Tyr Gly
        355             360             365

Ile Pro Gln Tyr Asn Ile Pro Ser Leu Lys Ser Lys Ile Asp Pro Leu
370             375             380

Leu Ile Ala Arg Arg Asp Tyr Ala Tyr Gly Thr Gln His Asp Tyr Leu
385             390             395             400

Asp His Ser Asp Ile Ile Gly Trp Thr Arg Glu Gly Thr Glu Lys Pro
                405             410             415

Gly Ser Gly Leu Ala Ala Leu Ile Thr Asp Gly Pro Gly Gly Ser Lys
            420             425             430

Trp Met Tyr Val Gly Lys Gln His Ala Gly Lys Val Phe Tyr Asp Leu
        435             440             445

Thr Gly Asn Arg Ser Asp Thr Val Thr Ile Asn Ser Asp Gly Trp Gly
        450             455             460

Glu Phe Lys Val Asn Gly Gly Ser Val Ser Val Trp Val Pro Arg Lys
465             470             475             480

Thr Thr Val Ser
```

US 8,084,240 B2

GEOBACILLUS STEAROTHERMOPHILUS α-AMYLASE (AMYS) VARIANTS WITH IMPROVED PROPERTIES

PRIORITY

The present application claim priority to U.S. Provisional Patent Application Ser. No. 61/059,423, filed Jun. 6, 2008, which is herein incorporated by reference.

TECHNICAL FIELD

Described are variants of a parent α-amylase that exhibits an alteration in at least one of the following properties relative to said parent α-amylase: specific activity, substrate specificity, substrate binding, substrate cleavage, thermal stability, pH-dependent activity, pH-dependent stability, oxidative stability, $Ca^{2+}$ dependency, pI, and wash performance. The variants are suitable for starch conversion, ethanol production, laundry washing, dish washing, hard surface cleaning, textile desizing, and/or sweetener production.

BACKGROUND

Alpha (α)-amylases (α-1,4-glucan-4-glucanohydrolases, E.C. 3.2.1.1) constitute a group of enzymes, which catalyze the hydrolysis of starch and other linear and branched 1,4-glucosidic oligo- and polysaccharides. α-amylases can be used commercially in the initial stages of starch processing (liquefaction); in wet corn milling; in alcohol production; as cleaning agents in detergent matrices; in the textile industry for starch desizing; in baking applications; in the beverage industry; in oilfields in drilling processes; in deinking of recycled paper and in animal feed.

Although currently available α-amylases have been used with some success in these applications, there remains a need for α-amylases with increased specific activity, tailored substrate specificity, improved thermal, pH, and oxidative stability, and reduced $Ca^{2+}$ dependency.

SUMMARY

In one aspect, novel α-amylolytic variants (mutants) of a SPEZYME® Xtra or AmyS-like α-amylase, are provided, in particular variants that exhibit altered properties which are advantageous in connection with the industrial processing of starch (starch liquefaction, saccharification, cleaning, and the like).

Such alterations in properties may be achieved by introducing mutations into a parental α-amylase that affect, e.g., specific activity, substrate specificity, substrate binding, the substrate cleavage pattern, thermal stability, the pH/activity profile, the pH/stability profile, stability towards oxidation, $Ca^{2+}$ dependency, and other properties of interest. For instance, the alteration may result in a variant which, as compared to the parent Spezyme Xtra-like α-amylase, has a reduced $Ca^{2+}$ dependency and/or an altered pH/activity profile and/or thermostability.

In some embodiments, the variants are based on the parent *Geobacillus stearothermophilus* α-amylase, or have a specified degree of amino acid sequence identity to this α-amylase, e.g., 60%, 65%, 70%, 75%, 80%, 85%, 90%, 91%, 92%, 93%, 94%, 95%, 96%, 97%, 98%, or even 99%. In other embodiments, the variants are based on related parent α-amylase, e.g., those which have at least 60%, 65%, 70%, 75%, 80%, 85%, 90%, 91%, 92%, 93%, 94%, 95%, 96%, 97%, 98%, or even 99% amino acid sequence identity to *Geobacillus stearothermophilus* α-amylase.

In some embodiments, a variant polypeptide having α-amylase activity and at least one altered characteristic that improves enzyme performance is provided, the variant polypeptide comprising an amino acid sequence having at least 60% amino acid sequence identity to a parental α-amylase polypeptide selected from AmyS (SEQ ID NO: 1) or a truncated variant of AmyS (SEQ ID NO: 2), and having at least one of the following mutations at an amino acid residue corresponding to that of the parental α-amylase polypeptide as determined by aligning the variant polypeptides with the parental polypeptide, wherein the mutation changes the amino acid residue from that of the parental polypeptides:

a) a substitution that introduces a positively charged amino acid residue one or more positions selected from the group consisting of D19, N28, E29, Q86, Q89, Q97, N224, N271, N281, D306, D318, Q319, Q358, D393, Q443, and D458;

b) a substitution that introduces one or more of the amino acid residues selected from the group consisting of 74A, 115L, 124K, 124R, 132A, 132C, 135A, 145A, 146A, 148A, 148N, 159A, 159C, 159D, 159E, 159F, 159G, 159H, 159K, 159L, 159N, 159R, 159S, 159T, 159V, 169A, 169L, 169M, 169Y, 179A, 181A, 181C, 181D, 181E, 181L, 181P, 181Q, 181V, 181Y, 242A, 242D, 242E, 242Q, 261L, 271A, 271V, 278A, 278H, 278K, 278N, 278R, 281A, 281L, 281M, 302D, 302M, 304D, 304E, 304M, 321A, 321H, 321Q, 321R, 333Q, 378D, 378N, 378R, 382D, 398A, 418A, 418M, 418N, 420A, 421R, 432A, 432D, 432L, 432M, 432N, 432Q, 432R, 432Y, 437D, 437G, 437H, 437L, 437M, 437Y, 446A, 446Y, 454A, 464Q, 464Y, 474A, 474E, 474K, 474L, 474M, 474N, 474P, 474Q, 474R, 474S, and 474V;

c) a substitution that introduces one or more of the amino acid residues selected from the group consisting of 6I, 6N, 6Q, 6T, 6V, 14T, 16F, 25A, 25C, 25G, 25Q, 27M, 36Q, 36S, 39G, 39V, 50I, 50L, 50M, 50N, 50Q, 52S, 53T, 67N, 67S, 80D, 80I, 90E, 133P, 133V, 137M, 137S, 141E, 141I, 141L, 141M, 141Q, 141R, 141S, 141V, 150E, 151I, 152G, 155S, 155Y, 168W, 173T, 188P, 193F, 193K, 193L, 193Y, 213L, 213M, 213V, 217Q, 220P, 220Q, 220R, 220S, 220V, 221I, 221S, 249E, 250F, 250I, 250M, 252L, 253Y, 254E, 254F, 254T, 254V, 255F, 255K, 255W, 257L, 257M, 257S, 257V, 258D, 258G, 258H, 258K, 258Q, 258T, 258V, 268F, 274W, 283M, 283N, 283V, 285E, 285Q, 293G, 293K, 294W, 301F, 301I, 301P, 301R, 301T, 301W, 309D, 309V, 312H, 312S, 312V, 312Y, 313G, 313H, 313I, 313L, 313S, 313V, 318T, 338A, 338C, 338G, 338M, 338T, 339K, 339T, 339V, 340A, 340M, 340Q, 340T, 343C, 343I, 343P, 343R, 343Y, 345I, 345Q, 369I, 369T, 370G, 375T, 385T, 386K, 394L, 394V, 400A, 400N, 400V, 402H, 402I, 402T, 402V, 402W, 403A, 403E, 403G, 403Q, 403R, 403T, 403V, 404C, 404E, 404G, 404I, 404V, 419A, 419C, 419M, 419T, 422E, 422G, 433A, 433H, 433I, 433K, 433L, 433M, 433V, 433Y, 442A, 442G, 442N, 442R, 442S, 442T, 442V, 442W, 442Y, 445G, 445I, 445N, 445T, 445V, 445W, 447I, 447N, 447Q, 447W, 447Y, 448C, 448F, 448G, 448H, 448I, 448N, 448Y, 450C, 450H, 450M, 450N, 450R, 450S, 450T, 450W, 455G, 455I, 455P, 455V, 463A, 463M, 463S, 463T, 463V, 463W, 465G, 465I, 465K, 465N, 465T, 465V, 469D, 469W, 469Y, 471I, 471V, 473G, 473Y, 476A, 476G, 476L, 476M, 476N, and 476T d) a substitution that introduces one or more of the amino acid residues selected from the group consisting of 124N, 125A, 125K, 125N, 130A, 130S, 159A, 159D, 159E, 159G, 159H, 159K, 159L, 159N, 159R, 159S, 159T, 166F, 166G, 166H, 166S, 166Y, 169L, 179A, 179P, 180A, 180D, 180H, 180K, 180L, 180N, 180T, 180V, 180Y, 181A, 181D, 181E, 181G, 181P, 181R, 181S, 181V, 187A, 187C, 187K, 187N, 187P, 187Q, 187R, 187S, 242H, 242N, 278H, 278K, 278N, 278R, 281M, 302D, 304M, 304Y, 321H, 321Q, 321R, 333Q, 432Q, 437Y, 446A, 474Q, and 474S, e) a substitution that introduces one or more of the amino acid residues selected from the group consisting of 6A, 6D, 6E, 6H, 6I, 6K, 6L, 6M, 6N, 6P, 6Q, 6R, 6S, 6T, 6V, 6W, 6Y, 13K, 14F, 14T, 14Y, 15A, 15D, 15E, 015G, 15H, 15K, 15N, 15P, 15Q, 15R, 15S, 15T, 15W, 16A, 16E, 16G, 16H, 16K, 16N, 16P, 16Q, 16R, 16T, 25C, 39D, 39E, 39N, 39Q, 81Y, 121P, 139D, 139H, 139R, 139Y, 177A, 188D, 191H, 191K, 192A, 192D, 192G, 192N, 192P, 192Q, 192S, 192T, 192V, 192Y, 196A, 196C, 196D, 196E, 196F, 196H, 196I, 196K, 196P, 196R, 196S, 196T, 196V, 201A, 201E, 201G, 201H, 201M, 202H, 216E, 216G, 216H, 216M, 216Q, 216R, 216S, 216T, 216Y, 221A, 221D, 221F, 221I, 221L, 221M, 221N, 221R, 221S, 221V, 221Y, 237G, 240G, 240N, 240P, 240Q, 240R, 240T, 246R, 250A, 250D, 250E, 250F, 250G, 250I, 250K, 250L, 250M, 250N, 250Q, 250R, 250S, 250W, 252K, 268A, 268D, 268E, 268G, 268H, 268K, 268N, 268P, 268Q, 268R, 268S, 274A, 274D, 274G, 274I, 274K, 274L, 274N, 274Q, 274R, 274S, 274T, 275K, 285Q, 285Y, 293K, 293R, 318A, 318F, 318G, 318I, 318K, 318L, 318M, 318R, 318S, 318T, 318V, 318Y, 319C, 319D, 319H, 319I, 319K, 319R, 319Y, 320K, 320R, 320T, 338A, 338G, 338I, 338M, 338P, 338S, 338V, 339G, 339P, 340A, 340D, 340E, 340H, 340K, 340N, 340Q, 345E, 363D, 363E, 363M, 363N, 363Q, 363S, 366Q, 370A, 370D, 370E, 370H, 370K, 370N, 370Q, 370S, 375A, 375D, 375E, 375K, 375N, 375Q, 375R, 375S, 419A, 419I, 419M, 419P, 419S, 419V, 448Y, 452N, 452Q, 452R, 452S, 471R, and 471Y; and f) a substitution that introduces one or more of the amino acid residues selected from the group consisting of I181A, I181P, I181C, I181E, I181Y, S242A, S242E, G132A, N193Y, and E188P.

In some embodiments, the variant includes a mutation that introduces a positively charged amino acid residue one or more positions selected from the group consisting of D19, N28, E29, Q86, Q89, Q97, N224, N271, N281, D306, D318, Q319, Q358, D393, Q443, and D458, and the variant polypeptides exhibits improved cleaning performance. In particular embodiments, the improved cleaning is under North American laundry conditions, and is determined using a microswatch assay. In particular embodiments, the positively charged amino acid residue is arginine.

In some embodiments, the variant include a substitution that introduces one or more of the amino acid residues selected from the group consisting of 74A, 115L, 124K, 124R, 132A, 132C, 135A, 145A, 146A, 148A, 148N, 159A, 159C, 159D, 159E, 159F, 159G, 159H, 159K, 159L, 159N, 159R, 159S, 159T, 159V, 169A, 169L, 169M, 169Y, 179A, 181A, 181C, 181D, 181E, 181L, 181P, 181Q, 181V, 181Y, 242A, 242D, 242E, 242Q, 261L, 271A, 271V, 278A, 278H, 278K, 278N, 278R, 281A, 281L, 281M, 302D, 302M, 304D, 304E, 304M, 321A, 321H, 321Q, 321R, 333Q, 378D, 378N, 378R, 383D, 398A, 418A, 418M, 418N, 420A, 421R, 432A, 432D, 432L, 432M, 432N, 432Q, 432R, 432Y, 437D, 437G, 437H, 437L, 437M, 437Y, 446A, 446Y, 454A, 464Q, 464Y, 474A, 474E, 474K, 474L, 474M, 474N, 474P, 474Q, 474R, 474S, and 474V, and the variant has improved thermostability compared to the parental polypeptide.

In some embodiments, the variant include a substitution substitution that introduces one or more of the amino acid residues selected from the group consisting of 6I, 6N, 6Q, 6T, 6V, 14T, 16F, 25A, 25C, 25G, 25Q, 27M, 36Q, 36S, 39G, 39V, 50I, 50L, 50M, 50N, 50Q, 52S, 53T, 67N, 67S, 80D, 80I, 90E, 133P, 133V, 137M, 137S, 141E, 141I, 141L, 141M, 141Q, 141R, 141S, 141V, 150E, 151I, 152G, 155S, 155Y, 168W, 173T, 188P, 193F, 193K, 193L, 193Y, 213L, 213M, 213V, 217Q, 220P, 220Q, 220R, 220S, 220V, 221I, 221S, 249E, 250F, 250I, 250M, 252L, 253Y, 254E, 254F, 254T, 254V, 255F, 255K, 255W, 257L, 257M, 257S, 257V, 258D, 258G, 258H, 258K, 258Q, 258T, 258V, 268F, 274W, 283M, 283N, 283V, 285E, 285Q, 293G, 293K, 294W, 301T, 301I, 301P, 301R, 301T, 301W, 309D, 309V, 312H, 312S, 312V, 312Y, 313G, 313H, 313I, 313L, 313S, 313V, 318T, 338A, 338C, 338G, 338M, 338T, 339K, 339T, 339V, 340A, 340M, 340Q, 340T, 343C, 343I, 343P, 343R, 343Y, 345I, 345Q, 369I, 369T, 370G, 375T, 385T, 386K, 394L, 394V, 400A, 400N, 400V, 402H, 402I, 402T, 402V, 402W, 403A, 403E, 403G, 403Q, 403R, 403T, 403V, 404C, 404E, 404G, 404I, 404V, 419A, 419C, 419M, 419T, 422E, 422G, 433A, 433H, 433I, 433K, 433L, 433M, 433V, 433Y, 442A, 442G, 442N, 442R, 442S, 442T, 442V, 442W, 442Y, 445G, 445I, 445N, 445T, 445V, 445W, 447I, 447N, 447Q, 447W, 447Y, 448C, 448F, 448G, 448H, 448I, 448N, 448Y, 450C, 450H, 450M, 450N, 450R, 450S, 450T, 450W, 455G, 455I, 455P, 455V, 463A, 463M, 463S, 463T, 463V, 463W, 465G, 465I, 465K, 465N, 465T, 465V, 469D, 469W, 469Y, 471I, 471V, 473G, 473Y, 476A, 476G, 476L, 476M, 476N, and 476T, and the variant has improved thermostability compared to the parental polypeptide.

In some embodiments, the variant include a substitution that introduces one or more of the amino acid residues selected from the group consisting of 124N, 125A, 125K, 125N, 130A, 130S, 159A, 159D, 159E, 159G, 159H, 159K, 159L, 159N, 159R, 159S, 159T, 166F, 166G, 166H, 166S, 166Y, 169L, 179A, 179P, 180A, 180D, 180H, 180K, 180L, 180N, 180T, 180V, 180Y, 181A, 181D, 181E, 181G, 181P, 181R, 181S, 181V, 187A, 187C, 187K, 187N, 187P, 187Q, 187R, 187S, 242H, 242N, 278H, 278K, 278N, 278R, 281M, 302D, 304M, 304Y, 321H, 321Q, 321R, 333Q, 432Q, 437Y, 446A, 474Q, and 474S, and the variant exhibits increased activity or expression compared to the parental polypeptide.

In some embodiments, the variant include a substitution that introduces one or more of the amino acid residues selected from the group consisting of 6A, 6D, 6E, 6H, 6I, 6K, 6L, 6M, 6N, 6P, 6Q, 6R, 6S, 6T, 6V, 6W, 6Y, 13K, 14F, 14T, 14Y, 15A, 15D, 15E, 015G, 15H, 15K, 15N, 15P, 15Q, 15R, 15S, 15T, 15W, 16A, 16E, 16G, 16H, 16K, 16N, 16P, 16Q, 16R, 16T, 25C, 39D, 39E, 39N, 39Q, 81Y, 121P, 139D, 139H, 139R, 139Y, 177A, 188D, 191H, 191K, 192A, 192D, 192G, 192N, 192P, 192Q, 192S, 192T, 192V, 192Y, 196A, 196C, 196D, 196E, 196F, 196H, 196I, 196K, 196P, 196R, 196S, 196T, 196V, 201A, 201E, 201G, 201H, 201M, 202H, 216E, 216G, 216H, 216M, 216Q, 216R, 216S, 216T, 216Y, 221A, 221D, 221F, 221I, 221L, 221M, 221N, 221R, 221S, 221V, 221Y, 237G, 240G, 240N, 240P, 240Q, 240R, 240T, 246R, 250A, 250D, 250E, 250F, 250G, 250I, 250K, 250L, 250M, 250N, 250Q, 250R, 250S, 250W, 252K, 268A, 268D, 268E, 268G, 268H, 268K, 268N, 268P, 268Q, 268R, 268S, 274A, 274D, 274G, 274I, 274K, 274L, 274N, 274Q, 274R, 274S, 274T, 275K, 285Q, 285Y, 293K, 293R, 318A, 318F, 318G, 318I, 318K, 318L, 318M, 318R, 318S, 318T, 318V, 318Y, 319C, 319D, 319H, 319I, 319K, 319R, 319Y, 320K, 320R, 320T, 338A, 338G, 338I, 338M, 338P, 338S, 338V, 339G, 339P, 340A, 340D, 340E, 340H, 340K, 340N, 340Q, 345E, 363D, 363E, 363M, 363N, 363Q, 363S, 366Q, 370A, 370D, 370E, 370H, 370K, 370N, 370Q, 370S, 375A, 375D, 375E, 375K, 375N, 375Q, 375R, 375S, 419A, 419I, 419M, 419P, 419S, 419V, 448Y, 452N, 452Q, 452R, 452S, 471R, and 471Y, and the variant exhibits increased activity or expression compared to the parental polypeptide.

In some embodiments, the variant include a substitution that introduces one or more of the amino acid residues selected from the group consisting of I181A, I181P, I181C, I181E, I181Y, S242A, S242E, G132A, N193Y, and E188P, and the variant exhibits increased viscosity reduction in a starch liquefaction assay compared to the parental polypeptide.

In some embodiments, a variant α-amylase polypeptide is provided, comprising an amino acid sequence derived from a parental α-amylase polypeptide, and having a combination of three or more mutations at positions selected from the group consisting of 5, 6, 13, 14, 15, 16, 18, 20, 25, 27, 29, 36, 39, 50, 52, 53, 54, 67, 71, 73, 75, 77, 80, 81, 83, 85, 90, 92, 107, 111, 113, 114, 120, 121, 126, 128, 131, 133, 137, 138, 139, 141, 143, 147, 149, 150, 151, 152, 155, 160, 165, 168, 172, 173, 177, 188, 191, 192, 193, 196, 200, 201, 202, 213, 216, 217, 220, 221, 227, 232, 235, 237, 238, 240, 246, 249, 250, 252, 253, 254, 255, 257, 258, 268, 272, 274, 275, 279, 283, 285, 293, 294, 297, 300, 301, 306, 309, 312, 313, 317, 318, 319, 320, 338, 339, 340, 343, 345, 363, 366, 369, 370, 375, 379, 381, 385, 386, 391, 392, 393, 394, 400, 402, 403, 404, 406, 407, 410, 413, 414, 416, 419, 422, 427, 433, 436, 439, 442, 445, 447, 448, 450, 452, 455, 463, 465, 469, 471, 473, and 476, wherein the polypeptides has α-amylase activity, and where each of the at least three or more mutations introduces an amino acid residue that differs from that in the parental polypeptide. In particular embodiments, the number of mutations is 4, 5, 6, 7, 8, 9, 10, or more.

In some embodiments, where the mutation is not already at position 242, the mutation is present in combination with the substitutions S242A, S242E, S242Q, S242F, S242H, or S242N. In particular embodiments, the substitution is S242Q. In some embodiments, where the mutation is not already at position 179 or 180, the mutation is present in combination with a deletion at positions 179 and 180. In some embodiments, where the mutation is not already at position 349 or 428, the mutation is present in combination with a substitution of a cysteine at one or more of these amino acids.

In some embodiments, where the mutation is not already at one of the following positions, the mutation is present in combination with a substitution at position P17, D19, T21, N28, S51, G72, V74, A82, Q86, Q89, A93, G95, Q97, W115, D117, P123, S124, D125, N127, I130, G132, Q135, P145, G146, G148, S153, Y159, W166, S169, K171, W187, P209, N224, S242, G256, D269, N271, T278, N281, G302, A304, R308, T321, Q358, P378, S382, K383, T398, H405, T417, E418, P420, G421, P432, W437, G446, G454, S457, T459, T461, S464, G474, or R483.

In some embodiments, where the mutation is not already at one of the following positions, the mutation is present in combination with a substitution at position M8, M9, M15, M96, V128, A111, H133, W138, T149, M197, N188, M200, M206, A209, A210, M284, M307, M311, M316, H405, T412, M438, N193F, and V416G.

In some embodiments, the parental polypeptide has at least 80%, at least 85%, at least 90%, or even at least 95% amino acid sequence identity to the polypeptide of SEQ ID NO: 1.

In some embodiments, the parental polypeptide has at least 80%, at least 85%, at least 90%, or even at least 95% amino acid sequence identity to the polypeptide of SEQ ID NO: 2.

In some embodiments, the parental polypeptide has at least 80%, at least 85%, at least 90%, or even at least 95% amino acid sequence identity to a polypeptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, and SEQ ID NO: 16. In some embodiments, the parental polypeptide includes a truncation of the C-terminal amino acid residues. In particular embodiments, the truncation is of the C-terminal 29 amino acid residues.

In some embodiments, the variant polypeptide does not include a mutations at either position 106 or 199, or both.

In some embodiments, one or more mutations can be added or deleted from a list of mutations without departing from the description. Relatedly, any one or more mutations that appear in the context of a list of mutations can be combined as a subset of mutations.

In another aspect, a composition comprising one or more of the aforementioned variant α-amylases is provided. In particular embodiments, the composition is a cleaning composition, such as a laundry detergent, a dishwashing detergent, a hard-surface-cleaning composition, or the like. The composition may include a detergent.

In another aspect, a method for hydrolyzing a soluble starch substrate using an α-amylase variant is provided. In some embodiments, the variant includes a substitution that introduces one or more of the amino acid residues selected from the group consisting of I181A, I181P, I181C, I181E, I181Y, S242A, S242E, S242Q, G132A, N193Y, and E188P.

In some embodiments, the variant α-amylase is used in combination with a phytic acid hydrolyzing enzyme, wherein the ratio of α-amylase activity (in α-amylase units) to phytic acid activity (in phytase units), i.e., AAU:FTU, is from about 1:15 to about 15:1, and preferably from 1:10 to about 10:1. In particular embodiments, the ratio of AAU:FTU is from 1:4 to 3:1, or even 1:1.

In a further aspect, a method for liquefying starch in a slurry is provided, involving a substrate that includes plant material such as granular starch from either a dry or wet milling process, the method comprising a primary and/or secondary liquefaction step, invoilving adding to the slurry in the primary and/or secondary liquefaction step, in any order, a combination of at least one phytic acid hydrolyzing enzyme and at least one variant α-amylase, either simultaneously or separately. The method can further comprise saccharifying the liquefied starch to obtain fermentable sugars; and recovering the fermentable sugars. In some embodiments, the method further comprises fermenting the fermentable sugars under suitable fermentation conditions to obtain end-products such as alcohol. In some embodiments the enzyme composition contains at least one variant α-amylase and a phytase. In some embodiments, the enzyme composition is in blended form.

In a further aspect, a method for fermenting a starch substrate is provided, the method comprising adding in any order a combination of a variant α-amylase and a phytase in a single or split dose. In another aspect, the treated starch substrate is fermented to ethanol.

In a further aspect, a starch conversion process and/or an ethanol fermentation process is provided that does not require addition of acid or alkali to adjust the pH. One embodiment relates to a pH adjustment free liquefaction step, wherein the pH of the liquefaction is in the range of pH 4.5 to 5.4 and acid neutralizing chemicals are not added to the liquefaction process step. In another embodiment, the pH of the liquefaction is in the range of pH 4.8 to 5.8 and acid neutralizing chemicals are not added to the liquefaction process step.

In another aspect, a method of obtaining a fermentable substrate is provided, involving contacting a slurry of milled grain containing granular starch with a phytic acid hydrolyzing enzyme at a temperature 0-30° C. less than the starch gelatinization temperature, contacting the slurry with a variant α-amylase, raising the temperature above the gelatinization temperature for the granular starch to allow gelatinization of the starch, and hydrolyzing the gelatinized starch by contacting the gelatinized starch with the α-amylase for a time sufficient to hydrolyze the starch, and obtaining a fermentable substrate. The phytic acid hydrolyzing enzyme can be a bacterial or fungal phytase. The fungal phytase can be an *Aspergillus* phytase or a *Buttiauxella* phytase. In some embodiments, the bacterial phytase is from *Escherichia coli*.

In another aspect, the a process for producing a fermentable sugar is provided, comprising (a) mixing milled starch-containing material with water and thin stillage, wherein the thin stillage is in the range of 10 to 70% v/v and obtaining a slurry comprising starch and having a dry solids (ds) content of 20 to 50% w/w, (b) treating the slurry with a phytase prior to or simultaneously with liquefying the starch, (c) liquefying the starch, (d) adding a variant α-amylase to the starch either during step (b) and/or simultaneously with the liquefying step, and (e) saccharifying the liquefied starch to obtain fermentable sugars, wherein the pH is not adjusted during any of the steps (a), (b), (c), (d), or (e). In some embodiments, the fermentable sugar is recovered and purified or isomerized. In other embodiments, the phytase is added prior to the liquefaction step. In some embodiments, the α-amylase is added with the phytase. In yet further embodiments, a second α-amylase dose is added during the liquefaction step.

In a further aspect, a process of producing alcohol from the starch-containing material, is provided, comprising liquefying and saccharifying the liquefied starch as disclosed above to obtain fermentable sugars and further fermenting the fermentable sugars under suitable fermentation conditions using a fermenting microorganism to obtain alcohol. In some embodiments, the saccharification and fermentation steps are simultaneous. In some embodiments, the alcohol is ethanol.

In another aspect, DNA constructs, including expression vectors, that encode variants α-amylases are provided, along with methods of expressing and using the variant α-amylases, alone or in combination with other α-amylolytic enzymes, e.g., in various industrial processes, such as starch liquefaction and cleaning.

BRIEF DESCRIPTION OF THE DRAWINGS

FIG. 1 shows an alignment of the amino acid sequences of several AmyS-related α-amylases. (Consensus sequence corresponds to SEQ ID NO: 26)

FIGS. 4A-4I shows pairwise alignments of the amino acid sequences shown in FIG. 1. (Consensus sequences correspond to SEQ ID NOS: 27 through 35, respectively)

FIG. 20 shows a comparison of sulfate and phytic acid content in DDGS: 1) from a conventional process, and 2) from the process with no pH adjustment. Reference is made to Example 10.

BRIEF DESCRIPTION OF THE SEQUENCES

Figure 2:
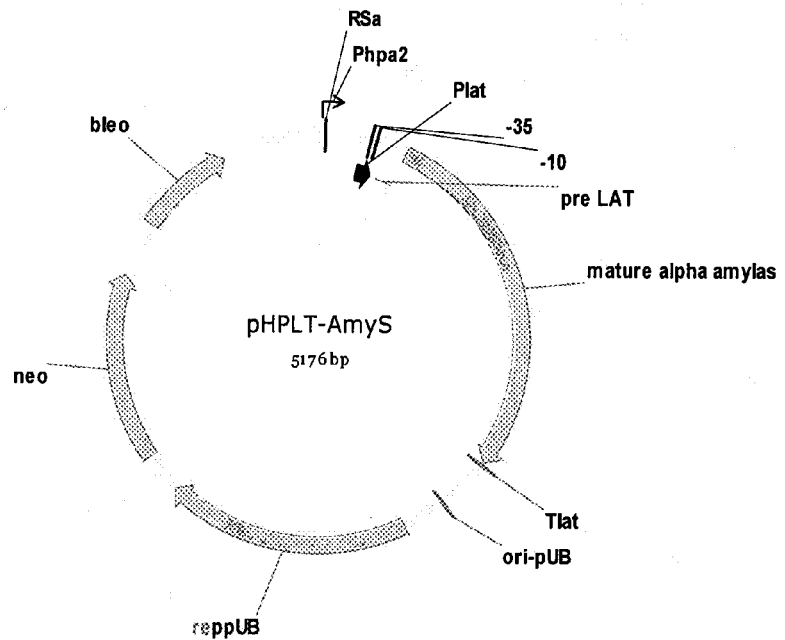
FIG. 2 shows the pHPLT-AmyS plasmid.

The following amino acid and nucleotide sequences are referred to herein.

```
(full-length, wild-type AmyS)
                                       SEQ ID NO: 1
AAPFNGTMMQ YFEWYLPDDG TLWTKVANEA NNLSSLGITA
LWLPPAYKGT SRSDVGYGVY DLYDLGEFNQ KGTVRTKYGT
KAQYLQAIQA AHAAGMQVYA DVVFDHKGGA DGTEWVDAVE
VNPSDRNQEI SGTYQIQAWT KFDFPGRGNT YSSFKWRWYH
FDGVDWDESR KLSRIYKFRG IGKAWDWEVD TENGNYDYLM
YADLDMDHPE VVTELKNWGK WYVNTTNIDG FRLDAVKHIK
FSFFPDWLSY VRSQTGKPLF TVGEYWSYDI NKLHNYITKT
NGTMSLFDAP LHNKFYTASK SGGAFDMRTL MTNTLMKDQP
TLAVTFVDNH DTEPGQALQS WVDPWFKPLA YAFILTRQEG
YPCVFYGDYY GIPQYNIPSL KSKIDPLLIA RRDYAYGTQH
DYLDHSDIIG WTREGVTEKP GSGLAALITD GPGGSKWMYV
GKQHAGKVFY DLTGNRSDTV TINSDGWGEF KVNGGSVSVW
VPRKTTVSTI ARPITTRPWT GEFVRWTEPR LVAWP (truncated, wild-type AmyS; SPEZYM ® Xtra)
                                       SEQ ID NO: 2
AAPFNGTMMQ YFEWYLPDDG TLWTKVANEA NNLSSLGITA
LWLPPAYKGT SRSDVGYGVY DLYDLGEFNQ KGTVRTKYGT
KAQYLQAIQA AHAAGMQVYA DVVFDHKGGA DGTEWVDAVE
VNPSDRNQEI SGTYQIQAWT KFDFPGRGNT YSSFKWRWYH
FDGVDWDESR KLSRIYKFRG IGKAWDWEVD TENGNYDYLM
YADLDMDHPE VVTELKNWGK WYVNTTNIDG FRLDAVKHIK
FSFFPDWLSY VRSQTGKPLF TVGEYWSYDI NKLHNYITKT
NGTMSLFDAP LHNKFYTASK SGGAFDMRTL MTNTLMKDQP
TLAVTFVDNH DTEPGQALQS WVDPWFKPLA YAFILTRQEG
YPCVFYGDYY GIPQYNIPSL KSKIDPLLIA RRDYAYGTQH
DYLDHSDIIG WTREGVTEKP GSGLAALITD GPGGSKWMYV
GKQHAGKVFY DLTGNRSDTV TINSDGWGEF KVNGGSVSVW
VPRKTT (full-length, S242A AmyS)
                                       SEQ ID NO: 3
AAPFNGTMMQ YFEWYLPDDG TLWTKVANEA NNLSSLGITA
LWLPPAYKGT SRSDVGYGVY DLYDLGEFNQ KGTVRTKYGT
KAQYLQAIQA AHAAGMQVYA DVVFDHKGGA DGTEWVDAVE
VNPSDRNQEI SGTYQIQAWT KFDFPGRGNT YSSFKWRWYH
FDGVDWDESR KLSRIYKFRG IGKAWDWEVD TENGNYDYLM
YADLDMDHPE VVTELKNWGK WYVNTTNIDG FRLDAVKHIK
FAFFPDWLSY VRSQTGKPLF TVGEYWSYDI NKLHNYITKT
NGTMSLFDAP LHNKFYTASK SGGAFDMRTL MTNTLMKDQP
TLAVTFVDNH DTEPGQALQS WVDPWFKPLA YAFILTRQEG
YPCVFYGDYY GIPQYNIPSL KSKIDPLLIA RRDYAYGTQH
DYLDHSDIIG WTREGVTEKP GSGLAALITD GPGGSKWMYV
GKQHAGKVFY DLTGNRSDTV TINSDGWGEF KVNGGSVSVW
VPRKTTVSTI ARPITTRPWT GEFVRWTEPR LVAWP (full-length, S242Q AmyS)
                                       SEQ ID NO: 4
AAPFNGTMMQ YFEWYLPDDG TLWTKVANEA NNLSSLGITA
LWLPPAYKGT SRSDVGYGVY DLYDLGEFNQ KGTVRTKYGT
KAQYLQAIQA AHAAGMQVYA DVVFDHKGGA DGTEWVDAVE
VNPSDRNQEI SGTYQIQAWT KFDFPGRGNT YSSFKWRWYH
FDGVDWDESR KLSRIYKFRG IGKAWDWEVD TENGNYDYLM
YADLDMDHPE VVTELKNWGK WYVNTTNIDG FRLDAVKHIK
FQFFPDWLSY VRSQTGKPLF TVGEYWSYDI NKLHNYITKT
NGTMSLFDAP LHNKFYTASK SGGAFDMRTL MTNTLMKDQP
TLAVTFVDNH DTEPGQALQS WVDPWFKPLA YAFILTRQEG
YPCVFYGDYY GIPQYNIPSL KSKIDPLLIA RRDYAYGTQH
DYLDHSDIIG WTREGVTEKP GSGLAALITD GPGGSKWMYV
GKQHAGKVFY DLTGNRSDTV TINSDGWGEF KVNGGSVSVW
VPRKTTVSTI ARPITTRPWT GEFVRWTEPR LVAWP (full-length, S242E AmyS)
                                       SEQ ID NO: 5
AAPFNGTMMQ YFEWYLPDDG TLWTKVANEA NNLSSLGITA
LWLPPAYKGT SRSDVGYGVY DLYDLGEFNQ KGTVRTKYGT
KAQYLQAIQA AHAAGMQVYA DVVFDHKGGA DGTEWVDAVE
VNPSDRNQEI SGTYQIQAWT KFDFPGRGNT YSSFKWRWYH
FDGVDWDESR KLSRIYKFRG IGKAWDWEVD TENGNYDYLM
YADLDMDHPE VVTELKNWGK WYVNTTNIDG FRLDAVKHIK
FEFFPDWLSY VRSQTGKPLF TVGEYWSYDI NKLHNYITKT
NGTMSLFDAP LHNKFYTASK SGGAFDMRTL MTNTLMKDQP
TLAVTFVDNH DTEPGQALQS WVDPWFKPLA YAFILTRQEG
YPCVFYGDYY GIPQYNIPSL KSKIDPLLIA RRDYAYGTQH
DYLDHSDIIG WTREGVTEKP GSGLAALITD GPGGSKWMYV
GKQHAGKVFY DLTGNRSDTV TINSDGWGEF KVNGGSVSVW
VPRKTTVSTI ARPITTRPWT GEFVRWTEPR LVAWP (Yamane 707)
                                       SEQ ID NO: 6
HHNGTNGTMMQYFEWYLPNDGNHWNRLNSDASNLKSKGITAVWIPPAWKG
ASQNDVGYGAYDLYDLGEFNQKGTVRTKYGTRSQLQAAVTSLKNNGIQVY
GDVVMNHKGGADATEMVRAVEVNPNNRNQEVTGEYTIEAWTRFDFPGRGN
THSSFKWRWYHFDGVDWDQSRRLNNRIYKFRGHGKAWDWEVDTENGNYDY
LMYADIDMDHPEVVNELRNWGVWYTNTLGLDGFRIDAVKHIKYSFTRDWI
NHVRSATGKNMFAVAEFWKNDLGAIENYLQKTNWNHSVFDVPLHYNLYNA
SKSGGNYDMRNIFNGTVVQRHPSHAVTFVDNHDSQPEEALESFVEEWFKP
LAYALTLTREQGYPSVFYGDYYGIPTHGVPAMRSKIDPILEARQKYAYGK
QNDYLDHHNIIGWTREGNTAHPNSGLATIMSDGAGGSKWMFVGRNKAGQV
WSDITGNRTGTVTINADGWGNFSVNGGSVSIWVNK (wild-type AmyL; LAT)
                                       SEQ ID NO: 7
ANLNGTLMQYFEWYMPNDGQHWKRLQNDSAYLAEHGITAVWIPPAYKGTS
QADVGYGAYDLYDLGEFHQKGTVRTKYGTKGELQSAIKSLHSRDINVYGD
VVINHKGGADATEDVTAVEVDPADRNRVISGEHLIKAWTHFHFPGRGSTY
SDFKWHWYHFDGTDWDESRKLNRIYKFQGKAWDWEVSNENGNYDYLMYAD
IDYDHPDVAAEIKRWGTWYANELQLDGFRLDAVKHIKFSFLRDWVNHVRE
KTGKEMFTVAEYWQNDLGALENYLNKTNFNHSVFDVPLHYQFHAASTQGG
GYDMRKLLNGTVVSKHPLKSVTFVDNHDTQPGQSLESTVQTWFKPLAYAF
ILTRESGYPQVFYGDMYGTKGDSQREIPALKHKIEPILKARKQYAYGAQH
DYFDHHDIVGWTREGDSSVANSGLAALITDGPGGAKRMYVGRQNAGETWH
DITGNRSEPVVINSEGWGEFHVNGGSVSIYVQR
```

(wild-type AmyL; Termamyl)
SEQ ID NO: 8
ANLNGTLMQYFEWYMPNDGQHWRRLQNDSAYLAEHGITAVWIPPAYKGTS
QADVGYGAYDLYDLGEFHQKGTVRTKYGTKGELQSAIKSLHSRDINVYGD
VVINHKGGADATEDVTAVEVDPADRNRVISGEHLIKAWTHFHFPGRGSTY
SDFKWHWYHFDGTDWDESRKLNRIYKFQGKAWDWEVSNENGNYDYLMYAD
IDYDHPDVAAEIKRWGTWYANELQLDGFRLDAVKHIKFSFLRDWVNHVRE
KTGKEMFTVAEYWQNDLGALENYLNKTNFNHSVFDVPLHYQFHAASTQGG
GYDMRKLLNGTVVSKHPLKSVTFVDNHDTQPGQSLESTVQTWFKPLAYAF
ILTRESGYPQVFYGDMYGTKGDSQREIPALKHKIEPILKARKQYAYGAQH
DYFDHHDIVGWTREGDSSVANSGLAALITDGPGGAKRMYVGRQNAGETWH
DITGNRSEPVVINSEGWGEFHVNGGSVSIYVQR (B. amyloliquefaciens amylase)
SEQ ID NO: 9
VNGTLMQYFEWYTPNDGQHWKRLQNDAEHLSDIGITAVWIPPAYKGLSQS
DNGYGPYDLYDLGEFQQKGTVRTKYGTKSELQDAIGSLHSRNVQVYGDVV
LNHKAGADATEDVTAVEVNPANRNQETSEEYQIKAWTDFRFPGRNTYSD
FKWHWYHFDGADWDESRKISRIFKFRGEGKAWDWEVSSENGNYDYLMYAD
VDYDHPDVVAETKKWGIWYANELSLDGFRIDAAKHIKFSFLRDWVQAVRQ
ATGKEMFTVAEYWQNNAGKLENYLNKTSFNQSVFDVPLHFNLQAASSQGG
GYDMRRLLDGTVVSRHPEKAVTFVENHDTQPGQSLESTVQTWFKPLAYAF
ILTRESGYPQVFYGDMYKTGTSPKEIPSLKDNIEPILKARKEYAYGPQH
DYIDHPDVIGWTREGDSSAAKSGLAALITDGPGGSKRMYAGLKNAGETWY
DITGNRSDTVKIGSDGWGEFHVNDGSVSIYVQK (STAINZYME ™)
SEQ ID NO: 10
HHNGTNGTMM QYFEWYLPND GNHWNRLRSD ASNLKDKGIS
AVWIPPAWKG ASQNDVGYGA YDLYDLGEFN QKGTIRTKYG
TRNQLQAAVN ALKSNGIQVY GDVVMNHKGG ADATEMVRAV
EVNPNNRNQE VSGEYTIEAW TKFDPFGRGN THSNFKWRWY
HFDGVDWDQS RKLNNRIYKF RGDGKGWDWE VDTENGNYDY
LMYADIDMDH PEVVNELRNW GVWYNTLGL DGFRIDAVKH
IKYSFTRDWI NHVRSATGKN MFAVAEFWKN DLGAIENYLN
KTNWNHSVFD VPLHYNLYNA SKSGGNYDMR QIFNGTVVQR
HPMHAVTFVD NHDSQPEEAL ESFVEEWFKP LAYALTLTRE
QGYPSVFYGD YYGIPTHGVP AMKSKIDPIL EARQKYAYGR
QNDYLDHHNI IGWTREGNTA HPNSGLATIM SDGAGGNKWM
FVGRNKAGQV WTDITGNRAG TVTINADGWG NFSVNGGSVS
IWVNK (NATALASE ™)
SEQ ID NO: 11
HHNGTNGTMMQYFEWHLPNDGNHWNRLRDDASNLRNRGITAIWIPPAWKG
TSQNDVGYGAYDLYDLGEFNQKGTVRTKYGTRSQLESAIHALKNNGVQVY
GDVVMNHKGGADATENVLAVEVNPNNRNQEISGDYTIEAWTKFDFPGRGN
TYSDFKWRWYHFDGVDWDQSRQFQNRIYKFRGDGKAWDWEVDSENGNYDY
LMYADVDMDHPEVVNELRRWGEWYTNTLNLDGFRIDAVKHIKYSFTRDWL
THVRNATGKEMFAVAEFWKNDLGALENYLNKTNWNHSVFDVPLHYNLYNA
SNSGGNYDMAKLLNGTVVQKHPMHAVTFVDNHDSQPGEALESFVQEWFKP
LAYALILTREQGYPSVFYGDYYGIPTHSVPAMKAKIDPILEARQNFAYGT
QHDYFDHHNIIGWTREGNTTHPNSGLATIMSDGPGGEKWMYVGQNKAGQV
WHDITGNKPGTVTINADGWANFSVNGGSVSIWVKR (KAO KSM 1378)
SEQ ID NO: 12
HHNGTNGTMMQYFEWHLPNDGNHWNRLRDDAANLKSKGITAVWIPPAWKG
TSQNDVGYGAYDLYDLGEFNQKGTVRTKYGTRSQLQQGAVTSLKNNGIQVY
GDVVMNHKGGADGTEMVNAVEVNRSNRNQEISGEYTIEAWTKFDFPGRGN
THSNFKWRYHFDGTDWDQSRQLQNKIYKFRGTGKAWDWEVDIENGNYDY
LMYADIDMDHPEVINELRNWGVWYTNTLNLDGFRIDAVKHIKYSYTRDWL
THVRNTTGKPMFAVAEFWKNDLAAIENYLNKTSWNHSVFDVPLHYNLYNA
SNSGGYFDMRNILNGSVVQKHPIHAVTFVDNHDSQPGEALESFVQSWFKP
LAYALILTREQGYPSVFYGDYYGIPTHGVPSMKSKIDPLLQARQTYAYGT
QHDYFDHHDIIGWTREGDSSHPNSGLATIMSDGPGGNKWMYVGKHKAGQV
WRDITGNRSGTVTINADGWGNFTVNGGAVSVWVKQ (KAO KSM K38)
SEQ ID NO: 13
DGLNGTMMQYYEWHLENDGQHWNRLHDDAAALSDAGITAIWIPPAYKGNS
QADVGYGAYDLYDLGEFNQKGTVRTKYGTKAQLERAIGSLKSNDINVYGD
VVMNHKMGADFTEAVQAVQVNPTNRWQDISGAYTIDAWTGFDFSGRNNAY
SDFKRWRWFHFNGVDWDQRYQENHIFRFANTNWNWRVDEENGNYDYLLGSN
IDFSHPEVQDELKDWGSWFTDELDLDGYRLDAIKHIPFWYTSDWVRHQRN
EADQDLFVVGEYWKDDVGALEFYLDEMNWEMSLFDVPLNYNFYRASQQGG
SYDMRNILRGSLVEAHPMHAVTFVDNHDTQPGESLESWVADWFKPLAYAT
ILTREGGYPNVFYGDYYGIPNDNISAKKDMIDELLDARQNYAYGTQHDYF
DHWDVVGWTREGSSSRPNSGLATIMSNGPGGSKWMYVGRQNAGOPGTWTDLT
GNNGASVTINGDGWGEFFTNGGSVSVYVNQ (KAO KSM K36)
SEQ ID NO: 14
DGLNGTMMQYYEWHLENDGQHWNRLHDDAEALSNAGITAIWIPPAYKGNS
QADVGYGAYDLYDLGEFNQKGTVRTKYGTKAQLERAIGSLKSNDINVYGD
VVMNHKLGADFTEAVQAVQVNPSNRWQDISGVYTIDAWTGFDFPGRNNAY
SDFKWRWFHFNGVDWDQRYQENHLFRFANTNWNWRVDEENGNYDYLLGSN
IDFSHPEVQEELKDWGSWFTDELDLDGYRLDAIKHIPPFWYTSDWVRHQRS
EADQDLFVVGEYWKDDVGALEFYLDEMNWEMSLFDVPLNYNFYRASKQGG
SYDMRNILRGSLVEAHPIHAVTFVDNHDTQPGESLESWVADWFKPLAYAT
ILTREGGYPNVFYGDYYGIPNDNISAKKDMIDELLDARQNYAYGTQHDYF
DHWDIVGWTREGTSSRPNSGLATIMSNGPGGSKWMYVGQQHAGQTWTDLT
GNHAASVTINGDGWGEFFTNGGSVSVYVNQ (LIQUIZYME® SC)
SEQ ID NO: 15
AAPFNGTMMQYFEWYLPDDGTLWTKVANEANNLSSLGITALWLPPAYKGT
SRSDVGYGVYDLYDLGEFNQKGTVRTKYGTKAQYLQAIQAAHAAGMQVYA
DVVFDHKGGADGTEWVDAVEVNPSDRNQEISGTYQIQAWTKFDFPGRGNT
YSSFKWRWYHFDGVDWDESRKLSRIYKFRGKAWDWEVDTEFGNYDYLMYA
DLDMDHPEVVTELKNWGKWYVNTTNIDGFRLDAVKHIKFSFFPDWLSYVR
SQTGKPLFTVGEYWSYDINKLHNYITKTNGTMSLFDAPLHNKFYTASKSG
GAFDMRTLMTNTLMKDQPTLAVTFVDNHDTEPGQALQSWVDPWFKPLAYA
FILTRQEGYPCVFYGDYYGIPQYNIPSLKSKIDPLLIARRDYAYGTQHDY
LDHSDIIGWTREGGTEKPGSGLAALITDGPGGSKWMYVKQHAGKVFYDL
TGNRSDTVTINSDGWGEFKVNGGSVSVWVPRKTTVS (SPEZYME® Ethyl)
SEQ ID NO: 16
AAPFNGTMMQYFEWYLPDDGTLWTKVANEANNLSSLGITALWLPPAYKGT
SRSDVGYGVYDLYDLGEFNQKGTVRTKYGTKAQYLQAIQAAHAAGMQVYA
DVVFDHKGGADGTEWVDAVEVNPSDRNQEISGTYQIQAWTKFDFPGRGNT
YSSFKWRWYHFDGVDWDESRKLSRIYKFIGKAWDWEVDTENGNYDYLMYA
DLDMDHPEVVTELKNWGKWYVNTTNIDGFRLDAVKHIKFSFFPDWLSYVR
SQTGKPLFTVGEYWSYDINKLHNYITKTNGTMSLFDAPLHNKFYTASKSG
GAFDMRTLMTNTLMKDQPTLAVTFVDNHDTEPGQALQSWVDPWFKPLAYA
FILTRQEGYPCVFYGDYYGIPQYNIPSLKSKIDPLLIARRDYAYGTQHDY
LDHSDIIGWTREGVTEKPGSGLAALITDGPGGSKWMYVGKQHAGKVFYDL
TGNRSDIVIINSDGWGEFKVNGGSVSVWVPRKTT (primer S242 F)
SEQ ID NO: 17
5'-[Phos]GTCAAGCATATTAAGTTCNNSTTTTTTCCTGATTGGTT
G-3'

(primer S242 R)
SEQ ID NO: 18
5'-[Phos]CAACCAATCAGGAAAAAASNNGAACTTAATATGCTTGA
C-3'

(BP17 phytase)
SEQ ID NO: 19
NDTPASGYQV EKVVILSRHG VRAPTKMTQT MRDVTPNTWP
EWPVKLGYIT PRGEHLISLM GGFYRQKFQQ QGILSQGSCP
TPNSIYVWAD VDQRTLKTGE AFLAGLAPQC GLTIHHQQNL
EKADPLFHPV KAGTCSMDKT QVQQAVEKEA QTPIDNLNQH
YIPFLALMNT TLNFSTSAWC QKHSADKSCD LGLSMPSKLS
IKDNGNKVAL DGAIGLSSTL AEIFLLEYAQ GMPQAAWGNI
HSEQEWASLL KLHNVQFDLM ARTPYIARHN GTPLLQAISN
ALNPNATESK LPDISPDNKI LFIAGHDTNI ANIAGMLNMR
WTLPGQPDNT PPGGALVFER LADKSGKQYV SVSMVYQTLE
QLRSQTPLSL NQPAGSVQLK IPGCNDQTAE GYCPLSTFTR
VVSQSVEPGC QLQ (coding sequence for the LAT signal peptide)
SEQ ID NO: 20
atgaaacaac aaaaacggct ttacgcccga ttgctgacgc
tgttatttgc gctcatcttc ttgctgcctc attctgcagc
ttcagca (LAT signal peptide)
SEQ ID NO: 21
MKQQKRLYAR LLTLLFALIF LLPHSAASA (truncated S242Q AmyS)
SEQ ID NO: 22
AAPFNGTMMQ YFEWYLPDDG TLWTKVANEA NNLSSLGITA
LWLPPAYKGT SRSDVGYGVY DLYDLGEFNQ KGTVRTKYGT
KAQYLQAIQA AHAAGMQVYA DVVFDHKGGA DGTEWVDAVE
VNPSDRNQEI SGTYQIQAWT KFDFPGRGNT YSSFKWRWYH
FDGVDWDESR KLSRIYKFRG IGKAWDWEVD TENGNYDYLM
YADLDMDHPE VVTELKNWGK WYVNTTNIDG FRLDAVKHIK -continued
FQFFPDWLSY VRSQTGKPLF TVGEYWSYDI NKLHNYITKT
NGTMSLFDAP LHNKFYTASK SGGAFDMRTL MTNTLMKDQP
TLAVTFVDNH DTEPGQALQS WVDPWFKPLA YAFILTRQEG
YPCVFYGDYY GIPQYNIPSL KSKIDPLLIA RRDYAYGTQH
DYLDHSDIIG WTREGVTEKP GSGLAALITD GPGGSKWMYV
GKQHAGKVFY DLTGNRSDTV TINSDGWGEF KVNGGSVSVW
VPRKTI (coding sequence for mature AmyS)
SEQ ID NO: 23
```
gccgcaccgt ttaacggtac catgatgcag tattttgaat
ggtacttgcc ggatgatggc acgttatgga ccaaagtggc
caatgaagcc aacaacttat ccagccttgg catcaccgct
ctttggctgc cgcccgctta caaaggaaca agccgcagcg
acgtagggta cggagtatac gacttgtatg acctcggcga
attcaatcaa aaagggaccg tccgcacaaa atatggaaca
aaagctcaat atcttcaagc cattcaagcc gcccacgccg
ctggaatgca agtgtacgcc gatgtcgtgt tcgaccataa
aggcggcgct gacggcacgg aatgggtgga cgccgtcgaa
gtcaatccgt ccgaccgcaa ccaagaaatc tcgggcacct
atcaaatcca agcatggacg aaatttgatt ttcccgggcg
gggcaacacc tactccagct ttaagtggcg ctggtaccat
tttgacggcg ttgactggga cgaaagccga aaattaagcc
gcatttacaa attccgcggc atcggcaaag cgtgggattg
ggaagtagac acggaaaacg gaaactatga ctacttaatg
tatgccgacc ttgatatgga tcatcccgaa gtcgtgaccg
agctgaaaaa ctgggggaaa tggtatgtca acacaacgaa
cattgatggg ttccggcttg atgccgtcaa gcatattaag
ttcagttttt ttcctgattg gttgtcgtat gtgcgttctc
agactggcaa gccgctattt accgtcgggg aatattggag
ctatgacatc aacaagttgc acaattacat tacgaaaaca
aacggaacga tgtctttgtt tgatgccccg ttacacaaca
aattttatac cgcttccaaa tcagggggcg catttgatat
gcgcacgtta atgaccaata ctctcatgaa agatcaaccg
acattggccg tcaccttcgt tgataatcat gacaccgaac
ccggccaagc gctgcagtca tgggtcgacc catggttcaa
accgttggct tacgccttta ttctaactcg gcaggaagga
tacccgtgcg tcttttatgg tgactattat ggcattccac
aatataacat tccttcgctg aaaagcaaaa tcgatccgct
cctcatcgcg cgcagggatt atgcttacgg aacgcaacat
gattatcttg atcactccga catcatcggg tggacaaggg
aaggggtcac tgaaaaacca ggatccgggc tggccgcact
gatcaccgat gggccgggag gaagcaaatg gatgtacgtt
ggcaaacaac acgctggaaa agtgttctat gaccttaccg
gcaaccggag tgcaccgtc accatcaaca gtgatggatg
gggggaattc aaagtcaatg gcggttcggt ttcggtttgg
gttcctagaa aaacgaccgt ttctaccatc gctcggccga
tcacaacccg accgtggact ggtgaattcg tccgttggac
cgaaccacgg ttggtggcat ggcct
```

(Satori F)
SEQ ID NO: 24
5'-CTCATCTTCTTGCTGCCTCATTCTGCAGCTTC-3'

(Satori R)
SEQ ID NO: 25
5'-TTATCCTTTACCTTGTCTCCAAGC-3'

DETAILED DESCRIPTION

I. Introduction

The present composition and methods relate to variants of a parent α-amylase that exhibit an alteration in at least one of the following properties relative to said parent α-amylase: specific activity, substrate specificity, substrate binding, substrate cleavage, thermal stability, pH-dependent activity, pH-dependent stability, oxidative stability, $Ca^{2+}$ dependency, pI, and wash performance. The variants are suitable for starch conversion, ethanol production, laundry washing, dish washing, hard surface cleaning, and other industrial use.

Although numerous mutations are described, they have in the common the ability to improve the performance of parental α-amylases that share structural features in terms of amino acid sequence identity and three dimension structure. Several of these mutations have been found to be combinable with other mutations, which make them of particular value in designing variant α-amylases with preselected properties. Also described are positions that are either not amenable to mutation, in general, or not amenable to mutation and combination with other mutations. The identification of these positions is also important in designing variant α-amylases with preselected properties.

Although studies performed in support of the present compositions and methods were performed primarily using a particular parental α-amylase from *Geobacillus stearothermophilus*, structurally-related α-amylases are likely to benefit from equivalent mutations. Accordingly, the present description provides a roadmap for modifying any of a large number of α-amylases to produce beneficial changes in performance characteristics and for identifying novel α-amylases likely to have desirable performance characteristic based on the presence of certain amino acid residues at specified positions.

These and other aspects and embodiments of the compositions and methods are described in more detail, below.

II. Definitions and Nomenclature

Prior to describing the present compositions and methods in more detail, various terminology, nomenclature, and general principles are set forth, below.

A. Definitions

The following terms and phrases are defined for clarity. Terms and phrases that are not defined should be given their ordinary meaning as used in the art. Reference is made to standard molecular biology references, such as Sambrook et al., MOLECULAR CLONING: A LABORATORY MANUAL (2nd Ed., 1989); Kreigler, GENE TRANSFER AND EXPRESSION; A LABORATORY MANUAL (1990); Ausubel et al. (eds.) CURRENT PROTOCOLS IN MOLECULAR BIOLOGY (1994); Singleton, et al., DICTIONARY OF MICROBIOLOGY AND MOLECULAR BIOLOGY, 2D ED., John Wiley and Sons, New York (1994); and Hale and Markham, THE HARPER COLLINS DICTIONARY OF BIOLOGY, Harper Perennial, N.Y. (1991).

As used herein, the term "starch" refers to any material comprised of the complex polysaccharide carbohydrates of plants, comprised of amylose and amylopectin with the formula $(C_6H_{10}O_5)_x$, wherein X can be any number. Exemplary sources of starch include but are not limited to grains, grasses, tubers, and roots, and more specifically wheat, barley, corn, rye, rice, sorghum, brans, cassava, millet, potato, sweet potato, and tapioca.

As used herein, the term "alpha (α)-amylase" refers to enzymes that catalyze the hydrolysis of α-1,4-glucosidic linkages, e.g., E.C. class 3.2.1.1. These enzymes have also been described as effecting the exo or endohydrolysis of 1,4-α-D-glucosidic linkages in polysaccharides containing 1,4-α-linked D-glucose units. Another term used to describe these enzymes is "glycogenases." Exemplary enzymes include α-1,4-glucan 4-glucanohydrase glucanohydrolase.

As used here, the term "recombinant," when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, the terms "protein" and "polypeptide" are used interchangeably to refer to a contiguous chain of amino acid residue linked by peptide bonds. The conventional one-letter or three-letter code for amino acid residues is used.

As used herein, a "signal sequence" refers to a sequence of amino acid residues at the N-termus of a polypeptide, which facilitates the secretion of an extracellular polypeptide outside the cell. The mature form of the extracellular protein lacks the signal sequence, which is cleaved off during the secretion process.

As used herein, a "gene" refers to a DNA segment that is involved in producing a polypeptide and includes regions preceding and following the coding regions as well as intervening sequences (introns) between individual coding segments (exons). The name of a gene is generally italicized, while the name of a corresponding protein is generally not italicized and the first letter is capitalized.

As used herein, the terms "nucleic acid" and "polynucleotide" are used interchangeably to refers to a contiguous chain of nucleosides linked by phosphodiester or similar bonds, and" encompasses DNA, RNA, whether single-stranded, double-stranded, or partially double-stranded, as well as chemically modified DNA or RNA or synthetic derivatives, thereof. Unless other wise specified, the sequences of nucleic acids are present in a 5' to 3' direction. The skilled person will appreciate that because the genetic code is degenerate, more than one codon may encode a particular amino acid.

As used herein, a "vector" refers to a polynucleotide sequence designed to introduce nucleic acids into one or more cell types. Vectors include cloning vectors, expression vectors, shuttle vectors, plasmids, phage particles, cassettes, and the like.

As used herein, an "expression vector" refers to a DNA construct comprising a DNA sequence that is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

As used herein, a "promoter" is a regulatory sequence that is involved in binding RNA polymerase to initiate transcription of a gene. A promoter may be an inducible promoter or a constitutive promoter. An exemplary promoter is from the *Trichoderma reesei* cbh1 gene, which is an inducible promoter.

As used herein, the term "under transcriptional control" indicates that the transcription of a specified polynucleotide, usually a DNA sequence, depends on its being operably linked to a specified promoter and/or other element(s), which regulate its transcription.

As used herein, the term "under translational control" indicates that the translation of a specified polynucleotide, usually a mRNA sequence, depends on its being operably linked to a specified element(s), which regulate its translation.

As used herein, the term "derived" encompasses the terms "originated from," "obtained from," "obtainable from," and "isolated from," and is used to indicate that a specified polypeptide, polynucleotide, expression vector, host cell, or the like, is a modified variant of a parental polypeptide, polynucleotide, expression vector, host cell, or the like.

As used herein, "operably-linked" means that the described components are in a relationship permitting them to function in their intended manner. For example, a regulatory sequence can be "operably-linked" to a coding sequence in such a way that expression of the coding sequence is achieved under conditions compatible with the regulatory sequence.

The term "selective/selectable marker" refers to a gene capable of being expressed in a host cell that allows for ease of selection of those host cells using a media component or growth condition. Examples of selectable markers include but are not limited to gene that confer antibiotic/antimicrobial resistence (e.g., hygromycin, bleomycin, or chloramphenicol) and/or genes that confer a metabolic or nutritional advantage.

As used herein, a polynucleotide or a polypeptide has a certain "percent/percentage sequence identity" (e.g., 80%, 85%, 90%, 91%, 92%, 93%, 94%, 95%, 96%, 97%, 98%, or 99%) with another sequence when the specified percentage of bases or amino acid residues are the same following alignment the sequences. Alignment and the percent homology or identity can be determined using any suitable software program known in the art, for example those described in CURRENT PROTOCOLS IN MOLECULAR BIOLOGY (Ausubel et al. (eds) (1987) Supplement 30, section 7.7.18). Preferred programs include the Vector NTI Advance™ 9.0 (Invitrogen Corp. Carlsbad, Calif.), GCG Pileup, FASTA (Pearson et al. (1988) *Proc. Natl, Acad. Sci USA* 85:2444-2448), and BLAST (BLAST Manual, Altschul et al., Natl Cent. Biotechnol. Inf., Natl Lib. Med. (NCIB NLM NIH), Bethesda, Md., and Altschul et al. (1997) *NAR* 25:3389-3402) programs. Another preferred alignment program is ALIGN Plus (Scientific and Educational Software, PA), preferably using default parameters. Another sequence software program that finds use is the TFASTA Data Searching Program available in the Sequence Software Package Version 6.0 (Genetics Computer Group, University of Wisconsin, Madison, Wis.).

As used herein, a "host strain" or "host cell" refers to an organism suitable for introducing an expression vector or DNA construct comprising a polynucleotide encoding a subject polypeptide. Host cells are preferably bacterial or fungal cells but may also be plant cells (e.g., protoplasts), insect cells, or mammalian cells.

As used herein, the term "culturing" refers to growing a population of microbial cells under suitable conditions in liquid or solid medium. Culturing includes fermentative bioconversion of a starch substrate containing granular starch to an end-product (typically in a vessel or reactor).

As used herein, the term "fermentation" refers to the enzymatic and substantially anaerobic breakdown of organic substances by microorganisms to produce simpler organic compounds. While fermentation generally occurs under anaerobic conditions it is not intended that the term be solely limited to strict anaerobic conditions, as fermentation also occurs in the presence of oxygen.

As used herein, the term "contacting," with reference to an enzyme and its substrate, refers to the placing of the enzyme in sufficiently close proximity to the substrate to enable the enzyme to convert the substrate to an end-product (i.e., act on the substrate). Contacting can be brought about by mixing solutions or suspensions of enzymes and substrates.

As used herein, the term "enzymatic conversion" generally refers to the modification of a substrate by enzyme action, for example, the modification of a starch substrate by the action of an amylase, glucoamylase, or other enzyme.

As used herein, the term "saccharification" refers to enzymatic conversion of starch to glucose.

As used herein, the term "gelatinization" refers to solubilization of starch (e.g., raw or crystalline starch) by cooking to form a viscous suspension.

As used herein, the term "liquefaction" refers to the stage in starch conversion in which gelatinized starch is hydrolyzed to lower molecular weight soluble dextrins.

As used herein, the term "degree of polymerization (DP)" refers to the number (n) of anhydroglucopyranose units in a given saccharide. Examples of DP1 saccharides are monosaccharides, such as glucose and fructose. Examples of DP2 saccharides are disaccharides, such as maltose and sucrose. A DP>3 saccharide has a degree of polymerization greater than 3.

As used herein, the terms "end-product" or "desired end-product" refer to a molecule that is enzymatically derived from a substrate, such as starch.

As used herein, the term "dry solids content (ds)" refers to the total solids of a slurry expressed in terms of % on a dry weight basis (% wt/wt).

As used herein, the term "slurry" refers to an aqueous mixture containing insoluble solids.

As used herein, the term "residual starch" refers to the remaining starch (soluble or insoluble) in a starch composition after fermentation.

As used herein, a "recycling step" refers to the recycling of mash components, which may include residual starch, enzymes, and/or microorganisms to affect or participate in the fermentation of additional starch compositions.

As used herein, the term "mash" refers to a mixture of fermentable carbon molecules (e.g., carbohydrates) in water, which may be used to produce a fermented product, such as an alcohol. The terms "beer" and "mash" may be used interchangeability.

As used herein, the term "stillage" refers to a mixture of non-fermented solids and water, which is the residue after removal of alcohol from a fermented mash.

As used herein, the terms "distillers dried grain (DDG)" and "distillers dried grain with solubles (DDGS)" refer to a useful by-product of grain fermentation.

As used herein, an "ethanologenic microorganism" refers to a microorganism capable of converting a sugar or oligosaccharide to ethanol. Ethanologenic microorganisms are generally ethanologenic by virtue of their ability to express one or more enzymes that individually or together convert sugar to ethanol.

As used herein, the term "ethanol producer" or ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast. Preferred yeast includes strains of *Sacchromyces*, particularly, *S. cerevisiae*.

As used herein, the term "heterologous," with reference to a polynucleotide or polypeptide, refers to a polynucleotide or polypeptide that does not naturally occur in a host cell. The protein may be a commercially important industrial polypeptide, such as an enzyme. It is intended that the term encompasses polynucleotides and polypeptides that are (or are encoded by) naturally occurring genes, mutated genes, and/or synthetic genes.

As used herein, the term "endogenous," with reference to a polynucleotide or polypeptide, refers to a polynucleotide or polypeptide that occurs naturally in the host cell.

As used herein, the terms "recovered," "isolated," and "separated" refer to a compound, protein, cell, nucleic acid or amino acid that is removed from at least one component with which it is naturally associated.

As used herein, the terms "transformed," "stably transformed," and "transgenic," used in reference to a cell, means the cell includes a non-native (e.g., heterologous) nucleic acid sequence integrated into its genome or carried as an episomal plasmid that is maintained through multiple generations.

As used herein, the term "expression" refers to the process by which a polypeptide is produced based on the nucleotide sequence of a gene. The process includes both transcription and translation.

As used herein, the term "introduced," in the context of inserting a nucleic acid sequence into a cell, refers to "transfection," "transformation," or "transduction," and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, the term "specific activity" refers to the number of moles of substrate that can be converted to product by an enzyme or enzyme preparation per unit time under specific conditions. Specific activity is generally expressed as units (U)/mg of protein.

As used herein, the term "yield" refers to the amount of end-product produced using a specified method and specified reagents (including enzymes). The amount of end-product may be expressed in terms of mass, volume, concentration, or the like, and may include a reference to the amount of starting material (e.g., substrate), time, or other conditions.

As used herein, there term "performance index (PI)" refers to the ratio of performance of a variant enzyme to the parent or reference enzyme. Within this context, various further terms and phrases are used to characterize the performance of variants: "up mutations" have a PI>1; neutral mutations have a PI>0.5; non-deleterious mutations have a PI>0.05; deleterious mutations have a PI=0.05; combinable mutations have a PI=0.5 for at least one property, and >0.05 for all properties.

As used herein, "combinable mutations" are mutations that can be combined to deliver proteins with preselected performance indices (PI) for one or more desired properties (see above).

As used herein, "ATCC" refers to the American Type Culture Collection located in Manassas, Va., USA.

As used herein, "NRRL" refers to the Agricultural Research Service Culture Collection, National Center for Agricultural Utilization Research (previously known as USDA Northern Regional Research Laboratory) in Peoria, Ill., USA.

In general, numeric ranges are inclusive of the numbers defining the range. The singular articles "a," "an," and "the" include plural referents, unless the context clearly dictates otherwise. The headings are provided for ease of reading and should not be construed as confining described subject matter to a portion of the specification. All patents and publications, including all sequences disclosed within such patents and publications, are expressly incorporated by reference.

B. Nomenclature

The conventional one-letter and three-letter codes for amino acid residues are used unless otherwise specified. Variant polypeptides are described using the following nomenclature: original amino acid(s): position(s): substituted amino acid(s).

According to this nomenclature, for instance the substitution of serine by an alanine in position 242 is shown as:
Ser242Ala or S242A A deletion of alanine in position 30 is shown as:
Ala30* or A30* or ΔA30

And an insertion of an additional amino acid residue, such as lysine, is shown as:

Ala30AlaLys or A30AK

A deletion of a consecutive stretch of amino acid residues, such as amino acid residues 30-33, is indicated as (30-33)* or Δ(A30-N33).

Where a polypeptide contains a "deletion" in comparison with other polypeptides (or a parent polypeptide) and an insertion is made in this position it is indicated as:

*36Asp or *36D, where the example represents for insertion of an aspartic acid in position 36.

Multiple mutations are separated by plus signs. For example, mutations at positions 30 and 34, substituting alanine and glutamic acid for asparagine and serine, respectively, are represented by:

Ala30Asp+Glu34Ser or A30N+E34S

When one or more alternative amino acid residues may be inserted in a given position it is indicated as A30N,E or A30N or A30E Furthermore, when a position suitable for modification is identified without any specific modification being suggested, it is to be understood that any amino acid residue may be substituted for the amino acid residue present in the position. For instance, when a modification of an alanine in position 30 is mentioned, but not specified, it is to be understood that the alanine may be deleted or substituted for any other amino acid, i.e., any one of:

R, N, D, A, C, Q, E, G, H, I, L, K, M, F, P, S, T, W, Y, V.

Further, "A30X" means any one of the following substitutions:

A30R, A30N, A30D, A30C, A30Q, A30E, A30G, A30H, A30I, A30L, A30K, A30M, A30F, A30P, A30S, A30T, A30W, A30Y, or A30V; which may also be presented as:

A30R, N, D, C, Q, E, G, H, I, L, K, M, F, P, S, T, W, Y, V.

If the parent enzyme used for the numbering already has the amino acid residue in question suggested for substitution in that position, the following nomenclature is used:

"X30N" or "X30N,V" in the case where for instance one or N or V is present in the wildtype.

Thus, it means that other corresponding parent enzymes are substituted to an "Asn" or "Val" in position 30.

C. Characteristics of Amino Acid Residues

The following general information characteristic of amino acid residues are provided for reference.

Charged amino acids:

Asp, Glu, Arg, Lys, His

Negatively charged amino acids (with the most negative residue first):

Asp, Glu

Positively charged amino acids (with the most positive residue first):

Arg, Lys, His

Neutral amino acids:

Gly, Ala, Val, Leu, lie, Phe, Tyr, Trp, Met, Cys, Asn, Gln, Ser, Thr, Pro

Hydrophobic amino acid residues (with the most hydrophobic residue listed last):

Gly, Ala, Val, Pro, Met, Leu, lie, Tyr, Phe, Trp,

Hydrophilic amino acids (with the most hydrophilic residue listed last):

Thr, Ser, Cys, Gln, Asn

III. α-amylases for Use in the Present Compositions and Methods

The following paragraphs describe "Spezyme® Xtra-like" or "AmyS-like" α-amylases that can be modified and used according as described herein.

A. Homology Among α-amylases

Experiments performed in support of the present compositions and methods have been performed using *Geobacillus* (formerly *Bacillus*) *stearothermophilus* α-amylase (i.e., AmyS), exemplified by SEQ ID NO: 2. A variant of this amylase is commercially available as SPEZYME® Xtra (Danisco US Inc, Genencor Division, Palo Alto, Calif., USA).

A number of α-amylases produced by *Bacillus* spp. are highly homologous (identical) on the amino acid level to AmyS, and the many of mutations described herein are expected to produce similar effects when made in these amylase, which are collectively referred to as "SPEZYME® Xtra-like" α-amylases or "AmyS-like" α-amylases. The identity of a number of known *Bacillus* α-amylases is summarized in Table A:

TABLE A

| | Percent identity | | | | | | | |
|---|---|---|---|---|---|---|---|---|
| | 707 | AP1378 | BAN | BSG | SP690 | SP722 | AA560 | LAT |
| 707 | 100.0 | 86.4 | 66.9 | 66.5 | 87.6 | 86.2 | 95.5 | 68.1 |
| AP1378 | 86.4 | 100.0 | 67.1 | 68.1 | 95.1 | 86.6 | 86.0 | 69.4 |
| BAN | 66.9 | 67.1 | 100.0 | 65.6 | 67.1 | 68.8 | 66.9 | 80.7 |
| BSG | 66.5 | 68.1 | 65.6 | 100.0 | 67.9 | 67.1 | 66.3 | 65.4 |
| SP690 | 87.6 | 95.1 | 67.1 | 67.9 | 100.0 | 87.2 | 87.0 | 69.2 |
| SP722 | 86.2 | 86.6 | 68.8 | 67.1 | 87.2 | 100.0 | 86.8 | 70.8 |
| AA560 | 95.5 | 86.0 | 66.9 | 66.3 | 87.0 | 86.8 | 100.0 | 68.3 |
| LAT | 68.1 | 69.4 | 80.7 | 65.4 | 69.2 | 70.8 | 68.3 | 100.0 |

The *B. licheniformis* α-amylase (LAT) having the amino acid sequence shown in SEQ ID NO: 7 has been found to be about 81% homologous with the *B. amyloliquefaciens* α-amylase having the amino acid sequence shown in SEQ ID NO: 9, and about 65% homologous with the *Geobacillus* (formerly *Bacillus*) *stearothermophilus* α-amylase (BSG; AmyS) comprising the amino acid sequence shown in SEQ ID NO: 1. Further homologous α-amylases include SP690 and SP722 disclosed in WO 95/26397 and the #707 α-amylase derived from *Bacillus* sp., shown in SEQ ID NO: 6 and described by Tsukamoto et al. (1988) *Biochemical and Biophysical Research Communications* 151:25-31. The KSM AP1378 α-amylase (SEQ ID NO: 12) is disclosed in WO 97/00324 (from KAO Corporation).

Still further homologous α-amylases include the α-amylase produced by the *B. licheniformis* strain described in EP 0 252 666. (ATCC 27811), and the α-amylases identified in WO 91/00353 and WO 94/18314. Other commercial SPEZYME® Xtra-like α-amylases are comprised in the products sold under the following tradenames: SPEZYME® AA and Ultraphlow (available from Danisco US Inc, Genencor Division), and KEISTASE™ (available from Daiwa) and LIQUEZYME® SC (SEQ ID NO: 15) available from Novozymes, DK). Other related α-amylases include Termamyl® (SEQ ID NO: 8; Novozymes), STAINZYME™ (SEQ ID NO: 10; Novozymes), NATALASE™ (SEQ ID NO: 11; Novozymes), KAO KSM K38 (SEQ ID NO: 13), KAO KSM K36 (SEQ ID NO: 14), other α-amylases mentioned in the Table, and other α-amylases described herein.

Because of the substantial homology found between these α-amylases, they are considered to belong to the same class of α-amylases and are encompassed by the present compositions and methods. While *G. stearothermophilus* α-amylase (SEQ ID NO: 2) is used as a starting point, corresponding positions in these and other α-amylases, e.g., the SP722, BLA, BAN, AA560, SP690, KSM AP1378, #707 and other *Bacillus* α-amylases are also expected to benefit from modifications to be described.

Accordingly, the terms SPEZYME® Xtra-like α-amylase or AmyS-like α-amylase are intended to include an α-amylase having the amino acid sequence of SEQ ID NOs: 1, 2, 6, 7, 8, 9, 10, 11, 12, 15, and 16. In some embodiments, SPEZYME® Xtra-like α-amylase or AmyS-like α-amylase also include α-amylases that exhibits substantial identity at the amino acid level to SEQ ID NO: 2, for example, at least 60%, at least 70%, at least 75%, at least 80%, at least 85%, at least 90%, at least 91%, at least 92%, at least 93%, at least 94%, at least 95%, at least 96%, at least 97%, at least 98%, or even at least 99% homology (identity). In further embodiments, SPEZYME® Xtra-like α-amylase or AmyS-like α-amylase also include α-amylases that exhibits substantial identity at the amino acid level to one or more of SEQ ID NOs: 1, 2, 6, 7, 8, 9, 10, 11, 12, 15, and 16, for example, at least 60%, at least 70%, at least 75%, at least 80%, at least 85%, at least 90%, at least 91%, at least 92%, at least 93%, at least 94%, at least 95%, at least 96%, at least 97%, at least 98%, or even at least 99% homology (identity).

The homology of known or suspected α-amylases to a reference α-amylase may be determined by means of computer programs known in the art. Generally, a structural alignment between SPEZYME® Xtra (SEQ ID NO: 2) and, e.g., another α-amylase may be used to identify equivalent/corresponding positions in other SPEZYME® Xtra-like α-amylases, which can be mutated as described herein to produce similar effects. One exemplary program is GAP, which is provided in the GCG program package (described above). In particular, Gap GCG v8 may be used with the default scoring matrix for identity and the following default parameters: GAP creation penalty of 5.0 and GAP extension penalty of 0.3, respectively for nucleic acidic sequence comparison, and GAP creation penalty of 3.0 and GAP extension penalty of 0.1, respectively, for protein sequence comparison. GAP uses the method of Needleman and Wunsch, (1970), *J. Mol. Biol.* 48:443-453, to make alignments and to calculate the identity. Other programs and methods are known in tha art.

Another method of obtaining structural alignments is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149-155) and reverse threading (Huber, T; Torda, AE, PROTEIN SCIENCE Vol. 7, No. 1 pp. 142-149 (1998).

SPEZYME® Xtra-like α-amylases or AmyS-like α-amylases further include polypeptides encoded by a DNA sequence that hybridizes to a DNA sequence encoding one or more of the aforementioned α-amylases, as exemplified by SEQ ID NOs: 9 (BAN), 5 (BSG; AmyS), 3 (SP722), 1 (SP690), 7 (LAT), and 11 (AA560) of WO 06/002643 and polynucleotides encoding the amino acid sequences of SEQ ID NOs: 1, 2, 6, 7, 8, 9, 10, 11, 12, 15 and 16. A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (see, e.g., Sambrook (1989) supra, particularly chapters 9 and 11). An oligonucleotide probe used in the characterization of a known or suspected SPEZYME® Xtra-like α-amylase above may suitably be prepared on the basis of the full or partial nucleotide or amino acid sequence of the α-amylase in question.

Suitable conditions for testing hybridization involve pre-soaking in 5×SSC and prehybridizing for 1 hour at 40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at 40° C., followed by three times washing of the filter in 2×SSC, 0.2% SDS at 40° C. for 30 minutes (low stringency), preferred at 50° C. (medium stringency), more preferably at 65° C. (high stringency), even more preferably at 75° C. (very high stringency). More details about the hybridization method can be found in Sambrook et a., Molecular Cloning: A Laboratory Manual, 2nd Ed., Cold Spring Harbor, 1989. In some embodiments, stringent conditions correspond to a Tm of 65° C. and 0.1×SSC, 0.1% SDS.

B. Parental α-amylases

Any of the aforemtioned SPEZYME® Xtra/AmyS-like α-amylases may serve as a parental α-amylase to be modified and used as described herein. The parental/parent α-amylase may also be referred to as a "backbone" or "template," and variant amylases may be derived, therefrom. In some embodiments, the parent α-amylase is derived from *G. stearothermophilus*. In a particular embodiment, the the parent α-amylase has the amino acid sequence of SEQ ID NO: 2. In other embodiments, the parental α-amylase has the amino acid sequence of SEQ ID NOs: 1, 6, 7, 8, 9, 10, 11, 12, 15, and 16, or exhibits substantial identity at the amino acid level to SEQ ID NOs: 1, 2, 6, 7, 8, 9, 10, 11, 12, 15, and/or 16, for example, at least 60%, at least 70%, at least 75%, at least 80%, at least 85%, at least 90%, at least 91%, at least 92%, at least 93%, at least 94%, at least 95%, at least 96%, at least 97%, at least 98%, or even at least 99% homology (identity).

A parental α-amylase may also be a hybrid α-amylase, i.e., an α-amylase, which comprises a combination of partial amino acid sequences derived from at least two α-amylases, such as those described, above. In addition the hybrid α-amylase may include a portion of a SPEZYME® Xtra/AmyS-like α-amylase and portion of one or more other α-amylases of microbial (bacterial or fungal) and/or mammalian origin.

Thus, the parent hybrid α-amylase may comprise a combination of partial amino acid sequences deriving from at least two SPEZYME® Xtra-like α-amylases, or from at least one SPEZYME® Xtra-like and at least one non-SPEZYME® Xtra-like bacterial α-amylase, or from at least one SPEZYME® Xtra-like and at least one fungal α-amylase, and so forth. For instance, the parent α-amylase may comprise a C-terminal part of an α-amylase derived from a strain of B. licheniformis, and an N-terminal part of an α-amylase derived from a strain of G. stearothermophilus.

IV. Altered Properties of α-amylase Variants

The following section describes the relationship between mutations, which are present in the variant polypeptides described herein, and desirable alterations in properties (relative to those of a parent SPEZYME® Xtra-like α-amylase), which result therefrom.

In a first aspect a variant of a parent G. stearothermophilus α-amylase is provided, comprising an alteration at one or more positions (using SEQ ID NO: 1 or SEQ ID NO: 2 for the amino acid numbering) selected from the group of:
P17, D19, T21, N28, S51, G72, V74, A82, Q86, Q89, A93, G95, Q97, W115, D117, P123, S124, D125, N127, I130, G132, Q135, P145, G146, G148, S153, Y159, W166, S169, K171, W187, P209, N224, S242, G256, D269, N271, T278, N281, G302, A304, R308, T321, Q358, P378, S382, K383, T398, H405, T417, E418, P420, G421, P432, W437, G446, G454, S457, T459, T461, S464, G474, R483.
wherein
(a) the alteration(s) are independently
(i) an insertion of an amino acid downstream of the amino acid which occupies the position,
(ii) a deletion of the amino acid which occupies the position, or
(iii) a substitution of the amino acid which occupies the position with a different amino acid,
(b) the variant has α-amylase activity and (c) each position corresponds to a position of the amino add sequence of the parent G. stearothermophilus α-amylase having the amino acid sequence shown in SEQ ID NO: 1 or 2.

Specifically contemplated herein are S242A, S242Q, S242N and S242E, which may be combined with mutations at R179, G180, I181, G182, and/or K183, associated with calcium-sodium binding, and/or a mutations at P245 in the middle of an α-helix.

Corresponding positions in other parent SPEZYME® Xtra-like α-amylases can be found by alignment as described above and shown in the alignment in FIG. 4.
Stability In the context of the variants described herein, mutations (including amino acid substitutions and deletion) of importance with respect to achieving altered stability, in particular improved stability (i.e., higher or lower), at especially high temperatures (i.e., 70-120° C.) and/or extreme pH (i.e., low or high pH, i.e, pH 4-6 or pH 8-11, respectively), in particular at free (i.e., unbound, therefore in solution) calcium concentrations below 60 ppm, include any of the mutations listed in the "Altered Properties" section. The stability may be determined as described in the "Methods" section below.

Exemplary mutations in SPEZYME® Extra and related α-amylases that increase stability include:
(a) a substitution that introduces one or more of the amino acid residues: 74A, 115L, 124K, 124R, 132A, 132C, 135A, 145A, 146A, 148A, 148N, 159A, 159C, 159D, 159E, 159F, 159G, 159H, 159K, 159L, 159N, 159R, 159S, 159T, 159V, 169A, 169L, 169M, 169Y, 179A, 181A, 181C, 181D, 181E, 181L, 181P, 181Q, 181V, 181Y, 242A, 242D, 242E, 242Q, 261L, 271A, 271V, 278A, 278H, 278K, 278N, 278R, 281A, 281L, 281M, 302D, 302M, 304D, 304E, 304M, 321A, 321H, 321Q, 321R, 333Q, 378D, 378 N, 378R, 382D, 398A, 418A, 418M, 418N, 420A, 421R, 432A, 432D, 432L, 432M, 432N, 432Q, 432R, 432Y, 437D, 437G, 437H, 437L, 437M, 437Y, 446A, 446Y, 454A, 464Q, 464Y, 474A, 474E, 474K, 474L, 474M, 474N, 474P, 474Q, 474R, 474S, and 474V, or
(b) a substitution that introduces one or more of the amino acid residues: 6I, 6N, 6Q, 6T, 6V, 14T, 16F, 25A, 25C, 25G, 25Q, 27M, 36Q, 36S, 39G, 39V, 50I, 50L, 50M, 50N, 50Q, 52S, 53T, 67N, 67S, 80D, 80I, 90E, 133P, 133V, 137M, 137S, 141E, 141I, 141L, 141M, 141Q, 141R, 141S, 141V, 150E, 151I, 152G, 155S, 155Y, 168W, 173T, 188P, 193F, 193K, 193L, 193Y, 213L, 213M, 213V, 217Q, 220P, 220Q, 220R, 220S, 220V, 221I, 221S, 249E, 250F, 250I, 250M, 252L, 253Y, 254E, 254F, 254T, 254V, 255F, 255K, 255W, 257L, 257M, 257S, 257V, 258D, 258G, 258H, 258K, 258Q, 258T, 258V, 268F, 274W, 283M, 283N, 283V, 285E, 285Q, 293G, 293K, 294W, 301F, 301I, 301P, 301R, 301T, 301W, 309D, 309V, 312H, 312S, 312V, 312Y, 313G, 313H, 313I, 313L, 313S, 313V, 318T, 338A, 338C, 338G, 338M, 338T, 339K, 339T, 339V, 340A, 340M, 340Q, 340T, 343C, 343I, 343P, 343R, 343Y, 345I, 345Q, 369I, 369T, 370G, 375T, 385T, 386K, 394L, 394V, 400A, 400N, 400V, 402H, 402I, 402T, 402V, 402W, 403A, 403E, 403G, 403Q, 403R, 403T, 403V, 404C, 404E, 404G, 404I, 404V, 419A, 419C, 419M, 419T, 422E, 422G, 433A, 433H, 433I, 433K, 433L, 433M, 433V, 433Y, 442A, 442G, 442N, 442R, 442S, 442T, 442V, 442W, 442Y, 445G, 445I, 445N, 445T, 445V, 445W, 447I, 447N, 447Q, 447W, 447Y, 448C, 448F, 448G, 448H, 448I, 448N, 448Y, 450C, 450H, 450M, 450N, 450R, 450S, 450T, 450W, 455G, 455I, 455P, 455V, 463A, 463M, 463S, 463T, 463V, 463W, 465G, 465I, 465K, 465N, 465T, 465V, 469D, 469W, 469Y, 471I, 471V, 473G, 473Y, 476A, 476G, 476L, 476M, 476N, and 476T $Ca^{2+}$ Stability Altered $Ca^{2+}$ stability means the stability of the enzyme under $Ca^{2+}$ depletion has been improved, i.e., higher or lower stability. In the context of the presently described variants, mutations (including amino acid substitutions and deletions) of importance with respect to achieving altered $Ca^{2+}$ stability, in particular improved $Ca^{2+}$ stability, i.e., higher or lower stability, at especially high pH (i.e., pH 8-10.5) include any of the mutations listed in the in "Altered Properties" section.

Specific Activity and or Increased Expression

In a further aspect, important mutations (including amino acid substitutions and deletions) with respect to obtaining variants exhibiting altered specific activity, in particular increased or decreased specific activity, especially at temperatures from 10-60° C., preferably 20-50° C., especially 30-40° C., include any of the mutations listed in the in "Altered properties" section. The specific activity may be determined as described in the "Methods" section below. In some cases, the mutations increase expression rather than or in addition to increasing specific activity. Exemplary mutations are as follows:

(a) a substitution that introduces one or more of the amino acid residues selected from the group consisting of 124N, 125A, 125K, 125N, 130A, 130S, 159A, 159D, 159E, 159G, 159H, 159K, 159L, 159N, 159R, 159S, 159T, 166F, 166G, 166H, 166S, 166Y, 169L, 179A, 179P, 180A, 180D, 180H, 180K, 180L, 180N, 180T, 180V, 180Y, 181A, 181D, 181E, 181G, 181P, 181R, 181S, 181V, 187A, 187C, 187K, 187N, 187P, 187Q, 187R, 187S, 242H, 242N, 278H, 278K, 278N, 278R, 281M, 302D, 304M, 304Y, 321H, 321Q, 321R, 333Q, 432Q, 437Y, 446A, 474Q, and 474S, or (b) a substitution that introduces one or more of the amino acid residues selected from the group consisting of 6A, 6D, 6E, 6H, 6I, 6K, 6L, 6M, 6N, 6P, 6Q, 6R, 6S, 6T, 6V, 6W, 6Y, 13K, 14F, 14T, 14Y, 15A, 15D, 15E, 015G, 15H, 15K, 15N, 15P, 15Q, 15R, 15S, 15T, 15W, 16A, 16E, 16G, 16H, 16K, 16N, 16P, 16Q, 16R, 16T, 25C, 39D, 39E, 39N, 39Q, 81Y, 121P, 139D, 139H, 139R, 139Y, 177A, 188D, 191H, 191K, 192A, 192D, 192G, 192N, 192P, 192Q, 192S, 192T, 192V, 192Y, 196A, 196C, 196D, 196E, 196F, 196H, 196I, 196K, 196P, 196R, 196S, 196T, 196V, 201A, 201E, 201G, 201H, 201M, 202H, 216E, 216G, 216H, 216M, 216Q, 216R, 216S, 216T, 216Y, 221A, 221D, 221F, 221I, 221L, 221M, 221N, 221R, 221S, 221V, 221Y, 237G, 240G, 240N, 240P, 240Q, 240R, 240T, 246R, 250A, 250D, 250E, 250F, 250G, 250I, 250K, 250L, 250M, 250N, 250Q, 250R, 250S, 250W, 252K, 268A, 268D, 268E, 268G, 268H, 268K, 268N, 268P, 268Q, 268R, 268S, 274A, 274D, 274G, 274I, 274K, 274L, 274N, 274Q, 274R, 274S, 274T, 275K, 285Q, 285Y, 293K, 293R, 318A, 318F, 318G, 318I, 318K, 318L, 318M, 318R, 318S, 318T, 318V, 318Y, 319C, 319D, 319H, 319I, 319K, 319R, 319Y, 320K, 320R, 320T, 338A, 338G, 338I, 338M, 338P, 338S, 338V, 339G, 339P, 340A, 340D, 340E, 340H, 340K, 340N, 340Q, 345E, 363D, 363E, 363M, 363N, 363Q, 363S, 366Q, 370A, 370D, 370E, 370H, 370K, 370N, 370Q, 370S, 375A, 375D, 375E, 375K, 375N, 375Q, 375R, 375S, 419A, 419I, 419M, 419P, 419S, 419V, 448Y, 452N, 452Q, 452R, 452S, 471R, and 471Y.

Oxidation Stability

The described variants may have altered oxidation stability, in particular higher oxidation stability, in comparison to the parent α-amylase. Increased oxidation stability is advantageous in, e.g., detergent compositions and decreased oxidation stability may be advantageous in composition for starch liquefaction. Oxidation stability may be determined as described in the "Methods" section below.

Altered pH Profile

Important positions and mutations with respect to obtaining variants with altered pH profile, in particular improved activity at especially high pH (i.e., pH 8-10.5) or low pH (i.e., pH 4-6) include mutations of amino residues located close to the active site residues. In some cases, the improved activity is observed, e.g., at pH<6, at pH<5, or at pH>9.

Preferred specific mutations/substitutions are the ones listed above in the section "Altered Properties" for the positions in question. Suitable assays are described in the "Methods" section below.

Wash Performance

Important positions and mutations with respect to obtaining variants with improved wash performance at especially high pH (i.e., pH 8.5-11) include the specific mutations/substitutions listed above in the section "Altered Properties" for the positions in question. The wash performance may be tested as described below in the "Methods" section.

Starch Liquifaction

Some mutations have the effect of reducing the viscosity of a starch composition compared that observed using a "wild-type" α-amylase, such as SPEZYME® Extra. Exemplary mutations include a substitution that introduces one or more of the amino acid residues selected from the group consisting of I181A, I181P, I181C, I181E, I181Y, S242A, S242E, S242Q, G132A, N193Y, and E188P.

Other Mutations in Variants

In some embodiments, the present variants include one or more modifications in addition to those outlined above. For example, it may be advantageous that one or more proline residues is replaced with a non-proline residue. Exemplary non-proline residues include alanine, glycine, serine, threonine, valine, and leucine. Similarly, it may be advantageous to replace one or more cysteine residues with a non-cysteine residue. Exemplary non-cysteine residues include serine, alanine, threonine, glycine, valine, and leucine.

Furthermore, it may be advantageous to introduce mutations at one or more of the following positions (using SEQ ID NO: 7 for the numbering): M15, V128, A111, H133, W138, T149, M197, N188, A209, A210, H405, T412, in particular the following single, double or triple or multi mutations:

M15X, in particular M15T,L;
V128X, in particular V128E;
H133X, in particular H133Y;
N188X, in particular N188S,T,P;
M197X, in particular M197T,L;
A209X, in particular A209V;
M197T/W138F; M197T/138Y; M15T/H133Y/N188S;
M15N128E/H133Y/N188S; E119C/S130C; D124C/R127C; H133Y/T149I;
G475R, H133Y/S187D; H133Y/A209V.

In the case of the parent α-amylase having the amino acid sequence shown in SEQ ID NO: 7, relevant amino acid residues which may be deleted or substituted with a view to improving the oxidation stability include the single cysteine residue (C363) and the methionine residues located in positions M8, M9, M96, M200, M206, M284, M307, M311, M316 and M438 in SEQ ID NO: 2.

With respect to increasing the thermal stability of an α-amylase variant relative to its parent α-amylase, it appears to be particularly desirable to delete at least one, and preferably two or even three, of the following amino acid residues in the amino acid sequence shown in SEQ ID NO: 2 are F178, R179, G180, I181, G182 and K183. Particularly valuable pairwise deletions of this type are R179*+G180*; and I181*+G182* (SEQ ID NO. 16 or 15, respectively) (or equivalents of these pairwise deletions in another α-amylase meeting the requirements of a parent α-amylase in the context of the present disclosure).

Other mutations of interest include N193F and V416G, as exemplified in the amino acid sequence shown as SEQ ID NO: 2.

V. Methods of Preparing α-amylase Variants

Several methods for introducing mutations into genes are known in the art. After a brief discussion of the cloning of α-amylase-encoding DNA sequences, methods for generating mutations at specific sites within the α-amylase-encoding sequence will be discussed.

A. Cloning and Expression of Nucleic Acids Encoding an α-amylase

The DNA sequence encoding a parent α-amylase may be isolated from any cell or microorganism producing the α-amylase in question, using various methods well known in the art. First, a genomic DNA and/or cDNA library should be constructed using chromosomal DNA or messenger RNA from the organism that produces the α-amylase to be studied. Then, if the amino acid sequence of the α-amylase is known, homologous, labelled oligonucleotide probes may be synthesized and used to identify α-amylase-encoding clones from a genomic library prepared from the organism in question. Alternatively, a labelled oligonucleotide probe containing sequences homologous to a known α-amylase gene could be used as a probe to identify α-amylase-encoding clones, using hybridization and washing conditions of lower stringency.

Another method for identifying α-amylase-encoding clones would involve inserting fragments of genomic DNA into an expression vector, such as a plasmid, transforming α-amylase-negative bacteria with the resulting genomic DNA library, and then plating the transformed bacteria onto agar containing a substrate for α-amylase, thereby allowing clones expressing the α-amylase to be identified.

Alternatively, the DNA sequence encoding the enzyme may be prepared synthetically by established standard methods, e.g. the phosphoamidite method described by S. L. Beaucage and M. H. Caruthers (1981) or the method described by Matthes et al. (1984). In the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202.

B. Site-Directed Mutagenesis

Once an α-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the α-amylase-encoding sequence, is created in a vector carrying the α-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase.

Another method of introducing mutations into α-amylase-encoding DNA sequences involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Alternative methods for providing variants include gene shuffling, e.g., as described in WO 95/22625 (from Affymax Technologies N.V.) or in WO 96/00343 (from Novo Nordisk A/S), or other corresponding techniques resulting in a hybrid enzyme comprising the mutation(s), e.g., substitution(s) and/or deletion(s), in question.

C. Expression of α-amylase Variants

A DNA sequence encoding a variant produced by methods described above, or by alternative methods, can be expressed using an expression vector, which typically includes control sequences encoding a promoter, operator, ribosome binding site, translation initiation signal, and, optionally, a repressor gene or various activator genes.

The recombinant expression vector carrying the DNA sequence encoding an α-amylase variant may be any vector, which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

The DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an α-amylase variant, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *G. stearothermophilus* maltogenic amylase gene (amyM), the promoters of the *B. amyloliquefaciens* α-amylase (amyQ), the promoters of the *B. subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector may also comprise a suitable transcription terminator and, in eukaryotes, polyadenylation sequences operably connected to the DNA sequence encoding an α-amylase variant. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* α-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct encoding an α-amylase variant, the promoter, terminator and other elements, respectively, and to insert them into suitable vectors containing the information necessary for replication, are well known to persons skilled in the art (e.g., Sambrook et al., Molecular Cloning: A Laboratory Manual, 2nd Ed., Cold Spring Harbor, 1989).

The cell comprising a DNA construct or an expression vector is advantageously used as a host cell in the recombinant production of an α-amylase variant. The cell may be transformed with the DNA construct encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell may be a cell of a higher organism such as a mammal or an insect, but is preferably a microbial cell, e.g., a bacterial or a fungal (including yeast) cell.

Examples of suitable bacteria are Gram-positive bacteria such as *Bacillus subtilis, Bacillus licheniformis, Bacillus lentus, Bacillus brevis, Geobacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus*, or gram-negative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*. The filamentous fungus may advantageously belong to a species of *Aspergillus*, e.g., *A. oryzae* or *A. niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

An aspect of the present compositions and methods relates producing an α-amylase variant by cultivating a host cell under conditions conducive to the production of the variant amylase and recovering the variant amylase from the cells and/or culture medium. The medium used to cultivate the cells may be any conventional medium suitable for growing the host cell in question and obtaining expression of the α-amylase variant. Suitable media are available from commercial suppliers or may be prepared according to published recipes (e.g., as described in catalogues of the ATCC).

The α-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

VI. Industrial Applications

The present variant α-amylases possess valuable properties allowing for a variety of industrial applications. For example, the variants may be used for starch processesing/conversion, e.g., for starch liquefaction (see, e.g., U.S. Pat. No. 3,912,590, EP patent application nos. 252 730 and 63 909, WO 99/19467, and WO 96/28567 all references hereby incorporated by reference). The variants may further be useful in the production of sweeteners and ethanol (see, e.g., U.S. Pat. No. 5,231,017 hereby incorporated by reference), such as fuel, drinking and industrial ethanol, from starch or whole grains. The variants may further be useful for beer making or brewing. The variants may be in the form of compositions, which may further include, e.g., a glucoamylase, a pullulanase, and another α-amylase, in addition to suitable buffers, stabilizing agents, preservatives, and the like.

The amylase variants are also useful in laundry and dishwashing and hard surface cleaning, as components of detergent compositions. The variants may also be useful for desizing of textiles, fabrics and garments (see, e.g., WO 95/21247, U.S. Pat. No. 4,643,736, EP 119,920 hereby incorporated by reference), and in pulp and paper production.

These and other uses of the present compositions and methods are described in more detail, below.

A. Grain Processing and Starch Conversion Applications

Grain processing and starch conversion applications are divided into two catagories, namely (1) general starch conversion, which covers the conversion of starch into, e.g., maltodextrins, dextrose syrup, and high fructose syrup, (2) ethanol production, and (3) bearmaking. Although many steps involved in these processes are the similar, they are described separately. In some cases, the variant α-amylase is used in combination with a phytase (4). Compositions for performing these applications are also described (5).

1. General Starch Conversion

Conventional starch-conversion processes, such as liquefaction and saccharification processes are described, e.g., in U.S. Pat. No. 3,912,590 and EP patent publications Nos. 252,730 and 63,909, hereby incorporated by reference. Generally, the starch conversion process degrades starch to lower molecular weight carbohydrate components. In the case of converting starch into a sugar, the starch is depolymerized in a process involving of a pre-treatment step and two or three consecutive process steps, i.e., a liquefaction process, a saccharification process, and depending on the desired end product, and optional isomerization process.

a. Pre-Treatment of Native/Raw Starch

Native/raw starch consists of microscopic granules, which are insoluble in water at room temperature. When an aqueous starch slurry is heated, the granules swell and eventually burst, dispersing the starch molecules into the solution. During this "gelatinization" process, there is a dramatic increase in viscosity. As the solids level is 30-40% in a typical industrial process, the starch has to be thinned or "liquefied" so that it can be handled. This reduction in viscosity is conventionally obtained by enzymatic degradation.

b. Liquefaction

During the liquefaction step, long-chained starch molecules are degraded into shorter branched and linear molecules (maltodextrins) by an α-amylase. The liquefaction process is generally carried out at about 105-110° C. for about 5 to 10 minutes followed by 1-2 hours at 95° C. The pH is typically between about 5.5 and 6.2. To ensure optimal enzyme stability under these conditions, 1 mM of calcium is typically added (40 ppm free calcium ions). After this treatment the liquefied starch will have a "dextrose equivalent" (DE) of 10-15.

c. Saccharification

After the liquefaction process, the maltodextrins are converted into dextrose by addition of a glucoamylase (e.g., OPTIDEX® L-400) and a debranching enzyme, such as an isoamylase (U.S. Pat. No. 4,335,208) or a pullulanase. Before this step the pH is reduced to a value below about 4.5, while maintaining the high temperature (above 95° C.), to inactivate the liquefying α-amylase to reduce the formation of short oligosaccharides called "panose precursors" which cannot be hydrolyzed properly by the debranching enzyme. The temperature is lowered to 60° C., and glucoamylase and debranching enzyme are added. The saccharification process proceeds for 24-72 hours.

Normally, when denaturing the α-amylase after the liquefaction step, about 0.2-0.5% of the saccharification product is the branched trisaccharide Glc pα1-6Glc pα1-4Glc (panose) which cannot be degraded by a pullulanase. If active amylase from the liquefaction step is present during saccharification (i.e., no denaturing), this level can be as high as 1-2%, which is highly undesirable as it lowers the saccharification yield significantly.

d. Isomerization

When the desired final sugar product is, e.g., high fructose syrup the dextrose syrup may be converted into fructose. After the saccharification process, the pH is increased to a value in the range of about 6-8, preferably pH 7.5, and the calcium is removed by ion exchange. The dextrose syrup is then converted into high fructose syrup using, e.g., an immmobilized glucose isomerase (such as GENSWEET® IGI-HF).

2. Ethanol Production

In general alcohol production (ethanol) from whole grain can be separated into 4 main steps, i.e, (a) milling, (b) liquefaction, (c) saccharification, and (d) fermentation. Some of these steps are similar to those described, above.

a. Milling and Slurry Production

A starch-containing substrate, such as grain, corn, milo, or the like, is milled in order to open up the structure and allow for further processing. The two processes used are generally referred to as wet or dry milling. In dry milling, the whole kernel is milled and used in the remaining part of the process. Wet milling gives a very good separation of germ and meal (starch granules and protein) and is with a few exceptions applied at locations where there is a parallel production of syrups.

The milled starch-containing material is be combined with water and recycled thin-stillage resulting in an aqueous slurry. The slurry will comprise between 15 to 55% ds w/w (e.g., 20 to 50%, 25 to 50%, 25 to 45%, 25 to 40%, 20 to 35% and 30-36% ds). The recycled thin-stillage (backset) is typically in the range of 10 to 70% v/v (e.g., 10 to 60%, 10 to 50%, 10 to 40%, 10 to 30%, 10 to 20%, 20 to 60%, 20 to 50%, 20 to 40% and also 20 to 30%). 25 to 40% ds is fairly common.

Once the milled starch-containing material is combined with water and backset, the pH is generally not adjusted in the slurry. Further, the pH is not adjusted after the addition of phytase (see below) and α amylase to the slurry. The pH of the slurry will typically be in the range of pH 4.5 to less than 6.0 (e.g., pH 4.5 to 5.8, pH 4.5 to 5.6, pH 4.8 to 5.8, pH 5.0 to 5.8, pH 5.0 to 5.4, pH 5.2 to 5.5 and pH 5.2 to 5.9). The pH of the slurry may be between pH 4.5 and 5.2 depending on the amount of thin stillage added to the slurry and the type of material comprising the thin stillage. For example, the pH of the thin stillage may be between pH 3.8 and pH 4.5. Table B illustrates the pH change that occurs with addition of increasing amounts of thin stillage to a whole ground corn slurry (32% ds) after stirring for 2 hours at 155° F.

TABLE B pH change that occurs with addition of increasing amounts of thin stillage

| Thin stillage w/w % | Final pH |
|---|---|
| 0 | 5.52 |
| 20 | 5.29 |
| 40 | 5.16 |
| 50 | 5.09 |
| 60 | 5.05 |
| 80 | 4.98 |
| 100 | 4.94 |

It should be mentioned that during ethanol production, acids can be added to lower the pH in the beer well to reduce the risk of microbial contamination prior to distillation.

In some cases, phytase is added to the slurry. Phytases are described in more detail, below. In some cases, an α-amylase is added to the slurry. In some cases, a phytase and an α amylase are added to the slurry sequentially. In some cases, a phytase and an α-amylase are added simultaneously. In some cases, the slurry comprising the phytase and α-amylase are incubated (pretreated) for a period of 5 minutes to 8 hours (e.g., 5 minutes to 6 hours, 5 minutes to 4 hours 5 minutes to 2 hours, and 15 minutes to 4 hours). In other cases the slurry are incubated at a temperature in the range of 40 to 115° C., (e.g. 45 to 80° C., 50 to 70° C., 50 to 75° C., 60 to 110° C., 60 to 95° C., 70 to 110° C., 70 to 85° C. and 77 to 86° C.).

In some cases, the slurry is incubated at a temperature of 0 to 30° C. (e.g., 0 to 25° C., 0 to 20° C., 0 to 15° C., 0 to 10° C. and 0 to 5° C.) below the starch geltinization temperature of the starch-containing material. In some cases, the temperature is below 68° C., below 65° C., below 62° C., below 60° C., or even below 55° C. In some embodiments, the temperature is above 45° C., above 50° C., above 55° C., and even above 60° C. Incubation of the slurry comprising a phytase and an α-amylase at a temperature below the starch gelatinization temperature may be referred to as a primary (1°) liquefaction.

Currently, it is believed that commercially available microbial α-amylases used in the liquefaction process are not sufficiently stable to produce liquefied starch substrate from a dry mill process using whole ground grain at a temperature above about 80° C. at a pH less than pH 5.6. Generally, the stability of many commercially available α-amylases is reduced at a pH of less than about 4.0.

b. Liquefaction

In the liquefaction process, the starch granules are solubilized by hydrolysis to maltodextrins mostly of a DP higher than 4. The raw material can be milled whole grain or a side stream from starch processing. Milled and liquefied grain is also known as mash. The hydrolysis may be carried out by acid treatment or enzymatically by α-amylase. Acid hydrolysis is used on a limited basis.

Enzymatic liquefaction is typically carried out as a three-step hot slurry process. The slurry is heated to between 60-95° C. (preferably 77-86° C., 80-85° C., and 83-85° C.) and the enzyme(s) is (are) added. Then the slurry is jet-cooked at between 95-140° C., preferably 105-125° C., cooled to 60-95° C. and more enzyme(s) is (are) added to obtain the final hydrolysis. The liquefaction process is carried out at pH 4.0-6.5, typically at a pH between 5 and 6.

The slurry may be incubated with an α-amylase and, optionally, a phytase (discussed herein) and incubated for 5 minutes to 2 hours, at a temperature range of 60 to 75° C. In a further liquefaction step, the incubated or pretreated starch-containing material may be exposed to an increase in temperature such as 0 to 45° C. above the starch gelatinization temperature of the starch-containing material (e.g., 70° C. to 120° C., 70° C. to 110° C., and 70° C. to 90° C.) for a period of time of 2 minutes to 6 hours (e.g., 2 minutes to 4 hrs, 90 minutes, 140 minutes and 90 to 140 minutes) at a pH of about 4.0 to 5.5 more preferably between 1 hour to 2 hours. The temperature can be increased by a conventional high temperature jet cooking system for a short period of time for example for 1 to 15 minutes. Then the starch maybe further hydrolyzed at a temperature ranging from 75° C. to 95° C., (e.g., 80° C. to 90° C. and 80° C. to 85° C.) for a period of 15 to 150 minutes (e.g., 30 to 120 minutes). The pH may not be adjusted during these process steps and the pH of the liquefied mash is in the range of pH 4.0 to pH 5.8 (e.g., pH 4.5 to 5.8, pH 4.8 to 5.4, and pH 5.0 to 5.2). In some embodiments, a second dose of thermostable α amylase will be added to the secondary liquefaction step, but in other embodiments there will not be an additional dosage of α-amylase.

The incubation and liquefaction steps according to the invention may be followed by saccharification and fermentation steps.

c. Fermentation

The fermentable sugars obtained during the liquefaction process steps may be used to produce alcohol, particularly ethanol, via microbial fermentation. The organism used in fermentations will depend on the desired end-product.

Typically if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g. to produce at least 10% ethanol from a substrate having between 25-40% DS in less than 72 hours). Yeast cells are generally supplied in amounts of $10^4$ to $10^{12}$, and preferably from $10^7$ to $10^{10}$ viable yeast count per ml of fermentation broth. The fermentation will include in addition to a fermenting microorganisms (e.g. yeast), nutrients, optionally additional enzymes, including but not limited to phytases. The use of yeast in fermentation is well known and reference is made to THE ALCOHOL TEXTBOOK, K. JACQUES ET AL., EDS. 1999, NOTTINGHAM UNIVERSITY PRESS, UK. Yeast fermentation is usually performed for 24-96 hours, typically 35-60 hours. The temperature of fermentation is usually between 26-34° C., e.g., about 32° C., and the pH is bout 3-6, preferably around 4-5.

By using appropriate fermenting microorganisms, other end products may be obtained, including without limitation, glycerol, 1,3-propanediol, gluconate, 2-keto-D-gluconate, 2,5-diketo-D-gluconate, 2-keto-L-gulonic acid, succinic acid, lactic acid, amino acids and derivatives thereof. For example, when lactic acid is the desired end product, a *Lactobacillus* sp. (*L. casei*) may be used. When glycerol or 1,3-propanediol are the desired end-products *E. coli* may be used. When 2-keto-D-gluconate, 2,5-diketo-D-gluconate, and 2-keto-L-gulonic acid are the desired end products, *Pantoea citrea* may be used.

d. Saccharification and SSF

Liquefied starch-containing material is saccharified in the presence of saccharifying enzymes such as glucoamylases. The saccharification process may last for 12 hours to 120 hours (e.g. 12 to 90 hours, 12 to 60 hours and 12 to 48 hours). However, it is common to perform a pre-saccharification step for about 30 minutes to 2 hours (e.g., 30 to 90 minutes) in a temperature range of 30 to 65° C., typically above 50° C. and often around 60° C., which is followed by a complete saccharification during fermentation. This latter step may be referred to as simultaneous saccharification and fermentation (SSF). SSF is common in ethanol production, where the saccharifying enzymes and fermenting organisms (e.g., yeast) are added together and then carried out at a temperature of 30° C. to 40° C. and at a pH between 4.2-4.8, preferably pH 4.5.

Fermentable sugars (e.g., dextrins, monosaccharides, particularly glucose) are produced from enzymatic saccharification. These fermentable sugars may be further purified and/or converted to useful sugar products. In addition the sugars may be used as a fermentation feedstock in a microbial fermentation process for producing end-products, such as alcohol (e.g., ethanol and butanol), organic acids (e.g., succinic acid and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

e. Distillation

Optionally, following fermentation, alcohol (e.g., ethanol) may be recovered by distillation. The yield of ethanol is typically at least 8%, at least 10%, at least 12%, at least 14%, at least 15%, at least 16%, at least 17%, at least 18% (v/v), and is some cases, at least 19%, at least 20%, at least 21%, at least 22%, and even at least 23% (v/v). The ethanol obtained may be used as, for example, fuel ethanol, drinking ethanol, i.e., potable neutral spirits, or industrial ethanol.

f. By-Products

Left over from the fermentation process is the spent grain, which is typically used in animal feed either in liquid form or dried. The spent grain may take the form of so-called "fermentation co-products" such as distillers dried grains (DDG) and distiller's dried grain plus solubles (DDGS), which may also be used in animal feed.

3. Beer Making

The present variant α-amylases may be useful in a beer-making process. Typically, the α-amylases are added during the mashing process, where their advantages, in terms of stability, specific activity, and the like, are realized as in the case of starch conversion.

4. Use of Variant α-amylases in Combination with a Other Enzymes

In all aspects of liquefaction, saccharification, SSF, and carbohydrate processing, generally, the present variant α-amylase polypeptides can be used in combination with one or more addition enzymes, for example, an additional α-amylase, a glucoamylase, an iso-amylase, a β-amylase, a maltogenic amylase, a protease, a lipase, a peroxidase, an esterase, an oxidase, a pectinase, a pectine lyase, a cutinase, a laccase, and/or a phytase. Many of these enzymes are described in more detail with respect to cleaning applications.

Phytases are enzymes capable of breaking down phytic acid (phytate) found in grains and oil seeds. Phytate, as well as intermediates in it degradation, are believed to destabilize or otherwise adversely affect α-amylases, thereby reducing their efficiency.

Phytases that can be used in combination with variant α-amylases are capable of hydrolyzing phytic acid under the defined conditions of the incubation and liquefaction steps. In some embodiments, the phytase is capable of liberating at least one inorganic phosphate from an inositol hexaphosphate (phytic acid). Phytases can be grouped according to their preference for a specific position of the phosphate ester group on the phytate molecule at which hydrolysis is initiated, (e.g., as 3-phytases (EC 3.1.3.8) or as 6-phytases (EC 3.1.3.26)). A typical example of phytase is myo-inositol-hexakiphosphate-3-phosphohydrolase.

Phytases can be obtained from microorganisms such as fungal and bacterial organisms. Some of these microorganisms include e.g. *Aspergillus* (e.g., *A. niger, A. terreus, A. ficum* and *A. fumigatus*), *Myceliophthora* (*M. thermophila*), *Talaromyces* (*T. thermophilus*) *Trichoderma* spp (*T. reesei*). and *Thermomyces* (WO 99/49740). Also phytases are available from *Penicillium* species, e.g., *P. hordei* (ATCC No. 22053), *P. piceum* (ATCC No. 10519), or *P. brevi-compactum* (ATCC No. 48944). See, for example U.S. Pat. No. 6,475, 762. In addition, phytases are available from *Bacillus* (e.g., *B. subtilis, Pseudomonas, Peniophora, E. coli, Citrobacter, Enterbacter* and *Buttiauxella* (see WO2006/043178).

Commercial phytases are available such as NATUPHOS® (BASF), RONOZYME® P (Novozymes A/S), PHZYME® (Danisco A/S, Diversa) and FINASE® (AB Enzymes). The method for determining microbial phytase activity and the definition of a phytase unit has been published by Engelen et al. (1994) *J. AOAC Int.* 77:760-764. The phytase may be a wild-type phytase, a variant or fragment thereof.

Exemplary phytases are derived from species of the bacterium *Buttiauxiella*. *Buttiauxiella* spp. includes *B. agrestis, B. brennerae, B. ferragutiase, B. gaviniae, B. izardii, B. noackiae,* and *B. warmboldiae*. Strains of *Buttiauxella* species are available from DSMZ, the German National Resource Center for Biological Material (Inhoffenstrabe 7B, 38124 Braunschweig, Del.). *Buttiauxella* sp. strain P1-29 deposited under accession number NCIMB 41248 is an example of a particularly useful strain from which a phytase may be obtained. The phytase may be BP-wild type, a variant thereof (such as BP-11) described in WO 06/043178, or a variant as described in U.S. Patent Pub. No. US20080220498, filed Mar. 6, 2007 (see, e.g., Table 1 and SEQ ID NO: 3).

The phytase may also be the BP-17 variant of *Buttiauxiella* phytase, having the amino acid sequence of SEQ ID NO: 19, shown below, or a phytase having at least 75%, at least 80%, at least 85%, at least 88%, at least 90%, at least 91%, at least 92%, at least 93%, at least 94%, at least 95%, at least 96%, at least 97%, at least 98% and even at least 99% sequence identity to the amino acid sequence set forth in SEQ ID NO: 19.

```
                                                (SEQ ID NO: 19)
NDTPASGYQV EKVVILSRHG VRAPTKMTQT MRDVTPNTWP

EWPVKLGYIT PRGEHLISLM GGFYRQKFQQ QGILSQGSCP

TPNSIYVWAD VDQRTLKTGE AFLAGLAPQC GLTIHHQQNL

EKADPLFHPV KAGTCSMDKT QVQQAVEKEA QTPIDNLNQH

YIPFLALMNT TLNFSTSAWC QKHSADKSCD LGLSMPSKLS

IKDNGNKVAL DGAIGLSSTL AEIFLLEYAQ GMPQAAWGNI

HSEQEWASLL KLHNVQFDLM ARTPYIARHN GTPLLQAISN

ALNPNATESK LPDISPDNKI LFIAGHDTNI ANIAGMLNMR
```

-continued
```
WTLPGQPDNT PPGGALVFER LADKSGKQYV SVSMVYQTLE

QLRSQTPLSL NQPAGSVQLK IPGCNDQTAE GYCPLSTFTR

VVSQSVEPGC QLQ
```

The amount (dosage) of phytase used in the incubation and/or liquefaction processes may be in the range of about 0.001 to 50 FTU/g ds, (e.g., in the range of about 0.01 to 25 FTU/g ds, about 0.01 to 15 FTU/g ds, about 0.01 to 10 FTU/g ds, about 0.05 to 15 FTU/g ds, and about 0.05 to 5.0 FTU/g.

5. Compositions for Grain Processing and Starch Conversion

One aspect of the present compositions and methods is a composition comprising one or more of the variant α-amylases for use in starch conversion, including general starch conversion, alcohol fermentation, beer making, and the like. Such compositions may include buffers, salts, minerals, stabilizers, preservatives, antimicrobial agents, dyes, fragrances, and the like, selected to protect the variant α-amylase(s) from premature degredation (including proteolysis), to prolong storage, improve appearance, to color-code the composition, and the like.

The compositions may further include additional enzymes relating to starch conversion, including, e.g., glucoamylases and phytases. Particular a glucoamylases are G1 or G2 AMG from *Aspegillis niger*, which is described in Boel et al. (1984) *EMBO J.* 3:1097-1102 or a variant, thereof, as described in WO 00/04136 or WO 01/04273), the AMG from *Talaromyces emersonii*, as described in WO 99/28448, or glucoamylase from *Trichoderma reesei*, as described in WO 06/060062.

B. Pulp and Paper Production

The present variant α-amylases may also be used in the production of lignocellulosic materials, such as pulp, paper and cardboard, from starch reinforced waste paper and cardboard, especially where repulping occurs at pH above 7 and where the amylases facilitate the disintegration of the waste material through degradation of the reinforcing starch. The variant α-amylases are especially useful in a process for producing a papermaking pulp from starch-coated printed-paper. The process may be performed as described in WO 95/14807, comprising the steps of: (a) disintegrating the paper to produce a pulp, (b) treating with a starch-degrading enzyme before, during or after step (a), and (c) separating ink particles from the pulp after steps (a) and (b).

The α-amylases may also be useful where enzymatically modified starch is used in papermaking together with alkaline fillers such as calcium carbonate, kaolin and clays. With the present variant α-amylases, it is possible to modify the starch in the presence of the filler thus allowing for a simpler integrated process.

C. Desizing of Textiles, Fabrics and Garments

The present variant α-amylases may also be useful in textile, fabric or garment desizing. In the textile processing industry, α-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material.

To reduce processing cost and increase mill throughput, the desizing processing is sometimes combined with the scouring and bleaching steps. In such cases, non-enzymatic auxiliaries such as alkali or oxidation agents are used to break down the starch, because traditional α-amylases are not very compatible with high pH levels and bleaching agents. The non-enzymatic breakdown of the starch size leads to some fiber damage because of the rather aggressive chemicals used. Accordingly, it would be desirable to use variant α-amylases that offer improved performance in alkaline solutions. Such variants may be used alone or in combination with a cellulase when desizing cellulose-containing fabric or textile.

Desizing and bleaching processes are well known in the art. For instance, such processes are described in WO 95/21247, U.S. Pat. No. 4,643,736, EP 119,920 hereby incorporated by reference. A current commercially available products for desizing include OPTISIZE® FLEX from Genencor.

D. Cleaning and Detergent Compositions

The present variant α-amylases may be added to, and thus become a component of, a detergent composition. The detergent composition may be formulated as a hand or machine-laundry detergent, including a laundry additive suitable for pretreatment of stained fabrics and a rinse-added fabric softener composition. The detergent composition may also be formulated for hand or machine-dishwashing operations, or for use in general household hard surface cleaning operations. In general the properties of the variant α-amylase should be compatible with the selected detergent in terms of its pH and other enzymatic and non-enzymatic ingredients.

The detergent composition or additive may comprise one or more additional enzymes such as a protease, a lipase, a peroxidase, another amylolytic enzyme (e.g., another α-amylase), a glucoamylase, a maltogenic amylase, a CGTase and/or a cellulase mannanase (such as MANNASTAR™ from Danisco US Inc., Genencor Division)), a pectinase, a pectine lyase, a cutinase, and/or laccase, which are described in more detail, below:

Proteases: Suitable proteases may be derived from any organism, and include chemically modified or engineered variants. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like pro-teases are trypsin (e.g., of porcine or bovine origin) and the *Fusarium* protease described in WO 89/06270 and WO 94/25583.

Examples of useful proteases are the variants described in WO98/23732, WO99/20770, WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include ALCALASE®, SAVINASE®, PRIMASE®, DURALASE®, ESPERASE®, and KANNASE® (from Novozymes A/S), MAXATASE®, MAXACAL, MAXAPEM®, PROPERASE®, PURAFECT®, PURAFECT OXP®, FN2®, FN3®, FN4® (Genencor International Inc.).

Lipases: Suitable lipases include those of bacterial or fungal origin, and include chemically modified or engineered variant. Examples of useful lipases include lipases from *Humicola* (synonym *Thermomyces*), e.g., from *H. Ianuginosa* (*T. Ianuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), *Biochemica* et *Biophysic Acta,* 1131, 253-360), *B. stearothermophilus* (JP 64/744992) or *B. pumilus* (WO 91/16422). Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202. Preferred commercially available lipase enzymes include LIPOLASE™ and LIPOLASE ULTRA™ (Novozymes A/S).

Amylases: One or more additional amylases may also be included. Suitable amylases (α and/or β) include those of bacterial or fungal origin, and include chemically modified or engineered variants. Amylases include, for example, α-amylases obtained from *Bacillus*, e.g., a special strain of *B. licheniformis*, described in more detail in GB 1,296,839. Examples of useful α-amylases are the variants described in WO 94/18314, WO 96/39528, WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available α-amylases are DURAMYL™, LIQUEZYME™, TERMAMY™, NATALASE™, FUNGAMYL™ and BAN™ (Novozymes A/S), RAPIDASE™ and PURASTAR™ (from Genencor).

Cellulases: Suitable cellulases include those of bacterial or fungal origin. Chemically modified or protein engineered mutants are included. Suitable cellulases include cellulases from the genera *Bacillus, Pseudomonas, Trichoderma, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691, 178, U.S. Pat. No. 5,776,757 and WO 89/09259. The *Trichoderma reesei* cellulases are disclosed in U.S. Pat. No. 4,689, 297, U.S. Pat. No. 5,814,501, U.S. Pat. No. 5,324,649, WO 92/06221 and WO 92/06165. *Bacillus* cellulases are disclosed in U.S. Pat. No. 6,562,612. Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases: Suitable peroxidases/oxidases include those of plant, bacterial or fungal origin, and include chemically modified or engineered variants. Examples of useful peroxidases include peroxidases from *Coprinus*, e.g., from *C. cinereus*, and variants thereof as those described in WO 93/24618, WO 95/10602, and WO 98/15257. Commercially available peroxidases include GUARDZYME® (Novozymes A/S).

The detergent enzyme(s) may be included in a detergent composition by adding separate additives containing one or more enzymes, or by adding a combined additive comprising all of these enzymes. A detergent additive can be formulated as a liquid, a slurry, a bar, a tablet, a powder, a granule, a paste, etc. Exemplary detergent additive formulations are non-dusting granulates and stabilized liquids or slurries. A liquid detergent may be aqueous, typically containing up to 70% water and 0-30% organic solvent, or non-aqueous.

Non-dusting granulates may be produced, e.g., as disclosed in U.S. Pat. Nos. 4,106,991 and 4,661,452, and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition typically comprises one or more surfactants, which may be non-ionic (including semi-polar), anionic, cationic, and/or zwitterionic. The surfactants are typically present at a level of from 0.1% to 60% by weight. Exemplary detergent compositions include from about 1% to about 40% of an anionic surfactant such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid or soap, and/or from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent composition may include 0-65% detergent builder or complexing agent such as zeolite, diphosphate, tripho-sphate, phosphonate, carbonate, citrate, nitrilotriacetic acid, ethylenediaminetetraacetic acid, diethylenetri-aminepen-taacetic acid, alkyl- or alkenylsuccinic acid, soluble silicates or layered silicates (e.g. SKS-6 from Hoechst). The detergent composition may include one or more polymers, such as carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent may contain a bleaching system, which may include a $H_2O_2$ source such as perborate or percarbonate which may be combined with a peracid-forming bleach activator such as tetraacetylethylenediamine or nonanoyloxy-ben-zenesul-fonate. Alternatively, the bleaching system may comprise peroxyacids of, e.g., the amide, imide, or sulfone type.

The enzyme(s) of the detergent composition may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent composition may also contain other conventional detergent composition ingredients, such as fabric conditioners, clays, foam boosters, suds suppressors, anti-corrosion agents, soil-suspending agents, anti-soil re-deposition agents, dyes, bactericides, optical brighteners, hydrotropes, tarnish inhibitors, or perfumes.

The variant α-amylase should be present in an effective amount, which can readily be determined using the assays described, herein. As a starting point, it is contemplated that one (or more) variant α-amylases be added in an amount corresponding to 0.01-100 mg of enzyme protein per liter of wash liquor, and preferably about 0.1-1 mg of enzyme protein per liter of wash liquor. An exemplary amount is about 0.055 mg of enzyme protein per liter of wash liquor.

Exemplary dish washing detergent compositions, include the following:

| 1) POWDER AUTOMATIC DISHWASHING COMPOSITION | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

| 2) POWDER AUTOMATIC DISHWASHING COMPOSITION | |
|---|---|
| Nonionic surfactant (e.g., alcohol ethoxylate) | 1-2% |
| Sodium disilicate | 2-30% |
| Sodium carbonate | 10-50% |
| Sodium phosphonate | 0-5% |
| Trisodium citrate dihydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g., maleic acid/acrylic acid copolymer) | 6-25% |
| Enzymes | 0.0001-0.1% |
| Perfume | 0.1-0.5% |
| Water | 5-10% |

| 3) POWDER AUTOMATIC DISHWASHING COMPOSITION | |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

| 4) POWDER AUTOMATIC DISHWASHING COMPOSITION | |
|---|---|
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) Polymer | 0-3% |
| | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

| 5) POWDER AUTOMATIC DISHWASHING COMPOSITION | |
| --- | --- |
| Nonionic surfactant | 1-7% |
| Sodium disilicate | 18-30% |
| Trisodium citrate | 10-24% |
| Sodium carbonate | 12-20% |
| Monopersulphate ($2\,KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

| 6) POWDER AND LIQUID DISHWASHING COMPOSITION WITH CLEANING SURFACTANT SYSTEM | |
| --- | --- |
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |

| 7) NON-AQUEOUS LIQUID AUTOMATIC DISHWASHING COMPOSITION | |
| --- | --- |
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

| 8) NON-AQUEOUS LIQUID DISHWASHING COMPOSITION | |
| --- | --- |
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |

| 8) NON-AQUEOUS LIQUID DISHWASHING COMPOSITION | |
| --- | --- |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

| 9) THIXOTROPIC LIQUID AUTOMATIC DISHWASHING COMPOSITION | |
| --- | --- |
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

| 10) LIQUID AUTOMATIC DISHWASHING COMPOSITION | |
| --- | --- |
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

| 11) LIQUID AUTOMATIC DISHWASHING COMPOSITION CONTAINING PROTECTED BLEACH PARTICLES | |
| --- | --- |
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

12) Automatic dishwashing compositions as described in 1), 2), 3), 4), 6) and 10), wherein perborate is replaced by percarbonate.

13) Automatic dishwashing compositions as described in 1)-6) which additionally contain a manganese catalyst. The manganese catalyst may, e.g., be one of the compounds described in "Efficient manganese catalysts for low-temperature bleaching", Nature 369, 1994, pp. 637-639.

VII. Methods for Measuring α-amylase Properties

This section describes basic assays for measuring properties of α-amylases. Additional assays are described in the Examples section.

A. Filter Screening Assays

The following assays may be used to screening of SPEZYME® Xtra-like α-amylase variants having altered stability at high or low pH and/or under $Ca^{2+}$ depleted conditions compared to the parent enzyme and SPEZYME® Xtra-like α-amylase.

1. High pH Filter Assay

*Bacillus* libraries are plated on a sandwich of cellulose acetate (OE 67, Schleicher & Schuell, Dassel, Del.)—and nitrocellulose filters (Protran-Ba 85, Schleicher & Schuell, Dassel, Del.) on TY agar plates with 10 micro g/ml kanamycin at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with glycin-NaOH buffer, pH 8.6-10.6 and incubated at room temperature (can be altered from 10-60° C.) for 15 min. The cellulose acetate filters with colonies are stored on the TY-plates at room temperature until use. After incubation, residual activity is detected on plates containing 1% agarose, 0.2% starch in glycin-NaOH buffer, pH 8.6-10.6. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

2. Low Calcium Filter Assay

*Bacillus* libraries are plated on a sandwich of cellulose acetate (OE 67, Schleicher & Schuell, Dassel, Del.)—and nitrocellulose filters (Protran-Ba 85, Schleicher & Schuell, Dassel, Del.) on TY agar plates with a relevant antibiotic, e.g., kanamycin or chloramphenicol, at 37° C. for at least 21 hours. The cellulose-acetate layer is located on the TY agar plate.

Each filter sandwich is specifically marked with a needle after plating, but before incubation in order to be able to localize positive variants on the filter and the nitrocellulose filter with bound variants is transferred to a container with carbonatelbicarbonate buffer pH 8.5-10 and with different EDTA concentrations (0.001 mM-100 mM). The filters are incubated at room temperature for 1 hour. The cellulose acetate filters with colonies are stored on the TY-plates at room temperature until use. After incubation, residual activity is detected on plates containing 1% agarose, 0.2% starch in carbonatelbicarbonate buffer pH 8.5-10. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

3. Low pH Filter Assay

*Bacillus* libraries are plated on a sandwich of cellulose acetate (OE 67, Schleicher & Schuell, Dassel, Del.)—and nitrocellulose filters (Protran-Ba 85, Schleicher & Schuell, Dasseli, Del.) on TY agar plates with 10 micro g/ml chloramphenicol at 37° C. for at least 21 hours. The cellulose acetate layer is located on the TY agar plate.

Each filter sandwich is specifically marked with a needle after plating, but before incubation in order to be able to localize positive variants on the filter, and the nitrocellulose filter with bound variants is transferred to a container with citrate buffer, pH 4.5 and incubated at 80° C. for 20 minutes (when screening for variants in the wild type backbone) or 85° C. for 60 minutes (when screening for variants of the parent α-amylase). The cellulose acetate filters with colonies are stored on the TY-plates at room temperature until use. After incubation, residual activity is detected on assay plates containing 1% agarose, 0.2% starch in citrate buffer, pH 6.0. The assay plates with nitrocellulose filters are marked the same way as the filter sandwich and incubated for 2 hours at 50° C. After removal of the filters the assay plates are stained with 10% Lugol solution. Starch degrading variants are detected as white spots on dark blue background and then identified on the storage plates. Positive variants are re-screened twice under the same conditions as the first screen.

3. Secondary Screening

Positive transformants after rescreening are picked from the storage plate and tested in a secondary plate assay. Positive transformants are grown for 22 hours at 37° C. in 5 ml LB+chloramphenicol. The *Bacillus* culture of each positive transformant and as a control a clone expressing the corresponding backbone are incubated in citrate buffer, pH 4.5 at 90° C. and samples are taken at 0, 10, 20, 30, 40, 60 and 80 minutes. A 3 µL sample is spotted on an assay plate. The assay plate is stained with 10% Lugol solution. Improved variants are seen as variants with higher residual activity (detected as halos on the assay plate) than the backbone. The improved variants are determined by nucleotide sequencing.

B. Stability Assay of Unpurified Variants

The stability of the variants may be assayed as follows: *Bacillus* cultures expressing the variants to be analyzed are grown for 21 hours at 37° C. in 10 ml LB+chloramphenicol. 800 µL culture is mixed with 200 µL citrate buffer, pH 4.5. A number of 70 µL aliquots corresponding to the number of sample time points are made in PCR tubes and incubated at 70° C. or 90° C. for various time points (typically 5, 10, 15, 20, 25 and 30 minutes) in a PCR machine. The 0 min sample is not incubated at high temperature. Activity in the sample is measured by transferring 20 µL to 200 µL of the α-amylase PNP-$G_7$ substrate MPR3 ((Boehringer Mannheim Cat. no. 1660730) as described below under "Assays for α-Amylase Activity". Results are plotted as percentage activity (relative to the 0 time point) versus time, or stated as percentage residual activity after incubation for a certain period of time.

C. Fermentation and Purification of α-Amylase Variants

A *B. subtilis* strain harboring the relevant expression plasmid may be fermented and purified as follows: The strain is streaked on a LB-agar plate with 10 µg/ml kanamycin from −80° C. stock, and grown overnight at 37° C. The colonies are transferred to 100 ml PS-1 media supplemented with 10 micro g/ml chloamphinicol in a 500 ml shaking flask. The culture is shaken at 37° C. at 270 rpm for 5 days.

| Composition of PS-1 medium: | |
|---|---|
| Pearl sugar | 100 g/l |
| Soy Bean Meal | 40 g/l |
| Na$_2$HPO$_4$, 12 H$_2$O | 10 g/l |
| Pluronic ™ PE 6100 | 0.1 g/l |
| CaCO$_3$ | 5 g/l |

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10,000 MW cut-off membrane) and the buffer is changed to 20 mM Acetate pH 5.5. The UF-filtrate is applied on an S-sepharose FF column and elution is carried out by step elution with 0.2 M NaCl in the same buffer. The eluate is dialysed against 10 mM Tris, pH 9.0 and applied on a Q-sepharose FF column and eluted with a linear gradient from 0-0.3 M NaCl over 6 column-volumes. The fractions that contain the activity (measured by the Phadebas assay) are pooled, pH was adjusted to pH 7.5 and remaining color was removed by a treatment with 0.5% w/vol. activated charcoal for 5 minutes.

D. Specific Activity Determination

The specific activity is determined using the PHADEBAS® assay (Pharmacia) as activity/mg enzyme. The manufactures instructions are followed (see also below under "Assay for α-Amylase Activity).

E. Determination of Isoelectric Point

The pI is determined by isoelectric focusing (e.g., Pharmacia, Ampholine, pH 3.5-9.3).

F. Stability Determination

The amylase stability may be measured using the method as follows:

The enzyme is incubated under the relevant conditions. Samples are taken at various time points, e.g., after 0, 5, 10, 15 and 30 minutes and diluted 25 times (same dilution for all taken samples) in assay buffer (50 mM Britton buffer pH 7.3) and the activity is measured using the Phadebas assay (Pharmacia) under standard conditions pH 7.3, 37° C.

The activity measured before incubation (0 minutes) is used as reference (100%). The decline in percent is calculated as a function of the incubation time. The table shows the residual activity after, e.g., 30 minutes of incubation.

G. Assays for α-Amylase Activity

1. PHADEBAS® Assay

α-amylase activity is determined by a method employing PHADEBAS® tablets as substrate. Phadebas tablets (PHADEBAS® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric add, 50 mM boricacid, 0.1 mM CaCl$_2$, pH adjusted to the value of interest with NaOH). The test is performed in a water bath at the temperature of interest. The α-amylase to be tested is diluted in x ml of 50 mM Britton-Robinson buffer. 1 ml of this α-amylase solution is added to the 5 ml 50 mM Britton-Robinson buffer. The starch is hydrolyzed by the α-amylase giving soluble blue fragments. The absorbance of the resulting blue solution, measured spectrophotometrically at 620 nm, is a function of the α-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given α-amylase will hydrolyze a certain amount of substrate and a blue color will be produced. The color intensity is measured at 620 nm. The measured absorbance is directly proportional to the specific activity (activity/mg of pure α-amylase protein) of the α-amylase in question under the given set of conditions.

2. Alternative Method

α-amylase activity is determined by a method employing the PNP-G$_7$ substrate. PNP-G$_7$ which is a abbreviation for p-nitrophenyl-α, D-maltoheptaoside is a blocked oligosaccharide which can be cleaved by an endo-amylase. Following the cleavage, the α-Glucosidase included in the kit digest the substrate to liberate a free PNP molecule which has a yellow color and thus can be measured by visible spectophometry at λ=405 nm (400-420 nm). Kits containing PNP-G$_7$ substrate and α-Glucosidase is manufactured by Boehringer-Mannheim (cat. No. 1054635).

To prepare the reagent solution 10 ml of substrate/buffer solution is added to 50 ml enzyme/buffer solution as recommended by the manufacturer. The assay is performed by transferring 20 μL sample to a 96 well microtitre plate and incubating at 25° C. 200 μL reagent solution pre-equilibrated to 25° C. is added. The solution is mixed and pre-incubated 1 minute and absorption is measured every 30 seconds over 4 minutes at OD 405 nm in an ELISA reader.

The slope of the time dependent absorption-curve is directly proportional to the activity of the α-amylase in question under the given set of conditions.

H. Determination of LAS Sensitivity

The variant is incubated with different concentrations of LAS (linear alkyl benzene sulphonate; Nansa 1169/P) for 10 minutes at 40° C. The residual activity is determined using the PHADEBAS® assay method or the alternative method employing the PNP-G$_7$ substrate. LAS is diluted in 0.1 M phosphate buffer pH 7.5. The following concentrations are used: 500 ppm, 250 ppm, 100 ppm, 50 ppm, 25 ppm, and 10 ppm on no LAS.

The variant is diluted in the different LAS buffers to concentration of 0.01-5 mg/l in a total volume of 10 ml and incubated for 10 minutes in a temperature controlled water bath. The incubation is stopped by transferring a small aliquot into cold assay buffer. It is important that during activity measurement the LAS concentration is below 1 ppm, in order not to affect the activity measurement.

Then the residual activity is determined in duplicate using the above mentioned PHADEBAS® assay or alternative method. The activity is measured after subtraction of the blank. The activity with no LAS is 100%.

G. Determination of Phytase Activity (FTU)

Phytase activity (FTU) is measured by the release of inorganic phosphate. The inorganic phosphate forms a yellow complex with acidic molybdate/vanadate reagent and the yellow complex is measured at a wavelength of 415 nm in a spectrophotometer and the released inorganic phosphate is quantified with a phosphate standard curve. One unit of phytase (FTU) is the amount of enzyme that releases 1 micromole of inorganic phosphate from phytate per minute under the reaction conditions given in the European Standard (CEN/TC 327,2005-TC327WI 003270XX).

H. Determination of Phytic Acid Content

To determine phytic acid content, phytic acid was extracted from sample by adjusting the pH of the 5% slurry (if it is dry sample) to pH 10 and then determined by an HPLC method using an ion exchange column. Phytic acid was eluted from the column using a NaOH gradient system. Phytic acid content in the liquid was then calculated by comparing to a phytic acid standard.

The present compositions and methods are described in further detail in the following examples which are not in any way intended to be limiting in scope. All references cited are herein specifically incorporated by reference for all that is described therein.

EXAMPLES

In the disclosure and experimental section which follows, the following abbreviations apply: wt % (weight percent); ° C. (degrees Centigrade); H$_2$O (water); dH$_2$O (deionized water); dIH$_2$O (deionized water, Milli-Q filtration); g or gm (grams); μg (micrograms); mg (milligrams); kg (kilograms); μL and μt (microliters); mL and ml (milliliters); mm (millimeters); μm (micrometer); M (molar); mM (millimolar); μM (micromolar); U (units); MW (molecular weight); sec (seconds); min(s) (minute/minutes); hr(s) (hour/hours); DO (dissolved oxygen); W/V (weight to volume); W/W (weight to weight); V/V (volume to volume); IKA (IKA Works Inc. 2635 North Chase Parkway SE, Wilmington, N.C.); Genencor (Danisco US Inc, Genencor Division, Palo Alto, Calif.); Ncm (Newton centimeter) and ETOH (ethanol). eq (equivalents); N (Normal); ds or DS (dry solids content), SAPU (spectrophotometric acid protease unit, wherein in 1 SAPU is the amount of protease enzyme activity that liberates one micromole of tyrosine per minute from a casein substrate under conditions of the assay) and GAU (glucoamylase unit, which is defined as the amount of enzyme that will produce 1 g of reducing sugar calculated as glucose per hour from a soluble starch substrate at pH 4.2 and 60° C.).

Example 1

Construction of Variants

Variants in the mature sequence of AmyS were constructed using a site directed approach. For example, position S242 variants were constructed as follows:

The template for mutagenesis was methylated pHPLT-AmyS (see FIG. 2) using dam-Methylase from New England Biolabs (Massachusetts). Degenerate primers (S242F(orward) and S242R(everse), given below) were synthesized and diluted to 10 μM at Operon (Huntsville, Ala.) with complementary forward and reverse sequences both containing a 5' phosphate for ligation in the reaction. The sequence of the parent α-amylase is shown as SEQ ID NO: 2. Libraries were created with the Stratagene QUIK-CHANGE™ Multi-site kit (Stratagene, La Jolla Calif.) using oligonucleotide primers randomized with NN(G/C) at the target position. The selected amino acid (e.g., S242) was randomly replaced with all 19 possible alternatives.

S242 Primers for Mutagenesis:

S242 F:
SEQ ID NO: 17
5'-[Phos]GTCAAGCATATTAAGTTCNNSTTTTTTCCTGATTGGTT
G-3'

S242 R:
SEQ ID NO: 18
5'-[Phos]CAACCAATCAGGAAAAAASNNGAACTTAATATGCTTGA
C-3'

The reaction was performed as follows:
Quik-Change Reaction:

The reaction consisted of 18 μL of sterile distilled H$_2$O, 2.5 μL of 10× buffer from the kit, 1 μL dNTPs from the kit, 1.25 μL of the forward primers (of 10 uM stock), 1.25 μL of the reverse primers (of 10 uM stock), 1 μL of pHPLT-AmyS plasmid DNA as template (~70 ng), and 1 μL of the enzyme blend from the kit for a total of 26.5 μL.

Cycling Conditions:

The cycling conditions were 95° C. for 1 min once, then 95° C. for 1 min, 55° C. for 1 min, 65° C. for 10 min for 25 cycles. One μL Dpn I (10 U/μL) was added to the Multi-site Quik-Change reaction mixture and incubated at 37° C. for 18 hours and then another 0.5 μl was added for an additional 3 hours.

One μL of DpnI digested reaction was used as template for rolling circle amplification with the Templiphi amplification kit (Amersham Biosciences, Piscataway, N.J.) and the reaction was performed according to the Amersham protocol. One μL of rolling circle DNA was transformed into 100 μL of *Bacillus subtilis* competent cells (two protease deleted *B. subtilis* strain (ΔaprE, ΔnprE, amyE::xylRPxylAcomK-phleo)) and shaken at 37° C. for 1 hour. The entire transformation was next plated on LA+10 ppm Neo+1% insoluble starch plates (25 μL one plate, 75 μL on another plate) and incubated overnight at 37° C. 96 transformants were picked into 150 μL of LB+10 ppm Neo in a micro-titer plate and grown overnight at 37° C. The overnight plate was stamped onto a large LA+10 ppm Neo+1% insoluble starch plate with a 96-pin replicating tool and submitted to Quintara Biosciences (Berkeley, Calif., USA) for colony PCR and sequencing.

After variant sequences were determined, the variants were picked into a 96-well micro-titer plates containing 125 μL of LB+10 ppm Neo, arraying the variants into a quad format with controls. The arrayed micro-titer plate was grown for 6 hours at 37° C. and 250 rpm. Using a replicating tool (Enzyscreen, Leiden, The Netherlands) the micro-titer culture plate was used to inoculate a new micro-titer plate (micro-titer plate and plate lids from Enzyscreen, Leiden, The Netherlands) containing 150 μL of MBD medium for protein expression (G. Vogtentanz et al, A *Bacillus subtilis* fusion protein system to produce soybean Bowman-Birk protease inhibitor, Prot. Expr. & Purif., 55 (2007) 40-52) and supplemented with 5 mM CaCl$_2$ for protein expression. Expression plates were grown for 64 hours at 37 C., 250 rpm, and 70% humidity. Expression cultures were next filtered through a micro-filter plate (0.22 um, Millipore, Billerica, Mass.) and screened for improved thermostability (see Example 3).

AmyS Libraries

Site evaluation libraries were made for the following AmyS variants:

P17, D19, T21, N28, S51, G72, V74, A82, Q86, Q89, A93, W115, D117, P123, S124, D125, N127, I130, G132, Q135, P145, G146, G148A, S153A, Y159, W166, S169, K171, R179, G180, I181, G182, K183, W187, G194, P209, N224, S242, P245, G256, D269, N271, T278, N281, G302, A304, R308, T321, Q358, P378, S382, K383, T398, H405, T417, E418, P420, G421, P432, W437, Q443, G446, G454, S457, T459, T461, S464, G474, R483.

Example 2

Expression, Purification, and Characterization of Variants

Colonies were streaked from the microtiter plates from Example 1 and put onto starch plates with 10 ppm Neomycin.

The plates were incubated overnight at 37° C. and singles colonies were picked and used to inoculate shake flasks (250 mL with 25 mL media) containing media (see below) and 20 ppm Neomycin. These were grown up at 37° C., 275 rpm, for about 8 hrs (until an OD (600 nm) of 2.0 was reached). Whereupon the culture broths were mixed with 50% glycerol at 2:1 ratio, put into individually labeled culture vials and frozen at −80° C. It was from these glycerol stocks that subsequent production of the selected amylases were made.

Fermentations for amylases were carried out in 500 mL shake flasks grown at 37° C. for 60 hours in minimal MOPS culture medium (Neidhardt et al., *J. Bacteriol*. (1974) 119(3): 736-747) with 1% (w/v) Soytone. Enzymes were purified from the fermentation broth using hydrophobic interaction chromatography. In brief, the broth were concentrated 10-fold then diluted back with 50 mM MES, 2 mM $CaCl_2$, pH 6.8 with 1M ammonium sulfate and sterile filtered using glass fiber filter. Samples were then load onto phenyl sepharose FF high density column (20×95 mm; Amersham, GE Healthcare Bio-Sciences, Sweden) pre-equilibrated with the same buffer. Non-amlyase proteins were washed off with 10 column volumes of the same buffer without ammonium sulfate followed by 5 column volumes of water. Finally, enzymes of interest were eluted with 50 mM MES, 2 mM $CaCl_2$, pH 6.8 containing 40% propylene glycol.

Protein concentrations were determined either by a standard quantitative SDS page gel densitometry method or by an activity assay using a standard amylase assay kit from Megazyme (Wicklow, Ireland). Assays were converted using a standard curve generated using purified amylase (*Bacillus* 707 amylase; SEQ ID NO: 6).

Example 3

Determination of Altered Properties: Thermal Stress

This example shows that the variants described herein may have an altered property relative to the parent α-amylase. A high throughput thermal stability screen of *G. stearothermophilus* α-amylase (AmyS) variants was carried out.

Heat stress conditions were investigated and chosen such that after the heat stress the starting wild-type enzyme showed approximately 40% of its unstressed activity (i.e., activity after heat stress/activity before heat stress was approximately 0.4). Libraries of mutants were screened in quadruplicate, and potential winners were identified as those that showed residual activity after heat stress that was at least two standard deviations more than the average residual activity of the starting wildtype enzyme.

Amylase expression was approximately 100 ppm in the culture supernatants of the expression plates. After 60-65 hours of growth at 37° C. in a humidified shaker (250 rpm and 70% relative humidity), the culture supernatants were clarified to remove cellular material using filter plates. The clarified supernatants were diluted 10-fold into buffer containing 50 mM NaOAc/2.6 mM $CaCl_2$/0.002% Tween-20, pH 5.8, to a final concentration of approximately 10 ppm. One aliquot of the supernatant was further diluted to 0.02 ppm, and activity of the enzyme variants were determined as described below using a fluorescently-labeled corn starch substrate. A second aliquot of the supernatant was subjected to a 30 minute heat stress at 95° C. in a thermocycler before being diluted to 0.02 ppm in 50 mM NaOAc/2.6 mM $CaCl_2$/0.002% Tween-20, pH 5.8 and assayed for residual activity using the same fluorescent substrate and assay described below.

Amylase activity was determined using the amylase EnzCheck assay essentially as described by the manufacturer (Invitrogen, San Diego Calif.). Final concentration of the amylase in the assay was approximately 0.02 ppm. Assay buffer was 50 mM NaOAc/2.6 mM $CaCl_2$/0.002% Tween-20, pH 5.8. The substrate was BODIPY fluorescence dye conjugated 100 μg/mL DQ™ starch from corn (Invitrogen—Eugene, Oreg.). Increased fluorescence, indicating amylase activity, was measured using a Spectomax M2 (Molecular Devices, Sunnyvale, Calif.). The reaction was monitored at room temperature for 5 minutes with the instrument recording in kinetic mode. Excitation wavelength was 485 nm; emission was monitored at 520 nm with a cutoff filter at 515 nm.

Figure 3:
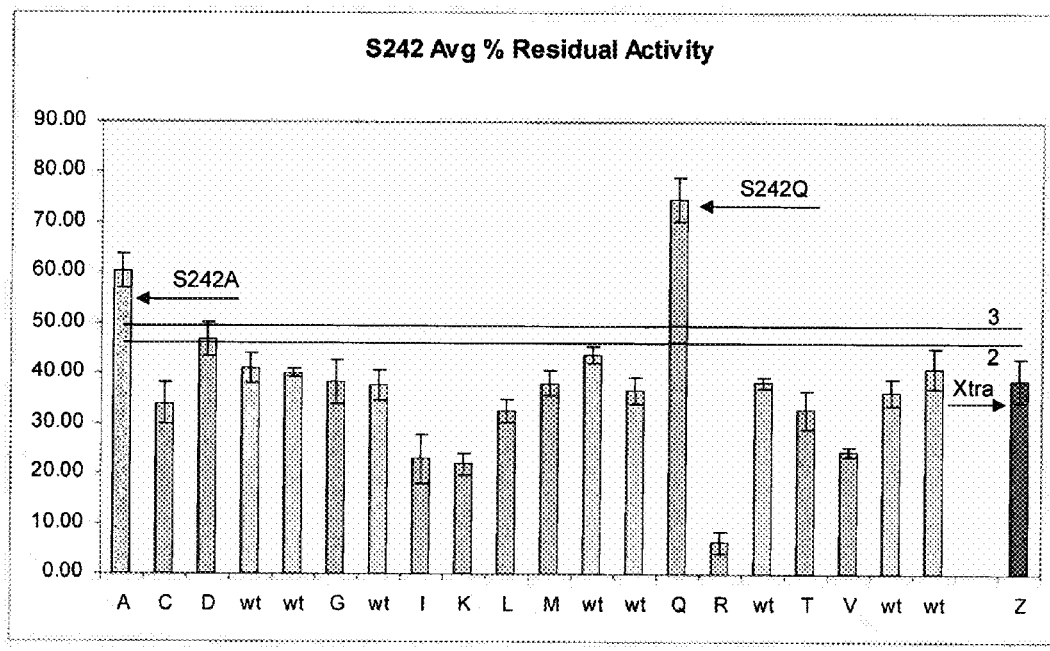
FIG. 3 shows percent residual activity of S242 library variants after heat stress at 95° C. for 30 minutes. Variant positions P, S, W, and Y are missing and are replaced by wild type AmyS (SPEZYME® Xtra-labeled "Z"). Lines indicate 2× and 3× above the standard deviation of the percent residual activity of the wildtype enzyme. S242A and S242Q clearly show higher residual activities than the wild type.

The wild type AmyS (SPEZYME® Xtra) showed 33-43% residual activity after being subject to thermal stress for 30 minutes at 95° C. AmyS variants, S242A and S242Q, retained 55-65% and 70-80% residual activities, respectively, following the same thermal stress conditions. See FIG. 3 and Table 3-1. These residual activity measurements indicate the two variants are more thermostable than the wild type α amylase. Some variants were missing from the libraries and are indicated by position letter within parenthesis marks. In its place, wild type (SPEZYME® Xtra) was placed instead; (WT) indicates the wild type was placed instead. Each plate includes SPEZYME® Xtra (labeled Z) as a control.

TABLE 3-1

Percent residual activities of each variant samples.

| Variants | % Residual Activity | | | | Average | Stdev | % CV |
|---|---|---|---|---|---|---|---|
| A | 60.6 | 59.8 | 56.5 | 64.6 | 60.4 | 3.3 | 5 |
| C | 38.1 | 35.6 | 28.3 | 34.5 | 34.1 | 4.2 | 12 |
| D | 50.6 | 42.9 | 45.0 | 48.7 | 46.8 | 3.5 | 7 |
| (WT) | 45.3 | 38.6 | 39.5 | 40.7 | 41.0 | 3.0 | 7 |
| (WT) | 40.5 | 40.2 | 41.2 | 38.9 | 40.2 | 1.0 | 2 |
| G | 36.4 | 35.7 | 44.8 | 36.7 | 38.4 | 4.3 | 11 |
| (WT) | 34.9 | 36.9 | 37.0 | 42.1 | 37.7 | 3.0 | 8 |
| I | 20.9 | 26.7 | 27.5 | 17.2 | 23.1 | 4.9 | 21 |
| K | 22.6 | 21.5 | 19.3 | 24.5 | 22.0 | 2.2 | 10 |
| L | 34.9 | 30.7 | 34.5 | 30.7 | 32.7 | 2.3 | 7 |
| M | 35.3 | 37.3 | 38.3 | 41.3 | 38.1 | 2.5 | 1 |
| (WT) | 43.9 | 43.2 | 46.0 | 42.2 | 43.8 | 1.6 | 4 |
| (WT) | 33.8 | 35.6 | 40.2 | 37.4 | 36.8 | 2.7 | 7 |
| Q | 80.6 | 71.0 | 75.9 | 71.5 | 74.8 | 4.5 | 6 |
| R | 9.6 | 4.5 | 6.1 | 5.4 | 6.4 | 2.2 | 35 |
| (WT) | 38.6 | 39.9 | 37.2 | 37.3 | 38.3 | 1.3 | 3 |
| T | 36.8 | 31.5 | 35.1 | 27.8 | 32.8 | 4.0 | 12 |
| V | 25.0 | 24.7 | 25.0 | 22.9 | 24.4 | 1.0 | 4 |
| (WT) | 32.7 | 37.5 | 36.3 | 38.8 | 36.3 | 2.6 | 7 |
| (WT) | 37.1 | 42.6 | 46.0 | 38.6 | 41.1 | 4.0 | 10 |
| Z(Xtra) | 38.8 | 41.5 | 42.5 | 32.7 | 38.9 | 4.4 | 11 |

Example 4

Determination of Altered Properties by DSC

SPEZYME® Xtra, S242A and S242Q were purified from shake flask fermentation broth (see Example 2) using hydrophobic interaction chromatography. The protein was eluted from the column in purified form using 50 mM MES, pH 6.8, containing 40% propylene glycol and 2 mM $CaCl_2$.

Figure 5:
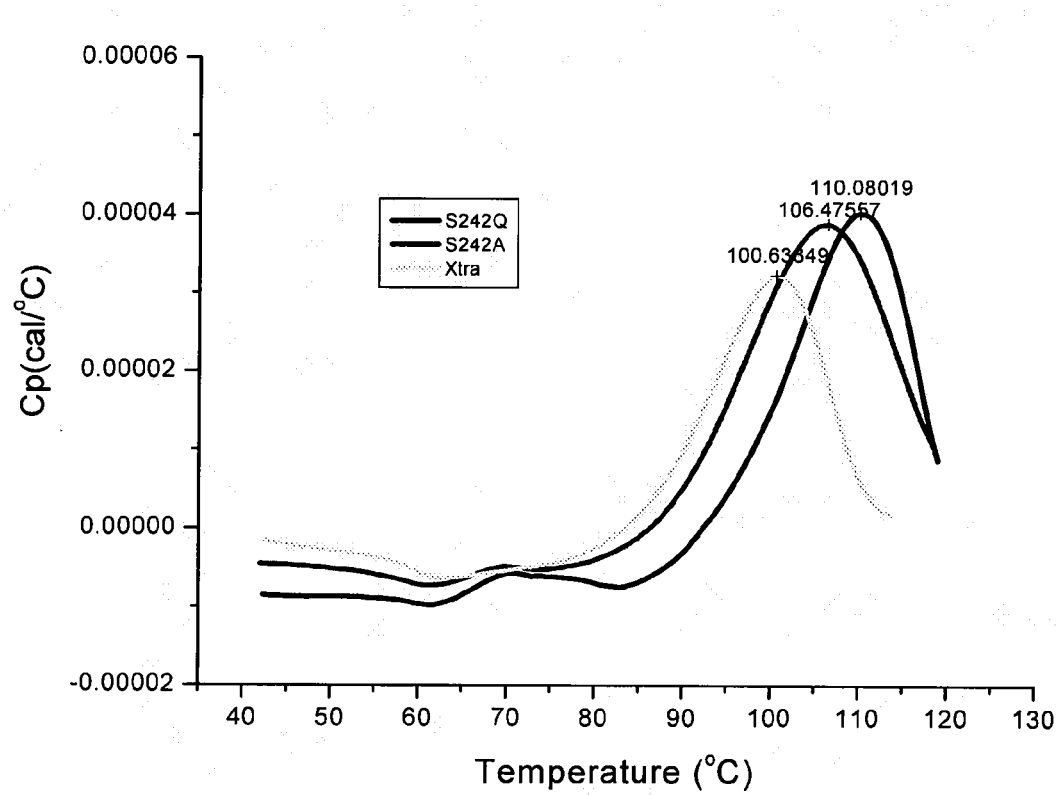
FIG. 5 shows the thermal melting curves and the melting points for the wild type and amylase variants without added calcium.
Figure 6:
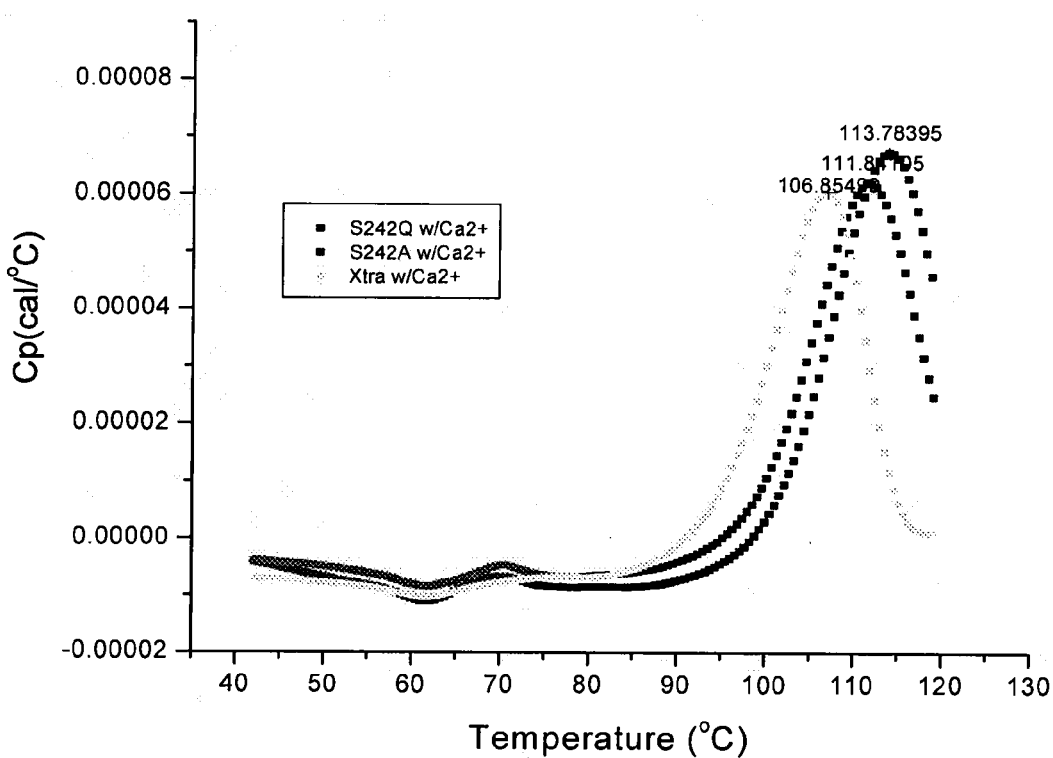
FIG. 6 shows the thermal melting curves and the melting points for the wild type and amylase variants with 2 mM calcium.

Excessive heat capacity curves were measured using an ultrasensitive scanning high-throughput microcalorimeter, VP-Cap DSC (MicroCal, Inc., Northampton, Mass.). The standard procedure for DSC measurements and the theory of the technique is previously published (Freire, E. (1995) Differential Scanning Calorimetry *Methods. Mol. Biol*. 41, 191-218). Approximately 500 μL of 0.5 mg/ml wild type *Bacillus stearothermophilus* α-amylase or variant S242S and S242Q (in the absence and presence of 2 mM calcium chloride) were scanned over 30-120° C. temperature range. The same sample was then re-scanned to check the reversibility of the process. For α-amylase the thermal unfolding process was irreversible. The buffer used was 10 mM sodium acetate, pH 5.5. A 200° C./hr scan rate was used to minimize any artifacts that may result from aggregation. The thermal midpoint (Tm) of the DSC curves was used as an indicator of the thermal stability. Table 4-1 shows the thermal melting points for the amylase proteins tested. The thermal melting curves and the melting points for the wild type and amylase variants are shown in FIG. 5.

The thermal unfolding for the amylase variants S242A and S242Q in the absence and presence of 2 mM calcium chloride show considerable increase in the melting points for the variants when compared to that for the wild type. In the absence of added calcium chloride, the wild type amylase has a thermal melting point of 100.8° C. whilst the Tm's for S242A and S242Q are 106.5° C. and 110.1° C., respectively. Thus, the substitution of S242 with A results in an increase in the Tm of 5.7° C., and the substitution of S242 with Q results in an increase in the Tm of 9.3° C.

In the presence of 2 mM calcium chloride, the wild type amylase characterized has a thermal melting point of 106.8° C. whilst the Tm's for S242A and S242Q are 111.8° C. and 113.8° C., respectively. Thus, in the presence of 2 mM calcium chloride all three proteins displayed increased Tm values. The increase in Tm for wild type and the S242A variants was 6° C. and 5.3° C., respectively. The increase in Tm for the S242Q variants was 3.7° C. This suggests that the S242Q variants is stabilized less by calcium or is less dependent on calcium for stability. The increase in the Tm of the S242A and S242Q relative to wild type in the presence of calcium chloride was 5° C. and 3° C., respectively. This suggests that the thermodynamic properties of the variants differ from those of SPEZYME® Xtra, and is consistent with its enhanced performance in application studies (see Example 5).

TABLE 4-1

|  | Tm (no Ca$_2^+$) | Tm (w/2 mM Ca$_2^+$) |
| --- | --- | --- |
| SPEZYME ® Xtra | 100.8 | 106.8 |
| S242A | 106.5 | 111.8 |
| S242Q | 110.1 | 113.8 |

Example 5

Activity Profiles

This example shows that the tested variants have altered activity profiles relative not only to the parent α-amylase but also to an industry standard. Protein determinations were made on purified or plate samples. All experimental variants and standard α-amylases were dosed on equal protein concentrations.

Either plate or purified variants were diluted down to approximately 20 ppm using pH 5.6 malic acid buffer. The substrate consisted of 15% corn starch in the same 50 mM Malic acid buffer, pH 5.6. 400 μL of the starch suspension was equilibrated to 70° C. for 2.5 minutes. Then 7 μL of the diluted enzyme was quickly added to the equilibrated starch (final protein concentration of around 0.36 ppm). The reaction mix was then put into a pre-heated 85° C. shaking heating block and mixed at 300 rpm. At predetermined time intervals the reactions were quenched with 50 μL of 125 mM NaOH. The reaction tubes were then spun and the supernatent was diluted 10-fold into 10 mM NaOH, to be analyzed for DP profile by HPAEC-PAD.

Reactions were set up for 4, 10 and 20 minutes. Total area from DP2 to the end of the HPLC run was integrated and the area was divided by the total protein and reaction time.

Figure 7:
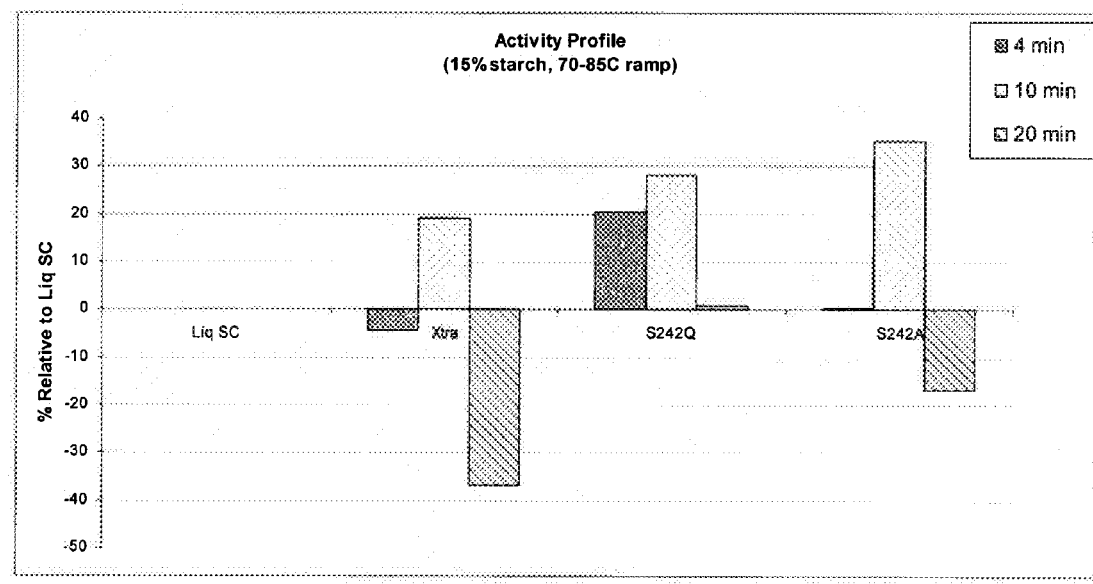
FIG. 7 shows the activity profile of SPEZYME® Xtra and two variants relative to Liquozyme SC for three time points.
Figure 8:
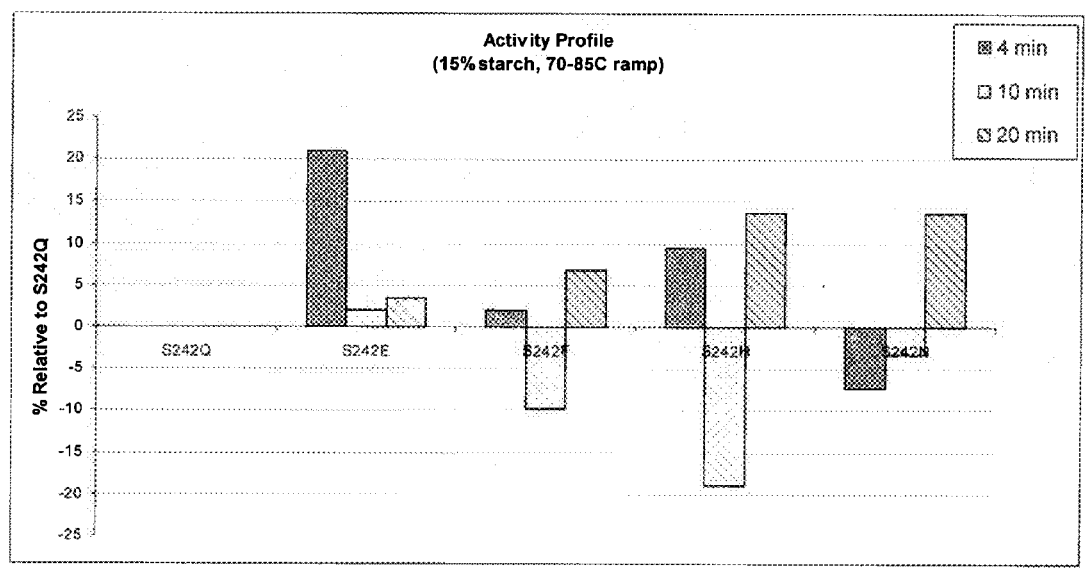
FIG. 8 shows the activity profile of four variants relative to the S242Q variant for three time points.

The 4-minute reaction provides an indication of how quickly the enzyme begins to break down the substrate; the 10-minute reaction provides an indication of the enzyme's thermal activity, and the 20-minute reaction provides an indication of the enzyme's thermal stability. The results are provided in FIGS. 7 and 8.

Example 6

Liquefaction in the Viscometer

This example shows that the S242A and S242Q variants of Example 3 that had altered residual activity relative to the wild-type parent also have altered performance relative to the parent α-amylase. The variant α-amylases of Example 2 were purified and characterized for total protein and specific activity before its test in the application.

Viscosity reduction of corn flour due to the action of the α-amylase was monitored using a HAAKE Viscotester 550 instrument. The substrate slurry is made up fresh daily in batch mode with 30% corn flour dry solids. The pH was adjusted to 5.8 using sulfuric acid. 50 g of the slurry (15 g dry solids) is weighed out and pre-incubated, with stirring, for 10 minutes to warm up to 70° C. Upon α amylase addition the temperature is immediately ramped up from 70° C. to 85° C. with a rotation speed of 75. Once the temperature of the slurry and enzyme mixture reaches 85° C., its temperature is held constant and viscosity is monitored for an additional 30 minutes. The viscosity was measured throughout the run and is reported in μNm. Wildtype AmyS, S242A, and S242Q were all dosed at equal protein concentrations (20 or 30 μg/50 g of corn flour slurry).

Figure 9:
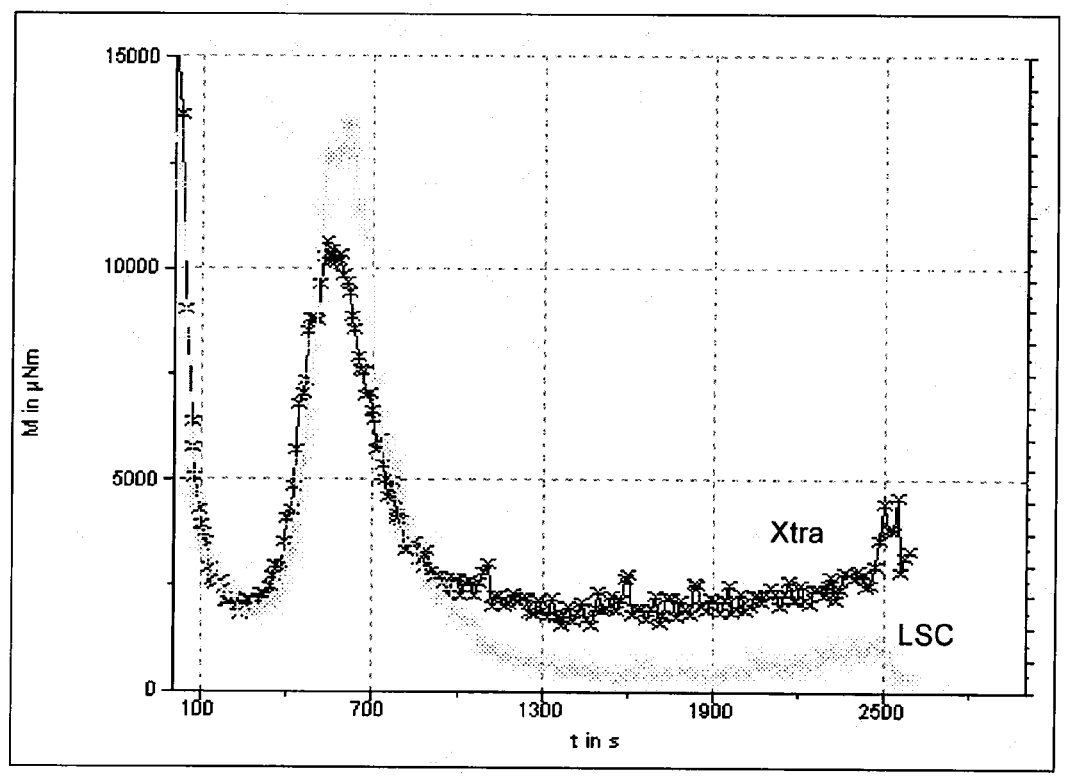
FIG. 9 shows the viscosity reduction of corn flour due to the action of the α-amylases LIQUOZYME® SC or SPEZYME® Xtra at a 30 μg dose.
Figure 10:
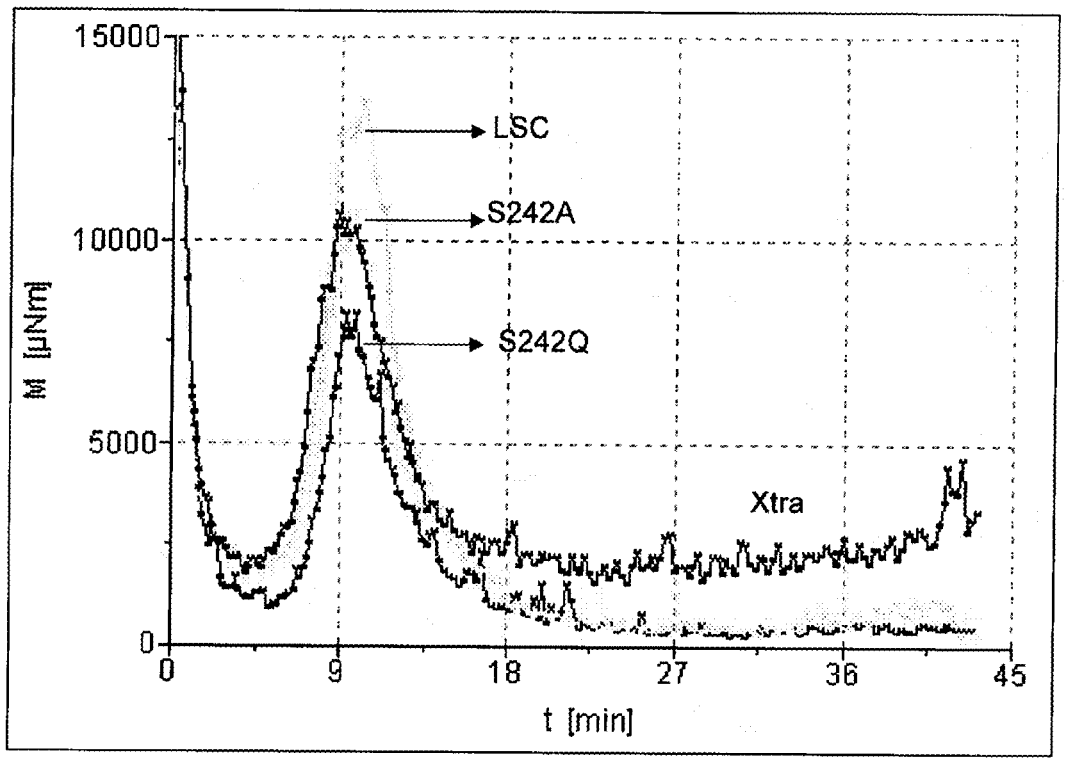
FIG. 10 shows the viscosity reduction of corn flour due to the action of the α-amylases LIQUOZYME® SC or SPEZYME® Xtra, or one of two variants (S242A and S242Q) at a 30 μg dose.
Figure 11:
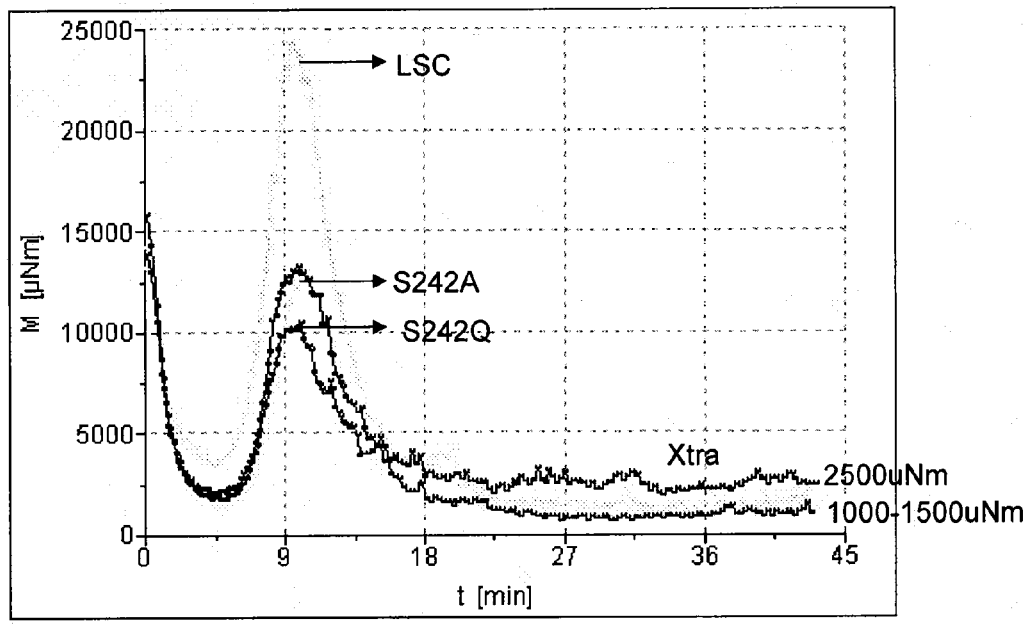
FIG. 11 shows the viscosity reduction of corn flour due to the action of the α-amylase LIQUOZYME® SC or SPEZYME® Xtra, or one of two variants (S242A and S242Q) at a 20 μg dose.

The viscometer application test resulted in both AmyS variants, S242A and S242Q, having better performance than the benchmark α amylases—LIQUOZYME® SC and SPEZYME® Xtra. Both variants exhibit the low peak viscosity characteristic of SPEZYME® Xtra and low final viscosity of LIQUOZYME® SC. When loaded at the lower concentration of 20 μg total protein, the differences of lower peak viscosities of the variants compared to that of LIQUOZYME® SC are further enhanced. See FIGS. 9, 10 and 11.

Example 7

Liquefaction in a Jet Cooker

Figure 12:
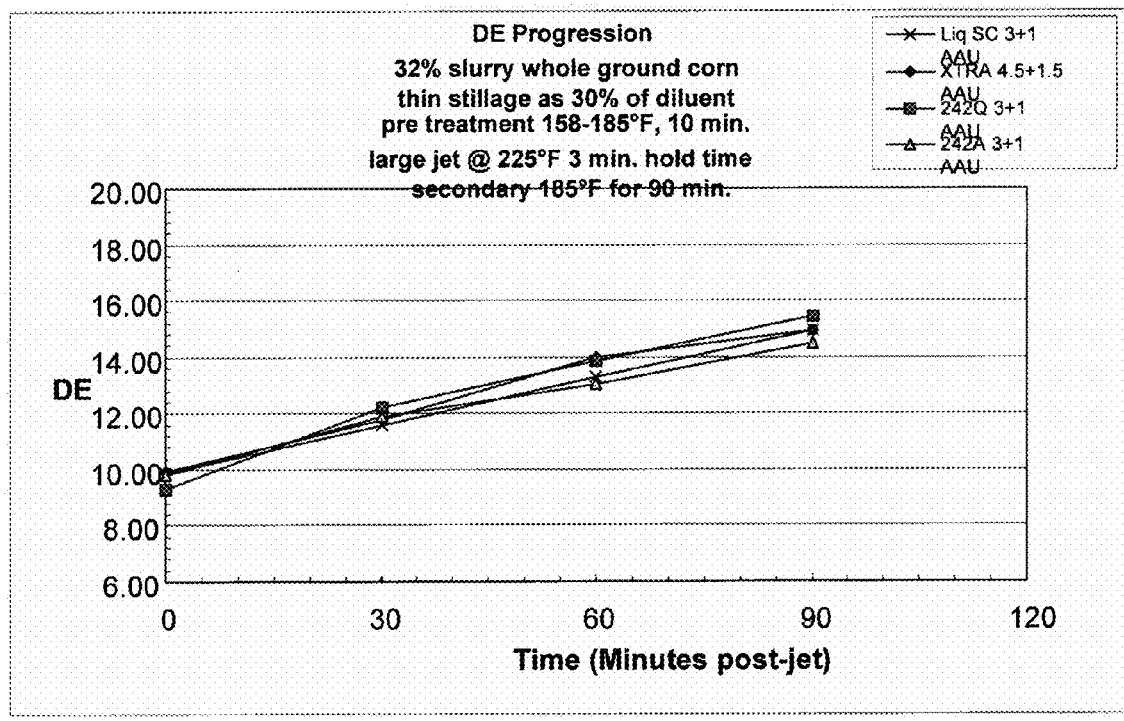
FIG. 12 shows the DE progression of whole ground corn treated with LIQUOZYME® SC, SPEZYME® Xtra, or one of two variants (S242A and S242Q) over time (0, 30, 60, and 90 minutes).
Figure 13:
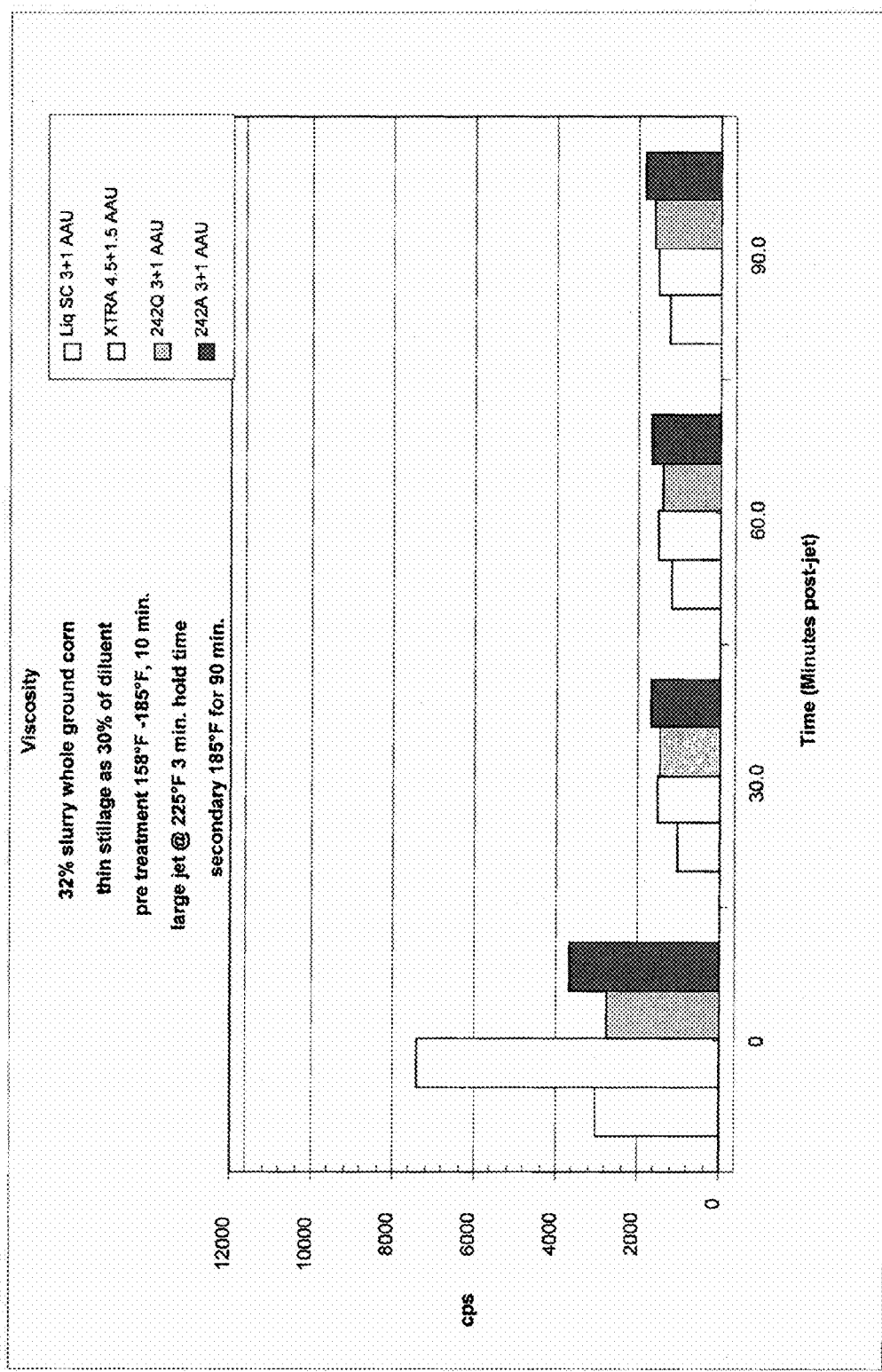
FIG. 13 shows the viscosity post-jet of whole ground corn treated with LIQUOZYME® SC, SPEZYME® Xtra, or one of two variants (S242A and S242Q) over time (0, 30, 60, and 90 minutes).

Whole ground corn was slurried to a 32% (dry solids corn) slurry by using a 70:30 ratio of water to thin stillage. The slurry pH was adjusted to pH 5.8 with 10 N NaOH. The slurry was heated to 70° C. (158° F.) using water and steam in a jacketed kettle. The liquefaction enzymes (SPEZYME® Xtra, LIQUOZYME® SC, or S242Q) were added and the slurry was heated to 85° C. (185° F.) over approximately 10 minutes. After an additional 10 minutes of incubation at 85° C., the slurry was passed through a jet-cooker maintained at 107° C. (225° F.) with a 3-minute hold time using a large pilot plant jet (equipped with an M103 hydro-heater from Hydro-thermal Corp., Waukesha, Wis.). The liquefact was collected from the jet and placed in an 85° C. water bath. A second dose of liquefaction enzyme was added post-jet. The liquefact was continuously stirred and held at 85° C. for 90 minutes. Samples were collected at 0, 30, 60 and 90 minutes. All samples were tested post-jet for DE (using the Schoorls method; method available upon request), and for viscosity (Brookfield-type viscometer (Lab-line Instruments Inc. of Melrose Park, Ill.) spindle 3 at 20 rpm). Dosing of liquefaction enzymes pre- and post-jet are indicated in the following Figures as "X+Y" where X represents the number of units of enzyme added before the jet, and Y represents the number of units added to the liquefact after it passes through the jet cooker. Results are shown in FIGS. 12 and 13.

Example 8

Effect of Removal of Phytic Acid Inhibition on α amylase Thermostability

In this example, the effect of the removal of phytic acid inhibition on the thermostability of liquefying thermostable α amylases was examined.

A. No Jet Cooking (Single Enzyme Dose)

A slurry of whole ground corn (obtained from Badger State Ethanol, Monroe, Wis., USA) was made with water containing 30% v/v thin stillage to a final concentration of about 32% ds. Corn solids were prepared in a jacked kettle. The slurry was mixed well and the pH of the slurry was measured (pH 5.2) and was used without further pH adjustment. This slurry was mixed in a jacketed kettle and brought up to the pretreatment temperature of 70° C. Just prior to reaching 70° C., the liquefying enzyme, i.e., an α amylase (4 AAU per gram ds corn), and phytase (4 FTU per gram ds corn) were added and a timer was started to begin the incubation or primary liquefaction step. The slurry was allowed to incubate for 30 minutes in the presence of the amylase with or without added phytase. The phytase used in this experiment was BP-17 (see, supra). Although the phytase was added at the same time as the α-amylase in this example it may be added prior to the amylase.

Figure 14:
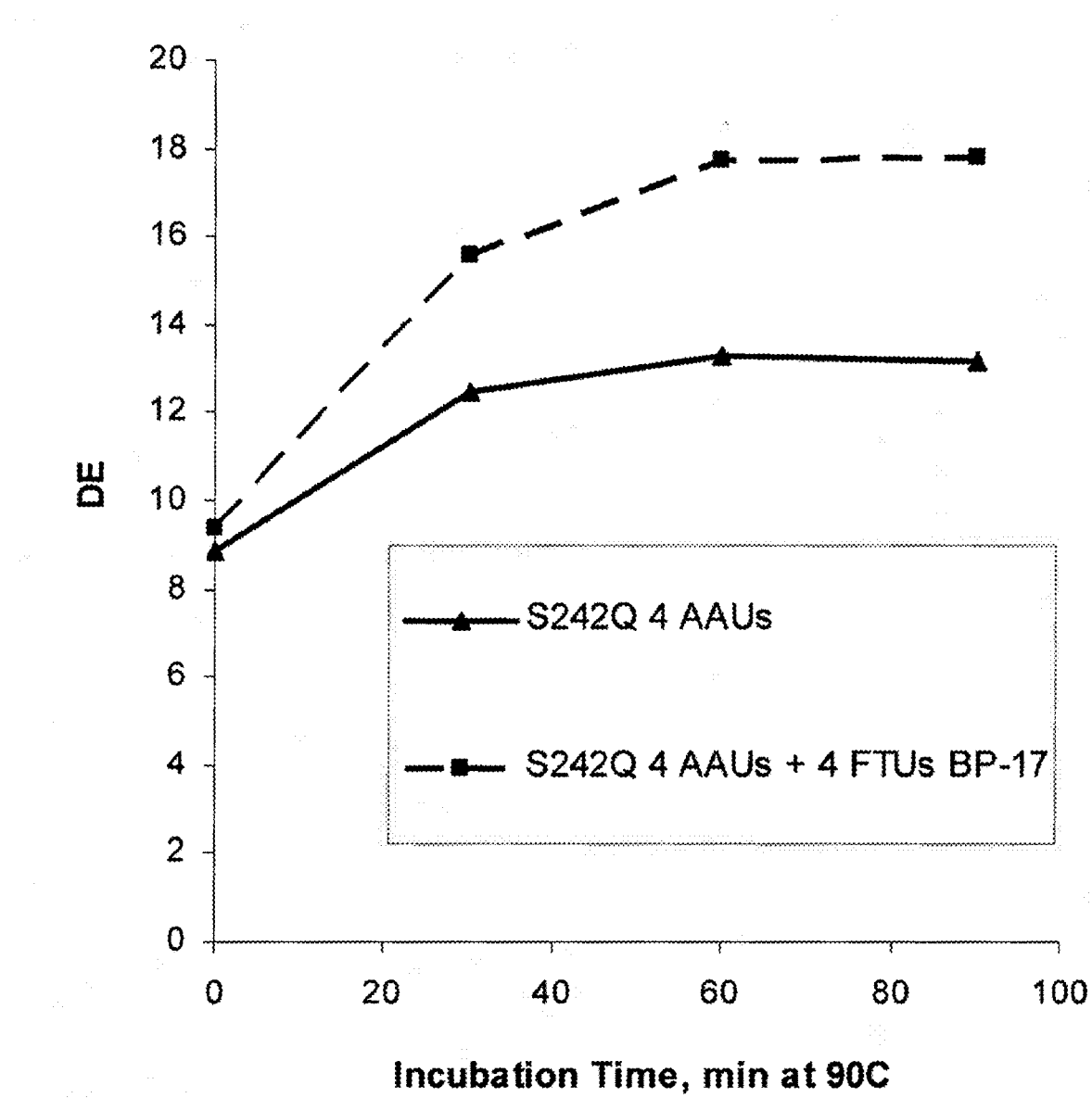
FIG. 14 shows the DE progression of whole ground corn treated with phytase and an amylase (SPEZYME® Xtra or S242Q variant) over time (0, 30, 60 and 90 minutes). MAX-ALIQ® is a phytase/amylase blend available from Genencor, a Danisco Division. Reference is made to Example 8.
Figure 15:
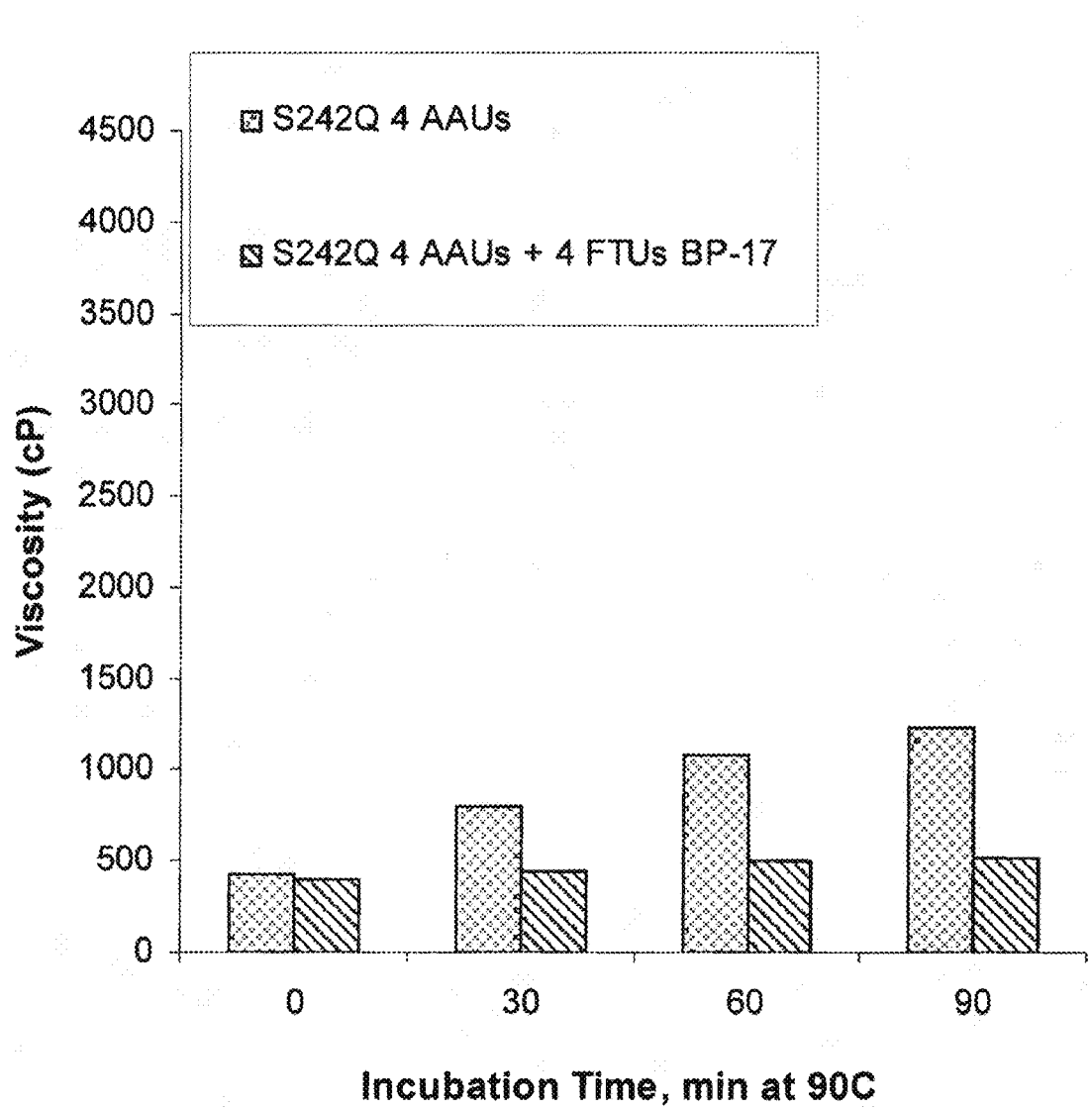
FIG. 15 shows the viscosity post-jet of whole ground corn treated with phytase and an amylase (SPEZYME® Xtra or S242Q variant) over time (0, 30, 60, and 90 minutes).

The treated slurry was then placed in a water bath maintained at 90° C. to begin the secondary liquefaction step (2° liquefaction). Samples were taken to test for viscosity (by Brookfield) and DE (by Schoorls) at 0, 30, 60 and 90 minutes. The results are shown in FIGS. 14 and 15.

B. With Jet Cooking (Split Enzyme Dose)

A slurry of whole ground corn (obtained from Badger State Ethanol, Monroe, Wis.) was made with water containing 30% v/v thin stillage to a final concentration of about 32% ds. Corn solids were prepared in a jacked kettle. The slurry was mixed well and the pH of the slurry was measured (pH 5.2). This slurry was mixed in a jacketed kettle and brought up to the pretreatment temperature of 70° C. Just prior to reaching 70° C., the liquefying enzyme, i.e., an S242Q variant α amylase (3 AAU per gram ds corn), was added and a timer was started to begin the incubation or primary liquefaction step. The slurry was allowed to incubate for 30 minutes in the presence of the α-amylase with or without added phytase (4 FTU per gram ds corn). Although the phytase was added at the same time as the α-amylase in this example it may be added prior to the amylase.

The incubated slurry was then passed through a jet cooker (225° F.; 107.2° C.) which was preheated to the desired temperature using steam and water. The slurry was sent through the jet at maximum speed (1.5 setting) about 4 liters/minute. Using the first three loops of the hold coil resulted in a hold time of just over 3 minutes. After all of the water was displaced and the desired temperature held steady, an aliquot of solubilized corn mash was collected and placed in a secondary bath (overhead stirring) at 85° C. to begin the secondary liquefaction step (2° liquefaction). A second dose of the S242Q (1 AAU/gm ds) was added and the liquefaction continued for an additional 90 minutes. Samples were taken to test for viscosity (by Brookfield) and DE (by Schoorls) at 0, 30, 60 and 90 minutes. This liquefact was used in Example 10B.

C. Jet Cooking, Conventional

A slurry of whole ground corn (obtained from Badger State Ethanol, Monroe, Wis.) was made with water containing 30% v/v thin stillage to a final concentration of about 32% ds. Corn solids were prepared in a jacked kettle. The slurry was mixed well and the pH of the slurry was measured (pH 5.2) and adjusted to pH 5.8 with dilute NaOH. This slurry was mixed in a jacketed kettle and brought up to the pretreatment temperature of 70° C. Just prior to reaching 70° C., the liquefying enzyme, i.e., an S242Q variant α amylase (3 AAU per gram ds corn), was added and a timer was started to begin the incubation or primary liquefaction step. The slurry was allowed to incubate for 30 minutes in the presence of the α-amylase without added phytase.

Figure 22:
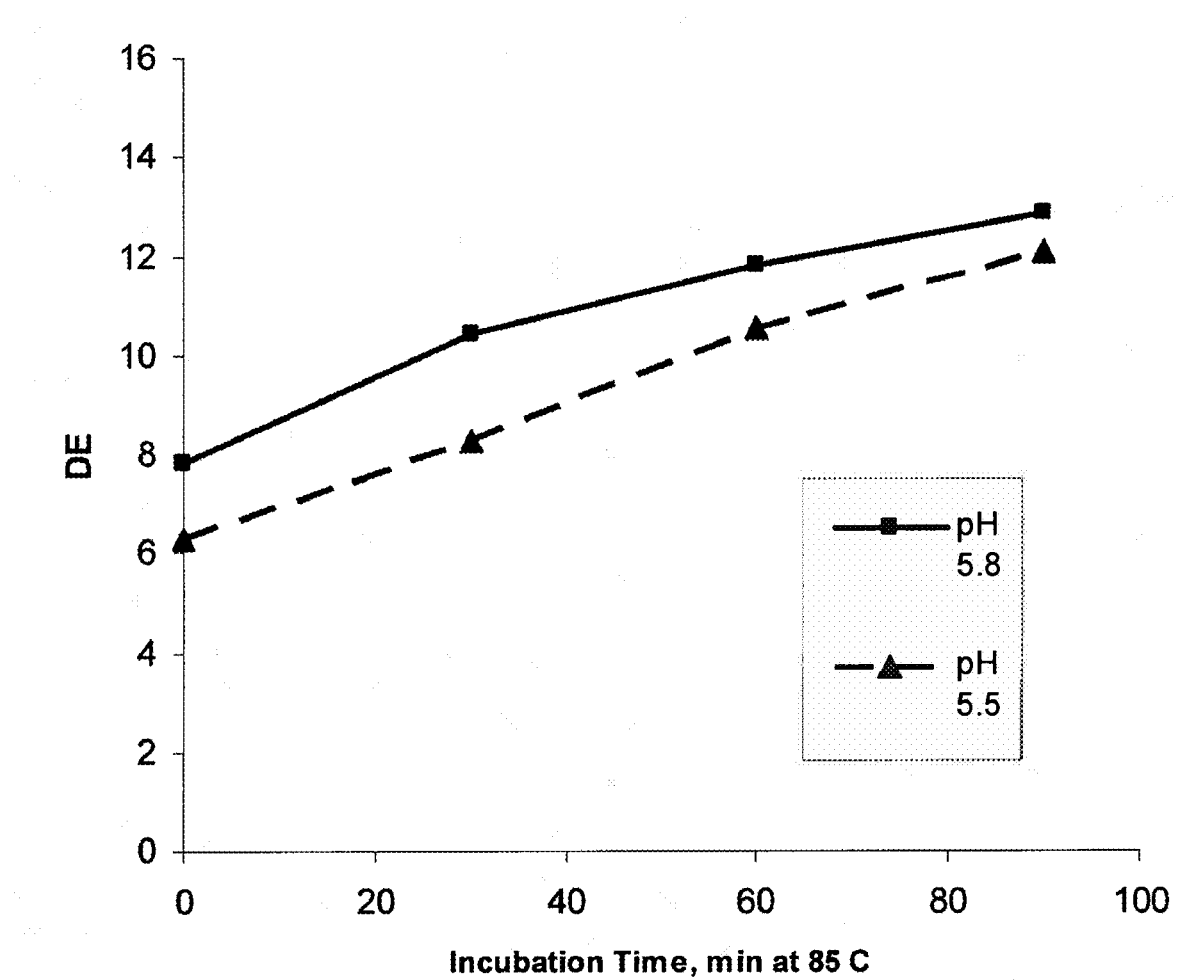
FIG. 22 is a graph showing the effect of the S242Q variant α-amylase on DE progression under conventional processing conditions. Reference is made to Example 8.

The incubated slurry was then passed through a jet cooker (225° F.; 107.2° C.) which was preheated to the desired temperature using steam and water. The slurry was sent through the jet at maximum speed (1.5 setting) about 4 liters/minute. Using the first three loops of the hold coil resulted in a hold time of just over 3 minutes. After all of the water was displaced and the desired temperature held steady, an aliquot of solubilized corn mash was collected and placed in a secondary bath (overhead stirring) at 85° C. to begin the secondary liquefaction step (2° liquefaction). A second dose of the S242Q variant α-amylase (1 AAU/gm ds) was added and the liquefaction continued for an additional 90 minutes. Samples were taken to test for viscosity (by Brookfield) and DE (by Schoorls) at 0, 30, 60 and 90 minutes. The above experiment at a slurry pH of 5.5. See FIG. 22. This liquefact was used in Example 10A.

D. Results With and Without Jet Cooking

Figure 21:
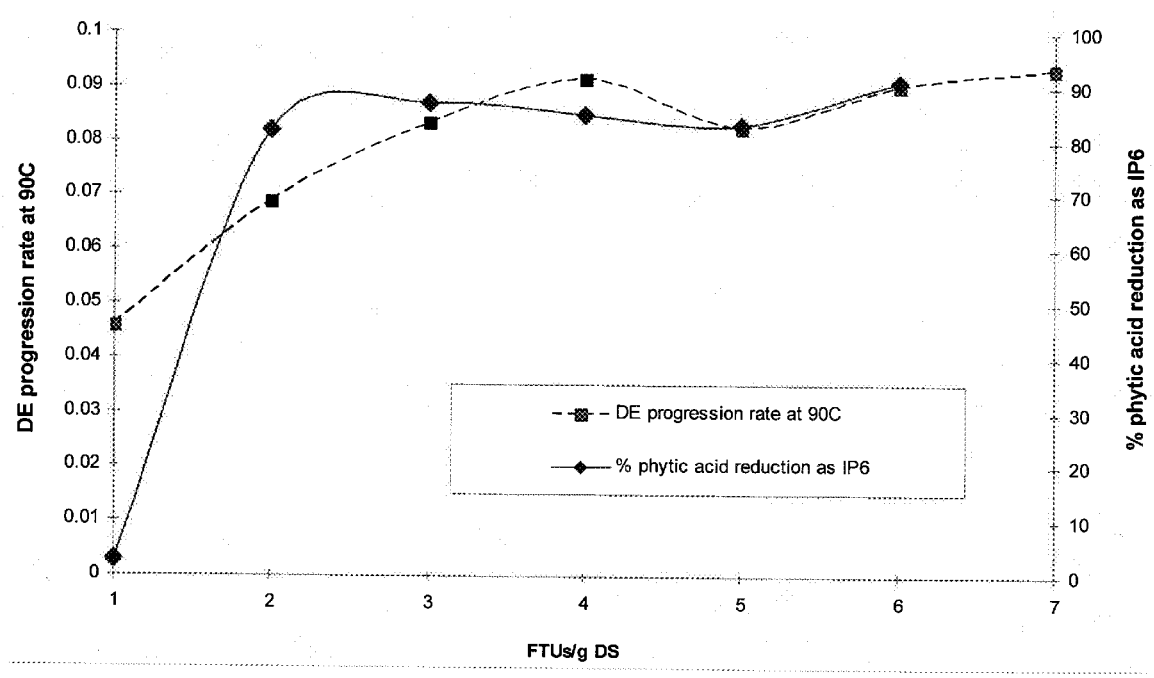
FIG. 21 is a graph showing the rate of DE progression and the percent phytic acid reduction as IP6.

Addition of BP-17 phytase during incubation (primary liquefaction) reduced the phytic acid content of the whole ground corn from 0.60% ds corn to 0.09% ds corn (>85% reduction) (FIG. 21). It is also very clear from FIGS. 14 and 15 that the α amylase were inactivated at a jet cooking temperature of 225° F. (107° C.) based on DE development or viscosity reduction. However, the inclusion of phytase prior to jet cooking (which it is believed to remove the phytic acid inhibition) resulted in a significant increase in the thermostability of the α amylases as shown by DE progression and viscosity reduction at 90° C. during the secondary liquefaction step. Similar results were seen with jet cooking (data not shown) as shown in FIGS. 14 and 15.

Example 9

Effect of BP-17 Phytase Concentration on α Amylase Stability at Low pH

The increase in the thermostability of α amylase due to the removal of the phytic acid inhibition of α amylase was further studied. The phytic acid was hydrolyzed using phytase prior to the secondary liquefaction of whole ground corn and the improvement in the pH stability at low pH was determined.

In a typical experiment, whole ground corn was slurried to a 32% (ds corn) by using a 70:30 ratio of water and thin stillage. The slurry pH was measured and found to be pH 5.2. The slurry was heated to 70° C. using water and steam in a jacketed kettle. The liquefaction enzyme, i.e., the S242Q variant α-amylase (4 AAU/gm ds corn), and varying concentrations of BP-17 (0-12 FTU/gm ds corn) were added and the slurry was pretreated by holding the temperature at 70° C. for 45 minutes. After 45 minutes of pretreatment, the slurry was placed in a 90° C. water bath. The liquefact was continuously stirred and held at 90° C. for 90 minutes. Samples were collected at 0, 30, 60 and 90 minutes. All samples were tested for DE (using the Schoorls method), and for viscosity (Brookfield viscometer spindle 2 at 20 rpm). The DE progression and viscosity data are summarized in FIGS. 16 and 17.

Figure 16:
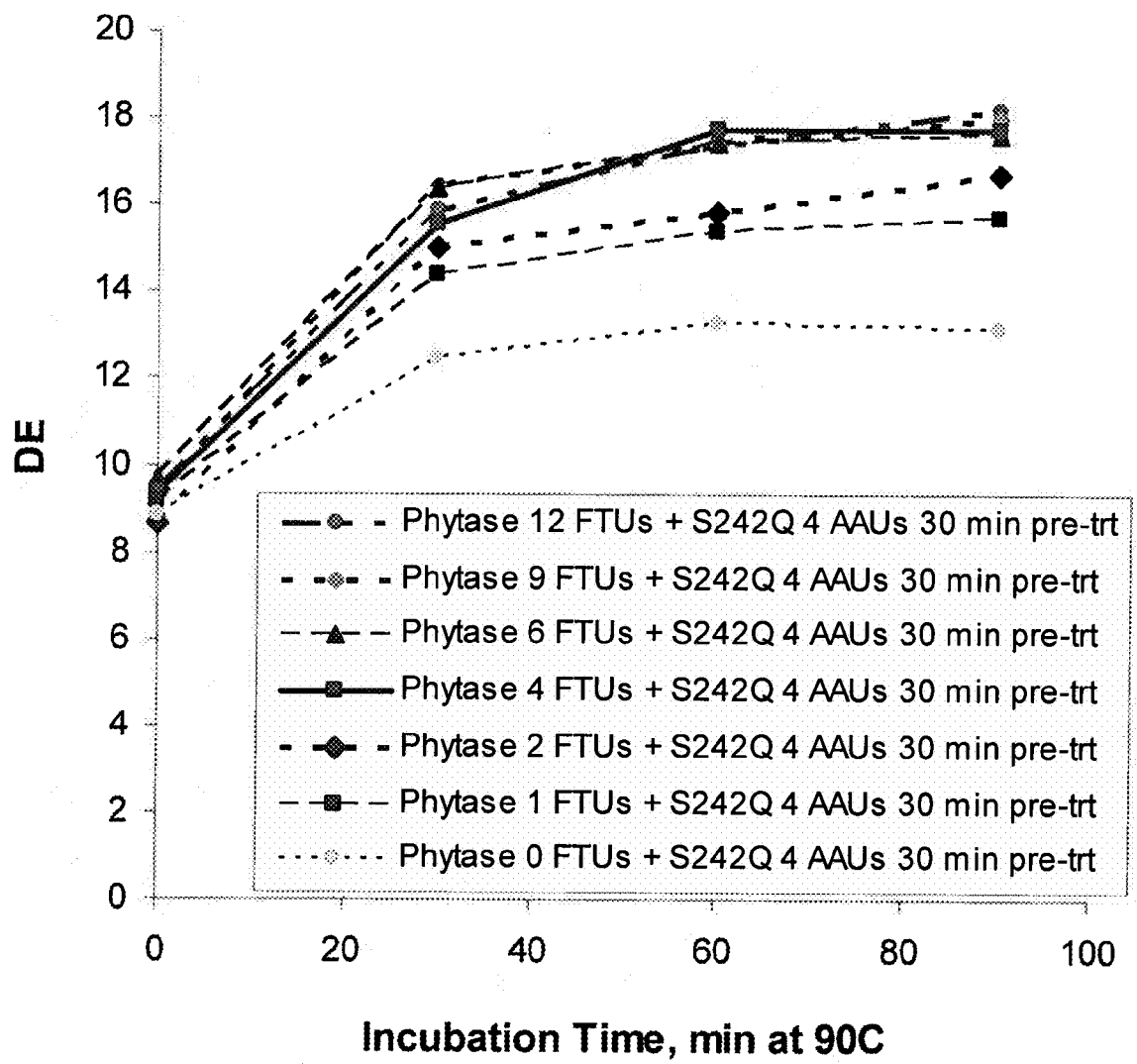
FIG. 16 shows the DE progression of whole ground corn treated with of the S242Q variant and phytase. Reference is made to Example 9.
Figure 17:
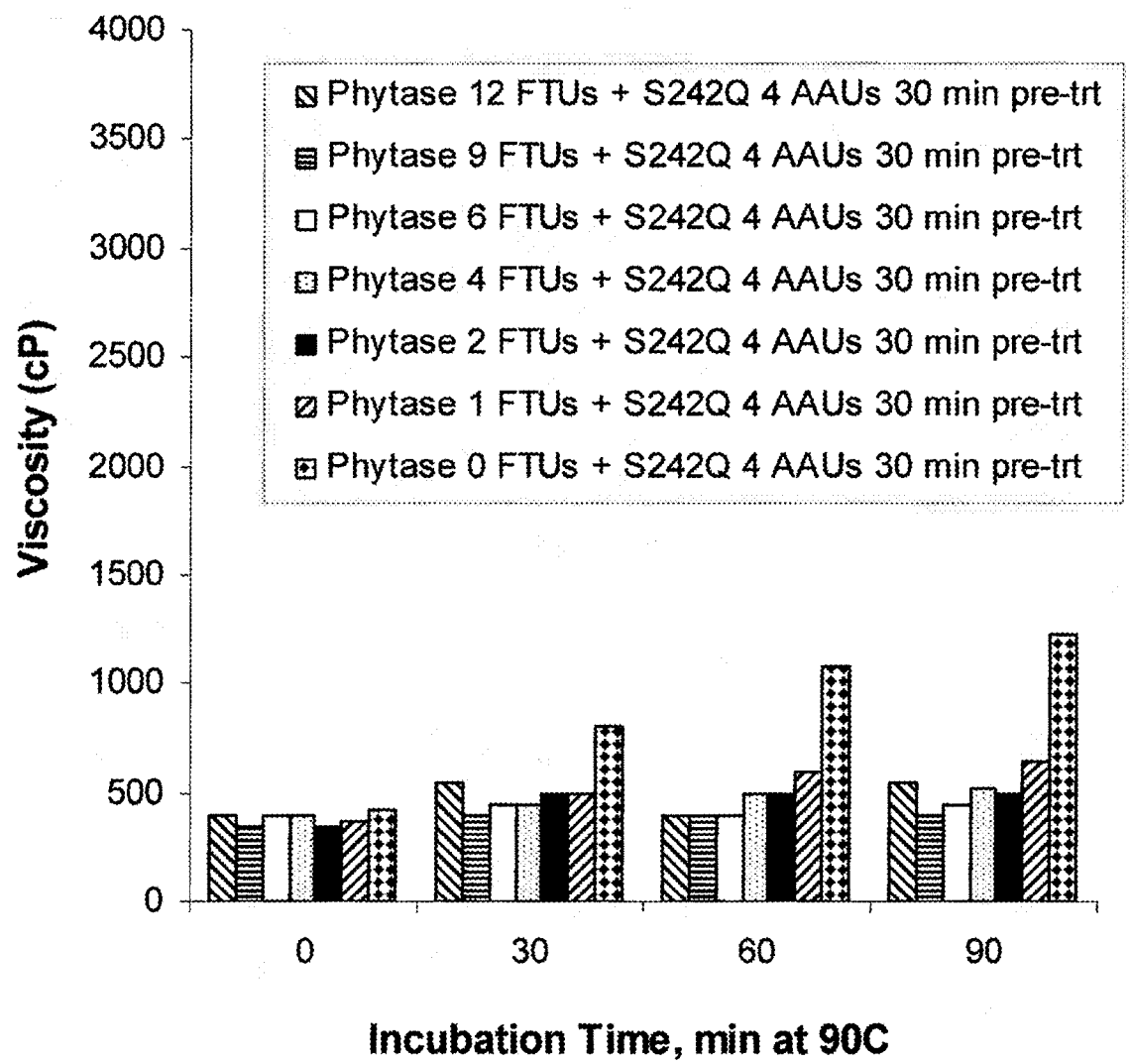
FIG. 17 shows the viscosity post-jet of whole ground corn treated with of the S242Q variant and phytase. Reference is made to Example 9.

The results in FIGS. 16 and 17 show that the reduction of phytic acid inhibition of the S242Q variant α-amylase resulted in a significant increase in the low pH stability for activity as evidenced by a steady increase in the DE progression at 90° C. with a concomitant decrease in the viscosity of the liquefact. The data clearly showed that the S242Q variant α amylase can be successfully used in the liquefaction process for whole ground corn at a pH 5.2 if the inhibition of the phytic acid is eliminated. In FIG. 21, it can be seen that the rate of DE progression increases with the increased removal of phytic acid and reaches a maximum at 4 FTU/gm ds indicating that the phytase increases the thermostability of the S242Q variant α-amylase by removing phytic acid from the slurry.

Example 10

Effect of pH

In this example, the effect of pH on the S242Q variant α-amylase was examined.

Figure 18:
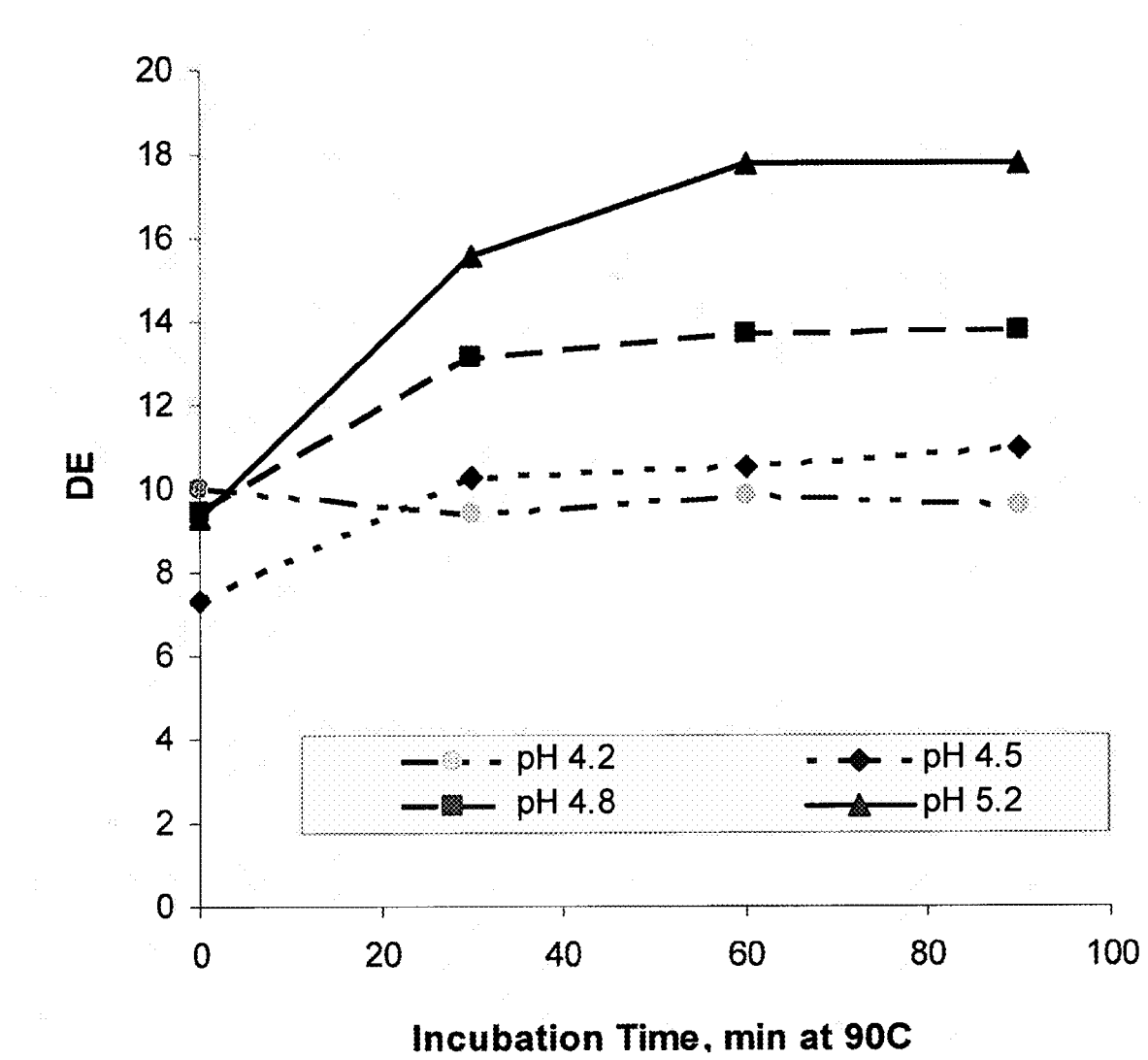
FIG. 18 shows the effect of phytase treatment of whole ground corn on the increase in the thermostability and low pH stability of the S242Q variant and reference is made to Example 9.
Figure 19:
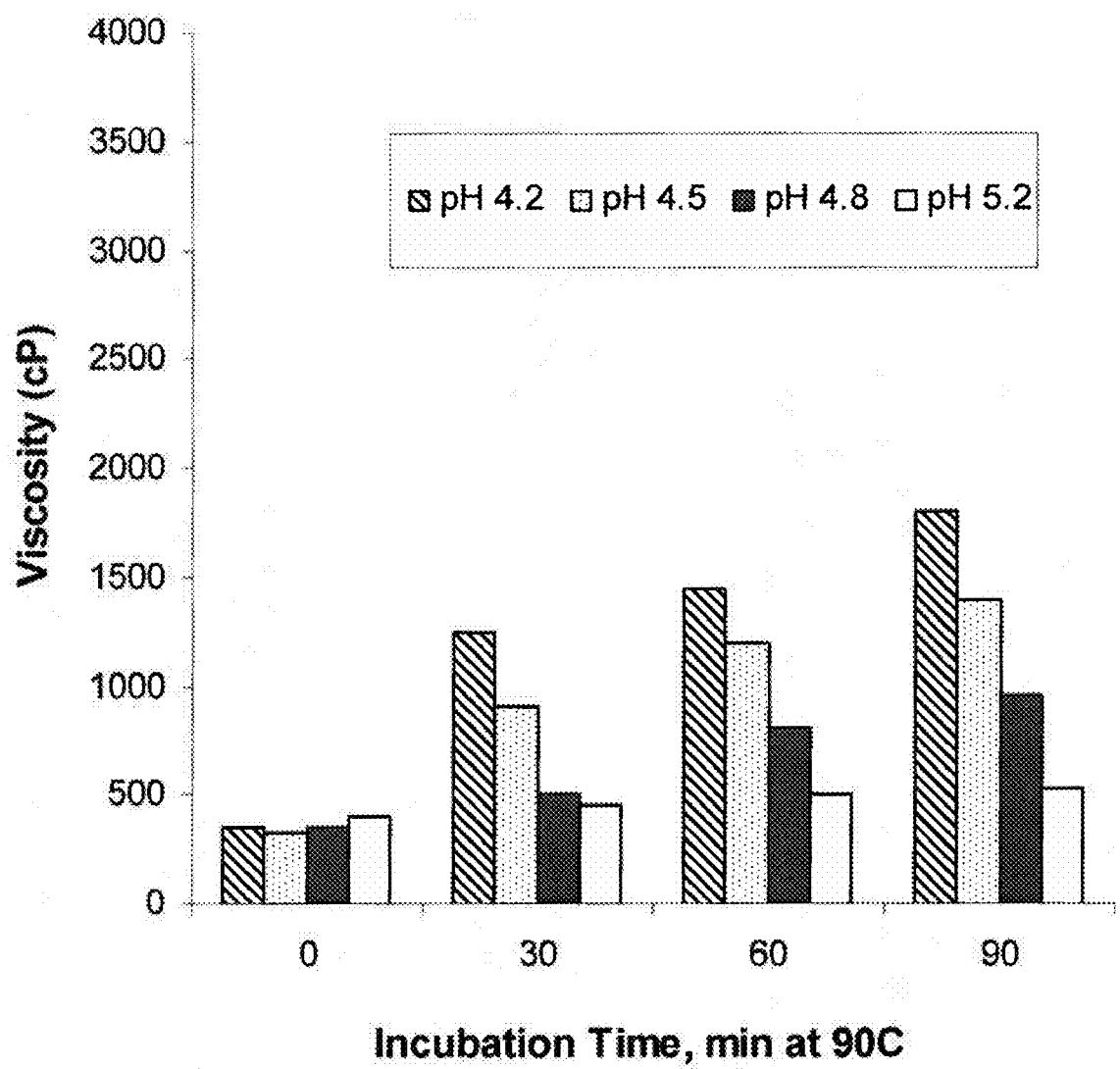
FIG. 19 shows the effect of phytase addition during primary liquefaction of whole ground corn on the viscosity reduction after jet cooking and reference is made to Example 9.

In a typical experiment, whole ground corn was slurried to a 32% (ds corn) by using a 70:30 ratio of water and thin stillage. The slurry pH was measured and found to be pH 5.2. The pH was lowered to between 4.2 and 4.8 using $H_2SO_4$. The slurry was heated to 70° C. using water and steam in a jacketed kettle. The liquefaction enzyme, i.e., the S242Q variant (4 AAU/gm ds), and BP-17 (4 FTU/gm ds) were added and the slurry was pretreated by holding the temperature at 70° C. for 45 minutes. After 45 minutes of pretreatment, the slurry was placed in a 90° C. water bath. The liquefact was continuously stirred and held at 90° C. for 90 minutes. Samples were collected at 0, 30, 60 and 90 minutes. All samples were tested for DE (using the Schoorls method), and for viscosity (Brookfield viscometer spindle 2 at 20 rpms). The DE progression and viscosity data are summarized in FIGS. 18 and 19.

The results showed that DE progression decreased with decreasing pH from 5.2 to 4.5. The enzyme was completely inactivated at pH 4.2.

Example 11

Effect on Ethanol Production

Liquefacts were used as fermentation feedstocks in ethanol fermentation for alcohol production. A slurry of whole ground corn (obtained from Badger State Ethanol, Monroe, Wis.) was mixed with water containing 30% v/v thin stillage to a final concentration of about 32% ds.

A. Conventional Process

The liquefact from Example 8C was used (Liquefact A). The pH of the secondary liquefact was adjusted to 4.2 using $H_2SO_4$ prior to the simultaneous saccharification and fermentation (SSF) stage.

B. Low pH, Jet Cooking (Split Dose)

The liquefact from Example 8B was used (Liquefact B). No pH adjustment was done prior to SSF.

C. Simultaneous Saccharification and Sermentation

In each experiment tare weights of the vessels were obtained prior to preparation of media. A 32% DS corn ds liquefact (2 liters) was taken in a 2 L flask. Red Star Ethanol Red yeast (RED STAR (Lesaffre) inoculums were prepared by adding 10 grams of yeast and 1 gram of glucose to 40 grams of water under mild agitation for one hour. Five mls of each inoculum was added to equilibrated fermentors followed by the addition of G Zyme™ 480 Ethanol (Danisco US Inc, Genencor Division) at 0.4 GAU/gds.corn to initiate the simultaneous saccharification and fermentation. The initial gross weight was noted and the flask was placed in a water bath maintained at 32° C. The samples were taken at different intervals of time and analyzed for carbohydrate and ethanol content using HPLC. Fermentations were also carried out using one kilogram of each liquefact and weight loss during fermentation was measured at different intervals of time. Based on the weight loss due to loss of carbon dioxide, the alcohol was measured. At the conclusion of the fermentation, a final gross weight was obtained. The broth was quantitatively transferred into a 5 L round bottom vessel. Distillation was performed under vacuum until approximately 800 mls of ethanol was collected in a receptacle containing 200 mls water. The ethanol was diluted to 2 L and was analyzed by HPLC. The weight and DS of the still bottoms was obtained prior to drying. Residual starch analysis was performed on the DDGS. Stoichiometric calculations were performed based on weight loss, distillation, and residual starch analysis.

Ethanol calculation using $CO_2$ weight loss:

Ethanol production(mmol)=$CO_2$ loss(g)/88

Ethanol production(g)=($CO_2$ loss(g)/88)*92=>$CO_2$ loss(g)*1.045

Ethanol production(ml)=(($CO_2$ loss(g)/88)*92)/0.789=>$CO_2$ loss(g)×1.325

The data in FIG. 20 shows major difference in free sulphate and phytic acid content between the conventional process and the no pH adjustment process according to the invention. Removal of phytic acid inhibition of thermostable α amylase in the incubation resulted in the DDGS with reduced phytic acid content, higher free available phosphate and reduced sulfate. Thus, the process with no pH adjustment confers pH stability at low pH for liquefying thermostable α amylases in the starch liquefaction.

Example 12

Additional Methods

The following assays were used in the Examples described below. Any deviations from the protocols provided below are indicated in the Examples. In these experiments, a spectrophotometer was used to measure the absorbance of the products formed after the completion of the reactions.

A. Protein Content Determination
BCA (Bicinchoninic Acid) Assay

In these assays, BCA (Pierce) assay was used to determine the protein concentration in samples on microtiter plate (MTP) scale. In this assay system, the chemical and reagent solutions used were: BCA protein assay reagent, and Pierce dilution buffer (50 mM MES, pH 6.5, 2 mM $CaCl_2$, 0.005% TWEEN®-80). The equipment used was a SpectraMAX (type 340; Molecular Devices) MTP reader. The MTPs were obtained from Costar (type 9017).

In the test, 200 μl BCA Reagent was pipetted into each well, followed by 20 μl diluted protein. After thorough mixing, the MTPs were incubated for 30 minutes at 37° C. Air bubbles were removed, and the optical density (OD) of the solution within the wells was read at 562 nm. To determine the protein concentration, the background reading was subtracted form the sample readings. The $OD_{562}$ was plotted for protein standards (purified enzyme), to produce a standard curve. The protein concentration of the samples were interpolated from the standard curve.

Bradford Assay

In these assays, the Bradford dye reagent (Quick Start) assay was used to determine the protein concentration in samples on MTP scale. In this assay system, the chemical and reagent solutions used were: Quick Start Bradford Dye Reagent (BIO-RAD Catalog No. 500-0205), Dilution buffer (10 mM NaCl, 0.1 mM $CaCl_2$, 0.005% TWEEN®-80). The equipment used was a Biomek FX Robot (Beckman) and a SpectraMAX (type 340) MTP reader. The MTPs were from Costar (type 9017).

In the test, 200 µl Bradford dye reagent was pipetted into each well, followed by 15 µl dilution buffer. Finally 10 µl of filtered culture broth were added to the wells. After thorough mixing, the MTPs were incubated for at least 10 minutes at room temperature. Air bubbles were blown away and the ODs of the wells were read at 595 nm. To determine the protein concentration, the background reading (i.e., from un-inoculated wells) was subtracted form the sample readings. The obtained $OD_{595}$ values provide a relative measure of the protein content in the samples.

B. Microswatch Assay for Testing Enzyme Performance

The detergents used in this assay did not contain enzymes or the enzymes present in commercial detergents had been destroyed through heat deactivation as described elsewhere in this document. The equipment used included an Eppendorf Thermomixer and a SpectraMAX (type 340) MTP reader. The MTPs were obtained from Costar (type 9017).

Detergent Preparation (AATCC HDL; US Conditions)

Milli-Q water was adjusted to 6 gpg water hardness (Ca/Mg=3/1), and 1.5 g/l AATCC 2003 standard reference liquid detergent without brightener was added. The detergent solution was vigorously stirred for at least 15 minutes. Then, 5 mM HEPES (free acid) was added and the pH adjusted to 8.0.

Rice Starch Microswatch Assay for Testing Amylase Performance

Test detergents were prepared as described elsewhere in this document. The equipment used included a New Brunswick Innova 4230 shaker/incubator and a SpectraMAX (type 340) MTP reader. The MTPs were obtained from Coming (type 3641). Aged rice starch with orange pigment swatches (CS-28) were obtained from Center for Test Materials (Vlaardingen, Netherlands). Before cutting 0.25-inch circular microswatches, the fabric was washed with water. Two microswatches were placed in each well of a 96-well microtiter plate. The test detergent was equilibrated at 20° C. (North America) or 40° C. (Western Europe). 190 µl of detergent solution was added to each well of the MTP, containing microswatches. To this mixture, 10 µl of the diluted enzyme solution was added. The MTP was sealed with adhesive foil and placed in the incubator for 1 hour with agitation at 750 rpm at the desired test temperature (typically 20° C. or 40° C.). Following incubation, 150 µl of the solution from each well was transferred into a fresh MTP. This MTP was read at 488 nm using a SpectraMax MTP reader to quantify cleaning. Blank controls, as well as controls containing microswatches and detergent but no enzyme were also included.

Calculation of Enzyme Performance

The obtained absorbance value was corrected for the blank value (i.e., obtained after incubation of microswatches in the absence of enzyme). The resulting absorbance was a measure for the hydrolytic activity.

C. Amylase Concentration Determination by Antibody Titration

As described herein, α-amylase concentration and specific activity was determined by titration with an inhibitory polyclonal antibody. Polyclonal antibodies raised to *Bacillus stearothermophilus* α-amylase (AmyS) were found to be strongly inhibitory of AmyS and the α-amylase from *Bacillus* sp. TS23 (e.g., the binding is tight enough to produce a linear titration of activity loss). Therefore, this antibody can be used to measure enzyme concentration, which in turn is used to calculate specific activity. Briefly, the amount of enzyme inhibition produced by several known concentrations of antibody is measured. From this information, the concentration of antibody required for complete inhibition is extrapolated, which is equivalent to the enzyme concentration in the sample. A-amylase activity and inhibition was measured using the fluorogenic BODIPY-starch assay. The buffer was 50 mM MOPS, pH 7.0, containing 0.005% Tween-80.

A polyclonal antibody directed against purified AmyS was raised in a rabbit and purified by standard methods. An empirical "apparent concentration" value of an antibody stock solution was determined by measuring the inhibition of a sample of AmyS of known specific activity. Then the antibody sample was used to determine the concentration and specific activity of AmyS and TS23t variants. These values were used to create normalized 96-well enzyme stock plates, where all of the variants were diluted to a common concentration.

D. Native Protein Gel Electrophoresis

Electrophoretic mobility of variant protein samples was measured using the PhastGel system (GE Healthcare) on pre-cast native polyacrylamide gels (PhastGel Homogeneous) at either 7.5% or 12.5% concentration. Buffer strips (PhastGel Native) were used and consisted of pH 8.8 in 0.88 M L-Alanine, 0.25 M Tris buffer. Typical run conditions consisted of 400 V for 12.75 minutes with an anode-to-cathode distance of 3.7 cm.

Alternatively, electrophoretic mobility of variant protein samples was measured on 1 mm thick 0.5-1.5% agarose gels at various pH values (i.e. 5.8, 8.0 and 10.0) through a choice of a suitable buffer system. The electrophoresis is carried out under non-denaturing conditions. The Cathode—Anode length was 13.9 cm. A sample of 1-2 µg protein was mixed with 5% glycerol+0.05% bromophenol blue and loaded on each lane. Gels were run typically for 1 hour at 100V.

In either case gels were stained with Louiseville blue dye dissolved in 10% acetic acid and destained with 10% methanol and 10% acidic acid in water. It is possible to load between 12 and 20 protein variants simultaneously depending on native gel system used. As a consequence the electrophoretic mobility of a protein variant can be immediately assessed relative to charge ladder standards loaded on the same gel.

E. Detergent Heat Inactivation

Heat inactivation of commercial detergent formulas serves to destroy the enzymatic activity of any protein components while retaining the properties of non-enzymatic components. Thus this method was suitable for preparing commercially purchased detergents for use in testing the enzyme variants of the present invention. For North American (NA) and Western European (WE) heavy duty liquid laundry (HDL) detergents, heat inactivation was performed by placing pre-weighed liquid detergent (in a glass bottle) in a water bath at 95° C. for 2 hours. The incubation time for heat inactivation of North American (NA) and Japanese (JPN) heavy duty granular laundry (HDG) detergent was 8 hours and that for Western European (WE) HDG detergent was 5 hours. The incubation time for heat inactivation of NA and WE auto dish washing (ADW) detergents was 8 hours. The detergents were purchased from local supermarket stores. Both un-heated and heated detergents were assayed within 5 minutes of dissolving the detergent to accurately determine percentage deactivated. Enzyme activity was tested by the suc-AAPF-pNA assay.

For testing of enzyme activity in heat-inactivated detergents, working solutions of detergents were made from the heat inactivated stocks. Appropriate amounts of water hardness (6 gpg or 12 gpg) and buffer were added to the detergent solutions to match the desired conditions (Table 12-1). The solutions were mixed by vortexing or inverting the bottles.

TABLE 12-1

Laundry and Dish Washing Conditions

| Region | Form | Dose | Detergent* | Buffer | Gpg | pH | T (° C.) |
|---|---|---|---|---|---|---|---|
| Laundry (heavy duty liquid and granular) | | | | | | | |
| NA | HDL | 0.78 g/l | P&G TIDE ® 2X | 5 mM HEPES | 6 | 8.0 | 20 |
| WE | HDL | 5.0 g/L | Henkel Persil | 5 mM HEPES | 12 | 8.2 | 40 |
| WE | HDG | 8.0 g/L | P&G Ariel | 2 mM $Na_2CO_3$ | 12 | 10.5 | 40 |
| JPN | HDG | 0.7 g/L | P&G TIDE ® | 2 mM $Na_2CO_3$ | 6 | 10.0 | 20 |
| NA | HDG | 1.0 g/L | P&G TIDE ® | 2 mM $Na_2CO_3$ | 6 | 10.0 | 20 |
| Automatic Dish Washing | | | | | | | |
| WE | ADW | 3.0 g/L | RB Calgonit | 2 mM $Na_2CO_3$ | 21 | 10.0 | 40 |
| NA | ADW | 3.0 g/L | P&G Cascade | 2 mM $Na_2CO_3$ | 9 | 10.0 | 40 |

*Abbreviations: Procter & Gamble (P&G); and Reckitt Benckiser (RB).

F. Terg-O-Tometer Assay for Cleaning Performance Determination

A standard protocol for assessing protein and carbohydrate soil cleaning was used whereby the soil level on a fabric swatch was measured before and after cleaning under standard conditions. The fabric swatches consisted of woven cotton fabric soiled with either maize starch, rice starch or a blood, milk and carbon black mixture, and were purchased from Testfabrics, Inc. (West Pittiston, Pa.). Maize Starch (EMPA 161) and Blood, Milk, Carbon Black (EMPA 116) technical soils were produced by EMPA Test materials AG (St. Gallen, Switzerland). Rice Starch (CFT CS-28) soils were produced by the Center for Testmaterials BV (Vlaardingen, Netherlands). Each stain was measured before and after treatment by optical reflectance using a Minolta Reflectometer CR-410 set to a D65 (6500° K) standard illuminant. The difference in the L, a, b values was converted to total color difference (dE), as defined by the CIE-LAB color space. Cleaning of the stains are expressed as percent stain removal index (% SRI) by taking a ratio between the color difference before and after washing and comparing it to the difference of unwashed soils (before wash) to unsoiled fabric.

Cleaning experiments were conducted in a Terg-o-tometer (United States Testing Co., Hoboken, N.J.) equipped with 6 stainless steel 2 L pots fitted with overhead agitators. Each treatment was conducted in 1 L total volume consisting of either 6 grains per gallon 3:1 (calcium:magnesium) water hardness or 12 grains per gallon water hardness. Detergents used in the wash experiments were 1.5 g/L AATCC HDL WOB 2003 liquid detergent with 5 mM HEPES buffer at pH 8, 0.7 g/L AATCC HDD WOB 1993 granular detergent, 8 g/L IEC A* 60456 granular detergent with perborate and TAED bleach, or 5 g/L Persil Power Gel liquid detergent. Enzyme was added directly into the wash solution and reactions were then initiated by addition of either 40 g/L or 200 g/L of soiled and ballast fabric. The washing reactions were agitated at 100 rpm for 10, 15, or 40 minutes at 20° C., 25° C., 30° C., 40° C., or 50° C. Following cleaning, swatches were rinsed for 3 minutes in tap water, spun in a front-loading washing machine at 1000 rpm to remove excess water, and dried in a dryer at low heat on a permanent press cycle for approximately 45 minutes. Comparison of the extent of soil removal was assessed by reflectometry and expressed as the percent soil removal index (% SRI). The control condition did not contain enzyme and the positive control consisted of various doses of benchmark commercial enzymes.

G. Bodipy-Starch Assay for Determination of Amylase Activity

The Bodipy-starch assay was performed using the ENZCHEK® Ultra Amylase Assay Kit (E33651, Invitrogen). A 1 mg/mL stock solution of the DQ starch substrate was prepared by dissolving the contents of the vial containing the lyophilized substrate in 100 µL of 50 mM sodium acetate buffer at pH 4.0. The vial was vortexed for about 20 seconds and left at room temperature, in the dark, with occasional mixing until dissolved. 900 µL of assay buffer (50 mM sodium acetate with 2.6 mM $CaCl_2$ pH 5.8) was added and the vial vortexed for about 20 seconds. The substrate solution was stored at room temperature, in the dark, until ready to use or at 4° C. For the assay, a 100 µg/mL of working solution of the DQ substrate was prepared from the 1 mg/mL substrate solution in the assay buffer. 190 µL of 100 µg/mL substrate solution was added to each well in a 96-well flat-bottom microtiter plate. 10 µL of the enzyme samples were added to the wells, mix for 30 seconds using a thermomixer at 800 rpms. A blank sample that contains buffer and substrate only (no-enzyme blank) was included in the assay. The rate of change of fluorescence intensity was measured (excitation: 485 nm, emission: 520 nm) in a fluorescence microtiter plate reader at 25° C. for 5 minutes.

H. Corn Flour Hydrolysis for Determination of Amylase Activity

Starch Hydrolysis of Corn Flour Substrate Assay for Enymatic Activity. Organic corn flour (Azure Farms, lot no. 03227) was evenly spread into Greiner 96-well microplate, polypropylene, black, flat bottom chimney wells, (Cat. No. 655209), using a solids dispensing device (V&P Scientific). 85 μL of 20 mM sodium acetate pH 5.6 were added to each well and mixed. A foil seal was applied to the top of the plate and the plate pre-incubated at 70° C. in the Thermomixer for 20-30 minutes. Enzyme samples were diluted in Agilent polypropylene plate (5042-1385) in 20 mM sodium acetate buffer. 11 μL of diluted enzyme samples were added to the substrate plate and the plate sealed firmly with another foil. Plates were then transferred to Labnet VorTemp 56 Incubator/Shaker with metal blocks, (Cat. No. S2056A) pre-heated to 95° C. and the shake speed set to 500 rpm. The incubation was continued for 30 minutes. At the end of the incubation, the plates were rapidly cooled in an ice bucket and the starch hydrolysis reaction was stopped by addition of 100 μL of 0.1 N $H_2SO_4$ to each well. The plate was mixed briefly and the starch hydrolysis reaction products were either analyzed by the PAHBAH assay or HPLC.

Colorimetric detection of Soluble Sugar Concentrations from Enzymatic Hydrolysis of Corn Flour Substrate. Aliquots of 80 μL of 0.5 N NaOH were added to all wells of an empty PCR plate followed by 20 μL of PAHBAH reagent (5% w/v p-hydroxybenzoic acid hydrazide (PAHBAH, Sigma #H9882, dissolved in 0.5 N HCl) and mixed (PAHBAH reaction plate). 10 μL of the starch hydrolysis reaction supernatants were added to the PAHBAH reaction plate. All plates were sealed and placed in the thermocycler (MJ Research Tetrad), programmed for 2 minutes at 95° C., and then cooled to 20° C. Samples of 80 μL of the developed PAHBAH reaction mixtures were transferred to a read plate and absorbance was measured at 405 nm in a spectrophotometer.

HPLC Determination of Soluble Sugar Concentrations from Enzymatic Hydrolysis of Corn Flour Substrate. Soluble sugar standards (DP1-DP7) obtained from Sigma (St. Louis, Mo.) were all diluted in Milli-Q water to 100 mg/mL and used for converting peak area for the sugars to actual sugar concentrations. The quenched plate from the starch hydrolysis assay was spun in a Beckman Coulter Allegra 6R Centrifuge for 5 minutes at 3000 rpm 25° C. The supernatant was pipetted from the spun plate and transferred to a Multiscreen-HV filter plate (Catalog No. MAHVN4550). The filter plate was spun over an Agilent HPLC plate in the Hettich Rotanta centrifuge for 10 minutes at 6,000 rpm 25° C. 50 μL of 0.01 N sulfuric acid mobile phase (0.1 N sulfuric acid diluted 10× with Milli-Q water) was transferred to each well of another clean Agilent HPLC plate. The filtered plate was briefly mixed and 50 μL of the filtrate was transferred the corresponding wells in the plate with 50 μL per well of mobile phase. Diluted sugar standards were added to empty wells in the plate to be included in the calibration. The contents were mixed briefly on a platform shaker and the plate covered with a Nalgene Pre-slit Well Cap. The HPLC column (Bio-Rad Aminex HPX-87H column Cat No. 125-0140) was prepared ahead of time with 2 L of mobile phase running at a constant flow rate of 0.6 mL/minute. All samples in the plate were run with 20 μL injection volume and analyzed using AMINEXH.M and RID (refractive index) as the detector. After the run was completed, the flow rate in the HPLC was dropped down to 0.05 mL/min.

I. Determination of Starch Viscosity Reduction by Amylase

In this assay, viscosity reduction of corn starch substrate solution was measured in a viscometer. The corn starch substrate slurry was made up fresh in batch mode with 30% corn flour dry solids in distilled water and adjusted to pH 5.8 using sulfuric acid. For each run, 50 grams of the slurry (15 grams dry solids) was weighed out and pre-incubated for 10 minutes to warm up to 70° C. Upon amylase addition, the temperature was immediately ramped up from 70° C. to 85° C. with a rotation speed of 75 rpm. Once the temperature of the slurry and amylase mixture reached 85° C., the temperature was held constant and viscosity was monitored for an additional 30 minutes.

J. Measurement of Enzyme Binding to Macromolecular Substrates

Binding assays were done to determine substrate binding of Amylase (AmyS) charge ladder variants (charge change=−12 to +12 relative to wild-type AmyS) to corn stover and bagasse. Substrates used included bagasse (sugarcane bagasse from Brazil, dilute-acid pre-treated by National Renewable Energy Laboratory, washed and buffered at pH 5), AFEX (ammonia fiber expansion corn stover), and PCS (dilute sulfuric acid pre-treated corn stover, washed and adjusted to pH 5). All substrates were brought to the desired percentage solids prior to use.

Amylase Binding: Amylase charge ladder variants were purified and diluted to 200 ppm for testing. A 1% cellulose bagasse solution was prepared in borate buffer (40 mM, pH8.5, 0.016% Tween80). 150 μl of the bagasse solution was added into each well in a microtiter filtration plate. 150 μl of borate buffer was added into a set of separate wells, which served as controls. 10 μl of amylase charge ladder variants was added into the filtration plate, each condition was in duplicates. The plate was incubated at room temperature for 2 hours. The filtrate was collected and amylase activity in the supernatant was measured by BODIPY-starch assay.

Measurement of Enzyme Binding to Microswatches: Amylase variants were incubated with or without CS-28 rice starch microswatches under standard wash conditions for 30 min. The amount of free enzyme was measured by the BODIPY-starch assay. The fraction of enzyme bound to the microswatches was calculated as follows: Fraction bound= (Activity of enzyme in absence of swatch−Activity of enzyme in presence of swatch)/(Activity of enzyme in absence of swatch).

K. *Geobacillus stearothermophilus* Amylase Protein Quantitation

The *G. stearothermophilus* amylase protein was quantitated by competitive immunoassay. Briefly, purified *G. stearothermophilus* amylase was labeled with a fluorescent dye (fluorescein) and antibody to *G. stearothermophilus* amylase was labeled with a quencher dye (tetramethylrhodamine). The fluorescence signal of the fluorescein-amylase conjugate is quenched upon binding of the quencher-labeled antibody. The presence of free amylase in the sample competes for the quencher-labeled antibody, resulting in an increase of the fluorescence signal. Therefore, the strength of the fluorescence signal is proportional to the amount of free amylase in the sample. The assay was calibrated with purified *G. stearothermophilus* amylase of known concentrations.

Labeling of *G. stearothermophilus*_Amylase with Fluorescent Dye: Purified *Geobacillus stearothermophilus* amylase was labeled with fluorescein isothiocyanate (Molecular Probes, Eugene Oreg.) at pH 9.5 in 50 mM sodium carbonate buffer according to the manufacturer's protocol. At the end of the reaction, the protein was separated from unbound dye by gel filtration over Sephadex G-25 (Sigma, St Louis, Mo., USA) in phosphate-buffered saline.

Antibody Preparation and Labeling with Quencher Dye: Antibody to *Geobacillus stearothermophilus* amylase was prepared by immunization of rabbits and recovery of the antiserum. The antiserum was stored at −20° C. until use. Preparation of the immunoglobulin fraction by carried out by ammonium sulfate precipitation; 15 ml. 3.75 M ammonium sulfate was added to 20 ml antiserum and allowed to sit at 4° C. for 60 minutes before centrifugation at 2,000 g to recover the precipitate. The recovered precipitate was washed twice by resuspension and sedimentation in 10 ml ice-cold 1.6 M ammonium sulfate. The final precipitate was dissolved in 4 ml. water and dialyzed against 50 mM sodium carbonate pH 9.5 at 4° C. The protein concentration was estimated to be 29.2 mg/ml. by $A_{280}$ using the extinction coefficient $\in_{1\%}=15$. The immunoglobulin fraction was labeled with tetramethyl rhodamine isothiocyanate (Sigma, St. Louis, Mo.) in 50 mM sodium carbonate pH 9.5. Unbound dye was then removed by gel filtration on a column of Sephadex G-25 equilibrated with phosphate-buffered saline containing 0.1% deoxycholate.

Assay Procedure: The immunoassay was carried out in 96-well microtiter plates (Corning #3650). The concentration of the fluorescein-amylase was adjusted such that the final concentration in the assay would be the middle of the desired standard curve. Similarly, the concentration of the quencher-antibody was adjusted such that the final concentration would allow for maximum modulation of the fluorescence signal. Using an automated liquid handling system, 5 µL each of sample, fluorescein-amylase, and quencher antibody were added to 180 µL phosphate-buffered saline containing 2% (w/v) polyethylene glycol 8000 (Sigma, St. Louis, Mo., USA). After briefly shaking, the plates were allowed to incubate at room temperature for one hour the fluorescence signal was determined using a fluorescence plate reader (Molecular Devices) with excitation and emission filters set to 495 nm and 520 nm, respectively.

Example 13

Amylase Production in *B. subtilis*

In this Example, production of a mutant truncated form *G. stearothermophilus* amylase α amylase (having a S242Q mutation and a 29 amino acid deletion from the C-terminus; also referred to herein as S242Q) and variants thereof in *B. subtilis* are described. Transformation was performed as known in the art (see, e.g., WO 02/14490). Briefly, the gene encoding the parent amylases was cloned into the pHPLT expression vector, which contains the LAT promoter (PLAT), a sequence encoding the LAT signal peptide (preLAT), followed by PstI and HpaI restriction sites for cloning.

The coding region for the LAT signal peptide is shown below:

```
                                      (SEQ ID NO: 20)
atgaaacaac aaaaacggct ttacgcccga ttgctgacgc tgttatttgc gctcatcttc ttgctgcctc attctgcagc ttcagca.
```

The amino acid sequence of the LAT signal peptide is shown below:

MKQQKRLYAR LLTLLFALIF LLPHSAASA (SEQ ID NO: 21)

The amino acid sequence of the mature truncated S242Q amylase with the substituted amino acid shown in italics was used as the basis for making the variant libraries described herein:

```
                                      (SEQ ID NO: 22)
AAPFNGTMMQ YFEWYLPDDG TLWTKVANEA NNLSSLGITA

LWLPPAYKGT SRSDVGYGVY DLYDLGEFNQ KGTVRTKYGT

KAQYLQAIQA AHAAGMQVYA DVVFDHKGGA DGTEWVDAVE

VNPSDRNQEI SGTYQIQAWT KFDFPGRGNT YSSFKWRWYH

FDGVDWDESR KLSRIYKFRG IGKAWDWEVD TENGNYDYLM

YADLDMDHPE VVTELKNWGK WYVNTTNIDG FRLDAVKHIK

FQFFPDWLSY VRSQTGKPLF TVGEYWSYDI NKLHNYITKT

NGTMSLFDAP LHNKFYTASK SGGAFDMRTL MTNTLMKDQP

TLAVTFVDNH DTEPGQALQS WVDPWFKPLA YAFILTRQEG

YPCVFYGDYY GIPQYNIPSL KSKIDPLLIA RRDYAYGTQH

DYLDHSDIIG WTREGVTEKP GSGLAALITD GPGGSKWMYV

GKQHAGKVFY DLTGNRSDTV TINSDGWGEF KVNGGSVSVW

VPRKTT.
```

The coding region for the mature AmyS amylase is shown below:

```
                                      (SEQ ID NO: 23)
gccgcaccgt taacggtac catgatgcag tattttgaat ggtacttgcc ggatgatggc acgttatgga ccaaagtggc caatgaagcc aacaacttat ccagccttgg catcaccgct ctttggctgc cgcccgctta caaaggaaca agccgcagcg acgtagggta cggagtatac gacttgtatg acctcggcga attcaatcaa aaagggaccg tccgcacaaa atatggaaca aaagctcaat atcttcaagc cattcaagcc gcccacgccg ctggaatgca agtgtacgcc gatgtcgtgt tcgaccataa aggcggcgct gacggcacgg aatgggtgga cgccgtcgaa gtcaatccgt ccgaccgcaa ccaagaaatc tcgggcacct atcaaatcca agcatggacg aaatttgatt ttcccggcg gggcaacacc tactccagct ttaagtggcg ctggtaccat tttgacggcg ttgactggga cgaaagccga aaattaagcc gcatttacaa attccgcggc atcggcaaag cgtgggattg ggaagtagac acggaaaacg gaaactatga ctacttaatg tatgccgacc ttgatatgga tcatcccgaa gtcgtgaccg agctgaaaaa ctggggggaaa tggtatgtca acacaacgaa cattgatggg ttccggcttg atgccgtcaa gcatattaag ttcagttttt ttcctgattg gttgtcgtat gtgcgttctc agactggcaa gccgctattt accgtcgggg aatattggag ctatgacatc aacaagttgc acaattacat tacgaaaaca aacggaacga tgtctttgtt tgatgccccg ttacacaaca aatttatac cgcttccaaa tcaggggcg catttgatat gcgcacgtta atgaccaata ctctcatgaa agatcaaccg
```

```
acattggccg tcaccttcgt tgataatcat gacaccgaac ccggccaagc gctgcagtca tgggtcgacc catggttcaa accgttggct tacgccttta ttctaactcg gcaggaagga tacccgtgcg tcttttatgg tgactattat ggcattccac aatataacat tccttcgctg aaaagcaaaa tcgatccgct cctcatcgcg cgcagggatt atgcttacgg aacgcaacat gattatcttg atcactccga catcatcggg tggacaaggg aaggggtcac tgaaaaacca ggatccgggc tggccgcact gatcaccgat gggccgggag gaagcaaatg gatgtacgtt ggcaaacaac acgctggaaa agtgttctat gaccttaccg gcaaccggag tgacaccgtc accatcaaca gtgatggatg gggggaattc aaagtcaatg gcggttcggt ttcggtttgg gttcctagaa aaacgaccgt ttctaccatc gctcggccga tcacaacccg accgtggact ggtgaattcg tccgttggac cgaaccacgg ttggtggcat ggcct
```

The amino acid sequence of the mature AmyS amylase was used as the basis for making the AmyS variant libraries, and is provided as SEQ ID NO:2.

The PCR products were purified using Qiaquik columns from Qiagen, and resuspended in 50 µL of deionized water. 50 µL of the purified DNA was digested with HpaI (Roche) and PstI (Roche) and the resultant DNA resuspended in 30 µL of deionized water. 10-20 ng/µL of the DNA was cloned into plasmid pHPLT using PstI and HpaI cloning sites. The ligation mixtures were directly transformed into competent B. subtilis cells (genotype: Δvpr, ΔwprA, Δmpr-ybfj, ΔnprB). The B. subtilis cells have a competency gene (comK) which is placed under a xylose inducible promoter, so xylose was used to induce competency for DNA binding and uptake (see Hahn et al. (1996) Mol. Microbiol. 21:763-775).

The elements of plasmid pHPLT-AmyS include: pUB110=DNA fragment from plasmid pUB110 (McKenzie et al. (1986) Plasmid 15: 93-103). Plasmid features include: ori-pUB110=origin of replication from pUB110, neo=neomycin resistance gene from pUB110, Plat=transcriptional promoter from B. licheniformis amylase, Pre LAT=signal peptide from B. licheniformis amylase, SAMY 425ss=The coding region for truncated AmyS gene sequence (replaced by the coding regions for each truncated AmyS variant expressed in this study), Terminator=transcriptional terminator from B. licheniformis amylase.

Example 14

Expression of Enzyme Variants

This Example describes the methods used to express various recombinant enzymes of the transformed B. subtilis of the preceding Examples on a 2 ml scale.

B. subtilis clones containing AmyS (or a variant thereof) or S242Q (or a variant thereof) expression vectors were replicated with a steel 96-well replicator from glycerol stocks into 96-well culture plates (BD, 353075) containing 150 µl of LB media+10 µg/ml neomycin, grown overnight at 37° C., 220 rpm in a humidified enclosure. A 100 µl aliquot from the overnight culture was used to inoculate 2,000 µl defined media+10 µg/ml neomycin in 5 ml plastic culture tubes. The cultivation media was an enriched semi-defined media based on MOPS buffer, with urea as major nitrogen source, glucose as the main carbon source, and supplemented with 1% soytone and 5 mM calcium for robust cell growth. Culture tubes were incubated at 37° C., 250 rpm, for 72 hours. Following this incubation, the culture broths were centrifuged for 10 minutes at 3,000× g. The supernatant solution was decanted into 15 ml polypropylene conical tubes and 80 µL of each sample were aliquoted into 96 well plates for protein quantitation.

Example 15

Production of Enzyme Variants

This Example describes the production of enzyme charge ladders and combinatorial charge libraries.

Enzyme Charge Ladders

Multiple protein variants spanning a range of physical properties of interest are selected from existing libraries or are generated by site-directed mutagenesis techniques as known in the art (see, e.g., U.S. Pat. Pub. No. 2008-0293610). This defined set of probe proteins is then assayed in a test of interest.

Exemplary amylase charge ladder variants are shown in the following tables and assayed as described herein. In these tables, the charge change is relative to the parent enzyme.

The sequence of the AmyS gene was provided to Gene Oracle (Mountain View, Calif.) for the synthesis of the 28 charge ladder variants shown in Tables 15-1 and 15-2. Gene Oracle synthesized and cloned the AmyS variants into vector pGov4 and transformed them into E. coli. DNA isolated from minipreps, as well as an agar stab were supplied for each variant.

The variants were PCR amplified and cloned into the pHPLT B. subtilis expression vector. The variants were amplified as a PstI-HindIII fragment from plasmid pGov4 using primers:

```
Satori F
                                      (SEQ ID NO: 24)
5'-CTCATCTTCTTGCTGCCTCATTCTGCAGCTTC-3';
and Satori R
                                      (SEQ ID NO: 25)
5'-TTATCCTTTACCTTGTCTCCAAGC-3'.
```

The PCR products were purified using Qiagen Qiaquik columns, and resuspended in 50 µL of milliQ water. 50 µL of the purified DNA was digested with HindIII (Roche) and PstI (Roche) and the resultant DNA resuspended in 30 µL of deionized water. 10-20 ng/µL of the DNA was cloned into plasmid pHPLT using PstI and HpaI cloning sites. The ligation mixtures were directly transformed into competent B. subtilis cells (genotype: amyE::xylRPxylAcomK-phleo). These B. subtilis cells have a competency gene (comK) which is placed under a xylose inducible promoter, so xylose was used to induce competency for DNA binding and uptake.

TABLE 15-1

First AmyS Charge Ladder

| Number | AmyS Variant | Δ Charge |
|---|---|---|
| 1-6 | R308Q R483Q K171Q K383Q K447Q K471Q N28D N224D N271D N281D Q86E Q89E | −12 |
| 1-5 | R308Q R483Q K171Q K383Q K447Q N28D N224D N271D N281D Q86E | −10 |
| 1-4 | R308Q R483Q K171Q K383Q N28D N224D N271D N281D | −8 |
| 1-3 | R308Q R483Q K171Q N28D N224D N271D | −6 |
| 1-2 | R308Q R483Q N28D N224D | −4 |
| 1-1 | R308Q N28D | −2 |
| AmyS | Parent | 0 |
| 2-1 | D318N N28R | +2 |
| 2-2 | D318N D306N N28R N224R | +4 |
| 2-3 | D318N D306N D19N N28R N224R N271R | +6 |
| 2-4 | D318N D306N D19N D393N N28R N224R N271R N281R | +8 |
| 2-5 | D318N D306N D19N D393N D458N N28R N224R N271R N281R Q86R | +10 |
| 2-6 | D318N D306N D19N D393N D458N E29Q N28R N224R N271R N281R Q86R Q89R | +12 |

TABLE 15-2

Second AmyS Charge Ladder

| | AmyS Variant | Δ Charge |
|---|---|---|
| 3-7 | Q97R Q319R Q358E Q443E N28D N224D N271D N281D Q86E Q89E R308Q R483Q K171Q K383Q K447Q K471Q | −12 |
| 3-6 | Q97R Q319R Q358E Q443E N28D N224D N271D N281D Q86E R308Q R483Q K171Q K383Q K447Q | −10 |
| 3-5 | Q97R Q319R Q358E Q443E N28D N224D N271D N281D R308Q R483Q K171Q K383Q | −8 |
| 3-4 | Q97R Q319R Q358E Q443E N28D N224D N271D R308Q R483Q K171Q | −6 |
| 3-3 | Q97R Q319R Q358E Q443E N28D N224D R308Q R483Q | −4 |
| 3-2 | Q97R Q319R Q358E Q443E N28D | −2 |
| 3-1 | Q97R Q319R Q358E Q443E | 0 |
| 4-1 | Q97R Q319R Q358E Q443E N28K D318N | +2 |
| 4-2 | Q97R Q319R Q358E Q443E N28K N224K D318N D306N | +4 |
| 4-3 | Q97R Q319R Q358E Q443E N28K N224K N271K D318N D306N D19N | +6 |
| 4-4 | Q97R Q319R Q358E Q443E N28K N224K N271K N281K D318N D306N D19N D393N | +8 |
| 4-5 | Q97R Q319R Q358E Q443E N28K N224K N271K N281K Q86R D318N D306N D19N D393N D458N | +10 |
| 4-6 | Q97R Q319R Q358E Q443E N28K N224K N271K N281K Q86R Q89R D318N D306N D19N D393N D458N E29Q | +12 |
| 5-1 | Q97R Q319R Q358E Q443E N28D R308Q S242E | −3 |
| 5-2 | Q97R Q319R Q358E Q443E N28D N224D R308Q S242E | −4 |
| 5-3 | Q97R Q319R Q358E Q443E N28D N224D R308Q S242Q | −3 |

TABLE 15-3

AmyS-S242Q Charge Ladder

| AmyS-S242Q Variant | Δ Charge |
|---|---|
| Q97E-Q319E-Q358E-Q443E | −4 |
| Q97E-Q319E-Q358E | −3 |
| Q97E-Q319E | −2 |
| Q97E | −1 |
| Q97R-Q319E | 0 |
| Parent AmyS-S242Q | 0 |
| Q97R | +1 |
| Q97R-Q319R | +2 |
| Q97R-Q319R-Q358R | +3 |
| Q97R-Q319R-Q358R | +4 |

Enzyme Combinatorial Charge Libraries (CCL): Generation of *G. stearothermophilus* AmyS-S242Q CCL The AmyS-S242Q plasmid DNA was isolated from a transformed *B. subtilis* strain (gentoype: ΔaprE, ΔnprE, amyE::xylRPxylAcomK-phleo) and sent to DNA2.0 Inc. as the template for CCL construction. A request was made to DNA2.0 Inc. (Mountain View, Calif., USA) for the generation of positional libraries at each of the four sites in AmyS-S242Q (S242Q) amylase that are shown in Table 15-4. Variants were supplied as glycerol stocks in 96-well plates.

The AmyS S242Q combinatorial charge library was designed by identifying the following four residues: Gln-97, Gln 319, Gln 358, and Gln 443. A four site, 81-member CCL was created by making all combinations of three possibilities at each site: wild-type, arginine, or aspartic acid.

TABLE 15-4

S242Q CCL Variants

| Variant # | Q97 | Q319 | Q358 | Q443 | Δ Charge |
|---|---|---|---|---|---|
| 1 | Q97E | Q319E | Q358E | Q443E | −4 |
| 2 | Q97E | Q319E | Q358E | Q443R | −2 |
| 3 | Q97E | Q319E | Q358E | — | −3 |
| 4 | Q97E | Q319E | Q358E | Q443E | −2 |
| 5 | Q97E | Q319E | Q358E | Q443R | 0 |
| 6 | Q97E | Q319E | Q358R | — | −1 |
| 7 | Q97E | Q319E | — | Q443E | −3 |
| 8 | Q97E | Q319E | — | Q443R | −1 |
| 9 | Q97E | Q319E | — | — | −2 |
| 10 | Q97E | Q319R | Q358E | Q443E | −2 |
| 11 | Q97E | Q319R | Q358E | Q443R | 0 |
| 12 | Q97E | Q319R | Q358E | — | −1 |
| 13 | Q97E | Q319R | Q358R | Q443E | 0 |
| 14 | Q97E | Q319R | Q358R | Q443R | +2 |
| 15 | Q97E | Q319R | Q358R | — | +1 |
| 16 | Q97E | Q319R | — | Q443E | −1 |
| 17 | Q97E | Q319R | — | Q443R | +1 |
| 18 | Q97E | Q319R | — | — | 0 |
| 19 | Q97E | — | Q358E | Q443E | −3 |
| 20 | Q97E | — | Q358E | Q443R | −1 |
| 21 | Q97E | — | Q358E | — | −2 |
| 22 | Q97E | — | Q358R | Q443E | −1 |
| 23 | Q97E | — | Q358R | Q443R | +1 |
| 24 | Q97E | — | Q358R | — | 0 |
| 25 | Q97E | — | — | Q443E | −2 |
| 26 | Q97E | — | — | Q443R | 0 |
| 27 | Q97E | — | — | — | −1 |
| 28 | Q97R | Q319E | Q358E | Q443E | −2 |
| 29 | Q97R | Q319E | Q358E | Q443R | 0 |
| 30 | Q97R | Q319E | Q358E | — | −1 |
| 31 | Q97R | Q319E | Q358R | Q443E | 0 |
| 32 | Q97R | Q319E | Q358R | Q443R | +2 |
| 33 | Q97R | Q319E | Q358R | — | +1 |
| 34 | Q97R | Q319E | — | Q443E | −1 |
| 35 | Q97R | Q319E | — | Q443R | +1 |
| 36 | Q97R | Q319E | — | — | 0 |
| 37 | Q97R | Q319R | Q358E | Q443E | 0 |
| 38 | Q97R | Q319R | Q358E | Q443R | +2 |
| 39 | Q97R | Q319R | Q358E | — | +1 |
| 40 | Q97R | Q319R | Q358R | Q443E | +2 |
| 41 | Q97R | Q319R | Q358R | Q443R | +4 |
| 42 | Q97R | Q319R | Q358R | — | +3 |
| 43 | Q97R | Q319R | — | Q443E | +1 |
| 44 | Q97R | Q319R | — | Q443R | +3 |
| 45 | Q97R | Q319R | — | — | +2 |
| 46 | Q97R | — | Q358E | Q443E | −1 |
| 47 | Q97R | — | Q358E | Q443R | +1 |
| 48 | Q97R | — | Q358E | — | 0 |
| 49 | Q97R | — | Q358R | Q443E | +1 |
| 50 | Q97R | — | Q358R | Q443R | +3 |
| 51 | Q97R | — | Q358R | — | +2 |
| 52 | Q97R | — | — | Q443E | 0 |
| 53 | Q97R | — | — | Q443R | +2 |
| 54 | Q97R | — | — | — | +1 |
| 55 | — | Q319E | Q358E | Q443E | −3 |
| 56 | — | Q319E | Q358E | Q443R | −1 |
| 57 | — | Q319E | Q358E | — | −2 |
| 58 | — | Q319E | Q358R | Q443E | −1 |
| 59 | — | Q319E | Q358R | Q443R | +1 |
| 60 | — | Q319E | Q358R | — | 0 |
| 61 | — | Q319E | — | Q443E | −2 |
| 62 | — | Q319E | — | Q443R | 0 |

TABLE 15-4-continued

S242Q CCL Variants

| Variant # | Q97 | Q319 | Q358 | Q443 | Δ Charge |
|---|---|---|---|---|---|
| 63 | — | Q319E | — | — | −1 |
| 64 | — | Q319R | Q358E | Q443E | −1 |
| 65 | — | Q319R | Q358E | Q443R | +1 |
| 66 | — | Q319R | Q358E | — | 0 |
| 67 | — | Q319R | Q358R | Q443E | +1 |
| 68 | — | Q319R | Q358R | Q443R | +3 |
| 69 | — | Q319R | Q358R | — | +2 |
| 70 | — | Q319R | — | Q443E | 0 |
| 71 | — | Q319R | — | Q443R | +2 |
| 72 | — | Q319R | — | — | +1 |
| 73 | — | — | Q358E | Q443E | −2 |
| 74 | — | — | Q358E | Q443R | 0 |
| 75 | — | — | Q358E | — | −1 |
| 76 | — | — | Q358R | Q443E | 0 |
| 77 | — | — | Q358R | Q443R | +2 |
| 78 | — | — | Q358R | — | +1 |
| 79 | — | — | — | Q443E | −1 |
| 80 | — | — | — | Q443R | +1 |
| 81 (parent) | Q97 | Q319 | Q358 | Q443 | 0 |

Example 16

Enzyme Wash Performance

This Example describes the testing of S242Q variant in a microswatch assay 1.0 μg/ml in AATCC HDL detergent or 5 mM HEPES buffer under varying ionic strength. The methods provided in Example 12 were used (see, e.g., "Rice Starch Microswatch Assay for testing Amylase Performance").

There is an optimal net charge change for cleaning performance for enzyme in AATCC HDL detergent. Performance is measured in terms of relative cleaning performance observed in a rice starch microswatch activity assay. A value of around 1.0 indicates top cleaning performance in this assay. This is an example of optimizing a protein physical property (e.g., net charge) for improving a given outcome or benefit (e.g., cleaning performance in a liquid laundry detergent). The charge optimum identified with this limited set of probe proteins coincides with the optimum charge observed when measuring the entire charge combinatorial library. The use of probe proteins is therefore predictive of the behavior of the entire library.

According to the Debye-Hückel theory (Israelachivili, Intermolecular and Surface Forces, Second Edition: With Applications to Colloidal and Biological Systems, Academic Press $2^{nd}$ Ed. [1992]), electrostatic interactions are governed primarily by the strength of double-layer forces between interacting species at constant potential or constant charge (enzymes, substrates, fabric, and detergent), their size, and the dielectric constant of the surrounding medium. In order to characterize the electrostatic behavior of particles in a complex medium, such as a detergent formulation, their interaction in a reduced environment possessing the same Debye screening length is sufficient. This was accomplished by choosing a buffer of matching pH and conductivity to that of the detergent under wash conditions. An appropriate buffer for such testing is 5 mM HEPES buffer at pH 8.0 with varying amounts of indifferent electrolyte, such as NaCl. Addition of 2.5 mM NaCl to this buffer matches the pH and conductivity of typical North American wash conditions. Addition of 100 mM NaCl is representative of Japanese and European wash conditions, typically higher in ionic strength due to both increased water hardness and detergent concentrations.

Figure 23:
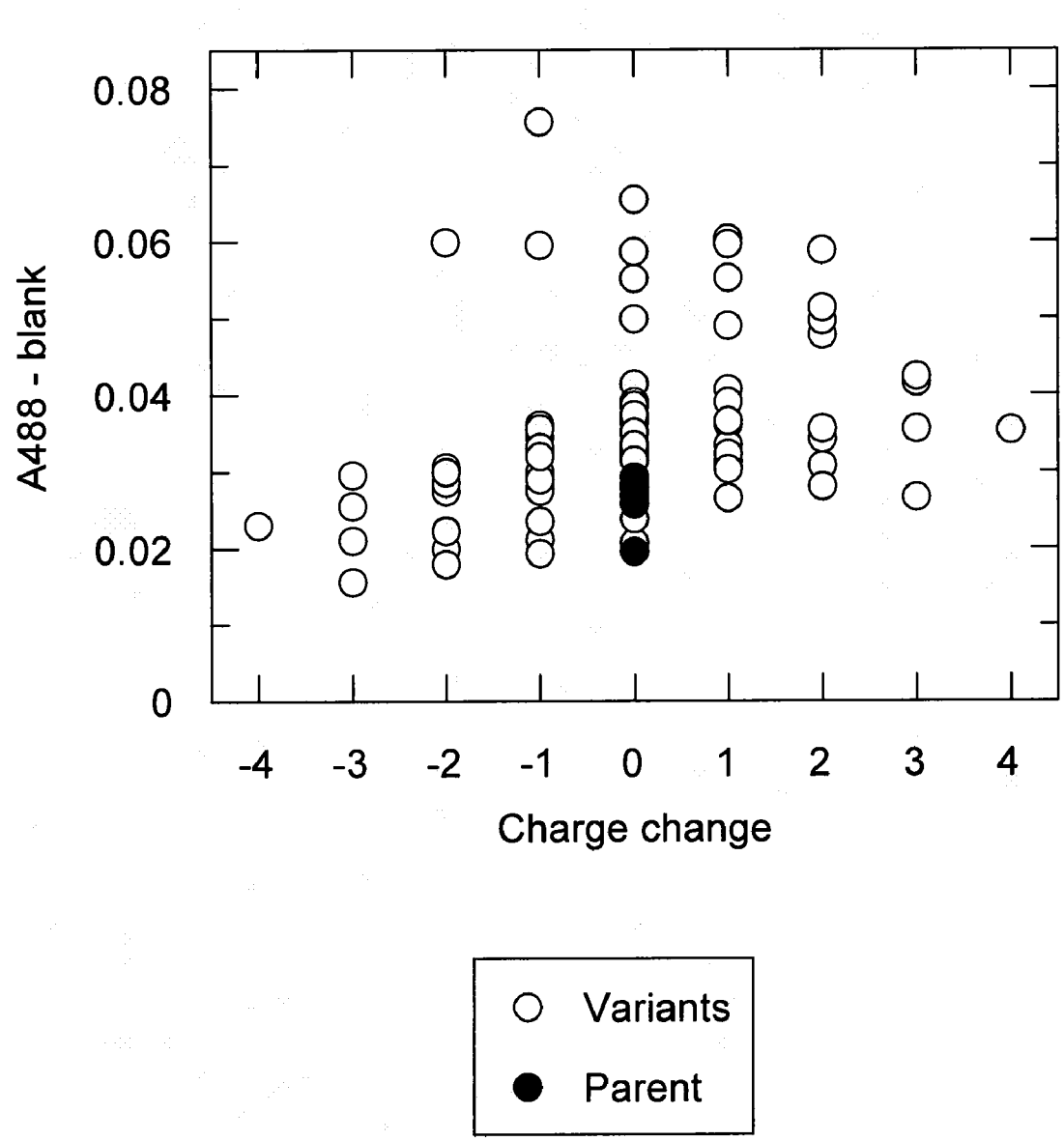
FIG. 23 is a graph depicting the performance of S242Q and its variants in the rice starch microswatch assay as a function of charge under North American laundry conditions. The conditions were TIDE® 2× at 20° C. Reference is made to Example 16.
Figure 24:
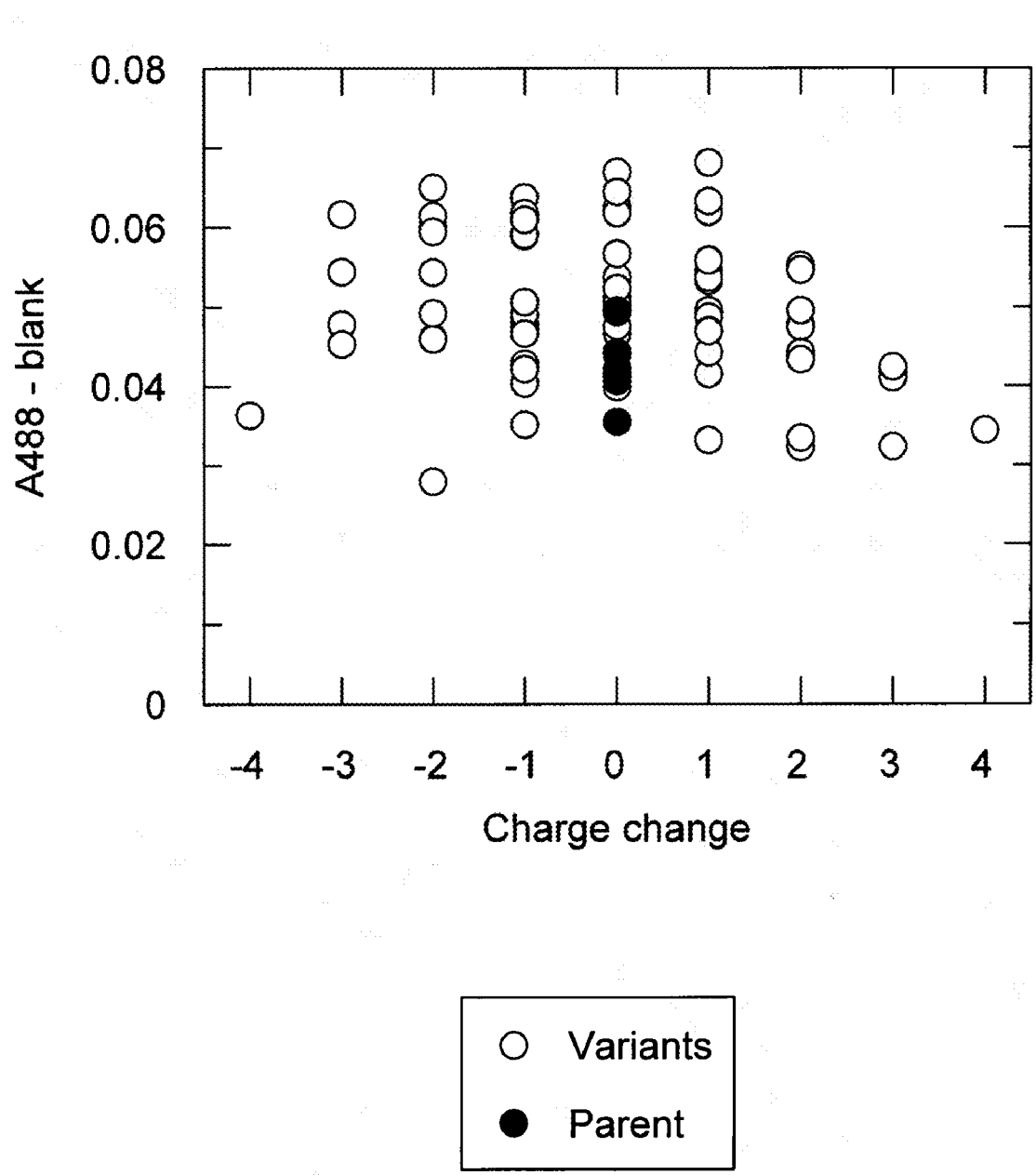
FIG. 24 is a graph depicting the performance of another α-amylase (i.e., truncated *Bacillus* sp. TS-23 amylase with the charge mutations in the rice starch microswatch assay under Western European laundry conditions. The conditions were PERSIL® at 40° C. Reference is made to Example 16.
Figure 25:
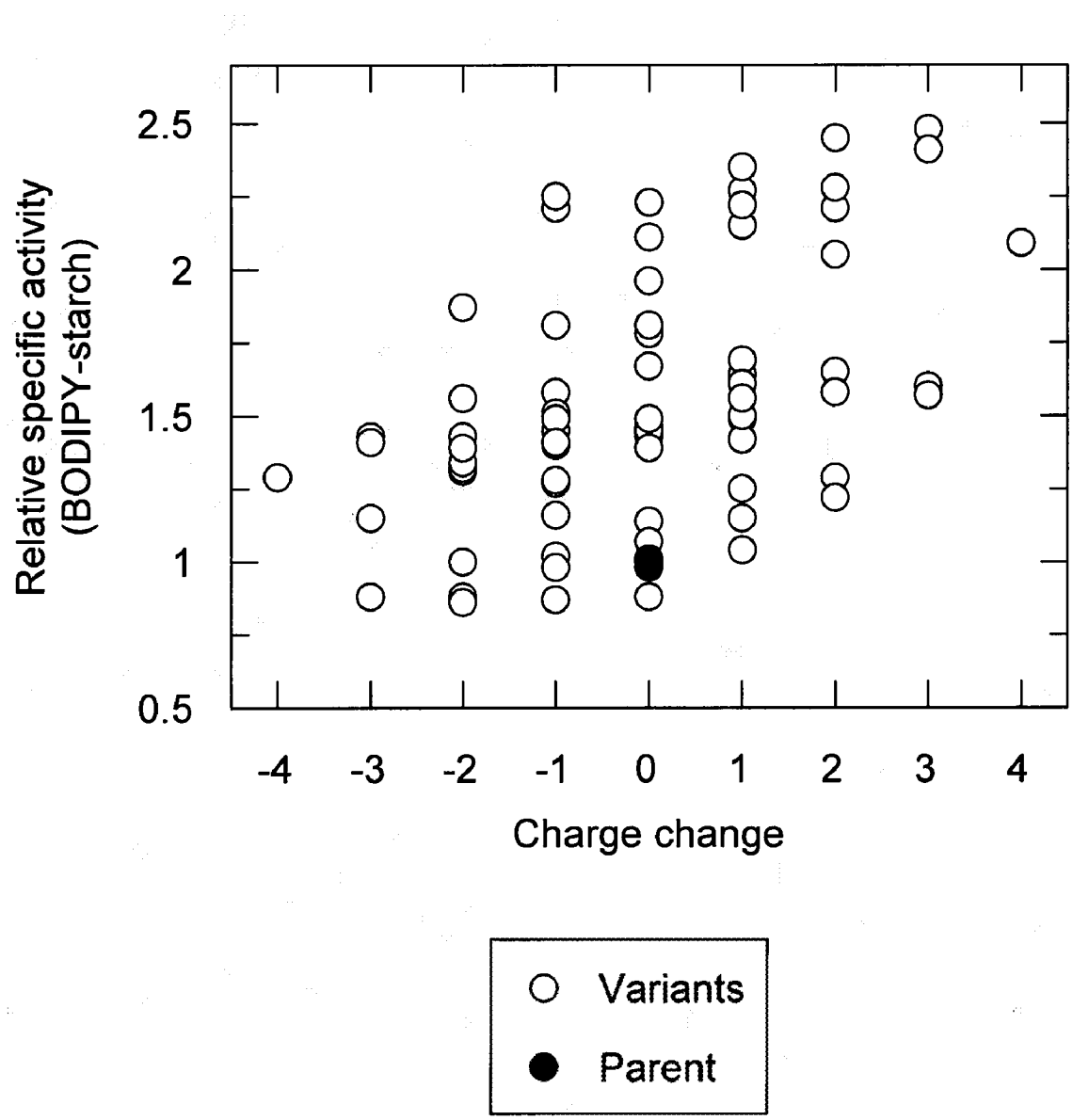
FIG. 25 is a graph depicting the performance of S242Q and its variants in the BODIPY-starch assay as a function of charge. Reference is made to Example 16.

FIG. 23 shows that positive charge S242Q variants were superior for cleaning of rice starch microswatch under North American laundry conditions. Similarly, positive charge variants of another α-amylase (i.e., TS23t) were superior for cleaning of rice starch microswatch under North American laundry conditions (FIG. 24), demonstrating that charge mutations have a similar effect in different α-amylases. Positive charge S242Q variants also exhibit higher specific activity for granular corn starch substrates hydrolysis (FIG. 25).

Starch liquefaction by the AmyS charge ladder variants was determined by monitoring the final viscosity following liquefaction of corn starch. A low viscosity value is indicative of breakdown of starch polysaccharides. As shown in FIG. 14 a charge optimum (e.g., −4 to −2) was observed for liquefaction. AmyS variants that were too negative (e.g., −12 to −10) exhibited very high final viscosities, and variants that were too positive (e.g., +6 or greater) exhibited even higher final viscosities (e.g., beyond limits of lab instrumentation due to torque overload).

Example 17

Thermostability

This Example describes determining the relationship between protein charge and thermal stability. Amylase assays were based on BODIPY starch hydrolysis before and after heating the culture supernatant. The same chemical and reagent solutions were used as described in Example 12.

Thermal Stability Assay for α-amylases

The filtered culture supernatants were serially diluted in 50 mM sodium acetate+2 mM $CaCl_2$ pH 5.8 with 0.002% Tween. 10 μl of each diluted culture supernatant was assayed to determine the initial amylase activity by the BODIPY starch assay. 50 μl of each diluted culture supernatant was placed in a VWR low profile PCR 96 well plate. 30 μl of mineral oil was added to each well as a sealant. The plate was incubated in a BioRad DNA engine Peltier Thermal Cycler at 95° C. for 30 or 60 minutes depending on the stability of the parent enzyme. Following incubation, the plate was cooled to 4° C. for 5 min and then kept at room temperature. 10 μl of each sample was added to a fresh plate and assayed to determine the final amylase activity by the BODIPY starch assay as described in Example 1.

Calculation of Thermostability

The residual activity of a sample was expressed as the ratio of the final absorbance and the initial absorbance, both corrected for blanks. A higher index indicates a more thermally stable variant. This is an example of optimizing a protein physical property, in this case net charge, for improving enzyme thermal stability for a liquid laundry application.

Figure 30:
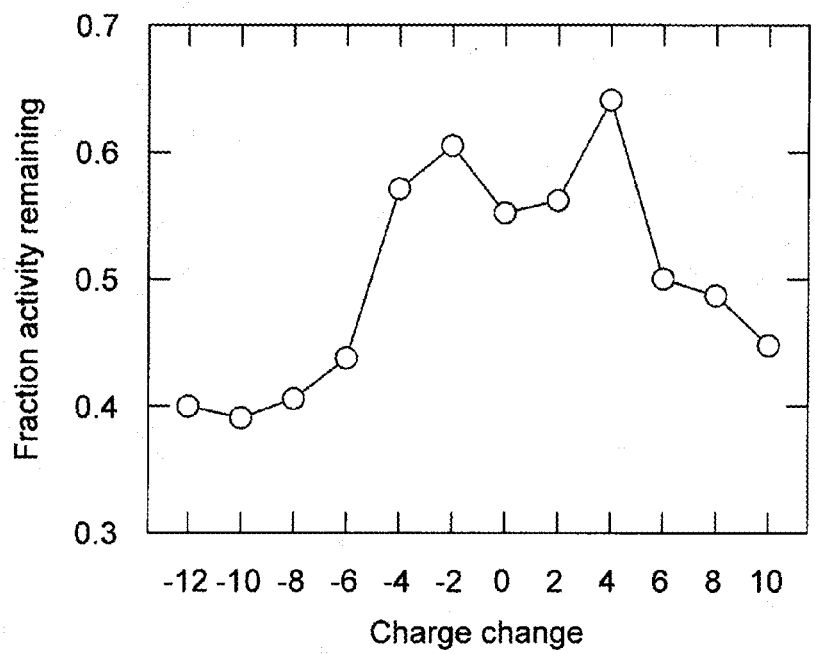
FIG. 30 is a graph depicting the thermal stability of the first AmyS charge ladder as a function of charge change relative to wild type. Experiment performed using standard amylase thermal stability assay. Reference is made to Example 17.

Thermostability of the variants were assessed as described above. Thermostability winners from the S242Q CCL are listed in Table 17-1. Winners were defined as those having a ratio of mutant residual activity to parent (i.e., S242Q) residual activity greater than 1. FIG. 30 shows the residual activity of the AmyS first charge ladder as a function of charge change relative to wild type. The thermal stability employed in this assay is described in example 12. Once again as evidenced from the Figure accumulation of extreme negative charges (−12) or positive charges (+4) relative to the wild type enzyme are detrimental for thermal stability. This is an example of optimizing a protein physical property, in this case net charge, for improving enzyme thermal stability for a liquid laundry application.

TABLE 17-1

S242Q CCL - thermal stability winners

| Variant # | 97 | 319 | 358 | 443 | Mut residual act./WT residual act. |
|---|---|---|---|---|---|
| 2 | Q97E | Q319E | Q358E | Q443R | 1.12 |
| 10 | Q97E | Q319R | Q358E | Q443E | 1.12 |
| 13 | Q97E | Q319R | Q358R | Q443E | 1.36 |
| 14 | Q97E | Q319R | Q358R | Q443R | 1.16 |
| 15 | Q97E | Q319R | Q358R | | 1.37 |
| 17 | Q97E | Q319R | | Q443R | 1.29 |
| 18 | Q97E | Q319R | | | 1.11 |
| 27 | Q97E | | | | 1.16 |
| 32 | Q97R | Q319E | Q358R | Q443R | 1.18 |
| 37 | Q97R | Q319R | Q358E | Q443E | 1.29 |
| 38 | Q97R | Q319R | Q358E | Q443R | 1.22 |
| 39 | Q97R | Q319R | Q358E | | 1.21 |
| 40 | Q97R | Q319R | Q358R | Q443E | 1.20 |
| 41 | Q97R | Q319R | Q358R | Q443R | 1.26 |
| 42 | Q97R | Q319R | Q358R | | 1.48 |
| 43 | Q97R | Q319R | | Q443E | 1.21 |
| 44 | Q97R | Q319R | | Q443R | 1.21 |
| 45 | Q97R | Q319R | | | 1.14 |
| 50 | Q97R | | Q358R | Q443R | 1.14 |
| 62 | | Q319E | | Q443R | 1.26 |
| 63 | | Q319E | | | 1.18 |
| 64 | | Q319R | Q358E | Q443E | 1.19 |
| 65 | | Q319R | Q358E | Q443R | 1.28 |
| 68 | | Q319R | Q358R | Q443R | 1.14 |
| 70 | | Q319R | | Q443E | 1.22 |
| 73 | | | Q358E | Q443E | 1.15 |
| 74 | | | Q358E | Q443R | 1.15 |
| 75 | | | Q358E | | 1.18 |

Example 18

Enzyme Performance

This Example demonstrates that enzyme performance may be affected by charge. Enzyme performance was assessed using heat inactivated detergents as described above in Example 12. Winners were defined as those having Performance Index (PI) a greater than 1. PI is the ratio of mutant residual activity to parent (i.e., S242Q) residual activity. Results are shown in Tables 18-1 and 18-2.

TABLE 18-1

S242Q CCL - CS-28 rice starch microswatch winners, Tide 2x (North American conditions as described in Example 12)

| Variant # | 97 | 319 | 358 | 443 | rel charge | PI |
|---|---|---|---|---|---|---|
| 13 | Q97E | Q319R | Q358R | Q443E | 0 | 1.44 |
| 14 | Q97E | Q319R | Q358R | Q443R | 2 | 1.32 |
| 15 | Q97E | Q319R | Q358R | | 1 | 1.40 |
| 16 | Q97E | Q319R | | Q443E | -1 | 1.33 |
| 17 | Q97E | Q319R | | Q443R | 1 | 1.40 |
| 18 | Q97E | Q319R | | | 0 | 1.41 |
| 20 | Q97E | | Q358E | Q443R | -1 | 1.15 |
| 23 | Q97E | | Q358R | Q443R | 1 | 1.21 |
| 25 | Q97E | | | Q443E | -2 | 1.18 |
| 26 | Q97E | | | Q443R | 0 | 1.25 |
| 27 | Q97E | | | | -1 | 1.16 |
| 28 | Q97R | Q319E | Q358E | Q443E | -2 | 2.32 |
| 29 | Q97R | Q319E | Q358E | Q443R | 0 | 2.54 |
| 30 | Q97R | Q319E | Q358E | | -1 | 2.93 |
| 31 | Q97R | Q319E | Q358R | Q443E | 0 | 2.27 |
| 32 | Q97R | Q319E | Q358R | Q443R | 2 | 2.28 |
| 33 | Q97R | Q319E | Q358R | | 1 | 2.34 |
| 34 | Q97R | Q319E | | Q443E | -1 | 2.31 |
| 35 | Q97R | Q319E | | Q443R | 1 | 2.31 |
| 36 | Q97R | Q319E | | | 0 | 2.14 |
| 37 | Q97R | Q319R | Q358E | Q443E | 0 | 1.93 |
| 38 | Q97R | Q319R | Q358E | Q443R | 2 | 1.85 |
| 39 | Q97R | Q319R | Q358E | | 1 | 2.14 |
| 40 | Q97R | Q319R | Q358R | Q443E | 2 | 1.92 |
| 41 | Q97R | Q319R | Q358R | Q443R | 4 | 1.37 |
| 42 | Q97R | Q319R | Q358R | | 3 | 1.61 |
| 43 | Q97R | Q319R | | Q443E | 1 | 1.90 |
| 44 | Q97R | Q319R | | Q443R | 3 | 1.64 |
| 45 | Q97R | Q319R | | | 2 | 1.99 |
| 46 | Q97R | | Q358E | Q443E | -1 | 1.40 |
| 47 | Q97R | | Q358E | Q443R | 1 | 1.29 |
| 48 | Q97R | | Q358E | | 0 | 1.60 |
| 49 | Q97R | | Q358R | Q443E | 1 | 1.57 |
| 50 | Q97R | | Q358R | Q443R | 3 | 1.38 |
| 51 | Q97R | | Q358R | | 2 | 1.37 |
| 52 | Q97R | | | Q443E | 0 | 1.51 |
| 54 | Q97R | | | | 1 | 1.51 |
| 55 | | Q319E | Q358E | Q443E | -3 | 1.14 |
| 56 | | Q319E | Q358E | Q443R | -1 | 1.38 |
| 57 | | Q319E | Q358E | | -2 | 1.10 |
| 58 | | Q319E | Q358R | Q443E | -1 | 1.25 |
| 59 | | Q319E | Q358R | Q443R | 1 | 1.41 |
| 60 | | Q319E | Q358R | | 0 | 1.49 |
| 61 | | Q319E | | Q443E | -2 | 1.16 |
| 62 | | Q319E | | Q443R | 0 | 1.45 |
| 63 | | Q319E | | | -1 | 1.28 |
| 64 | | Q319R | Q358E | Q443E | -1 | 1.12 |
| 65 | | Q319R | Q358E | Q443R | 1 | 1.19 |
| 66 | | Q319R | Q358E | | 0 | 1.36 |
| 67 | | Q319R | Q358R | Q443E | 1 | 1.24 |
| 69 | | Q319R | Q358R | | 2 | 1.19 |
| 70 | | Q319R | | Q443E | 0 | 1.29 |
| 76 | | | Q358E | Q443E | 0 | 1.22 |
| 78 | | | Q358R | | 1 | 1.25 |
| 79 | | | | Q443E | -1 | 1.24 |
| 80 | | | | Q443R | 1 | 1.17 |

TABLE 18-2

S242Q CCL - CS-28 rice starch microswatch winners, Persil (Western European conditions)

| Variant # | 97 | 319 | 358 | 443 | rel charge | PI |
|---|---|---|---|---|---|---|
| 2 | Q97E | Q319E | Q358E | Q443R | -2 | 1.41 |
| 3 | Q97E | Q319E | Q358E | | -3 | 1.94 |
| 4 | Q97E | Q319E | Q358R | Q443E | -2 | 1.61 |
| 5 | Q97E | Q319E | Q358R | Q443R | 0 | 1.39 |
| 6 | Q97E | Q319E | Q358R | | -1 | 2.04 |
| 7 | Q97E | Q319E | | Q443E | -3 | 2.05 |
| 8 | Q97E | Q319E | | Q443R | -1 | 1.84 |
| 9 | Q97E | Q319E | | | -2 | 2.27 |
| 10 | Q97E | Q319R | Q358E | Q443E | -2 | 1.35 |
| 13 | Q97E | Q319R | Q358R | Q443E | 0 | 1.45 |
| 14 | Q97E | Q319R | Q358R | Q443R | 2 | 1.17 |
| 15 | Q97E | Q319R | Q358R | | 1 | 1.22 |
| 16 | Q97E | Q319R | | Q443E | -1 | 1.26 |
| 17 | Q97E | Q319R | | Q443R | 1 | 1.29 |
| 18 | Q97E | Q319R | | | 0 | 1.76 |
| 26 | Q97E | | | Q443R | 0 | 1.36 |
| 27 | Q97E | | | | -1 | 1.31 |
| 28 | Q97R | Q319E | Q358E | Q443E | -2 | 2.21 |
| 29 | Q97R | Q319E | Q358E | Q443R | 0 | 1.96 |
| 30 | Q97R | Q319E | Q358E | | -1 | 1.94 |
| 31 | Q97R | Q319E | Q358R | Q443E | 0 | 2.11 |
| 32 | Q97R | Q319E | Q358R | Q443R | 2 | 1.87 |
| 33 | Q97R | Q319E | Q358R | | 1 | 2.41 |
| 34 | Q97R | Q319E | | Q443E | -1 | 2.20 |
| 35 | Q97R | Q319E | | Q443R | 1 | 2.21 |
| 36 | Q97R | Q319E | | | 0 | 2.07 |
| 37 | Q97R | Q319R | Q358E | Q443E | 0 | 1.86 |
| 38 | Q97R | Q319R | Q358E | Q443R | 2 | 1.83 |
| 39 | Q97R | Q319R | Q358E | | 1 | 1.99 |

TABLE 18-2-continued

S242Q CCL - CS-28 rice starch microswatch winners, Persil (Western European conditions)

| Variant # | 97 | 319 | 358 | 443 | rel charge | PI |
|---|---|---|---|---|---|---|
| 40 | Q97R | Q319R | Q358R | Q443E | 2 | 1.85 |
| 41 | Q97R | Q319R | Q358R | Q443R | 4 | 1.36 |
| 42 | Q97R | Q319R | Q358R |  | 3 | 1.90 |
| 43 | Q97R | Q319R |  | Q443E | 1 | 1.99 |
| 44 | Q97R | Q319R |  | Q443R | 3 | 1.94 |
| 45 | Q97R | Q319R |  |  | 2 | 1.75 |
| 46 | Q97R |  | Q358R | Q443E | -1 | 1.71 |
| 47 | Q97R |  | Q358E | Q443R | 1 | 1.39 |
| 48 | Q97R |  | Q358E |  | 0 | 1.85 |
| 50 | Q97R |  | Q358R | Q443R | 3 | 1.24 |
| 51 | Q97R |  | Q358R |  | 2 | 1.36 |
| 52 | Q97R |  |  | Q443E | 0 | 1.25 |
| 54 | Q97R |  |  |  | 1 | 1.88 |
| 55 |  | Q319E | Q358E | Q443E | -3 | 1.12 |
| 56 |  | Q319E | Q358E | Q443R | -1 | 1.17 |
| 58 |  | Q319E | Q358R | Q443E | -1 | 1.16 |
| 59 |  | Q319E | Q358R | Q443R | 1 | 1.25 |
| 60 |  | Q319E | Q358R |  | 0 | 1.50 |
| 63 |  | Q319E |  |  | -1 | 1.36 |
| 64 |  | Q319R | Q358E | Q443E | -1 | 1.10 |
| 65 |  | Q319R | Q358E | Q443R | 1 | 1.18 |
| 66 |  | Q319R | Q358E |  | 0 | 1.25 |
| 67 |  | Q319R | Q358R | Q443E | 1 | 1.29 |
| 70 |  | Q319R |  | Q443E | 0 | 1.15 |

Activity was also measured using the BODIPY starch hydrolysis assay as provided herein. The results are shown in Table 18-3. A relative specific activity on this starch substrate (a corn starch) greater than 1 indicates the variant has higher specific activity than the S242Q parent. Relative ppm is the expression titer of the variant relative to the parent, greater than 1 indicates higher titers (in shake tubes) than the S242Q parent.

TABLE 18-3

S242Q CCL - titer and/or BODIPY-starch winners

| Variant # | 97 | 319 | 358 | 443 | Charge | Rel ppm | Rel Sp act |
|---|---|---|---|---|---|---|---|
| 1 | Q97E | Q319E | Q358E | Q443E | -4 | 1.27 | 1.29 |
| 2 | Q97E | Q319E | Q358E | Q443R | -2 | 1.19 | 1.31 |
| 3 | Q97E | Q319E | Q358E |  | -3 | 1.00 | 1.43 |
| 4 | Q97E | Q319E | Q358R | Q443E | -2 | 1.23 | 1.43 |
| 5 | Q97E | Q319E | Q358R | Q443R | 0 | 0.94 | 1.78 |
| 6 | Q97E | Q319E | Q358R |  | -1 | 0.89 | 1.81 |
| 7 | Q97E | Q319E |  | Q443E | -3 | 1.40 | 1.41 |
| 8 | Q97E | Q319E |  | Q443R | -1 | 1.12 | 1.58 |
| 9 | Q97E | Q319E |  |  | -2 | 1.09 | 1.56 |
| 10 | Q97E | Q319R | Q358E | Q443E | -2 | 1.45 | 1.32 |
| 11 | Q97E | Q319R | Q358E | Q443R | 0 | 1.32 | 1.49 |
| 12 | Q97E | Q319R | Q358E |  | -1 | 1.58 | 1.27 |
| 13 | Q97E | Q319R | Q358R | Q443E | 0 | 0.65 | 1.44 |
| 14 | Q97E | Q319R | Q358R | Q443R | 2 | 0.66 | 1.65 |
| 15 | Q97E | Q319R | Q358R |  | 1 | 0.80 | 1.64 |
| 16 | Q97E | Q319R |  | Q443E | -1 | 1.09 | 1.51 |
| 17 | Q97E | Q319R |  | Q443R | 1 | 1.00 | 1.42 |
| 18 | Q97E | Q319R |  |  | 0 | 0.87 | 1.78 |
| 19 | Q97E |  | Q358E | Q443E | -3 | 1.22 | 0.88 |
| 21 | Q97E |  | Q358E |  | -2 | 1.12 | 0.88 |
| 22 | Q97E |  | Q358R | Q443E | -1 | 0.91 | 1.16 |
| 23 | Q97E |  | Q358R | Q443R | 1 | 0.78 | 1.25 |
| 24 | Q97E |  | Q358R |  | 0 | 1.08 | 1.14 |
| 25 | Q97E |  |  | Q443E | -2 | 1.12 | 1.00 |
| 28 | Q97R | Q319E | Q358E | Q443E | -2 | 0.78 | 1.87 |
| 29 | Q97R | Q319E | Q358E | Q443R | 0 | 0.80 | 1.81 |
| 30 | Q97R | Q319E | Q358E |  | -1 | 0.68 | 2.21 |
| 31 | Q97R | Q319E | Q358R | Q443E | 0 | 0.68 | 1.96 |
| 32 | Q97R | Q319E | Q358R | Q443R | 2 | 0.70 | 2.05 |
| 33 | Q97R | Q319E | Q358R |  | 1 | 0.60 | 2.27 |
| 34 | Q97R | Q319E |  | Q443E | -1 | 0.65 | 2.25 |
| 35 | Q97R | Q319E |  | Q443R | 1 | 0.70 | 2.15 |
| 36 | Q97R | Q319E |  |  | 0 | 0.73 | 2.23 |
| 37 | Q97R | Q319R | Q358E | Q443E | 0 | 0.93 | 2.11 |
| 38 | Q97R | Q319R | Q358E | Q443R | 2 | 0.65 | 2.21 |
| 39 | Q97R | Q319R | Q358E |  | 1 | 0.82 | 2.22 |
| 40 | Q97R | Q319R | Q358R | Q443E | 2 | 0.74 | 2.28 |
| 41 | Q97R | Q319R | Q358R | Q443R | 4 | 0.55 | 2.09 |
| 42 | Q97R | Q319R | Q358R |  | 3 | 0.67 | 2.48 |
| 43 | Q97R | Q319R |  | Q443E | 1 | 0.84 | 2.35 |
| 44 | Q97R | Q319R |  | Q443R | 3 | 0.73 | 2.41 |
| 45 | Q97R | Q319R |  |  | 2 | 0.76 | 2.45 |
| 46 | Q97R |  | Q358E | Q443E | -1 | 0.79 | 1.45 |
| 47 | Q97R |  | Q358E | Q443R | 1 | 0.75 | 1.42 |
| 48 | Q97R |  | Q358E |  | 0 | 0.82 | 1.46 |
| 49 | Q97R |  | Q358R | Q443E | 1 | 0.67 | 1.69 |
| 50 | Q97R |  | Q358R | Q443R | 3 | 0.60 | 1.60 |
| 51 | Q97R |  | Q358R |  | 2 | 0.64 | 1.29 |
| 52 | Q97R |  |  | Q443E | 0 | 0.83 | 1.43 |
| 54 | Q97R |  |  |  | 1 | 0.72 | 1.49 |
| 55 |  | Q319E | Q358E | Q443E | -3 | 0.99 | 1.15 |
| 56 |  | Q319E | Q358E | Q443R | -1 | 0.77 | 1.40 |
| 57 |  | Q319E | Q358E |  | -2 | 0.83 | 1.34 |
| 58 |  | Q319E | Q358R | Q443E | -1 | 0.73 | 1.49 |
| 59 |  | Q319E | Q358R | Q443R | 1 | 0.67 | 1.61 |
| 60 |  | Q319E | Q358R |  | 0 | 0.80 | 1.67 |
| 61 |  | Q319E |  | Q443E | -2 | 0.91 | 1.39 |
| 62 |  | Q319E |  | Q443R | 0 | 0.73 | 1.45 |
| 63 |  | Q319E |  |  | -1 | 0.75 | 1.41 |
| 64 |  | Q319R | Q358E | Q443E | -1 | 1.05 | 1.28 |
| 65 |  | Q319R | Q358E | Q443R | 1 | 0.94 | 1.42 |
| 66 |  | Q319R | Q358E |  | 0 | 0.96 | 1.39 |
| 67 |  | Q319R | Q358R | Q443E | 1 | 1.02 | 1.50 |
| 68 |  | Q319R | Q358R | Q443R | 3 | 0.71 | 1.57 |
| 69 |  | Q319R | Q358R |  | 2 | 0.71 | 1.58 |
| 70 |  | Q319R |  | Q443E | 0 | 0.91 | 1.49 |
| 72 |  | Q319R |  |  | 1 | 0.95 | 1.56 |
| 77 |  |  | Q358R | Q443R | 2 | 0.67 | 1.22 |
| 78 |  |  | Q358R |  | 1 | 0.66 | 1.15 |

Example 19

Balancing Mutational Effects on Amylase Activity and Expression

This Example illustrates that two conflicting enzyme properties can be simultaneously optimized by the introduction of multiple amino acid substitutions.

As determined during development of the present invention, the median expression of AmyS-242Q decreased with increasing positive charge. However, specific BODIPY starch hydrolysis increased with increasing positive charge. Enhanced recombinant amylase expression and starch hydrolysis are desirable in an engineered variant of AmyS-242Q suitable for starch liquefaction in the fuel ethanol industry or cleaning in detergent applications for instance. These properties, however, are apparently conflicting properties. As determined during development of the present invention, using the methods of the present invention, it is possible to produce a more highly expressed amylase variant without severely compromising starch hydrolysis by selectively combining single mutations. The strategy described herein was successfully used to produce and select multiply-substituted AmyS-242Q variants having improvements in a first property (e.g., expression as the primary property), while improving or not sacrificing a second property (e.g., starch hydrolysis as the secondary property).

In addition, in converse to median expression of AmyS-242Q variants, corn starch microswatch cleaning increased with increasing positive charge. Enhanced recombinant amylase expression and cleaning performance are desirable in an engineered variant of AmyS-242Q. These properties, however, are also apparently conflicting properties. As determined during development of the present invention, using the methods of the present invention, it is possible to produce a more highly expressed amylase variant without severely compromising cleaning performance by selectively combining single mutations. The strategy described herein was successfully used to produce and select multiply-substituted AmyS-242Q variants having improvements in a first property (e.g., expression as the primary property), while improving or not sacrificing a second property (e.g., rice starch microswatch cleaning as the secondary property).

In particular, an eighty member AmyS-S242Q charge combinatorial library (CCL) comprising variants having combinations of from one to four substitutions of charged residues was tested for shake tube expression, BODIPY-starch hydrolysis, and rice starch cleaning activity. AmyS-S242Q winners are shown in Tables 19-1 and 19-2. Importantly, the multiply-substituted variants of Table 19-1 have equal or improved expression and equal or improved BODIPY-starch hydrolysis as compared to the parent enzyme. Similarly, the multiply-substituted variants of Table 19-2 have equal or improved expression and equal or improved rice starch cleaning activity as compared to the parent enzyme.

and 26B). However, there are a number of variants that are improved in both expression and activity, and analyzing the library in this manner allows them to be identified.

Although demonstrated with amylases this method is applicable to other enzyme classes such as proteases, lipases, cellulases, transferases and pectinases. Moreover any combination of two or more properties can be analyzed simultaneously such as expression, activity, binding, thermal stability, detergent and chelant stability.

Example 20

Microswatch Cleaning and Starch Hydrolysis

Enzyme performance was assessed using heat inactivated detergents as described above. Assays were performed as described above in Example 12 (see Rice Starch Microswatch Assay for testing Amylase Performance and Bodipy-Starch Assay For Determination Of Amylase Activity). Winners are defined as those having Performance Index (PI) a greater than 1. PI is the ratio of mutant residual activity to WT residual activity. Table 20-1 shows the calculations for AmyS variants that are better than wild type ($\Delta\Delta G<0$) compared to the charge change scores ($\Delta$CHRG). The charge change, Kyte-Doolittle, Eisenberg and hydrogen bonding are defined in WO 2008/153925, filed 6 Jun. 2008. In addition Table 20-1 shows the results for Kyte-Doolittle hydropathicity ($\Delta$ K-D) and Eisenberg hydrophobicity scales ($\Delta$E). Table 20-1 also shows val-

TABLE 19-1

AmyS-S242Q Expression and BODIPY-Starch Hydrolysis Winners

| Variant | 97 | 319 | 358 | 443 | Charge | Expression (PI) | BODIPY (PI) |
|---|---|---|---|---|---|---|---|
| 1 | Q97E | Q319E | Q358E | Q443E | −4 | 1.27 | 1.29 |
| 2 | Q97E | Q319E | Q358E | Q443R | −2 | 1.19 | 1.31 |
| 3 | Q97E | Q319E | Q358E |  | −3 | 1.00 | 1.43 |
| 4 | Q97E | Q319E | Q358R | Q443E | −2 | 1.23 | 1.43 |
| 7 | Q97E | Q319E |  | Q443E | −3 | 1.40 | 1.41 |
| 8 | Q97E | Q319E |  | Q443R | −1 | 1.12 | 1.58 |
| 9 | Q97E | Q319E |  |  | −2 | 1.09 | 1.56 |
| 10 | Q97E | Q319R | Q358E | Q443E | −2 | 1.45 | 1.32 |
| 11 | Q97E | Q319R | Q358E | Q443R | 0 | 1.32 | 1.49 |
| 12 | Q97E | Q319R | Q358E |  | −1 | 1.58 | 1.27 |
| 16 | Q97E | Q319R |  | Q443E | −1 | 1.09 | 1.51 |
| 17 | Q97E | Q319R |  | Q443R | +1 | 1.00 | 1.42 |
| 24 | Q97E |  | Q358R |  | 0 | 1.08 | 1.14 |
| 25 | Q97E |  |  | Q443E | −2 | 1.12 | 1.00 |
| 64 |  | Q319R | Q358E | Q443E | −1 | 1.05 | 1.28 |
| 67 |  | Q319R | Q358R | Q443E | +1 | 1.02 | 1.50 |

TABLE 19-2

AmyS-S242Q Expression and Rice-Starch Hydrolysis Winners

| Variant | 97 | 319 | 358 | 443 | Charge | Expression | CS-28 |
|---|---|---|---|---|---|---|---|
| 1 | Q97E | Q319E | Q358E | Q443E | −4 | 1.27 | 1.01 |
| 11 | Q97E | Q319R | Q358E | Q443R | 0 | 1.32 | 1.18 |
| 12 | Q97E | Q319R | Q358E |  | −1 | 1.58 | 1.13 |
| 16 | Q97E | Q319R |  | Q443E | −1 | 1.09 | 1.43 |
| 17 | Q97E | Q319R |  | Q443R | +1 | 1.00 | 1.55 |
| 24 | Q97E |  | Q358R |  | 0 | 1.08 | 1.15 |
| 25 | Q97E |  |  | Q443E | −2 | 1.12 | 1.09 |
| 64 |  | Q319R | Q358E | Q443E | −1 | 1.05 | 1.18 |
| 67 |  | Q319R | Q358R | Q443E | +1 | 1.02 | 1.15 |

Figure 26:
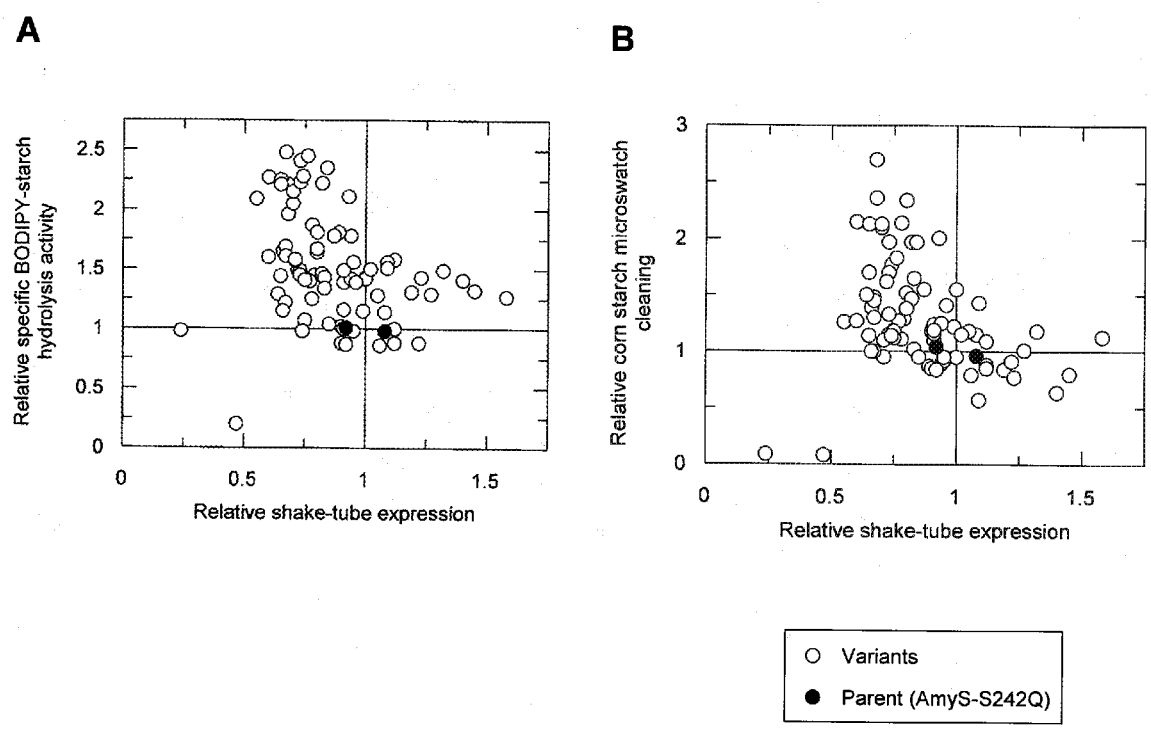
FIG. 26A is a graph depicting the relative BODIPY-starch hydrolysis as a function of relative shake tube expression (i.e., relative BODIPY-starch hydrolysis vs. relative shake tube expression).
FIG. 26B is a graph depicting the relative microswatch-starch hydrolysis as a function of relative shake tube expression (i.e., relative microswatch-starch hydrolysis vs. relative shake tube expression). Reference is made to Example 19.
Figure 27:
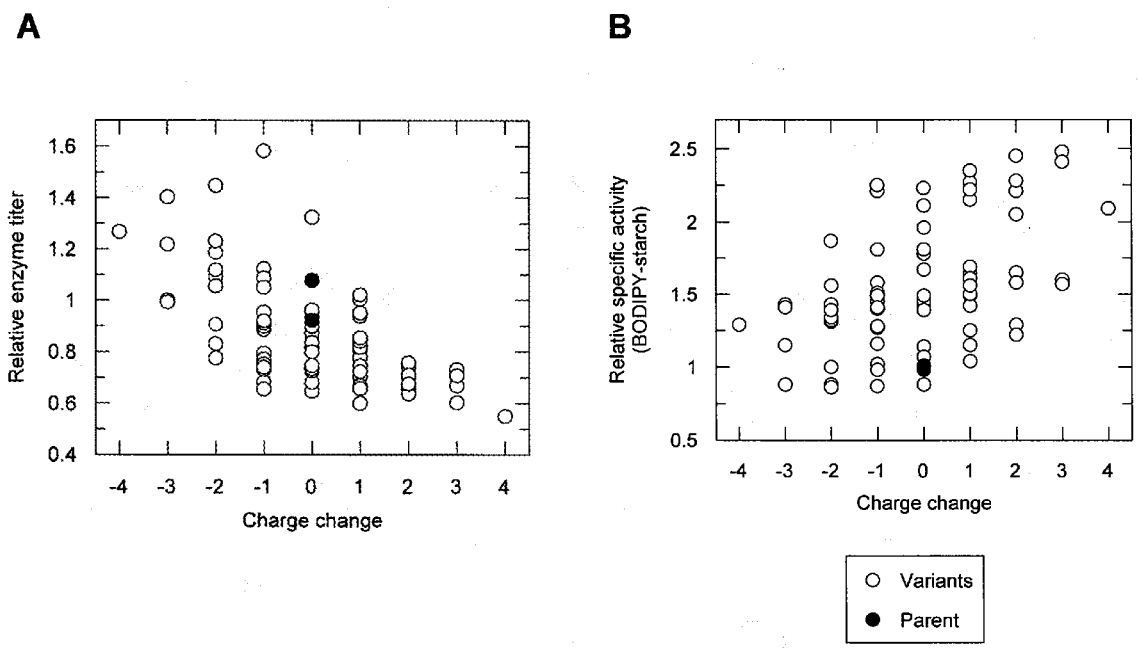
FIG. 27A is a graph depicting the relative shake tube expression as a function of charge.
FIG. 27B is a graph depicting the relative BODIPY-starch hydrolysis as a function of charge. Reference is made to Example 19.
Figure 28:
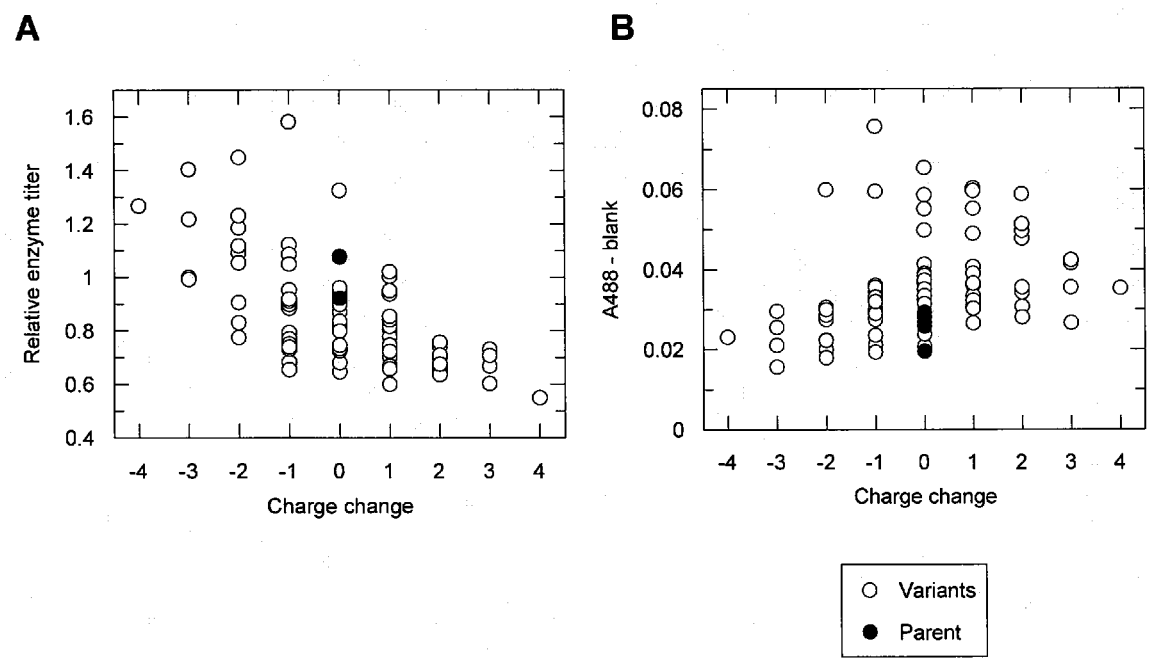
FIG. 28A is a graph depicting the relative shake tube expression as a function of charge.
FIG. 28B is a graph depicting the relative microswatch cleaning activity as a function of charge. Reference is made to Example 19.
Figure 29:
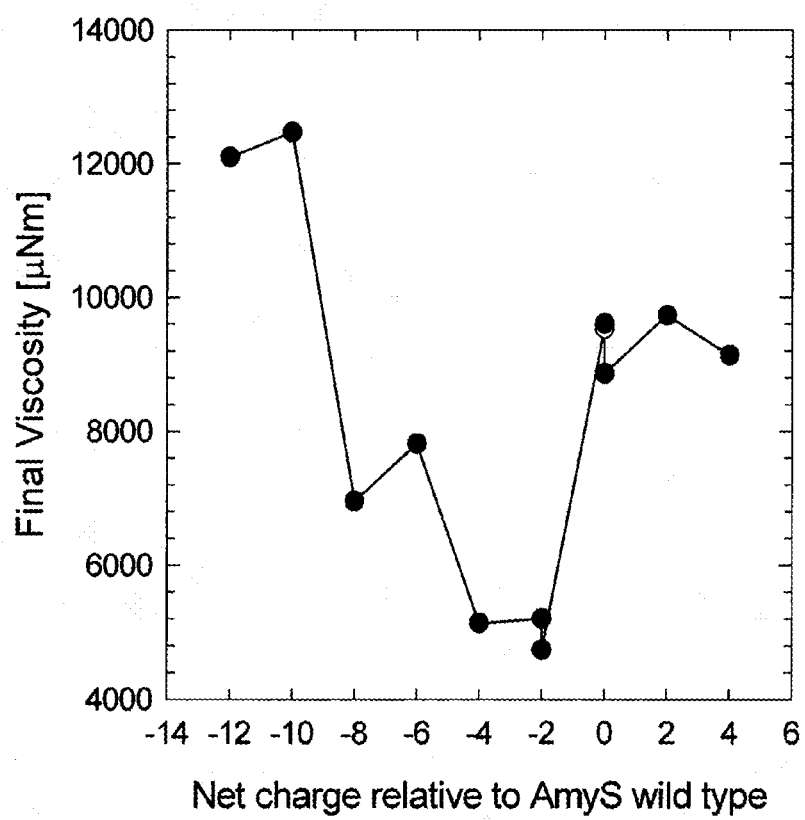
FIG. 29 is a graph depicting the final viscosity after corn starch liquefaction using 1st AmyS Ladder 30% DS, pH 5.8, enzyme dose 30 mg. For the +6 variant final viscosity is so high and cannot be measured (instrument overload). Reference is made to Example 16.
Figure 31:
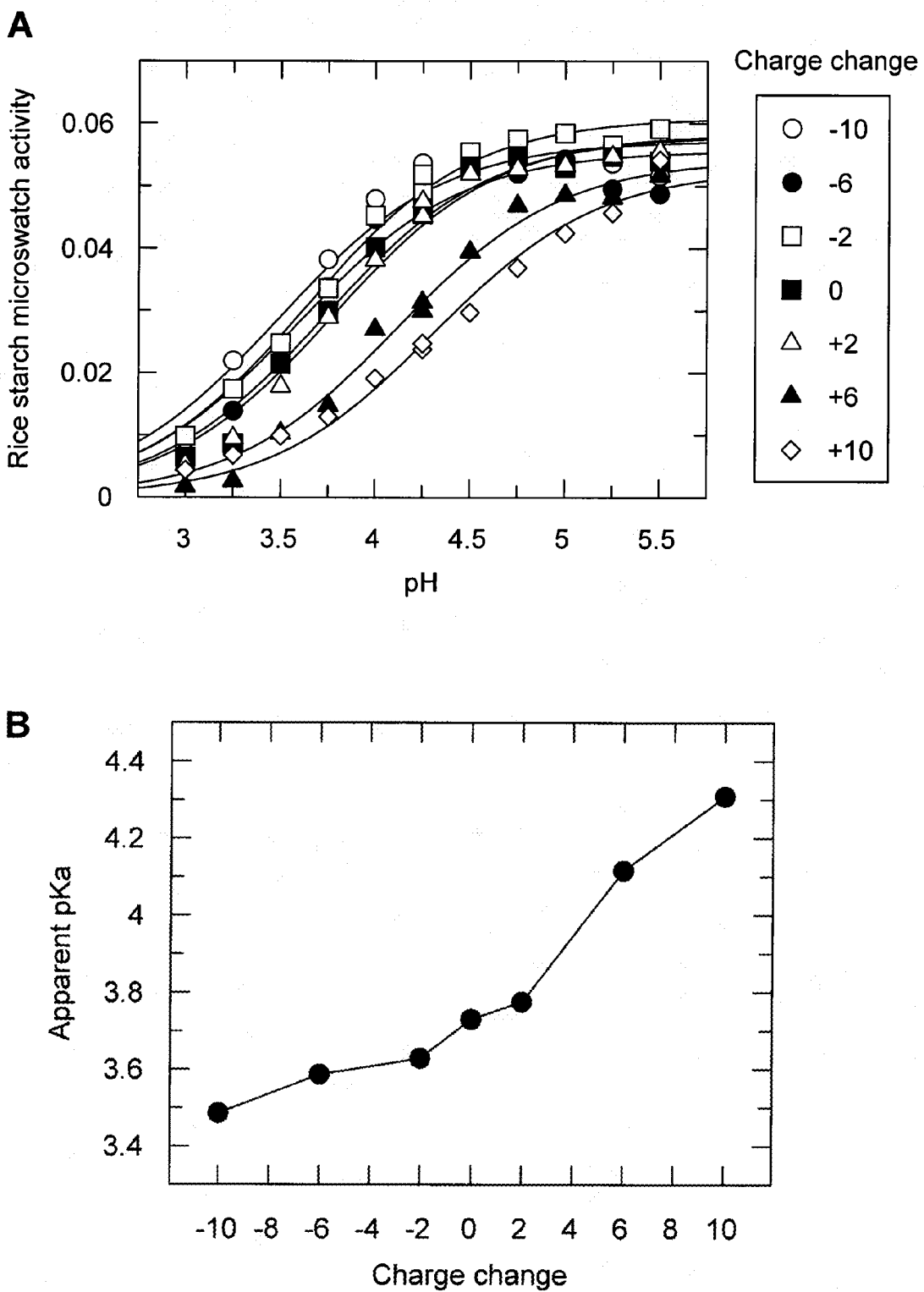
FIG. 31A is a graph depicting the rice starch cleaning activity of first AmyS charge ladder as a function of pH. pH 3.0-4.25 is 200 mM Na formate+0.01% Tween-80. pH 4.25-5.5 is 200 mM Na acetate+0.01% Tween-80. The data are fit to titration curves, each with a single pKa value. Reference is made to Example 21.
FIG. 31B is a graph depicting the effect of charge mutations on apparent pKa for AmyS catalysis (first charge ladder). Reference is made to Example 21.

In sum, because enzyme activity and enzyme production have different charge dependencies (see FIGS. 27A, 27B, 28A, and 28B) they are negatively correlated (See FIGS. 26A ues for hydrogen bonding ($\Delta$HB), with a score of −2 meaning the loss of hydrogen bonding ability. Table 20-1 shows the calculations for AmyS variants that are better than wild type for corn flour hydrolysis at 5, 10, and 60 min (CF5, CF10, CF60), activity on DP7 substrates at pH 4.0 and 5.8 (pH 4, pH 5.8), rice starch cleaning at pH 8.6 and 10 (Clean 8 and Clean 10), and protein expression in *B. subtilis* (EXP). The effect of charge on activity has the opposite direction to the effect of charge on expression. Hydrogen bonding and hydrophobicity also demonstrate statistically relevant effects on these properties. Clearly, properties of amino acid substitutions such as charge and hydrophobicity can affect expression levels in *B. subtilis* and *E. coli*, as well as basic activity and stability of proteins.

from 4.25 to 5.5 was in 200 mM Na acetate containing 0.01% Tween-80. The data are fit to titration curves, each with a single pKa value. FIG. 31B show an apparent pKa for AmyS catalysis as a function of charge change for the first AmyS charge ladder of Example 15. These data demonstrate that pH-activity profiles for an α-amylase can be significantly shifted by surface charge mutations, even in 200 mM buffer. Although this had been reported at very low ionic strength for subtilisin (Russell et al. (1987) *J Mol Biol.* 193: 803-13) and for D-xylose isomerase (Cha et al. (1998) *Mol Cell.* 8:374-

TABLE 20-1

AmyS Quintiles for Multiple Properties

| AmyS | o/e | AmyS | o/e | AmyS | o/e | AmyS | o/e |
|---|---|---|---|---|---|---|---|
| CF5 ΔΔG | 1.60 | CF5 ΔΔG | 0.84 | CF5 ΔΔG | 1.12 | CF5 ΔΔG | 1.13 |
| Δ CHRG −2 | | Δ HB −2 | | Δ K-D −2 | | Δ E −2 | |
| Δ CHRG −1 | 1.29 | Δ HB −1 | 0.98 | Δ K-D −1 | 1.19 | Δ E −1 | 1.09 |
| Δ CHRG 0 | 0.97 | Δ HB 0 | 1.02 | Δ K-D 0 | 0.83 | Δ E 0 | 1.05 |
| Δ CHRG +1 | 0.84 | Δ HB +1 | 0.92 | Δ K-D +1 | 1.15 | Δ E +1 | 0.89 |
| Δ CHRG +2 | 0.56 | Δ HB +2 | 1.19 | Δ K-D +2 | 0.77 | Δ E +2 | 1.12 |
| CF10 ΔΔG | 1.66 | CF10 ΔΔG | 0.86 | CF10 ΔΔG | 1.10 | CF10 ΔΔG | 1.26 |
| Δ CHRG −2 | | Δ HB −2 | | Δ K-D −2 | | Δ E −2 | |
| Δ CHRG −1 | 1.18 | Δ HB −1 | 1.00 | Δ K-D −1 | 1.15 | Δ E −1 | 1.04 |
| Δ CHRG 0 | 0.97 | Δ HB 0 | 1.02 | Δ K-D 0 | 0.86 | Δ E 0 | 1.08 |
| Δ CHRG +1 | 0.91 | Δ HB +1 | 0.97 | Δ K-D +1 | 1.12 | Δ E +1 | 0.90 |
| Δ CHRG +2 | 0.77 | Δ HB +2 | 1.12 | Δ K-D +2 | 0.82 | Δ E +2 | 1.16 |
| CF60 ΔΔG | 1.46 | CF60 ΔΔG | 1.00 | CF60 ΔΔG | 0.94 | CF60 ΔΔG | 0.98 |
| Δ CHRG −2 | | Δ HB −2 | | Δ K-D −2 | | Δ E −2 | |
| Δ CHRG −1 | 1.33 | Δ HB −1 | 0.96 | Δ K-D −1 | 1.15 | Δ E −1 | 1.01 |
| Δ CHRG 0 | 0.96 | Δ HB 0 | 1.01 | Δ K-D 0 | 0.79 | Δ E 0 | 1.05 |
| Δ CHRG +1 | 0.84 | Δ HB +1 | 0.95 | Δ K-D +1 | 1.16 | Δ E +1 | 0.94 |
| Δ CHRG +2 | 0.82 | Δ HB +2 | 1.05 | Δ K-D +2 | 0.89 | Δ E +2 | 1.54 |
| pH4 ΔΔG | 1.63 | pH4 ΔΔG | 0.91 | pH4 ΔΔG | 1.29 | pH4 ΔΔG | 1.07 |
| Δ CHRG −2 | | Δ HB −2 | | Δ K-D −2 | | Δ E −2 | |
| Δ CHRG −1 | 1.28 | Δ HB −1 | 0.89 | Δ K-D −1 | 1.19 | Δ E −1 | 1.13 |
| Δ CHRG 0 | 0.96 | Δ HB 0 | 0.97 | Δ K-D 0 | 0.72 | Δ E 0 | 1.01 |
| Δ CHRG +1 | 0.88 | Δ HB +1 | 0.93 | Δ K-D +1 | 1.12 | Δ E +1 | 0.89 |
| Δ CHRG +2 | 0.19 | Δ HB +2 | 1.26 | Δ K-D +2 | 0.86 | Δ E +2 | 0.95 |
| pH5.8 ΔΔG | 1.66 | pH5.8 ΔΔG | 0.99 | pH5.8 ΔΔG | 1.00 | pH5.8 ΔΔG | 1.23 |
| Δ CHRG −2 | | Δ HB −2 | | Δ K-D −2 | | Δ E −2 | |
| Δ CHRG −1 | 1.26 | Δ HB −1 | 0.99 | Δ K-D −1 | 1.17 | Δ E −1 | 1.06 |
| Δ CHRG 0 | 0.95 | Δ HB 0 | 0.95 | Δ K-D 0 | 0.80 | Δ E 0 | 0.99 |
| Δ CHRG +1 | 0.94 | Δ HB +1 | 0.90 | Δ K-D +1 | 1.08 | Δ E +1 | 0.94 |
| Δ CHRG +2 | 0.83 | Δ HB +2 | 1.15 | Δ K-D +2 | 0.92 | Δ E +2 | 1.16 |
| Clean8 ΔΔG | 1.34 | Clean8 ΔΔG | 1.07 | Clean8 ΔΔG | 0.89 | Clean8 ΔΔG | 0.88 |
| Δ CHRG −2 | | Δ HB −2 | | Δ K-D −2 | | Δ E −2 | |
| Δ CHRG −1 | 1.22 | Δ HB −1 | 1.02 | Δ K-D −1 | 1.10 | Δ E −1 | 0.98 |
| Δ CHRG 0 | 0.96 | Δ HB 0 | 0.96 | Δ K-D 0 | 0.83 | Δ E 0 | 1.00 |
| Δ CHRG +1 | 0.94 | Δ HB +1 | 0.90 | Δ K-D +1 | 1.07 | Δ E +1 | 1.01 |
| Δ CHRG +2 | 0.62 | Δ HB +2 | 1.05 | Δ K-D +2 | 1.02 | Δ E +2 | 1.32 |
| Clean10 ΔΔG | 1.32 | Clean10 ΔΔG | 0.86 | Clean10 ΔΔG | 1.03 | Clean10 ΔΔG | 0.81 |
| Δ CHRG −2 | | Δ HB −2 | | Δ K-D −2 | | Δ E −2 | |
| Δ CHRG −1 | 1.43 | Δ HB −1 | 1.36 | Δ K-D −1 | 1.11 | Δ E −1 | 1.03 |
| Δ CHRG 0 | 0.92 | Δ HB 0 | 0.72 | Δ K-D 0 | 0.80 | Δ E 0 | 1.00 |
| Δ CHRG +1 | 0.88 | Δ HB +1 | 1.07 | Δ K-D +1 | 1.16 | Δ E +1 | 0.97 |
| Δ CHRG +2 | 0.74 | Δ HB +2 | 1.11 | Δ K-D +2 | 0.91 | Δ E +2 | 1.48 |
| EXP ΔΔG | 0.00 | EXP ΔΔG | 0.63 | EXP ΔΔG | 0.65 | EXP ΔΔG Δ E −2 | 0.71 |
| Δ CHRG −2 | | Δ HB −2 | | Δ K-D −2 | | | |
| Δ CHRG −1 | 0.35 | Δ HB −1 | 0.91 | Δ K-D −1 | 1.11 | Δ E −1 | 1.29 |
| Δ CHRG 0 | 1.08 | Δ HB 0 | 0.95 | Δ K-D 0 | 1.49 | Δ E 0 | 1.06 |
| Δ CHRG +1 | 1.35 | Δ HB +1 | 1.39 | Δ K-D +1 | 0.77 | Δ E +1 | 0.79 |
| Δ CHRG +2 | 1.64 | Δ HB +2 | 1.16 | Δ K-D +2 | 0.72 | Δ E +2 | 0.20 |

Example 21

Modulating of an Enzyme's pH-Activity Profile

This Example describes the use of surface charge mutations to optimize an enzyme's pH-activity profile for a given reaction. FIG. 31A shows rice starch microswatch cleaning activity as a function of pH for the first AmyS charge ladder of Example 15. The pH range from 3.0 to 4.25 was in 200 mM Na formate containing 0.01% Tween-80, while the pH range 82), this is believed to be the first time this has been accomplished with α-amylase, and, surprisingly, even at high ionic strength.

Example 22

AmyS Superscreen

The following assays were used in the examples described below. Any deviations from the protocols provided below are indicated in the examples. In these experiments, a 96 well spectrophotometer was used to measure the absorbance of the products formed after the completion of the reactions.

Starch Hydrolysis Assay for Specific Activity Determination and Thermal Stability α-amylase activity assay on corn flour was performed to measure specific activity and stability of *B. subtilis* AmyS and AmyS variants. Conditions that closely mimic real-world applications in cleaning and grain processing were used. Activity is defined as reducing ends generated due to the enzymatic breakdown of corn flour, determined by the PAH-BAH (p-hydroxybenzoic acid hydrazide) method. Stability is defined as sustained activity at 85° C.

Hardware: Inheco Variomag Teleshake 95 with PCR plate adapter, Thermo Electron Multidrop, Axygen PCR-96-FS-C full-skirt PCR plate, Thermocyclers—with a minimum of 4 96-well blocks (an MJ Research Tetrad), Biomek FX liquid handlers.

Starch Hydrolysis: Azure Farms Organic Corn Flour, sifted for liquid-handling purposes was used to obtain the <600 micron fraction, baked 4 hours at 80° C., then allowed to equilibrate overnight at room temperature. A 2% w/w suspension was prepared in 500-g and 1000-g batches. The suspension was stirred vigorously and continuously during pH adjustment, pH equilibration, and transfer from beaker to PCR plate. For 1,000 g, 23 g pre-baked corn flour and 977 g house deionized water were stirred for 15 minutes, adjusted with H2SO4 to pH 5.8, and allowed to equilibrate for 30 minutes, at which point a final pH adjustment was performed if necessary. 8-channel pipets bearing tips trimmed to an opening size of approximately 1.5 mm were used to deliver the suspension into the wells of Axygen PCR plates.

Culture supernatants of AmyS and AmyS variants were diluted to approximately 1 µg/mL in dilution buffer (water+ 0.005% Tween-80) and 10 µL diluted supernatant each were transferred to the 5-minute, 10-minute and 60-minute reaction plates and mixed once by pipetting sample up and down. An aliquot of 50 µL light mineral oil was transferred to each well. Plates were transferred to the Inheco units pre-heated to 85° C. At the indicated time points following incubation (5, 10 and 60 minutes), the starch hydrolysis reaction was stopped by addition of 10 µL of 4N NaOH to each well. The starch hydrolysis reaction products were analyzed by the PAHBAH assay.

PAHBAH assay: Aliquots of 80 µL of 0.5 N NaOH were added to all wells of an empty PCR plate followed by 20 µL of PAHBAH reagent (5% w/v p-hydroxybenzoic acid hydrazide (PAHBAH, Sigma #H9882, dissolved in 0.5 N HCl) and mixed by pipetting up and down (PAHBAH reaction plate). 10 µL of the starch hydrolysis reaction supernatants were added to the PAHBAH reaction plate. All plates were sealed and placed in the thermocycler, programmed for 2 minutes at 95° C., and then cooled to 20° C. Samples of 80 µL of the developed PAHBAH reaction mixtures were transferred to a fresh (read) plate and absorbance was measured at 405 nm in a spectrophotometer.

Cleaning Swatch Assay for Stain Removal Performance

In this assay, the stain removal performance of *B. subtilis* AmyS and AmyS variants was determined in a microtiter plate scale using CS-28 rice starch stain microswatches. Microswatches of ¼" circular diameter were obtained from CFT Vlaardingen (Netherlands). Two microswatches were placed into each well of a 96-well microtiter plate.

The filtered culture broth samples were tested at an appropriate concentration by dilution with a mixture of 10 mM NaCl, 0.1 mM CaCl$_2$, 0.005% Tween-80 to 20× the desired final concentration in the performance test (final conc. in test 0.025-0.10 ppm).

Amylase performance was measured at both pH 8 and pH 10.

Either 190 µl of buffer solution, containing 25 mM HEPES (Sigma, H7523), 2 mM CaCl$_2$, 0.005% Tween-80, pH 8.0, or 190 µl of buffer solution, containing 25 mM CAPS (Sigma, C2632), 2 mM CaCl$_2$, 0.005% Tween-80, pH 10.0 were added to each well of the plates containing microswatches. 10 µL of diluted amylase samples were added to each microswatch containing well (to provide a total volume of 200 µL/well). The plate was covered with a plate seal and placed in an incubator for 60 minutes at 40° C., with agitation at 1150 rpm (iEMS incubator). Following incubation under the appropriate conditions, 100 µL of solution from each well was removed, placed into a fresh microtiter plate and absorbance was measured at 488 nm in a spectrophotometer. "Blank controls", containing 2 microswatches per well and detergent but no amylase samples were also included in the test.

Calculation of the CS-28 rice starch hydrolysis performance: The obtained absorbance value was corrected for the blank value (microswatches incubated in the absence of enzyme). The resulting absorbance—ΔOD488—was a measure for the amylolytic activity. For each sample (AmyS or AmyS variant) the performance index was calculated by dividing the activity of the variant by the activity of the wildtype enzyme. The performance index compared the performance of the variant (actual value) and the standard AmyS reference enzyme (theoretical value) at the same protein concentration.

A performance index (PI) that is greater than 1 (PI>1) identified a better variant (as compared to the standard, e.g., wild-type), while a PI of 1 (PI=1) identified a variant that performs the same as the standard, and a PI that is less than 1 (PI<1) identified a variant that performs worse than the standard. Thus, the PI identified variants with performance differences over the wildtype enzyme.

The following site variants were evaluated using the assays described in this Example:

```
P17A, C, D, E, F, G, H, I, K, L, M, N, P, Q, R, S,
T, V, W, Y

D19A, C, D, E, F, G, H, I, K, L, M, N, P, Q, R, S,
T, V, W, Y

T21A, C, D, E, F, G, H, I, K, L, M, N, P, Q, R, S,
T, V, W, Y

N28A, C, D, E, F, G, H, I, K, L, M, N, P, Q, R, S,
T, V, W, Y

S51A, C, D, E, F, G, H, I, K, L, M, N, P, Q, R, S,
T, V, W, Y

G72A, C, D, E, F, G, H, I, K, L, M, N, P, Q, R, S,
T, V, W, Y

V74A, C, D, E, F, G, H, I, K, L, M, N, Q, R, S, T,
V, W, Y

A82A, C, E, F, G, H, I, K, L, M, N, P, Q, R, S, T,
V, W, Y

Q86A, C, D, E, F, G, H, I, K, L, N, P, Q, R, S, T,
V, W, Y
```

-continued

Q89A, C, D, E, F, G, H, I, K, L, M, N, P, Q, R, T, V, W, Y

A93A, C, D, E, F, G, H, I, K, L, M, N, P, Q, R, S, T, V, W, Y

W115D, E, F, G, K, L, N, P, Q, R, S, V, Y

D117A, E, G, H, I, K, L, M, N, P, Q, R, S, T, V, W

P123A, D, E, G, K, L, M, P, Q, R, S, T, V

S124A, C, D, E, F, G, H, I, K, L, N, P, Q, R, S, T, V, Y

D125A, D, E, G, K, M, Q, R, S, T, V

N127A, C, D, F, G, H, K, L, M, N, P, Q, R, S, T, V, W, Y

I130A, G, H, I, K, L, M, N, P, Q, R, S, T, V, W

G132A, C, D, E, F, G, H, L, M, N, P, R, S, T, V, W, Y

Q135A, F, G, K, L, M, P, Q, R, S, T, V, Y

P145A, D, E, F, H, I, K, L, N, P, R, S, T, V, Y

G146A, C, D, E, G, H, K, L, P, R, S, T, V, W

G148A, C, D, E, F, G, H, L, N, P, Q, R, S, T, V, W, Y

S153A, C, D, E, F, G, H, I, K, L, N, P, Q, R, S, T, V, W, Y

Y159A, C, D, E, F, G, H, K, L, N, R, S, T, V, W

W166C, E, F, G, H, I, K, L, M, P, R, S, T, V, Y

S169A, C, D, E, F, G, I, K, L, M, N, P, Q, R, T, V, Y

K171C, D, E, G, H, K, L, M, P, Q, R, S, T, V, W, Y

R179A, G, H, L, M, P, Q, R, S, T, V, W, Y

G180A, C, D, F, G, H, I, K, L, N, P, R, S, T, V, Y

I181A, C, D, E, F, G, H, I, K, L, P, R, S, T, V, Y

G182A, C, D, E, F, G, H, K, L, P, R, S, T, V, Y

K183A, C, E, F, G, H, K, L, M, P, Q, R, S, T, V, W, Y

W187A, C, E, G, I, K, L, N, P, R, S, V, W

G194A, E, G, H, K, L, M, P, R, S, T, V, W

P209A, C, D, E, F, G, H, I, K, L, M, N, P, Q, R, S, T, V, W, Y

N224A, C, D, E, F, G, H, I, K, L, M, N, P, Q, R, S, T, V, W, Y

S242A, C, D, G, I, K, L, M, Q, R, S, T, V

P245A, C, D, E, F, H, I, L, M, N, P, Q, R, S, V, Y

G256A, C, D, E, G, H, I, K, L, M, N, P, R, S, T, V, W

D269A, C, D, F, G, H, I, K, M, N, P, R, S, T, Y

N271A, D, F, H, I, K, L, M, N, P, S, T, V, W, Y

T278A, E, G, H, I, K, L, M, N, P, R, S, T, W, Y

-continued

N281A, D, G, H, I, L, M, N, P, Q, R, S, T, V, Y

G302C, D, E, F, G, H, I, L, M, N, P, R, S, T, V, W, Y

A304A, D, E, F, H, L, M, N, P, R, S, T, V, W, Y

R308A, C, D, E, F, G, H, I, K, L, M, N, P, R, S, T, V, W, Y

T321A, C, F, H, I, L, P, Q, R, S, T, V, Y

Q358A, C, D, E, F, G, H, L, M, N, P, Q, R, S, T, V

P378C, D, F, G, H, I, L, N, P, R, S, T, V, Y

S382A, C, D, E, G, H, I, K, L, M, N, P, R, S, T, V, W

K383A, C, D, E, F, H, K, L, M, N, P, Q, R, S, T, W, Y

T398A, C, D, E, I, K, L, M, N, P, Q, R, S, T, V

H405A, C, D, F, G, H, K, L, M, N, P, Q, R, S, T, W, Y

T417A, D, E, H, I, L, M, P, Q, R, S, T, V, W

E418A, C, D, E, G, H, I, K, L, M, N, P, Q, R, S, T, V, Y

P420A, C, D, E, H, I, L, M, N, P, R, S, T, V, W, Y

G421A, D, E, F, G, H, I, L, N, P, Q, R, S, T, W, Y

P432A, D, E, H, K, L, M, N, P, Q, R, S, T, Y

W437C, D, E, F, G, H, L, M, N, Q, R, S, T, V, W, Y

Q443A, C, F, G, K, L, N, P, Q, R, S, T, V, W, Y

G446A, C, D, F, G, H, I, K, L, M, N, P, Q, R, S, T, V, W, Y

G454A, C, D, E, G, H, I, K, L, M, N, P, R, S, T, V

S457A, C, D, E, G, H, K, L, M, N, P, R, S, T, V, W, Y

T459A, D, G, I, K, L, Q, R, S, T, V, Y

T461A, D, E, F, G, I, K, L, N, P, R, S, T, V, W, Y

S464D, E, G, H, I, K, L, M, N, P, Q, S, V, W, Y

G474A, C, D, E, F, G, H, I, K, L, M, N, P, Q, R, S, T, V

R483A, C, F, G, K, L, M, N, P, Q, R, S, T, V, Y

Example 23

Performance of AmyS Variants

The performance of AmyS variants (e.g., as described in Example 22) were tested for protein expression (expression), hydrolysis of corn flour for 10 minutes (Corn Flour 10) or hydrolysis of corn flour for 60 minutes (Corn Flour 60), activity on DP7 substrate at pH 4 (DP7 pH 4) or activity on DP7 substrate at pH5.8 (DP7 pH 5.8), and CS 28 rice starch stained microswatch cleaning at pH 8 (cleaning pH 8) or CS 28 rice starch stained microswatch cleaning at pH 10 (cleaning 10). The results are shown in Table 23-1. Protein expression was measured by Bradford assay described in Example 12. The corn flour hydrolysis and cleaning swatch assays were performed as described in Example 22. Functionality of AmyS variants was quantified as a performance index (Pi) (i.e., the ratio of performance of a variant relative to wild type AmyS). A PI>1 for any property indicates that the variant is improved (compared to the control) for that property. ND indicates that the value obtained was outside the range of the assay.

TABLE 23-1

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 017 | P017A | 1.08 | 1.07 | 1.13 | 1.32 | 1.35 | 1.04 | 0.58 |
| 017 | P017C | 1.38 | 1.46 | 1.20 | 1.41 | 1.47 | 1.29 | 0.50 |
| 017 | P017D | 1.30 | 1.30 | 1.02 | 1.24 | 1.33 | 1.10 | 0.58 |
| 017 | P017E | 1.07 | 1.20 | 1.03 | 1.18 | 1.29 | 1.04 | 0.70 |
| 017 | P017F | 0.95 | 1.10 | 0.84 | 0.95 | 1.37 | 0.83 | 0.59 |
| 017 | P017G | 0.90 | 0.83 | 0.83 | 0.90 | 1.04 | 0.84 | 0.88 |
| 017 | P017H | 0.91 | 0.84 | 1.03 | 1.03 | 1.07 | 0.86 | 0.96 |
| 017 | P017I | 0.78 | 0.83 | 0.79 | 0.91 | 0.83 | 0.77 | 0.87 |
| 017 | P017K | 0.88 | 0.64 | 0.83 | 0.96 | 1.11 | 0.88 | 0.90 |
| 017 | P017L | 0.69 | 0.64 | 0.44 | 0.32 | 0.91 | 0.92 | 0.67 |
| 017 | P017M | 1.19 | 1.46 | 1.13 | 1.32 | 1.58 | 0.83 | 0.50 |
| 017 | P017N | 1.05 | 1.16 | 1.13 | 1.30 | 1.14 | 0.81 | 0.70 |
| 017 | P017Q | 1.24 | 1.31 | 1.19 | 1.21 | 1.09 | 0.90 | 0.73 |
| 017 | P017R | 1.21 | 1.23 | 0.93 | 1.13 | 1.40 | 1.01 | 0.71 |
| 017 | P017S | 0.97 | 0.85 | 0.78 | 0.84 | 1.00 | 0.87 | 0.76 |
| 017 | P017T | 0.81 | 0.91 | 0.68 | 0.75 | 1.12 | 0.73 | 0.76 |
| 017 | P017V | 0.79 | 0.79 | 0.70 | 0.75 | 0.94 | 0.82 | 0.81 |
| 017 | P017W | 0.81 | 0.77 | 0.70 | 0.82 | 0.89 | 0.77 | 0.75 |
| 017 | P017Y | 0.75 | 0.79 | 0.98 | 0.97 | 1.01 | 0.95 | 0.96 |
| 019 | D019A | 1.50 | 1.69 | 1.29 | 1.55 | 2.01 | 1.42 | 0.48 |
| 019 | D019C | 1.34 | 1.49 | 1.29 | 1.47 | 1.59 | 1.25 | 0.51 |
| 019 | D019E | 1.39 | 1.38 | 1.41 | 1.48 | 1.69 | 1.40 | 0.67 |
| 019 | D019F | 3.22 | 3.51 | 0.75 | 0.87 | 6.54 | 3.43 | 0.10 |
| 019 | D019G | 1.20 | 1.29 | 1.19 | 1.20 | 0.98 | 1.22 | 0.75 |
| 019 | D019H | 0.93 | 0.97 | 0.91 | 1.05 | 1.32 | 0.98 | 0.93 |
| 019 | D019I | 1.13 | 0.90 | 0.93 | 1.05 | 1.82 | 0.96 | 0.38 |
| 019 | D019K | 0.90 | 0.81 | 0.97 | 1.09 | 0.93 | 0.91 | 0.99 |
| 019 | D019L | 0.84 | 0.65 | −0.65 | −0.23 | 1.79 | 1.94 | 0.13 |
| 019 | D019M | 1.60 | 1.98 | 1.07 | 1.40 | 1.63 | 1.41 | 0.35 |
| 019 | D019N | 1.34 | 1.16 | 1.69 | 1.23 | 1.20 | 1.06 | 0.71 |
| 019 | D019P | 0.93 | 1.14 | 1.00 | 1.27 | 1.56 | 1.32 | 0.53 |
| 019 | D019Q | 1.35 | 1.24 | 1.94 | 1.65 | 1.31 | 1.20 | 0.74 |
| 019 | D019R | 1.02 | 1.05 | 0.94 | 1.03 | 1.44 | 1.12 | 0.80 |
| 019 | D019S | 1.03 | 1.12 | 1.08 | 1.12 | 1.09 | 0.89 | 0.95 |
| 019 | D019T | 1.04 | 1.06 | 1.07 | 1.11 | 1.22 | 0.89 | 0.97 |
| 019 | D019V | 1.05 | 1.28 | 1.07 | 1.27 | 2.16 | 1.52 | 0.36 |
| 019 | D019W | 0.64 | 0.93 | 0.52 | 0.71 | 1.24 | 0.81 | 0.56 |
| 019 | D019Y | 0.98 | 1.10 | 1.43 | 1.32 | 1.34 | 1.03 | 0.69 |
| 021 | T021A | 1.25 | 1.34 | 1.36 | 1.50 | 1.41 | 1.19 | 0.75 |
| 021 | T021C | 1.59 | 1.73 | 1.42 | 1.58 | 1.79 | 1.26 | 0.49 |
| 021 | T021D | 1.23 | 1.39 | 1.63 | 1.54 | 1.48 | 1.27 | 0.78 |
| 021 | T021E | 1.32 | 1.35 | 1.53 | 1.59 | 1.48 | 1.05 | 0.72 |
| 021 | T021F | 1.26 | 1.36 | 1.66 | 1.48 | 1.42 | 1.11 | 0.71 |
| 021 | T021G | 1.11 | 1.14 | 1.35 | 1.29 | 1.24 | 1.05 | 0.91 |
| 021 | T021H | 0.87 | 0.85 | 0.95 | 0.98 | 1.08 | 0.86 | 1.10 |
| 021 | T021I | 1.04 | 1.04 | 1.31 | 1.31 | 1.57 | 1.14 | 0.71 |
| 021 | T021K | 0.89 | 0.88 | 1.02 | 1.07 | 1.02 | 1.01 | 1.07 |
| 021 | T021L | 0.80 | 0.92 | 1.33 | 1.20 | 1.08 | 0.88 | 0.89 |
| 021 | T021M | 1.37 | 1.40 | 1.34 | 1.55 | 1.48 | 1.34 | 0.75 |
| 021 | T021N | 1.36 | 1.42 | 1.28 | 1.47 | 1.23 | 1.16 | 0.75 |
| 021 | T021P | 1.13 | 1.25 | 1.14 | 1.27 | 1.30 | 1.20 | 0.82 |
| 021 | T021Q | 1.32 | 1.42 | 1.50 | 1.55 | 1.33 | 1.20 | 0.79 |
| 021 | T021R | 1.17 | 1.26 | 1.14 | 1.21 | 1.23 | 1.11 | 0.86 |
| 021 | T021S | 1.08 | 1.28 | 1.09 | 1.17 | 1.12 | 0.97 | 0.91 |
| 021 | T021V | 1.10 | 1.19 | 1.12 | 1.24 | 1.35 | 0.95 | 0.73 |
| 021 | T021W | 0.98 | 1.01 | 0.91 | 0.95 | 1.17 | 1.11 | 0.75 |
| 021 | T021Y | 0.81 | 0.89 | 1.02 | 1.07 | 1.03 | 0.62 | 0.87 |
| 028 | N028A | 1.28 | 1.51 | 1.24 | 1.42 | 1.64 | 1.39 | 0.74 |
| 028 | N028C | −0.92 | −2.93 | 1.18 | 0.31 | 1.18 | 2.17 | −0.05 |
| 028 | N028D | 1.29 | 1.39 | 1.69 | 1.63 | 1.37 | 1.23 | 0.77 |
| 028 | N028E | 1.26 | 1.36 | 1.21 | 1.38 | 1.21 | 1.06 | 0.79 |
| 028 | N028F | 1.29 | 1.34 | 1.16 | 1.35 | 1.48 | 1.26 | 0.54 |
| 028 | N028G | 0.98 | 1.05 | 0.99 | 1.08 | 0.98 | 0.81 | 1.06 |
| 028 | N028H | 0.98 | 1.09 | 1.06 | 1.18 | 1.20 | 1.01 | 0.94 |
| 028 | N028I | 0.88 | 1.02 | 0.86 | 0.97 | 1.17 | 0.87 | 0.71 |
| 028 | N028K | 0.93 | 0.95 | 1.01 | 1.09 | 0.84 | 0.94 | 0.98 |
| 028 | N028L | 0.79 | 1.00 | 0.91 | 1.02 | 1.11 | 0.87 | 0.74 |
| 028 | N028M | 1.48 | 1.67 | 1.62 | 1.79 | 2.01 | 1.57 | 0.53 |
| 028 | N028P | 1.47 | 1.60 | 2.00 | 2.47 | 1.89 | 1.47 | 0.48 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 028 | N028Q | 1.19 | 1.23 | 1.01 | 1.18 | 1.20 | 1.24 | 0.75 |
| 028 | N028R | 1.11 | 1.07 | 1.10 | 1.27 | 1.38 | 1.10 | 0.80 |
| 028 | N028S | 1.11 | 1.23 | 0.98 | 1.08 | 1.03 | 0.94 | 0.91 |
| 028 | N028T | 1.13 | 1.22 | 1.07 | 1.21 | 1.22 | 0.99 | 0.84 |
| 028 | N028V | 0.98 | 0.97 | 1.12 | 1.13 | 1.35 | 0.90 | 0.75 |
| 028 | N028W | 1.00 | 1.05 | 0.92 | 1.08 | 1.25 | 0.92 | 0.65 |
| 028 | N028Y | 0.92 | 1.00 | 0.87 | 0.88 | 1.13 | 0.76 | 0.86 |
| 051 | S051A | 1.01 | 0.99 | 1.39 | 1.21 | 1.11 | 1.14 | 0.97 |
| 051 | S051C | 0.96 | 1.01 | 1.06 | 1.36 | 0.91 | 0.51 | 0.80 |
| 051 | S051D | 0.94 | 1.00 | 1.34 | 1.42 | 0.95 | 1.07 | 0.97 |
| 051 | S051E | 0.71 | 0.64 | 1.10 | 1.25 | 0.79 | 1.02 | 1.11 |
| 051 | S051F | 0.96 | 0.93 | 1.04 | 1.29 | 1.06 | 1.06 | 0.89 |
| 051 | S051G | 0.83 | 0.77 | 0.81 | 0.82 | 0.80 | 1.09 | 1.24 |
| 051 | S051H | 0.74 | 0.70 | 0.56 | 0.86 | 0.93 | 0.99 | 1.20 |
| 051 | S051I | 0.75 | 0.73 | 0.80 | 0.83 | 0.82 | 0.74 | 1.18 |
| 051 | S051K | 0.62 | 0.58 | 0.54 | 0.67 | 0.68 | 0.82 | 1.39 |
| 051 | S051L | 0.71 | 0.72 | 0.85 | 0.88 | 0.74 | 0.83 | 1.41 |
| 051 | S051M | 0.97 | 1.00 | 1.24 | 1.26 | 1.11 | 1.01 | 0.94 |
| 051 | S051N | 1.04 | 1.05 | 0.99 | 1.02 | 0.64 | 1.02 | 0.96 |
| 051 | S051P | 0.81 | 0.79 | 0.31 | 1.23 | 1.22 | 0.78 | 0.75 |
| 051 | S051Q | 1.01 | 0.96 | 1.07 | 1.08 | 1.07 | 1.06 | 1.03 |
| 051 | S051R | 0.88 | 0.88 | 0.66 | 0.89 | 0.92 | 1.09 | 1.02 |
| 051 | S051T | 0.89 | 0.80 | 0.76 | 0.79 | 0.96 | 0.91 | 1.17 |
| 051 | S051V | 0.78 | 0.70 | 0.70 | 0.75 | 0.86 | 0.78 | 1.21 |
| 051 | S051W | 0.81 | 0.76 | 0.81 | 0.94 | 0.87 | 0.81 | 1.17 |
| 051 | S051Y | 0.70 | 0.76 | 0.98 | 0.96 | 0.83 | 0.93 | 1.16 |
| 072 | G072A | 1.53 | 1.40 | 1.25 | 1.36 | 1.46 | 1.46 | 0.65 |
| 072 | G072C | 1.53 | 1.39 | 1.52 | 1.68 | 1.40 | 1.20 | 0.61 |
| 072 | G072D | 1.36 | 1.38 | 1.69 | 1.72 | 1.36 | 1.59 | 0.78 |
| 072 | G072E | 0.13 | 0.59 | 0.75 | 0.39 | −0.18 | −0.75 | −0.19 |
| 072 | G072F | 0.07 | 0.74 | 1.79 | 0.84 | 0.39 | 0.30 | −0.07 |
| 072 | G072H | 0.97 | 0.96 | 0.95 | 1.09 | 1.05 | 1.11 | 0.98 |
| 072 | G072I | 12.27 | −18.04 | −7.88 | −5.43 | −47.34 | −40.91 | 0.00 |
| 072 | G072K | 0.20 | −2.21 | −4.25 | −2.09 | 3.20 | −0.46 | 0.04 |
| 072 | G072L | 0.21 | −1.59 | −3.13 | −1.59 | −0.59 | −0.13 | 0.04 |
| 072 | G072M | 0.09 | 0.37 | 0.78 | 0.27 | 0.06 | 0.01 | −0.16 |
| 072 | G072N | −0.09 | 0.41 | 0.34 | 0.12 | 0.01 | 0.12 | −0.17 |
| 072 | G072P | −0.20 | 0.29 | 1.24 | 0.48 | 0.06 | −0.23 | −0.11 |
| 072 | G072Q | 1.68 | 1.60 | 1.60 | 1.66 | 1.62 | 1.60 | 0.68 |
| 072 | G072R | 1.23 | 1.19 | 0.83 | 1.05 | 1.06 | 1.42 | 0.80 |
| 072 | G072S | 0.77 | −1.60 | −0.59 | 2.54 | 0.70 | 8.99 | −0.01 |
| 072 | G072T | 0.93 | 0.98 | 0.88 | 0.94 | 1.08 | 1.05 | 1.02 |
| 072 | G072V | 1.31 | 1.27 | 1.19 | 1.30 | 1.48 | 1.22 | 0.68 |
| 072 | G072W | 0.10 | −0.61 | −1.03 | −0.54 | 0.41 | −0.49 | 0.12 |
| 072 | G072Y | 1.11 | 1.01 | 1.28 | 1.31 | 1.21 | 1.01 | 0.84 |
| 074 | V074A | 1.43 | 1.43 | 1.55 | 1.54 | 1.43 | 1.38 | 0.79 |
| 074 | V074C | 0.05 | 0.20 | 0.77 | 0.33 | −0.16 | 0.40 | −0.19 |
| 074 | V074D | −0.22 | 0.91 | 2.69 | 1.24 | 0.32 | −0.58 | −0.05 |
| 074 | V074E | 1.65 | 1.71 | 1.69 | 1.69 | 1.56 | 1.84 | 0.65 |
| 074 | V074F | 2.44 | 2.48 | 0.48 | 0.33 | 3.48 | 3.18 | 0.13 |
| 074 | V074G | 1.29 | 1.28 | 1.15 | 1.14 | 0.98 | 1.08 | 0.97 |
| 074 | V074H | 0.79 | 0.78 | 0.82 | 0.89 | 0.84 | 0.78 | 1.19 |
| 074 | V074I | 1.15 | 1.16 | 1.26 | 1.26 | 1.21 | 1.01 | 0.98 |
| 074 | V074K | 0.08 | −0.61 | −1.67 | −0.73 | 1.78 | 0.54 | 0.07 |
| 074 | V074L | 0.77 | −0.57 | −2.18 | −1.10 | 0.59 | −1.43 | 0.07 |
| 074 | V074M | −0.14 | −0.19 | 1.02 | 0.48 | 0.45 | −0.53 | −0.13 |
| 074 | V074N | −0.22 | 0.25 | 1.07 | 0.53 | 0.05 | 0.15 | −0.13 |
| 074 | V074Q | 1.57 | 1.60 | 1.61 | 1.59 | 1.30 | 1.16 | 0.78 |
| 074 | V074R | −0.93 | −0.49 | 1.45 | 0.77 | −0.63 | −1.66 | −0.08 |
| 074 | V074S | −3.20 | −3.28 | −0.69 | −1.93 | −2.28 | −5.92 | 0.05 |
| 074 | V074T | 7.70 | −8.69 | −7.16 | −3.32 | −0.73 | −6.93 | 0.02 |
| 074 | V074W | 0.47 | −0.38 | −3.18 | −1.38 | 0.49 | 0.72 | 0.04 |
| 074 | V074Y | 1.12 | 1.08 | 0.88 | 0.91 | 0.97 | 1.00 | 0.93 |
| 082 | A082C | 1.45 | 1.58 | 1.16 | 1.26 | 1.31 | 1.25 | 0.64 |
| 082 | A082E | 1.37 | 1.32 | 1.36 | 1.39 | 1.12 | 1.02 | 0.89 |
| 082 | A082F | 1.36 | 1.33 | 1.07 | 1.14 | 1.25 | 1.19 | 0.84 |
| 082 | A082G | 1.17 | 1.33 | 0.79 | 0.93 | 1.18 | 1.07 | 0.68 |
| 082 | A082H | 1.08 | 1.04 | 0.95 | 0.96 | 0.90 | 1.13 | 1.15 |
| 082 | A082I | 0.96 | 1.00 | 1.04 | 1.03 | 0.97 | 0.82 | 1.15 |
| 082 | A082K | 9.74 | 1.65 | −13.38 | −6.33 | −9.02 | 35.95 | 0.01 |
| 082 | A082L | 1.00 | 0.96 | 0.94 | 0.99 | 0.82 | 0.84 | 1.08 |
| 082 | A082M | −0.42 | 0.35 | 0.64 | 0.22 | 0.16 | −0.23 | −0.20 |
| 082 | A082N | 1.36 | 1.39 | 1.35 | 1.45 | 1.38 | 1.31 | 0.83 |
| 082 | A082P | 1.54 | 1.45 | 1.25 | 1.38 | 1.44 | 1.14 | 0.76 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 082 | A082Q | −0.19 | 0.28 | 1.16 | 0.54 | 0.15 | 1.37 | −0.12 |
| 082 | A082R | 1.17 | 1.17 | 1.29 | 1.34 | 1.42 | 1.45 | 0.99 |
| 082 | A082S | 1.02 | 1.07 | 0.92 | 1.01 | 0.90 | 0.86 | 1.06 |
| 082 | A082T | 1.08 | 1.08 | 0.99 | 1.06 | 1.00 | 1.32 | 1.02 |
| 082 | A082V | 0.98 | 1.08 | 0.97 | 1.05 | 1.02 | 0.90 | 1.02 |
| 082 | A082W | 1.16 | 1.16 | 0.83 | 0.99 | 1.08 | 0.97 | 0.96 |
| 082 | A082Y | 0.81 | 0.87 | 0.95 | 0.95 | 0.95 | 1.06 | 1.14 |
| 086 | Q086A | 1.00 | 1.11 | 1.43 | 1.46 | 1.25 | 1.02 | 0.83 |
| 086 | Q086C | 1.00 | 1.11 | 1.01 | 1.19 | 1.09 | 0.64 | 0.73 |
| 086 | Q086D | 0.96 | 1.03 | 1.22 | 1.29 | 1.11 | 0.99 | 0.87 |
| 086 | Q086E | 0.92 | 0.93 | 1.12 | 1.15 | 0.80 | 0.97 | 0.97 |
| 086 | Q086F | 0.26 | −0.46 | −3.07 | −1.44 | −0.60 | −1.61 | 0.05 |
| 086 | Q086G | 0.21 | 1.02 | −1.18 | −0.54 | −0.42 | −2.55 | 0.12 |
| 086 | Q086H | 1.34 | 1.23 | −1.23 | −0.61 | −2.15 | −1.84 | 0.10 |
| 086 | Q086I | 0.84 | 0.85 | 0.88 | 0.95 | 0.85 | 0.81 | 0.99 |
| 086 | Q086K | 0.64 | 0.66 | 0.88 | 0.84 | 0.71 | 0.81 | 1.42 |
| 086 | Q086L | 0.71 | 0.71 | 0.78 | 0.80 | 0.71 | 0.70 | 1.24 |
| 086 | Q086N | −4.91 | −2.76 | 5.03 | 2.01 | 3.01 | 2.98 | −0.02 |
| 086 | Q086P | 1.13 | 1.17 | 1.36 | 1.48 | 1.31 | 1.11 | 0.86 |
| 086 | Q086R | −7.06 | 24.56 | −23.74 | −11.36 | −12.19 | −55.94 | 0.00 |
| 086 | Q086S | 0.44 | 1.09 | −1.75 | −0.70 | −0.40 | −2.57 | 0.08 |
| 086 | Q086T | 0.94 | 0.91 | 0.90 | 0.99 | 0.78 | 0.91 | 1.03 |
| 086 | Q086V | 0.88 | 0.89 | 0.85 | 0.91 | 0.81 | 0.71 | 0.93 |
| 086 | Q086W | 0.78 | 0.74 | 0.81 | 0.85 | 0.80 | 0.69 | 1.24 |
| 086 | Q086Y | 0.72 | 0.74 | 0.94 | 0.91 | 0.77 | 0.82 | 1.13 |
| 089 | Q089A | 0.33 | −0.78 | 0.99 | 0.42 | −0.25 | 3.87 | −0.12 |
| 089 | Q089C | −0.69 | 0.00 | 0.05 | −0.23 | −0.17 | 0.59 | −0.11 |
| 089 | Q089D | 1.32 | 1.36 | 1.41 | 1.47 | 1.37 | 1.07 | 0.73 |
| 089 | Q089E | −0.37 | −0.82 | 0.68 | 0.35 | 0.65 | 1.13 | −0.12 |
| 089 | Q089F | 1.56 | 1.48 | 1.17 | 1.25 | 1.54 | 1.00 | 0.44 |
| 089 | Q089G | 1.13 | 1.03 | 1.21 | 1.15 | 1.10 | 1.02 | 0.93 |
| 089 | Q089H | 1.82 | 1.91 | 0.35 | 0.65 | 1.10 | 1.61 | 0.17 |
| 089 | Q089I | 1.16 | 1.01 | 1.04 | 1.10 | 1.15 | 0.90 | 0.77 |
| 089 | Q089K | 0.85 | 0.87 | 1.20 | 1.06 | 1.11 | 0.87 | 1.10 |
| 089 | Q089L | 0.95 | 0.94 | 0.97 | 0.98 | 0.72 | 0.77 | 0.86 |
| 089 | Q089M | 1.29 | 1.21 | 1.53 | 1.56 | 1.40 | 1.16 | 0.64 |
| 089 | Q089N | 1.40 | 1.30 | 1.64 | 1.67 | 1.56 | 1.26 | 0.71 |
| 089 | Q089P | −0.80 | 0.03 | 1.23 | 0.45 | 0.97 | 2.98 | −0.11 |
| 089 | Q089R | 1.15 | 1.00 | 1.27 | 1.34 | 1.15 | 1.13 | 0.95 |
| 089 | Q089T | 11.41 | −3.81 | −9.90 | −2.46 | −5.57 | −36.35 | 0.02 |
| 089 | Q089V | 1.15 | 0.96 | 1.24 | 1.23 | 1.20 | 0.84 | 0.90 |
| 089 | Q089W | 0.84 | 0.66 | 0.84 | 0.84 | 0.79 | 0.69 | 1.11 |
| 089 | Q089Y | 0.97 | 0.97 | 1.23 | 1.19 | 1.06 | 0.88 | 0.95 |
| 093 | A093C | 1.36 | 1.43 | 1.51 | 1.80 | 1.74 | 1.33 | 0.57 |
| 093 | A093D | 1.21 | 1.41 | 1.52 | 1.53 | 1.26 | 1.12 | 0.80 |
| 093 | A093E | 1.53 | 1.50 | 1.78 | 1.75 | 1.55 | 1.55 | 0.71 |
| 093 | A093F | 1.24 | 1.42 | 1.20 | 1.45 | 1.54 | 1.13 | 0.72 |
| 093 | A093G | 1.20 | 1.15 | 1.23 | 1.29 | 1.35 | 1.10 | 0.89 |
| 093 | A093H | 0.98 | 0.88 | 1.01 | 1.03 | 1.01 | 0.91 | 1.11 |
| 093 | A093I | 0.97 | 1.11 | 1.11 | 1.39 | 1.28 | 1.16 | 0.76 |
| 093 | A093K | 0.93 | 0.92 | 1.10 | 1.07 | 0.87 | 0.86 | 1.14 |
| 093 | A093L | 0.90 | 0.91 | 1.08 | 1.09 | 0.97 | 1.03 | 0.96 |
| 093 | A093M | 1.10 | 1.13 | 1.45 | 1.53 | 1.42 | 1.34 | 0.82 |
| 093 | A093N | 1.52 | 1.46 | 1.77 | 1.72 | 1.46 | 1.59 | 0.73 |
| 093 | A093P | −0.84 | −0.82 | 0.20 | −0.65 | −0.46 | −0.39 | −0.09 |
| 093 | A093Q | 1.36 | 1.45 | 1.41 | 1.56 | 1.41 | 1.40 | 0.76 |
| 093 | A093R | 1.15 | 1.13 | 1.23 | 1.32 | 1.29 | 1.04 | 0.91 |
| 093 | A093S | 1.09 | 1.11 | 1.30 | 1.22 | 1.02 | 0.93 | 0.94 |
| 093 | A093T | 0.93 | 0.90 | 1.02 | 1.05 | 0.89 | 0.98 | 1.02 |
| 093 | A093V | 1.02 | 1.08 | 1.11 | 1.16 | 1.10 | 0.93 | 0.87 |
| 093 | A093W | 1.02 | 0.97 | 0.98 | 1.05 | 0.92 | 0.82 | 0.88 |
| 093 | A093Y | 0.93 | 0.91 | 1.17 | 1.22 | 1.12 | 1.12 | 0.83 |
| 115 | W115D | 0.97 | 1.05 | 0.95 | 1.04 | 1.15 | 1.05 | 0.91 |
| 115 | W115E | 0.88 | 0.90 | 0.91 | 0.96 | 0.69 | 0.88 | 1.09 |
| 115 | W115F | 0.87 | 0.92 | 0.79 | 0.85 | 0.95 | 0.73 | 1.11 |
| 115 | W115G | 0.81 | 0.81 | 0.93 | 0.89 | 0.84 | 1.10 | 1.28 |
| 115 | W115K | 0.67 | 0.64 | 0.75 | 0.74 | 0.73 | 0.62 | 1.44 |
| 115 | W115L | 0.58 | 0.58 | 0.67 | 0.65 | 0.62 | 0.69 | 1.63 |
| 115 | W115N | 0.87 | 0.94 | 1.13 | 1.07 | 1.08 | 0.98 | 1.02 |
| 115 | W115P | 1.12 | 1.12 | 1.18 | 1.20 | 1.22 | 1.29 | 0.87 |
| 115 | W115Q | 0.96 | 0.96 | 1.01 | 1.04 | 0.99 | 0.85 | 1.00 |
| 115 | W115R | 0.79 | 0.83 | 0.92 | 0.94 | 0.95 | 0.65 | 1.07 |
| 115 | W115S | 0.92 | 0.87 | 1.02 | 0.98 | 0.96 | 1.00 | 1.14 |
| 115 | W115V | 0.77 | 0.81 | 0.83 | 0.79 | 0.89 | 0.82 | 1.27 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 115 | W115Y | 0.56 | 0.63 | 0.74 | 0.73 | 0.77 | 0.69 | 1.41 |
| 117 | D117A | 1.29 | 1.21 | 1.20 | 1.32 | 1.83 | 1.39 | 0.45 |
| 117 | D117E | 1.40 | 1.34 | 1.30 | 1.21 | 1.65 | 1.33 | 0.65 |
| 117 | D117G | 1.10 | 1.02 | 1.08 | 1.08 | 1.19 | 1.33 | 0.78 |
| 117 | D117H | 0.92 | 0.82 | 0.84 | 0.89 | 1.21 | 1.08 | 0.87 |
| 117 | D117I | 0.98 | 0.70 | 0.65 | 0.79 | 1.49 | 1.26 | 0.50 |
| 117 | D117K | 0.68 | 0.57 | 0.93 | 0.89 | 0.82 | 0.86 | 1.30 |
| 117 | D117L | 0.81 | 0.77 | 0.94 | 0.86 | 1.09 | 0.86 | 0.64 |
| 117 | D117M | 1.21 | 1.13 | 1.23 | 1.32 | 1.44 | 0.97 | 0.53 |
| 117 | D117N | 1.30 | 1.26 | 1.63 | 1.48 | 1.48 | 1.23 | 0.71 |
| 117 | D117P | 1.07 | 1.04 | 1.27 | 1.17 | 1.29 | 1.10 | 0.88 |
| 117 | D117Q | 1.63 | 1.62 | 1.46 | 1.51 | 2.08 | 1.57 | 0.56 |
| 117 | D117R | 1.06 | 1.12 | 1.12 | 1.05 | 1.25 | 0.83 | 0.95 |
| 117 | D117S | 0.89 | 0.90 | 0.92 | 0.98 | 1.09 | 0.94 | 0.81 |
| 117 | D117T | 0.93 | 0.83 | 0.82 | 0.88 | 1.03 | 1.20 | 0.91 |
| 117 | D117V | 1.08 | 0.86 | 0.91 | 1.08 | 2.00 | 1.98 | 0.40 |
| 117 | D117W | 0.76 | 0.56 | 0.82 | 0.82 | 0.74 | 0.70 | 1.20 |
| 123 | P123A | 1.06 | 1.01 | 1.43 | 1.25 | 1.10 | 0.95 | 0.84 |
| 123 | P123D | 1.19 | 1.05 | 1.18 | 1.22 | 1.38 | 1.34 | 0.84 |
| 123 | P123E | 1.49 | 1.39 | 1.45 | 1.41 | 1.65 | 1.24 | 0.66 |
| 123 | P123G | 1.10 | 0.96 | 1.18 | 1.07 | 1.18 | 1.10 | 0.90 |
| 123 | P123K | 0.84 | 0.62 | 1.09 | 0.96 | 1.00 | 0.89 | 1.18 |
| 123 | P123L | 0.83 | 0.72 | 1.03 | 1.00 | 1.21 | 0.98 | 0.93 |
| 123 | P123M | 1.14 | 1.00 | 1.13 | 1.29 | 1.52 | 1.25 | 0.61 |
| 123 | P123Q | 1.25 | 1.15 | 1.19 | 1.35 | 1.55 | 1.30 | 0.68 |
| 123 | P123R | 1.02 | 0.95 | 1.28 | 1.28 | 1.12 | 1.11 | 0.96 |
| 123 | P123S | 1.07 | 0.84 | 0.88 | 0.92 | 1.17 | 0.97 | 0.96 |
| 123 | P123T | 1.00 | 0.89 | 0.83 | 0.90 | 1.13 | 0.83 | 0.97 |
| 123 | P123V | 0.83 | 0.79 | 0.97 | 1.08 | 1.23 | 0.99 | 0.83 |
| 124 | S124A | 1.33 | 1.45 | 1.31 | 1.39 | 1.27 | 1.34 | 0.79 |
| 124 | S124C | 1.28 | 1.32 | 0.93 | 1.15 | 1.54 | 1.21 | 0.77 |
| 124 | S124D | 1.19 | 1.20 | 1.14 | 1.24 | 1.35 | 1.31 | 0.88 |
| 124 | S124E | 1.15 | 1.22 | 1.16 | 1.19 | 1.24 | 1.11 | 0.93 |
| 124 | S124F | 1.12 | 1.19 | 1.05 | 1.16 | 1.05 | 0.98 | 1.01 |
| 124 | S124G | 0.92 | 0.81 | 0.79 | 0.84 | 1.14 | 0.80 | 1.08 |
| 124 | S124H | 0.91 | 0.98 | 0.97 | 1.02 | 1.12 | 1.11 | 0.98 |
| 124 | S124I | 0.93 | 0.92 | 0.92 | 0.91 | 0.99 | 1.05 | 1.10 |
| 124 | S124K | 0.89 | 0.89 | 0.95 | 0.90 | 0.92 | 0.77 | 1.24 |
| 124 | S124L | 0.70 | 0.73 | 0.74 | 0.62 | 0.74 | 0.61 | 1.36 |
| 124 | S124N | 1.16 | 1.18 | 1.00 | 1.15 | 1.17 | 0.96 | 0.87 |
| 124 | S124P | 1.08 | 0.97 | 1.06 | 1.25 | 1.43 | 1.02 | 0.71 |
| 124 | S124Q | 1.16 | 1.22 | 1.09 | 1.18 | 1.27 | 1.20 | 0.82 |
| 124 | S124R | 1.26 | 1.24 | 1.05 | 1.16 | 1.35 | 1.21 | 0.88 |
| 124 | S124T | 1.03 | 1.09 | 0.90 | 0.92 | 1.06 | 1.03 | 1.02 |
| 124 | S124V | 0.97 | 0.96 | 0.81 | 0.86 | 0.98 | 1.00 | 1.01 |
| 124 | S124Y | 0.87 | 0.88 | 0.74 | 0.83 | 0.86 | 0.75 | 1.13 |
| 125 | D125A | 0.75 | 0.72 | 1.11 | 1.21 | 1.17 | 1.04 | 0.82 |
| 125 | D125E | 1.02 | 1.00 | 0.92 | 1.01 | 0.96 | 0.77 | 0.94 |
| 125 | D125G | 0.51 | 0.48 | 0.91 | 0.90 | 0.46 | 0.77 | 1.15 |
| 125 | D125K | 0.37 | 0.34 | 0.65 | 0.80 | 0.79 | 0.68 | 1.23 |
| 125 | D125M | 1.08 | 1.06 | 1.02 | 1.11 | 1.11 | 0.98 | 0.93 |
| 125 | D125Q | 0.87 | 0.74 | 0.92 | 1.03 | 0.85 | 0.81 | 0.94 |
| 125 | D125R | 0.43 | 0.43 | 0.69 | 0.92 | 0.74 | 0.61 | 1.06 |
| 125 | D125S | 0.67 | 0.57 | 0.96 | 1.03 | 0.80 | 0.82 | 1.12 |
| 125 | D125T | 0.91 | 0.92 | 0.78 | 0.80 | 0.78 | 0.59 | 1.17 |
| 125 | D125V | 0.38 | 0.36 | 0.67 | 0.81 | 0.78 | 1.01 | 1.17 |
| 127 | N127A | 0.80 | 0.88 | 1.41 | 1.37 | 1.42 | 1.34 | 0.69 |
| 127 | N127C | 1.25 | 1.40 | 1.26 | 1.39 | 1.48 | 1.45 | 0.69 |
| 127 | N127D | 1.21 | 1.24 | 1.24 | 1.31 | 1.19 | 1.41 | 0.78 |
| 127 | N127F | 0.98 | 0.84 | 1.27 | 1.23 | 1.09 | 0.90 | 0.82 |
| 127 | N127G | 0.86 | 0.71 | 1.05 | 1.04 | 1.03 | 1.05 | 0.93 |
| 127 | N127H | 0.70 | 0.63 | 0.83 | 0.89 | 0.86 | 0.81 | 1.02 |
| 127 | N127K | 0.51 | 0.47 | 0.77 | 0.86 | 0.95 | 1.01 | 1.03 |
| 127 | N127L | 0.71 | 0.67 | 0.99 | 1.04 | 1.12 | 1.01 | 0.93 |
| 127 | N127M | 1.00 | 1.15 | 1.47 | 1.46 | 1.35 | 1.23 | 0.73 |
| 127 | N127P | 1.10 | 1.04 | 1.30 | 1.39 | 1.16 | 1.21 | 0.65 |
| 127 | N127Q | 1.04 | 1.01 | 1.42 | 1.47 | 1.33 | 1.00 | 0.71 |
| 127 | N127R | 0.88 | 0.87 | 1.04 | 1.10 | 1.14 | 0.89 | 0.96 |
| 127 | N127S | 0.87 | 0.71 | 1.08 | 1.06 | 1.04 | 0.91 | 0.90 |
| 127 | N127T | 0.78 | 0.68 | 0.79 | 0.79 | 0.93 | 0.75 | 1.08 |
| 127 | N127V | 0.75 | 0.78 | 1.34 | 1.27 | 1.11 | 0.97 | 0.75 |
| 127 | N127W | 0.79 | 0.73 | 0.76 | 0.80 | 0.84 | 0.82 | 1.16 |
| 127 | N127Y | 1.16 | 1.12 | 1.23 | 1.15 | 1.21 | 1.14 | 0.82 |
| 130 | I130A | 1.15 | 1.06 | 1.61 | 1.47 | 1.25 | 1.13 | 0.82 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 130 | I130G | 0.81 | 0.71 | 1.10 | 1.12 | 1.25 | 1.11 | 0.91 |
| 130 | I130H | 0.58 | 0.51 | 0.83 | 0.87 | 0.92 | 0.79 | 1.18 |
| 130 | I130K | 0.73 | 0.64 | 1.06 | 0.96 | 0.94 | 0.84 | 1.14 |
| 130 | I130L | 0.80 | 0.77 | 1.08 | 1.04 | 0.99 | 0.92 | 0.96 |
| 130 | I130M | 1.45 | 1.37 | 1.42 | 1.44 | 1.33 | 1.19 | 0.77 |
| 130 | I130N | 1.08 | 0.95 | 1.48 | 1.46 | 1.11 | 1.01 | 0.78 |
| 130 | I130P | 0.29 | 0.41 | 0.91 | 1.29 | 1.33 | 1.36 | 0.76 |
| 130 | I130Q | −0.18 | −1.25 | 1.18 | 0.52 | −0.19 | 0.03 | −0.12 |
| 130 | I130R | 1.09 | 0.91 | 1.30 | 1.34 | 0.91 | 1.00 | 0.85 |
| 130 | I130S | 1.02 | 0.81 | 1.02 | 1.06 | 1.07 | 0.84 | 0.97 |
| 130 | I130T | 0.97 | 0.99 | 1.09 | 1.04 | 0.97 | 0.99 | 0.98 |
| 130 | I130V | 1.12 | 1.21 | 1.12 | 1.12 | 0.94 | 0.96 | 0.83 |
| 130 | I130W | 0.85 | 0.69 | 0.95 | 1.01 | 1.11 | 0.89 | 0.89 |
| 132 | G132A | 1.52 | 1.66 | 1.32 | 1.47 | 1.60 | 1.39 | 0.68 |
| 132 | G132C | 1.38 | 1.47 | 1.26 | 1.28 | 1.10 | 0.87 | 0.79 |
| 132 | G132D | 1.84 | 1.78 | 1.18 | 1.50 | 1.56 | 1.56 | 0.51 |
| 132 | G132E | 1.17 | 1.33 | 1.11 | 1.21 | 0.90 | 0.86 | 0.86 |
| 132 | G132F | 1.20 | 1.21 | 1.03 | 1.18 | 1.03 | 1.03 | 0.91 |
| 132 | G132H | 0.98 | 1.03 | 0.93 | 0.97 | 1.04 | 0.99 | 1.02 |
| 132 | G132L | 0.98 | 1.03 | 0.76 | 0.84 | 0.88 | 0.85 | 0.95 |
| 132 | G132M | 1.81 | 1.76 | 1.51 | 1.61 | 1.81 | 1.73 | 0.61 |
| 132 | G132N | 1.18 | 1.23 | 1.11 | 1.27 | 1.15 | 1.08 | 0.82 |
| 132 | G132P | 1.51 | 1.59 | 1.28 | 1.40 | 1.26 | 1.34 | 0.75 |
| 132 | G132R | 1.35 | 1.32 | 0.97 | 1.12 | 1.02 | 1.06 | 0.87 |
| 132 | G132S | 1.32 | 1.34 | 1.08 | 1.22 | 1.15 | 0.96 | 0.77 |
| 132 | G132T | 1.09 | 1.05 | 0.87 | 0.96 | 0.94 | 0.98 | 1.03 |
| 132 | G132V | 0.99 | 1.09 | 0.96 | 1.02 | 0.95 | 1.03 | 0.98 |
| 132 | G132W | 1.17 | 1.13 | 0.95 | 1.07 | 1.02 | 0.84 | 0.91 |
| 132 | G132Y | 0.93 | 0.87 | 0.81 | 0.86 | 0.80 | 0.81 | 1.15 |
| 135 | Q135A | 0.95 | 0.99 | 1.00 | 1.20 | 1.13 | 0.99 | 0.84 |
| 135 | Q135F | 0.93 | 1.05 | 0.91 | 1.03 | 1.04 | 1.39 | 0.94 |
| 135 | Q135G | 0.77 | 0.80 | 0.75 | 0.84 | 0.97 | 1.05 | 1.08 |
| 135 | Q135K | 0.59 | 0.69 | 0.63 | 0.71 | 0.70 | 0.74 | 1.27 |
| 135 | Q135L | 0.40 | 0.22 | −0.66 | −0.33 | 0.38 | −0.14 | 0.19 |
| 135 | Q135M | 0.91 | 1.03 | 1.01 | 1.14 | 0.90 | 1.01 | 0.86 |
| 135 | Q135P | 1.12 | 1.16 | 0.96 | 1.07 | 0.85 | 1.16 | 0.87 |
| 135 | Q135R | 0.92 | 1.01 | 0.95 | 1.00 | 0.95 | 1.14 | 1.08 |
| 135 | Q135S | 0.93 | 0.93 | 0.80 | 0.95 | 0.91 | 0.87 | 0.94 |
| 135 | Q135T | 0.84 | 0.83 | 0.73 | 0.80 | 0.79 | 0.83 | 1.19 |
| 135 | Q135V | 0.92 | 0.84 | 0.66 | 0.75 | 0.98 | 1.23 | 0.76 |
| 135 | Q135Y | 0.75 | 0.75 | 0.69 | 0.79 | 0.75 | 0.91 | 1.16 |
| 145 | P145A | 1.15 | 1.17 | 1.44 | 1.50 | 1.30 | 1.29 | 0.71 |
| 145 | P145D | 1.35 | 1.61 | 1.15 | 1.33 | 1.45 | 1.48 | 0.57 |
| 145 | P145E | 1.55 | 1.48 | 1.26 | 1.45 | 1.34 | 1.65 | 0.63 |
| 145 | P145F | 1.34 | 1.32 | 1.02 | 1.20 | 1.12 | 1.32 | 0.74 |
| 145 | P145H | 0.98 | 0.88 | 0.81 | 0.99 | 1.13 | 1.03 | 0.90 |
| 145 | P145I | 1.20 | 1.06 | 0.84 | 0.98 | 1.10 | 1.20 | 0.85 |
| 145 | P145K | 0.90 | 0.89 | 0.88 | 1.05 | 1.15 | 1.02 | 0.88 |
| 145 | P145L | 1.03 | 0.90 | 0.81 | 1.01 | 0.97 | 1.23 | 0.85 |
| 145 | P145N | 1.19 | 1.43 | 1.41 | 1.58 | 1.49 | 1.48 | 0.61 |
| 145 | P145R | 1.22 | 1.11 | 1.10 | 1.29 | 1.14 | 1.11 | 0.86 |
| 145 | P145S | 1.12 | 1.04 | 1.03 | 1.10 | 1.08 | 1.12 | 0.85 |
| 145 | P145T | 1.15 | 0.99 | 0.91 | 1.00 | 0.92 | 0.81 | 0.89 |
| 145 | P145V | 1.09 | 1.18 | 1.08 | 1.19 | 1.24 | 1.25 | 0.73 |
| 145 | P145Y | 1.14 | 1.12 | 0.89 | 1.15 | 1.08 | 1.16 | 0.75 |
| 146 | G146A | 1.18 | 1.00 | 1.34 | 1.41 | 1.19 | 1.05 | 0.77 |
| 146 | G146C | 2.03 | 1.89 | 1.71 | 1.89 | 2.19 | 1.52 | 0.40 |
| 146 | G146D | 1.32 | 1.35 | 1.45 | 1.52 | 1.50 | 1.17 | 0.70 |
| 146 | G146E | 1.43 | 1.43 | 1.63 | 1.62 | 1.38 | 1.33 | 0.82 |
| 146 | G146H | 1.00 | 0.99 | 0.77 | 0.88 | 1.01 | 0.93 | 1.06 |
| 146 | G146K | 0.94 | 0.84 | 1.06 | 1.07 | 1.05 | 1.10 | 1.08 |
| 146 | G146L | 0.99 | 0.80 | 0.85 | ND | 0.97 | 0.74 | 0.97 |
| 146 | G146P | 1.33 | 1.24 | 1.30 | 1.36 | 1.43 | 1.31 | 0.76 |
| 146 | G146R | 1.21 | 1.07 | 1.12 | 1.30 | 1.21 | 1.41 | 0.85 |
| 146 | G146S | 1.18 | 1.13 | 1.02 | 1.04 | 0.97 | 0.94 | 0.91 |
| 146 | G146T | 0.91 | 0.83 | 0.98 | 1.00 | 0.97 | 0.78 | 1.13 |
| 146 | G146V | 1.19 | 1.04 | 1.15 | 1.21 | 1.22 | 1.16 | 0.79 |
| 146 | G146W | 0.94 | 0.88 | 0.83 | 0.91 | 0.80 | 1.01 | 0.93 |
| 148 | G148A | 1.20 | 1.28 | 1.37 | 1.49 | 1.22 | 1.10 | 0.71 |
| 148 | G148C | 1.09 | 0.94 | 1.25 | 1.28 | 1.17 | 1.19 | 0.84 |
| 148 | G148D | −1.07 | −0.40 | 0.77 | 0.36 | 0.81 | 1.35 | −0.11 |
| 148 | G148E | 1.17 | 1.19 | 1.27 | 1.27 | 1.37 | 1.02 | 0.89 |
| 148 | G148F | 1.08 | 1.07 | 1.13 | 1.16 | 1.03 | 1.27 | 0.97 |
| 148 | G148H | 0.89 | 0.90 | 1.00 | 0.97 | 0.91 | 0.66 | 1.13 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 148 | G148L | 0.88 | 0.83 | 0.89 | 0.90 | 0.94 | 0.91 | 1.16 |
| 148 | G148N | 1.00 | 0.98 | 1.20 | 1.17 | 1.13 | 1.18 | 1.01 |
| 148 | G148P | 1.30 | 1.33 | 1.34 | 1.45 | 1.35 | 1.09 | 0.76 |
| 148 | G148Q | −1.69 | −1.32 | 1.69 | 0.84 | −0.01 | 0.58 | −0.07 |
| 148 | G148R | 1.27 | 1.20 | 1.12 | 1.24 | 1.14 | 0.71 | 0.85 |
| 148 | G148S | 0.96 | 0.97 | 0.92 | 0.96 | 0.84 | 1.05 | 1.03 |
| 148 | G148T | 1.35 | 1.20 | 0.70 | 0.86 | 1.35 | 0.90 | 0.49 |
| 148 | G148V | 0.96 | 0.95 | 0.95 | 1.02 | 1.04 | 0.69 | 1.03 |
| 148 | G148W | 1.00 | 0.88 | 0.90 | 0.96 | 0.89 | 0.83 | 1.00 |
| 148 | G148Y | 0.82 | 0.74 | 0.86 | 0.93 | 0.91 | 0.87 | 1.14 |
| 153 | S153A | 1.14 | 1.15 | 1.09 | 1.23 | 1.21 | 1.09 | 0.86 |
| 153 | S153C | 1.70 | 1.78 | 1.37 | 1.54 | 1.51 | 1.61 | 0.53 |
| 153 | S153D | 1.34 | 1.25 | 0.99 | 1.11 | 1.18 | 1.02 | 0.88 |
| 153 | S153E | 1.76 | 1.18 | 1.20 | 1.34 | 1.54 | 1.36 | 0.61 |
| 153 | S153F | 1.42 | 1.35 | 1.07 | 1.18 | 1.22 | 1.36 | 0.80 |
| 153 | S153G | 1.35 | 1.16 | 0.97 | 1.03 | 1.08 | 1.25 | 0.88 |
| 153 | S153H | 0.98 | 0.91 | 0.72 | 0.77 | 0.92 | 1.00 | 1.05 |
| 153 | S153I | 1.31 | 1.09 | 0.95 | 1.05 | 1.28 | 1.35 | 0.74 |
| 153 | S153K | 0.79 | 0.82 | 0.80 | 0.87 | 1.02 | 1.00 | 1.08 |
| 153 | S153L | 1.11 | 0.96 | 0.92 | 0.98 | 1.03 | 1.26 | 0.92 |
| 153 | S153N | 1.29 | 1.38 | 1.38 | 1.43 | 1.20 | 1.75 | 0.76 |
| 153 | S153P | 1.09 | 1.19 | 1.21 | 1.28 | 1.15 | 1.15 | 1.00 |
| 153 | S153Q | 1.14 | 1.22 | 0.95 | 1.21 | 1.39 | 1.47 | 0.73 |
| 153 | S153R | 1.29 | 1.16 | 1.00 | 1.12 | 1.18 | 1.16 | 0.95 |
| 153 | S153T | 0.93 | 1.02 | 0.82 | 0.89 | 0.88 | 0.97 | 1.01 |
| 153 | S153V | 1.30 | 1.16 | 0.97 | 1.07 | 1.08 | 1.26 | 0.77 |
| 153 | S153W | 0.94 | 0.95 | 0.75 | 0.86 | 0.85 | 1.21 | 0.90 |
| 153 | S153Y | 1.15 | 1.03 | 0.96 | 1.00 | 1.03 | 1.13 | 0.86 |
| 159 | Y159A | 1.17 | 1.17 | 1.42 | 1.52 | 1.50 | 1.70 | 0.74 |
| 159 | Y159C | 1.46 | 1.19 | 1.80 | 1.73 | 1.10 | 1.66 | 0.66 |
| 159 | Y159D | 1.08 | 1.21 | 1.89 | 1.88 | 1.63 | 2.01 | 0.78 |
| 159 | Y159E | 1.23 | 1.25 | 1.34 | 1.50 | 1.31 | 1.66 | 0.73 |
| 159 | Y159F | 1.11 | 1.10 | 1.03 | 1.10 | 0.96 | 1.17 | 0.97 |
| 159 | Y159G | 0.92 | 0.79 | 0.95 | 1.02 | 1.22 | 1.44 | 0.94 |
| 159 | Y159H | 0.97 | 0.86 | 0.97 | 1.05 | 1.07 | 1.17 | 1.01 |
| 159 | Y159K | 1.03 | 0.78 | 1.20 | 1.21 | 0.96 | 1.71 | 0.90 |
| 159 | Y159L | 0.77 | 0.61 | 0.95 | 1.00 | 1.24 | 1.41 | 0.98 |
| 159 | Y159N | 0.97 | 0.94 | 1.46 | 1.56 | 1.40 | 1.85 | 0.78 |
| 159 | Y159R | 1.10 | 0.86 | 1.19 | 1.40 | 1.39 | 1.75 | 0.80 |
| 159 | Y159S | 0.97 | 0.82 | 1.01 | 1.09 | 1.25 | 1.44 | 0.94 |
| 159 | Y159T | 0.93 | 0.93 | 1.18 | 1.20 | 1.26 | 1.74 | 0.87 |
| 159 | Y159V | 1.09 | 0.95 | 0.96 | 1.07 | 1.12 | 1.48 | 0.87 |
| 159 | Y159W | 1.08 | 1.12 | 0.98 | 1.08 | 0.73 | 0.96 | 0.88 |
| 166 | W166C | 0.57 | 0.71 | 0.61 | 0.60 | 0.90 | 1.03 | 0.80 |
| 166 | W166E | 0.58 | 0.78 | 0.94 | 0.74 | 1.09 | 1.12 | 0.97 |
| 166 | W166F | 0.75 | 0.82 | 0.73 | 0.81 | 0.82 | 1.06 | 1.07 |
| 166 | W166G | 0.65 | 0.57 | 0.42 | 0.50 | 0.84 | 0.93 | 1.18 |
| 166 | W166H | 0.59 | 0.64 | 0.57 | 0.67 | 0.90 | 0.92 | 1.26 |
| 166 | W166I | 0.56 | 0.65 | 0.85 | 0.79 | 0.65 | 1.16 | 1.13 |
| 166 | W166K | 0.47 | 0.49 | 0.96 | 0.81 | 0.60 | 1.09 | 1.49 |
| 166 | W166L | 0.45 | 0.54 | 0.79 | 0.64 | 0.58 | 0.91 | 1.46 |
| 166 | W166M | 0.70 | 0.83 | 0.96 | 0.82 | 0.89 | 1.24 | 1.00 |
| 166 | W166P | 0.16 | 0.30 | −0.15 | −0.02 | 1.19 | 1.09 | 0.69 |
| 166 | W166R | 0.67 | 0.86 | 1.40 | 1.17 | 0.83 | 0.76 | 0.94 |
| 166 | W166S | 0.61 | 0.64 | 0.63 | 0.57 | 0.90 | 0.95 | 1.14 |
| 166 | W166T | 0.60 | 0.73 | 0.92 | 0.76 | 0.70 | 0.33 | 1.15 |
| 166 | W166V | 0.51 | 0.61 | 0.88 | 0.75 | 0.49 | 0.98 | 1.10 |
| 166 | W166Y | 0.65 | 0.70 | 0.73 | 0.78 | 0.81 | 0.96 | 1.16 |
| 169 | S169A | 1.10 | 1.14 | 1.17 | 1.30 | 1.17 | 1.35 | 0.85 |
| 169 | S169C | 1.05 | 1.37 | 1.33 | 1.43 | 1.54 | 1.47 | 0.74 |
| 169 | S169D | 0.91 | 1.17 | 1.21 | 1.26 | 1.36 | 1.42 | 0.71 |
| 169 | S169E | 1.24 | 1.36 | 1.37 | 1.59 | 1.65 | 1.81 | 0.67 |
| 169 | S169F | 1.04 | 1.33 | 1.01 | 1.13 | 1.15 | 1.36 | 0.74 |
| 169 | S169G | 1.05 | 0.90 | 0.97 | 0.99 | 0.99 | 1.22 | 0.97 |
| 169 | S169I | 0.84 | 0.82 | 0.84 | 1.02 | 1.18 | 1.00 | 0.93 |
| 169 | S169K | 0.81 | 0.85 | 0.78 | 0.94 | 0.88 | 1.03 | 1.00 |
| 169 | S169L | 0.82 | 0.65 | 0.83 | 0.95 | 0.99 | 1.00 | 1.09 |
| 169 | S169M | 0.98 | 0.71 | 1.05 | 1.17 | 0.98 | 1.17 | 0.92 |
| 169 | S169N | 0.88 | 1.09 | 1.28 | 1.35 | 1.43 | 1.41 | 0.76 |
| 169 | S169P | 0.55 | 0.85 | 0.74 | 1.10 | 1.25 | 0.96 | 0.78 |
| 169 | S169Q | 1.08 | 1.18 | 1.27 | 1.43 | 1.43 | 1.54 | 0.75 |
| 169 | S169R | 0.95 | 0.88 | 1.01 | 1.13 | 1.08 | 1.26 | 0.96 |
| 169 | S169T | 0.78 | 0.75 | 0.87 | 0.96 | 0.92 | 0.79 | 1.07 |
| 169 | S169V | 0.78 | 0.88 | 0.78 | 1.01 | 1.10 | 1.00 | 0.94 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 169 | S169Y | 0.91 | 0.87 | 1.00 | 1.11 | 0.97 | 1.10 | 0.93 |
| 171 | K171C | 1.20 | 1.53 | 1.27 | 1.46 | 1.71 | 1.56 | 0.54 |
| 171 | K171D | 1.22 | 1.28 | 1.11 | 1.32 | 1.03 | 1.49 | 0.75 |
| 171 | K171E | 1.18 | 1.46 | 1.26 | 1.33 | 1.61 | 1.36 | 0.65 |
| 171 | K171G | 1.03 | 1.06 | 0.87 | 0.91 | 1.08 | 1.29 | 0.80 |
| 171 | K171H | 0.90 | 0.76 | 0.82 | 0.90 | 0.93 | 0.94 | 1.20 |
| 171 | K171L | 0.70 | 0.76 | 0.84 | 0.88 | 0.88 | 0.86 | 1.05 |
| 171 | K171M | 1.11 | 1.32 | 1.25 | 1.34 | 1.43 | 1.08 | 0.67 |
| 171 | K171P | 0.99 | 1.09 | 1.19 | 1.31 | 1.36 | 1.32 | 0.73 |
| 171 | K171Q | 1.08 | 1.15 | 1.05 | 1.26 | 1.66 | 1.37 | 0.67 |
| 171 | K171R | 1.01 | 0.96 | 0.96 | 1.08 | 1.10 | 1.42 | 0.92 |
| 171 | K171S | 1.12 | 0.97 | 0.86 | 0.96 | 0.90 | 1.17 | 0.93 |
| 171 | K171T | 1.00 | 0.88 | 0.87 | 0.93 | 0.96 | 1.03 | 1.09 |
| 171 | K171V | 0.87 | 0.92 | 0.81 | 0.92 | 1.13 | 0.97 | 0.89 |
| 171 | K171W | 0.74 | 0.74 | 0.59 | 0.82 | 0.88 | 0.86 | 1.03 |
| 171 | K171Y | 0.86 | 0.73 | 0.70 | 0.90 | 0.96 | 1.06 | 0.92 |
| 179 | R179A | 0.88 | 0.88 | 1.28 | 1.47 | 1.62 | 1.55 | 0.83 |
| 179 | R179G | 0.53 | 0.56 | 0.93 | 1.05 | 1.02 | 1.09 | 1.05 |
| 179 | R179H | 0.82 | 0.78 | 1.07 | 1.19 | 1.25 | 1.32 | 1.00 |
| 179 | R179L | 0.71 | 0.62 | 0.79 | 0.93 | 1.00 | 1.28 | 0.99 |
| 179 | R179M | 0.81 | 1.14 | 1.24 | 1.51 | 1.58 | 1.52 | 0.66 |
| 179 | R179P | 0.33 | 0.50 | 1.14 | 1.33 | 1.42 | 1.61 | 0.79 |
| 179 | R179Q | 1.07 | 0.98 | 1.03 | 1.27 | 1.31 | 1.39 | 0.82 |
| 179 | R179S | 0.86 | 0.62 | 0.94 | 1.12 | 1.11 | 1.21 | 1.02 |
| 179 | R179T | 0.97 | 0.78 | 1.00 | 1.16 | 1.31 | 1.32 | 0.94 |
| 179 | R179V | 0.90 | 0.89 | 0.84 | 1.03 | 1.26 | 1.12 | 0.91 |
| 179 | R179W | 0.81 | 0.70 | 0.92 | 1.19 | 1.17 | 1.71 | 0.87 |
| 179 | R179Y | 0.64 | 0.49 | 0.81 | 0.95 | 0.89 | 1.22 | 1.06 |
| 180 | G180A | 0.82 | 0.75 | 1.37 | 0.96 | 1.25 | 1.45 | 0.76 |
| 180 | G180C | 0.43 | 0.46 | 1.29 | 0.82 | 1.35 | 1.56 | 0.73 |
| 180 | G180D | 0.50 | 0.54 | 1.39 | 0.99 | 1.37 | 1.36 | 0.81 |
| 180 | G180F | 0.32 | 0.32 | 1.19 | 1.03 | 0.90 | 1.75 | 0.72 |
| 180 | G180H | 0.38 | 0.36 | 0.95 | 0.80 | 0.89 | 1.00 | 1.12 |
| 180 | G180I | 0.21 | 0.21 | 0.87 | 0.73 | 1.17 | 1.09 | 0.84 |
| 180 | G180K | 0.13 | 0.16 | 0.77 | ND | 0.99 | 1.02 | 1.26 |
| 180 | G180L | 0.22 | 0.25 | 1.02 | 0.72 | 0.81 | 0.94 | 1.38 |
| 180 | G180N | 0.46 | 0.52 | 1.41 | 1.13 | 1.24 | 0.89 | 0.81 |
| 180 | G180P | 0.42 | 0.45 | 1.39 | ND | 1.46 | 1.74 | 0.75 |
| 180 | G180R | 1.27 | 0.83 | ND | ND | −0.82 | −12.79 | −0.03 |
| 180 | G180S | 0.82 | 0.70 | 0.98 | 0.79 | 0.90 | 0.92 | 0.96 |
| 180 | G180T | 0.46 | 0.37 | 0.91 | 0.76 | 1.02 | 0.77 | 1.07 |
| 180 | G180V | 0.25 | 0.18 | 0.89 | ND | 1.01 | 0.98 | 0.96 |
| 180 | G180Y | 0.29 | 0.34 | 0.91 | 0.75 | 1.03 | 1.11 | 1.03 |
| 181 | I181A | 1.16 | 1.15 | 1.60 | 1.19 | 1.45 | 1.48 | 0.78 |
| 181 | I181C | 1.18 | 1.21 | 1.79 | ND | 1.10 | 1.35 | 0.68 |
| 181 | I181D | 1.19 | 1.29 | 1.61 | 1.22 | 1.64 | 1.19 | 0.74 |
| 181 | I181E | 1.44 | 1.47 | 1.54 | 1.27 | 1.48 | 1.55 | 0.72 |
| 181 | I181F | 1.11 | 1.04 | 1.20 | 0.92 | 1.24 | 0.84 | 0.87 |
| 181 | I181G | 0.69 | 0.59 | 1.20 | 1.02 | 1.15 | 1.12 | 0.94 |
| 181 | I181H | 0.88 | 0.73 | 1.13 | ND | 0.95 | 0.95 | 0.98 |
| 181 | I181K | 0.58 | 0.43 | 1.15 | ND | 0.96 | 0.87 | 1.04 |
| 181 | I181L | 0.76 | 0.75 | 1.09 | ND | 0.91 | 0.78 | 1.01 |
| 181 | I181P | 1.04 | 1.07 | 1.35 | ND | 1.30 | 1.34 | 0.85 |
| 181 | I181R | 0.49 | 0.47 | 0.78 | 0.87 | 1.43 | 1.64 | 0.87 |
| 181 | I181S | 0.93 | 0.83 | 1.09 | 0.80 | 1.02 | 1.15 | 0.97 |
| 181 | I181T | 0.80 | 0.75 | 1.02 | 0.85 | 0.94 | 1.13 | 1.09 |
| 181 | I181V | 1.20 | 1.04 | 1.39 | 1.12 | 1.18 | 1.16 | 0.81 |
| 181 | I181Y | 0.83 | 0.69 | 1.06 | 0.89 | 0.94 | 0.87 | 0.95 |
| 182 | G182A | 0.82 | 0.87 | 1.36 | 1.14 | 1.24 | 1.11 | 0.72 |
| 182 | G182C | 1.18 | 1.14 | 1.73 | 1.58 | 1.96 | 1.42 | 0.45 |
| 182 | G182D | 0.79 | 0.71 | 1.40 | 1.17 | 1.40 | 1.56 | 0.77 |
| 182 | G182E | 0.68 | 0.64 | 1.45 | 1.26 | 1.73 | 1.43 | 0.66 |
| 182 | G182F | 1.30 | 1.21 | 1.10 | 1.06 | 1.50 | 1.46 | 0.46 |
| 182 | G182H | 0.64 | 0.53 | 1.01 | ND | 1.13 | 1.22 | 1.01 |
| 182 | G182K | −0.04 | −0.01 | −0.15 | ND | 0.07 | −0.08 | 0.91 |
| 182 | G182L | 0.53 | 0.48 | 1.12 | ND | 1.26 | 0.86 | 0.70 |
| 182 | G182P | 0.61 | 0.47 | 1.45 | 1.23 | 1.57 | 1.40 | 0.73 |
| 182 | G182R | 0.77 | 0.69 | 1.32 | 0.99 | 1.30 | 1.56 | 0.81 |
| 182 | G182S | 0.68 | 0.57 | 0.99 | 0.87 | 1.16 | 1.10 | 0.85 |
| 182 | G182T | 0.49 | 0.49 | 1.00 | 0.89 | 1.22 | 1.12 | 0.84 |
| 182 | G182V | 0.61 | 0.46 | 1.26 | 1.12 | 1.38 | 1.18 | 0.66 |
| 182 | G182Y | 0.61 | 0.48 | 0.85 | 0.88 | 1.00 | 0.96 | 0.84 |
| 183 | K183A | 0.20 | 0.17 | 1.19 | 1.20 | 1.58 | 1.99 | 0.66 |
| 183 | K183C | 0.18 | 0.19 | 1.35 | 1.24 | 1.38 | 2.02 | 0.62 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 183 | K183E | 0.14 | 0.02 | 1.20 | 1.10 | 1.37 | 1.55 | 0.72 |
| 183 | K183F | 0.15 | −0.05 | 1.11 | 1.08 | 1.61 | 2.04 | 0.59 |
| 183 | K183G | 0.15 | 0.13 | 0.96 | ND | 1.24 | 1.35 | 0.94 |
| 183 | K183H | 0.27 | 0.15 | 0.93 | 0.84 | 1.31 | 1.26 | 0.86 |
| 183 | K183L | 0.05 | 0.10 | 0.91 | 0.93 | 1.15 | 1.44 | 0.86 |
| 183 | K183M | 0.14 | 0.18 | 1.42 | 1.40 | 1.60 | 2.40 | 0.58 |
| 183 | K183P | 0.03 | 0.17 | 1.27 | 1.06 | 1.73 | 1.64 | 0.58 |
| 183 | K183Q | 0.12 | 0.14 | 1.30 | 1.21 | 1.51 | 2.11 | 0.71 |
| 183 | K183R | 0.20 | 0.11 | 1.03 | 1.00 | 1.13 | 2.07 | 0.82 |
| 183 | K183S | 0.15 | 0.18 | 0.92 | 0.83 | 1.18 | 1.33 | 0.93 |
| 183 | K183T | 0.20 | 0.01 | 1.10 | 1.11 | 1.16 | 1.71 | 0.80 |
| 183 | K183V | 0.10 | 0.07 | 0.82 | 0.89 | 1.38 | 1.73 | 0.62 |
| 183 | K183W | 0.07 | 0.13 | 0.66 | 0.77 | 1.23 | 1.09 | 0.70 |
| 183 | K183Y | 0.08 | 0.14 | 0.66 | 0.73 | 1.10 | 1.32 | 0.88 |
| 187 | W187A | 0.45 | 0.36 | 1.67 | 1.77 | 1.21 | 1.02 | 0.90 |
| 187 | W187C | 0.48 | 0.40 | 1.23 | 1.49 | 1.19 | 1.13 | 0.88 |
| 187 | W187E | 0.62 | 0.51 | 1.18 | 1.22 | 1.14 | 1.08 | 1.04 |
| 187 | W187G | 0.16 | 0.13 | 0.57 | 0.86 | 0.86 | 0.73 | 1.13 |
| 187 | W187I | 0.70 | 0.57 | 0.83 | 0.86 | 0.78 | 0.82 | 1.29 |
| 187 | W187K | 0.16 | 0.16 | 0.85 | 0.90 | 0.71 | 0.64 | 1.72 |
| 187 | W187L | 0.69 | 0.69 | 0.72 | 0.78 | 0.75 | 0.66 | 1.29 |
| 187 | W187N | 0.53 | 0.62 | 1.29 | 1.41 | 1.10 | 1.08 | 0.91 |
| 187 | W187P | 0.17 | 0.14 | 0.29 | 1.65 | 1.19 | 1.15 | 0.85 |
| 187 | W187Q | 0.41 | 0.35 | 1.27 | 1.30 | 1.09 | 0.92 | 1.03 |
| 187 | W187R | 0.29 | 0.28 | 0.96 | 1.19 | 0.92 | 0.92 | 1.08 |
| 187 | W187S | 0.40 | 0.28 | 1.01 | 1.07 | 0.86 | 0.76 | 1.25 |
| 187 | W187V | 0.20 | −0.60 | −0.25 | 0.12 | 0.26 | 0.77 | 0.20 |
| 194 | G194A | 1.33 | 1.26 | 1.40 | 1.36 | 1.55 | 1.18 | 0.68 |
| 194 | G194E | 1.28 | 1.12 | 1.13 | 1.10 | 1.37 | 1.25 | 0.79 |
| 194 | G194H | 1.09 | 1.02 | 0.91 | 0.92 | 1.10 | 0.72 | 0.97 |
| 194 | G194K | 0.77 | 0.75 | 0.80 | 0.80 | 1.01 | 0.68 | 1.18 |
| 194 | G194L | 0.74 | 0.64 | 0.81 | 0.85 | 0.97 | 0.78 | 1.01 |
| 194 | G194M | 1.38 | 1.33 | 1.65 | 1.48 | 1.40 | 1.19 | 0.69 |
| 194 | G194P | 0.04 | 0.01 | 0.00 | 2.12 | 1.14 | 0.37 | 0.78 |
| 194 | G194R | 1.04 | 0.96 | 0.98 | 1.05 | 1.08 | 0.86 | 1.01 |
| 194 | G194S | 1.08 | 1.02 | 1.14 | 1.09 | 0.94 | 0.70 | 1.03 |
| 194 | G194T | 0.93 | 0.77 | 0.87 | 0.92 | 1.05 | 0.71 | 1.07 |
| 194 | G194V | 1.26 | 1.08 | 0.97 | 1.01 | 1.14 | 0.80 | 0.84 |
| 194 | G194W | 0.61 | 0.51 | 0.60 | 0.62 | 0.75 | 0.48 | 1.31 |
| 209 | P209A | 1.22 | 1.30 | 1.67 | 1.68 | 1.52 | 1.20 | 0.68 |
| 209 | P209C | 1.24 | 1.20 | 1.01 | 1.00 | 1.37 | 1.29 | 0.58 |
| 209 | P209D | 1.35 | 1.33 | 1.41 | 1.57 | 1.39 | 1.30 | 0.76 |
| 209 | P209E | 1.34 | 1.25 | 1.31 | 1.47 | 1.34 | 1.35 | 0.82 |
| 209 | P209F | 1.23 | 1.36 | 1.22 | 1.48 | 1.51 | 1.50 | 0.62 |
| 209 | P209G | 1.09 | 0.92 | 1.10 | 1.09 | 0.98 | 0.91 | 1.01 |
| 209 | P209H | 1.02 | 0.91 | 1.20 | 1.15 | 0.97 | 1.00 | 1.00 |
| 209 | P209I | 0.94 | 0.85 | 1.01 | 1.03 | 0.91 | 0.84 | 0.95 |
| 209 | P209K | 1.24 | 0.95 | 1.22 | 1.23 | 0.99 | 1.03 | 0.98 |
| 209 | P209L | 0.83 | 0.92 | 1.00 | 1.06 | 1.02 | 1.02 | 0.87 |
| 209 | P209M | 1.34 | 1.34 | 1.48 | 1.61 | 1.81 | 1.18 | 0.65 |
| 209 | P209N | 1.65 | 2.42 | 0.99 | 1.11 | 2.77 | 2.36 | 0.21 |
| 209 | P209Q | −0.73 | −0.45 | ND | ND | −0.20 | 0.55 | −0.12 |
| 209 | P209R | 1.38 | 1.03 | 1.41 | 1.45 | 1.08 | 1.22 | 0.91 |
| 209 | P209S | 1.14 | 1.02 | 1.13 | 1.21 | 1.02 | 0.86 | 0.89 |
| 209 | P209T | 1.12 | 1.10 | 1.37 | 1.35 | 1.35 | 0.97 | 0.84 |
| 209 | P209V | 0.98 | 0.83 | 1.10 | 0.93 | 1.16 | 1.04 | 0.82 |
| 209 | P209W | 0.99 | 1.06 | 1.03 | 1.10 | 1.16 | 0.86 | 0.80 |
| 209 | P209Y | 0.64 | 0.73 | 0.53 | 0.76 | 0.96 | 1.10 | 0.82 |
| 224 | N224A | 0.65 | 1.07 | 1.11 | 1.13 | 1.47 | 1.19 | 0.81 |
| 224 | N224C | 0.91 | 1.07 | 1.05 | 1.08 | 1.22 | 1.00 | 0.82 |
| 224 | N224D | 0.81 | 1.10 | 0.96 | 1.08 | 0.85 | 0.75 | 0.82 |
| 224 | N224E | 0.93 | 1.78 | 0.68 | 0.91 | 1.68 | 1.83 | 0.31 |
| 224 | N224F | 0.79 | 1.11 | 0.81 | 0.93 | 1.33 | 1.31 | 0.67 |
| 224 | N224G | 0.72 | 0.80 | 0.82 | 0.87 | 0.72 | 0.97 | 1.26 |
| 224 | N224H | 0.60 | 0.80 | 0.74 | 0.84 | 0.66 | 0.83 | 1.20 |
| 224 | N224I | 0.71 | 0.95 | 0.85 | 0.99 | 0.95 | 0.97 | 0.86 |
| 224 | N224K | 0.56 | 0.64 | 0.78 | 0.81 | 0.58 | 0.78 | 1.42 |
| 224 | N224L | 0.55 | 0.72 | 0.69 | 0.75 | 0.89 | 0.73 | 1.11 |
| 224 | N224M | 0.84 | 1.07 | 1.07 | 1.13 | 1.22 | 1.27 | 0.73 |
| 224 | N224P | 1.21 | 1.26 | 0.87 | 1.03 | 1.04 | 1.19 | 0.83 |
| 224 | N224Q | 0.97 | 1.03 | 0.98 | 0.98 | 1.12 | 1.07 | 0.90 |
| 224 | N224R | 0.89 | 1.22 | 0.65 | 0.76 | 1.15 | 1.34 | 0.53 |
| 224 | N224S | 0.91 | 0.84 | 0.88 | 0.93 | 0.78 | 0.82 | 1.11 |
| 224 | N224T | 0.90 | 0.86 | 0.93 | 0.95 | 0.78 | 0.99 | 1.17 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 224 | N224V | 0.83 | 0.88 | 0.78 | 0.89 | 0.92 | 0.89 | 0.92 |
| 224 | N224W | 0.82 | 0.87 | 0.70 | 0.80 | 0.79 | 0.88 | 1.02 |
| 224 | N224Y | 0.92 | 1.03 | 0.81 | 0.89 | 0.87 | 0.77 | 0.93 |
| 242 | S242A | 1.44 | 1.56 | 1.59 | 1.45 | 1.19 | 1.10 | 0.72 |
| 242 | S242C | 1.73 | 1.99 | 1.84 | 1.93 | 1.97 | 1.06 | 0.46 |
| 242 | S242D | 1.36 | 1.51 | 1.45 | 1.43 | 1.29 | 1.11 | 0.81 |
| 242 | S242G | 1.24 | 1.20 | 1.29 | 1.22 | 1.12 | 0.92 | 0.93 |
| 242 | S242I | 1.36 | 1.12 | 1.14 | 1.24 | 1.43 | 1.34 | 0.55 |
| 242 | S242K | 0.80 | 0.70 | 0.92 | 0.92 | 0.99 | 0.86 | 1.26 |
| 242 | S242L | 0.77 | 0.75 | 1.26 | 1.08 | 1.06 | 0.99 | 0.93 |
| 242 | S242M | 1.56 | 1.70 | 1.48 | 1.78 | 1.54 | 1.10 | 0.55 |
| 242 | S242Q | 1.44 | 1.62 | 1.28 | 1.34 | 1.34 | 1.14 | 0.84 |
| 242 | S242R | 0.98 | 0.82 | 1.14 | 1.15 | 1.02 | 1.07 | 1.05 |
| 242 | S242T | 1.06 | 0.93 | 0.90 | 0.91 | 1.08 | 0.71 | 0.99 |
| 242 | S242V | 1.19 | 1.00 | 0.90 | 1.00 | 1.28 | 0.94 | 0.65 |
| 245 | P245A | 1.53 | 1.58 | 1.74 | 1.69 | 1.46 | 1.09 | 0.68 |
| 245 | P245C | 1.18 | 1.01 | 1.45 | 1.43 | 1.25 | 1.07 | 0.63 |
| 245 | P245D | 1.52 | 1.36 | 1.65 | 1.61 | 1.45 | 1.53 | 0.77 |
| 245 | P245E | 1.39 | 1.24 | 1.28 | 1.40 | 1.24 | 0.80 | 0.95 |
| 245 | P245F | 1.28 | 1.35 | 1.13 | 1.15 | 1.23 | 0.93 | 0.77 |
| 245 | P245H | 1.11 | 0.94 | 1.16 | 1.06 | 1.03 | 0.75 | 1.09 |
| 245 | P245I | 0.81 | 0.61 | 1.05 | 0.96 | 0.93 | 0.90 | 0.97 |
| 245 | P245L | 0.82 | 0.71 | 0.92 | 0.92 | 1.05 | 0.90 | 0.98 |
| 245 | P245M | 1.18 | 1.20 | 1.76 | 1.74 | 1.60 | 1.27 | 0.67 |
| 245 | P245N | 1.70 | 1.40 | 1.62 | 1.60 | 1.40 | 1.42 | 0.79 |
| 245 | P245Q | 1.49 | 1.22 | 1.61 | 1.52 | 1.26 | 0.99 | 0.96 |
| 245 | P245R | 1.37 | 1.23 | 1.19 | 1.26 | 1.47 | 1.08 | 0.88 |
| 245 | P245S | 1.16 | 1.01 | 1.20 | 1.21 | 1.07 | 0.88 | 1.07 |
| 245 | P245T | 1.31 | 0.99 | 1.26 | 1.23 | 1.13 | 0.97 | 0.92 |
| 245 | P245V | 1.03 | 0.95 | 0.97 | 1.00 | 0.94 | 0.75 | 1.00 |
| 245 | P245Y | 0.89 | 0.87 | 1.09 | 0.99 | 0.88 | 0.65 | 1.15 |
| 256 | G256A | 1.13 | 1.22 | 1.07 | 1.22 | 1.09 | 1.29 | 0.70 |
| 256 | G256C | 0.94 | 1.02 | 0.83 | 0.95 | 0.92 | 1.05 | 0.64 |
| 256 | G256D | 0.98 | 1.00 | 1.18 | 1.17 | 1.01 | 1.15 | 0.95 |
| 256 | G256E | 0.84 | 0.87 | 0.81 | 0.86 | 0.71 | 1.24 | 1.04 |
| 256 | G256H | 0.71 | 0.74 | 0.74 | 0.77 | 0.83 | 0.70 | 1.18 |
| 256 | G256I | 0.75 | 0.93 | 0.43 | 0.54 | 0.96 | 0.78 | 0.71 |
| 256 | G256K | 0.58 | 0.60 | 0.56 | 0.65 | 0.68 | 0.84 | 1.38 |
| 256 | G256L | 0.60 | 0.68 | 0.56 | 0.66 | 0.76 | 0.86 | 0.91 |
| 256 | G256M | 1.15 | 1.07 | 0.97 | 1.13 | 1.14 | 1.24 | 0.67 |
| 256 | G256N | 0.94 | 0.97 | 1.18 | 1.23 | 1.05 | 1.01 | 0.98 |
| 256 | G256P | 1.50 | 1.45 | 0.71 | 0.89 | 1.51 | 1.67 | 0.46 |
| 256 | G256R | 1.02 | 0.96 | 0.86 | 0.96 | 1.08 | 0.32 | 0.91 |
| 256 | G256S | 0.96 | 0.96 | 0.79 | 0.87 | 0.82 | 0.98 | 0.95 |
| 256 | G256T | 0.90 | 0.93 | 0.62 | 0.67 | 0.87 | 0.80 | 0.96 |
| 256 | G256V | 0.89 | 0.84 | 0.77 | 0.77 | 1.07 | 1.11 | 0.72 |
| 256 | G256W | 0.74 | 0.77 | 0.53 | 0.60 | 0.78 | 0.84 | 0.81 |
| 269 | D269A | 1.71 | 1.92 | 1.19 | 1.67 | 1.38 | 2.24 | 0.23 |
| 269 | D269C | 1.67 | 1.68 | 1.02 | 1.35 | 1.95 | 2.39 | 0.28 |
| 269 | D269F | −8.17 | −9.85 | 2.60 | 1.57 | −14.68 | −4.97 | 0.02 |
| 269 | D269G | 1.18 | 1.30 | 0.68 | 0.96 | 1.59 | 1.43 | 0.37 |
| 269 | D269H | 0.88 | 0.93 | 0.86 | 1.01 | 1.21 | 1.07 | 0.56 |
| 269 | D269I | −4.21 | −1.61 | −2.68 | −0.84 | 1.26 | 3.06 | 0.03 |
| 269 | D269K | 0.61 | 0.49 | 0.73 | 0.93 | 0.98 | 1.08 | 0.68 |
| 269 | D269M | 2.30 | 4.29 | 1.94 | 2.82 | 6.32 | 9.02 | 0.02 |
| 269 | D269N | 1.20 | 1.07 | 1.39 | 1.58 | 1.07 | 1.36 | 0.68 |
| 269 | D269P | 1.10 | 1.31 | 0.98 | 1.54 | 2.14 | 2.17 | 0.19 |
| 269 | D269Q | 1.53 | 1.50 | 1.31 | 1.60 | 1.53 | 1.51 | 0.44 |
| 269 | D269R | 1.11 | 1.09 | 0.80 | 1.25 | 1.59 | 1.26 | 0.39 |
| 269 | D269S | 0.82 | 0.86 | 0.93 | 0.96 | 0.89 | 0.91 | 1.07 |
| 269 | D269T | 0.76 | 0.98 | 0.78 | 0.96 | 1.43 | 1.43 | 0.30 |
| 269 | D269Y | 1.05 | 0.91 | 0.73 | 1.06 | 1.46 | 1.47 | 0.20 |
| 271 | N271A | 1.26 | 1.33 | 1.32 | 1.38 | 1.07 | 1.21 | 0.79 |
| 271 | N271D | 1.25 | 1.29 | 1.25 | 1.37 | 1.21 | 1.35 | 0.80 |
| 271 | N271F | 1.75 | 1.69 | 1.17 | 1.33 | 1.37 | 1.75 | 0.64 |
| 271 | N271H | 0.79 | 0.76 | 0.84 | 0.80 | 0.89 | 0.91 | 1.10 |
| 271 | N271I | 1.19 | 1.10 | 1.12 | 1.21 | 1.16 | 1.42 | 0.67 |
| 271 | N271K | 0.79 | 0.75 | 0.92 | 0.93 | 0.94 | 1.20 | 1.15 |
| 271 | N271L | 0.98 | 0.95 | 1.24 | 1.07 | 0.93 | 0.93 | 0.81 |
| 271 | N271M | 1.25 | 1.29 | 1.40 | 1.44 | 1.16 | 1.59 | 0.68 |
| 271 | N271P | 1.42 | 1.54 | 1.12 | 1.23 | 1.61 | 1.59 | 0.40 |
| 271 | N271S | 0.99 | 1.03 | 0.96 | 1.04 | 1.02 | 1.10 | 0.97 |
| 271 | N271T | 0.91 | 0.89 | 1.00 | 0.99 | 0.90 | 0.83 | 0.98 |
| 271 | N271V | 0.70 | 0.88 | 0.80 | 1.01 | 1.07 | 1.08 | 0.76 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 271 | N271W | 0.99 | 0.93 | 0.83 | 0.96 | 1.02 | 0.69 | 0.80 |
| 271 | N271Y | 0.95 | 0.87 | 0.86 | 0.96 | 0.84 | 0.94 | 0.78 |
| 278 | T278A | 1.17 | 1.21 | 1.25 | 1.41 | 1.11 | 1.35 | 0.84 |
| 278 | T278E | 0.92 | 0.80 | 0.99 | 1.13 | 1.06 | 1.35 | 0.88 |
| 278 | T278G | −1.12 | 0.26 | −4.08 | −1.79 | 3.31 | 1.75 | 0.04 |
| 278 | T278H | 0.89 | 0.89 | 0.92 | 1.02 | 0.94 | 1.03 | 1.00 |
| 278 | T278I | 0.89 | 0.87 | 0.81 | 0.86 | 0.82 | 0.89 | 1.10 |
| 278 | T278K | 0.84 | 0.75 | 0.91 | 0.96 | 0.82 | 0.91 | 1.08 |
| 278 | T278L | 0.82 | 0.80 | 1.02 | 0.99 | 0.82 | 0.93 | 0.96 |
| 278 | T278M | 1.26 | 1.35 | 1.27 | 1.47 | 1.32 | 1.35 | 0.70 |
| 278 | T278N | 1.22 | 1.19 | 1.17 | 1.30 | 1.00 | 1.35 | 0.86 |
| 278 | T278P | 1.78 | 1.71 | 1.06 | 1.79 | 2.30 | 3.46 | 0.19 |
| 278 | T278R | 1.13 | 1.07 | 1.00 | 1.24 | 1.10 | 1.47 | 0.83 |
| 278 | T278S | 0.91 | 0.92 | 0.86 | 1.00 | 0.99 | 1.01 | 1.06 |
| 278 | T278W | 0.92 | 0.99 | 0.84 | 1.00 | 1.04 | 1.08 | 0.85 |
| 278 | T278Y | 0.76 | 0.84 | 0.79 | 0.90 | 0.72 | 0.87 | 1.04 |
| 281 | N281A | 1.06 | 1.16 | 1.13 | 1.25 | 1.06 | 1.07 | 0.82 |
| 281 | N281D | 1.08 | 1.33 | 1.09 | 1.22 | 1.41 | 1.29 | 0.61 |
| 281 | N281G | 0.78 | 0.79 | 0.93 | 0.93 | 0.82 | 0.90 | 1.21 |
| 281 | N281H | 0.76 | 0.82 | 0.83 | 0.87 | 0.73 | 0.63 | 1.10 |
| 281 | N281I | 0.84 | 0.81 | 0.79 | 0.84 | 0.79 | 0.78 | 1.17 |
| 281 | N281L | 0.66 | 0.72 | 0.77 | 0.78 | 0.58 | 0.55 | 1.43 |
| 281 | N281M | 1.15 | 1.12 | 0.98 | 1.12 | 0.93 | 1.08 | 0.84 |
| 281 | N281P | 1.15 | 1.18 | 1.09 | 1.18 | 1.05 | 0.89 | 0.85 |
| 281 | N281Q | 1.22 | 1.33 | 1.00 | 1.13 | 1.10 | 1.16 | 0.62 |
| 281 | N281R | 1.03 | 1.05 | 0.98 | 1.02 | 0.95 | 0.97 | 0.96 |
| 281 | N281S | 0.90 | 0.91 | 0.88 | 0.89 | 0.72 | 1.01 | 1.09 |
| 281 | N281T | −0.21 | 1.17 | −0.65 | −0.27 | −0.63 | −0.72 | 0.14 |
| 281 | N281V | 0.85 | 0.88 | 0.80 | 0.87 | 0.76 | 1.07 | 0.86 |
| 281 | N281Y | 0.79 | 0.84 | 0.75 | 0.80 | 0.59 | 0.73 | 1.18 |
| 302 | G302C | 1.40 | 1.39 | 1.42 | 1.50 | 1.34 | 1.39 | 0.66 |
| 302 | G302D | 1.10 | 1.14 | 1.13 | 1.17 | 1.14 | 0.96 | 0.88 |
| 302 | G302E | 1.25 | 1.34 | 1.43 | 1.42 | 1.38 | 1.28 | 0.75 |
| 302 | G302F | 1.26 | 1.51 | 1.02 | 1.22 | 1.42 | 1.77 | 0.50 |
| 302 | G302H | 0.95 | 0.94 | 0.94 | 0.92 | 0.80 | 0.84 | 1.09 |
| 302 | G302I | 1.34 | 1.31 | 1.13 | 1.25 | 1.63 | 1.52 | 0.67 |
| 302 | G302L | 0.84 | 0.86 | 0.92 | 0.98 | 0.78 | 0.86 | 0.98 |
| 302 | G302M | 1.31 | 1.35 | 1.35 | 1.51 | 1.31 | 1.52 | 0.69 |
| 302 | G302N | 1.38 | 1.39 | 1.48 | 1.48 | 1.17 | 1.18 | 0.70 |
| 302 | G302P | 1.24 | 1.29 | 1.32 | 1.43 | 1.23 | 1.03 | 0.59 |
| 302 | G302R | 1.13 | 1.19 | 1.06 | 1.14 | 0.99 | 0.94 | 0.89 |
| 302 | G302S | 1.05 | 1.11 | 0.91 | 0.96 | 0.87 | 0.99 | 1.01 |
| 302 | G302T | 0.89 | 0.92 | 0.94 | 0.95 | 0.77 | 0.70 | 1.05 |
| 302 | G302V | 1.08 | 1.16 | 1.09 | 1.15 | 0.76 | 0.96 | 0.88 |
| 302 | G302W | 0.79 | 0.75 | 0.85 | 0.83 | 0.80 | 0.75 | 1.30 |
| 302 | G302Y | 0.91 | 0.98 | 0.91 | 0.99 | 0.75 | 0.92 | 0.93 |
| 304 | A304D | 1.19 | 1.30 | 1.42 | 1.44 | 1.16 | 1.22 | 0.75 |
| 304 | A304E | 1.70 | 1.57 | 1.41 | 1.47 | 1.45 | 1.45 | 0.69 |
| 304 | A304F | 1.14 | 1.14 | 1.27 | 1.18 | 0.86 | 0.87 | 1.02 |
| 304 | A304H | 0.85 | 0.85 | 0.77 | 0.83 | 0.81 | 0.68 | 1.15 |
| 304 | A304L | 0.92 | 0.95 | 0.91 | 0.96 | 0.80 | 0.74 | 1.00 |
| 304 | A304M | 1.18 | 1.21 | 1.45 | 1.49 | 0.98 | 1.18 | 0.72 |
| 304 | A304N | 1.42 | 1.41 | 1.30 | 1.44 | 1.43 | 1.28 | 0.71 |
| 304 | A304P | 1.24 | 1.30 | 1.24 | 1.35 | 1.49 | 1.34 | 0.77 |
| 304 | A304R | 1.14 | 1.16 | 1.05 | 1.13 | 0.93 | 1.03 | 0.90 |
| 304 | A304S | 0.84 | 0.94 | 0.80 | 1.15 | 0.87 | 0.71 | 0.67 |
| 304 | A304T | 1.00 | 1.07 | 0.89 | 0.99 | 0.98 | 0.75 | 0.92 |
| 304 | A304V | 1.16 | 1.18 | 1.13 | 1.21 | 0.94 | 0.70 | 0.81 |
| 304 | A304W | 0.88 | 0.89 | 0.89 | 0.93 | 0.73 | 0.94 | 1.07 |
| 304 | A304Y | 0.89 | 0.93 | 0.87 | 0.95 | 0.66 | 0.77 | 1.01 |
| 308 | R308A | 1.52 | 1.58 | 1.23 | 1.51 | 1.40 | 1.34 | 0.52 |
| 308 | R308C | 1.61 | 2.01 | 0.97 | 1.22 | 1.95 | 1.87 | 0.39 |
| 308 | R308D | 2.54 | 2.88 | 1.75 | 2.01 | 3.24 | 2.75 | 0.24 |
| 308 | R308E | 1.54 | 1.66 | 1.15 | 1.34 | 1.42 | 1.45 | 0.53 |
| 308 | R308F | 1.91 | 2.67 | 0.69 | 1.30 | 1.80 | 1.55 | 0.18 |
| 308 | R308G | 1.27 | 1.29 | 0.81 | 0.95 | 1.02 | 1.10 | 0.59 |
| 308 | R308H | 1.10 | 1.08 | 0.77 | 0.92 | 1.06 | 0.97 | 0.66 |
| 308 | R308I | 1.13 | 1.55 | 0.57 | 0.76 | 0.92 | 0.84 | 0.43 |
| 308 | R308K | 1.00 | 0.97 | 1.00 | 0.99 | 0.99 | 0.92 | 0.95 |
| 308 | R308L | 0.97 | 1.33 | 0.36 | 0.67 | 0.93 | 0.19 | 0.33 |
| 308 | R308M | 1.94 | 2.07 | 1.31 | 1.66 | 1.65 | 1.92 | 0.38 |
| 308 | R308N | 1.72 | 1.86 | 1.09 | 1.37 | 1.94 | 1.71 | 0.41 |
| 308 | R308P | 4.38 | 4.55 | 1.93 | 2.52 | 5.05 | 3.89 | 0.12 |
| 308 | R308S | 1.06 | 1.00 | 0.84 | 0.97 | 0.84 | 0.87 | 1.00 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 308 | R308T | 1.36 | 1.34 | 0.91 | 1.08 | 1.16 | 1.24 | 0.73 |
| 308 | R308V | 1.31 | 1.47 | 0.62 | 0.88 | 1.06 | 0.97 | 0.42 |
| 308 | R308W | 0.92 | 1.50 | 0.34 | 0.70 | 1.29 | 1.01 | 0.31 |
| 308 | R308Y | 0.90 | 1.28 | 0.46 | 0.70 | 0.92 | 1.14 | 0.41 |
| 321 | T321A | 1.07 | 1.20 | 0.95 | 1.19 | 1.44 | 1.33 | 0.84 |
| 321 | T321C | 1.35 | 1.36 | 0.92 | 1.09 | 1.63 | 1.10 | 0.52 |
| 321 | T321F | 1.00 | 0.96 | 0.90 | 1.00 | 1.14 | 1.07 | 1.03 |
| 321 | T321H | 0.89 | 0.85 | 0.81 | 0.90 | 1.03 | 1.37 | 1.14 |
| 321 | T321I | 0.81 | 0.87 | 0.66 | 0.77 | 1.13 | 0.93 | 0.83 |
| 321 | T321L | 0.74 | 0.77 | 0.67 | 0.75 | 0.91 | 0.96 | 1.11 |
| 321 | T321P | 1.23 | 1.25 | 1.08 | 1.18 | 1.69 | 1.22 | 0.79 |
| 321 | T321Q | 1.12 | 1.15 | 1.05 | 1.10 | 1.14 | 1.27 | 0.93 |
| 321 | T321R | 1.02 | 0.92 | 1.02 | 0.96 | 1.09 | 0.96 | 1.04 |
| 321 | T321S | 1.02 | 0.91 | 0.88 | 0.99 | 1.14 | 0.84 | 1.08 |
| 321 | T321V | 0.95 | 0.92 | 0.72 | 0.81 | 1.34 | 0.43 | 0.84 |
| 321 | T321Y | 0.76 | 0.82 | 0.69 | 0.77 | 1.23 | 0.79 | 1.04 |
| 358 | Q358A | 1.07 | 1.42 | 1.63 | 1.45 | 1.54 | 1.31 | 0.65 |
| 358 | Q358C | 1.95 | 2.35 | 1.34 | 1.85 | 2.83 | 1.62 | 0.26 |
| 358 | Q358D | 1.35 | 1.37 | 1.21 | 1.29 | 1.55 | 1.10 | 0.79 |
| 358 | Q358E | 1.30 | 1.35 | 1.22 | 1.27 | 1.57 | 1.02 | 0.74 |
| 358 | Q358F | 1.35 | 1.32 | 1.05 | 1.14 | 1.49 | 1.19 | 0.71 |
| 358 | Q358G | 1.15 | 1.03 | 0.90 | 0.96 | 1.10 | 1.06 | 0.74 |
| 358 | Q358H | 1.05 | 0.99 | 0.95 | 0.97 | 1.15 | 1.40 | 0.94 |
| 358 | Q358L | 0.92 | 1.06 | 1.05 | 1.06 | 1.24 | 0.84 | 0.83 |
| 358 | Q358M | 1.12 | 1.37 | 1.42 | 1.41 | 1.52 | 1.17 | 0.72 |
| 358 | Q358N | 1.27 | 1.37 | 1.32 | 1.42 | 1.63 | 1.06 | 0.73 |
| 358 | Q358P | 1.27 | 1.33 | 1.10 | 1.23 | 1.72 | 1.17 | 0.65 |
| 358 | Q358R | 1.03 | 1.07 | 1.08 | 1.07 | 1.18 | 1.15 | 0.91 |
| 358 | Q358S | 1.09 | 0.99 | 1.02 | 1.04 | 1.01 | 0.91 | 0.93 |
| 358 | Q358T | 1.05 | 1.05 | 1.04 | 1.00 | 1.17 | 1.10 | 0.95 |
| 358 | Q358V | 1.15 | 1.18 | 1.02 | 1.13 | 1.35 | 1.35 | 0.67 |
| 378 | P378C | 28.49 | 39.29 | 11.48 | 19.82 | 40.84 | 34.77 | 0.05 |
| 378 | P378D | 1.13 | 1.20 | 1.15 | 1.18 | 1.12 | 0.99 | 0.88 |
| 378 | P378F | 1.84 | 2.17 | 0.62 | 1.01 | 2.97 | 0.36 | 0.15 |
| 378 | P378G | 1.21 | 1.20 | 1.00 | 1.06 | 1.44 | 1.30 | 0.75 |
| 378 | P378H | 0.90 | 0.94 | 0.80 | 0.85 | 1.11 | 0.50 | 1.06 |
| 378 | P378I | 1.16 | 1.20 | 1.03 | 1.15 | 1.33 | 1.26 | 0.62 |
| 378 | P378L | 0.78 | 0.89 | 0.88 | 0.97 | 1.08 | 0.79 | 0.82 |
| 378 | P378N | 1.31 | 1.39 | 1.19 | 1.37 | 1.42 | 0.97 | 0.71 |
| 378 | P378R | 0.94 | 0.93 | 1.10 | 1.07 | 1.05 | 1.03 | 1.28 |
| 378 | P378S | 1.15 | 1.09 | 0.99 | 1.04 | 1.08 | 1.11 | 0.90 |
| 378 | P378T | 0.83 | 0.96 | 0.90 | 0.93 | 0.87 | 0.73 | 1.04 |
| 378 | P378V | 1.08 | 1.08 | 1.09 | 1.10 | 1.15 | 0.94 | 0.87 |
| 378 | P378Y | 0.87 | 0.92 | 0.78 | 0.91 | 1.11 | 0.97 | 0.67 |
| 382 | S382A | 1.05 | 1.33 | 1.16 | 1.30 | 1.57 | 1.17 | 0.76 |
| 382 | S382C | 1.20 | 1.19 | 1.01 | 1.12 | 1.27 | 1.05 | 0.87 |
| 382 | S382D | 1.43 | 1.42 | 1.19 | 1.34 | 1.35 | 1.41 | 0.74 |
| 382 | S382E | 1.23 | 1.39 | 1.14 | 1.27 | 1.47 | 1.23 | 0.83 |
| 382 | S382G | 1.05 | 1.06 | 0.90 | 0.96 | 0.96 | 0.95 | 1.02 |
| 382 | S382H | 1.10 | 1.02 | 0.96 | 0.99 | 1.10 | 0.98 | 1.00 |
| 382 | S382I | 1.03 | 1.07 | 0.82 | 0.88 | 1.07 | 0.96 | 0.79 |
| 382 | S382K | 0.94 | 0.84 | 0.95 | 0.98 | 1.12 | 0.78 | 1.09 |
| 382 | S382L | 0.93 | 0.93 | 0.69 | 0.82 | 0.95 | 0.70 | 0.79 |
| 382 | S382M | 1.51 | 1.84 | 1.25 | 1.51 | 2.20 | 1.47 | 0.54 |
| 382 | S382N | 1.39 | 1.43 | 1.15 | 1.35 | 1.55 | 1.16 | 0.72 |
| 382 | S382P | 1.41 | 1.42 | 1.22 | 1.33 | 1.65 | 1.25 | 0.70 |
| 382 | S382R | 1.23 | 1.19 | 0.97 | 1.17 | 1.14 | 0.78 | 0.91 |
| 382 | S382T | 1.18 | 1.15 | 0.98 | 1.08 | 1.30 | 1.14 | 0.90 |
| 382 | S382V | 1.13 | 1.07 | 0.85 | 0.98 | 1.22 | 0.89 | 0.81 |
| 382 | S382W | 1.08 | 1.03 | 0.90 | 0.98 | 1.19 | 0.94 | 0.98 |
| 383 | K383A | 1.26 | 1.16 | 1.24 | 1.35 | 1.17 | 0.86 | 0.66 |
| 383 | K383C | 1.85 | 2.15 | 0.60 | 1.01 | 1.16 | 0.02 | 0.16 |
| 383 | K383D | 1.14 | 1.17 | 1.16 | 1.13 | 1.04 | 0.89 | 0.69 |
| 383 | K383E | 1.04 | 0.98 | 0.98 | 1.00 | 1.00 | 0.82 | 0.94 |
| 383 | K383F | 1.43 | 1.44 | 0.93 | 1.01 | 1.47 | 0.86 | 0.50 |
| 383 | K383H | 0.80 | 0.78 | 0.79 | 0.84 | 0.97 | 1.03 | 0.96 |
| 383 | K383L | 0.64 | 0.66 | 0.50 | 0.60 | 0.66 | 0.92 | 0.76 |
| 383 | K383M | 1.32 | 1.19 | 0.94 | 1.10 | 1.20 | 1.01 | 0.57 |
| 383 | K383N | 1.27 | 1.20 | 0.98 | 1.11 | 1.07 | 1.16 | 0.64 |
| 383 | K383P | 1.89 | 2.46 | 1.17 | 1.37 | 1.82 | 2.31 | 0.22 |
| 383 | K383Q | 1.03 | 0.98 | 1.01 | 1.06 | 0.95 | 1.15 | 0.94 |
| 383 | K383R | 1.02 | 0.91 | 1.00 | 0.95 | 1.10 | 0.84 | 0.99 |
| 383 | K383S | 0.92 | 0.92 | 0.87 | 0.92 | 0.97 | 0.74 | 0.86 |
| 383 | K383T | 0.79 | 0.76 | 0.83 | 0.84 | 0.90 | 0.83 | 0.98 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 383 | K383W | 0.70 | 0.78 | 0.62 | 0.68 | 0.74 | 0.39 | 0.61 |
| 383 | K383Y | 0.62 | 0.72 | 0.78 | 0.75 | 0.73 | 0.67 | 0.87 |
| 398 | T398A | 1.28 | 1.18 | 1.34 | 1.43 | 1.37 | 1.17 | 0.73 |
| 398 | T398C | 1.58 | 1.46 | 1.20 | 1.39 | 1.61 | 1.35 | 0.46 |
| 398 | T398D | 1.29 | 1.24 | 1.33 | 1.33 | 0.88 | 1.42 | 0.75 |
| 398 | T398E | 1.33 | 1.24 | 1.31 | 1.32 | 1.17 | 1.38 | 0.81 |
| 398 | T398I | 0.81 | 0.87 | 0.91 | 0.96 | 0.91 | 0.86 | 1.04 |
| 398 | T398K | 0.92 | 0.76 | 0.99 | 0.97 | 0.97 | 0.66 | 1.06 |
| 398 | T398L | 0.76 | 0.68 | 0.85 | 0.87 | 0.86 | 1.14 | 0.99 |
| 398 | T398M | 1.29 | 1.24 | 1.39 | 1.38 | 1.18 | 1.03 | 0.75 |
| 398 | T398N | 1.96 | 1.88 | 1.34 | 1.58 | 1.23 | 1.31 | 0.37 |
| 398 | T398P | 1.38 | 1.29 | 1.33 | 1.35 | 0.97 | 1.29 | 0.77 |
| 398 | T398Q | 1.47 | 1.41 | 1.61 | 1.52 | 1.46 | 1.51 | 0.74 |
| 398 | T398R | 1.16 | 1.08 | 1.25 | 1.16 | 1.25 | 1.02 | 0.98 |
| 398 | T398S | 1.03 | 0.94 | 1.08 | 1.05 | 0.92 | 0.67 | 1.07 |
| 398 | T398V | 1.00 | 1.06 | 1.20 | 1.19 | 1.03 | 0.96 | 0.87 |
| 405 | H405A | 1.61 | 1.64 | 1.45 | 1.54 | 1.54 | 1.15 | 0.56 |
| 405 | H405C | 1.92 | 2.06 | 1.69 | 1.91 | 2.68 | 1.40 | 0.33 |
| 405 | H405D | 1.45 | 1.44 | 1.25 | 1.30 | 1.37 | 1.21 | 0.47 |
| 405 | H405F | 2.03 | 2.09 | 1.28 | 1.41 | 3.15 | 1.98 | 0.20 |
| 405 | H405G | 1.16 | 1.20 | 1.10 | 1.14 | 1.50 | 1.14 | 0.72 |
| 405 | H405K | 0.71 | 0.58 | 0.87 | 0.89 | 1.05 | 0.64 | 0.72 |
| 405 | H405L | 0.79 | 0.89 | 0.77 | 0.94 | 0.97 | 0.72 | 0.49 |
| 405 | H405M | 1.65 | 1.66 | 1.28 | 1.51 | 1.67 | 1.22 | 0.41 |
| 405 | H405N | 1.42 | 1.26 | 1.37 | 1.42 | 1.43 | 1.09 | 0.69 |
| 405 | H405P | −12.67 | −11.60 | −0.88 | −2.21 | −6.12 | −0.26 | −0.03 |
| 405 | H405Q | 1.50 | 1.53 | 1.33 | 1.42 | 1.76 | 1.33 | 0.59 |
| 405 | H405R | 1.54 | 1.56 | 1.22 | 1.36 | 1.29 | 0.84 | 0.51 |
| 405 | H405S | 1.09 | 1.00 | 1.05 | 1.03 | 1.10 | 0.91 | 0.90 |
| 405 | H405T | 0.99 | 0.94 | 0.86 | 0.89 | 0.96 | 0.77 | 0.87 |
| 405 | H405W | 0.86 | 0.83 | 0.43 | 0.64 | 1.32 | 0.50 | 0.35 |
| 405 | H405Y | 0.96 | 1.07 | 0.84 | 0.93 | 1.37 | 0.96 | 0.50 |
| 417 | T417A | 1.55 | 1.30 | 1.42 | 1.39 | 1.28 | 1.05 | 0.71 |
| 417 | T417D | 1.55 | 1.28 | 1.40 | 1.43 | 1.14 | 1.34 | 0.80 |
| 417 | T417E | 1.22 | 1.07 | 1.16 | 1.17 | 1.12 | 1.07 | 0.89 |
| 417 | T417H | 0.98 | 0.89 | 0.91 | 0.95 | 1.07 | 0.89 | 0.98 |
| 417 | T417I | 1.00 | 0.99 | 0.79 | 0.84 | 0.90 | 0.82 | 0.82 |
| 417 | T417L | 0.87 | 0.79 | 0.88 | 0.89 | 0.98 | 1.03 | 0.92 |
| 417 | T417M | 1.65 | 1.65 | 1.39 | 1.52 | 1.82 | 1.41 | 0.49 |
| 417 | T417P | 1.38 | 1.25 | 1.34 | 1.35 | 1.26 | 1.12 | 0.74 |
| 417 | T417Q | 1.47 | 1.24 | 1.21 | 1.24 | 1.40 | 1.26 | 0.84 |
| 417 | T417R | 1.34 | 1.15 | 1.36 | 1.31 | 1.13 | 1.08 | 0.85 |
| 417 | T417S | 1.10 | 0.95 | 1.01 | 1.03 | 0.96 | 1.13 | 1.02 |
| 417 | T417V | 0.88 | 0.86 | 0.85 | 0.92 | 0.97 | 0.94 | 0.97 |
| 417 | T417W | 0.97 | 0.84 | 0.72 | 0.89 | 1.01 | 0.77 | 0.90 |
| 418 | E418A | 1.16 | 1.16 | 1.32 | 1.29 | 1.44 | 0.99 | 0.83 |
| 418 | E418C | 1.14 | 1.24 | 0.98 | 1.10 | 1.21 | 0.73 | 0.66 |
| 418 | E418D | 0.94 | 0.94 | 1.06 | 1.11 | 0.98 | 0.84 | 0.96 |
| 418 | E418G | 0.68 | 0.70 | 0.81 | 0.82 | 0.82 | 0.58 | 1.17 |
| 418 | E418H | 0.71 | 0.73 | 0.76 | 0.80 | 0.87 | 0.75 | 1.04 |
| 418 | E418I | 0.80 | 0.75 | 0.76 | 0.79 | 1.09 | 0.70 | 0.97 |
| 418 | E418K | 0.68 | 0.62 | 0.68 | 0.71 | 0.77 | 0.79 | 1.27 |
| 418 | E418L | 0.69 | 0.64 | 0.72 | 0.78 | 0.39 | 0.47 | 1.08 |
| 418 | E418M | 0.96 | 0.95 | 1.01 | 1.07 | 1.33 | 0.81 | 0.86 |
| 418 | E418N | 1.00 | 1.01 | 1.18 | 1.20 | 1.11 | 0.87 | 0.83 |
| 418 | E418P | 1.04 | 1.03 | 1.15 | 1.19 | 1.09 | 0.72 | 0.87 |
| 418 | E418Q | 1.11 | 1.13 | 1.05 | 1.16 | 1.22 | 0.76 | 0.84 |
| 418 | E418R | 1.08 | 1.01 | 0.95 | 1.03 | 1.26 | 1.01 | 0.86 |
| 418 | E418S | 1.03 | 0.94 | 0.80 | 0.85 | 0.94 | 0.85 | 0.86 |
| 418 | E418T | 0.87 | 0.80 | 0.82 | 0.84 | 0.91 | 0.50 | 1.09 |
| 418 | E418V | 0.71 | 0.65 | 0.66 | 0.82 | 0.83 | 0.34 | 1.22 |
| 418 | E418Y | 0.80 | 0.77 | 0.65 | 0.79 | 0.88 | 0.59 | 0.81 |
| 420 | P420A | 1.16 | 1.17 | 1.41 | 1.49 | 1.36 | 0.97 | 0.81 |
| 420 | P420C | 1.17 | 1.32 | 1.37 | 1.47 | 1.09 | 1.02 | 0.70 |
| 420 | P420D | 1.29 | 1.25 | 1.37 | 1.38 | 1.35 | 0.90 | 0.75 |
| 420 | P420E | 1.32 | 1.27 | 1.32 | 1.35 | 1.45 | 0.79 | 0.75 |
| 420 | P420H | 1.05 | 0.95 | 0.95 | 1.01 | 1.11 | 0.69 | 0.98 |
| 420 | P420I | 0.98 | 0.95 | 0.87 | 0.95 | 1.07 | 0.62 | 0.98 |
| 420 | P420L | 0.85 | 0.82 | 0.87 | 0.91 | 1.07 | 0.74 | 0.97 |
| 420 | P420M | 1.37 | 1.41 | 1.33 | 1.29 | 1.28 | 0.75 | 0.73 |
| 420 | P420N | 1.42 | 1.38 | 1.30 | 1.41 | 1.50 | 0.95 | 0.73 |
| 420 | P420R | 0.49 | −5.15 | −1.38 | −0.61 | −11.09 | −1.99 | −0.01 |
| 420 | P420S | 1.01 | 0.88 | 1.10 | 1.09 | 0.93 | 0.81 | 1.11 |
| 420 | P420T | 0.97 | 0.87 | 0.94 | 0.95 | 0.68 | 0.87 | 1.10 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 420 | P420V | 1.11 | 1.06 | 1.10 | 1.12 | 1.21 | 0.77 | 0.84 |
| 420 | P420W | 0.72 | 0.69 | 0.71 | 0.75 | 0.80 | 0.54 | 1.29 |
| 420 | P420Y | 0.90 | 0.83 | 0.80 | 0.76 | 1.05 | 0.85 | 0.96 |
| 421 | G421A | 1.36 | 1.28 | 1.23 | 1.30 | 1.31 | 0.79 | 0.79 |
| 421 | G421D | 1.23 | 1.28 | 1.43 | 1.38 | 1.28 | 0.99 | 0.72 |
| 421 | G421E | 1.44 | 1.43 | 1.47 | 1.46 | 1.48 | 1.23 | 0.66 |
| 421 | G421F | 1.23 | 1.19 | 1.13 | 1.13 | 1.50 | 0.75 | 0.79 |
| 421 | G421H | 0.91 | 0.81 | 0.80 | 0.84 | 0.69 | 0.71 | 1.19 |
| 421 | G421I | 1.19 | 1.13 | 0.97 | 1.08 | 1.38 | 0.80 | 0.65 |
| 421 | G421L | 0.80 | 0.77 | 0.91 | 0.95 | 1.24 | 0.74 | 0.97 |
| 421 | G421N | 1.28 | 1.30 | 1.23 | 1.34 | 1.49 | 0.82 | 0.75 |
| 421 | G421P | 1.20 | 1.22 | 1.22 | 1.27 | 1.41 | 0.83 | 0.74 |
| 421 | G421Q | 1.31 | 1.27 | 1.27 | 1.29 | 1.30 | 1.15 | 0.75 |
| 421 | G421R | 1.17 | 1.04 | 1.05 | 1.09 | 1.08 | 0.85 | 1.00 |
| 421 | G421S | 1.11 | 1.02 | 1.05 | 1.04 | 1.05 | 0.80 | 0.97 |
| 421 | G421T | 1.04 | 0.91 | 0.95 | 0.98 | 1.05 | 0.86 | 1.05 |
| 421 | G421W | 0.84 | 0.85 | 0.86 | 0.94 | 0.94 | 0.74 | 0.96 |
| 421 | G421Y | 0.98 | 0.86 | 0.89 | 0.94 | 1.12 | 0.64 | 0.95 |
| 432 | P432A | 1.40 | 1.30 | 1.44 | 1.53 | 1.64 | 1.26 | 0.75 |
| 432 | P432D | 1.77 | 1.59 | 1.72 | 1.77 | 1.95 | 1.24 | 0.61 |
| 432 | P432E | 1.39 | 1.29 | 1.40 | 1.41 | 1.33 | 1.19 | 0.77 |
| 432 | P432H | 1.14 | 1.07 | 0.83 | 1.01 | 1.35 | 0.97 | 0.80 |
| 432 | P432K | 1.21 | 0.96 | 1.05 | 1.08 | 1.22 | 1.02 | 0.91 |
| 432 | P432L | 1.06 | 0.90 | 0.98 | 0.98 | 1.26 | 0.63 | 0.97 |
| 432 | P432M | 1.48 | 1.47 | 1.72 | 1.71 | 2.15 | 1.45 | 0.65 |
| 432 | P432N | 1.31 | 1.38 | 1.28 | 1.41 | 1.59 | 1.02 | 0.73 |
| 432 | P432Q | 1.62 | 1.39 | 1.31 | 1.46 | 1.69 | 1.46 | 0.70 |
| 432 | P432R | 1.60 | 1.35 | 1.36 | 1.43 | 1.27 | 1.21 | 0.78 |
| 432 | P432S | 1.16 | 1.02 | 0.94 | 1.00 | 1.07 | 0.78 | 1.04 |
| 432 | P432T | 1.19 | 0.99 | 1.33 | 1.13 | 1.27 | 1.08 | 0.98 |
| 432 | P432Y | 1.14 | 0.98 | 0.82 | 0.94 | 1.21 | 0.69 | 0.90 |
| 437 | W437C | 0.83 | 0.77 | 1.09 | 1.15 | 0.89 | 0.84 | 1.01 |
| 437 | W437D | 0.97 | 0.85 | 1.12 | 1.15 | 0.98 | 0.97 | 1.08 |
| 437 | W437E | 0.99 | 1.00 | 0.79 | 0.87 | 0.95 | 0.76 | 0.59 |
| 437 | W437F | 1.01 | 0.81 | 0.94 | 1.00 | 0.74 | 0.80 | 1.22 |
| 437 | W437G | 0.83 | 0.72 | 0.82 | 0.82 | 0.78 | 0.66 | 1.42 |
| 437 | W437H | 0.65 | 0.64 | 0.83 | 0.84 | 0.78 | 0.71 | 1.52 |
| 437 | W437L | 0.64 | 0.60 | 0.73 | 0.75 | 0.59 | 0.68 | 1.55 |
| 437 | W437M | 1.03 | 0.86 | 1.01 | 1.06 | 0.83 | 0.63 | 1.11 |
| 437 | W437N | 1.01 | 0.94 | 1.02 | 1.06 | 0.87 | 1.07 | 1.04 |
| 437 | W437Q | 1.05 | 0.90 | 1.08 | 1.11 | 0.90 | 0.77 | 1.12 |
| 437 | W437R | 0.91 | 0.83 | 1.07 | 1.02 | 0.83 | 0.53 | 1.19 |
| 437 | W437S | 0.96 | 0.75 | 0.99 | 0.96 | 0.86 | 0.90 | 1.24 |
| 437 | W437T | 0.78 | 0.71 | 0.92 | 0.89 | 0.77 | 0.71 | 1.32 |
| 437 | W437V | 0.75 | 0.73 | 0.90 | 0.87 | 0.81 | 0.87 | 1.36 |
| 437 | W437Y | 0.66 | 0.59 | 0.78 | 0.77 | 0.64 | 0.68 | 1.50 |
| 443 | Q443A | 1.24 | 1.01 | 1.35 | 1.32 | 1.08 | 1.08 | 0.83 |
| 443 | Q443C | 1.27 | 1.23 | 1.16 | 1.22 | 1.02 | 1.22 | 0.80 |
| 443 | Q443F | 1.26 | 1.14 | 1.18 | 1.20 | 1.10 | 1.15 | 0.86 |
| 443 | Q443G | 1.12 | 0.94 | 1.11 | 1.02 | 1.01 | 1.00 | 1.08 |
| 443 | Q443K | 0.79 | 0.75 | 0.93 | 0.90 | 0.83 | 0.76 | 1.10 |
| 443 | Q443L | 0.84 | 0.81 | 1.07 | 1.02 | 0.89 | 0.85 | 1.09 |
| 443 | Q443N | 1.22 | 1.18 | 1.41 | 1.53 | 1.21 | 1.23 | 0.77 |
| 443 | Q443P | 1.02 | 0.97 | 1.08 | 1.16 | 1.03 | 0.64 | 0.92 |
| 443 | Q443R | 1.06 | 1.03 | 1.03 | 1.10 | 0.99 | 0.98 | 0.98 |
| 443 | Q443S | 0.89 | 0.82 | 0.95 | 0.94 | 0.84 | 0.87 | 1.20 |
| 443 | Q443T | 1.01 | 0.76 | 0.88 | 0.89 | 0.89 | 0.69 | 1.15 |
| 443 | Q443V | 1.02 | 0.90 | 1.09 | 1.10 | 1.23 | 1.03 | 0.95 |
| 443 | Q443W | 0.57 | 0.59 | 0.57 | 0.63 | 0.65 | 0.63 | 0.87 |
| 443 | Q443Y | 0.82 | 0.87 | 0.95 | 0.97 | 0.97 | 0.86 | 0.92 |
| 446 | G446A | 1.00 | 0.91 | 1.25 | 1.26 | 0.97 | 1.08 | 0.95 |
| 446 | G446C | 1.39 | 1.31 | 1.84 | 1.78 | 1.40 | 1.23 | 0.73 |
| 446 | G446D | 1.12 | 0.99 | 1.15 | 1.25 | 1.15 | 0.97 | 0.93 |
| 446 | G446F | 1.34 | 1.37 | 1.00 | 1.15 | 1.03 | 1.22 | 0.75 |
| 446 | G446H | 0.93 | 0.80 | 0.65 | 0.70 | 0.84 | 0.83 | 1.32 |
| 446 | G446I | 1.22 | 1.07 | 0.97 | 1.04 | 1.39 | 1.05 | 0.70 |
| 446 | G446K | 0.97 | 0.83 | 0.80 | 0.86 | 0.70 | 0.87 | 1.10 |
| 446 | G446L | 0.80 | 0.78 | 0.86 | 0.88 | 0.94 | 0.85 | 1.07 |
| 446 | G446M | 1.21 | 1.05 | 0.85 | 0.99 | 1.06 | 1.16 | 0.87 |
| 446 | G446N | 1.17 | 1.08 | 1.05 | 1.21 | 1.07 | 1.07 | 0.88 |
| 446 | G446P | 1.21 | 1.09 | 1.07 | 1.16 | 1.09 | 0.95 | 0.74 |
| 446 | G446Q | 1.28 | 1.21 | 1.16 | 1.23 | 1.09 | 1.01 | 0.83 |
| 446 | G446R | 0.37 | 0.07 | 0.71 | 1.10 | 0.22 | 0.65 | 0.75 |
| 446 | G446S | 1.07 | 0.95 | 0.95 | 0.95 | 0.75 | 1.01 | 1.11 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 446 | G446T | 1.03 | 0.88 | 0.69 | 0.81 | 0.91 | 0.96 | 1.09 |
| 446 | G446V | 1.17 | 1.09 | 0.91 | 0.98 | 1.14 | 0.90 | 0.82 |
| 446 | G446W | 0.85 | 0.72 | 0.83 | 0.89 | 0.92 | 0.80 | 1.05 |
| 446 | G446Y | 0.88 | 0.76 | 1.02 | 1.00 | 0.83 | 0.91 | 1.09 |
| 454 | G454A | 1.33 | 1.25 | 1.61 | 1.60 | 1.14 | 1.26 | 0.88 |
| 454 | G454C | 1.33 | 1.18 | 1.15 | 1.20 | 1.14 | 1.37 | 0.78 |
| 454 | G454D | 1.40 | 1.30 | 1.27 | 1.36 | 1.18 | 1.09 | 0.76 |
| 454 | G454E | 1.36 | 1.21 | 1.08 | 1.19 | 0.99 | 0.91 | 0.83 |
| 454 | G454H | 0.92 | 0.83 | 0.89 | 0.95 | 0.83 | 0.83 | 1.10 |
| 454 | G454I | 0.87 | 0.79 | 0.77 | 0.82 | 0.88 | 0.75 | 1.02 |
| 454 | G454K | 0.86 | 0.80 | 0.99 | 0.97 | 0.82 | 0.81 | 1.13 |
| 454 | G454L | 0.12 | −0.34 | −0.62 | −0.26 | 0.50 | −0.62 | 0.11 |
| 454 | G454M | 1.39 | 1.26 | 1.14 | 1.42 | 1.26 | 1.30 | 0.68 |
| 454 | G454N | 1.20 | 1.09 | 1.07 | 1.20 | 1.11 | 1.10 | 0.91 |
| 454 | G454P | 1.41 | 1.34 | 1.14 | 1.29 | 1.16 | 0.96 | 0.77 |
| 454 | G454R | 1.25 | 1.09 | 0.99 | 1.12 | 1.07 | 1.01 | 0.92 |
| 454 | G454S | 0.83 | 0.80 | 0.83 | 0.90 | 0.89 | 0.79 | 1.17 |
| 454 | G454T | 1.04 | 0.93 | 0.90 | 0.98 | 0.99 | 0.94 | 1.02 |
| 454 | G454V | 1.20 | 1.07 | 1.05 | 1.10 | 1.18 | 0.89 | 0.93 |
| 457 | S457A | 1.05 | 0.95 | 1.22 | 1.27 | 1.23 | 1.21 | 0.89 |
| 457 | S457C | 1.27 | 1.23 | 0.72 | 0.72 | 1.53 | 1.44 | 0.59 |
| 457 | S457D | 1.02 | 0.89 | 1.05 | 1.16 | 0.93 | 0.81 | 0.99 |
| 457 | S457E | 1.10 | 0.95 | 0.97 | 1.06 | 0.97 | 0.79 | 0.95 |
| 457 | S457G | 0.82 | 0.71 | 0.82 | 0.87 | 0.80 | 0.88 | 1.21 |
| 457 | S457H | 0.83 | 0.72 | 0.81 | 0.90 | 0.89 | 1.12 | 1.17 |
| 457 | S457K | 0.74 | 0.63 | 0.79 | 0.86 | 0.76 | 0.62 | 1.37 |
| 457 | S457L | 0.67 | 0.61 | 0.68 | 0.79 | 0.64 | 0.63 | 1.27 |
| 457 | S457M | 1.07 | 0.98 | 0.96 | 1.08 | 1.03 | 0.99 | 0.92 |
| 457 | S457N | 1.08 | 0.92 | 1.10 | 1.19 | 1.13 | 1.15 | 0.86 |
| 457 | S457P | 1.29 | 1.21 | 1.09 | 1.18 | 1.30 | 1.19 | 0.88 |
| 457 | S457Q | 1.10 | 1.01 | 1.06 | 1.13 | 1.14 | 0.96 | 0.91 |
| 457 | S457R | 1.58 | 1.31 | 0.89 | 1.10 | 1.59 | 1.89 | 0.42 |
| 457 | S457T | 0.88 | 0.70 | 0.94 | 0.94 | 0.85 | 1.01 | 1.18 |
| 457 | S457V | 0.89 | 0.82 | 0.83 | 0.88 | 0.84 | 0.78 | 1.11 |
| 457 | S457W | 0.87 | 0.69 | 0.64 | 0.74 | 0.84 | 0.60 | 1.05 |
| 457 | S457Y | 0.81 | 0.70 | 0.70 | 0.80 | 0.80 | 0.79 | 1.15 |
| 459 | T459A | 1.10 | 1.03 | 1.25 | 1.34 | 1.46 | 1.18 | 0.83 |
| 459 | T459D | 1.20 | 1.17 | 1.19 | 1.24 | 1.37 | 1.44 | 0.82 |
| 459 | T459G | 1.15 | 1.01 | 0.98 | 0.97 | 0.81 | 1.36 | 1.08 |
| 459 | T459I | 1.05 | 0.95 | 0.95 | 1.01 | 1.04 | 1.04 | 1.02 |
| 459 | T459K | 1.04 | 0.91 | 0.86 | 0.90 | 0.80 | 0.72 | 1.08 |
| 459 | T459L | 0.93 | 0.83 | 1.19 | 1.10 | 0.91 | 0.81 | 1.04 |
| 459 | T459Q | 1.46 | 1.43 | 1.40 | 1.47 | 1.29 | 1.24 | 0.72 |
| 459 | T459R | 1.09 | 1.00 | 1.09 | 1.09 | 0.90 | 0.97 | 1.05 |
| 459 | T459S | 0.99 | 1.00 | 0.85 | 0.87 | 1.04 | 0.90 | 1.06 |
| 459 | T459V | 1.11 | 1.02 | 0.92 | 0.99 | 1.07 | 1.35 | 0.93 |
| 459 | T459Y | 1.10 | 1.02 | 0.97 | 1.06 | 1.14 | 0.74 | 0.92 |
| 461 | T461A | 1.40 | 1.44 | 1.16 | 1.28 | 1.74 | 1.18 | 0.47 |
| 461 | T461D | 1.26 | 1.09 | 1.21 | 1.25 | 1.25 | 1.10 | 0.92 |
| 461 | T461E | 1.52 | 1.44 | 1.49 | 1.43 | 1.22 | 1.06 | 0.74 |
| 461 | T461F | 1.29 | 1.22 | 1.31 | 1.25 | 1.14 | 1.12 | 0.79 |
| 461 | T461G | 1.09 | 1.03 | 1.08 | 1.04 | 1.16 | 1.14 | 0.98 |
| 461 | T461I | 1.11 | 1.00 | 0.99 | 1.05 | 1.03 | 1.33 | 0.93 |
| 461 | T461K | 0.89 | 0.75 | 0.78 | 0.91 | 0.98 | 0.99 | 1.01 |
| 461 | T461L | 0.92 | 0.85 | 1.03 | 1.02 | 1.15 | 0.91 | 0.87 |
| 461 | T461N | 1.18 | 1.18 | 1.35 | 1.37 | 1.36 | 1.30 | 0.81 |
| 461 | T461P | 1.19 | 1.10 | 1.37 | 1.33 | 1.14 | 1.17 | 0.92 |
| 461 | T461R | 1.19 | 1.04 | 1.13 | 1.18 | 1.11 | 0.91 | 0.99 |
| 461 | T461S | 1.12 | 1.04 | 0.87 | 0.88 | 1.03 | 0.90 | 0.88 |
| 461 | T461V | 0.95 | 1.00 | 1.01 | 1.05 | 1.11 | 1.28 | 0.87 |
| 461 | T461W | 0.97 | 0.82 | 0.77 | 0.86 | 0.75 | 0.67 | 0.87 |
| 461 | T461Y | 1.02 | 0.93 | 0.90 | 1.02 | 1.01 | 1.11 | 0.87 |
| 464 | S464D | 1.45 | 1.23 | 1.24 | 1.31 | 1.51 | 1.21 | 0.73 |
| 464 | S464E | 0.95 | 0.98 | 1.04 | 1.06 | 1.06 | 1.23 | 1.03 |
| 464 | S464G | 0.94 | 0.86 | 0.92 | 1.00 | 0.98 | 0.97 | 1.04 |
| 464 | S464H | 0.88 | 0.84 | 0.82 | 0.87 | 0.99 | 1.04 | 1.10 |
| 464 | S464I | 0.94 | 0.80 | 0.78 | 0.83 | 0.96 | 1.15 | 1.00 |
| 464 | S464K | 0.94 | 0.85 | 0.88 | 0.93 | 0.93 | 0.81 | 0.97 |
| 464 | S464L | 0.77 | 0.81 | 0.79 | 0.91 | 0.88 | 0.86 | 1.02 |
| 464 | S464M | 1.32 | 1.27 | 1.35 | 1.50 | 1.18 | 1.42 | 0.81 |
| 464 | S464N | 1.15 | 1.03 | 1.16 | 1.25 | 1.18 | 1.38 | 0.85 |
| 464 | S464P | 1.42 | 1.38 | 1.32 | 1.42 | 1.40 | 1.56 | 0.76 |
| 464 | S464Q | 1.33 | 1.30 | 1.12 | 1.29 | 1.28 | 1.21 | 0.80 |
| 464 | S464V | 0.94 | 0.96 | 0.94 | 1.02 | 1.12 | 1.33 | 0.89 |

TABLE 23-1-continued

Performance of AmyS variants

| Position | variant | Corn Flour 10 | Corn Flour 60 | DP7 pH 4 | DP7 pH 5.8 | Cleaning pH 8 | Cleaning pH 10 | Expression |
|---|---|---|---|---|---|---|---|---|
| 464 | S464W | 1.06 | 0.95 | 0.94 | 1.08 | 0.98 | 0.84 | 1.01 |
| 464 | S464Y | 0.81 | 0.71 | 1.01 | 1.02 | 0.75 | 0.84 | 1.33 |
| 474 | G474A | 1.03 | 1.20 | 1.25 | 1.35 | 1.12 | 1.27 | 0.81 |
| 474 | G474C | 1.05 | 1.30 | 1.18 | 1.31 | 1.55 | 1.04 | 0.66 |
| 474 | G474D | 1.13 | 1.26 | 1.35 | 1.41 | 1.26 | 1.28 | 0.78 |
| 474 | G474E | 1.13 | 1.13 | 1.17 | 1.27 | 1.16 | 1.23 | 0.87 |
| 474 | G474F | 1.23 | 1.34 | 1.20 | 1.29 | 1.22 | 1.47 | 0.80 |
| 474 | G474H | 0.86 | 0.95 | 0.94 | 1.02 | 1.06 | 1.11 | 1.07 |
| 474 | G474I | 0.79 | 0.99 | 0.91 | 0.97 | 0.95 | 0.81 | 0.99 |
| 474 | G474K | 0.81 | 0.82 | 0.92 | 0.97 | 1.06 | 0.97 | 1.07 |
| 474 | G474L | 0.70 | 0.75 | 0.81 | 0.87 | 0.88 | 0.91 | 1.12 |
| 474 | G474M | 1.18 | 1.26 | 1.24 | 1.40 | 1.20 | 1.05 | 0.74 |
| 474 | G474N | 1.14 | 1.02 | 1.09 | 1.16 | 1.29 | 1.29 | 0.89 |
| 474 | G474P | 1.53 | 1.45 | 1.25 | 1.38 | 1.39 | 0.36 | 0.72 |
| 474 | G474Q | 1.19 | 1.14 | 1.26 | 1.33 | 1.35 | 1.37 | 0.79 |
| 474 | G474R | 1.15 | 1.17 | 1.16 | 1.29 | 1.31 | 1.41 | 0.82 |
| 474 | G474S | 0.87 | 0.89 | 0.97 | 0.99 | 1.00 | 0.93 | 1.09 |
| 474 | G474T | 0.97 | 1.01 | 1.13 | 1.06 | 1.03 | 1.00 | 1.01 |
| 474 | G474V | 0.88 | 0.91 | 1.03 | 1.02 | 1.03 | 0.94 | 1.01 |
| 483 | R483A | 1.25 | 1.23 | 1.35 | 1.43 | 1.43 | 1.34 | 0.74 |
| 483 | R483C | 1.19 | 1.17 | 1.73 | 1.51 | 1.19 | 1.59 | 0.70 |
| 483 | R483F | 1.08 | 1.49 | 1.36 | 1.23 | 1.51 | 1.18 | 0.57 |
| 483 | R483G | 1.07 | 1.13 | 1.07 | 1.12 | 1.14 | 1.08 | 0.86 |
| 483 | R483K | 0.82 | 0.73 | 0.86 | 0.90 | 0.91 | 0.69 | 1.12 |
| 483 | R483L | 1.10 | 1.03 | 1.29 | 1.20 | 1.06 | 0.93 | 0.94 |
| 483 | R483M | 1.31 | 1.50 | 1.42 | 1.56 | 1.51 | 1.26 | 0.66 |
| 483 | R483N | 1.17 | 1.32 | 1.46 | 1.39 | 1.34 | 1.09 | 0.75 |
| 483 | R483P | 1.19 | 1.17 | 1.37 | 1.35 | 1.17 | 1.05 | 0.83 |
| 483 | R483Q | 1.38 | 1.48 | 1.84 | 1.67 | 1.72 | 1.51 | 0.65 |
| 483 | R483S | 0.99 | 1.05 | 0.92 | 0.96 | 1.04 | 0.94 | 1.02 |
| 483 | R483T | 1.10 | 1.03 | 1.04 | 0.98 | 0.98 | 0.93 | 0.93 |
| 483 | R483V | 1.11 | 1.18 | 1.25 | 1.26 | 1.25 | 1.20 | 0.80 |
| 483 | R483Y | 0.81 | 0.86 | 1.07 | 1.06 | 1.04 | 0.81 | 0.96 |

It will be apparent that a large number of substitutions produced variant α-amylases having one or more improved properties compared to the wild-type α-amylase. These substitutions are included in the present compositions and methods.

Example 24

Altered Property of AmyS Variants

This example shows that some *G. stearothermophilus* α-amylase (AmyS) variants (described in Example 22) have an altered property relative to the parent α-amylase. A high throughput thermal stability screen of AmyS variants was carried out as described in Example 3. Performance indices for activity (measured as BODIPY assay) and residual activity (after thermal stress) are shown in Tables 24-1, 24-2, 24-3.

TABLE 24-1

Positions in AmyS protein with mutations (shown in column labeled variant) that have performance indices for both activity and residual activity after heat stress better than wildtype AmyS.

| Variant | Activity | Residual Activity |
|---|---|---|
| 72D | 1.0300361 | 1.0701945 |
| 74A | 1.0821966 | 1.2443197 |
| 74E | 1.0425346 | 1.0348158 |
| 74G | 1.1272413 | 1.0873821 |
| 74H | 1.0489031 | 1.0047597 |
| 74I | 1.0441329 | 1.0204416 |

TABLE 24-1-continued

Positions in AmyS protein with mutations (shown in column labeled variant) that have performance indices for both activity and residual activity after heat stress better than wildtype AmyS.

| Variant | Activity | Residual Activity |
|---|---|---|
| 74Y | 1.0962024 | 1.0243028 |
| 86E | 1.0744425 | 1.0082956 |
| 86K | 1.0320588 | 1.0003874 |
| 115E | 1.0371929 | 1.0263233 |
| 115K | 1.0983963 | 1.1179136 |
| 115L | 1.0304852 | 1.2220073 |
| 115N | 1.0617811 | 1.0373701 |
| 115Q | 1.0585819 | 1.0086197 |
| 115R | 1.0362569 | 1.0196812 |
| 115Y | 1.0818022 | 1.0155115 |
| 124A | 1.0066154 | 1.0764058 |
| 124K | 1.0875013 | 1.3977188 |
| 124N | 1.2073767 | 1.1957849 |
| 124Q | 1.0581528 | 1.1748222 |
| 124R | 1.0401245 | 1.2046408 |
| 125N | 1.2111343 | 1.111989 |
| 132A | 1.0229275 | 1.3339209 |
| 135F | 1.0125922 | 1.1400675 |
| 145A | 1.0535347 | 1.269397 |
| 146A | 1.0159296 | 1.2695343 |
| 146D | 1.0111003 | 1.0989512 |
| 146E | 1.0209598 | 1.076157 |
| 146T | 1.0557131 | 1.0905141 |
| 146W | 1.0503671 | 1.0446909 |
| 148A | 1.1550962 | 1.3714229 |
| 148E | 1.0257123 | 1.1367377 |
| 148F | 1.0047267 | 1.0833811 |
| 148R | 1.1439066 | 1.0724962 |

TABLE 24-1-continued

Positions in AmyS protein with mutations (shown in column labeled variant) that have performance indices for both activity and residual activity after heat stress better than wildtype AmyS.

| Variant | Activity | Residual Activity |
| --- | --- | --- |
| 153A | 1.0933406 | 1.1903028 |
| 153D | 1.047218 | 1.0763254 |
| 153G | 1.0314126 | 1.0393344 |
| 153H | 1.0243746 | 1.0325474 |
| 153N | 1.0749307 | 1.1537286 |
| 153P | 1.1090313 | 1.1653113 |
| 153R | 1.0695773 | 1.050884 |
| 159A | 1.2514424 | 1.8489959 |
| 159C | 1.1389324 | 1.4229765 |
| 159D | 1.3042895 | 1.616517 |
| 159E | 1.3048703 | 1.6426287 |
| 159F | 1.0692526 | 1.2740874 |
| 159G | 1.309088 | 1.4806394 |
| 159H | 1.2239861 | 1.4766606 |
| 159K | 1.3024788 | 1.6188749 |
| 159L | 1.2438467 | 1.7685564 |
| 159N | 1.4021695 | 1.747298 |
| 159R | 1.3445318 | 1.6062932 |
| 159S | 1.3352659 | 1.5322275 |
| 159T | 1.2115923 | 1.5982316 |
| 159V | 1.1075763 | 1.5364844 |
| 169L | 1.2709 | 1.221157 |
| 169M | 1.0720854 | 1.2525822 |
| 169Y | 1.1519097 | 1.3009779 |
| 179A | 1.2856782 | 1.4150905 |
| 179Q | 1.0837406 | 1.0777175 |
| 180A | 1.223674 | 1.1463487 |
| 181A | 1.5853606 | 2.5498838 |
| 181C | 1.0805237 | 1.2359592 |
| 181D | 1.2451756 | 1.4958763 |
| 181E | 1.2126846 | 1.3673333 |
| 181F | 1.1174172 | 1.0714025 |
| 181L | 1.0562715 | 1.2603028 |
| 181M | 1.0553459 | 1.1115696 |
| 181N | 1.0657087 | 1.058626 |
| 181P | 1.3407541 | 1.8191875 |
| 181Q | 1.1827757 | 1.3094913 |
| 181R | 2.1023852 | 1.000651 |
| 181V | 1.2072805 | 1.2882775 |
| 181Y | 1.1468422 | 1.2888335 |
| 187L | 1.0631177 | 1.1713174 |
| 242D | 1.053295 | 1.2659451 |
| 242E | 1.1904636 | 1.4089496 |
| 242G | 1.0897161 | 1.0670134 |
| 259M | 1.054788 | 1.1174398 |
| 261L | 1.1311136 | 1.2682418 |
| 271K | 1.0660617 | 1.1281026 |
| 271V | 1.0912656 | 1.3024768 |
| 278A | 1.1681249 | 1.3749858 |
| 278H | 1.2287582 | 1.3214257 |
| 278K | 1.2908668 | 1.3351968 |
| 278N | 1.2587781 | 1.4816971 |
| 278R | 1.2602246 | 1.3802029 |
| 278S | 1.0407916 | 1.051006 |
| 281A | 1.0778757 | 1.302493 |
| 281I | 1.0773434 | 1.0691046 |
| 281L | 1.0664433 | 1.5428781 |
| 281M | 1.2357293 | 1.317267 |
| 281P | 1.1452343 | 1.1634661 |
| 281R | 1.1498741 | 1.1898966 |
| 281Y | 1.0366211 | 1.0814182 |
| 302C | 1.0627926 | 1.0743991 |
| 302D | 1.3067743 | 1.3085968 |
| 302E | 1.0492343 | 1.1151221 |
| 302M | 1.0807557 | 1.2463993 |
| 304D | 1.1358974 | 1.304862 |
| 304E | 1.1872403 | 1.2138013 |
| 304F | 1.1250781 | 1.0476505 |
| 304M | 1.2316987 | 1.2224245 |
| 304N | 1.0270711 | 1.0584592 |
| 304P | 1.0166456 | 1.0403283 |
| 304R | 1.0960387 | 1.0336549 |
| 304V | 1.0716606 | 1.0416779 |
| 304W | 1.1600113 | 1.0109269 |
| 304Y | 1.3289811 | 1.1964204 |
| 308A | 1.0074309 | 1.189004 |
| 321A | 1.0826055 | 1.2311805 |
| 321H | 1.384587 | 1.4691649 |
| 321Q | 1.3306703 | 1.3485614 |
| 321R | 1.2446359 | 1.3138378 |
| 321S | 1.1483705 | 1.1251132 |
| 321Y | 1.0396471 | 1.1263643 |
| 333Q | 1.425789 | 1.6656427 |
| 378D | 1.0880667 | 1.2202146 |
| 378N | 1.0064817 | 1.2616767 |
| 378R | 1.0264777 | 1.2826859 |
| 378T | 1.042994 | 1.0795534 |
| 382D | 1.1628676 | 1.2206133 |
| 382G | 1.0050534 | 1.009576 |
| 382K | 1.1896345 | 1.178075 |
| 382N | 1.0241429 | 1.1576205 |
| 382P | 1.001145 | 1.0672392 |
| 398A | 1.0127464 | 1.2067063 |
| 418A | 1.070915 | 1.3701437 |
| 418M | 1.101424 | 1.3091549 |
| 418N | 1.1440828 | 1.4650527 |
| 420A | 1.1288416 | 1.2216203 |
| 420D | 1.0368387 | 1.065286 |
| 420M | 1.011372 | 1.1274183 |
| 420N | 1.0213745 | 1.1440374 |
| 421E | 1.010536 | 1.0961403 |
| 421H | 1.0434891 | 1.0576175 |
| 421L | 1.0197128 | 1.0679988 |
| 421N | 1.092512 | 1.1299631 |
| 421Q | 1.0784982 | 1.1126707 |
| 421R | 1.142674 | 1.2396538 |
| 421T | 1.0098565 | 1.023113 |
| 432A | 1.1828859 | 1.4534375 |
| 432D | 1.1261465 | 1.2701694 |
| 432E | 1.0932052 | 1.1438228 |
| 432K | 1.0432215 | 1.1145887 |
| 432L | 1.1040571 | 1.2896033 |
| 432M | 1.1530369 | 1.3947422 |
| 432N | 1.1373288 | 1.2843802 |
| 432Q | 1.2305257 | 1.3438957 |
| 432R | 1.1226193 | 1.2108348 |
| 432S | 1.1383528 | 1.1690319 |
| 432T | 1.0946975 | 1.1651163 |
| 432Y | 1.0242088 | 1.2209025 |
| 437C | 1.0389223 | 1.0550093 |
| 437D | 1.0648095 | 1.2263069 |
| 437F | 1.0884138 | 1.0761389 |
| 437G | 1.1270339 | 1.2057266 |
| 437H | 1.0624587 | 1.2128077 |
| 437L | 1.0706178 | 1.2702869 |
| 437M | 1.1727007 | 1.3357945 |
| 437N | 1.0678835 | 1.1245993 |
| 437Q | 1.0533035 | 1.1845926 |
| 437R | 1.0211609 | 1.01587 |
| 437S | 1.0996009 | 1.0837657 |
| 437V | 1.0035949 | 1.1373234 |
| 437Y | 1.2190374 | 1.428939 |
| 443D | 1.039287 | 1.0340347 |
| 443L | 1.0229234 | 1.0966951 |
| 443P | 1.0219417 | 1.0948128 |
| 446A | 1.2002798 | 1.498028 |
| 446D | 1.0773299 | 1.1176728 |
| 446H | 1.0897531 | 1.071114 |
| 446K | 1.039616 | 1.0263734 |
| 446N | 1.1867752 | 1.1501356 |
| 446R | 1.0179243 | 1.035122 |
| 446S | 1.00426 | 1.0219768 |
| 446Y | 1.1205486 | 1.2525673 |
| 459I | 1.0404304 | 1.0379194 |
| 459M | 1.0320006 | 1.1066777 |
| 459Y | 1.0131462 | 1.0198803 |

TABLE 24-1-continued

Positions in AmyS protein with mutations (shown in column labeled variant) that have performance indices for both activity and residual activity after heat stress better than wildtype AmyS.

| Variant | Activity | Residual Activity |
|---|---|---|
| 461P | 1.084833 | 1.1869717 |
| 464D | 1.0164453 | 1.0297077 |
| 464H | 1.0355113 | 1.0962268 |
| 464L | 1.0084324 | 1.0510274 |
| 464M | 1.0026999 | 1.1589373 |
| 464N | 1.0727228 | 1.1205096 |
| 464Q | 1.0719588 | 1.2199585 |
| 464Y | 1.1888873 | 1.3747167 |
| 474A | 1.1556971 | 1.3935021 |
| 474D | 1.0692943 | 1.1879003 |
| 474E | 1.1729152 | 1.3481142 |
| 474F | 1.0633952 | 1.1462803 |
| 474H | 1.0620029 | 1.1722857 |
| 474I | 1.0766474 | 1.1352128 |
| 474K | 1.1240341 | 1.2036886 |
| 474L | 1.110407 | 1.267509 |
| 474M | 1.1869843 | 1.3422689 |
| 474N | 1.1135684 | 1.2124349 |
| 474P | 1.0761861 | 1.2293237 |
| 474Q | 1.2580448 | 1.3477339 |
| 474R | 1.1994238 | 1.3506214 |
| 474S | 1.2348915 | 1.2615358 |
| 474T | 1.1757697 | 1.1841873 |
| 474V | 1.0823992 | 1.2078523 |

TABLE 24-2

Positions in AmyS protein with mutations (shown in column labeled variant) that have performance indices for residual activity after heat stress at least 20% better than wildtype AmyS and performance indices for starting activity or expression at least half of wildtype AmyS.

| Variant | Activity | Residual Activity |
|---|---|---|
| 74A | 1.0821966 | 1.2443197 |
| 115L | 1.0304852 | 1.2220073 |
| 124K | 1.0875013 | 1.3977188 |
| 124R | 1.0401245 | 1.2046408 |
| 132A | 1.0229275 | 1.3339209 |
| 132C | 0.9072598 | 1.2271522 |
| 135A | 0.9014583 | 1.2604591 |
| 145A | 1.0535347 | 1.269397 |
| 146A | 1.0159296 | 1.2695343 |
| 148A | 1.1550962 | 1.3714229 |
| 148N | 0.8803735 | 1.202166 |
| 159A | 1.2514424 | 1.8489959 |
| 159C | 1.1389324 | 1.4229765 |
| 159D | 1.3042895 | 1.616517 |
| 159E | 1.3048703 | 1.6426287 |
| 159F | 1.0692526 | 1.2740874 |
| 159G | 1.309088 | 1.4806394 |
| 159H | 1.2239861 | 1.4766606 |
| 159K | 1.3024788 | 1.6188749 |
| 159L | 1.2438467 | 1.7685564 |
| 159N | 1.4021695 | 1.747298 |
| 159R | 1.3445318 | 1.6062932 |
| 159S | 1.3352659 | 1.5322275 |
| 159T | 1.2115923 | 1.5982316 |
| 159V | 1.1075763 | 1.5364844 |
| 169A | 0.9976004 | 1.3149706 |
| 169L | 1.2709 | 1.221157 |
| 169M | 1.0720854 | 1.2525822 |
| 169Y | 1.1519097 | 1.3009779 |
| 179A | 1.2856782 | 1.4150905 |
| 181A | 1.5853606 | 2.5498838 |
| 181C | 1.0805237 | 1.2359592 |
| 181D | 1.2451756 | 1.4958763 |
| 181E | 1.2126846 | 1.3673333 |

TABLE 24-2-continued

Positions in AmyS protein with mutations (shown in column labeled variant) that have performance indices for residual activity after heat stress at least 20% better than wildtype AmyS and performance indices for starting activity or expression at least half of wildtype AmyS.

| Variant | Activity | Residual Activity |
|---|---|---|
| 181L | 1.0562715 | 1.2603028 |
| 181P | 1.3407541 | 1.8191875 |
| 181Q | 1.1827757 | 1.3094913 |
| 181V | 1.2072805 | 1.2882775 |
| 181Y | 1.1468422 | 1.2888335 |
| 242A | 0.8658592 | 1.3402797 |
| 242D | 1.053295 | 1.2659451 |
| 242E | 1.1904636 | 1.4089496 |
| 242Q | 0.9905304 | 1.8848517 |
| 261L | 1.1311136 | 1.2682418 |
| 271A | 0.9883235 | 1.3367718 |
| 271V | 1.0912656 | 1.3024768 |
| 278A | 1.1681249 | 1.3749858 |
| 278H | 1.2287582 | 1.3214257 |
| 278K | 1.2908668 | 1.3351968 |
| 278N | 1.2587781 | 1.4816971 |
| 278R | 1.2602246 | 1.3802029 |
| 281A | 1.0778757 | 1.302493 |
| 281L | 1.0664433 | 1.5428781 |
| 281M | 1.2357293 | 1.317267 |
| 302D | 1.3067743 | 1.3085968 |
| 302M | 1.0807557 | 1.2463993 |
| 304D | 1.1358974 | 1.304862 |
| 304E | 1.1872403 | 1.2138013 |
| 304M | 1.2316987 | 1.2224245 |
| 321A | 1.0826055 | 1.2311805 |
| 321H | 1.384587 | 1.4691649 |
| 321Q | 1.3306703 | 1.3485614 |
| 321R | 1.2446359 | 1.3138378 |
| 333Q | 1.425789 | 1.6656427 |
| 378D | 1.0880667 | 1.2202146 |
| 378N | 1.0064817 | 1.2616767 |
| 378R | 1.0264777 | 1.2826859 |
| 382D | 1.1628676 | 1.2206133 |
| 398A | 1.0127464 | 1.2067063 |
| 418A | 1.070915 | 1.3701437 |
| 418M | 1.101424 | 1.3091549 |
| 418N | 1.1440828 | 1.4650527 |
| 420A | 1.1288416 | 1.2216203 |
| 421R | 1.142674 | 1.2396538 |
| 432A | 1.1828859 | 1.4534375 |
| 432D | 1.1261465 | 1.2701694 |
| 432L | 1.1040571 | 1.2896033 |
| 432M | 1.1530369 | 1.3947422 |
| 432N | 1.1373288 | 1.2843802 |
| 432Q | 1.2305257 | 1.3438957 |
| 432R | 1.1226193 | 1.2108348 |
| 432Y | 1.0242088 | 1.2209025 |
| 437D | 1.0648095 | 1.2263069 |
| 437G | 1.1270339 | 1.2057266 |
| 437H | 1.0624587 | 1.2128077 |
| 437L | 1.0706178 | 1.2702869 |
| 437M | 1.1727007 | 1.3357945 |
| 437Y | 1.2190374 | 1.428939 |
| 446A | 1.2002798 | 1.498028 |
| 446Y | 1.1205486 | 1.2525673 |
| 454A | 0.9816646 | 1.2570919 |
| 464Q | 1.0719588 | 1.2199585 |
| 464Y | 1.1888873 | 1.3747167 |
| 474A | 1.1556971 | 1.3935021 |
| 474E | 1.1729152 | 1.3481142 |
| 474K | 1.1240341 | 1.2036886 |
| 474L | 1.110407 | 1.267509 |
| 474M | 1.1869843 | 1.3422689 |
| 474N | 1.1135684 | 1.2124349 |
| 474P | 1.0761861 | 1.2293237 |
| 474Q | 1.2580448 | 1.3477339 |
| 474R | 1.1994238 | 1.3506214 |
| 474S | 1.2348915 | 1.2615358 |
| 474V | 1.0823992 | 1.2078523 |

TABLE 24-3

Positions in AmyS protein with mutations (shown in column labeled variant) that have performance indices for activity or expression at least 20% greater than wildtype AmyS

| Variant | Activity | Residual Activity |
|---|---|---|
| 124N | 1.2073767 | 1.1957849 |
| 125A | 1.372718 | −0.3461869 |
| 125K | 1.2754087 | −0.3195654 |
| 125N | 1.2111343 | 1.111989 |
| 130A | 1.2829276 | −0.1606582 |
| 130S | 1.2547959 | −0.2396474 |
| 159A | 1.2514424 | 1.8489959 |
| 159D | 1.3042895 | 1.616517 |
| 159E | 1.3048703 | 1.6426287 |
| 159G | 1.309088 | 1.4806394 |
| 159H | 1.2239861 | 1.4766606 |
| 159K | 1.3024788 | 1.6188749 |
| 159L | 1.2438467 | 1.7685564 |
| 159N | 1.4021695 | 1.747298 |
| 159R | 1.3445318 | 1.6062932 |
| 159S | 1.3352659 | 1.5322275 |
| 159T | 1.2115923 | 1.5982316 |
| 166F | 1.3226117 | 0.9751853 |
| 166G | 1.3251188 | −0.8989095 |
| 166H | 1.5608888 | 0.889625 |
| 166S | 1.5553953 | −0.4698927 |
| 166Y | 1.3161377 | 0.9404254 |
| 169L | 1.2709 | 1.221157 |
| 179A | 1.2856782 | 1.4150905 |
| 179P | 1.2367832 | −0.2832651 |
| 180A | 1.223674 | 1.1463487 |
| 180D | 1.3732003 | 0.5446904 |
| 180H | 1.3854073 | −0.9190277 |
| 180K | 1.4038831 | −1.1078033 |
| 180L | 1.6414819 | −0.6936105 |
| 180N | 1.2646998 | −1.0108408 |
| 180T | 1.4553893 | −0.8759486 |
| 180V | 1.2190216 | −1.0611484 |
| 180Y | 1.3113267 | 0.6162484 |
| 181A | 1.5853606 | 2.5498838 |
| 181D | 1.2451756 | 1.4958763 |
| 181E | 1.2126846 | 1.3673333 |
| 181G | 1.2893058 | 0.9117403 |
| 181P | 1.3407541 | 1.8191875 |
| 181R | 2.1023852 | 1.000651 |
| 181S | 1.2285225 | 0.9373869 |
| 181V | 1.2072805 | 1.2882775 |
| 187A | 1.3658382 | −0.221251 |
| 187C | 1.3181513 | −0.2335241 |
| 187K | 1.2523832 | −0.2685104 |
| 187N | 1.2632558 | 0.127576 |
| 187P | 1.4102122 | −0.2495879 |
| 187Q | 1.2477941 | −0.2008265 |
| 187R | 1.3445711 | −0.2482154 |
| 187S | 1.2513011 | −0.2208563 |
| 242H | 1.280464 | 0.7629545 |
| 242N | 1.29758 | 0.8729278 |
| 278H | 1.2287582 | 1.3214257 |
| 278K | 1.2908668 | 1.3351968 |
| 278N | 1.2587781 | 1.4816971 |
| 278R | 1.2602246 | 1.3802029 |
| 281M | 1.2357293 | 1.317267 |
| 302D | 1.3067743 | 1.3085968 |
| 304M | 1.2316987 | 1.2224245 |
| 304Y | 1.3289811 | 1.1964204 |
| 321H | 1.384587 | 1.4691649 |
| 321Q | 1.3306703 | 1.3485614 |
| 321R | 1.2446359 | 1.3138378 |
| 333Q | 1.425789 | 1.6656427 |
| 432Q | 1.2305257 | 1.3438957 |
| 437Y | 1.2190374 | 1.428939 |
| 446A | 1.2002798 | 1.498028 |
| 474Q | 1.2580448 | 1.3477339 |
| 474S | 1.2348915 | 1.2615358 |

Based on the relative performance data and stability data for the AmyS positions described in Table 23-1, 24-1, 24-2, and Table 24-3, AmyS positions were classified as restrictive versus non-restrictive as follows: Non-restrictive positions have ≧20% neutral mutations for at least one property. These positions are good candidates for mutation when making engineered α-amylases because mutations at these position have a high probability of improving performance. Restrictive positions have <20% neutral mutations for activity and stability. These positioned are generally left alone (i.e., not mutated) when engineering α-amylase variants, as mutation at these positions tend to reduce, rather than increase performance. All the positions/sites described in Table 23-1 are non-restrictive.

Example 25

Additional Positional Libraries in AmyS Protein

In addition to the AmyS variants described in Example 22, positional libraries at additional sites were generated in *G. stearothermophilus* α-amylase with a truncation (SEQ ID NO: 2). The libraries were produced by Geneart (Geneart GmbH, Josef-Engert-strasse 11, D-93053 Regensburg, Del.). Table 25-1 shows the site variants that were generated:

TABLE 25-1

Site variants generated in AmyS

N5: A, C, E, F, G, H, I, K, L, M, P, Q, R, S, T, V, W, Y

G6: A, D, E, H, I, K, L, M, N, P, Q, R, S, T, V, W, Y

E13: A, C, D, F, G, H, I, K, L, M, N, P, Q, R, S, T, V, W, Y

W14: A, C, D, E, F, G, H, I, K, L, M, N, P, Q, R, S, T, V, Y

Y15: A, C, D, E, G, H, I, K, L, M, N, P, Q, R, S, T, W

L16: A, D, E, F, G, H, I, K, M, N, P, Q, R, S, T, V, W, Y

D18: A, F, G, H, I, K, L, N, P, Q, R, S, T, V, W, Y

G20: A, C, D, E, F, H, I, K, L, M, N, P, Q, R, S, T, V, W, Y

K25: A, C, D, E, F, G, H, L, M, N, P, Q, R, S, T, Y

A27: C, D, E, F, G, H, I, K, L, M, N, P, Q, R, S, T, V, W, Y

E29: A, D, G, H, K, L, M, N, P, Q, R, S, T, W, Y

L36: A, C, D, E, F, G, H, I, K, M, N, P, Q, R, S, T, V, W, Y

T39: C, D, E, F, G, H, K, M, N, P, Q, R, S, V, W

T50: A, C, D, E, F, G, H, I, K, L, M, N, P, Q, R, S, V, W, Y

R52: A, C, D, E, G, H, K, L, M, N, P, Q, S, T, V, W, Y

S53: A, C, D, E, F, G, H, I, K, L, M, P, Q, R, T, V, W, Y

D54: A, C, E, F, G, H, I, K, L, M, N, P, Q, R, S, T, V, W, Y

TABLE 25-1-continued

Site variants generated in AmyS

E67: A, C, D, G, H, K, L, M, N, P, Q, R, S, T, W, Y

K71: A, C, D, E, F, G, H, I, L, M, N, P, Q, R, S, T, V, W, Y

T73: A, C, D, E, F, G, H, I, K, L, M, N, P, R, S, V, W, Y

R75: A, C, D, E, F, G, H, I, L, M, P, Q, S, T, V, W, Y

K77: A, C, D, E, F, G, I, L, M, N, P, Q, R, S, T, V, W

T80: A, C, D, E, F, G, H, I, K, L, M, N, P, Q, R, S, V, W, Y

K81: A, C, D, E, F, G, H, I, L, M, N, P, S, T, V, W, Y

Q83: A, C, D, E, G, G, H, I, L, M, P, R, S, T, V, W, Y

L85: A, C, D, E, G, H, I, K, M, N, P, Q, R, S, T, W, Y

A90: C, D, E, F, G, H, I, K, L, M, N, O, Q, R, S, T, V, W, Y

H92: C, D, E, F, G, K, L, N, P, Q, R, S, T, V, W, Y

H106: A, C, D, E, G, I, K, L, N, P, Q, R, S, T, V, W, Y

K107: A, C, D, E, F, G, H, I, L, M, N, P, Q, R, S, T, V, W, Y

D111: A, C, E, F, G, H, I, K, L, M, N, P, Q, R, S, T, V, W, Y

T113: A, C, D, E, F, G, H, I, K, L, M, P, Q, R, V, W

E114: A, C, D, F, G, H, I, L, M, N, P, R, T, V, W, Y

E120: A, C, D, F, G, H, I, L, M, N, P, Q, R, S, T, V, W, Y

V121: A, C, D, E, F, G, H, I, L, M, P, Q, R, S, T, W, Y

R126: A, D, E, F, G, H, I, L, M, N, P, Q, T, V, W, Y

Q128: A, C, D, E, G, H, I, K, L, N, P, R, S, T, V, W, Y

S131: A, C, D, E, F, G, H, I, K, M, N, P, R, T, W, Y

T133: A, C, D, E, F, G, H, I, K, L, M, N, P, Q, R, S, V, W, Y

Q137: A, C, D, E, F, G, H, I, L, M, P, R, S, T, V, W, Y

A138: C, D, E, F, G, H, I, K, L, M, N, P, Q, R, S, T, V, W, Y

W139: A, C, D, E, G, H, I, K, L, M, N, Q, R, S, T, V, Y

K141: A, C, D, E, F, G, H, I, L, M, N, P, Q, R, S, T, V, W, Y

D143: A, C, E, G, H, I, K, L, M, N, P, T, V, W, Y

R147: A, C, D, E, F, G, H, I, K, L, M, N, P, Q, S, T, V, W, Y

N149: A, D, E, F, G, H, I, K, L, M, Q, R, S, V, W

T150: A, C, D, E, F, G, I, K, L, M, N, Q, R, S, V, Y

Y151: A, C, D, E, F, G, H, I, L, M, N, P, Q, R, S, T, V, W

S152: A, C, D, E, F, G, H, I, K, M, N, Q, R, T, V, W, Y

K155: A, C, D, E, G, H, L, M, N, P, Q, R, S, T, V, W, Y

H160: A, C, D, E, F, G, I, L, M, N, P, Q, R, S, T, V, W, Y

D165: A, C, E, F, G, H, I, K, L, M, N, P, Q, R, S, T, V, W, Y

E168: A, C, D, F, G, H, I, K, L, M, N, P, Q, R, S, T, V, W, Y

L172: A, C, D, E, G, H, I, K, M, N, P, Q, R, S, T, V, W, Y

S173: A, C, D, E, F, G, H, I, K, L, M, N, Q, R, T, V, W, Y

K177: A, C, D, E, F, G, H, I, L, M, N, P, Q, R, S, T, W, Y

E188: A, C, D, F, G, H, I, K, M, N, P, Q, S, T, V, W, Y

T191: A, C, D, F, G, H, I, K, L, M, N, P, Q, R, S, V, W

E192: A, C, D, G, H, I, K, M, N, P, Q, R, S, T, V, W, Y

N193: A, C, D, E, F, G, H, I, K, L, M, P, R, S, T, W, Y

Y196: A, C, D, E, F, G, H, I, K, L, N, P, R, S, V, W

L199: A, E, G, H, I, K, M, N, P, Q, R, S, T, V, W, Y

M200: A, C, D, E, F, G, H, I, K, L, N, P, Q, S, T, V, W

Y201: A, C, D, E, F, G, H, I, K, L, M, N, P, Q, R, S, T, V, W

A202: C, D, E, F, G, H, I, K, L, M, N, P, Q, R, S, T, V, Y

T213: A, C, D, E, F, G, H, I, K, L, M, N, P, Q, R, S, V, W

K216: A, D, E, F, G, H, I, L, M, P, Q, R, S, T, V, W, Y

N217: A, C, E, F, G, H, I, L, M, P, Q, R, S, T, V, W, Y

K220: A, C, D, E, F, G, H, I, M, N, P, Q, R, S, T, V, W, Y

W221: A, C, D, E, F, G, H, I, K, L, M, N, P, R, S, V, Y

TABLE 25-1-continued

Site variants generated in AmyS

N227: A, C, D, E, F, G, H, I, K, L, M, P, Q, R, S, T, V, W, Y

R232: A, C, D, E, G, H, K, M, N, P, Q, S, T, V, W, Y

A235: C, D, E, F, G, H, I, K, L, M, N, P, Q, R, S, T, V, W, Y

K237: A, C, D, E, F, G, H, I, L, M, N, P, Q, R, T, V, W, Y

H238: A, C, D, F, G, I, K, L, M, N, P, Q, R, T, V, Y

K240: A, D, E, F, G, H, I, M, N, P, Q, R, S, T, V, W, Y

D246: A, E, F, G, H, I, K, L, M, N, P, Q, R, S, T, Y

S249: A, C, D, E, F, G, H, K, L, M, P, Q, R, T, V, W, Y

Y250: A, C, D, E, F, G, I, K, L, M, N, P, Q, R, S, T, V, W

R252: A, C, D, E, F, G, I, K, L, M, N, P, Q, S, T, V, Y

S253: A, D, E, F, G, H, I, K, L, M, N, P, Q, T, V, W, Y

Q254: A, C, D, E, F, G, H, I, K, L, M, N, R, S, T, V, W, Y

T255: A, C, D, E, F, G, H, I, K, L, M, N, P, R, S, V, W, Y

K257: A, C, D, E, F, G, H, I, L, M, N, P, Q, R, S, T, V, W

P258: A, C, D, E, F, G, H, I, K, L, M, N, Q, R, S, T, V, W, Y

Y268: A, C, D, E, F, G, H, I, K, L, M, N, P, Q, R, S, T, V, W

K272: A, C, D, E, F, G, H, I, M, N, P, R, S, T, V, W, Y

N275: A, C, D, E, F, G, H, I, K, L, M, P, Q, R, S, T, V, W, Y

K279: C, E, F, G, H, I, L, M, N, P, Q, S, T, V, W, Y

T283: A, C, D, E, G, H, I, K, L, M, N, P, R, S, V, W, Y

S285: A, C, D, E, F, H, I, K, L, M, Q, R, T, V, W, Y

N293: A, C, D, E, F, G, H, I, K, L, M, P, Q, R, S, T, V, W, Y

K294: A, C, D, E, F, G, H, I, L, M, N, P, Q, R, S, T, V, W, Y

T297: C, D, E, F, G, H, I, K, L, M, N, P, Q, R, S, V, W, Y

K300: A, C, D, E, F, G, H, I, L, M, N, P, Q, R, S, T, V, W

S301: A, E, F, G, H, I, K, L, M, N, P, Q, R, T, V, W, Y

D306: A, C, E, F, G, H, I, K, L, N, P, Q, R, S, T, V, W, Y

T309: A, C, D, E, F, G, H, I, K, L, M, N, P, Q, R, S, V, W, Y

T312: A, C, D, E, F, G, H, K, L, M, N, P, Q, R, S, V, W, Y

N313: A, C, D, E, F, G, H, I, K, L, M, P, Q, R, S, V, W

K317: A, C, D, E, F, G, L, M, N, P, Q, R, S, T, V, W, Y

D318: A, E, F, G, H, I, K, L, M, N, P, Q, R, S, T, V, W, Y

Q319: A, C, D, E, F, G, H, I, K, L, M, N, P, R, S, T, V, W, Y

P320: A, C, D, E, F, G, H, I, K, L, M, Q, R, S, T, V, W, Y

L338: A, C, D, E, F, G, H, I, K, M, P, Q, R, S, T, V, W, Y

Q339: A, C, D, E, F, G, H, K, L, M, P, R, S, T, V, W, Y

S340: A, C, D, E, F, H, I, K, L, M, N, P, Q, T, V, Y

D343: A, C, E, F, H, I, L, M, N, P, Q, R, T, W, Y

W345: A, C, D, E, F, H, I, K, L, M, N, P, Q, S, T, V

C363: A, D, E, F, G, H, I, L, M, N, P, Q, R, S, T, V, W, Y

Y366: A, C, D, E, F, G, H, I, K, L, M, N, P, Q, R, S, T, V, W

Y369: A, C, E, F, G, H, I, K, M, P, Q, R, S, T, V, W

Y370: A, C, D, E, F, G, H, I, K, L, M, N, P, Q, S, T, V, W

Y375: A, C, D, E, F, G, H, I, K, L, M, N, P, Q, R, S, T, W

S379: A, C, D, E, F, G, H, I, K, L, M, N, P, Q, R, T, V, W, Y

K381: A, C, D, E, F, G, H, I, L, M, N, P, Q, R, S, T, V, W, Y

D385: A, C, E, F, G, H, I, K, L, N, P, Q, R, S, T, V, W

P386: A, C, D, E, F, G, H, I, K, L, M, N, Q, S, T, V, W, Y

R391: A, C, E, G, H, K, L, N, P, Q, S, T, V, W, Y

R392: A, C, E, F, G, H, I, K, L, M, N, P, Q, S, T, V, W, Y

D393: A, C, E, F, G, H, I, K, L, N, P, Q, R, S, T, V, W, Y

Y394: A, D, E, F, G, H, I, K, L, M, N, P, Q, S, V, W

TABLE 25-1-continued

Site variants generated in AmyS

H400: A, C, D, E, F, G, I, K, L, M, N, P, Q, R, S, T, V, W, Y

Y402: A, C, D, E, F, G, H, I, K, L, M, N, P, Q, R, T, V, W

L403: A, C, D, E, F, G, H, M, N, P, Q, R, S, T, V, W, Y

D404: A, C, E, G, I, K, L, M, N, P, Q, R, S, V, W, Y

S406: A, C, D, E, F, G, H, I, K, L, M, N, P, Q, T, V, Y

D407: C, E, F, G, H, I, K, L, M, N, P, Q, R, S, T, V, W, Y

G410: A, C, D, E, F, H, I, L, M, N, P, Q, R, T, V, W, Y

R413: A, D, E, G, H, I, K, L, M, N, P, Q, S, T, V, W, Y

E414: A, C, D, F, G, H, I, K, L, M, N, P, Q, R, S, T, W, Y

V416: A, C, D, F, H, I, K, L, M, N, P, Q, R, S, T, W, Y

K419: A, C, D, E, F, H, I, L, M, N, P, Q, R, S, T, V, W, Y

S422: A, C, D, E, F, G, H, I, K, L, M, N, P, Q, R, T, V, W, Y

L427: A, C, D, E, F, G, H, I, K, M, N, P, Q, R, S, T, V, W, Y

G433: A, C, D, E, F, H, I, K, L, M, N, P, W, R, S, T, V, Y

K436: A, C, D, E, F, G, H, I, L, M, N, P, Q, R, S, T, V, W, Y

Y439: A, D, E, F, G, H, I, K, L, M, N, P, Q, R, S, T, V, W

K442: A, C, F, G, H, I, N, P, Q, R, S, T, V, W, Y

A445: C, D, G, H, I, K, L, N, P, Q, R, S, T, V, W

K447: A, C, D, E, F, G, H, I, L, M, N, Q, R, S, T, V, W, Y

V448: A, C, D, E, F, G, H, I, K, L, M, N, P, Q, R, S, T, W, Y

Y450: A, C, D, E, G, H, K, L, M, N, P, Q, R, S, T, V, W

L452: A, C, D, E, F, G, H, K, M, N, P, Q, R, S, T, V, Y

N455: A, C, D, E, G, H, I, K, L, M, P, Q, R, S, T, V, W, Y

N463: A, D, F, G, H, I, K, L, M, P, Q, R, S, T, V, W, Y

D465: A, C, E, F, G, H, I, K, L, M, N, P, Q, R, S, T, V, W, Y

E469: A, C, D, F, G, H, K, L, M, N, R, S, T, V, W, Y

K471: A, C, D, F, G, H, I, L, M, N, P, R, S, T, V, Y

N473: A, C, D, E, F, G, H, I, K, L, M, P, Q, R, S, T, V, W, Y

S476: A, C, D, E, F, G, H, I, K, L, M, N, P, Q, R, T, V, W, Y

Example 26

Altered Properties of Variants Described in Example 25

This example shows that *G. stearothermophilus* alpha-amylase (AmyS) variants (described in Example 25) may have an altered property relative to the parent α-amylase. A high throughput thermal stability screen of AmyS variants was carried out as described in Example 3. Performance indices for activity (measured as BODIPY assay) and residual activity (after thermal stress) are shown in Tables 26-1, 26-2, 26-3.

TABLE 26-1

Positions in AmyS protein with mutations (shown in column labeled variant) that have performance indices for both activity and residual activity after heat stress better than wildtype AmyS.

| Variant | Activity | Residual Activity |
| --- | --- | --- |
| 006A | 1.59 | 1.10 |
| 006D | 1.64 | 1.14 |
| 006E | 1.93 | 1.08 |
| 006I | 1.47 | 1.23 |
| 006L | 1.61 | 1.15 |
| 006M | 1.60 | 1.11 |
| 006N | 1.61 | 1.21 |
| 006P | 2.47 | 1.10 |
| 006Q | 1.34 | 1.26 |
| 006S | 1.86 | 1.12 |
| 006T | 2.01 | 1.21 |
| 006V | 1.54 | 1.29 |
| 006W | 1.32 | 1.13 |
| 006Y | 1.88 | 1.07 |
| 014F | 1.25 | 1.06 |
| 014T | 1.22 | 1.22 |
| 014Y | 1.71 | 1.08 |
| 015A | 1.48 | 1.05 |
| 015H | 1.85 | 1.01 |
| 016E | 1.21 | 1.09 |
| 025C | 1.46 | 1.33 |
| 025D | 1.03 | 1.06 |
| 025H | 1.06 | 1.03 |
| 025Q | 1.07 | 1.24 |
| 027N | 1.00 | 1.06 |
| 036K | 1.05 | 1.01 |
| 036M | 1.05 | 1.05 |
| 039C | 1.05 | 1.09 |
| 039D | 1.47 | 1.15 |
| 039E | 1.32 | 1.15 |
| 039G | 1.05 | 1.23 |
| 039H | 1.10 | 1.16 |
| 039K | 1.10 | 1.12 |
| 039N | 1.64 | 1.14 |
| 039Q | 1.43 | 1.20 |
| 039R | 1.10 | 1.01 |
| 039S | 1.02 | 1.15 |
| 050G | 1.18 | 1.00 |
| 050N | 1.12 | 1.20 |
| 050Q | 1.08 | 1.31 |
| 050S | 1.09 | 1.07 |
| 052M | 1.00 | 1.01 |

TABLE 26-1-continued

Positions in AmyS protein with mutations (shown in column labeled variant) that have performance indices for both activity and residual activity after heat stress better than wildtype AmyS.

| Variant | Activity | Residual Activity |
|---|---|---|
| 052T | 1.00 | 1.11 |
| 053A | 1.00 | 1.03 |
| 053H | 1.00 | 1.12 |
| 053K | 1.10 | 1.03 |
| 053T | 1.02 | 1.25 |
| 067G | 1.13 | 1.01 |
| 067H | 1.03 | 1.04 |
| 071R | 1.10 | 1.10 |
| 075A | 1.14 | 1.05 |
| 075M | 1.04 | 1.04 |
| 085E | 1.02 | 1.09 |
| 085M | 1.04 | 1.01 |
| 085S | 1.04 | 1.02 |
| 090H | 1.03 | 1.05 |
| 090M | 1.02 | 1.02 |
| 113L | 1.08 | 1.08 |
| 133P | 1.08 | 1.41 |
| 138P | 1.15 | 1.07 |
| 138S | 1.02 | 1.12 |
| 138T | 1.05 | 1.16 |
| 139Y | 1.63 | 1.14 |
| 141M | 1.01 | 1.23 |
| 141N | 1.02 | 1.11 |
| 143G | 1.09 | 1.13 |
| 143V | 1.01 | 1.00 |
| 150M | 1.00 | 1.05 |
| 160N | 1.02 | 1.11 |
| 165N | 1.10 | 1.16 |
| 172A | 1.06 | 1.14 |
| 172R | 1.06 | 1.16 |
| 173K | 1.03 | 1.17 |
| 188P | 1.16 | 1.40 |
| 193K | 1.17 | 1.28 |
| 193Y | 1.10 | 1.89 |
| 201H | 1.44 | 1.06 |
| 201M | 1.21 | 1.16 |
| 213Q | 1.02 | 1.12 |
| 213R | 1.05 | 1.05 |
| 213S | 1.08 | 1.10 |
| 216E | 1.30 | 1.03 |
| 216Q | 1.34 | 1.04 |
| 221F | 1.28 | 1.07 |
| 221I | 1.23 | 1.33 |
| 221M | 1.35 | 1.16 |
| 221N | 1.57 | 1.11 |
| 221S | 1.40 | 1.34 |
| 221V | 1.31 | 1.13 |
| 221Y | 1.36 | 1.14 |
| 227A | 1.02 | 1.01 |
| 227D | 1.06 | 1.01 |
| 227E | 1.06 | 1.03 |
| 227G | 1.09 | 1.05 |
| 227K | 1.13 | 1.00 |
| 235R | 1.14 | 1.03 |
| 246E | 1.03 | 1.18 |
| 249K | 1.02 | 1.15 |
| 249R | 1.03 | 1.07 |
| 250C | 1.12 | 1.03 |
| 250E | 1.33 | 1.13 |
| 250F | 1.28 | 1.29 |
| 250G | 1.33 | 1.09 |
| 250I | 1.27 | 1.35 |
| 250K | 1.48 | 1.07 |
| 250L | 1.32 | 1.02 |
| 250M | 1.39 | 1.35 |
| 250N | 1.40 | 1.05 |
| 250Q | 1.54 | 1.01 |
| 250S | 1.41 | 1.02 |
| 252A | 1.08 | 1.12 |
| 252E | 1.12 | 1.09 |
| 252K | 1.21 | 1.19 |
| 252Q | 1.04 | 1.16 |
| 252S | 1.01 | 1.04 |
| 253D | 1.04 | 1.07 |
| 253K | 1.01 | 1.10 |
| 253N | 1.03 | 1.06 |
| 258D | 1.10 | 1.33 |
| 258G | 1.02 | 1.30 |
| 258H | 1.13 | 1.38 |
| 258K | 1.11 | 1.29 |
| 258N | 1.01 | 1.07 |
| 258Q | 1.13 | 1.31 |
| 258R | 1.13 | 1.02 |
| 258S | 1.08 | 1.12 |
| 258T | 1.10 | 1.27 |
| 258Y | 1.08 | 1.16 |
| 268F | 1.07 | 1.28 |
| 268G | 1.21 | 1.03 |
| 268S | 1.22 | 1.06 |
| 274Y | 1.07 | 1.05 |
| 283K | 1.01 | 1.14 |
| 283S | 1.06 | 1.02 |
| 283Y | 1.04 | 1.01 |
| 285F | 1.02 | 1.18 |
| 285Q | 1.22 | 1.38 |
| 285W | 1.08 | 1.13 |
| 293H | 1.05 | 1.12 |
| 293K | 1.41 | 1.42 |
| 293Q | 1.06 | 1.14 |
| 293T | 1.12 | 1.10 |
| 297R | 1.14 | 1.03 |
| 301G | 1.05 | 1.02 |
| 301K | 1.05 | 1.08 |
| 309K | 1.08 | 1.18 |
| 309R | 1.08 | 1.12 |
| 312A | 1.00 | 1.01 |
| 312G | 1.07 | 1.18 |
| 313R | 1.13 | 1.19 |
| 313S | 1.05 | 1.25 |
| 318H | 1.10 | 1.12 |
| 318S | 1.37 | 1.11 |
| 318T | 1.32 | 1.40 |
| 318Y | 1.33 | 1.10 |
| 319A | 1.13 | 1.02 |
| 319G | 1.03 | 1.14 |
| 319K | 1.52 | 1.10 |
| 319R | 1.44 | 1.18 |
| 319V | 1.08 | 1.07 |
| 319W | 1.08 | 1.05 |
| 319Y | 1.41 | 1.04 |
| 320S | 1.03 | 1.16 |
| 320T | 1.28 | 1.11 |
| 320Y | 1.03 | 1.05 |
| 338A | 1.29 | 1.36 |
| 338G | 1.34 | 1.38 |
| 338I | 1.32 | 1.12 |
| 338M | 1.27 | 1.20 |
| 338P | 1.23 | 1.11 |
| 338S | 1.51 | 1.13 |
| 338T | 1.05 | 1.42 |
| 338V | 1.55 | 1.14 |
| 339A | 1.13 | 1.08 |
| 339G | 1.21 | 1.17 |
| 339H | 1.04 | 1.03 |
| 339K | 1.13 | 1.26 |
| 339P | 1.24 | 1.02 |
| 339S | 1.02 | 1.02 |
| 339T | 1.01 | 1.35 |
| 340A | 1.43 | 1.23 |
| 340H | 1.45 | 1.12 |
| 340I | 1.07 | 1.07 |
| 340M | 1.20 | 1.24 |
| 340N | 1.75 | 1.10 |
| 340Q | 1.76 | 1.21 |
| 340T | 1.14 | 1.21 |
| 343E | 1.07 | 1.00 |

TABLE 26-1-continued

Positions in AmyS protein with mutations (shown in column labeled variant) that have performance indices for both activity and residual activity after heat stress better than wildtype AmyS.

| Variant | Activity | Residual Activity |
|---|---|---|
| 343P | 1.03 | 1.30 |
| 343Q | 1.01 | 1.14 |
| 343R | 1.03 | 1.25 |
| 345D | 1.15 | 1.10 |
| 345E | 1.24 | 1.06 |
| 345H | 1.10 | 1.15 |
| 345M | 1.01 | 1.02 |
| 345N | 1.10 | 1.07 |
| 345Q | 1.10 | 1.26 |
| 345S | 1.12 | 1.01 |
| 345T | 1.15 | 1.15 |
| 345V | 1.02 | 1.16 |
| 366H | 1.12 | 1.07 |
| 366Q | 1.49 | 1.03 |
| 366S | 1.02 | 1.07 |
| 369M | 1.02 | 1.06 |
| 370A | 1.21 | 1.03 |
| 370G | 1.18 | 1.21 |
| 370N | 1.41 | 1.04 |
| 370S | 1.50 | 1.06 |
| 370T | 1.10 | 1.07 |
| 370V | 1.13 | 1.05 |
| 375A | 1.39 | 1.03 |
| 375L | 1.07 | 1.03 |
| 375T | 1.04 | 1.25 |
| 379A | 1.02 | 1.01 |
| 385Q | 1.01 | 1.02 |
| 392K | 1.09 | 1.10 |
| 394K | 1.07 | 1.09 |
| 394L | 1.11 | 1.22 |
| 394Q | 1.13 | 1.09 |
| 394S | 1.15 | 1.11 |
| 394W | 1.16 | 1.11 |
| 402T | 1.02 | 1.32 |
| 403R | 1.01 | 1.36 |
| 403V | 1.00 | 1.34 |
| 413A | 1.06 | 1.02 |
| 419A | 1.29 | 1.36 |
| 419I | 1.32 | 1.12 |
| 419M | 1.27 | 1.20 |
| 419P | 1.23 | 1.11 |
| 419S | 1.51 | 1.13 |
| 419T | 1.05 | 1.42 |
| 419V | 1.55 | 1.14 |
| 422N | 1.03 | 1.12 |
| 433A | 1.08 | 1.27 |
| 433K | 1.05 | 1.27 |
| 433M | 1.01 | 1.23 |
| 433Y | 1.01 | 1.26 |
| 442G | 1.02 | 1.23 |
| 442H | 1.04 | 1.07 |
| 442N | 1.03 | 1.39 |
| 442P | 1.03 | 1.11 |
| 442Q | 1.05 | 1.11 |
| 442R | 1.01 | 1.33 |
| 442S | 1.07 | 1.24 |
| 442T | 1.06 | 1.34 |
| 442Y | 1.08 | 1.24 |
| 445G | 1.01 | 1.21 |
| 447A | 1.06 | 1.09 |
| 447L | 1.01 | 1.06 |
| 448D | 1.02 | 1.15 |
| 448F | 1.01 | 1.48 |
| 448G | 1.05 | 1.26 |
| 448H | 1.03 | 1.37 |
| 448K | 1.07 | 1.20 |
| 448L | 1.08 | 1.04 |
| 448Q | 1.16 | 1.18 |
| 448S | 1.10 | 1.20 |
| 448Y | 1.27 | 1.33 |
| 450R | 1.02 | 1.22 |
| 450S | 1.01 | 1.22 |
| 452A | 1.06 | 1.08 |
| 452G | 1.00 | 1.07 |
| 452K | 1.08 | 1.11 |
| 452M | 1.09 | 1.13 |
| 452N | 1.28 | 1.06 |
| 452T | 1.18 | 1.02 |
| 452V | 1.14 | 1.14 |
| 452Y | 1.07 | 1.17 |
| 455A | 1.04 | 1.07 |
| 455G | 1.00 | 1.23 |
| 455H | 1.01 | 1.05 |
| 455K | 1.08 | 1.10 |
| 455R | 1.02 | 1.13 |
| 463A | 1.06 | 1.25 |
| 463G | 1.00 | 1.04 |
| 463L | 1.01 | 1.16 |
| 463M | 1.08 | 1.24 |
| 469A | 1.01 | 1.16 |
| 469D | 1.02 | 1.22 |
| 469F | 1.00 | 1.11 |
| 469Q | 1.04 | 1.03 |
| 469T | 1.06 | 1.15 |
| 469V | 1.08 | 1.15 |
| 469Y | 1.09 | 1.35 |
| 471A | 1.09 | 1.09 |
| 471D | 1.06 | 1.01 |
| 471F | 1.05 | 1.10 |
| 471G | 1.12 | 1.13 |
| 471I | 1.02 | 1.22 |
| 471N | 1.12 | 1.04 |
| 471T | 1.09 | 1.11 |
| 471V | 1.11 | 1.28 |
| 471Y | 1.36 | 1.15 |
| 473K | 1.02 | 1.02 |
| 473M | 1.00 | 1.11 |
| 473R | 1.05 | 1.08 |
| 473T | 1.04 | 1.04 |
| 476A | 1.02 | 1.51 |
| 476M | 1.08 | 1.58 |
| 476Q | 1.03 | 1.13 |
| 476R | 1.08 | 1.01 |
| 476T | 1.01 | 1.78 |

TABLE 26-2

Positions in AmyS protein with mutations (shown in column labeled variant) that have performance indices for residual activity after heat stress at least 20% better than wildtype AmyS and performance indices for starting activity or expression at least half of wildtype AmyS.

| Variant | Activity | Residual Activity |
|---|---|---|
| 006I | 1.47 | 1.23 |
| 006N | 1.61 | 1.21 |
| 006Q | 1.34 | 1.26 |
| 006T | 2.01 | 1.21 |
| 006V | 1.54 | 1.29 |
| 014T | 1.22 | 1.22 |
| 016F | 0.98 | 2.17 |
| 025A | 0.82 | 1.22 |
| 025C | 1.46 | 1.33 |
| 025G | 0.97 | 1.27 |
| 025Q | 1.07 | 1.24 |
| 027M | 0.88 | 1.21 |
| 036Q | 0.78 | 1.40 |
| 036S | 0.69 | 1.25 |
| 039G | 1.05 | 1.23 |
| 039V | 0.82 | 1.30 |
| 050I | 0.61 | 1.24 |
| 050L | 0.67 | 1.22 |

TABLE 26-2-continued

Positions in AmyS protein with mutations (shown in column labeled variant) that have performance indices for residual activity after heat stress at least 20% better than wildtype AmyS and performance indices for starting activity or expression at least half of wildtype AmyS.

| Variant | Activity | Residual Activity |
|---|---|---|
| 050M | 0.62 | 1.32 |
| 050N | 1.12 | 1.20 |
| 050Q | 1.08 | 1.31 |
| 052S | 0.92 | 1.21 |
| 053T | 1.02 | 1.25 |
| 067N | 0.95 | 1.32 |
| 067S | 1.00 | 1.23 |
| 080D | 0.86 | 1.22 |
| 080I | 0.82 | 1.29 |
| 090E | 0.92 | 1.20 |
| 133P | 1.08 | 1.41 |
| 133V | 0.92 | 1.25 |
| 137M | 0.83 | 1.30 |
| 137S | 0.98 | 1.45 |
| 141E | 0.92 | 3.48 |
| 141I | 0.87 | 1.40 |
| 141L | 0.85 | 1.22 |
| 141M | 1.01 | 1.23 |
| 141Q | 0.97 | 1.28 |
| 141R | 0.99 | 1.23 |
| 141S | 0.98 | 1.21 |
| 141V | 1.00 | 1.21 |
| 150E | 0.87 | 4.54 |
| 151I | 0.78 | 1.22 |
| 152G | 0.91 | 1.25 |
| 155S | 0.85 | 1.22 |
| 155Y | 0.80 | 1.21 |
| 168W | 0.66 | 1.23 |
| 173T | 0.86 | 1.33 |
| 188P | 1.16 | 1.40 |
| 193F | 0.98 | 1.71 |
| 193K | 1.17 | 1.28 |
| 193L | 0.78 | 1.22 |
| 193Y | 1.10 | 1.89 |
| 213L | 0.75 | 1.26 |
| 213M | 0.78 | 1.26 |
| 213V | 0.76 | 1.35 |
| 217Q | 0.74 | 1.31 |
| 220P | 0.89 | 1.33 |
| 220Q | 0.87 | 1.21 |
| 220R | 0.83 | 1.26 |
| 220S | 0.81 | 1.30 |
| 220V | 0.82 | 1.21 |
| 221I | 1.23 | 1.33 |
| 221S | 1.40 | 1.34 |
| 249E | 0.92 | 1.27 |
| 250F | 1.28 | 1.29 |
| 250I | 1.27 | 1.35 |
| 250M | 1.39 | 1.35 |
| 252L | 0.96 | 1.32 |
| 253Y | 0.94 | 1.34 |
| 254E | 0.89 | 1.29 |
| 254F | 0.74 | 1.23 |
| 254T | 0.65 | 1.21 |
| 254V | 0.92 | 1.31 |
| 255F | 0.68 | 1.30 |
| 255K | 0.83 | 1.27 |
| 255W | 0.74 | 1.27 |
| 257L | 0.74 | 1.26 |
| 257M | 0.79 | 1.29 |
| 257S | 0.71 | 1.29 |
| 257V | 0.78 | 1.31 |
| 258D | 1.10 | 1.33 |
| 258G | 1.02 | 1.30 |
| 258H | 1.13 | 1.38 |
| 258K | 1.11 | 1.29 |
| 258Q | 1.13 | 1.31 |
| 258T | 1.10 | 1.27 |
| 258V | 0.80 | 1.29 |
| 268F | 1.07 | 1.28 |
| 274W | 0.79 | 1.26 |
| 283M | 0.93 | 1.26 |
| 283N | 0.96 | 1.29 |
| 283V | 0.81 | 1.23 |
| 285E | 0.89 | 1.33 |
| 285Q | 1.22 | 1.38 |
| 293G | 0.92 | 1.31 |
| 293K | 1.41 | 1.42 |
| 294W | 0.66 | 1.23 |
| 301F | 0.68 | 1.44 |
| 301I | 0.74 | 1.28 |
| 301P | 0.61 | 1.21 |
| 301R | 0.89 | 1.35 |
| 301T | 0.85 | 1.23 |
| 301W | 0.75 | 1.27 |
| 309D | 0.89 | 1.27 |
| 309V | 0.95 | 1.38 |
| 312H | 0.99 | 1.30 |
| 312S | 0.99 | 1.29 |
| 312V | 0.87 | 1.40 |
| 312Y | 0.92 | 1.31 |
| 313G | 0.96 | 1.25 |
| 313H | 0.94 | 1.25 |
| 313I | 0.55 | 1.44 |
| 313L | 0.85 | 1.21 |
| 313S | 1.05 | 1.25 |
| 313V | 0.74 | 1.28 |
| 318T | 1.32 | 1.40 |
| 338A | 1.29 | 1.36 |
| 338C | 0.67 | 1.24 |
| 338G | 1.34 | 1.38 |
| 338M | 1.27 | 1.20 |
| 338T | 1.05 | 1.42 |
| 339K | 1.13 | 1.26 |
| 339T | 1.01 | 1.35 |
| 339V | 0.76 | 1.23 |
| 340A | 1.43 | 1.23 |
| 340M | 1.20 | 1.24 |
| 340Q | 1.76 | 1.21 |
| 340T | 1.14 | 1.21 |
| 343C | 0.74 | 1.32 |
| 343I | 0.88 | 1.27 |
| 343P | 1.03 | 1.30 |
| 343R | 1.03 | 1.25 |
| 343Y | 0.82 | 1.29 |
| 345I | 0.90 | 1.28 |
| 345Q | 1.10 | 1.26 |
| 369I | 0.91 | 1.33 |
| 369T | 0.68 | 1.28 |
| 370G | 1.18 | 1.21 |
| 375T | 1.04 | 1.25 |
| 385T | 0.92 | 1.22 |
| 386K | 0.87 | 1.22 |
| 394L | 1.11 | 1.22 |
| 394V | 0.75 | 3.00 |
| 400A | 0.89 | 1.24 |
| 400N | 0.92 | 1.26 |
| 400V | 0.91 | 1.28 |
| 402H | 0.91 | 1.21 |
| 402I | 0.75 | 1.36 |
| 402T | 1.02 | 1.32 |
| 402V | 0.95 | 1.40 |
| 402W | 0.89 | 1.24 |
| 403A | 0.89 | 1.20 |
| 403E | 0.93 | 1.26 |
| 403G | 0.96 | 1.22 |
| 403Q | 0.98 | 1.24 |
| 403R | 1.01 | 1.36 |
| 403T | 0.99 | 1.53 |
| 403V | 1.00 | 1.34 |
| 404C | 0.61 | 1.28 |
| 404E | 0.78 | 1.38 |
| 404G | 0.77 | 1.25 |
| 404I | 0.84 | 1.20 |

TABLE 26-2-continued

Positions in AmyS protein with mutations (shown in column labeled variant) that have performance indices for residual activity after heat stress at least 20% better than wildtype AmyS and performance indices for starting activity or expression at least half of wildtype AmyS.

| Variant | Activity | Residual Activity |
|---|---|---|
| 404V | 0.79 | 1.28 |
| 419A | 1.29 | 1.36 |
| 419C | 0.67 | 1.24 |
| 419M | 1.27 | 1.20 |
| 419T | 1.05 | 1.42 |
| 422E | 0.78 | 1.31 |
| 422G | 0.99 | 1.20 |
| 433A | 1.08 | 1.27 |
| 433H | 0.99 | 1.27 |
| 433I | 0.86 | 1.37 |
| 433K | 1.05 | 1.27 |
| 433L | 0.90 | 1.30 |
| 433M | 1.01 | 1.23 |
| 433V | 0.95 | 1.27 |
| 433Y | 1.01 | 1.26 |
| 442A | 0.98 | 1.38 |
| 442G | 1.02 | 1.23 |
| 442N | 1.03 | 1.39 |
| 442R | 1.01 | 1.33 |
| 442S | 1.07 | 1.24 |
| 442T | 1.06 | 1.34 |
| 442V | 0.99 | 1.20 |
| 442W | 0.98 | 1.32 |
| 442Y | 1.08 | 1.24 |
| 445G | 1.01 | 1.21 |
| 445I | 0.84 | 1.25 |
| 445N | 0.91 | 1.20 |
| 445T | 0.88 | 1.29 |
| 445V | 0.93 | 1.27 |
| 445W | 0.80 | 1.25 |
| 447I | 0.91 | 1.22 |
| 447N | 0.97 | 1.43 |
| 447Q | 1.00 | 1.34 |
| 447W | 0.89 | 1.31 |
| 447Y | 0.96 | 1.21 |
| 448C | 0.98 | 1.36 |
| 448F | 1.01 | 1.48 |
| 448G | 1.05 | 1.26 |
| 448H | 1.03 | 1.37 |
| 448I | 0.97 | 1.44 |
| 448N | 0.70 | 1.24 |
| 448Y | 1.27 | 1.33 |
| 450C | 0.84 | 1.22 |
| 450H | 0.90 | 1.23 |
| 450M | 0.89 | 1.29 |
| 450N | 0.96 | 1.23 |
| 450R | 1.02 | 1.22 |
| 450S | 1.01 | 1.22 |
| 450T | 0.96 | 1.32 |
| 450W | 0.95 | 1.21 |
| 455G | 1.00 | 1.23 |
| 455I | 0.95 | 1.23 |
| 455P | 0.93 | 1.36 |
| 455V | 0.89 | 1.26 |
| 463A | 1.06 | 1.25 |
| 463M | 1.08 | 1.24 |
| 463S | 0.96 | 1.27 |
| 463T | 0.91 | 1.38 |
| 463V | 0.86 | 1.32 |
| 463W | 0.74 | 1.45 |
| 465G | 0.92 | 1.35 |
| 465I | 0.85 | 1.37 |
| 465K | 0.88 | 1.53 |
| 465N | 0.93 | 1.32 |
| 465T | 0.92 | 1.42 |
| 465V | 0.93 | 1.24 |
| 469D | 1.02 | 1.22 |
| 469W | 0.97 | 1.24 |
| 469Y | 1.09 | 1.35 |
| 471I | 1.02 | 1.22 |
| 471V | 1.11 | 1.28 |
| 473G | 0.99 | 1.35 |
| 473Y | 0.86 | 1.23 |
| 476A | 1.02 | 1.51 |
| 476G | 0.97 | 1.22 |
| 476L | 0.93 | 1.46 |
| 476M | 1.08 | 1.58 |
| 476N | 0.98 | 1.61 |
| 476T | 1.01 | 1.78 |

TABLE 26-3

Positions in AmyS protein with mutations (shown in column labeled variant) that have performance indices for activity or expression at least 20% greater than wildtype AmyS

| Variant | Activity |
|---|---|
| 006A | 1.59 |
| 006D | 1.64 |
| 006E | 1.93 |
| 006H | 2.29 |
| 006I | 1.47 |
| 006K | 2.36 |
| 006L | 1.61 |
| 006M | 1.60 |
| 006N | 1.61 |
| 006P | 2.47 |
| 006Q | 1.34 |
| 006R | 1.28 |
| 006S | 1.86 |
| 006T | 2.01 |
| 006V | 1.54 |
| 006W | 1.32 |
| 006Y | 1.88 |
| 013K | 1.22 |
| 014F | 1.25 |
| 014T | 1.22 |
| 014Y | 1.71 |
| 015A | 1.48 |
| 015D | 1.82 |
| 015E | 1.96 |
| 015G | 1.89 |
| 015H | 1.85 |
| 015K | 1.58 |
| 015N | 1.88 |
| 015P | 1.59 |
| 015Q | 1.74 |
| 015R | 1.60 |
| 015S | 1.78 |
| 015T | 1.47 |
| 015W | 1.44 |
| 016A | 1.31 |
| 016E | 1.21 |
| 016G | 1.35 |
| 016H | 1.21 |
| 016K | 1.41 |
| 016N | 1.32 |
| 016P | 1.30 |
| 016Q | 1.33 |
| 016R | 1.28 |
| 016T | 1.32 |
| 025C | 1.46 |
| 039D | 1.47 |
| 039E | 1.32 |
| 039N | 1.64 |
| 039Q | 1.43 |
| 081Y | 1.20 |
| 121P | 1.22 |
| 139D | 1.40 |
| 139H | 1.59 |

TABLE 26-3-continued

Positions in AmyS protein with mutations (shown in column labeled variant) that have performance indices for activity or expression at least 20% greater than wildtype AmyS

| Variant | Activity |
| --- | --- |
| 139R | 1.29 |
| 139Y | 1.63 |
| 177A | 1.20 |
| 188D | 1.21 |
| 191H | 1.27 |
| 191K | 1.33 |
| 192A | 1.26 |
| 192D | 1.50 |
| 192G | 1.38 |
| 192N | 1.35 |
| 192P | 1.33 |
| 192Q | 1.55 |
| 192S | 1.47 |
| 192T | 1.35 |
| 192V | 1.25 |
| 192Y | 1.30 |
| 196A | 1.57 |
| 196C | 1.36 |
| 196D | 1.29 |
| 196E | 1.29 |
| 196F | 1.38 |
| 196H | 1.92 |
| 196I | 1.61 |
| 196K | 1.29 |
| 196P | 1.50 |
| 196R | 1.29 |
| 196S | 1.59 |
| 196T | 1.65 |
| 196V | 1.55 |
| 201A | 1.41 |
| 201E | 1.36 |
| 201G | 1.63 |
| 201H | 1.44 |
| 201M | 1.21 |
| 202H | 1.30 |
| 216E | 1.30 |
| 216G | 1.20 |
| 216H | 1.28 |
| 216M | 1.39 |
| 216Q | 1.34 |
| 216R | 1.32 |
| 216S | 1.28 |
| 216T | 1.22 |
| 216Y | 1.31 |
| 221A | 1.54 |
| 221D | 1.31 |
| 221F | 1.28 |
| 221I | 1.23 |
| 221L | 1.50 |
| 221M | 1.35 |
| 221N | 1.57 |
| 221R | 1.29 |
| 221S | 1.40 |
| 221V | 1.31 |
| 221Y | 1.36 |
| 237G | 1.21 |
| 240G | 1.22 |
| 240N | 1.37 |
| 240P | 1.69 |
| 240Q | 1.21 |
| 240R | 1.41 |
| 240T | 1.23 |
| 246R | 1.31 |
| 250A | 1.21 |
| 250D | 1.29 |
| 250E | 1.33 |
| 250F | 1.28 |
| 250G | 1.33 |
| 250I | 1.27 |
| 250K | 1.48 |
| 250L | 1.32 |
| 250M | 1.39 |
| 250N | 1.40 |
| 250Q | 1.54 |
| 250R | 1.55 |
| 250S | 1.41 |
| 250W | 1.35 |
| 252K | 1.21 |
| 268A | 1.39 |
| 268D | 1.44 |
| 268E | 1.47 |
| 268G | 1.21 |
| 268H | 1.24 |
| 268K | 1.90 |
| 268N | 1.51 |
| 268P | 1.41 |
| 268Q | 1.30 |
| 268R | 1.49 |
| 268S | 1.22 |
| 274A | 1.40 |
| 274D | 1.20 |
| 274G | 1.36 |
| 274I | 1.39 |
| 274K | 1.60 |
| 274L | 1.40 |
| 274N | 1.50 |
| 274Q | 1.47 |
| 274R | 1.50 |
| 274S | 1.28 |
| 274T | 1.38 |
| 275K | 1.22 |
| 285Q | 1.22 |
| 285Y | 1.49 |
| 293K | 1.41 |
| 293R | 1.37 |
| 318A | 1.38 |
| 318F | 1.22 |
| 318G | 1.39 |
| 318I | 1.40 |
| 318K | 1.73 |
| 318L | 1.31 |
| 318M | 1.26 |
| 318R | 1.54 |
| 318S | 1.37 |
| 318T | 1.32 |
| 318V | 1.34 |
| 318Y | 1.33 |
| 319C | 1.38 |
| 319D | 1.31 |
| 319H | 1.28 |
| 319I | 1.32 |
| 319K | 1.52 |
| 319R | 1.44 |
| 319Y | 1.41 |
| 320K | 1.23 |
| 320R | 1.25 |
| 320T | 1.28 |
| 338A | 1.29 |
| 338G | 1.34 |
| 338I | 1.32 |
| 338M | 1.27 |
| 338P | 1.23 |
| 338S | 1.51 |
| 338V | 1.55 |
| 339G | 1.21 |
| 339P | 1.24 |
| 340A | 1.43 |
| 340D | 1.63 |
| 340E | 1.58 |
| 340H | 1.45 |
| 340K | 1.76 |
| 340N | 1.75 |
| 340Q | 1.76 |
| 345E | 1.24 |
| 363D | 1.74 |
| 363E | 1.34 |
| 363M | 1.36 |
| 363N | 1.86 |

TABLE 26-3-continued

Positions in AmyS protein with mutations (shown in column labeled variant) that have performance indices for activity or expression at least 20% greater than wildtype AmyS

| Variant | Activity |
|---|---|
| 363Q | 1.78 |
| 363S | 1.35 |
| 366Q | 1.49 |
| 370A | 1.21 |
| 370D | 1.35 |
| 370E | 1.35 |
| 370H | 1.36 |
| 370K | 1.65 |
| 370N | 1.41 |
| 370Q | 1.51 |
| 370S | 1.50 |
| 375A | 1.39 |
| 375D | 1.52 |
| 375E | 1.48 |
| 375K | 1.43 |
| 375N | 1.48 |
| 375Q | 1.56 |
| 375R | 1.61 |
| 375S | 1.29 |
| 419A | 1.29 |
| 419I | 1.32 |
| 419M | 1.27 |
| 419P | 1.23 |
| 419S | 1.51 |
| 419V | 1.55 |
| 448Y | 1.27 |
| 452N | 1.28 |
| 452Q | 1.22 |
| 452R | 1.26 |
| 452S | 1.21 |
| 471R | 1.33 |
| 471Y | 1.36 |

Table 26-4 shows the Performance index values (Pi) for 2,666 variants of AmyS at 152 positions. Performance indices less than or equal to 0.05 in the activity assay were fixed to 0.05 and indicated in bold italics in the Table 26-4. Also, for the stability measure, if the Performance index of activity in the stability assays was less than or equal to 0.05, the associated stability performance index was fixed to 0.05.

TABLE 26-4

Performance Indicies for stability and activity measurements for AmyS variants

| Position | Variant | Stability PI | Activity PI |
|---|---|---|---|
| 5 | N005A | 0.95 | 0.32 |
| 5 | N005C | 0.98 | 0.29 |
| 5 | N005E | 1.04 | 0.43 |
| 5 | N005F | 0.79 | 0.15 |
| 5 | N005G | 0.88 | 0.34 |
| 5 | N005H | 0.89 | 0.43 |
| 5 | N005I | 1.00 | 0.10 |
| 5 | N005K | 0.90 | 0.34 |
| 5 | N005L | 1.04 | 0.10 |
| 5 | N005M | 0.84 | 0.18 |
| 5 | N005P | 1.10 | 0.40 |
| 5 | N005Q | 1.07 | 0.58 |
| 5 | N005R | 0.94 | 0.40 |
| 5 | N005S | 0.98 | 0.35 |
| 5 | N005T | 0.83 | 0.35 |
| 5 | N005V | 0.88 | 0.16 |
| 5 | N005W | 0.94 | 0.07 |
| 5 | N005Y | 1.07 | 0.21 |
| 6 | G006A | 1.10 | 1.59 |
| 6 | G006D | 1.14 | 1.64 |
| 6 | G006E | 1.08 | 1.93 |
| 6 | G006H | 0.95 | 2.29 |
| 6 | G006I | 1.23 | 1.47 |
| 6 | G006K | 0.93 | 2.36 |
| 6 | G006L | 1.15 | 1.61 |
| 6 | G006M | 1.11 | 1.60 |
| 6 | G006N | 1.21 | 1.61 |
| 6 | G006P | 1.10 | 2.47 |
| 6 | G006Q | 1.26 | 1.34 |
| 6 | G006R | 0.98 | 1.28 |
| 6 | G006S | 1.12 | 1.86 |
| 6 | G006T | 1.21 | 2.01 |
| 6 | G006V | 1.29 | 1.54 |
| 6 | G006W | 1.13 | 1.32 |
| 6 | G006Y | 1.07 | 1.88 |
| 13 | E013A | 0.32 | 1.01 |
| 13 | E013C | 0.22 | 0.68 |
| 13 | E013D | 0.08 | 1.03 |
| 13 | E013F | *0.05* | 0.81 |
| 13 | E013G | 0.18 | 1.00 |
| 13 | E013H | 0.60 | 1.10 |
| 13 | E013I | 0.15 | 0.87 |
| 13 | E013K | 0.22 | 1.22 |
| 13 | E013L | 0.20 | 1.02 |
| 13 | E013M | 0.20 | 0.96 |
| 13 | E013N | *0.05* | *0.05* |
| 13 | E013P | *0.05* | 0.37 |
| 13 | E013Q | 0.21 | 0.96 |
| 13 | E013R | 0.28 | 1.04 |
| 13 | E013S | 0.28 | 0.92 |
| 13 | E013T | 0.19 | 0.79 |
| 13 | E013V | 0.19 | 0.76 |
| 13 | E013W | *0.05* | 0.76 |
| 13 | E013Y | 0.89 | 0.93 |
| 14 | W014A | 0.95 | 0.77 |
| 14 | W014C | 0.91 | 0.71 |
| 14 | W014D | 0.81 | 0.59 |
| 14 | W014E | 0.95 | 1.07 |
| 14 | W014F | 1.06 | 1.25 |
| 14 | W014G | 0.97 | 0.88 |
| 14 | W014H | *0.05* | *0.05* |
| 14 | W014I | 1.12 | 0.40 |
| 14 | W014K | 1.01 | 0.69 |
| 14 | W014L | 0.88 | 0.15 |
| 14 | W014M | 1.18 | 0.84 |
| 14 | W014N | 0.92 | 0.99 |
| 14 | W014P | 0.84 | 0.98 |
| 14 | W014Q | 0.94 | 0.67 |
| 14 | W014R | 0.97 | 0.67 |
| 14 | W014S | 0.97 | 1.02 |
| 14 | W014T | 1.22 | 1.22 |
| 14 | W014V | 1.17 | 0.81 |
| 14 | W014Y | 1.08 | 1.71 |
| 15 | Y015A | 1.05 | 1.48 |
| 15 | Y015C | 0.70 | 1.15 |
| 15 | Y015D | 0.77 | 1.82 |
| 15 | Y015E | 0.68 | 1.96 |
| 15 | Y015G | 0.69 | 1.89 |
| 15 | Y015H | 1.01 | 1.85 |
| 15 | Y015I | 0.63 | 0.91 |
| 15 | Y015K | 0.74 | 1.58 |
| 15 | Y015L | 0.67 | 0.76 |
| 15 | Y015M | 0.72 | 1.12 |
| 15 | Y015N | 0.99 | 1.88 |
| 15 | Y015P | 0.57 | 1.59 |
| 15 | Y015Q | 0.80 | 1.74 |
| 15 | Y015R | 0.72 | 1.60 |
| 15 | Y015S | 0.58 | 1.78 |
| 15 | Y015T | 0.87 | 1.47 |
| 15 | Y015W | 0.95 | 1.44 |
| 16 | L016A | 0.81 | 1.31 |
| 16 | L016D | 0.93 | 1.12 |
| 16 | L016E | 1.09 | 1.21 |
| 16 | L016F | 2.17 | 0.98 |
| 16 | L016G | 0.61 | 1.35 |
| 16 | L016H | 0.96 | 1.21 |

TABLE 26-4-continued

Performance Indicies for stability and activity measurements for AmyS variants

| Position | Variant | Stability PI | Activity PI |
|---|---|---|---|
| 16 | L016I | 0.79 | 1.12 |
| 16 | L016K | 0.79 | 1.41 |
| 16 | L016M | 0.94 | 1.15 |
| 16 | L016N | 0.92 | 1.32 |
| 16 | L016P | 0.35 | 1.30 |
| 16 | L016Q | 0.96 | 1.33 |
| 16 | L016R | 0.71 | 1.28 |
| 16 | L016S | 0.94 | 1.19 |
| 16 | L016T | 0.87 | 1.32 |
| 16 | L016V | 0.87 | 1.16 |
| 16 | L016W | 0.75 | 0.99 |
| 16 | L016Y | 0.97 | 1.10 |
| 18 | D018A | 1.08 | 0.89 |
| 18 | D018F | 0.68 | 0.58 |
| 18 | D018G | 0.88 | 0.87 |
| 18 | D018H | 0.84 | 0.84 |
| 18 | D018I | 0.79 | 0.70 |
| 18 | D018K | 0.88 | 0.65 |
| 18 | D018L | 0.60 | 0.72 |
| 18 | D018N | 0.73 | 1.01 |
| 18 | D018P | 0.84 | 1.04 |
| 18 | D018Q | 0.80 | 1.00 |
| 18 | D018R | 0.81 | 0.65 |
| 18 | D018S | 0.81 | 0.93 |
| 18 | D018T | 0.81 | 0.91 |
| 18 | D018V | 0.89 | 0.77 |
| 18 | D018W | 0.72 | 0.51 |
| 18 | D018Y | 0.72 | 0.87 |
| 20 | G020A | 0.79 | 0.25 |
| 20 | G020C | 0.58 | 0.24 |
| 20 | G020D | 0.92 | 0.96 |
| 20 | G020E | 0.89 | 0.95 |
| 20 | G020F | 0.65 | 0.13 |
| 20 | G020H | 0.75 | 0.11 |
| 20 | G020I | 0.96 | 0.28 |
| 20 | G020K | *0.05* | *0.05* |
| 20 | G020L | *0.05* | *0.05* |
| 20 | G020M | 0.69 | 0.10 |
| 20 | G020N | 0.78 | 0.09 |
| 20 | G020P | *0.05* | *0.05* |
| 20 | G020Q | 0.61 | 0.07 |
| 20 | G020R | *0.05* | *0.05* |
| 20 | G020S | *0.05* | *0.05* |
| 20 | G020T | 0.82 | 0.09 |
| 20 | G020V | 0.77 | 0.19 |
| 20 | G020W | 0.80 | 0.69 |
| 20 | G020Y | *0.05* | *0.05* |
| 25 | K025A | 1.22 | 0.82 |
| 25 | K025C | 1.33 | 1.46 |
| 25 | K025D | 1.06 | 1.03 |
| 25 | K025E | 1.07 | 0.95 |
| 25 | K025F | 1.00 | 0.58 |
| 25 | K025G | 1.27 | 0.97 |
| 25 | K025H | 1.03 | 1.06 |
| 25 | K025L | 1.12 | 0.64 |
| 25 | K025M | 1.03 | 0.61 |
| 25 | K025N | 0.91 | 1.06 |
| 25 | K025P | 0.98 | 0.55 |
| 25 | K025Q | 1.24 | 1.07 |
| 25 | K025R | 1.08 | 0.96 |
| 25 | K025S | 1.07 | 0.98 |
| 25 | K025T | 1.14 | 0.89 |
| 25 | K025Y | 0.98 | 0.65 |
| 27 | A027C | 0.79 | 0.55 |
| 27 | A027D | 1.01 | 0.95 |
| 27 | A027E | 0.93 | 0.95 |
| 27 | A027F | 0.88 | 0.85 |
| 27 | A027G | 1.20 | 0.98 |
| 27 | A027H | 1.05 | 1.00 |
| 27 | A027I | 1.05 | 0.87 |
| 27 | A027K | 0.86 | 1.01 |
| 27 | A027L | 1.06 | 0.86 |
| 27 | A027M | 1.21 | 0.88 |
| 27 | A027N | 1.06 | 1.00 |
| 27 | A027P | 1.13 | 0.43 |
| 27 | A027Q | 1.00 | 0.96 |
| 27 | A027R | 1.11 | 0.89 |
| 27 | A027S | 1.16 | 0.97 |
| 27 | A027T | 1.20 | 0.90 |
| 27 | A027V | 1.20 | 0.82 |
| 27 | A027W | 1.13 | 0.76 |
| 27 | A027Y | 0.97 | 0.28 |
| 29 | E029A | 1.05 | 0.50 |
| 29 | E029D | 0.94 | 1.11 |
| 29 | E029G | 0.75 | 0.37 |
| 29 | E029H | 0.83 | 0.83 |
| 29 | E029K | 1.05 | 0.89 |
| 29 | E029L | 0.76 | 0.22 |
| 29 | E029M | 0.76 | 0.15 |
| 29 | E029N | 1.02 | 0.89 |
| 29 | E029P | 0.87 | 0.33 |
| 29 | E029Q | 1.04 | 0.86 |
| 29 | E029R | 1.09 | 0.92 |
| 29 | E029S | 0.97 | 0.83 |
| 29 | E029T | 0.95 | 0.59 |
| 29 | E029W | 0.74 | 0.10 |
| 29 | E029Y | *0.05* | *0.05* |
| 36 | L036A | 0.95 | 0.85 |
| 36 | L036C | 0.83 | 0.43 |
| 36 | L036D | 0.91 | 0.27 |
| 36 | L036E | 0.90 | 0.40 |
| 36 | L036F | 1.14 | 0.90 |
| 36 | L036G | 0.92 | 0.34 |
| 36 | L036H | 0.92 | 0.77 |
| 36 | L036I | 1.17 | 0.89 |
| 36 | L036K | 1.01 | 1.05 |
| 36 | L036M | 1.05 | 1.05 |
| 36 | L036N | 1.02 | 0.68 |
| 36 | L036P | 0.90 | 0.06 |
| 36 | L036Q | 1.40 | 0.78 |
| 36 | L036R | 1.12 | 0.76 |
| 36 | L036S | 1.25 | 0.69 |
| 36 | L036T | 1.11 | 0.64 |
| 36 | L036V | 0.88 | 0.97 |
| 36 | L036W | 0.92 | 0.63 |
| 36 | L036Y | 1.07 | 0.91 |
| 39 | T039C | 1.09 | 1.05 |
| 39 | T039D | 1.15 | 1.47 |
| 39 | T039E | 1.15 | 1.32 |
| 39 | T039F | 1.16 | 0.48 |
| 39 | T039G | 1.23 | 1.05 |
| 39 | T039H | 1.16 | 1.10 |
| 39 | T039K | 1.12 | 1.10 |
| 39 | T039M | 1.18 | 0.54 |
| 39 | T039N | 1.14 | 1.64 |
| 39 | T039P | 1.11 | 0.26 |
| 39 | T039Q | 1.20 | 1.43 |
| 39 | T039R | 1.01 | 1.10 |
| 39 | T039S | 1.15 | 1.02 |
| 39 | T039V | 1.30 | 0.82 |
| 39 | T039W | 1.11 | 0.25 |
| 50 | T050A | 1.09 | 0.98 |
| 50 | T050C | 1.03 | 0.34 |
| 50 | T050D | 0.87 | 0.91 |
| 50 | T050E | *0.05* | *0.05* |
| 50 | T050F | 0.86 | 0.43 |
| 50 | T050G | 1.00 | 1.18 |
| 50 | T050H | 0.97 | 0.82 |
| 50 | T050I | 1.24 | 0.61 |
| 50 | T050K | 1.13 | 0.80 |
| 50 | T050L | 1.22 | 0.67 |
| 50 | T050M | 1.32 | 0.62 |
| 50 | T050N | 1.20 | 1.12 |
| 50 | T050P | 1.03 | 0.99 |
| 50 | T050Q | 1.31 | 1.08 |
| 50 | T050R | 1.13 | 0.79 |
| 50 | T050S | 1.07 | 1.09 |
| 50 | T050V | 1.02 | 0.79 |

TABLE 26-4-continued

Performance Indicies for stability and activity measurements for AmyS variants

| Position | Variant | Stability PI | Activity PI |
|---|---|---|---|
| 50 | T050W | 0.90 | 0.18 |
| 50 | T050Y | 1.14 | 0.42 |
| 52 | R052A | 0.99 | 1.02 |
| 52 | R052C | 0.87 | 0.62 |
| 52 | R052D | 0.76 | 0.85 |
| 52 | R052E | 0.77 | 0.97 |
| 52 | R052G | 0.96 | 0.93 |
| 52 | R052H | 0.91 | 0.99 |
| 52 | R052K | 0.93 | 1.02 |
| 52 | R052L | 1.10 | 0.98 |
| 52 | R052M | 1.01 | 1.00 |
| 52 | R052N | 0.95 | 0.99 |
| 52 | R052P | 1.05 | 0.95 |
| 52 | R052Q | *0.05* | *0.05* |
| 52 | R052S | 1.21 | 0.92 |
| 52 | R052T | 1.11 | 1.00 |
| 52 | R052V | 1.14 | 0.95 |
| 52 | R052W | 1.00 | 0.83 |
| 52 | R052Y | 0.99 | 0.96 |
| 53 | S053A | 1.03 | 1.00 |
| 53 | S053C | 0.73 | 0.58 |
| 53 | S053D | 0.75 | 0.83 |
| 53 | S053E | 1.05 | 0.88 |
| 53 | S053F | 0.87 | 0.85 |
| 53 | S053G | 1.14 | 0.93 |
| 53 | S053H | 1.12 | 1.00 |
| 53 | S053I | 0.99 | 1.12 |
| 53 | S053K | 1.03 | 1.10 |
| 53 | S053L | 0.93 | 0.96 |
| 53 | S053M | 0.96 | 0.97 |
| 53 | S053P | 0.88 | 1.00 |
| 53 | S053Q | 0.94 | 0.94 |
| 53 | S053R | 0.83 | 1.15 |
| 53 | S053T | 1.25 | 1.02 |
| 53 | S053V | 1.11 | 0.94 |
| 53 | S053W | 1.09 | 0.84 |
| 53 | S053Y | 0.94 | 0.93 |
| 54 | D054A | 0.34 | 0.88 |
| 54 | D054C | 0.64 | 0.38 |
| 54 | D054E | *0.05* | *0.05* |
| 54 | D054F | *0.05* | 0.60 |
| 54 | D054G | 0.11 | 0.97 |
| 54 | D054H | 0.11 | 1.04 |
| 54 | D054I | 0.30 | 0.83 |
| 54 | D054K | *0.05* | 1.08 |
| 54 | D054L | *0.05* | 0.89 |
| 54 | D054M | 0.11 | 0.88 |
| 54 | D054N | 0.94 | 1.05 |
| 54 | D054P | *0.05* | 1.03 |
| 54 | D054Q | *0.05* | *0.05* |
| 54 | D054R | 0.06 | 0.89 |
| 54 | D054S | 0.38 | 0.96 |
| 54 | D054T | 0.17 | 0.95 |
| 54 | D054V | 0.17 | 0.77 |
| 54 | D054W | *0.05* | *0.05* |
| 54 | D054Y | *0.05* | 0.64 |
| 67 | E067A | *0.05* | *0.05* |
| 67 | E067C | 1.08 | 0.75 |
| 67 | E067D | 0.90 | 1.07 |
| 67 | E067G | 1.01 | 1.13 |
| 67 | E067H | 1.04 | 1.03 |
| 67 | E067K | 0.98 | 0.94 |
| 67 | E067L | 0.97 | 0.95 |
| 67 | E067M | 0.93 | 0.91 |
| 67 | E067N | 1.32 | 0.95 |
| 67 | E067P | *0.05* | *0.05* |
| 67 | E067Q | 0.93 | 0.95 |
| 67 | E067R | 1.01 | 0.90 |
| 67 | E067S | 1.23 | 1.00 |
| 67 | E067T | 0.99 | 0.98 |
| 67 | E067W | *0.05* | *0.05* |
| 67 | E067Y | 1.11 | 0.93 |
| 71 | K071A | 0.72 | 0.81 |
| 71 | K071C | 0.80 | 0.61 |
| 71 | K071D | 0.69 | 0.71 |
| 71 | K071E | 0.80 | 0.84 |
| 71 | K071F | 0.47 | 0.61 |
| 71 | K071G | 0.74 | 0.91 |
| 71 | K071H | 0.96 | 0.88 |
| 71 | K071I | 0.83 | 0.75 |
| 71 | K071L | 0.55 | 0.61 |
| 71 | K071M | 0.80 | 0.68 |
| 71 | K071N | 1.11 | 0.89 |
| 71 | K071P | 0.92 | 0.86 |
| 71 | K071Q | 0.98 | 0.77 |
| 71 | K071R | 1.10 | 1.10 |
| 71 | K071S | 0.99 | 0.97 |
| 71 | K071T | 0.95 | 0.83 |
| 71 | K071V | 0.94 | 0.84 |
| 71 | K071W | 0.82 | 0.91 |
| 71 | K071Y | 0.52 | 0.71 |
| 73 | T073A | 0.97 | 1.11 |
| 73 | T073C | 0.91 | 0.60 |
| 73 | T073D | 0.89 | 1.02 |
| 73 | T073E | 0.75 | 1.08 |
| 73 | T073F | 0.73 | 0.99 |
| 73 | T073G | 0.79 | 1.12 |
| 73 | T073H | 0.86 | 0.88 |
| 73 | T073I | 0.66 | 1.02 |
| 73 | T073K | 0.20 | 0.97 |
| 73 | T073L | 0.47 | 1.17 |
| 73 | T073M | 0.59 | 0.64 |
| 73 | T073N | 0.73 | 1.08 |
| 73 | T073P | 0.57 | 0.98 |
| 73 | T073R | 0.40 | 1.11 |
| 73 | T073S | 0.87 | 1.10 |
| 73 | T073V | 0.67 | 1.09 |
| 73 | T073W | 0.83 | 1.07 |
| 73 | T073Y | 0.79 | 1.10 |
| 75 | R075A | 1.05 | 1.14 |
| 75 | R075C | 0.88 | 0.85 |
| 75 | R075D | 0.87 | 0.99 |
| 75 | R075E | 0.86 | 1.01 |
| 75 | R075F | 0.76 | 0.92 |
| 75 | R075G | 0.79 | 1.04 |
| 75 | R075H | 0.85 | 1.07 |
| 75 | R075I | 0.86 | 1.01 |
| 75 | R075L | 0.88 | 1.04 |
| 75 | R075M | 1.04 | 1.04 |
| 75 | R075P | 0.90 | 0.93 |
| 75 | R075Q | 0.90 | 0.95 |
| 75 | R075S | 0.66 | 0.60 |
| 75 | R075T | 0.98 | 0.88 |
| 75 | R075V | 0.78 | 0.94 |
| 75 | R075W | 0.75 | 0.93 |
| 75 | R075Y | 0.68 | 1.04 |
| 77 | K077A | 0.38 | 0.98 |
| 77 | K077C | 0.28 | 0.51 |
| 77 | K077D | *0.05* | 0.59 |
| 77 | K077E | 0.11 | 0.77 |
| 77 | K077F | 0.20 | 0.72 |
| 77 | K077G | 0.13 | 0.76 |
| 77 | K077I | 0.16 | 1.00 |
| 77 | K077L | 0.54 | 0.98 |
| 77 | K077M | 0.58 | 0.99 |
| 77 | K077N | *0.05* | *0.05* |
| 77 | K077P | *0.05* | 0.61 |
| 77 | K077Q | 0.07 | 0.86 |
| 77 | K077R | 0.77 | 1.07 |
| 77 | K077S | 0.11 | 0.89 |
| 77 | K077T | *0.05* | 0.86 |
| 77 | K077V | *0.05* | 0.83 |
| 77 | K077W | *0.05* | 0.77 |
| 80 | T080A | 0.88 | 1.01 |
| 80 | T080C | 0.91 | 0.69 |
| 80 | T080D | 1.22 | 0.86 |
| 80 | T080E | 0.71 | 0.92 |
| 80 | T080F | 1.10 | 0.50 |

TABLE 26-4-continued

Performance Indicies for stability and activity measurements for AmyS variants

| Position | Variant | Stability PI | Activity PI |
|---|---|---|---|
| 80 | T080G | 1.02 | 0.93 |
| 80 | T080H | 1.01 | 0.95 |
| 80 | T080I | 1.29 | 0.82 |
| 80 | T080K | 0.90 | 0.86 |
| 80 | T080L | 0.82 | 0.98 |
| 80 | T080M | 0.97 | 0.95 |
| 80 | T080N | 0.90 | 1.00 |
| 80 | T080P | 0.88 | 0.88 |
| 80 | T080Q | 0.87 | 0.88 |
| 80 | T080R | 0.99 | 0.76 |
| 80 | T080S | 0.83 | 1.09 |
| 80 | T080V | 0.87 | 0.87 |
| 80 | T080W | 0.77 | 0.89 |
| 80 | T080Y | 0.72 | 0.97 |
| 81 | K081A | 0.87 | 0.94 |
| 81 | K081C | 0.84 | 0.74 |
| 81 | K081D | 0.96 | 0.83 |
| 81 | K081E | 0.69 | 0.92 |
| 81 | K081G | 0.86 | 0.81 |
| 81 | K081H | 0.73 | 1.03 |
| 81 | K081I | 0.82 | 0.79 |
| 81 | K081L | 0.87 | 1.01 |
| 81 | K081M | 0.93 | 1.04 |
| 81 | K081N | *0.05* | *0.05* |
| 81 | K081P | 0.90 | 0.79 |
| 81 | K081Q | 0.84 | 1.03 |
| 81 | K081R | 0.90 | 1.04 |
| 81 | K081S | 0.74 | 0.98 |
| 81 | K081T | 0.80 | 0.93 |
| 81 | K081V | 0.66 | 1.03 |
| 81 | K081W | 0.60 | 0.98 |
| 81 | K081Y | 0.89 | 1.20 |
| 83 | Q083A | 1.20 | 0.98 |
| 83 | Q083C | 1.79 | 0.17 |
| 83 | Q083D | 0.94 | 0.92 |
| 83 | Q083E | 0.98 | 0.95 |
| 83 | Q083F | 0.87 | 0.80 |
| 83 | Q083G | 0.76 | 1.01 |
| 83 | Q083H | 0.78 | 0.86 |
| 83 | Q083I | 0.69 | 0.85 |
| 83 | Q083L | 0.77 | 0.91 |
| 83 | Q083M | 0.91 | 0.96 |
| 83 | Q083P | 1.01 | 0.82 |
| 83 | Q083R | 0.91 | 0.90 |
| 83 | Q083S | 0.75 | 0.99 |
| 83 | Q083T | 0.84 | 0.84 |
| 83 | Q083V | 0.73 | 0.80 |
| 83 | Q083W | 0.82 | 0.78 |
| 83 | Q083Y | 0.71 | 0.93 |
| 85 | L085A | 0.94 | 1.06 |
| 85 | L085C | 0.90 | 0.63 |
| 85 | L085D | 0.84 | 1.04 |
| 85 | L085E | 1.09 | 1.02 |
| 85 | L085G | 0.85 | 0.90 |
| 85 | L085H | 0.73 | 1.02 |
| 85 | L085I | 0.89 | 0.88 |
| 85 | L085K | 0.96 | 0.93 |
| 85 | L085M | 1.01 | 1.04 |
| 85 | L085N | 1.10 | 0.89 |
| 85 | L085P | 1.01 | 0.72 |
| 85 | L085Q | 0.91 | 0.99 |
| 85 | L085R | 0.96 | 1.01 |
| 85 | L085S | 1.02 | 1.04 |
| 85 | L085T | 0.83 | 1.12 |
| 85 | L085W | 0.93 | 0.95 |
| 85 | L085Y | 0.70 | 1.08 |
| 90 | A090C | 1.00 | 0.65 |
| 90 | A090D | 1.12 | 0.92 |
| 90 | A090E | 1.20 | 0.92 |
| 90 | A090F | 0.99 | 0.76 |
| 90 | A090G | 1.04 | 0.87 |
| 90 | A090H | 1.05 | 1.03 |
| 90 | A090I | 0.90 | 0.83 |
| 90 | A090K | 0.93 | 1.04 |
| 90 | A090L | 0.76 | 0.92 |
| 90 | A090M | 1.02 | 1.02 |
| 90 | A090N | 1.02 | 0.98 |
| 90 | A090P | 1.39 | 0.10 |
| 90 | A090Q | 0.94 | 0.93 |
| 90 | A090R | 0.90 | 0.90 |
| 90 | A090S | 1.16 | 0.99 |
| 90 | A090T | 0.78 | 0.88 |
| 90 | A090V | 0.79 | 0.87 |
| 90 | A090W | 0.69 | 0.84 |
| 90 | A090Y | 0.83 | 0.96 |
| 92 | H092C | 0.75 | 0.29 |
| 92 | H092D | 1.06 | 0.69 |
| 92 | H092E | 0.88 | 0.76 |
| 92 | H092F | 0.92 | 0.28 |
| 92 | H092G | 0.86 | 0.81 |
| 92 | H092K | 0.89 | 0.98 |
| 92 | H092L | 0.43 | 0.12 |
| 92 | H092N | 0.85 | 0.78 |
| 92 | H092P | *0.05* | *0.05* |
| 92 | H092Q | 0.80 | 0.89 |
| 92 | H092R | 0.75 | 0.96 |
| 92 | H092S | 0.70 | 0.87 |
| 92 | H092T | 0.68 | 0.47 |
| 92 | H092V | 0.70 | 0.28 |
| 92 | H092W | 0.83 | 0.44 |
| 92 | H092Y | 0.71 | 0.63 |
| 106 | H106A | 0.32 | 0.19 |
| 106 | H106C | 0.33 | 0.06 |
| 106 | H106D | 0.58 | 0.07 |
| 106 | H106E | *0.05* | *0.05* |
| 106 | H106G | 0.16 | 0.17 |
| 106 | H106I | *0.05* | *0.05* |
| 106 | H106K | *0.05* | *0.05* |
| 106 | H106L | *0.05* | 0.06 |
| 106 | H106N | 0.14 | 0.08 |
| 106 | H106P | 0.59 | 0.06 |
| 106 | H106Q | 0.07 | 0.39 |
| 106 | H106R | *0.05* | *0.05* |
| 106 | H106S | *0.05* | 0.20 |
| 106 | H106T | *0.05* | *0.05* |
| 106 | H106V | *0.05* | *0.05* |
| 106 | H106W | *0.05* | *0.05* |
| 106 | H106Y | *0.05* | *0.05* |
| 107 | K107A | 0.46 | 0.81 |
| 107 | K107C | 0.42 | 0.67 |
| 107 | K107D | 0.32 | 0.51 |
| 107 | K107E | 0.35 | 0.70 |
| 107 | K107F | 0.42 | 0.66 |
| 107 | K107G | 0.23 | 0.76 |
| 107 | K107H | 0.34 | 0.94 |
| 107 | K107I | 0.29 | 0.69 |
| 107 | K107L | 0.53 | 0.75 |
| 107 | K107M | 0.60 | 0.79 |
| 107 | K107N | 0.43 | 0.88 |
| 107 | K107P | *0.05* | 0.65 |
| 107 | K107Q | 0.63 | 0.74 |
| 107 | K107R | 1.05 | 0.71 |
| 107 | K107S | 0.30 | 0.78 |
| 107 | K107T | 0.38 | 0.72 |
| 107 | K107V | 0.41 | 0.70 |
| 107 | K107W | *0.05* | 0.44 |
| 107 | K107Y | 0.40 | 0.64 |
| 111 | D111A | 0.55 | 0.95 |
| 111 | D111C | 0.71 | 0.60 |
| 111 | D111E | 0.87 | 1.01 |
| 111 | D111F | 0.63 | 0.65 |
| 111 | D111G | 0.74 | 0.90 |
| 111 | D111H | 0.50 | 0.85 |
| 111 | D111I | 0.56 | 0.91 |
| 111 | D111K | 0.45 | 0.62 |
| 111 | D111L | 0.44 | 0.86 |
| 111 | D111M | 0.65 | 1.00 |
| 111 | D111N | 0.97 | 0.87 |

TABLE 26-4-continued

Performance Indicies for stability and activity measurements for AmyS variants

| Position | Variant | Stability PI | Activity PI |
|---|---|---|---|
| 111 | D111P | 0.78 | 0.71 |
| 111 | D111Q | 0.77 | 0.95 |
| 111 | D111R | 0.53 | 0.07 |
| 111 | D111S | 0.67 | 0.91 |
| 111 | D111T | 0.61 | 1.02 |
| 111 | D111V | 0.58 | 1.02 |
| 111 | D111W | 0.42 | 0.54 |
| 111 | D111Y | 0.49 | 0.92 |
| 113 | T113A | 0.89 | 0.97 |
| 113 | T113C | 0.80 | 0.82 |
| 113 | T113D | 0.94 | 0.95 |
| 113 | T113E | 0.92 | 0.91 |
| 113 | T113F | 0.76 | 0.92 |
| 113 | T113G | 0.88 | 1.08 |
| 113 | T113H | 0.88 | 0.96 |
| 113 | T113I | 1.14 | 0.88 |
| 113 | T113K | 0.93 | 1.13 |
| 113 | T113L | 1.08 | 1.08 |
| 113 | T113M | 0.83 | 0.99 |
| 113 | T113P | 1.05 | 0.96 |
| 113 | T113Q | 0.88 | 1.05 |
| 113 | T113R | 0.88 | 1.03 |
| 113 | T113V | 1.12 | 0.94 |
| 113 | T113W | 1.06 | 0.88 |
| 114 | E114A | 0.54 | 0.97 |
| 114 | E114C | 0.62 | 0.76 |
| 114 | E114D | 0.71 | 0.82 |
| 114 | E114F | 0.36 | 0.92 |
| 114 | E114G | 0.59 | 1.01 |
| 114 | E114H | 0.49 | 0.92 |
| 114 | E114I | 0.54 | 0.86 |
| 114 | E114L | 0.43 | 0.97 |
| 114 | E114M | 0.77 | 0.97 |
| 114 | E114N | 0.67 | 0.88 |
| 114 | E114P | 0.37 | 0.37 |
| 114 | E114R | 0.35 | 0.84 |
| 114 | E114T | 0.54 | 0.94 |
| 114 | E114V | 0.43 | 0.85 |
| 114 | E114W | 0.31 | 0.94 |
| 114 | E114Y | 0.26 | 0.93 |
| 120 | E120A | 0.29 | 1.20 |
| 120 | E120C | 0.24 | 0.89 |
| 120 | E120D | *0.05* | 1.02 |
| 120 | E120F | *0.05* | 0.88 |
| 120 | E120G | *0.05* | 1.14 |
| 120 | E120H | 0.09 | 0.90 |
| 120 | E120I | 0.60 | 0.87 |
| 120 | E120L | 0.20 | 0.97 |
| 120 | E120M | 0.39 | 0.96 |
| 120 | E120N | 0.16 | 1.02 |
| 120 | E120P | *0.05* | 1.12 |
| 120 | E120Q | 0.66 | 1.10 |
| 120 | E120R | 0.12 | 1.12 |
| 120 | E120S | 0.08 | 1.07 |
| 120 | E120T | 0.22 | 1.06 |
| 120 | E120V | 0.53 | 0.93 |
| 120 | E120W | 0.15 | 0.81 |
| 120 | E120Y | 0.07 | 0.98 |
| 121 | V121A | *0.05* | 1.04 |
| 121 | V121C | 0.92 | 0.55 |
| 121 | V121D | *0.05* | 0.91 |
| 121 | V121E | *0.05* | 0.93 |
| 121 | V121F | *0.05* | 0.77 |
| 121 | V121G | *0.05* | 0.92 |
| 121 | V121H | *0.05* | *0.05* |
| 121 | V121I | *0.05* | 0.79 |
| 121 | V121L | *0.05* | 0.98 |
| 121 | V121M | *0.05* | 0.97 |
| 121 | V121P | *0.05* | 1.22 |
| 121 | V121Q | *0.05* | 0.97 |
| 121 | V121R | *0.05* | 1.01 |
| 121 | V121S | *0.05* | 0.95 |
| 121 | V121T | 0.07 | 0.92 |
| 121 | V121W | *0.05* | 0.62 |
| 121 | V121Y | *0.05* | 0.88 |
| 126 | R126A | *0.05* | *0.05* |
| 126 | R126D | *0.05* | 0.46 |
| 126 | R126E | *0.05* | 0.82 |
| 126 | R126F | *0.05* | 1.03 |
| 126 | R126G | *0.05* | 0.89 |
| 126 | R126H | *0.05* | 1.06 |
| 126 | R126I | *0.05* | 0.95 |
| 126 | R126L | *0.05* | 0.97 |
| 126 | R126M | *0.05* | 1.01 |
| 126 | R126N | *0.05* | 1.07 |
| 126 | R126P | *0.05* | 0.67 |
| 126 | R126Q | *0.05* | 0.65 |
| 126 | R126T | *0.05* | 0.83 |
| 126 | R126V | *0.05* | 0.99 |
| 126 | R126W | *0.05* | 1.06 |
| 126 | R126Y | *0.05* | 1.01 |
| 128 | Q128A | *0.05* | *0.05* |
| 128 | Q128C | 0.42 | 0.95 |
| 128 | Q128D | 0.15 | 1.05 |
| 128 | Q128E | 0.90 | 1.00 |
| 128 | Q128G | *0.05* | 0.99 |
| 128 | Q128H | 0.34 | 1.05 |
| 128 | Q128I | 0.90 | 0.89 |
| 128 | Q128K | 0.52 | 1.15 |
| 128 | Q128L | 0.47 | 0.97 |
| 128 | Q128N | 0.12 | 1.05 |
| 128 | Q128P | *0.05* | 1.03 |
| 128 | Q128R | 0.31 | 1.14 |
| 128 | Q128S | 0.28 | 1.02 |
| 128 | Q128T | *0.05* | *0.05* |
| 128 | Q128V | 0.86 | 0.97 |
| 128 | Q128W | 0.07 | 0.76 |
| 128 | Q128Y | 0.13 | 0.86 |
| 131 | S131A | *0.05* | 1.15 |
| 131 | S131C | *0.05* | 0.98 |
| 131 | S131D | 0.26 | 1.08 |
| 131 | S131E | *0.05* | 1.14 |
| 131 | S131F | *0.05* | 0.92 |
| 131 | S131G | 0.24 | 0.86 |
| 131 | S131H | *0.05* | 1.13 |
| 131 | S131I | *0.05* | *0.05* |
| 131 | S131K | *0.05* | 1.13 |
| 131 | S131M | *0.05* | 0.99 |
| 131 | S131N | 0.76 | 1.02 |
| 131 | S131P | *0.05* | 1.05 |
| 131 | S131R | *0.05* | 1.05 |
| 131 | S131T | 0.49 | 0.90 |
| 131 | S131W | *0.05* | 0.82 |
| 131 | S131Y | *0.05* | 0.90 |
| 133 | T133A | 0.95 | 1.13 |
| 133 | T133C | 0.49 | 0.97 |
| 133 | T133D | 1.03 | 0.99 |
| 133 | T133E | 0.82 | 1.02 |
| 133 | T133F | 0.17 | 0.97 |
| 133 | T133G | 0.47 | 0.84 |
| 133 | T133H | 0.41 | 1.19 |
| 133 | T133I | 0.86 | 0.96 |
| 133 | T133K | 0.47 | 0.85 |
| 133 | T133L | 0.41 | 1.06 |
| 133 | T133M | 0.51 | 1.05 |
| 133 | T133N | 0.68 | 1.13 |
| 133 | T133P | 1.41 | 1.08 |
| 133 | T133Q | 0.63 | 1.10 |
| 133 | T133R | 0.18 | 1.13 |
| 133 | T133S | 0.72 | 1.08 |
| 133 | T133V | 1.25 | 0.92 |
| 133 | T133W | 0.14 | 0.98 |
| 133 | T133Y | 0.41 | 1.01 |
| 137 | Q137A | 0.92 | 0.97 |
| 137 | Q137C | 1.09 | 0.77 |
| 137 | Q137D | 0.89 | 0.96 |
| 137 | Q137E | 1.06 | 0.87 |
| 137 | Q137F | 0.85 | 0.86 |

TABLE 26-4-continued

Performance Indicies for stability and activity measurements for AmyS variants

| Position | Variant | Stability PI | Activity PI |
|---|---|---|---|
| 137 | Q137G | 1.13 | 0.94 |
| 137 | Q137H | 0.95 | 1.05 |
| 137 | Q137I | 0.93 | 0.22 |
| 137 | Q137L | 1.20 | 0.82 |
| 137 | Q137M | 1.30 | 0.83 |
| 137 | Q137P | 0.07 | 1.05 |
| 137 | Q137R | 0.95 | 1.05 |
| 137 | Q137S | 1.45 | 0.98 |
| 137 | Q137T | 1.12 | 0.91 |
| 137 | Q137V | 1.02 | 0.86 |
| 137 | Q137W | 1.06 | 0.88 |
| 137 | Q137Y | 0.94 | 0.89 |
| 138 | A138C | *0.05* | *0.05* |
| 138 | A138D | *0.05* | 0.37 |
| 138 | A138E | *0.05* | 0.54 |
| 138 | A138G | 0.90 | 1.02 |
| 138 | A138H | *0.05* | 0.60 |
| 138 | A138I | 0.23 | 0.90 |
| 138 | A138K | *0.05* | 0.15 |
| 138 | A138L | *0.05* | 0.90 |
| 138 | A138M | *0.05* | 0.94 |
| 138 | A138N | 0.50 | 0.94 |
| 138 | A138P | 1.07 | 1.15 |
| 138 | A138Q | 0.13 | 0.69 |
| 138 | A138R | *0.05* | 0.15 |
| 138 | A138S | 1.12 | 1.02 |
| 138 | A138T | 1.16 | 1.05 |
| 138 | A138V | 1.17 | 0.87 |
| 138 | A138W | *0.05* | 0.27 |
| 138 | A138Y | 0.14 | 0.97 |
| 139 | W139A | 0.82 | 0.89 |
| 139 | W139C | 0.75 | 0.39 |
| 139 | W139D | 0.93 | 1.40 |
| 139 | W139E | 0.81 | 0.97 |
| 139 | W139G | 0.79 | 0.74 |
| 139 | W139H | 0.97 | 1.59 |
| 139 | W139I | 0.74 | 0.58 |
| 139 | W139K | 0.68 | 0.42 |
| 139 | W139L | 0.78 | 0.59 |
| 139 | W139M | 0.87 | 1.00 |
| 139 | W139N | 1.13 | 0.85 |
| 139 | W139Q | 0.82 | 0.79 |
| 139 | W139R | 0.96 | 1.29 |
| 139 | W139S | 0.93 | 1.04 |
| 139 | W139T | 0.71 | 0.87 |
| 139 | W139V | 0.72 | 0.66 |
| 139 | W139Y | 1.14 | 1.63 |
| 141 | K141A | 1.09 | 0.73 |
| 141 | K141C | 1.03 | 0.85 |
| 141 | K141D | 0.89 | 0.98 |
| 141 | K141E | 3.48 | 0.92 |
| 141 | K141F | 0.89 | 0.80 |
| 141 | K141G | 1.18 | 0.96 |
| 141 | K141H | 1.13 | 0.99 |
| 141 | K141I | 1.40 | 0.87 |
| 141 | K141L | 1.22 | 0.85 |
| 141 | K141M | 1.23 | 1.01 |
| 141 | K141N | 1.11 | 1.02 |
| 141 | K141P | 1.07 | 0.96 |
| 141 | K141Q | 1.28 | 0.97 |
| 141 | K141R | 1.23 | 0.99 |
| 141 | K141S | 1.21 | 0.98 |
| 141 | K141T | 1.17 | 0.94 |
| 141 | K141V | 1.21 | 1.00 |
| 141 | K141W | 1.16 | 0.87 |
| 141 | K141Y | 1.17 | 0.88 |
| 143 | D143A | 0.95 | 1.04 |
| 143 | D143C | 1.11 | 0.84 |
| 143 | D143E | 1.12 | 0.98 |
| 143 | D143G | 1.13 | 1.09 |
| 143 | D143H | 0.91 | 0.98 |
| 143 | D143I | 1.05 | 0.94 |
| 143 | D143K | 0.86 | 0.96 |
| 143 | D143L | *0.05* | *0.05* |
| 143 | D143M | 0.86 | 1.05 |
| 143 | D143N | 1.10 | 0.99 |
| 143 | D143P | 0.98 | 0.84 |
| 143 | D143T | *0.05* | *0.05* |
| 143 | D143V | 1.00 | 1.01 |
| 143 | D143W | 1.00 | 0.99 |
| 143 | D143Y | 0.75 | 0.15 |
| 147 | R147A | 0.73 | 0.25 |
| 147 | R147C | *0.05* | *0.05* |
| 147 | R147D | 0.66 | 0.07 |
| 147 | R147E | *0.05* | *0.05* |
| 147 | R147F | *0.05* | *0.05* |
| 147 | R147G | 0.74 | 0.11 |
| 147 | R147H | 0.81 | 0.21 |
| 147 | R147I | *0.05* | *0.05* |
| 147 | R147K | 1.05 | 0.48 |
| 147 | R147L | *0.05* | *0.05* |
| 147 | R147M | 0.65 | 0.07 |
| 147 | R147N | 0.91 | 0.30 |
| 147 | R147P | *0.05* | *0.05* |
| 147 | R147Q | 0.88 | 0.30 |
| 147 | R147S | 0.90 | 0.39 |
| 147 | R147T | 0.90 | 0.10 |
| 147 | R147V | *0.05* | *0.05* |
| 147 | R147W | *0.05* | *0.05* |
| 147 | R147Y | *0.05* | *0.05* |
| 149 | N149A | 0.94 | 0.93 |
| 149 | N149D | 0.89 | 0.95 |
| 149 | N149E | 0.98 | 0.93 |
| 149 | N149F | 1.09 | 0.85 |
| 149 | N149G | 0.90 | 0.93 |
| 149 | N149H | 1.01 | 0.98 |
| 149 | N149I | 1.15 | 0.83 |
| 149 | N149K | 0.90 | 0.88 |
| 149 | N149L | 0.88 | 0.94 |
| 149 | N149M | *0.05* | *0.05* |
| 149 | N149Q | 1.00 | 0.93 |
| 149 | N149R | 0.80 | 0.95 |
| 149 | N149S | 0.94 | 1.03 |
| 149 | N149V | 1.06 | 0.87 |
| 149 | N149W | 1.01 | 0.87 |
| 150 | T150A | 0.90 | 0.96 |
| 150 | T150C | 1.03 | 0.72 |
| 150 | T150D | 0.82 | 0.87 |
| 150 | T150E | 4.54 | 0.87 |
| 150 | T150F | *0.05* | *0.05* |
| 150 | T150G | 0.99 | 0.86 |
| 150 | T150I | 0.82 | 0.93 |
| 150 | T150K | 0.86 | 0.96 |
| 150 | T150L | 0.83 | 0.07 |
| 150 | T150M | 1.05 | 1.00 |
| 150 | T150N | 0.98 | 1.08 |
| 150 | T150Q | 0.83 | 0.99 |
| 150 | T150R | 0.99 | 1.04 |
| 150 | T150S | 0.77 | 0.96 |
| 150 | T150V | 0.90 | 0.93 |
| 150 | T150Y | 1.18 | 1.00 |
| 151 | Y151A | 0.96 | 0.87 |
| 151 | Y151C | 0.80 | 0.67 |
| 151 | Y151D | 0.99 | 0.71 |
| 151 | Y151E | 0.76 | 0.71 |
| 151 | Y151F | 0.96 | 0.88 |
| 151 | Y151G | 1.17 | 0.79 |
| 151 | Y151H | 1.04 | 0.87 |
| 151 | Y151I | 1.22 | 0.78 |
| 151 | Y151L | 1.05 | 0.90 |
| 151 | Y151M | 1.02 | 0.83 |
| 151 | Y151N | 0.98 | 0.91 |
| 151 | Y151P | 0.89 | 0.77 |
| 151 | Y151Q | 1.07 | 0.75 |
| 151 | Y151R | 1.05 | 0.76 |
| 151 | Y151S | 0.85 | 0.80 |
| 151 | Y151T | 1.04 | 0.80 |
| 151 | Y151V | 1.14 | 0.80 |

TABLE 26-4-continued

Performance Indicies for stability and activity measurements for AmyS variants

| Position | Variant | Stability PI | Activity PI |
|---|---|---|---|
| 151 | Y151W | 1.16 | 0.79 |
| 152 | S152A | 0.95 | 0.88 |
| 152 | S152C | 0.83 | 0.75 |
| 152 | S152D | *0.05* | *0.05* |
| 152 | S152E | 1.09 | 0.71 |
| 152 | S152F | 0.75 | 0.22 |
| 152 | S152G | 1.25 | 0.91 |
| 152 | S152H | 0.99 | 0.71 |
| 152 | S152I | 0.81 | 0.22 |
| 152 | S152K | 0.74 | 0.58 |
| 152 | S152M | *0.05* | *0.05* |
| 152 | S152N | 1.20 | 0.43 |
| 152 | S152Q | 0.71 | 0.21 |
| 152 | S152R | 0.89 | 0.86 |
| 152 | S152T | 1.16 | 0.99 |
| 152 | S152V | 0.79 | 0.42 |
| 152 | S152W | 0.73 | 0.22 |
| 152 | S152Y | 0.91 | 0.26 |
| 155 | K155A | 1.10 | 0.85 |
| 155 | K155C | 0.92 | 0.72 |
| 155 | K155D | 0.94 | 0.85 |
| 155 | K155E | 0.82 | 0.79 |
| 155 | K155G | 1.05 | 0.58 |
| 155 | K155H | 1.04 | 0.84 |
| 155 | K155L | 1.05 | 0.89 |
| 155 | K155M | 0.91 | 0.91 |
| 155 | K155N | 1.18 | 0.90 |
| 155 | K155P | 0.99 | 0.94 |
| 155 | K155Q | 0.84 | 0.90 |
| 155 | K155R | 1.20 | 0.93 |
| 155 | K155S | 1.22 | 0.85 |
| 155 | K155T | 1.12 | 0.76 |
| 155 | K155V | 1.01 | 0.85 |
| 155 | K155W | 1.09 | 0.88 |
| 155 | K155Y | 1.21 | 0.80 |
| 160 | H160A | 0.89 | 0.89 |
| 160 | H160C | 0.84 | 0.98 |
| 160 | H160D | 0.89 | 0.69 |
| 160 | H160E | 0.86 | 0.52 |
| 160 | H160F | 0.77 | 0.79 |
| 160 | H160G | 0.82 | 0.36 |
| 160 | H160I | 0.36 | 0.58 |
| 160 | H160L | 1.03 | 0.92 |
| 160 | H160M | 0.56 | 0.97 |
| 160 | H160N | 1.11 | 1.02 |
| 160 | H160P | *0.05* | *0.05* |
| 160 | H160Q | 0.98 | 0.47 |
| 160 | H160R | 0.54 | 0.62 |
| 160 | H160S | *0.05* | *0.05* |
| 160 | H160T | 1.01 | 0.91 |
| 160 | H160V | 0.76 | 0.74 |
| 160 | H160W | 0.26 | 0.66 |
| 160 | H160Y | 0.86 | 0.89 |
| 165 | D165A | 0.53 | 0.12 |
| 165 | D165C | 1.01 | 0.07 |
| 165 | D165E | 1.14 | 0.07 |
| 165 | D165F | 0.09 | 0.07 |
| 165 | D165G | 0.63 | 0.20 |
| 165 | D165H | 0.46 | 0.18 |
| 165 | D165I | 0.06 | 0.15 |
| 165 | D165K | 0.07 | 0.14 |
| 165 | D165L | 0.30 | 0.11 |
| 165 | D165M | 0.58 | 0.10 |
| 165 | D165N | 1.16 | 1.10 |
| 165 | D165P | *0.05* | 0.50 |
| 165 | D165Q | 0.53 | 0.11 |
| 165 | D165R | 0.08 | 0.11 |
| 165 | D165S | 0.83 | 0.43 |
| 165 | D165T | *0.05* | 0.50 |
| 165 | D165V | *0.05* | 0.15 |
| 165 | D165W | *0.05* | *0.05* |
| 165 | D165Y | 0.31 | 0.07 |
| 168 | E168A | 0.83 | 0.92 |
| 168 | E168C | 0.83 | 0.50 |
| 168 | E168D | 0.82 | 0.57 |
| 168 | E168F | 0.69 | 0.59 |
| 168 | E168G | 0.92 | 0.75 |
| 168 | E168H | 0.84 | 0.90 |
| 168 | E168I | 1.08 | 0.71 |
| 168 | E168K | *0.05* | *0.05* |
| 168 | E168L | 0.80 | 0.92 |
| 168 | E168M | 1.12 | 0.80 |
| 168 | E168N | 0.97 | 0.83 |
| 168 | E168P | *0.05* | *0.05* |
| 168 | E168Q | 0.88 | 0.87 |
| 168 | E168R | 1.18 | 0.90 |
| 168 | E168S | 0.95 | 0.83 |
| 168 | E168T | 0.83 | 0.16 |
| 168 | E168V | 0.89 | 0.73 |
| 168 | E168W | 1.23 | 0.66 |
| 168 | E168Y | 0.76 | 0.82 |
| 172 | L172A | 1.14 | 1.06 |
| 172 | L172C | 1.07 | 0.89 |
| 172 | L172D | 0.83 | 0.91 |
| 172 | L172E | 0.97 | 1.01 |
| 172 | L172G | 0.50 | 0.60 |
| 172 | L172H | 0.93 | 1.06 |
| 172 | L172I | 0.97 | 0.90 |
| 172 | L172K | 0.98 | 1.12 |
| 172 | L172M | 0.86 | 0.91 |
| 172 | L172N | 0.91 | 0.96 |
| 172 | L172P | 0.17 | 0.83 |
| 172 | L172Q | 1.00 | 0.89 |
| 172 | L172R | 1.16 | 1.06 |
| 172 | L172S | 0.78 | 1.01 |
| 172 | L172T | 0.82 | 0.94 |
| 172 | L172V | 1.02 | 0.88 |
| 172 | L172W | 1.09 | 0.92 |
| 172 | L172Y | 1.06 | 0.98 |
| 173 | S173A | 0.92 | 0.74 |
| 173 | S173C | 0.82 | 0.57 |
| 173 | S173D | 0.63 | 0.71 |
| 173 | S173E | 1.07 | 0.65 |
| 173 | S173F | 0.82 | 0.25 |
| 173 | S173G | 0.73 | 0.78 |
| 173 | S173H | 0.85 | 0.66 |
| 173 | S173I | 1.20 | 0.59 |
| 173 | S173K | 1.17 | 1.03 |
| 173 | S173L | 0.75 | 0.20 |
| 173 | S173M | 1.05 | 0.48 |
| 173 | S173N | 1.02 | 0.84 |
| 173 | S173Q | 1.08 | 0.84 |
| 173 | S173R | 0.88 | 1.03 |
| 173 | S173T | 1.33 | 0.86 |
| 173 | S173V | 1.12 | 0.46 |
| 173 | S173W | 0.86 | 0.20 |
| 173 | S173Y | 0.90 | 0.25 |
| 177 | K177A | *0.05* | 1.20 |
| 177 | K177C | *0.05* | 0.76 |
| 177 | K177D | *0.05* | 1.07 |
| 177 | K177E | *0.05* | 1.08 |
| 177 | K177F | *0.05* | 1.01 |
| 177 | K177G | *0.05* | 1.03 |
| 177 | K177H | *0.05* | 1.07 |
| 177 | K177I | *0.05* | 0.89 |
| 177 | K177L | 0.89 | 0.91 |
| 177 | K177M | 0.10 | 0.90 |
| 177 | K177N | *0.05* | 1.15 |
| 177 | K177P | *0.05* | 1.11 |
| 177 | K177Q | 0.08 | 1.07 |
| 177 | K177R | 0.47 | 1.09 |
| 177 | K177S | *0.05* | 1.00 |
| 177 | K177T | *0.05* | 1.01 |
| 177 | K177W | *0.05* | 1.07 |
| 177 | K177Y | *0.05* | 0.97 |
| 188 | E188A | *0.05* | 1.10 |
| 188 | E188C | *0.05* | 0.85 |
| 188 | E188D | *0.05* | 1.21 |

TABLE 26-4-continued

Performance Indicies for stability and activity measurements for AmyS variants

| Position | Variant | Stability PI | Activity PI |
|---|---|---|---|
| 188 | E188F | *0.05* | 1.08 |
| 188 | E188G | *0.05* | 1.17 |
| 188 | E188H | *0.05* | 1.00 |
| 188 | E188I | *0.05* | 1.11 |
| 188 | E188K | *0.05* | 1.02 |
| 188 | E188M | *0.05* | 1.08 |
| 188 | E188N | *0.05* | 1.06 |
| 188 | E188P | 1.40 | 1.16 |
| 188 | E188Q | *0.05* | 1.06 |
| 188 | E188S | *0.05* | 1.10 |
| 188 | E188T | *0.05* | 1.17 |
| 188 | E188V | *0.05* | 1.08 |
| 188 | E188W | *0.05* | 1.07 |
| 188 | E188Y | *0.05* | 1.02 |
| 191 | T191A | 0.49 | 1.11 |
| 191 | T191C | 0.13 | 1.07 |
| 191 | T191D | 0.91 | 1.03 |
| 191 | T191F | *0.05* | 1.02 |
| 191 | T191G | 0.19 | 1.09 |
| 191 | T191H | *0.05* | 1.27 |
| 191 | T191I | 0.18 | 1.06 |
| 191 | T191K | *0.05* | 1.33 |
| 191 | T191L | *0.05* | 1.08 |
| 191 | T191M | 0.06 | 1.09 |
| 191 | T191N | 0.76 | 1.13 |
| 191 | T191P | 0.99 | 1.07 |
| 191 | T191Q | 0.18 | 1.17 |
| 191 | T191R | *0.05* | 1.20 |
| 191 | T191S | 0.72 | 1.05 |
| 191 | T191V | 0.16 | 1.02 |
| 191 | T191W | *0.05* | 0.91 |
| 192 | E192A | *0.05* | 1.26 |
| 192 | E192C | 0.55 | 1.12 |
| 192 | E192D | 0.42 | 1.50 |
| 192 | E192G | *0.05* | 1.38 |
| 192 | E192H | *0.05* | 0.78 |
| 192 | E192I | *0.05* | 1.00 |
| 192 | E192K | *0.05* | 0.33 |
| 192 | E192M | *0.05* | 1.19 |
| 192 | E192N | *0.05* | 1.35 |
| 192 | E192P | *0.05* | 1.33 |
| 192 | E192Q | 0.22 | 1.55 |
| 192 | E192R | *0.05* | 0.37 |
| 192 | E192S | *0.05* | 1.47 |
| 192 | E192T | 0.10 | 1.35 |
| 192 | E192V | *0.05* | 1.25 |
| 192 | E192W | *0.05* | 1.17 |
| 192 | E192Y | *0.05* | 1.30 |
| 193 | N193A | *0.05* | 0.98 |
| 193 | N193C | 0.73 | 0.62 |
| 193 | N193D | *0.05* | 0.95 |
| 193 | N193E | *0.05* | 0.74 |
| 193 | N193F | 1.71 | 0.98 |
| 193 | N193G | *0.05* | 0.96 |
| 193 | N193H | 1.10 | 0.92 |
| 193 | N193I | *0.05* | 0.78 |
| 193 | N193K | 1.28 | 1.17 |
| 193 | N193L | 1.22 | 0.78 |
| 193 | N193M | 0.81 | 0.96 |
| 193 | N193P | *0.05* | 0.90 |
| 193 | N193R | 0.87 | 0.97 |
| 193 | N193S | *0.05* | 1.15 |
| 193 | N193T | *0.05* | 0.86 |
| 193 | N193W | 1.09 | 0.73 |
| 193 | N193Y | 1.89 | 1.10 |
| 196 | Y196A | 0.74 | 1.57 |
| 196 | Y196C | *0.05* | 1.36 |
| 196 | Y196D | 0.29 | 1.29 |
| 196 | Y196E | *0.05* | 1.29 |
| 196 | Y196F | 0.74 | 1.38 |
| 196 | Y196G | *0.05* | 1.09 |
| 196 | Y196H | *0.05* | 1.92 |
| 196 | Y196I | *0.05* | 1.61 |
| 196 | Y196K | *0.05* | 1.29 |
| 196 | Y196L | *0.05* | 1.14 |
| 196 | Y196N | 0.54 | 0.94 |
| 196 | Y196P | *0.05* | 1.50 |
| 196 | Y196R | *0.05* | 1.29 |
| 196 | Y196S | 0.36 | 1.59 |
| 196 | Y196T | *0.05* | 1.65 |
| 196 | Y196V | *0.05* | 1.55 |
| 196 | Y196W | *0.05* | 0.57 |
| 199 | L199A | 0.16 | 0.42 |
| 199 | L199E | *0.05* | 0.34 |
| 199 | L199G | *0.05* | 0.31 |
| 199 | L199H | *0.05* | 0.18 |
| 199 | L199I | 0.14 | 0.30 |
| 199 | L199K | 0.22 | 0.15 |
| 199 | L199M | 0.30 | 0.14 |
| 199 | L199N | *0.05* | 0.07 |
| 199 | L199P | *0.05* | *0.05* |
| 199 | L199Q | *0.05* | 0.20 |
| 199 | L199R | *0.05* | 0.23 |
| 199 | L199S | *0.05* | 0.29 |
| 199 | L199T | 0.12 | 0.35 |
| 199 | L199V | 0.61 | 0.13 |
| 199 | L199W | *0.05* | *0.05* |
| 199 | L199Y | *0.05* | *0.05* |
| 200 | M200A | 1.03 | 0.68 |
| 200 | M200C | 0.84 | 0.53 |
| 200 | M200D | 0.71 | 0.81 |
| 200 | M200E | 0.54 | 0.55 |
| 200 | M200F | *0.05* | 0.25 |
| 200 | M200G | 0.23 | 0.41 |
| 200 | M200H | *0.05* | *0.05* |
| 200 | M200I | 1.14 | 0.57 |
| 200 | M200K | *0.05* | *0.05* |
| 200 | M200L | 0.68 | 1.11 |
| 200 | M200N | 0.46 | 0.72 |
| 200 | M200P | *0.05* | *0.05* |
| 200 | M200Q | 0.78 | 0.77 |
| 200 | M200S | 0.61 | 1.11 |
| 200 | M200T | 0.80 | 0.61 |
| 200 | M200V | 0.97 | 0.56 |
| 200 | M200W | *0.05* | *0.05* |
| 201 | Y201A | 0.90 | 1.41 |
| 201 | Y201C | 1.22 | 0.14 |
| 201 | Y201D | 0.60 | 0.73 |
| 201 | Y201E | 0.81 | 1.36 |
| 201 | Y201F | 0.85 | 0.81 |
| 201 | Y201G | 0.56 | 1.63 |
| 201 | Y201H | 1.06 | 1.44 |
| 201 | Y201I | 1.35 | 0.11 |
| 201 | Y201K | 0.89 | 0.08 |
| 201 | Y201L | 1.05 | 0.18 |
| 201 | Y201M | 1.16 | 1.21 |
| 201 | Y201N | 1.15 | 0.31 |
| 201 | Y201P | *0.05* | *0.05* |
| 201 | Y201Q | 1.11 | 0.79 |
| 201 | Y201R | 0.87 | 0.06 |
| 201 | Y201S | 0.74 | 1.11 |
| 201 | Y201T | 0.65 | 0.39 |
| 201 | Y201V | *0.05* | *0.05* |
| 201 | Y201W | 0.73 | 0.08 |
| 202 | A202C | 0.97 | 0.57 |
| 202 | A202D | 0.83 | 0.93 |
| 202 | A202E | 0.49 | 0.85 |
| 202 | A202F | *0.05* | 0.68 |
| 202 | A202G | 0.45 | 0.83 |
| 202 | A202H | *0.05* | 1.30 |
| 202 | A202I | 0.50 | 1.02 |
| 202 | A202K | 0.37 | 0.12 |
| 202 | A202L | 0.46 | 0.95 |
| 202 | A202M | 0.32 | 0.84 |
| 202 | A202N | 0.53 | 1.08 |
| 202 | A202P | *0.05* | 0.72 |
| 202 | A202Q | 0.47 | 1.01 |
| 202 | A202R | *0.05* | *0.05* |

TABLE 26-4-continued

Performance Indicies for stability and activity measurements for AmyS variants

| Position | Variant | Stability PI | Activity PI |
|---|---|---|---|
| 202 | A202S | 0.69 | 0.79 |
| 202 | A202T | 0.63 | 1.07 |
| 202 | A202V | 0.82 | 1.02 |
| 202 | A202Y | *0.05* | 0.43 |
| 213 | T213A | 1.11 | 0.98 |
| 213 | T213C | 0.97 | 0.77 |
| 213 | T213D | 1.12 | 0.91 |
| 213 | T213E | 1.11 | 0.88 |
| 213 | T213F | 1.13 | 0.75 |
| 213 | T213G | 1.11 | 0.91 |
| 213 | T213H | 0.92 | 1.00 |
| 213 | T213I | *0.05* | *0.05* |
| 213 | T213K | 0.90 | 1.11 |
| 213 | T213L | 1.26 | 0.75 |
| 213 | T213M | 1.26 | 0.78 |
| 213 | T213N | 1.11 | 0.91 |
| 213 | T213P | 0.94 | 0.91 |
| 213 | T213Q | 1.12 | 1.02 |
| 213 | T213R | 1.05 | 1.05 |
| 213 | T213S | 1.10 | 1.08 |
| 213 | T213V | 1.35 | 0.76 |
| 213 | T213W | 1.17 | 0.68 |
| 216 | K216A | 0.66 | 0.24 |
| 216 | K216D | *0.05* | *0.05* |
| 216 | K216E | 1.03 | 1.30 |
| 216 | K216F | *0.05* | *0.05* |
| 216 | K216G | 0.83 | 1.20 |
| 216 | K216H | 0.90 | 1.28 |
| 216 | K216I | *0.05* | *0.05* |
| 216 | K216L | *0.05* | *0.05* |
| 216 | K216M | 0.97 | 1.39 |
| 216 | K216P | 0.91 | 0.97 |
| 216 | K216Q | 1.04 | 1.34 |
| 216 | K216R | 0.77 | 1.32 |
| 216 | K216S | 0.97 | 1.28 |
| 216 | K216T | 0.99 | 1.22 |
| 216 | K216V | 0.95 | 1.07 |
| 216 | K216W | 1.00 | 1.13 |
| 216 | K216Y | 0.79 | 1.31 |
| 217 | N217A | 1.10 | 0.87 |
| 217 | N217C | 0.81 | 0.78 |
| 217 | N217E | *0.05* | 0.73 |
| 217 | N217F | 0.90 | 0.88 |
| 217 | N217G | 0.95 | 0.90 |
| 217 | N217H | 1.09 | 0.90 |
| 217 | N217I | 1.08 | 0.76 |
| 217 | N217L | 1.09 | 0.82 |
| 217 | N217M | 0.97 | 0.80 |
| 217 | N217P | 0.97 | 0.73 |
| 217 | N217Q | 1.31 | 0.74 |
| 217 | N217R | 1.19 | 0.87 |
| 217 | N217S | 1.05 | 0.87 |
| 217 | N217T | 1.01 | 0.87 |
| 217 | N217V | 1.18 | 0.69 |
| 217 | N217W | 0.99 | 0.80 |
| 217 | N217Y | *0.05* | *0.05* |
| 220 | K220A | 1.06 | 0.79 |
| 220 | K220C | 1.05 | 0.75 |
| 220 | K220D | 1.02 | 0.88 |
| 220 | K220E | 1.12 | 0.88 |
| 220 | K220F | 1.03 | 0.78 |
| 220 | K220G | 1.10 | 0.84 |
| 220 | K220H | 1.12 | 0.81 |
| 220 | K220I | 1.13 | 0.81 |
| 220 | K220M | 1.05 | 0.75 |
| 220 | K220N | 1.17 | 0.80 |
| 220 | K220P | 1.33 | 0.89 |
| 220 | K220Q | 1.21 | 0.87 |
| 220 | K220R | 1.26 | 0.83 |
| 220 | K220S | 1.30 | 0.81 |
| 220 | K220T | *0.05* | 0.09 |
| 220 | K220V | 1.21 | 0.82 |
| 220 | K220W | 1.01 | 0.81 |
| 220 | K220Y | 1.08 | 0.84 |
| 221 | W221A | 0.88 | 1.54 |
| 221 | W221C | 0.95 | 1.09 |
| 221 | W221D | 0.84 | 1.31 |
| 221 | W221E | *0.05* | *0.05* |
| 221 | W221F | 1.07 | 1.28 |
| 221 | W221G | *0.05* | *0.05* |
| 221 | W221H | *0.05* | *0.05* |
| 221 | W221I | 1.33 | 1.23 |
| 221 | W221K | *0.05* | *0.05* |
| 221 | W221L | 0.88 | 1.50 |
| 221 | W221M | 1.16 | 1.35 |
| 221 | W221N | 1.11 | 1.57 |
| 221 | W221P | *0.05* | *0.05* |
| 221 | W221R | 0.93 | 1.29 |
| 221 | W221S | 1.34 | 1.40 |
| 221 | W221V | 1.13 | 1.31 |
| 221 | W221Y | 1.14 | 1.36 |
| 227 | N227A | 1.01 | 1.02 |
| 227 | N227C | 0.92 | 0.95 |
| 227 | N227D | 1.01 | 1.06 |
| 227 | N227E | 1.03 | 1.06 |
| 227 | N227F | 0.72 | 0.81 |
| 227 | N227G | 1.05 | 1.09 |
| 227 | N227H | 0.95 | 1.13 |
| 227 | N227I | 1.03 | 0.76 |
| 227 | N227K | 1.00 | 1.13 |
| 227 | N227L | 0.84 | 0.75 |
| 227 | N227M | 0.84 | 0.87 |
| 227 | N227P | 1.08 | 0.88 |
| 227 | N227Q | 0.94 | 1.00 |
| 227 | N227R | 0.89 | 1.03 |
| 227 | N227S | 0.96 | 0.95 |
| 227 | N227T | 1.06 | 0.96 |
| 227 | N227V | 1.05 | 0.84 |
| 227 | N227W | 1.07 | 0.81 |
| 227 | N227Y | 1.01 | 0.85 |
| 232 | R232A | *0.05* | *0.05* |
| 232 | R232C | 0.40 | 0.14 |
| 232 | R232D | *0.05* | *0.05* |
| 232 | R232E | 0.41 | 0.12 |
| 232 | R232G | 0.06 | 0.23 |
| 232 | R232H | 0.66 | 0.34 |
| 232 | R232K | 0.52 | 0.47 |
| 232 | R232M | 0.62 | 0.12 |
| 232 | R232N | *0.05* | *0.05* |
| 232 | R232P | *0.05* | *0.05* |
| 232 | R232Q | 0.54 | 0.12 |
| 232 | R232S | 0.59 | 0.16 |
| 232 | R232T | 0.76 | 0.17 |
| 232 | R232V | 0.70 | 0.15 |
| 232 | R232W | *0.05* | *0.05* |
| 232 | R232Y | *0.05* | *0.05* |
| 235 | A235C | 0.86 | 0.53 |
| 235 | A235D | 0.70 | 0.98 |
| 235 | A235E | 0.93 | 0.84 |
| 235 | A235F | 1.01 | 0.68 |
| 235 | A235G | 1.17 | 0.78 |
| 235 | A235H | 0.80 | 1.01 |
| 235 | A235I | 1.07 | 0.84 |
| 235 | A235K | 0.93 | 1.14 |
| 235 | A235L | 0.89 | 0.97 |
| 235 | A235M | 0.99 | 0.91 |
| 235 | A235N | 0.78 | 1.03 |
| 235 | A235P | 0.97 | 0.48 |
| 235 | A235Q | 1.01 | 0.89 |
| 235 | A235R | 1.03 | 1.14 |
| 235 | A235S | 0.92 | 1.00 |
| 235 | A235T | *0.05* | *0.05* |
| 235 | A235V | 1.01 | 0.86 |
| 235 | A235W | 0.98 | 0.60 |
| 235 | A235Y | 0.91 | 0.93 |
| 237 | K237A | *0.05* | 0.78 |
| 237 | K237C | *0.05* | 0.57 |
| 237 | K237D | *0.05* | 0.08 |

TABLE 26-4-continued

Performance Indicies for stability and activity measurements for AmyS variants

| Position | Variant | Stability PI | Activity PI |
|---|---|---|---|
| 237 | K237E | 0.05 | 0.74 |
| 237 | K237F | 0.05 | 0.09 |
| 237 | K237G | 0.05 | 1.21 |
| 237 | K237H | 0.05 | 0.26 |
| 237 | K237I | 0.05 | 0.40 |
| 237 | K237L | 0.05 | 0.57 |
| 237 | K237M | 0.05 | 0.46 |
| 237 | K237N | 0.05 | 0.43 |
| 237 | K237P | 0.05 | 0.30 |
| 237 | K237Q | 0.05 | 0.77 |
| 237 | K237R | 0.48 | 0.88 |
| 237 | K237T | 0.05 | 0.69 |
| 237 | K237V | 0.05 | 0.54 |
| 237 | K237W | 0.05 | 0.05 |
| 237 | K237Y | 0.05 | 0.05 |
| 238 | H238A | 0.05 | 0.62 |
| 238 | H238C | 0.05 | 0.63 |
| 238 | H238D | 0.05 | 0.75 |
| 238 | H238F | 0.05 | 0.05 |
| 238 | H238G | 0.05 | 0.73 |
| 238 | H238I | 0.05 | 0.18 |
| 238 | H238K | 0.05 | 0.05 |
| 238 | H238L | 0.05 | 0.25 |
| 238 | H238M | 0.05 | 0.36 |
| 238 | H238N | 0.21 | 0.83 |
| 238 | H238P | 0.05 | 0.57 |
| 238 | H238Q | 0.05 | 1.18 |
| 238 | H238R | 0.05 | 0.05 |
| 238 | H238T | 0.05 | 0.74 |
| 238 | H238V | 0.05 | 0.52 |
| 238 | H238Y | 0.05 | 0.05 |
| 240 | K240A | 0.05 | 1.13 |
| 240 | K240D | 0.05 | 1.19 |
| 240 | K240E | 0.05 | 1.19 |
| 240 | K240F | 0.05 | 0.90 |
| 240 | K240G | 0.05 | 1.22 |
| 240 | K240H | 0.05 | 1.17 |
| 240 | K240I | 0.05 | 0.99 |
| 240 | K240M | 0.31 | 1.13 |
| 240 | K240N | 0.05 | 1.37 |
| 240 | K240P | 0.05 | 1.69 |
| 240 | K240Q | 0.12 | 1.21 |
| 240 | K240R | 0.27 | 1.41 |
| 240 | K240S | 0.05 | 1.07 |
| 240 | K240T | 0.05 | 1.23 |
| 240 | K240V | 0.05 | 1.09 |
| 240 | K240W | 0.05 | 1.01 |
| 240 | K240Y | 0.05 | 1.11 |
| 246 | D246A | 0.73 | 1.03 |
| 246 | D246E | 1.18 | 1.03 |
| 246 | D246F | 0.67 | 1.02 |
| 246 | D246G | 0.61 | 1.09 |
| 246 | D246H | 0.71 | 1.05 |
| 246 | D246I | 0.75 | 0.85 |
| 246 | D246K | 0.36 | 1.18 |
| 246 | D246L | 0.81 | 0.91 |
| 246 | D246M | 0.80 | 0.92 |
| 246 | D246N | 0.68 | 0.97 |
| 246 | D246P | 0.47 | 0.81 |
| 246 | D246Q | 0.78 | 0.98 |
| 246 | D246R | 0.24 | 1.31 |
| 246 | D246S | 0.97 | 1.01 |
| 246 | D246T | 0.83 | 1.14 |
| 246 | D246Y | 0.90 | 0.96 |
| 249 | S249A | 1.06 | 0.97 |
| 249 | S249C | 0.93 | 0.74 |
| 249 | S249D | 0.98 | 0.94 |
| 249 | S249E | 1.27 | 0.92 |
| 249 | S249F | 0.91 | 0.74 |
| 249 | S249G | 0.91 | 0.94 |
| 249 | S249H | 1.04 | 0.93 |
| 249 | S249K | 1.15 | 1.02 |
| 249 | S249L | 1.14 | 0.82 |
| 249 | S249M | 0.95 | 0.77 |
| 249 | S249P | 1.09 | 0.80 |
| 249 | S249Q | 1.20 | 0.94 |
| 249 | S249R | 1.07 | 1.03 |
| 249 | S249T | 1.17 | 0.91 |
| 249 | S249V | 1.01 | 0.74 |
| 249 | S249W | 1.13 | 0.77 |
| 249 | S249Y | 1.07 | 0.87 |
| 250 | Y250A | 0.99 | 1.21 |
| 250 | Y250C | 1.03 | 1.12 |
| 250 | Y250D | 0.97 | 1.29 |
| 250 | Y250E | 1.13 | 1.33 |
| 250 | Y250F | 1.29 | 1.28 |
| 250 | Y250G | 1.09 | 1.33 |
| 250 | Y250I | 1.35 | 1.27 |
| 250 | Y250K | 1.07 | 1.48 |
| 250 | Y250L | 1.02 | 1.32 |
| 250 | Y250M | 1.35 | 1.39 |
| 250 | Y250N | 1.05 | 1.40 |
| 250 | Y250P | 0.71 | 1.05 |
| 250 | Y250Q | 1.01 | 1.54 |
| 250 | Y250R | 0.99 | 1.55 |
| 250 | Y250S | 1.02 | 1.41 |
| 250 | Y250T | 0.05 | 0.05 |
| 250 | Y250V | 0.05 | 0.05 |
| 250 | Y250W | 0.99 | 1.35 |
| 252 | R252A | 1.12 | 1.08 |
| 252 | R252C | 0.97 | 0.81 |
| 252 | R252D | 0.89 | 0.86 |
| 252 | R252E | 1.09 | 1.12 |
| 252 | R252F | 1.01 | 0.89 |
| 252 | R252G | 0.76 | 1.00 |
| 252 | R252I | 1.07 | 0.97 |
| 252 | R252K | 1.19 | 1.21 |
| 252 | R252L | 1.32 | 0.96 |
| 252 | R252M | 0.98 | 0.96 |
| 252 | R252N | 1.15 | 0.97 |
| 252 | R252P | 0.72 | 0.83 |
| 252 | R252Q | 1.16 | 1.04 |
| 252 | R252S | 1.04 | 1.01 |
| 252 | R252T | 1.09 | 0.99 |
| 252 | R252V | 1.01 | 0.94 |
| 252 | R252Y | 1.14 | 0.86 |
| 253 | S253A | 1.09 | 0.97 |
| 253 | S253D | 1.07 | 1.04 |
| 253 | S253E | 0.05 | 0.05 |
| 253 | S253F | 1.19 | 0.82 |
| 253 | S253G | 1.18 | 0.92 |
| 253 | S253H | 1.13 | 0.97 |
| 253 | S253I | 1.13 | 0.84 |
| 253 | S253K | 1.10 | 1.01 |
| 253 | S253L | 1.09 | 0.79 |
| 253 | S253M | 0.05 | 0.05 |
| 253 | S253N | 1.06 | 1.03 |
| 253 | S253P | 0.95 | 0.90 |
| 253 | S253Q | 1.13 | 0.93 |
| 253 | S253T | 1.14 | 0.97 |
| 253 | S253V | 1.15 | 0.90 |
| 253 | S253W | 1.04 | 0.87 |
| 253 | S253Y | 1.34 | 0.94 |
| 254 | Q254A | 0.98 | 0.88 |
| 254 | Q254C | 0.94 | 0.66 |
| 254 | Q254D | 1.10 | 0.90 |
| 254 | Q254E | 1.29 | 0.89 |
| 254 | Q254F | 1.23 | 0.74 |
| 254 | Q254G | 1.15 | 0.77 |
| 254 | Q254H | 1.04 | 0.94 |
| 254 | Q254I | 1.12 | 0.91 |
| 254 | Q254K | 1.00 | 0.99 |
| 254 | Q254L | 1.09 | 0.82 |
| 254 | Q254M | 0.94 | 0.89 |
| 254 | Q254N | 1.17 | 0.90 |
| 254 | Q254R | 1.05 | 0.98 |
| 254 | Q254S | 1.07 | 0.98 |
| 254 | Q254T | 1.21 | 0.65 |

TABLE 26-4-continued

Performance Indicies for stability and activity measurements for AmyS variants

| Position | Variant | Stability PI | Activity PI |
|---|---|---|---|
| 254 | Q254V | 1.31 | 0.92 |
| 254 | Q254W | 1.17 | 0.69 |
| 254 | Q254Y | 1.03 | 0.87 |
| 255 | T255A | 1.09 | 0.73 |
| 255 | T255C | 0.89 | 0.78 |
| 255 | T255D | *0.05* | *0.05* |
| 255 | T255E | 1.09 | 0.64 |
| 255 | T255F | 1.30 | 0.68 |
| 255 | T255G | 1.15 | 0.73 |
| 255 | T255H | 1.10 | 0.74 |
| 255 | T255I | 1.18 | 0.70 |
| 255 | T255K | 1.27 | 0.83 |
| 255 | T255L | 0.97 | 0.73 |
| 255 | T255M | 0.98 | 0.72 |
| 255 | T255N | 0.83 | 0.76 |
| 255 | T255P | 0.77 | 0.59 |
| 255 | T255R | 1.12 | 0.85 |
| 255 | T255S | 1.10 | 0.84 |
| 255 | T255V | 1.17 | 0.70 |
| 255 | T255W | 1.27 | 0.74 |
| 255 | T255Y | 1.02 | 0.72 |
| 257 | K257A | 1.08 | 0.67 |
| 257 | K257C | 0.89 | 0.49 |
| 257 | K257D | 1.16 | 0.75 |
| 257 | K257E | 1.15 | 0.76 |
| 257 | K257F | 1.03 | 0.92 |
| 257 | K257G | 0.97 | 0.73 |
| 257 | K257H | 1.12 | 0.69 |
| 257 | K257I | 1.09 | 0.59 |
| 257 | K257L | 1.26 | 0.74 |
| 257 | K257M | 1.29 | 0.79 |
| 257 | K257N | 1.16 | 0.83 |
| 257 | K257P | 0.62 | 0.38 |
| 257 | K257Q | 1.18 | 0.82 |
| 257 | K257R | 1.03 | 0.89 |
| 257 | K257S | 1.29 | 0.71 |
| 257 | K257T | 1.04 | 0.77 |
| 257 | K257V | 1.31 | 0.78 |
| 257 | K257W | 0.99 | 0.72 |
| 258 | P258A | 0.97 | 1.08 |
| 258 | P258C | 1.17 | 0.85 |
| 258 | P258D | 1.33 | 1.10 |
| 258 | P258E | 0.95 | 1.05 |
| 258 | P258F | 0.96 | 0.75 |
| 258 | P258G | 1.30 | 1.02 |
| 258 | P258H | 1.38 | 1.13 |
| 258 | P258I | 1.27 | 0.25 |
| 258 | P258K | 1.29 | 1.11 |
| 258 | P258L | 1.08 | 0.61 |
| 258 | P258M | 1.09 | 0.91 |
| 258 | P258N | 1.07 | 1.01 |
| 258 | P258Q | 1.31 | 1.13 |
| 258 | P258R | 1.02 | 1.13 |
| 258 | P258S | 1.12 | 1.08 |
| 258 | P258T | 1.27 | 1.10 |
| 258 | P258V | 1.29 | 0.80 |
| 258 | P258W | 1.14 | 0.87 |
| 258 | P258Y | 1.16 | 1.08 |
| 268 | Y268A | 0.86 | 1.39 |
| 268 | Y268C | 0.47 | 1.10 |
| 268 | Y268D | 0.59 | 1.44 |
| 268 | Y268E | 0.55 | 1.47 |
| 268 | Y268F | 1.28 | 1.07 |
| 268 | Y268G | 1.03 | 1.21 |
| 268 | Y268H | 0.87 | 1.24 |
| 268 | Y268I | *0.05* | *0.05* |
| 268 | Y268K | 0.78 | 1.90 |
| 268 | Y268L | 0.72 | 1.10 |
| 268 | Y268M | 0.97 | 1.15 |
| 268 | Y268N | 0.69 | 1.51 |
| 268 | Y268P | 0.78 | 1.41 |
| 268 | Y268Q | 0.71 | 1.30 |
| 268 | Y268R | 0.76 | 1.49 |
| 268 | Y268S | 1.06 | 1.22 |
| 268 | Y268T | 0.99 | 1.12 |
| 268 | Y268V | 0.88 | 0.99 |
| 268 | Y268W | 0.97 | 1.07 |
| 272 | K272A | *0.05* | 0.73 |
| 272 | K272C | *0.05* | 0.68 |
| 272 | K272D | *0.05* | 0.86 |
| 272 | K272E | *0.05* | 0.85 |
| 272 | K272F | *0.05* | 0.56 |
| 272 | K272G | *0.05* | 0.60 |
| 272 | K272H | *0.05* | 0.78 |
| 272 | K272I | *0.05* | 0.81 |
| 272 | K272M | *0.05* | 0.77 |
| 272 | K272N | *0.05* | 0.67 |
| 272 | K272P | *0.05* | 0.38 |
| 272 | K272R | 0.90 | 0.86 |
| 272 | K272S | *0.05* | 0.79 |
| 272 | K272T | *0.05* | 0.99 |
| 272 | K272V | *0.05* | 0.64 |
| 272 | K272W | *0.05* | 0.48 |
| 272 | K272Y | *0.05* | 0.66 |
| 274 | H274A | 0.66 | 1.40 |
| 274 | H274C | 0.65 | 0.68 |
| 274 | H274D | 0.64 | 1.20 |
| 274 | H274E | 0.86 | 1.14 |
| 274 | H274F | 0.88 | 1.00 |
| 274 | H274G | 0.56 | 1.36 |
| 274 | H274I | 0.76 | 1.39 |
| 274 | H274K | 0.85 | 1.60 |
| 274 | H274L | 0.87 | 1.40 |
| 274 | H274N | 0.67 | 1.50 |
| 274 | H274P | *0.05* | 0.50 |
| 274 | H274Q | 0.84 | 1.47 |
| 274 | H274R | 0.80 | 1.50 |
| 274 | H274S | 0.67 | 1.28 |
| 274 | H274T | 0.69 | 1.38 |
| 274 | H274W | 1.26 | 0.79 |
| 274 | H274Y | 1.05 | 1.07 |
| 275 | N275A | 0.32 | 1.01 |
| 275 | N275C | 0.22 | 0.68 |
| 275 | N275D | 0.08 | 1.03 |
| 275 | N275E | *0.05* | 0.98 |
| 275 | N275F | *0.05* | 0.81 |
| 275 | N275G | 0.18 | 1.00 |
| 275 | N275H | 0.60 | 1.10 |
| 275 | N275I | 0.15 | 0.87 |
| 275 | N275K | 0.22 | 1.22 |
| 275 | N275L | 0.20 | 1.02 |
| 275 | N275M | 0.20 | 0.96 |
| 275 | N275P | *0.05* | 0.37 |
| 275 | N275Q | 0.21 | 0.96 |
| 275 | N275R | 0.28 | 1.04 |
| 275 | N275S | 0.28 | 0.92 |
| 275 | N275T | 0.19 | 0.79 |
| 275 | N275V | 0.19 | 0.76 |
| 275 | N275W | *0.05* | 0.76 |
| 275 | N275Y | 0.89 | 0.93 |
| 279 | K279C | *0.05* | 0.54 |
| 279 | K279E | *0.05* | 0.91 |
| 279 | K279F | *0.05* | 0.70 |
| 279 | K279G | *0.05* | 0.85 |
| 279 | K279H | *0.05* | 0.36 |
| 279 | K279I | *0.05* | 0.68 |
| 279 | K279L | *0.05* | 0.52 |
| 279 | K279M | *0.05* | 0.71 |
| 279 | K279N | *0.05* | 0.91 |
| 279 | K279P | *0.05* | 0.46 |
| 279 | K279Q | *0.05* | 0.86 |
| 279 | K279S | *0.05* | 0.94 |
| 279 | K279T | *0.05* | 0.92 |
| 279 | K279V | *0.05* | 0.78 |
| 279 | K279W | *0.05* | 0.76 |
| 279 | K279Y | *0.05* | 0.78 |
| 283 | T283A | 1.06 | 0.97 |
| 283 | T283C | 1.16 | 0.78 |

TABLE 26-4-continued

Performance Indicies for stability and activity measurements for AmyS variants

| Position | Variant | Stability PI | Activity PI |
|---|---|---|---|
| 283 | T283D | 0.92 | 1.03 |
| 283 | T283E | 0.95 | 1.01 |
| 283 | T283G | 0.97 | 1.01 |
| 283 | T283H | 1.09 | 0.84 |
| 283 | T283I | 1.10 | 0.72 |
| 283 | T283K | 1.14 | 1.01 |
| 283 | T283L | 1.07 | 0.76 |
| 283 | T283M | 1.26 | 0.93 |
| 283 | T283N | 1.29 | 0.96 |
| 283 | T283P | 0.46 | 0.56 |
| 283 | T283R | 0.82 | 1.08 |
| 283 | T283S | 1.02 | 1.06 |
| 283 | T283V | 1.23 | 0.81 |
| 283 | T283W | 1.07 | 0.75 |
| 283 | T283Y | 1.01 | 1.04 |
| 285 | S285A | 0.93 | 0.80 |
| 285 | S285C | 0.73 | 0.61 |
| 285 | S285D | 0.91 | 1.09 |
| 285 | S285E | 1.33 | 0.89 |
| 285 | S285F | 1.18 | 1.02 |
| 285 | S285H | 0.98 | 1.10 |
| 285 | S285I | 0.84 | 0.52 |
| 285 | S285K | 1.16 | 0.84 |
| 285 | S285L | 0.85 | 0.54 |
| 285 | S285M | 0.98 | 0.76 |
| 285 | S285Q | 1.38 | 1.22 |
| 285 | S285R | 0.84 | 0.96 |
| 285 | S285T | 0.98 | 0.79 |
| 285 | S285V | 0.70 | 0.63 |
| 285 | S285W | 1.13 | 1.08 |
| 285 | S285Y | 0.97 | 1.49 |
| 293 | N293A | 1.02 | 0.93 |
| 293 | N293C | 0.78 | 0.69 |
| 293 | N293D | 1.08 | 0.89 |
| 293 | N293E | 0.87 | 0.92 |
| 293 | N293F | 0.89 | 0.70 |
| 293 | N293G | 1.31 | 0.92 |
| 293 | N293H | 1.12 | 1.05 |
| 293 | N293I | 0.94 | 0.75 |
| 293 | N293K | 1.42 | 1.41 |
| 293 | N293L | 0.87 | 0.81 |
| 293 | N293M | 0.95 | 1.07 |
| 293 | N293P | 0.97 | 0.40 |
| 293 | N293Q | 1.14 | 1.06 |
| 293 | N293R | 0.86 | 1.37 |
| 293 | N293S | 0.93 | 0.95 |
| 293 | N293T | 1.10 | 1.12 |
| 293 | N293V | 1.04 | 0.82 |
| 293 | N293W | 1.09 | 0.78 |
| 293 | N293Y | 1.19 | 0.74 |
| 294 | K294A | 0.83 | 0.92 |
| 294 | K294C | 0.83 | 0.50 |
| 294 | K294D | 0.82 | 0.57 |
| 294 | K294E | 0.83 | 0.68 |
| 294 | K294F | 0.69 | 0.59 |
| 294 | K294G | 0.92 | 0.75 |
| 294 | K294H | 0.84 | 0.90 |
| 294 | K294I | 1.08 | 0.71 |
| 294 | K294L | 0.80 | 0.92 |
| 294 | K294M | 1.12 | 0.80 |
| 294 | K294N | 0.97 | 0.83 |
| 294 | K294P | *0.05* | *0.05* |
| 294 | K294Q | 0.88 | 0.87 |
| 294 | K294R | 1.18 | 0.90 |
| 294 | K294S | 0.95 | 0.83 |
| 294 | K294T | 0.83 | 0.16 |
| 294 | K294V | 0.89 | 0.73 |
| 294 | K294W | 1.23 | 0.66 |
| 294 | K294Y | 0.76 | 0.82 |
| 297 | T297C | 0.86 | 0.53 |
| 297 | T297D | 0.70 | 0.98 |
| 297 | T297E | 0.93 | 0.84 |
| 297 | T297F | 1.01 | 0.68 |
| 297 | T297G | 1.17 | 0.78 |
| 297 | T297H | 0.80 | 1.01 |
| 297 | T297I | 1.07 | 0.84 |
| 297 | T297K | 0.93 | 1.14 |
| 297 | T297L | 0.89 | 0.97 |
| 297 | T297M | 0.99 | 0.91 |
| 297 | T297N | 0.78 | 1.03 |
| 297 | T297P | 0.97 | 0.48 |
| 297 | T297Q | 1.01 | 0.89 |
| 297 | T297R | 1.03 | 1.14 |
| 297 | T297S | 0.92 | 1.00 |
| 297 | T297V | 1.01 | 0.86 |
| 297 | T297W | 0.98 | 0.60 |
| 297 | T297Y | 0.91 | 0.93 |
| 300 | K300A | 0.99 | 0.79 |
| 300 | K300C | 0.95 | 0.39 |
| 300 | K300D | 0.91 | 0.61 |
| 300 | K300E | 0.86 | 0.78 |
| 300 | K300F | 0.74 | 0.63 |
| 300 | K300G | 0.98 | 0.62 |
| 300 | K300H | 1.04 | 0.83 |
| 300 | K300I | 1.02 | 0.82 |
| 300 | K300L | 0.91 | 0.73 |
| 300 | K300M | 1.17 | 0.80 |
| 300 | K300N | 1.02 | 0.80 |
| 300 | K300P | *0.05* | *0.05* |
| 300 | K300Q | 0.90 | 0.86 |
| 300 | K300R | 1.20 | 0.92 |
| 300 | K300S | 0.93 | 0.80 |
| 300 | K300T | 1.16 | 0.87 |
| 300 | K300V | 1.15 | 0.84 |
| 300 | K300W | 0.97 | 0.57 |
| 301 | S301A | 1.10 | 0.89 |
| 301 | S301E | 1.12 | 0.94 |
| 301 | S301F | 1.44 | 0.68 |
| 301 | S301G | 1.02 | 1.05 |
| 301 | S301H | 1.12 | 0.87 |
| 301 | S301I | 1.28 | 0.74 |
| 301 | S301K | 1.08 | 1.05 |
| 301 | S301L | 1.09 | 0.97 |
| 301 | S301M | 1.09 | 0.87 |
| 301 | S301N | 1.16 | 0.64 |
| 301 | S301P | 1.21 | 0.61 |
| 301 | S301Q | 1.18 | 0.95 |
| 301 | S301R | 1.35 | 0.89 |
| 301 | S301T | 1.23 | 0.85 |
| 301 | S301V | 1.18 | 0.81 |
| 301 | S301W | 1.27 | 0.75 |
| 301 | S301Y | 1.10 | 0.80 |
| 306 | D306A | 0.82 | 0.40 |
| 306 | D306C | 0.74 | 0.30 |
| 306 | D306E | 0.80 | 0.71 |
| 306 | D306F | 0.71 | 0.10 |
| 306 | D306G | 0.76 | 0.26 |
| 306 | D306H | 0.84 | 0.35 |
| 306 | D306I | 0.80 | 0.18 |
| 306 | D306K | 0.77 | 0.41 |
| 306 | D306L | 0.78 | 0.18 |
| 306 | D306N | 1.15 | 0.89 |
| 306 | D306P | 0.82 | 0.39 |
| 306 | D306Q | 1.03 | 0.43 |
| 306 | D306R | 0.82 | 0.27 |
| 306 | D306S | 0.81 | 0.50 |
| 306 | D306T | 0.88 | 0.29 |
| 306 | D306V | 0.99 | 0.22 |
| 306 | D306W | *0.05* | *0.05* |
| 306 | D306Y | 0.94 | 0.12 |
| 309 | T309A | *0.05* | *0.05* |
| 309 | T309C | 1.15 | 0.59 |
| 309 | T309D | 1.27 | 0.89 |
| 309 | T309E | 0.95 | 0.91 |
| 309 | T309F | 1.15 | 0.80 |
| 309 | T309G | 1.17 | 1.00 |
| 309 | T309H | 0.94 | 0.97 |
| 309 | T309I | 1.17 | 0.82 |

TABLE 26-4-continued

Performance Indicies for stability and activity measurements for AmyS variants

| Position | Variant | Stability PI | Activity PI |
|---|---|---|---|
| 309 | T309K | 1.18 | 1.08 |
| 309 | T309L | 1.15 | 0.95 |
| 309 | T309M | 1.15 | 0.97 |
| 309 | T309N | 1.20 | 0.99 |
| 309 | T309P | 0.93 | 0.20 |
| 309 | T309Q | 1.19 | 0.98 |
| 309 | T309R | 1.12 | 1.08 |
| 309 | T309S | 1.00 | 1.04 |
| 309 | T309V | 1.38 | 0.95 |
| 309 | T309W | 1.08 | 0.77 |
| 309 | T309Y | 1.11 | 0.94 |
| 312 | T312A | 1.01 | 1.00 |
| 312 | T312C | 0.99 | 0.70 |
| 312 | T312D | 1.03 | 0.96 |
| 312 | T312E | 1.15 | 0.95 |
| 312 | T312F | 1.05 | 0.92 |
| 312 | T312G | 1.18 | 1.07 |
| 312 | T312H | 1.30 | 0.99 |
| 312 | T312K | 0.83 | 0.25 |
| 312 | T312L | 1.08 | 0.95 |
| 312 | T312M | 0.98 | 0.91 |
| 312 | T312N | 1.04 | 0.99 |
| 312 | T312P | 0.74 | 0.85 |
| 312 | T312Q | 1.05 | 0.94 |
| 312 | T312R | 1.13 | 1.00 |
| 312 | T312S | 1.29 | 0.99 |
| 312 | T312V | 1.40 | 0.87 |
| 312 | T312W | 1.14 | 0.83 |
| 312 | T312Y | 1.31 | 0.92 |
| 313 | N313A | 1.01 | 0.93 |
| 313 | N313C | 0.95 | 0.63 |
| 313 | N313D | 0.95 | 0.51 |
| 313 | N313E | 1.05 | 0.90 |
| 313 | N313F | 1.06 | 0.64 |
| 313 | N313G | 1.25 | 0.96 |
| 313 | N313H | 1.25 | 0.94 |
| 313 | N313I | 1.44 | 0.55 |
| 313 | N313K | 1.12 | 0.85 |
| 313 | N313L | 1.21 | 0.85 |
| 313 | N313M | 1.02 | 0.89 |
| 313 | N313P | 1.05 | 0.81 |
| 313 | N313Q | 1.00 | 1.00 |
| 313 | N313R | 1.19 | 1.13 |
| 313 | N313S | 1.25 | 1.05 |
| 313 | N313V | 1.28 | 0.74 |
| 313 | N313W | 1.01 | 0.67 |
| 313 | N313Y | 1.10 | 0.90 |
| 317 | K317A | 0.98 | 0.94 |
| 317 | K317C | 0.83 | 0.54 |
| 317 | K317D | 0.82 | 0.86 |
| 317 | K317E | 0.78 | 0.91 |
| 317 | K317F | 0.92 | 0.84 |
| 317 | K317G | 0.91 | 0.88 |
| 317 | K317L | 1.10 | 0.86 |
| 317 | K317M | 1.02 | 0.95 |
| 317 | K317N | 1.03 | 0.92 |
| 317 | K317P | 0.86 | 0.80 |
| 317 | K317Q | 0.76 | 0.94 |
| 317 | K317R | 0.78 | 0.89 |
| 317 | K317S | 1.04 | 0.93 |
| 317 | K317T | 0.94 | 0.88 |
| 317 | K317V | 1.00 | 0.93 |
| 317 | K317W | 1.08 | 0.83 |
| 317 | K317Y | 1.05 | 0.93 |
| 318 | D318A | 0.93 | 1.38 |
| 318 | D318E | 0.90 | 1.09 |
| 318 | D318F | 0.78 | 1.22 |
| 318 | D318G | 0.91 | 1.39 |
| 318 | D318H | 1.12 | 1.10 |
| 318 | D318I | 0.75 | 1.40 |
| 318 | D318K | 0.65 | 1.73 |
| 318 | D318L | 1.00 | 1.31 |
| 318 | D318M | 0.90 | 1.26 |
| 318 | D318N | 0.92 | 1.19 |
| 318 | D318P | 0.61 | 0.37 |
| 318 | D318Q | 0.93 | 1.14 |
| 318 | D318R | 0.71 | 1.54 |
| 318 | D318S | 1.11 | 1.37 |
| 318 | D318T | 1.40 | 1.32 |
| 318 | D318V | 0.81 | 1.34 |
| 318 | D318W | 0.90 | 1.07 |
| 318 | D318Y | 1.10 | 1.33 |
| 319 | Q319A | 1.02 | 1.13 |
| 319 | Q319C | 0.73 | 1.38 |
| 319 | Q319D | 0.85 | 1.31 |
| 319 | Q319E | 0.98 | 1.20 |
| 319 | Q319F | 0.87 | 1.11 |
| 319 | Q319G | 1.14 | 1.03 |
| 319 | Q319H | 0.94 | 1.28 |
| 319 | Q319I | 0.94 | 1.32 |
| 319 | Q319K | 1.10 | 1.52 |
| 319 | Q319L | 0.95 | 1.11 |
| 319 | Q319M | 0.90 | 1.09 |
| 319 | Q319N | 0.91 | 1.12 |
| 319 | Q319P | 1.13 | 0.57 |
| 319 | Q319R | 1.18 | 1.44 |
| 319 | Q319S | 0.91 | 1.12 |
| 319 | Q319T | 0.98 | 1.10 |
| 319 | Q319V | 1.07 | 1.08 |
| 319 | Q319W | 1.05 | 1.08 |
| 319 | Q319Y | 1.04 | 1.41 |
| 320 | P320A | 1.02 | 0.96 |
| 320 | P320C | 1.01 | 0.75 |
| 320 | P320D | 0.74 | 0.91 |
| 320 | P320E | 1.04 | 0.85 |
| 320 | P320F | 0.76 | 0.77 |
| 320 | P320G | 1.00 | 1.00 |
| 320 | P320H | 1.00 | 1.18 |
| 320 | P320I | 0.86 | 0.80 |
| 320 | P320K | 0.96 | 1.23 |
| 320 | P320L | 0.87 | 0.83 |
| 320 | P320M | 1.04 | 0.60 |
| 320 | P320Q | 0.95 | 1.08 |
| 320 | P320R | 0.79 | 1.25 |
| 320 | P320S | 1.16 | 1.03 |
| 320 | P320T | 1.11 | 1.28 |
| 320 | P320V | 1.08 | 0.88 |
| 320 | P320W | 0.90 | 1.03 |
| 320 | P320Y | 1.05 | 1.03 |
| 338 | L338A | 1.36 | 1.29 |
| 338 | L338C | 1.24 | 0.67 |
| 338 | L338D | 1.00 | 0.94 |
| 338 | L338E | 0.87 | 0.65 |
| 338 | L338F | 0.90 | 0.17 |
| 338 | L338G | 1.38 | 1.34 |
| 338 | L338H | *0.05* | *0.05* |
| 338 | L338I | 1.12 | 1.32 |
| 338 | L338K | *0.05* | *0.05* |
| 338 | L338M | 1.20 | 1.27 |
| 338 | L338P | 1.11 | 1.23 |
| 338 | L338Q | 0.96 | 0.61 |
| 338 | L338R | *0.05* | *0.05* |
| 338 | L338S | 1.13 | 1.51 |
| 338 | L338T | 1.42 | 1.05 |
| 338 | L338V | 1.14 | 1.55 |
| 338 | L338W | 0.98 | 0.14 |
| 338 | L338Y | 1.15 | 0.11 |
| 339 | Q339A | 1.08 | 1.13 |
| 339 | Q339C | 0.88 | 0.79 |
| 339 | Q339D | 0.93 | 0.11 |
| 339 | Q339E | 1.07 | 0.84 |
| 339 | Q339F | 0.86 | 0.55 |
| 339 | Q339G | 1.17 | 1.21 |
| 339 | Q339H | 1.03 | 1.04 |
| 339 | Q339K | 1.26 | 1.13 |
| 339 | Q339L | 1.12 | 0.70 |
| 339 | Q339M | 0.93 | 0.81 |
| 339 | Q339P | 1.02 | 1.24 |

TABLE 26-4-continued

Performance Indicies for stability and activity measurements for AmyS variants

| Position | Variant | Stability PI | Activity PI |
|---|---|---|---|
| 339 | Q339R | 0.81 | 0.35 |
| 339 | Q339S | 1.02 | 1.02 |
| 339 | Q339T | 1.35 | 1.01 |
| 339 | Q339V | 1.23 | 0.76 |
| 339 | Q339W | 0.05 | 0.05 |
| 339 | Q339Y | 1.14 | 0.78 |
| 340 | S340A | 1.23 | 1.43 |
| 340 | S340C | 0.74 | 0.75 |
| 340 | S340D | 0.97 | 1.63 |
| 340 | S340E | 0.92 | 1.58 |
| 340 | S340F | 0.83 | 0.82 |
| 340 | S340H | 1.12 | 1.45 |
| 340 | S340I | 1.07 | 1.07 |
| 340 | S340K | 0.99 | 1.76 |
| 340 | S340L | 0.05 | 0.05 |
| 340 | S340M | 1.24 | 1.20 |
| 340 | S340N | 1.10 | 1.75 |
| 340 | S340P | 0.69 | 0.81 |
| 340 | S340Q | 1.21 | 1.76 |
| 340 | S340T | 1.21 | 1.14 |
| 340 | S340V | 1.00 | 1.09 |
| 340 | S340Y | 1.02 | 0.97 |
| 343 | D343A | 0.96 | 0.35 |
| 343 | D343C | 1.32 | 0.74 |
| 343 | D343E | 1.00 | 1.07 |
| 343 | D343F | 0.91 | 0.79 |
| 343 | D343H | 0.98 | 1.02 |
| 343 | D343I | 1.27 | 0.88 |
| 343 | D343L | 0.95 | 1.08 |
| 343 | D343M | 0.99 | 1.02 |
| 343 | D343N | 1.05 | 0.88 |
| 343 | D343P | 1.30 | 1.03 |
| 343 | D343Q | 1.14 | 1.01 |
| 343 | D343R | 1.25 | 1.03 |
| 343 | D343T | 1.08 | 0.98 |
| 343 | D343W | 1.00 | 0.64 |
| 343 | D343Y | 1.29 | 0.82 |
| 345 | W345A | 1.05 | 0.90 |
| 345 | W345C | 0.97 | 0.43 |
| 345 | W345D | 1.10 | 1.15 |
| 345 | W345E | 1.06 | 1.24 |
| 345 | W345F | 1.07 | 0.55 |
| 345 | W345H | 1.15 | 1.10 |
| 345 | W345I | 1.28 | 0.90 |
| 345 | W345K | 0.05 | 0.05 |
| 345 | W345L | 1.07 | 0.99 |
| 345 | W345M | 1.02 | 1.01 |
| 345 | W345N | 1.07 | 1.10 |
| 345 | W345P | 1.00 | 0.94 |
| 345 | W345Q | 1.26 | 1.10 |
| 345 | W345S | 1.01 | 1.12 |
| 345 | W345T | 1.15 | 1.15 |
| 345 | W345V | 1.16 | 1.02 |
| 363 | C363A | 0.84 | 1.06 |
| 363 | C363D | 0.87 | 1.74 |
| 363 | C363E | 0.99 | 1.34 |
| 363 | C363F | 0.83 | 1.03 |
| 363 | C363G | 0.61 | 0.83 |
| 363 | C363H | 0.78 | 0.76 |
| 363 | C363I | 0.92 | 0.63 |
| 363 | C363L | 0.73 | 0.89 |
| 363 | C363M | 0.97 | 1.36 |
| 363 | C363N | 0.92 | 1.86 |
| 363 | C363P | 0.05 | 0.05 |
| 363 | C363Q | 0.88 | 1.78 |
| 363 | C363R | 0.05 | 0.05 |
| 363 | C363S | 0.88 | 1.35 |
| 363 | C363T | 1.15 | 0.18 |
| 363 | C363V | 1.02 | 0.99 |
| 363 | C363W | 0.35 | 0.70 |
| 363 | C363Y | 0.92 | 0.12 |
| 366 | Y366A | 0.96 | 1.14 |
| 366 | Y366C | 0.46 | 0.37 |
| 366 | Y366D | 0.52 | 1.18 |
| 366 | Y366E | 0.91 | 1.18 |
| 366 | Y366F | 0.91 | 0.87 |
| 366 | Y366G | 0.94 | 1.08 |
| 366 | Y366H | 1.07 | 1.12 |
| 366 | Y366I | 0.85 | 0.87 |
| 366 | Y366K | 0.72 | 0.82 |
| 366 | Y366L | 0.77 | 0.61 |
| 366 | Y366M | 0.92 | 0.79 |
| 366 | Y366N | 1.03 | 0.91 |
| 366 | Y366P | 0.54 | 0.78 |
| 366 | Y366Q | 1.03 | 1.49 |
| 366 | Y366R | 0.96 | 0.96 |
| 366 | Y366S | 1.07 | 1.02 |
| 366 | Y366T | 1.01 | 0.91 |
| 366 | Y366V | 1.04 | 0.94 |
| 366 | Y366W | 1.11 | 0.99 |
| 369 | Y369A | 0.05 | 0.05 |
| 369 | Y369C | 0.44 | 0.16 |
| 369 | Y369E | 0.98 | 0.87 |
| 369 | Y369F | 1.03 | 0.79 |
| 369 | Y369G | 0.86 | 0.33 |
| 369 | Y369H | 0.89 | 0.78 |
| 369 | Y369I | 1.33 | 0.91 |
| 369 | Y369K | 1.07 | 0.80 |
| 369 | Y369M | 1.06 | 1.02 |
| 369 | Y369P | 0.49 | 0.20 |
| 369 | Y369Q | 1.07 | 0.79 |
| 369 | Y369R | 1.11 | 0.95 |
| 369 | Y369S | 0.89 | 0.60 |
| 369 | Y369T | 1.28 | 0.68 |
| 369 | Y369V | 1.17 | 0.91 |
| 369 | Y369W | 1.09 | 0.95 |
| 370 | Y370A | 1.03 | 1.21 |
| 370 | Y370C | 0.44 | 0.19 |
| 370 | Y370D | 0.48 | 1.35 |
| 370 | Y370E | 0.98 | 1.35 |
| 370 | Y370F | 0.90 | 0.73 |
| 370 | Y370G | 1.21 | 1.18 |
| 370 | Y370H | 0.96 | 1.36 |
| 370 | Y370I | 0.99 | 1.00 |
| 370 | Y370K | 0.93 | 1.65 |
| 370 | Y370L | 0.93 | 0.88 |
| 370 | Y370M | 0.91 | 1.04 |
| 370 | Y370N | 1.04 | 1.41 |
| 370 | Y370P | 0.44 | 0.67 |
| 370 | Y370Q | 0.87 | 1.51 |
| 370 | Y370S | 1.06 | 1.50 |
| 370 | Y370T | 1.07 | 1.10 |
| 370 | Y370V | 1.05 | 1.13 |
| 370 | Y370W | 0.94 | 0.91 |
| 375 | Y375A | 1.03 | 1.39 |
| 375 | Y375C | 0.59 | 0.48 |
| 375 | Y375D | 0.96 | 1.52 |
| 375 | Y375E | 0.96 | 1.48 |
| 375 | Y375F | 0.90 | 1.00 |
| 375 | Y375G | 0.90 | 0.98 |
| 375 | Y375H | 0.98 | 1.16 |
| 375 | Y375I | 0.94 | 1.06 |
| 375 | Y375K | 0.96 | 1.43 |
| 375 | Y375L | 1.03 | 1.07 |
| 375 | Y375M | 0.98 | 1.05 |
| 375 | Y375N | 0.92 | 1.48 |
| 375 | Y375P | 0.92 | 0.89 |
| 375 | Y375Q | 0.92 | 1.56 |
| 375 | Y375R | 0.77 | 1.61 |
| 375 | Y375S | 0.92 | 1.29 |
| 375 | Y375T | 1.25 | 1.04 |
| 375 | Y375W | 0.98 | 0.88 |
| 379 | S379A | 1.01 | 1.02 |
| 379 | S379C | 0.60 | 0.44 |
| 379 | S379D | 0.92 | 0.96 |
| 379 | S379E | 0.99 | 1.01 |
| 379 | S379F | 0.48 | 0.43 |
| 379 | S379G | 0.90 | 0.91 |

TABLE 26-4-continued

Performance Indicies for stability and activity measurements for AmyS variants

| Position | Variant | Stability PI | Activity PI |
|---|---|---|---|
| 379 | S379H | *0.05* | *0.05* |
| 379 | S379I | 0.80 | 0.70 |
| 379 | S379K | 1.00 | 1.12 |
| 379 | S379L | 0.84 | 0.56 |
| 379 | S379M | 0.87 | 0.80 |
| 379 | S379N | 1.03 | 0.98 |
| 379 | S379P | 0.61 | 0.39 |
| 379 | S379Q | 0.94 | 0.98 |
| 379 | S379R | 0.96 | 1.01 |
| 379 | S379T | 1.07 | 0.95 |
| 379 | S379V | 0.90 | 0.75 |
| 379 | S379W | 0.70 | 0.35 |
| 379 | S379Y | 0.92 | 0.59 |
| 381 | K381A | 0.85 | 0.78 |
| 381 | K381C | 0.86 | 0.35 |
| 381 | K381D | 0.87 | 0.65 |
| 381 | K381E | 0.93 | 0.81 |
| 381 | K381F | 0.96 | 0.20 |
| 381 | K381G | 0.96 | 0.82 |
| 381 | K381H | 1.13 | 0.73 |
| 381 | K381I | 0.98 | 0.36 |
| 381 | K381L | 0.95 | 0.38 |
| 381 | K381M | 0.93 | 0.56 |
| 381 | K381N | 0.87 | 0.68 |
| 381 | K381P | 1.18 | 0.39 |
| 381 | K381Q | 1.03 | 0.90 |
| 381 | K381R | 1.20 | 0.95 |
| 381 | K381S | 1.18 | 0.89 |
| 381 | K381T | 1.01 | 0.60 |
| 381 | K381V | 1.00 | 0.43 |
| 381 | K381W | 0.90 | 0.22 |
| 381 | K381Y | 0.87 | 0.63 |
| 385 | D385A | 1.01 | 0.88 |
| 385 | D385C | *0.05* | *0.05* |
| 385 | D385E | 0.89 | 1.05 |
| 385 | D385F | 0.73 | 0.54 |
| 385 | D385G | 1.05 | 0.88 |
| 385 | D385H | 0.96 | 0.99 |
| 385 | D385I | 0.46 | 0.15 |
| 385 | D385K | 1.00 | 1.06 |
| 385 | D385L | 0.96 | 0.47 |
| 385 | D385N | 0.91 | 0.96 |
| 385 | D385P | *0.05* | *0.05* |
| 385 | D385Q | 1.02 | 1.01 |
| 385 | D385R | 0.86 | 0.95 |
| 385 | D385S | 1.10 | 1.00 |
| 385 | D385T | 1.22 | 0.92 |
| 385 | D385V | 0.85 | 0.43 |
| 385 | D385W | 0.98 | 0.53 |
| 386 | P386A | 0.90 | 0.80 |
| 386 | P386C | 0.72 | 0.69 |
| 386 | P386D | 0.85 | 0.94 |
| 386 | P386E | 0.94 | 0.87 |
| 386 | P386F | 0.72 | 0.66 |
| 386 | P386G | 1.02 | 0.77 |
| 386 | P386H | 0.89 | 0.93 |
| 386 | P386I | 1.12 | 0.73 |
| 386 | P386K | 1.22 | 0.87 |
| 386 | P386L | 0.96 | 0.73 |
| 386 | P386M | 0.94 | 0.70 |
| 386 | P386N | 0.91 | 0.86 |
| 386 | P386Q | 0.95 | 0.86 |
| 386 | P386S | 0.83 | 0.82 |
| 386 | P386T | 1.00 | 0.54 |
| 386 | P386V | 1.11 | 0.79 |
| 386 | P386W | 0.90 | 0.44 |
| 386 | P386Y | 0.91 | 0.78 |
| 391 | R391A | 0.58 | 0.22 |
| 391 | R391C | 0.28 | 0.12 |
| 391 | R391E | *0.05* | 0.08 |
| 391 | R391G | 0.42 | 0.16 |
| 391 | R391H | 0.59 | 0.29 |
| 391 | R391K | 0.88 | 0.59 |
| 391 | R391L | *0.05* | *0.05* |
| 391 | R391N | 0.71 | 0.38 |
| 391 | R391P | *0.05* | *0.05* |
| 391 | R391Q | 0.62 | 0.28 |
| 391 | R391S | *0.05* | 0.33 |
| 391 | R391T | 0.67 | 0.25 |
| 391 | R391V | 0.24 | 0.09 |
| 391 | R391W | *0.05* | *0.05* |
| 391 | R391Y | *0.05* | *0.05* |
| 392 | R392A | 0.89 | 0.73 |
| 392 | R392C | 0.74 | 0.66 |
| 392 | R392E | 0.79 | 0.46 |
| 392 | R392F | 1.03 | 0.43 |
| 392 | R392G | 0.99 | 0.65 |
| 392 | R392H | 0.86 | 0.96 |
| 392 | R392I | 1.08 | 0.57 |
| 392 | R392K | 1.10 | 1.09 |
| 392 | R392L | 0.91 | 0.63 |
| 392 | R392M | 1.07 | 0.72 |
| 392 | R392N | 0.89 | 0.90 |
| 392 | R392P | 0.67 | 0.31 |
| 392 | R392Q | 1.12 | 0.75 |
| 392 | R392S | 1.00 | 0.73 |
| 392 | R392T | 1.00 | 0.91 |
| 392 | R392V | 0.89 | 0.48 |
| 392 | R392W | 0.68 | 0.23 |
| 392 | R392Y | 1.00 | 0.60 |
| 393 | D393A | 0.98 | 0.77 |
| 393 | D393C | 0.69 | 0.48 |
| 393 | D393E | 0.92 | 0.81 |
| 393 | D393F | 0.84 | 0.61 |
| 393 | D393G | 1.08 | 0.75 |
| 393 | D393H | 0.88 | 0.75 |
| 393 | D393I | *0.05* | *0.05* |
| 393 | D393K | 1.09 | 0.80 |
| 393 | D393L | 1.04 | 0.70 |
| 393 | D393N | *0.05* | *0.05* |
| 393 | D393P | *0.05* | *0.05* |
| 393 | D393Q | 1.00 | 0.82 |
| 393 | D393R | 0.88 | 0.64 |
| 393 | D393S | 0.92 | 0.91 |
| 393 | D393T | 1.12 | 0.90 |
| 393 | D393V | 1.04 | 0.63 |
| 393 | D393W | 0.95 | 0.66 |
| 393 | D393Y | 1.01 | 0.66 |
| 394 | Y394A | 0.91 | 0.86 |
| 394 | Y394D | 0.98 | 0.84 |
| 394 | Y394E | 0.92 | 1.03 |
| 394 | Y394F | 1.07 | 0.98 |
| 394 | Y394G | 1.13 | 0.85 |
| 394 | Y394H | 1.04 | 0.99 |
| 394 | Y394I | 1.11 | 0.95 |
| 394 | Y394K | 1.09 | 1.07 |
| 394 | Y394L | 1.22 | 1.11 |
| 394 | Y394M | 0.74 | 0.23 |
| 394 | Y394N | 1.00 | 1.01 |
| 394 | Y394P | *0.05* | *0.05* |
| 394 | Y394Q | 1.09 | 1.13 |
| 394 | Y394S | 1.11 | 1.15 |
| 394 | Y394V | 3.00 | 0.75 |
| 394 | Y394W | 1.11 | 1.16 |
| 400 | H400A | 1.24 | 0.89 |
| 400 | H400C | 1.16 | 0.73 |
| 400 | H400D | 1.05 | 0.82 |
| 400 | H400E | 0.99 | 0.95 |
| 400 | H400F | 1.01 | 0.94 |
| 400 | H400G | 0.90 | 0.83 |
| 400 | H400I | 1.04 | 0.91 |
| 400 | H400K | 0.92 | 1.03 |
| 400 | H400L | 0.90 | 0.88 |
| 400 | H400M | 1.01 | 0.91 |
| 400 | H400N | 1.26 | 0.92 |
| 400 | H400P | *0.05* | *0.05* |
| 400 | H400Q | 0.96 | 0.94 |
| 400 | H400R | 1.03 | 0.87 |

TABLE 26-4-continued

Performance Indicies for stability and activity measurements for AmyS variants

| Position | Variant | Stability PI | Activity PI |
|---|---|---|---|
| 400 | H400S | 0.94 | 0.92 |
| 400 | H400T | 0.95 | 0.88 |
| 400 | H400V | 1.28 | 0.91 |
| 400 | H400W | 1.17 | 0.80 |
| 400 | H400Y | 1.15 | 0.92 |
| 402 | Y402A | 1.07 | 0.97 |
| 402 | Y402C | 0.92 | 0.76 |
| 402 | Y402D | 0.90 | 0.80 |
| 402 | Y402E | 1.09 | 0.77 |
| 402 | Y402F | 0.89 | 0.82 |
| 402 | Y402G | 0.92 | 0.81 |
| 402 | Y402H | 1.21 | 0.91 |
| 402 | Y402I | 1.36 | 0.75 |
| 402 | Y402K | 0.95 | 0.84 |
| 402 | Y402L | 1.09 | 0.49 |
| 402 | Y402M | 1.14 | 0.88 |
| 402 | Y402N | 1.06 | 0.86 |
| 402 | Y402P | 1.03 | 0.28 |
| 402 | Y402Q | 0.98 | 0.83 |
| 402 | Y402R | 1.16 | 0.75 |
| 402 | Y402T | 1.32 | 1.02 |
| 402 | Y402V | 1.40 | 0.95 |
| 402 | Y402W | 1.24 | 0.89 |
| 403 | L403A | 1.20 | 0.89 |
| 403 | L403C | 1.10 | 0.98 |
| 403 | L403D | 1.03 | 0.95 |
| 403 | L403E | 1.26 | 0.93 |
| 403 | L403F | 1.03 | 0.74 |
| 403 | L403G | 1.22 | 0.96 |
| 403 | L403H | 1.10 | 0.90 |
| 403 | L403M | 1.11 | 0.99 |
| 403 | L403N | 0.98 | 0.95 |
| 403 | L403P | 0.78 | 0.47 |
| 403 | L403Q | 1.24 | 0.98 |
| 403 | L403R | 1.36 | 1.01 |
| 403 | L403S | 1.17 | 1.00 |
| 403 | L403T | 1.53 | 0.99 |
| 403 | L403V | 1.34 | 1.00 |
| 403 | L403W | 1.15 | 0.85 |
| 403 | L403Y | 1.16 | 0.97 |
| 404 | D404A | 1.12 | 0.73 |
| 404 | D404C | 1.28 | 0.61 |
| 404 | D404E | 1.38 | 0.78 |
| 404 | D404G | 1.25 | 0.77 |
| 404 | D404I | 1.20 | 0.84 |
| 404 | D404K | 1.10 | 0.83 |
| 404 | D404L | 1.09 | 0.91 |
| 404 | D404M | 1.13 | 0.76 |
| 404 | D404N | 1.13 | 0.98 |
| 404 | D404P | 1.05 | 0.56 |
| 404 | D404Q | 1.17 | 0.91 |
| 404 | D404R | 1.15 | 0.77 |
| 404 | D404S | 1.19 | 0.99 |
| 404 | D404V | 1.28 | 0.79 |
| 404 | D404W | 1.05 | 0.76 |
| 404 | D404Y | 1.08 | 0.81 |
| 406 | S406A | 0.99 | 0.99 |
| 406 | S406C | 1.11 | 0.85 |
| 406 | S406D | 0.93 | 1.02 |
| 406 | S406E | 0.95 | 0.91 |
| 406 | S406F | 0.86 | 0.88 |
| 406 | S406G | 0.93 | 0.86 |
| 406 | S406H | 0.88 | 0.98 |
| 406 | S406I | 0.92 | 0.91 |
| 406 | S406K | 0.95 | 0.82 |
| 406 | S406L | 0.94 | 0.98 |
| 406 | S406M | 0.89 | 0.90 |
| 406 | S406N | 1.09 | 0.94 |
| 406 | S406P | 0.91 | 0.93 |
| 406 | S406Q | *0.05* | *0.05* |
| 406 | S406T | 1.18 | 0.97 |
| 406 | S406V | 1.14 | 0.87 |
| 406 | S406Y | 0.99 | 0.80 |
| 407 | D407C | 1.14 | 0.41 |
| 407 | D407E | 0.82 | 0.59 |
| 407 | D407F | 0.88 | 0.35 |
| 407 | D407G | 1.10 | 0.38 |
| 407 | D407H | 0.85 | 0.63 |
| 407 | D407I | 1.05 | 0.22 |
| 407 | D407K | 1.00 | 0.44 |
| 407 | D407L | 0.91 | 0.18 |
| 407 | D407M | 1.05 | 0.37 |
| 407 | D407N | 1.11 | 0.96 |
| 407 | D407P | *0.05* | *0.05* |
| 407 | D407Q | 0.94 | 0.53 |
| 407 | D407R | 0.78 | 0.36 |
| 407 | D407S | 0.93 | 0.65 |
| 407 | D407T | 1.06 | 0.49 |
| 407 | D407V | 0.93 | 0.29 |
| 407 | D407W | 1.06 | 0.20 |
| 407 | D407Y | 0.85 | 0.38 |
| 410 | G410A | 0.90 | 1.00 |
| 410 | G410C | 1.04 | 0.81 |
| 410 | G410D | *0.05* | *0.05* |
| 410 | G410E | *0.05* | *0.05* |
| 410 | G410F | 0.96 | 0.22 |
| 410 | G410H | 0.93 | 0.34 |
| 410 | G410I | *0.05* | *0.05* |
| 410 | G410L | *0.05* | *0.05* |
| 410 | G410M | 1.13 | 0.35 |
| 410 | G410N | 0.99 | 0.27 |
| 410 | G410P | *0.05* | *0.05* |
| 410 | G410Q | 1.05 | 0.14 |
| 410 | G410R | 0.98 | 0.27 |
| 410 | G410T | 1.08 | 0.70 |
| 410 | G410V | 1.10 | 0.42 |
| 410 | G410W | *0.05* | *0.05* |
| 410 | G410Y | 0.92 | 0.49 |
| 413 | R413A | 1.02 | 1.06 |
| 413 | R413D | 0.71 | 0.40 |
| 413 | R413E | 0.86 | 0.67 |
| 413 | R413G | 1.19 | 0.33 |
| 413 | R413H | 1.06 | 0.95 |
| 413 | R413I | 0.96 | 0.75 |
| 413 | R413K | 1.08 | 0.95 |
| 413 | R413L | 1.02 | 0.96 |
| 413 | R413M | 0.81 | 0.81 |
| 413 | R413N | 0.93 | 0.72 |
| 413 | R413P | *0.05* | *0.05* |
| 413 | R413Q | 0.81 | 0.35 |
| 413 | R413S | 0.85 | 0.87 |
| 413 | R413T | *0.05* | 0.74 |
| 413 | R413V | 0.93 | 0.73 |
| 413 | R413W | 0.92 | 0.41 |
| 413 | R413Y | 0.73 | 0.49 |
| 414 | E414A | 1.06 | 0.70 |
| 414 | E414C | 1.05 | 0.55 |
| 414 | E414D | 1.13 | 0.75 |
| 414 | E414F | 0.81 | 0.59 |
| 414 | E414G | 0.82 | 0.68 |
| 414 | E414H | 0.89 | 0.65 |
| 414 | E414I | 0.98 | 0.60 |
| 414 | E414K | 0.96 | 0.65 |
| 414 | E414L | 1.16 | 0.71 |
| 414 | E414M | 0.88 | 0.72 |
| 414 | E414N | 0.99 | 0.57 |
| 414 | E414P | 0.85 | 0.60 |
| 414 | E414Q | 0.85 | 0.70 |
| 414 | E414R | 1.00 | 0.65 |
| 414 | E414S | 0.91 | 0.63 |
| 414 | E414T | 0.79 | 0.67 |
| 414 | E414W | 1.03 | 0.25 |
| 414 | E414Y | 0.78 | 0.58 |
| 416 | V416A | 0.93 | 0.67 |
| 416 | V416C | 0.94 | 0.61 |
| 416 | V416D | 1.05 | 0.71 |
| 416 | V416F | *0.05* | *0.05* |
| 416 | V416H | 0.92 | 0.78 |

TABLE 26-4-continued

Performance Indicies for stability and activity measurements for AmyS variants

| Position | Variant | Stability PI | Activity PI |
|---|---|---|---|
| 416 | V416I | 0.83 | 0.74 |
| 416 | V416K | 0.71 | 0.65 |
| 416 | V416L | 0.96 | 0.81 |
| 416 | V416M | 1.06 | 0.78 |
| 416 | V416N | 0.92 | 0.66 |
| 416 | V416P | 1.18 | 0.53 |
| 416 | V416Q | 1.02 | 0.74 |
| 416 | V416R | 1.02 | 0.29 |
| 416 | V416S | 1.15 | 0.46 |
| 416 | V416T | 1.01 | 0.65 |
| 416 | V416W | 0.83 | 0.55 |
| 416 | V416Y | 0.89 | 0.69 |
| 419 | K419A | 1.36 | 1.29 |
| 419 | K419C | 1.24 | 0.67 |
| 419 | K419D | 1.00 | 0.94 |
| 419 | K419E | 0.87 | 0.65 |
| 419 | K419F | 0.90 | 0.17 |
| 419 | K419H | *0.05* | *0.05* |
| 419 | K419I | 1.12 | 1.32 |
| 419 | K419L | *0.05* | *0.05* |
| 419 | K419M | 1.20 | 1.27 |
| 419 | K419N | *0.05* | *0.05* |
| 419 | K419P | 1.11 | 1.23 |
| 419 | K419Q | 0.96 | 0.61 |
| 419 | K419R | *0.05* | *0.05* |
| 419 | K419S | 1.13 | 1.51 |
| 419 | K419T | 1.42 | 1.05 |
| 419 | K419V | 1.14 | 1.55 |
| 419 | K419W | 0.98 | 0.14 |
| 419 | K419Y | 1.15 | 0.11 |
| 422 | S422A | 0.64 | 0.97 |
| 422 | S422C | 0.96 | 0.71 |
| 422 | S422D | 0.97 | 0.96 |
| 422 | S422E | 1.31 | 0.78 |
| 422 | S422F | 0.96 | 0.71 |
| 422 | S422G | 1.20 | 0.99 |
| 422 | S422H | 1.06 | 0.66 |
| 422 | S422I | 1.11 | 0.85 |
| 422 | S422K | 1.16 | 0.96 |
| 422 | S422L | 0.99 | 0.74 |
| 422 | S422M | 1.04 | 0.94 |
| 422 | S422N | 1.12 | 1.03 |
| 422 | S422P | 0.84 | 0.70 |
| 422 | S422Q | 0.15 | 0.82 |
| 422 | S422R | 1.02 | 0.94 |
| 422 | S422T | 0.97 | 0.92 |
| 422 | S422V | 1.17 | 0.88 |
| 422 | S422W | 0.96 | 0.70 |
| 422 | S422Y | 1.09 | 0.92 |
| 427 | L427A | 0.93 | 0.66 |
| 427 | L427C | 1.02 | 0.68 |
| 427 | L427D | *0.05* | *0.05* |
| 427 | L427E | 0.86 | 0.27 |
| 427 | L427F | 0.89 | 0.30 |
| 427 | L427G | 0.63 | 0.26 |
| 427 | L427H | *0.05* | *0.05* |
| 427 | L427I | 1.08 | 0.64 |
| 427 | L427K | *0.05* | *0.05* |
| 427 | L427M | 0.86 | 0.79 |
| 427 | L427N | 0.76 | 0.31 |
| 427 | L427P | 1.13 | 0.06 |
| 427 | L427Q | 0.95 | 0.53 |
| 427 | L427R | *0.05* | *0.05* |
| 427 | L427S | 0.78 | 0.27 |
| 427 | L427T | 0.80 | 0.70 |
| 427 | L427V | 0.82 | 0.72 |
| 427 | L427W | *0.05* | *0.05* |
| 427 | L427Y | *0.05* | *0.05* |
| 433 | G433A | 1.27 | 1.08 |
| 433 | G433C | 1.15 | 0.69 |
| 433 | G433D | 1.05 | 0.96 |
| 433 | G433E | 0.92 | 0.99 |
| 433 | G433F | 1.04 | 0.92 |
| 433 | G433H | 1.27 | 0.99 |
| 433 | G433I | 1.37 | 0.86 |
| 433 | G433K | 1.27 | 1.05 |
| 433 | G433L | 1.30 | 0.90 |
| 433 | G433M | 1.23 | 1.01 |
| 433 | G433N | 1.07 | 0.75 |
| 433 | G433P | 1.13 | 0.95 |
| 433 | G433Q | 0.78 | 0.99 |
| 433 | G433R | 1.00 | 0.91 |
| 433 | G433S | 1.17 | 0.96 |
| 433 | G433T | 1.17 | 0.90 |
| 433 | G433V | 1.27 | 0.95 |
| 433 | G433Y | 1.26 | 1.01 |
| 436 | K436A | 0.92 | 0.94 |
| 436 | K436C | 0.90 | 0.84 |
| 436 | K436D | 0.86 | 0.93 |
| 436 | K436E | 0.70 | 0.87 |
| 436 | K436F | 0.81 | 0.64 |
| 436 | K436G | 0.84 | 0.77 |
| 436 | K436H | 1.09 | 0.89 |
| 436 | K436I | 1.08 | 0.81 |
| 436 | K436L | 1.01 | 0.78 |
| 436 | K436M | 0.76 | 0.85 |
| 436 | K436N | 0.98 | 0.92 |
| 436 | K436P | 0.88 | 0.71 |
| 436 | K436Q | 1.01 | 0.96 |
| 436 | K436R | 1.06 | 0.79 |
| 436 | K436S | 0.75 | 0.92 |
| 436 | K436T | 0.95 | 0.90 |
| 436 | K436V | 0.98 | 0.87 |
| 436 | K436W | 1.07 | 0.71 |
| 436 | K436Y | 0.99 | 0.80 |
| 439 | Y439A | 1.02 | 0.78 |
| 439 | Y439D | 1.01 | 0.85 |
| 439 | Y439E | *0.05* | *0.05* |
| 439 | Y439F | 0.77 | 0.78 |
| 439 | Y439G | 1.01 | 0.77 |
| 439 | Y439H | 0.96 | 0.73 |
| 439 | Y439I | *0.05* | *0.05* |
| 439 | Y439K | 0.96 | 0.74 |
| 439 | Y439L | *0.05* | *0.05* |
| 439 | Y439M | 1.04 | 0.77 |
| 439 | Y439N | 0.96 | 0.83 |
| 439 | Y439P | 0.87 | 0.85 |
| 439 | Y439Q | 0.90 | 0.88 |
| 439 | Y439R | 0.75 | 0.80 |
| 439 | Y439S | 0.94 | 0.82 |
| 439 | Y439T | 0.84 | 0.79 |
| 439 | Y439V | 1.04 | 0.70 |
| 439 | Y439W | 0.86 | 0.72 |
| 442 | K442A | 1.38 | 0.98 |
| 442 | K442C | *0.05* | *0.05* |
| 442 | K442F | 1.04 | 0.97 |
| 442 | K442G | 1.23 | 1.02 |
| 442 | K442H | 1.07 | 1.04 |
| 442 | K442I | 1.13 | 0.93 |
| 442 | K442N | 1.39 | 1.03 |
| 442 | K442P | 1.11 | 1.03 |
| 442 | K442Q | 1.11 | 1.05 |
| 442 | K442R | 1.33 | 1.01 |
| 442 | K442S | 1.24 | 1.07 |
| 442 | K442T | 1.34 | 1.06 |
| 442 | K442V | 1.20 | 0.99 |
| 442 | K442W | 1.32 | 0.98 |
| 442 | K442Y | 1.24 | 1.08 |
| 445 | A445C | 0.98 | 0.83 |
| 445 | A445D | 1.04 | 0.87 |
| 445 | A445G | 1.21 | 1.01 |
| 445 | A445H | 0.90 | 0.93 |
| 445 | A445I | 1.25 | 0.84 |
| 445 | A445K | 1.20 | 0.11 |
| 445 | A445L | 1.17 | 0.92 |
| 445 | A445N | 1.20 | 0.91 |
| 445 | A445P | 0.91 | 0.77 |
| 445 | A445Q | *0.05* | *0.05* |

TABLE 26-4-continued

Performance Indicies for stability and activity measurements for AmyS variants

| Position | Variant | Stability PI | Activity PI |
|---|---|---|---|
| 445 | A445R | 0.91 | 0.89 |
| 445 | A445S | 1.16 | 0.94 |
| 445 | A445T | 1.29 | 0.88 |
| 445 | A445V | 1.27 | 0.93 |
| 445 | A445W | 1.25 | 0.80 |
| 447 | K447A | 1.09 | 1.06 |
| 447 | K447C | 1.11 | 0.87 |
| 447 | K447D | 1.00 | 0.99 |
| 447 | K447F | 1.09 | 0.84 |
| 447 | K447G | 1.06 | 0.94 |
| 447 | K447H | 1.13 | 0.92 |
| 447 | K447I | 1.22 | 0.91 |
| 447 | K447L | 1.06 | 1.01 |
| 447 | K447M | 1.07 | 0.96 |
| 447 | K447N | 1.43 | 0.97 |
| 447 | K447Q | 1.34 | 1.00 |
| 447 | K447R | 1.10 | 0.96 |
| 447 | K447S | 0.90 | 0.92 |
| 447 | K447T | 1.21 | 0.37 |
| 447 | K447V | 0.69 | 0.86 |
| 447 | K447W | 1.31 | 0.89 |
| 447 | K447Y | 1.21 | 0.96 |
| 448 | V448A | 0.98 | 0.96 |
| 448 | V448C | 1.36 | 0.98 |
| 448 | V448D | 1.15 | 1.02 |
| 448 | V448E | *0.05* | *0.05* |
| 448 | V448F | 1.48 | 1.01 |
| 448 | V448G | 1.26 | 1.05 |
| 448 | V448H | 1.37 | 1.03 |
| 448 | V448I | 1.44 | 0.97 |
| 448 | V448K | 1.20 | 1.07 |
| 448 | V448L | 1.04 | 1.08 |
| 448 | V448M | 1.13 | 0.97 |
| 448 | V448N | 1.24 | 0.70 |
| 448 | V448P | 0.84 | 1.19 |
| 448 | V448Q | 1.18 | 1.16 |
| 448 | V448R | *0.05* | *0.05* |
| 448 | V448S | 1.20 | 1.10 |
| 448 | V448T | *0.05* | *0.05* |
| 448 | V448W | 1.08 | 0.89 |
| 448 | V448Y | 1.33 | 1.27 |
| 450 | Y450A | 0.95 | 0.94 |
| 450 | Y450C | 1.22 | 0.84 |
| 450 | Y450D | 1.19 | 0.95 |
| 450 | Y450E | 1.01 | 0.92 |
| 450 | Y450G | 1.02 | 0.93 |
| 450 | Y450H | 1.23 | 0.90 |
| 450 | Y450K | 1.18 | 0.94 |
| 450 | Y450L | 0.93 | 0.69 |
| 450 | Y450M | 1.29 | 0.89 |
| 450 | Y450N | 1.23 | 0.96 |
| 450 | Y450P | 0.75 | 0.30 |
| 450 | Y450Q | 1.00 | 0.95 |
| 450 | Y450R | 1.22 | 1.02 |
| 450 | Y450S | 1.22 | 1.01 |
| 450 | Y450T | 1.32 | 0.96 |
| 450 | Y450V | *0.05* | *0.05* |
| 450 | Y450W | 1.21 | 0.95 |
| 452 | L452A | 1.08 | 1.06 |
| 452 | L452C | 1.00 | 1.01 |
| 452 | L452D | 0.98 | 1.08 |
| 452 | L452E | 0.75 | 0.55 |
| 452 | L452F | 0.79 | 0.93 |
| 452 | L452G | 1.07 | 1.00 |
| 452 | L452H | 1.05 | 0.99 |
| 452 | L452K | 1.11 | 1.08 |
| 452 | L452M | 1.13 | 1.09 |
| 452 | L452N | 1.06 | 1.28 |
| 452 | L452P | 1.02 | 0.78 |
| 452 | L452Q | 0.92 | 1.22 |
| 452 | L452R | 0.93 | 1.26 |
| 452 | L452S | 0.86 | 1.21 |
| 452 | L452T | 1.02 | 1.18 |
| 452 | L452V | 1.14 | 1.14 |
| 452 | L452Y | 1.17 | 1.07 |
| 455 | N455A | 1.07 | 1.04 |
| 455 | N455C | 0.85 | 0.89 |
| 455 | N455D | 1.07 | 0.97 |
| 455 | N455E | 1.14 | 0.94 |
| 455 | N455G | 1.23 | 1.00 |
| 455 | N455H | 1.05 | 1.01 |
| 455 | N455I | 1.23 | 0.95 |
| 455 | N455K | 1.10 | 1.08 |
| 455 | N455L | 1.06 | 0.97 |
| 455 | N455M | 0.95 | 0.96 |
| 455 | N455P | 1.36 | 0.93 |
| 455 | N455Q | 0.96 | 0.91 |
| 455 | N455R | 1.13 | 1.02 |
| 455 | N455S | 1.04 | 0.91 |
| 455 | N455T | 1.16 | 0.90 |
| 455 | N455V | 1.26 | 0.89 |
| 455 | N455W | 1.12 | 0.76 |
| 455 | N455Y | 1.08 | 0.15 |
| 463 | N463A | 1.25 | 1.06 |
| 463 | N463D | 0.97 | 1.02 |
| 463 | N463F | 1.04 | 0.87 |
| 463 | N463G | 1.04 | 1.00 |
| 463 | N463H | 1.12 | 0.99 |
| 463 | N463I | *0.05* | *0.05* |
| 463 | N463K | 1.07 | 1.00 |
| 463 | N463L | 1.16 | 1.01 |
| 463 | N463M | 1.24 | 1.08 |
| 463 | N463P | 0.93 | 1.05 |
| 463 | N463Q | 0.98 | 1.04 |
| 463 | N463R | 0.95 | 0.93 |
| 463 | N463S | 1.27 | 0.96 |
| 463 | N463T | 1.38 | 0.91 |
| 463 | N463V | 1.32 | 0.86 |
| 463 | N463W | 1.45 | 0.74 |
| 463 | N463Y | 1.20 | 0.90 |
| 465 | D465A | 0.76 | 1.06 |
| 465 | D465C | 0.84 | 0.74 |
| 465 | D465E | 0.95 | 0.93 |
| 465 | D465F | 0.78 | 0.89 |
| 465 | D465G | 1.35 | 0.92 |
| 465 | D465H | 1.06 | 0.92 |
| 465 | D465I | 1.37 | 0.85 |
| 465 | D465K | 1.53 | 0.88 |
| 465 | D465L | 1.14 | 0.95 |
| 465 | D465M | 1.06 | 0.98 |
| 465 | D465N | 1.32 | 0.93 |
| 465 | D465P | 1.13 | 0.71 |
| 465 | D465Q | 0.86 | 0.94 |
| 465 | D465R | 1.18 | 0.90 |
| 465 | D465S | 0.87 | 0.98 |
| 465 | D465T | 1.42 | 0.92 |
| 465 | D465V | 1.24 | 0.93 |
| 465 | D465W | 1.00 | 0.83 |
| 465 | D465Y | 1.06 | 0.93 |
| 469 | E469A | 1.16 | 1.01 |
| 469 | E469C | 1.03 | 0.86 |
| 469 | E469D | 1.22 | 1.02 |
| 469 | E469F | 1.11 | 1.00 |
| 469 | E469G | 1.19 | 1.00 |
| 469 | E469H | 1.04 | 0.96 |
| 469 | E469K | 1.16 | 0.96 |
| 469 | E469L | 1.10 | 0.98 |
| 469 | E469M | *0.05* | *0.05* |
| 469 | E469N | 1.19 | 0.47 |
| 469 | E469P | 0.85 | 1.05 |
| 469 | E469Q | 1.03 | 1.04 |
| 469 | E469R | 1.01 | 0.75 |
| 469 | E469S | 0.91 | 1.08 |
| 469 | E469T | 1.15 | 1.06 |
| 469 | E469V | 1.15 | 1.08 |
| 469 | E469W | 1.24 | 0.97 |
| 469 | E469Y | 1.35 | 1.09 |
| 471 | K471A | 1.09 | 1.09 |

TABLE 26-4-continued

Performance Indicies for stability and activity measurements for AmyS variants

| Position | Variant | Stability PI | Activity PI |
|---|---|---|---|
| 471 | K471C | 1.04 | 0.91 |
| 471 | K471D | 1.01 | 1.06 |
| 471 | K471F | 1.10 | 1.05 |
| 471 | K471G | 1.13 | 1.12 |
| 471 | K471H | 1.00 | 1.10 |
| 471 | K471I | 1.22 | 1.02 |
| 471 | K471L | 0.99 | 1.07 |
| 471 | K471M | 0.95 | 1.14 |
| 471 | K471N | 1.04 | 1.12 |
| 471 | K471P | 0.84 | 0.98 |
| 471 | K471Q | 0.90 | 1.08 |
| 471 | K471R | 0.77 | 1.33 |
| 471 | K471S | 0.97 | 1.01 |
| 471 | K471T | 1.11 | 1.09 |
| 471 | K471V | 1.28 | 1.11 |
| 471 | K471Y | 1.15 | 1.36 |
| 473 | N473A | 1.03 | 0.99 |
| 473 | N473C | 1.15 | 0.74 |
| 473 | N473D | 1.14 | 0.98 |
| 473 | N473E | 1.20 | 0.99 |
| 473 | N473F | 1.10 | 0.83 |
| 473 | N473G | 1.35 | 0.99 |
| 473 | N473H | 1.02 | 0.91 |
| 473 | N473I | 0.66 | 0.45 |
| 473 | N473K | 1.02 | 1.02 |
| 473 | N473L | *0.05* | 0.97 |
| 473 | N473M | 1.11 | 1.00 |
| 473 | N473P | 1.01 | 0.95 |
| 473 | N473Q | 1.13 | 0.99 |
| 473 | N473R | 1.08 | 1.05 |
| 473 | N473S | 1.15 | 0.98 |
| 473 | N473T | 1.04 | 1.04 |
| 473 | N473V | *0.05* | *0.05* |
| 473 | N473W | 0.85 | 0.64 |
| 473 | N473Y | 1.23 | 0.86 |
| 476 | S476A | 1.51 | 1.02 |
| 476 | S476C | 0.91 | 0.89 |
| 476 | S476D | 0.98 | 0.91 |
| 476 | S476E | 1.08 | 0.91 |
| 476 | S476F | 1.09 | 0.87 |
| 476 | S476G | 1.22 | 0.97 |
| 476 | S476H | 1.07 | 0.96 |
| 476 | S476I | 1.03 | 0.78 |
| 476 | S476K | 1.01 | 0.97 |
| 476 | S476L | 1.46 | 0.93 |
| 476 | S476M | 1.58 | 1.08 |
| 476 | S476N | 1.61 | 0.98 |
| 476 | S476P | 1.02 | 0.62 |
| 476 | S476Q | 1.13 | 1.03 |
| 476 | S476R | 1.01 | 1.08 |
| 476 | S476T | 1.78 | 1.01 |
| 476 | S476V | 1.21 | 0.89 |
| 476 | S476W | 1.43 | 0.78 |
| 476 | S476Y | 1.79 | 0.94 |

Table 26-5 lists AmyS variants which are combinable mutations (2,250) for the 152 positions. These variants have Performance index values 0.5 for at least one property (activity or stability) and >0.05 for both properties.

TABLE 26-5

Combinable mutations in AmyS

| POS | variant | Stability PI | Activity PI |
|---|---|---|---|
| 5 | N005A | 0.95 | 0.32 |
| 5 | N005C | 0.98 | 0.29 |
| 5 | N005E | 1.04 | 0.43 |
| 5 | N005F | 0.79 | 0.15 |
| 5 | N005G | 0.88 | 0.34 |
| 5 | N005H | 0.89 | 0.43 |
| 5 | N005I | 1.00 | 0.10 |
| 5 | N005K | 0.90 | 0.34 |
| 5 | N005L | 1.04 | 0.10 |
| 5 | N005M | 0.84 | 0.18 |
| 5 | N005P | 1.10 | 0.40 |
| 5 | N005Q | 1.07 | 0.58 |
| 5 | N005R | 0.94 | 0.40 |
| 5 | N005S | 0.98 | 0.35 |
| 5 | N005T | 0.83 | 0.35 |
| 5 | N005V | 0.88 | 0.16 |
| 5 | N005W | 0.94 | 0.07 |
| 5 | N005Y | 1.07 | 0.21 |
| 6 | G006A | 1.10 | 1.59 |
| 6 | G006D | 1.14 | 1.64 |
| 6 | G006E | 1.08 | 1.93 |
| 6 | G006H | 0.95 | 2.29 |
| 6 | G006I | 1.23 | 1.47 |
| 6 | G006K | 0.93 | 2.36 |
| 6 | G006L | 1.15 | 1.61 |
| 6 | G006M | 1.11 | 1.60 |
| 6 | G006N | 1.21 | 1.61 |
| 6 | G006P | 1.10 | 2.47 |
| 6 | G006Q | 1.26 | 1.34 |
| 6 | G006R | 0.98 | 1.28 |
| 6 | G006S | 1.12 | 1.86 |
| 6 | G006T | 1.21 | 2.01 |
| 6 | G006V | 1.29 | 1.54 |
| 6 | G006W | 1.13 | 1.32 |
| 6 | G006Y | 1.07 | 1.88 |
| 13 | E013A | 0.32 | 1.01 |
| 13 | E013C | 0.22 | 0.68 |
| 13 | E013D | 0.08 | 1.03 |
| 13 | E013G | 0.18 | 1.00 |
| 13 | E013H | 0.60 | 1.10 |
| 13 | E013I | 0.15 | 0.87 |
| 13 | E013K | 0.22 | 1.22 |
| 13 | E013L | 0.20 | 1.02 |
| 13 | E013M | 0.20 | 0.96 |
| 13 | E013Q | 0.21 | 0.96 |
| 13 | E013R | 0.28 | 1.04 |
| 13 | E013S | 0.28 | 0.92 |
| 13 | E013T | 0.19 | 0.79 |
| 13 | E013V | 0.19 | 0.76 |
| 13 | E013W | 0.05 | 0.76 |
| 13 | E013Y | 0.89 | 0.93 |
| 14 | W014A | 0.95 | 0.77 |
| 14 | W014C | 0.91 | 0.71 |
| 14 | W014D | 0.81 | 0.59 |
| 14 | W014E | 0.95 | 1.07 |
| 14 | W014F | 1.06 | 1.25 |
| 14 | W014G | 0.97 | 0.88 |
| 14 | W014I | 1.12 | 0.40 |
| 14 | W014K | 1.01 | 0.69 |
| 14 | W014L | 0.88 | 0.15 |
| 14 | W014M | 1.18 | 0.84 |
| 14 | W014N | 0.92 | 0.99 |
| 14 | W014P | 0.84 | 0.98 |
| 14 | W014Q | 0.94 | 0.67 |
| 14 | W014R | 0.97 | 0.67 |
| 14 | W014S | 0.97 | 1.02 |
| 14 | W014T | 1.22 | 1.22 |
| 14 | W014V | 1.17 | 0.81 |
| 14 | W014Y | 1.08 | 1.71 |
| 15 | Y015A | 1.05 | 1.48 |
| 15 | Y015C | 0.70 | 1.15 |
| 15 | Y015D | 0.77 | 1.82 |
| 15 | Y015E | 0.68 | 1.96 |
| 15 | Y015G | 0.69 | 1.89 |
| 15 | Y015H | 1.01 | 1.85 |
| 15 | Y015I | 0.63 | 0.91 |
| 15 | Y015K | 0.74 | 1.58 |
| 15 | Y015L | 0.67 | 0.76 |
| 15 | Y015M | 0.72 | 1.12 |

TABLE 26-5-continued

Combinable mutations in AmyS

| POS | variant | Stability PI | Activity PI |
|---|---|---|---|
| 15 | Y015N | 0.99 | 1.88 |
| 15 | Y015P | 0.57 | 1.59 |
| 15 | Y015Q | 0.80 | 1.74 |
| 15 | Y015R | 0.72 | 1.60 |
| 15 | Y015S | 0.58 | 1.78 |
| 15 | Y015T | 0.87 | 1.47 |
| 15 | Y015W | 0.95 | 1.44 |
| 16 | L016A | 0.81 | 1.31 |
| 16 | L016D | 0.93 | 1.12 |
| 16 | L016E | 1.09 | 1.21 |
| 16 | L016F | 2.17 | 0.98 |
| 16 | L016G | 0.61 | 1.35 |
| 16 | L016H | 0.96 | 1.21 |
| 16 | L016I | 0.79 | 1.12 |
| 16 | L016K | 0.79 | 1.41 |
| 16 | L016M | 0.94 | 1.15 |
| 16 | L016N | 0.92 | 1.32 |
| 16 | L016P | 0.35 | 1.30 |
| 16 | L016Q | 0.96 | 1.33 |
| 16 | L016R | 0.71 | 1.28 |
| 16 | L016S | 0.94 | 1.19 |
| 16 | L016T | 0.87 | 1.32 |
| 16 | L016V | 0.87 | 1.16 |
| 16 | L016W | 0.75 | 0.99 |
| 16 | L016Y | 0.97 | 1.10 |
| 18 | D018A | 1.08 | 0.89 |
| 18 | D018F | 0.68 | 0.58 |
| 18 | D018G | 0.88 | 0.87 |
| 18 | D018H | 0.84 | 0.84 |
| 18 | D018I | 0.79 | 0.70 |
| 18 | D018K | 0.88 | 0.65 |
| 18 | D018L | 0.60 | 0.72 |
| 18 | D018N | 0.73 | 1.01 |
| 18 | D018P | 0.84 | 1.04 |
| 18 | D018Q | 0.80 | 1.00 |
| 18 | D018R | 0.81 | 0.65 |
| 18 | D018S | 0.81 | 0.93 |
| 18 | D018T | 0.81 | 0.91 |
| 18 | D018V | 0.89 | 0.77 |
| 18 | D018W | 0.72 | 0.51 |
| 18 | D018Y | 0.72 | 0.87 |
| 20 | G020A | 0.79 | 0.25 |
| 20 | G020C | 0.58 | 0.24 |
| 20 | G020D | 0.92 | 0.96 |
| 20 | G020E | 0.89 | 0.95 |
| 20 | G020F | 0.65 | 0.13 |
| 20 | G020H | 0.75 | 0.11 |
| 20 | G020I | 0.96 | 0.28 |
| 20 | G020M | 0.69 | 0.10 |
| 20 | G020N | 0.78 | 0.09 |
| 20 | G020Q | 0.61 | 0.07 |
| 20 | G020T | 0.82 | 0.09 |
| 20 | G020V | 0.77 | 0.19 |
| 20 | G020W | 0.80 | 0.69 |
| 25 | K025A | 1.22 | 0.82 |
| 25 | K025C | 1.33 | 1.46 |
| 25 | K025D | 1.06 | 1.03 |
| 25 | K025E | 1.07 | 0.95 |
| 25 | K025F | 1.00 | 0.58 |
| 25 | K025G | 1.27 | 0.97 |
| 25 | K025H | 1.03 | 1.06 |
| 25 | K025L | 1.12 | 0.64 |
| 25 | K025M | 1.03 | 0.61 |
| 25 | K025N | 0.91 | 1.06 |
| 25 | K025P | 0.98 | 0.55 |
| 25 | K025Q | 1.24 | 1.07 |
| 25 | K025R | 1.08 | 0.96 |
| 25 | K025S | 1.07 | 0.98 |
| 25 | K025T | 1.14 | 0.89 |
| 25 | K025Y | 0.98 | 0.65 |
| 27 | A027C | 0.79 | 0.55 |
| 27 | A027D | 1.01 | 0.95 |
| 27 | A027E | 0.93 | 0.95 |
| 27 | A027F | 0.88 | 0.85 |
| 27 | A027G | 1.20 | 0.98 |
| 27 | A027H | 1.05 | 1.00 |
| 27 | A027I | 1.05 | 0.87 |
| 27 | A027K | 0.86 | 1.01 |
| 27 | A027L | 1.06 | 0.86 |
| 27 | A027M | 1.21 | 0.88 |
| 27 | A027N | 1.06 | 1.00 |
| 27 | A027P | 1.13 | 0.43 |
| 27 | A027Q | 1.00 | 0.96 |
| 27 | A027R | 1.11 | 0.89 |
| 27 | A027S | 1.16 | 0.97 |
| 27 | A027T | 1.20 | 0.90 |
| 27 | A027V | 1.20 | 0.82 |
| 27 | A027W | 1.13 | 0.76 |
| 27 | A027Y | 0.97 | 0.28 |
| 29 | E029A | 1.05 | 0.50 |
| 29 | E029D | 0.94 | 1.11 |
| 29 | E029G | 0.75 | 0.37 |
| 29 | E029H | 0.83 | 0.83 |
| 29 | E029K | 1.05 | 0.89 |
| 29 | E029L | 0.76 | 0.22 |
| 29 | E029M | 0.76 | 0.15 |
| 29 | E029N | 1.02 | 0.89 |
| 29 | E029P | 0.87 | 0.33 |
| 29 | E029Q | 1.04 | 0.86 |
| 29 | E029R | 1.09 | 0.92 |
| 29 | E029S | 0.97 | 0.83 |
| 29 | E029T | 0.95 | 0.59 |
| 29 | E029W | 0.74 | 0.10 |
| 36 | L036A | 0.95 | 0.85 |
| 36 | L036C | 0.83 | 0.43 |
| 36 | L036D | 0.91 | 0.27 |
| 36 | L036E | 0.90 | 0.40 |
| 36 | L036F | 1.14 | 0.90 |
| 36 | L036G | 0.92 | 0.34 |
| 36 | L036H | 0.92 | 0.77 |
| 36 | L036I | 1.17 | 0.89 |
| 36 | L036K | 1.01 | 1.05 |
| 36 | L036M | 1.05 | 1.05 |
| 36 | L036N | 1.02 | 0.68 |
| 36 | L036P | 0.90 | 0.06 |
| 36 | L036Q | 1.40 | 0.78 |
| 36 | L036R | 1.12 | 0.76 |
| 36 | L036S | 1.25 | 0.69 |
| 36 | L036T | 1.11 | 0.64 |
| 36 | L036V | 0.88 | 0.97 |
| 36 | L036W | 0.92 | 0.63 |
| 36 | L036Y | 1.07 | 0.91 |
| 39 | T039C | 1.09 | 1.05 |
| 39 | T039D | 1.15 | 1.47 |
| 39 | T039E | 1.15 | 1.32 |
| 39 | T039F | 1.16 | 0.48 |
| 39 | T039G | 1.23 | 1.05 |
| 39 | T039H | 1.16 | 1.10 |
| 39 | T039K | 1.12 | 1.10 |
| 39 | T039M | 1.18 | 0.54 |
| 39 | T039N | 1.14 | 1.64 |
| 39 | T039P | 1.11 | 0.26 |
| 39 | T039Q | 1.20 | 1.43 |
| 39 | T039R | 1.01 | 1.10 |
| 39 | T039S | 1.15 | 1.02 |
| 39 | T039V | 1.30 | 0.82 |
| 39 | T039W | 1.11 | 0.25 |
| 50 | T050A | 1.09 | 0.98 |
| 50 | T050C | 1.03 | 0.34 |
| 50 | T050D | 0.87 | 0.91 |
| 50 | T050F | 0.86 | 0.43 |
| 50 | T050G | 1.00 | 1.18 |
| 50 | T050H | 0.97 | 0.82 |
| 50 | T050I | 1.24 | 0.61 |
| 50 | T050K | 1.13 | 0.80 |
| 50 | T050L | 1.22 | 0.67 |
| 50 | T050M | 1.32 | 0.62 |
| 50 | T050N | 1.20 | 1.12 |
| 50 | T050P | 1.03 | 0.99 |
| 50 | T050Q | 1.31 | 1.08 |

TABLE 26-5-continued

Combinable mutations in AmyS

| POS | variant | Stability PI | Activity PI |
|---|---|---|---|
| 50 | T050R | 1.13 | 0.79 |
| 50 | T050S | 1.07 | 1.09 |
| 50 | T050V | 1.02 | 0.79 |
| 50 | T050W | 0.90 | 0.18 |
| 50 | T050Y | 1.14 | 0.42 |
| 52 | R052A | 0.99 | 1.02 |
| 52 | R052C | 0.87 | 0.62 |
| 52 | R052D | 0.76 | 0.85 |
| 52 | R052E | 0.77 | 0.97 |
| 52 | R052G | 0.96 | 0.93 |
| 52 | R052H | 0.91 | 0.99 |
| 52 | R052K | 0.93 | 1.02 |
| 52 | R052L | 1.10 | 0.98 |
| 52 | R052M | 1.01 | 1.00 |
| 52 | R052N | 0.95 | 0.99 |
| 52 | R052P | 1.05 | 0.95 |
| 52 | R052S | 1.21 | 0.92 |
| 52 | R052T | 1.11 | 1.00 |
| 52 | R052V | 1.14 | 0.95 |
| 52 | R052W | 1.00 | 0.83 |
| 52 | R052Y | 0.99 | 0.96 |
| 53 | S053A | 1.03 | 1.00 |
| 53 | S053C | 0.73 | 0.58 |
| 53 | S053D | 0.75 | 0.83 |
| 53 | S053E | 1.05 | 0.88 |
| 53 | S053F | 0.87 | 0.85 |
| 53 | S053G | 1.14 | 0.93 |
| 53 | S053H | 1.12 | 1.00 |
| 53 | S053I | 0.99 | 1.12 |
| 53 | S053K | 1.03 | 1.10 |
| 53 | S053L | 0.93 | 0.96 |
| 53 | S053M | 0.96 | 0.97 |
| 53 | S053P | 0.88 | 1.00 |
| 53 | S053Q | 0.94 | 0.94 |
| 53 | S053R | 0.83 | 1.15 |
| 53 | S053T | 1.25 | 1.02 |
| 53 | S053V | 1.11 | 0.94 |
| 53 | S053W | 1.09 | 0.84 |
| 53 | S053Y | 0.94 | 0.93 |
| 54 | D054A | 0.34 | 0.88 |
| 54 | D054C | 0.64 | 0.38 |
| 54 | D054G | 0.11 | 0.97 |
| 54 | D054H | 0.11 | 1.04 |
| 54 | D054I | 0.30 | 0.83 |
| 54 | D054M | 0.11 | 0.88 |
| 54 | D054N | 0.94 | 1.05 |
| 54 | D054R | 0.06 | 0.89 |
| 54 | D054S | 0.38 | 0.96 |
| 54 | D054T | 0.17 | 0.95 |
| 54 | D054V | 0.17 | 0.77 |
| 67 | E067C | 1.08 | 0.75 |
| 67 | E067D | 0.90 | 1.07 |
| 67 | E067G | 1.01 | 1.13 |
| 67 | E067H | 1.04 | 1.03 |
| 67 | E067K | 0.98 | 0.94 |
| 67 | E067L | 0.97 | 0.95 |
| 67 | E067M | 0.93 | 0.91 |
| 67 | E067N | 1.32 | 0.95 |
| 67 | E067Q | 0.93 | 0.95 |
| 67 | E067R | 1.01 | 0.90 |
| 67 | E067S | 1.23 | 1.00 |
| 67 | E067T | 0.99 | 0.98 |
| 67 | E067Y | 1.11 | 0.93 |
| 71 | K071A | 0.72 | 0.81 |
| 71 | K071C | 0.80 | 0.61 |
| 71 | K071D | 0.69 | 0.71 |
| 71 | K071E | 0.80 | 0.84 |
| 71 | K071F | 0.47 | 0.61 |
| 71 | K071G | 0.74 | 0.91 |
| 71 | K071H | 0.96 | 0.88 |
| 71 | K071I | 0.83 | 0.75 |
| 71 | K071L | 0.55 | 0.61 |
| 71 | K071M | 0.80 | 0.68 |
| 71 | K071N | 1.11 | 0.89 |
| 71 | K071P | 0.92 | 0.86 |
| 71 | K071Q | 0.98 | 0.77 |
| 71 | K071R | 1.10 | 1.10 |
| 71 | K071S | 0.99 | 0.97 |
| 71 | K071T | 0.95 | 0.83 |
| 71 | K071V | 0.94 | 0.84 |
| 71 | K071W | 0.82 | 0.91 |
| 71 | K071Y | 0.52 | 0.71 |
| 73 | T073A | 0.97 | 1.11 |
| 73 | T073C | 0.91 | 0.60 |
| 73 | T073D | 0.89 | 1.02 |
| 73 | T073E | 0.75 | 1.08 |
| 73 | T073F | 0.73 | 0.99 |
| 73 | T073G | 0.79 | 1.12 |
| 73 | T073H | 0.86 | 0.88 |
| 73 | T073I | 0.66 | 1.02 |
| 73 | T073K | 0.20 | 0.97 |
| 73 | T073L | 0.47 | 1.17 |
| 73 | T073M | 0.59 | 0.64 |
| 73 | T073N | 0.73 | 1.08 |
| 73 | T073P | 0.57 | 0.98 |
| 73 | T073R | 0.40 | 1.11 |
| 73 | T073S | 0.87 | 1.10 |
| 73 | T073V | 0.67 | 1.09 |
| 73 | T073W | 0.83 | 1.07 |
| 73 | T073Y | 0.79 | 1.10 |
| 75 | R075A | 1.05 | 1.14 |
| 75 | R075C | 0.88 | 0.85 |
| 75 | R075D | 0.87 | 0.99 |
| 75 | R075E | 0.86 | 1.01 |
| 75 | R075F | 0.76 | 0.92 |
| 75 | R075G | 0.79 | 1.04 |
| 75 | R075H | 0.85 | 1.07 |
| 75 | R075I | 0.86 | 1.01 |
| 75 | R075L | 0.88 | 1.04 |
| 75 | R075M | 1.04 | 1.04 |
| 75 | R075P | 0.90 | 0.93 |
| 75 | R075Q | 0.90 | 0.95 |
| 75 | R075S | 0.66 | 0.60 |
| 75 | R075T | 0.98 | 0.88 |
| 75 | R075V | 0.78 | 0.94 |
| 75 | R075W | 0.75 | 0.93 |
| 75 | R075Y | 0.68 | 1.04 |
| 77 | K077A | 0.38 | 0.98 |
| 77 | K077C | 0.28 | 0.51 |
| 77 | K077E | 0.11 | 0.77 |
| 77 | K077F | 0.20 | 0.72 |
| 77 | K077G | 0.13 | 0.76 |
| 77 | K077I | 0.16 | 1.00 |
| 77 | K077L | 0.54 | 0.98 |
| 77 | K077M | 0.58 | 0.99 |
| 77 | K077Q | 0.07 | 0.86 |
| 77 | K077R | 0.77 | 1.07 |
| 77 | K077S | 0.11 | 0.89 |
| 77 | K077V | 0.05 | 0.83 |
| 80 | T080A | 0.88 | 1.01 |
| 80 | T080C | 0.91 | 0.69 |
| 80 | T080D | 1.22 | 0.86 |
| 80 | T080E | 0.71 | 0.92 |
| 80 | T080F | 1.10 | 0.50 |
| 80 | T080G | 1.02 | 0.93 |
| 80 | T080H | 1.01 | 0.95 |
| 80 | T080I | 1.29 | 0.82 |
| 80 | T080K | 0.90 | 0.86 |
| 80 | T080L | 0.82 | 0.98 |
| 80 | T080M | 0.97 | 0.95 |
| 80 | T080N | 0.90 | 1.00 |
| 80 | T080P | 0.88 | 0.88 |
| 80 | T080Q | 0.87 | 0.88 |
| 80 | T080R | 0.99 | 0.76 |
| 80 | T080S | 0.83 | 1.09 |
| 80 | T080V | 0.87 | 0.87 |
| 80 | T080W | 0.77 | 0.89 |
| 80 | T080Y | 0.72 | 0.97 |
| 81 | K081A | 0.87 | 0.94 |
| 81 | K081C | 0.84 | 0.74 |

TABLE 26-5-continued

Combinable mutations in AmyS

| POS | variant | Stability PI | Activity PI |
|---|---|---|---|
| 81 | K081D | 0.96 | 0.83 |
| 81 | K081E | 0.69 | 0.92 |
| 81 | K081G | 0.86 | 0.81 |
| 81 | K081H | 0.73 | 1.03 |
| 81 | K081I | 0.82 | 0.79 |
| 81 | K081L | 0.87 | 1.01 |
| 81 | K081M | 0.93 | 1.04 |
| 81 | K081P | 0.90 | 0.79 |
| 81 | K081Q | 0.84 | 1.03 |
| 81 | K081R | 0.90 | 1.04 |
| 81 | K081S | 0.74 | 0.98 |
| 81 | K081T | 0.80 | 0.93 |
| 81 | K081V | 0.66 | 1.03 |
| 81 | K081W | 0.60 | 0.98 |
| 81 | K081Y | 0.89 | 1.20 |
| 83 | Q083A | 1.20 | 0.98 |
| 83 | Q083C | 1.79 | 0.17 |
| 83 | Q083D | 0.94 | 0.92 |
| 83 | Q083E | 0.98 | 0.95 |
| 83 | Q083F | 0.87 | 0.80 |
| 83 | Q083G | 0.76 | 1.01 |
| 83 | Q083H | 0.78 | 0.86 |
| 83 | Q083I | 0.69 | 0.85 |
| 83 | Q083L | 0.77 | 0.91 |
| 83 | Q083M | 0.91 | 0.96 |
| 83 | Q083P | 1.01 | 0.82 |
| 83 | Q083R | 0.91 | 0.90 |
| 83 | Q083S | 0.75 | 0.99 |
| 83 | Q083T | 0.84 | 0.84 |
| 83 | Q083V | 0.73 | 0.80 |
| 83 | Q083W | 0.82 | 0.78 |
| 83 | Q083Y | 0.71 | 0.93 |
| 85 | L085A | 0.94 | 1.06 |
| 85 | L085C | 0.90 | 0.63 |
| 85 | L085D | 0.84 | 1.04 |
| 85 | L085E | 1.09 | 1.02 |
| 85 | L085G | 0.85 | 0.90 |
| 85 | L085H | 0.73 | 1.02 |
| 85 | L085I | 0.89 | 0.88 |
| 85 | L085K | 0.96 | 0.93 |
| 85 | L085M | 1.01 | 1.04 |
| 85 | L085N | 1.10 | 0.89 |
| 85 | L085P | 1.01 | 0.72 |
| 85 | L085Q | 0.91 | 0.99 |
| 85 | L085R | 0.96 | 1.01 |
| 85 | L085S | 1.02 | 1.04 |
| 85 | L085T | 0.83 | 1.12 |
| 85 | L085W | 0.93 | 0.95 |
| 85 | L085Y | 0.70 | 1.08 |
| 90 | A090C | 1.00 | 0.65 |
| 90 | A090D | 1.12 | 0.92 |
| 90 | A090E | 1.20 | 0.92 |
| 90 | A090F | 0.99 | 0.76 |
| 90 | A090G | 1.04 | 0.87 |
| 90 | A090H | 1.05 | 1.03 |
| 90 | A090I | 0.90 | 0.83 |
| 90 | A090K | 0.93 | 1.04 |
| 90 | A090L | 0.76 | 0.92 |
| 90 | A090M | 1.02 | 1.02 |
| 90 | A090N | 1.02 | 0.98 |
| 90 | A090P | 1.39 | 0.10 |
| 90 | A090Q | 0.94 | 0.93 |
| 90 | A090R | 0.90 | 0.90 |
| 90 | A090S | 1.16 | 0.99 |
| 90 | A090T | 0.78 | 0.88 |
| 90 | A090V | 0.79 | 0.87 |
| 90 | A090W | 0.69 | 0.84 |
| 90 | A090Y | 0.83 | 0.96 |
| 92 | H092C | 0.75 | 0.29 |
| 92 | H092D | 1.06 | 0.69 |
| 92 | H092E | 0.88 | 0.76 |
| 92 | H092F | 0.92 | 0.28 |
| 92 | H092G | 0.86 | 0.81 |
| 92 | H092K | 0.89 | 0.98 |
| 92 | H092N | 0.85 | 0.78 |
| 92 | H092Q | 0.80 | 0.89 |
| 92 | H092R | 0.75 | 0.96 |
| 92 | H092S | 0.70 | 0.87 |
| 92 | H092T | 0.68 | 0.47 |
| 92 | H092V | 0.70 | 0.28 |
| 92 | H092W | 0.83 | 0.44 |
| 92 | H092Y | 0.71 | 0.63 |
| 106 | H106D | 0.58 | 0.07 |
| 106 | H106P | 0.59 | 0.06 |
| 107 | K107A | 0.46 | 0.81 |
| 107 | K107C | 0.42 | 0.67 |
| 107 | K107D | 0.32 | 0.51 |
| 107 | K107E | 0.35 | 0.70 |
| 107 | K107F | 0.42 | 0.66 |
| 107 | K107G | 0.23 | 0.76 |
| 107 | K107H | 0.34 | 0.94 |
| 107 | K107I | 0.29 | 0.69 |
| 107 | K107L | 0.53 | 0.75 |
| 107 | K107M | 0.60 | 0.79 |
| 107 | K107N | 0.43 | 0.88 |
| 107 | K107Q | 0.63 | 0.74 |
| 107 | K107R | 1.05 | 0.71 |
| 107 | K107S | 0.30 | 0.78 |
| 107 | K107T | 0.38 | 0.72 |
| 107 | K107V | 0.41 | 0.70 |
| 107 | K107Y | 0.40 | 0.64 |
| 111 | D111A | 0.55 | 0.95 |
| 111 | D111C | 0.71 | 0.60 |
| 111 | D111E | 0.87 | 1.01 |
| 111 | D111F | 0.63 | 0.65 |
| 111 | D111G | 0.74 | 0.90 |
| 111 | D111H | 0.50 | 0.85 |
| 111 | D111I | 0.56 | 0.91 |
| 111 | D111K | 0.45 | 0.62 |
| 111 | D111L | 0.44 | 0.86 |
| 111 | D111M | 0.65 | 1.00 |
| 111 | D111N | 0.97 | 0.87 |
| 111 | D111P | 0.78 | 0.71 |
| 111 | D111Q | 0.77 | 0.95 |
| 111 | D111R | 0.53 | 0.07 |
| 111 | D111S | 0.67 | 0.91 |
| 111 | D111T | 0.61 | 1.02 |
| 111 | D111V | 0.58 | 1.02 |
| 111 | D111W | 0.42 | 0.54 |
| 111 | D111Y | 0.49 | 0.92 |
| 113 | T113A | 0.89 | 0.97 |
| 113 | T113C | 0.80 | 0.82 |
| 113 | T113D | 0.94 | 0.95 |
| 113 | T113E | 0.92 | 0.91 |
| 113 | T113F | 0.76 | 0.92 |
| 113 | T113G | 0.88 | 1.08 |
| 113 | T113H | 0.88 | 0.96 |
| 113 | T113I | 1.14 | 0.88 |
| 113 | T113K | 0.93 | 1.13 |
| 113 | T113L | 1.08 | 1.08 |
| 113 | T113M | 0.83 | 0.99 |
| 113 | T113P | 1.05 | 0.96 |
| 113 | T113Q | 0.88 | 1.05 |
| 113 | T113R | 0.88 | 1.03 |
| 113 | T113V | 1.12 | 0.94 |
| 113 | T113W | 1.06 | 0.88 |
| 114 | E114A | 0.54 | 0.97 |
| 114 | E114C | 0.62 | 0.76 |
| 114 | E114D | 0.71 | 0.82 |
| 114 | E114F | 0.36 | 0.92 |
| 114 | E114G | 0.59 | 1.01 |
| 114 | E114H | 0.49 | 0.92 |
| 114 | E114I | 0.54 | 0.86 |
| 114 | E114L | 0.43 | 0.97 |
| 114 | E114M | 0.77 | 0.97 |
| 114 | E114N | 0.67 | 0.88 |
| 114 | E114R | 0.35 | 0.84 |
| 114 | E114T | 0.54 | 0.94 |
| 114 | E114V | 0.43 | 0.85 |
| 114 | E114W | 0.31 | 0.94 |

TABLE 26-5-continued

Combinable mutations in AmyS

| POS | variant | Stability PI | Activity PI |
|---|---|---|---|
| 114 | E114Y | 0.26 | 0.93 |
| 120 | E120A | 0.29 | 1.20 |
| 120 | E120C | 0.24 | 0.89 |
| 120 | E120H | 0.09 | 0.90 |
| 120 | E120I | 0.60 | 0.87 |
| 120 | E120L | 0.20 | 0.97 |
| 120 | E120M | 0.39 | 0.96 |
| 120 | E120N | 0.16 | 1.02 |
| 120 | E120Q | 0.66 | 1.10 |
| 120 | E120R | 0.12 | 1.12 |
| 120 | E120S | 0.08 | 1.07 |
| 120 | E120T | 0.22 | 1.06 |
| 120 | E120V | 0.53 | 0.93 |
| 120 | E120W | 0.15 | 0.81 |
| 120 | E120Y | 0.07 | 0.98 |
| 121 | V121C | 0.92 | 0.55 |
| 121 | V121T | 0.07 | 0.92 |
| 128 | Q128C | 0.42 | 0.95 |
| 128 | Q128D | 0.15 | 1.05 |
| 128 | Q128E | 0.90 | 1.00 |
| 128 | Q128H | 0.34 | 1.05 |
| 128 | Q128I | 0.90 | 0.89 |
| 128 | Q128K | 0.52 | 1.15 |
| 128 | Q128L | 0.47 | 0.97 |
| 128 | Q128N | 0.12 | 1.05 |
| 128 | Q128R | 0.31 | 1.14 |
| 128 | Q128S | 0.28 | 1.02 |
| 128 | Q128V | 0.86 | 0.97 |
| 128 | Q128W | 0.07 | 0.76 |
| 128 | Q128Y | 0.13 | 0.86 |
| 131 | S131D | 0.26 | 1.08 |
| 131 | S131G | 0.24 | 0.86 |
| 131 | S131N | 0.76 | 1.02 |
| 131 | S131T | 0.49 | 0.90 |
| 133 | T133A | 0.95 | 1.13 |
| 133 | T133C | 0.49 | 0.97 |
| 133 | T133D | 1.03 | 0.99 |
| 133 | T133E | 0.82 | 1.02 |
| 133 | T133F | 0.17 | 0.97 |
| 133 | T133G | 0.47 | 0.84 |
| 133 | T133H | 0.41 | 1.19 |
| 133 | T133I | 0.86 | 0.96 |
| 133 | T133K | 0.47 | 0.85 |
| 133 | T133L | 0.41 | 1.06 |
| 133 | T133M | 0.51 | 1.05 |
| 133 | T133N | 0.68 | 1.13 |
| 133 | T133P | 1.41 | 1.08 |
| 133 | T133Q | 0.63 | 1.10 |
| 133 | T133R | 0.18 | 1.13 |
| 133 | T133S | 0.72 | 1.08 |
| 133 | T133V | 1.25 | 0.92 |
| 133 | T133W | 0.14 | 0.98 |
| 133 | T133Y | 0.41 | 1.01 |
| 137 | Q137A | 0.92 | 0.97 |
| 137 | Q137C | 1.09 | 0.77 |
| 137 | Q137D | 0.89 | 0.96 |
| 137 | Q137E | 1.06 | 0.87 |
| 137 | Q137F | 0.85 | 0.86 |
| 137 | Q137G | 1.13 | 0.94 |
| 137 | Q137H | 0.95 | 1.05 |
| 137 | Q137I | 0.93 | 0.22 |
| 137 | Q137L | 1.20 | 0.82 |
| 137 | Q137M | 1.30 | 0.83 |
| 137 | Q137P | 0.07 | 1.05 |
| 137 | Q137R | 0.95 | 1.05 |
| 137 | Q137S | 1.45 | 0.98 |
| 137 | Q137T | 1.12 | 0.91 |
| 137 | Q137V | 1.02 | 0.86 |
| 137 | Q137W | 1.06 | 0.88 |
| 137 | Q137Y | 0.94 | 0.89 |
| 138 | A138G | 0.90 | 1.02 |
| 138 | A138I | 0.23 | 0.90 |
| 138 | A138N | 0.50 | 0.94 |
| 138 | A138P | 1.07 | 1.15 |
| 138 | A138Q | 0.13 | 0.69 |
| 138 | A138S | 1.12 | 1.02 |
| 138 | A138T | 1.16 | 1.05 |
| 138 | A138V | 1.17 | 0.87 |
| 138 | A138Y | 0.14 | 0.97 |
| 139 | W139A | 0.82 | 0.89 |
| 139 | W139C | 0.75 | 0.39 |
| 139 | W139D | 0.93 | 1.40 |
| 139 | W139E | 0.81 | 0.97 |
| 139 | W139G | 0.79 | 0.74 |
| 139 | W139H | 0.97 | 1.59 |
| 139 | W139I | 0.74 | 0.58 |
| 139 | W139K | 0.68 | 0.42 |
| 139 | W139L | 0.78 | 0.59 |
| 139 | W139M | 0.87 | 1.00 |
| 139 | W139N | 1.13 | 0.85 |
| 139 | W139Q | 0.82 | 0.79 |
| 139 | W139R | 0.96 | 1.29 |
| 139 | W139S | 0.93 | 1.04 |
| 139 | W139T | 0.71 | 0.87 |
| 139 | W139V | 0.72 | 0.66 |
| 139 | W139Y | 1.14 | 1.63 |
| 141 | K141A | 1.09 | 0.73 |
| 141 | K141C | 1.03 | 0.85 |
| 141 | K141D | 0.89 | 0.98 |
| 141 | K141E | 3.48 | 0.92 |
| 141 | K141F | 0.89 | 0.80 |
| 141 | K141G | 1.18 | 0.96 |
| 141 | K141H | 1.13 | 0.99 |
| 141 | K141I | 1.40 | 0.87 |
| 141 | K141L | 1.22 | 0.85 |
| 141 | K141M | 1.23 | 1.01 |
| 141 | K141N | 1.11 | 1.02 |
| 141 | K141P | 1.07 | 0.96 |
| 141 | K141Q | 1.28 | 0.97 |
| 141 | K141R | 1.23 | 0.99 |
| 141 | K141S | 1.21 | 0.98 |
| 141 | K141T | 1.17 | 0.94 |
| 141 | K141V | 1.21 | 1.00 |
| 141 | K141W | 1.16 | 0.87 |
| 141 | K141Y | 1.17 | 0.88 |
| 143 | D143A | 0.95 | 1.04 |
| 143 | D143C | 1.11 | 0.84 |
| 143 | D143E | 1.12 | 0.98 |
| 143 | D143G | 1.13 | 1.09 |
| 143 | D143H | 0.91 | 0.98 |
| 143 | D143I | 1.05 | 0.94 |
| 143 | D143K | 0.86 | 0.96 |
| 143 | D143M | 0.86 | 1.05 |
| 143 | D143N | 1.10 | 0.99 |
| 143 | D143P | 0.98 | 0.84 |
| 143 | D143V | 1.00 | 1.01 |
| 143 | D143W | 1.00 | 0.99 |
| 143 | D143Y | 0.75 | 0.15 |
| 147 | R147A | 0.73 | 0.25 |
| 147 | R147D | 0.66 | 0.07 |
| 147 | R147G | 0.74 | 0.11 |
| 147 | R147H | 0.81 | 0.21 |
| 147 | R147K | 1.05 | 0.48 |
| 147 | R147M | 0.65 | 0.07 |
| 147 | R147N | 0.91 | 0.30 |
| 147 | R147Q | 0.88 | 0.30 |
| 147 | R147S | 0.90 | 0.39 |
| 147 | R147T | 0.90 | 0.10 |
| 149 | N149A | 0.94 | 0.93 |
| 149 | N149D | 0.89 | 0.95 |
| 149 | N149E | 0.98 | 0.93 |
| 149 | N149F | 1.09 | 0.85 |
| 149 | N149G | 0.90 | 0.93 |
| 149 | N149H | 1.01 | 0.98 |
| 149 | N149I | 1.15 | 0.83 |
| 149 | N149K | 0.90 | 0.88 |
| 149 | N149L | 0.88 | 0.94 |
| 149 | N149Q | 1.00 | 0.93 |
| 149 | N149R | 0.80 | 0.95 |
| 149 | N149S | 0.94 | 1.03 |

TABLE 26-5-continued

Combinable mutations in AmyS

| POS | variant | Stability PI | Activity PI |
|---|---|---|---|
| 149 | N149V | 1.06 | 0.87 |
| 149 | N149W | 1.01 | 0.87 |
| 150 | T150A | 0.90 | 0.96 |
| 150 | T150C | 1.03 | 0.72 |
| 150 | T150D | 0.82 | 0.87 |
| 150 | T150E | 4.54 | 0.87 |
| 150 | T150G | 0.99 | 0.86 |
| 150 | T150I | 0.82 | 0.93 |
| 150 | T150K | 0.86 | 0.96 |
| 150 | T150L | 0.83 | 0.07 |
| 150 | T150M | 1.05 | 1.00 |
| 150 | T150N | 0.98 | 1.08 |
| 150 | T150Q | 0.83 | 0.99 |
| 150 | T150R | 0.99 | 1.04 |
| 150 | T150S | 0.77 | 0.96 |
| 150 | T150V | 0.90 | 0.93 |
| 150 | T150Y | 1.18 | 1.00 |
| 151 | Y151A | 0.96 | 0.87 |
| 151 | Y151C | 0.80 | 0.67 |
| 151 | Y151D | 0.99 | 0.71 |
| 151 | Y151E | 0.76 | 0.71 |
| 151 | Y151F | 0.96 | 0.88 |
| 151 | Y151G | 1.17 | 0.79 |
| 151 | Y151H | 1.04 | 0.87 |
| 151 | Y151I | 1.22 | 0.78 |
| 151 | Y151L | 1.05 | 0.90 |
| 151 | Y151M | 1.02 | 0.83 |
| 151 | Y151N | 0.98 | 0.91 |
| 151 | Y151P | 0.89 | 0.77 |
| 151 | Y151Q | 1.07 | 0.75 |
| 151 | Y151R | 1.05 | 0.76 |
| 151 | Y151S | 0.85 | 0.80 |
| 151 | Y151T | 1.04 | 0.80 |
| 151 | Y151V | 1.14 | 0.80 |
| 151 | Y151W | 1.16 | 0.79 |
| 152 | S152A | 0.95 | 0.88 |
| 152 | S152C | 0.83 | 0.75 |
| 152 | S152E | 1.09 | 0.71 |
| 152 | S152F | 0.75 | 0.22 |
| 152 | S152G | 1.25 | 0.91 |
| 152 | S152H | 0.99 | 0.71 |
| 152 | S152I | 0.81 | 0.22 |
| 152 | S152K | 0.74 | 0.58 |
| 152 | S152N | 1.20 | 0.43 |
| 152 | S152Q | 0.71 | 0.21 |
| 152 | S152R | 0.89 | 0.86 |
| 152 | S152T | 1.16 | 0.99 |
| 152 | S152V | 0.79 | 0.42 |
| 152 | S152W | 0.73 | 0.22 |
| 152 | S152Y | 0.91 | 0.26 |
| 155 | K155A | 1.10 | 0.85 |
| 155 | K155C | 0.92 | 0.72 |
| 155 | K155D | 0.94 | 0.85 |
| 155 | K155E | 0.82 | 0.79 |
| 155 | K155G | 1.05 | 0.58 |
| 155 | K155H | 1.04 | 0.84 |
| 155 | K155L | 1.05 | 0.89 |
| 155 | K155M | 0.91 | 0.91 |
| 155 | K155N | 1.18 | 0.90 |
| 155 | K155P | 0.99 | 0.94 |
| 155 | K155Q | 0.84 | 0.90 |
| 155 | K155R | 1.20 | 0.93 |
| 155 | K155S | 1.22 | 0.85 |
| 155 | K155T | 1.12 | 0.76 |
| 155 | K155V | 1.01 | 0.85 |
| 155 | K155W | 1.09 | 0.88 |
| 155 | K155Y | 1.21 | 0.80 |
| 160 | H160A | 0.89 | 0.89 |
| 160 | H160C | 0.84 | 0.98 |
| 160 | H160D | 0.89 | 0.69 |
| 160 | H160E | 0.86 | 0.52 |
| 160 | H160F | 0.77 | 0.79 |
| 160 | H160G | 0.82 | 0.36 |
| 160 | H160I | 0.36 | 0.58 |
| 160 | H160L | 1.03 | 0.92 |
| 160 | H160M | 0.56 | 0.97 |
| 160 | H160N | 1.11 | 1.02 |
| 160 | H160Q | 0.98 | 0.47 |
| 160 | H160R | 0.54 | 0.62 |
| 160 | H160T | 1.01 | 0.91 |
| 160 | H160V | 0.76 | 0.74 |
| 160 | H160W | 0.26 | 0.66 |
| 160 | H160Y | 0.86 | 0.89 |
| 165 | D165A | 0.53 | 0.12 |
| 165 | D165C | 1.01 | 0.07 |
| 165 | D165E | 1.14 | 0.07 |
| 165 | D165G | 0.63 | 0.20 |
| 165 | D165M | 0.58 | 0.10 |
| 165 | D165N | 1.16 | 1.10 |
| 165 | D165Q | 0.53 | 0.11 |
| 165 | D165S | 0.83 | 0.43 |
| 168 | E168A | 0.83 | 0.92 |
| 168 | E168C | 0.83 | 0.50 |
| 168 | E168D | 0.82 | 0.57 |
| 168 | E168F | 0.69 | 0.59 |
| 168 | E168G | 0.92 | 0.75 |
| 168 | E168H | 0.84 | 0.90 |
| 168 | E168I | 1.08 | 0.71 |
| 168 | E168L | 0.80 | 0.92 |
| 168 | E168M | 1.12 | 0.80 |
| 168 | E168N | 0.97 | 0.83 |
| 168 | E168Q | 0.88 | 0.87 |
| 168 | E168R | 1.18 | 0.90 |
| 168 | E168S | 0.95 | 0.83 |
| 168 | E168T | 0.83 | 0.16 |
| 168 | E168V | 0.89 | 0.73 |
| 168 | E168W | 1.23 | 0.66 |
| 168 | E168Y | 0.76 | 0.82 |
| 172 | L172A | 1.14 | 1.06 |
| 172 | L172C | 1.07 | 0.89 |
| 172 | L172D | 0.83 | 0.91 |
| 172 | L172E | 0.97 | 1.01 |
| 172 | L172G | 0.50 | 0.60 |
| 172 | L172H | 0.93 | 1.06 |
| 172 | L172I | 0.97 | 0.90 |
| 172 | L172K | 0.98 | 1.12 |
| 172 | L172M | 0.86 | 0.91 |
| 172 | L172N | 0.91 | 0.96 |
| 172 | L172P | 0.17 | 0.83 |
| 172 | L172Q | 1.00 | 0.89 |
| 172 | L172R | 1.16 | 1.06 |
| 172 | L172S | 0.78 | 1.01 |
| 172 | L172T | 0.82 | 0.94 |
| 172 | L172V | 1.02 | 0.88 |
| 172 | L172W | 1.09 | 0.92 |
| 172 | L172Y | 1.06 | 0.98 |
| 173 | S173A | 0.92 | 0.74 |
| 173 | S173C | 0.82 | 0.57 |
| 173 | S173D | 0.63 | 0.71 |
| 173 | S173E | 1.07 | 0.65 |
| 173 | S173F | 0.82 | 0.25 |
| 173 | S173G | 0.73 | 0.78 |
| 173 | S173H | 0.85 | 0.66 |
| 173 | S173I | 1.20 | 0.59 |
| 173 | S173K | 1.17 | 1.03 |
| 173 | S173L | 0.75 | 0.20 |
| 173 | S173M | 1.05 | 0.48 |
| 173 | S173N | 1.02 | 0.84 |
| 173 | S173Q | 1.08 | 0.84 |
| 173 | S173R | 0.88 | 1.03 |
| 173 | S173T | 1.33 | 0.86 |
| 173 | S173V | 1.12 | 0.46 |
| 173 | S173W | 0.86 | 0.20 |
| 173 | S173Y | 0.90 | 0.25 |
| 177 | K177L | 0.89 | 0.91 |
| 177 | K177M | 0.10 | 0.90 |
| 177 | K177Q | 0.08 | 1.07 |
| 177 | K177R | 0.47 | 1.09 |
| 188 | E188P | 1.40 | 1.16 |
| 191 | T191A | 0.49 | 1.11 |

TABLE 26-5-continued

Combinable mutations in AmyS

| POS | variant | Stability PI | Activity PI |
|---|---|---|---|
| 191 | T191C | 0.13 | 1.07 |
| 191 | T191D | 0.91 | 1.03 |
| 191 | T191G | 0.19 | 1.09 |
| 191 | T191I | 0.18 | 1.06 |
| 191 | T191M | 0.06 | 1.09 |
| 191 | T191N | 0.76 | 1.13 |
| 191 | T191P | 0.99 | 1.07 |
| 191 | T191Q | 0.18 | 1.17 |
| 191 | T191S | 0.72 | 1.05 |
| 191 | T191V | 0.16 | 1.02 |
| 192 | E192C | 0.55 | 1.12 |
| 192 | E192D | 0.42 | 1.50 |
| 192 | E192Q | 0.22 | 1.55 |
| 192 | E192T | 0.10 | 1.35 |
| 193 | N193C | 0.73 | 0.62 |
| 193 | N193F | 1.71 | 0.98 |
| 193 | N193H | 1.10 | 0.92 |
| 193 | N193K | 1.28 | 1.17 |
| 193 | N193L | 1.22 | 0.78 |
| 193 | N193M | 0.81 | 0.96 |
| 193 | N193R | 0.87 | 0.97 |
| 193 | N193W | 1.09 | 0.73 |
| 193 | N193Y | 1.89 | 1.10 |
| 196 | Y196A | 0.74 | 1.57 |
| 196 | Y196D | 0.29 | 1.29 |
| 196 | Y196F | 0.74 | 1.38 |
| 196 | Y196N | 0.54 | 0.94 |
| 196 | Y196S | 0.36 | 1.59 |
| 199 | L199V | 0.61 | 0.13 |
| 200 | M200A | 1.03 | 0.68 |
| 200 | M200C | 0.84 | 0.53 |
| 200 | M200D | 0.71 | 0.81 |
| 200 | M200E | 0.54 | 0.55 |
| 200 | M200I | 1.14 | 0.57 |
| 200 | M200L | 0.68 | 1.11 |
| 200 | M200N | 0.46 | 0.72 |
| 200 | M200Q | 0.78 | 0.77 |
| 200 | M200S | 0.61 | 1.11 |
| 200 | M200T | 0.80 | 0.61 |
| 200 | M200V | 0.97 | 0.56 |
| 201 | Y201A | 0.90 | 1.41 |
| 201 | Y201C | 1.22 | 0.14 |
| 201 | Y201D | 0.60 | 0.73 |
| 201 | Y201E | 0.81 | 1.36 |
| 201 | Y201F | 0.85 | 0.81 |
| 201 | Y201G | 0.56 | 1.63 |
| 201 | Y201H | 1.06 | 1.44 |
| 201 | Y201I | 1.35 | 0.11 |
| 201 | Y201K | 0.89 | 0.08 |
| 201 | Y201L | 1.05 | 0.18 |
| 201 | Y201M | 1.16 | 1.21 |
| 201 | Y201N | 1.15 | 0.31 |
| 201 | Y201Q | 1.11 | 0.79 |
| 201 | Y201R | 0.87 | 0.06 |
| 201 | Y201S | 0.74 | 1.11 |
| 201 | Y201T | 0.65 | 0.39 |
| 201 | Y201W | 0.73 | 0.08 |
| 202 | A202C | 0.97 | 0.57 |
| 202 | A202D | 0.83 | 0.93 |
| 202 | A202E | 0.49 | 0.85 |
| 202 | A202G | 0.45 | 0.83 |
| 202 | A202I | 0.50 | 1.02 |
| 202 | A202L | 0.46 | 0.95 |
| 202 | A202M | 0.32 | 0.84 |
| 202 | A202N | 0.53 | 1.08 |
| 202 | A202Q | 0.47 | 1.01 |
| 202 | A202S | 0.69 | 0.79 |
| 202 | A202T | 0.63 | 1.07 |
| 202 | A202V | 0.82 | 1.02 |
| 213 | T213A | 1.11 | 0.98 |
| 213 | T213C | 0.97 | 0.77 |
| 213 | T213D | 1.12 | 0.91 |
| 213 | T213E | 1.11 | 0.88 |
| 213 | T213F | 1.13 | 0.75 |
| 213 | T213G | 1.11 | 0.91 |
| 213 | T213H | 0.92 | 1.00 |
| 213 | T213K | 0.90 | 1.11 |
| 213 | T213L | 1.26 | 0.75 |
| 213 | T213M | 1.26 | 0.78 |
| 213 | T213N | 1.11 | 0.91 |
| 213 | T213P | 0.94 | 0.91 |
| 213 | T213Q | 1.12 | 1.02 |
| 213 | T213R | 1.05 | 1.05 |
| 213 | T213S | 1.10 | 1.08 |
| 213 | T213V | 1.35 | 0.76 |
| 213 | T213W | 1.17 | 0.68 |
| 216 | K216A | 0.66 | 0.24 |
| 216 | K216E | 1.03 | 1.30 |
| 216 | K216G | 0.83 | 1.20 |
| 216 | K216H | 0.90 | 1.28 |
| 216 | K216M | 0.97 | 1.39 |
| 216 | K216P | 0.91 | 0.97 |
| 216 | K216Q | 1.04 | 1.34 |
| 216 | K216R | 0.77 | 1.32 |
| 216 | K216S | 0.97 | 1.28 |
| 216 | K216T | 0.99 | 1.22 |
| 216 | K216V | 0.95 | 1.07 |
| 216 | K216W | 1.00 | 1.13 |
| 216 | K216Y | 0.79 | 1.31 |
| 217 | N217A | 1.10 | 0.87 |
| 217 | N217C | 0.81 | 0.78 |
| 217 | N217F | 0.90 | 0.88 |
| 217 | N217G | 0.95 | 0.90 |
| 217 | N217H | 1.09 | 0.90 |
| 217 | N217I | 1.08 | 0.76 |
| 217 | N217L | 1.09 | 0.82 |
| 217 | N217M | 0.97 | 0.80 |
| 217 | N217P | 0.97 | 0.73 |
| 217 | N217Q | 1.31 | 0.74 |
| 217 | N217R | 1.19 | 0.87 |
| 217 | N217S | 1.05 | 0.87 |
| 217 | N217T | 1.01 | 0.87 |
| 217 | N217V | 1.18 | 0.69 |
| 217 | N217W | 0.99 | 0.80 |
| 220 | K220A | 1.06 | 0.79 |
| 220 | K220C | 1.05 | 0.75 |
| 220 | K220D | 1.02 | 0.88 |
| 220 | K220E | 1.12 | 0.88 |
| 220 | K220F | 1.03 | 0.78 |
| 220 | K220G | 1.10 | 0.84 |
| 220 | K220H | 1.12 | 0.81 |
| 220 | K220I | 1.13 | 0.81 |
| 220 | K220M | 1.05 | 0.75 |
| 220 | K220N | 1.17 | 0.80 |
| 220 | K220P | 1.33 | 0.89 |
| 220 | K220Q | 1.21 | 0.87 |
| 220 | K220R | 1.26 | 0.83 |
| 220 | K220S | 1.30 | 0.81 |
| 220 | K220V | 1.21 | 0.82 |
| 220 | K220W | 1.01 | 0.81 |
| 220 | K220Y | 1.08 | 0.84 |
| 221 | W221A | 0.88 | 1.54 |
| 221 | W221C | 0.95 | 1.09 |
| 221 | W221D | 0.84 | 1.31 |
| 221 | W221F | 1.07 | 1.28 |
| 221 | W221I | 1.33 | 1.23 |
| 221 | W221L | 0.88 | 1.50 |
| 221 | W221M | 1.16 | 1.35 |
| 221 | W221N | 1.11 | 1.57 |
| 221 | W221R | 0.93 | 1.29 |
| 221 | W221S | 1.34 | 1.40 |
| 221 | W221V | 1.13 | 1.31 |
| 221 | W221Y | 1.14 | 1.36 |
| 227 | N227A | 1.01 | 1.02 |
| 227 | N227C | 0.92 | 0.95 |
| 227 | N227D | 1.01 | 1.06 |
| 227 | N227E | 1.03 | 1.06 |
| 227 | N227F | 0.72 | 0.81 |
| 227 | N227G | 1.05 | 1.09 |
| 227 | N227H | 0.95 | 1.13 |

TABLE 26-5-continued

Combinable mutations in AmyS

| POS | variant | Stability PI | Activity PI |
|---|---|---|---|
| 227 | N227I | 1.03 | 0.76 |
| 227 | N227K | 1.00 | 1.13 |
| 227 | N227L | 0.84 | 0.75 |
| 227 | N227M | 0.84 | 0.87 |
| 227 | N227P | 1.08 | 0.88 |
| 227 | N227Q | 0.94 | 1.00 |
| 227 | N227R | 0.89 | 1.03 |
| 227 | N227S | 0.96 | 0.95 |
| 227 | N227T | 1.06 | 0.96 |
| 227 | N227V | 1.05 | 0.84 |
| 227 | N227W | 1.07 | 0.81 |
| 227 | N227Y | 1.01 | 0.85 |
| 232 | R232H | 0.66 | 0.34 |
| 232 | R232K | 0.52 | 0.47 |
| 232 | R232M | 0.62 | 0.12 |
| 232 | R232Q | 0.54 | 0.12 |
| 232 | R232S | 0.59 | 0.16 |
| 232 | R232T | 0.76 | 0.17 |
| 232 | R232V | 0.70 | 0.15 |
| 235 | A235C | 0.86 | 0.53 |
| 235 | A235D | 0.70 | 0.98 |
| 235 | A235E | 0.93 | 0.84 |
| 235 | A235F | 1.01 | 0.68 |
| 235 | A235G | 1.17 | 0.78 |
| 235 | A235H | 0.80 | 1.01 |
| 235 | A235I | 1.07 | 0.84 |
| 235 | A235K | 0.93 | 1.14 |
| 235 | A235L | 0.89 | 0.97 |
| 235 | A235M | 0.99 | 0.91 |
| 235 | A235N | 0.78 | 1.03 |
| 235 | A235P | 0.97 | 0.48 |
| 235 | A235Q | 1.01 | 0.89 |
| 235 | A235R | 1.03 | 1.14 |
| 235 | A235S | 0.92 | 1.00 |
| 235 | A235V | 1.01 | 0.86 |
| 235 | A235W | 0.98 | 0.60 |
| 235 | A235Y | 0.91 | 0.93 |
| 237 | K237R | 0.48 | 0.88 |
| 238 | H238N | 0.21 | 0.83 |
| 240 | K240M | 0.31 | 1.13 |
| 240 | K240Q | 0.12 | 1.21 |
| 240 | K240R | 0.27 | 1.41 |
| 246 | D246A | 0.73 | 1.03 |
| 246 | D246E | 1.18 | 1.03 |
| 246 | D246F | 0.67 | 1.02 |
| 246 | D246G | 0.61 | 1.09 |
| 246 | D246H | 0.71 | 1.05 |
| 246 | D246I | 0.75 | 0.85 |
| 246 | D246K | 0.36 | 1.18 |
| 246 | D246L | 0.81 | 0.91 |
| 246 | D246M | 0.80 | 0.92 |
| 246 | D246N | 0.68 | 0.97 |
| 246 | D246P | 0.47 | 0.81 |
| 246 | D246Q | 0.78 | 0.98 |
| 246 | D246R | 0.24 | 1.31 |
| 246 | D246S | 0.97 | 1.01 |
| 246 | D246T | 0.83 | 1.14 |
| 246 | D246Y | 0.90 | 0.96 |
| 249 | S249A | 1.06 | 0.97 |
| 249 | S249C | 0.93 | 0.74 |
| 249 | S249D | 0.98 | 0.94 |
| 249 | S249E | 1.27 | 0.92 |
| 249 | S249F | 0.91 | 0.74 |
| 249 | S249G | 0.91 | 0.94 |
| 249 | S249H | 1.04 | 0.93 |
| 249 | S249K | 1.15 | 1.02 |
| 249 | S249L | 1.14 | 0.82 |
| 249 | S249M | 0.95 | 0.77 |
| 249 | S249P | 1.09 | 0.80 |
| 249 | S249Q | 1.20 | 0.94 |
| 249 | S249R | 1.07 | 1.03 |
| 249 | S249T | 1.17 | 0.91 |
| 249 | S249V | 1.01 | 0.74 |
| 249 | S249W | 1.13 | 0.77 |
| 249 | S249Y | 1.07 | 0.87 |
| 250 | Y250A | 0.99 | 1.21 |
| 250 | Y250C | 1.03 | 1.12 |
| 250 | Y250D | 0.97 | 1.29 |
| 250 | Y250E | 1.13 | 1.33 |
| 250 | Y250F | 1.29 | 1.28 |
| 250 | Y250G | 1.09 | 1.33 |
| 250 | Y250I | 1.35 | 1.27 |
| 250 | Y250K | 1.07 | 1.48 |
| 250 | Y250L | 1.02 | 1.32 |
| 250 | Y250M | 1.35 | 1.39 |
| 250 | Y250N | 1.05 | 1.40 |
| 250 | Y250P | 0.71 | 1.05 |
| 250 | Y250Q | 1.01 | 1.54 |
| 250 | Y250R | 0.99 | 1.55 |
| 250 | Y250S | 1.02 | 1.41 |
| 250 | Y250W | 0.99 | 1.35 |
| 252 | R252A | 1.12 | 1.08 |
| 252 | R252C | 0.97 | 0.81 |
| 252 | R252D | 0.89 | 0.86 |
| 252 | R252E | 1.09 | 1.12 |
| 252 | R252F | 1.01 | 0.89 |
| 252 | R252G | 0.76 | 1.00 |
| 252 | R252I | 1.07 | 0.97 |
| 252 | R252K | 1.19 | 1.21 |
| 252 | R252L | 1.32 | 0.96 |
| 252 | R252M | 0.98 | 0.96 |
| 252 | R252N | 1.15 | 0.97 |
| 252 | R252P | 0.72 | 0.83 |
| 252 | R252Q | 1.16 | 1.04 |
| 252 | R252S | 1.04 | 1.01 |
| 252 | R252T | 1.09 | 0.99 |
| 252 | R252V | 1.01 | 0.94 |
| 252 | R252Y | 1.14 | 0.86 |
| 253 | S253A | 1.09 | 0.97 |
| 253 | S253D | 1.07 | 1.04 |
| 253 | S253F | 1.19 | 0.82 |
| 253 | S253G | 1.18 | 0.92 |
| 253 | S253H | 1.13 | 0.97 |
| 253 | S253I | 1.13 | 0.84 |
| 253 | S253K | 1.10 | 1.01 |
| 253 | S253L | 1.09 | 0.79 |
| 253 | S253N | 1.06 | 1.03 |
| 253 | S253P | 0.95 | 0.90 |
| 253 | S253Q | 1.13 | 0.93 |
| 253 | S253T | 1.14 | 0.97 |
| 253 | S253V | 1.15 | 0.90 |
| 253 | S253W | 1.04 | 0.87 |
| 253 | S253Y | 1.34 | 0.94 |
| 254 | Q254A | 0.98 | 0.88 |
| 254 | Q254C | 0.94 | 0.66 |
| 254 | Q254D | 1.10 | 0.90 |
| 254 | Q254E | 1.29 | 0.89 |
| 254 | Q254F | 1.23 | 0.74 |
| 254 | Q254G | 1.15 | 0.77 |
| 254 | Q254H | 1.04 | 0.94 |
| 254 | Q254I | 1.12 | 0.91 |
| 254 | Q254K | 1.00 | 0.99 |
| 254 | Q254L | 1.09 | 0.82 |
| 254 | Q254M | 0.94 | 0.89 |
| 254 | Q254N | 1.17 | 0.90 |
| 254 | Q254R | 1.05 | 0.98 |
| 254 | Q254S | 1.07 | 0.98 |
| 254 | Q254T | 1.21 | 0.65 |
| 254 | Q254V | 1.31 | 0.92 |
| 254 | Q254W | 1.17 | 0.69 |
| 254 | Q254Y | 1.03 | 0.87 |
| 255 | T255A | 1.09 | 0.73 |
| 255 | T255C | 0.89 | 0.78 |
| 255 | T255E | 1.09 | 0.64 |
| 255 | T255F | 1.30 | 0.68 |
| 255 | T255G | 1.15 | 0.73 |
| 255 | T255H | 1.10 | 0.74 |
| 255 | T255I | 1.18 | 0.70 |
| 255 | T255K | 1.27 | 0.83 |
| 255 | T255L | 0.97 | 0.73 |

TABLE 26-5-continued

Combinable mutations in AmyS

| POS | variant | Stability PI | Activity PI |
|---|---|---|---|
| 255 | T255M | 0.98 | 0.72 |
| 255 | T255N | 0.83 | 0.76 |
| 255 | T255P | 0.77 | 0.59 |
| 255 | T255R | 1.12 | 0.85 |
| 255 | T255S | 1.10 | 0.84 |
| 255 | T255V | 1.17 | 0.70 |
| 255 | T255W | 1.27 | 0.74 |
| 255 | T255Y | 1.02 | 0.72 |
| 257 | K257A | 1.08 | 0.67 |
| 257 | K257C | 0.89 | 0.49 |
| 257 | K257D | 1.16 | 0.75 |
| 257 | K257E | 1.15 | 0.76 |
| 257 | K257F | 1.03 | 0.92 |
| 257 | K257G | 0.97 | 0.73 |
| 257 | K257H | 1.12 | 0.69 |
| 257 | K257I | 1.09 | 0.59 |
| 257 | K257L | 1.26 | 0.74 |
| 257 | K257M | 1.29 | 0.79 |
| 257 | K257N | 1.16 | 0.83 |
| 257 | K257P | 0.62 | 0.38 |
| 257 | K257Q | 1.18 | 0.82 |
| 257 | K257R | 1.03 | 0.89 |
| 257 | K257S | 1.29 | 0.71 |
| 257 | K257T | 1.04 | 0.77 |
| 257 | K257V | 1.31 | 0.78 |
| 257 | K257W | 0.99 | 0.72 |
| 258 | P258A | 0.97 | 1.08 |
| 258 | P258C | 1.17 | 0.85 |
| 258 | P258D | 1.33 | 1.10 |
| 258 | P258E | 0.95 | 1.05 |
| 258 | P258F | 0.96 | 0.75 |
| 258 | P258G | 1.30 | 1.02 |
| 258 | P258H | 1.38 | 1.13 |
| 258 | P258I | 1.27 | 0.25 |
| 258 | P258K | 1.29 | 1.11 |
| 258 | P258L | 1.08 | 0.61 |
| 258 | P258M | 1.09 | 0.91 |
| 258 | P258N | 1.07 | 1.01 |
| 258 | P258Q | 1.31 | 1.13 |
| 258 | P258R | 1.02 | 1.13 |
| 258 | P258S | 1.12 | 1.08 |
| 258 | P258T | 1.27 | 1.10 |
| 258 | P258V | 1.29 | 0.80 |
| 258 | P258W | 1.14 | 0.87 |
| 258 | P258Y | 1.16 | 1.08 |
| 268 | Y268A | 0.86 | 1.39 |
| 268 | Y268C | 0.47 | 1.10 |
| 268 | Y268D | 0.59 | 1.44 |
| 268 | Y268E | 0.55 | 1.47 |
| 268 | Y268F | 1.28 | 1.07 |
| 268 | Y268G | 1.03 | 1.21 |
| 268 | Y268H | 0.87 | 1.24 |
| 268 | Y268K | 0.78 | 1.90 |
| 268 | Y268L | 0.72 | 1.10 |
| 268 | Y268M | 0.97 | 1.15 |
| 268 | Y268N | 0.69 | 1.51 |
| 268 | Y268P | 0.78 | 1.41 |
| 268 | Y268Q | 0.71 | 1.30 |
| 268 | Y268R | 0.76 | 1.49 |
| 268 | Y268S | 1.06 | 1.22 |
| 268 | Y268T | 0.99 | 1.12 |
| 268 | Y268V | 0.88 | 0.99 |
| 268 | Y268W | 0.97 | 1.07 |
| 272 | K272R | 0.90 | 0.86 |
| 274 | H274A | 0.66 | 1.40 |
| 274 | H274C | 0.65 | 0.68 |
| 274 | H274D | 0.64 | 1.20 |
| 274 | H274E | 0.86 | 1.14 |
| 274 | H274F | 0.88 | 1.00 |
| 274 | H274G | 0.56 | 1.36 |
| 274 | H274I | 0.76 | 1.39 |
| 274 | H274K | 0.85 | 1.60 |
| 274 | H274L | 0.87 | 1.40 |
| 274 | H274N | 0.67 | 1.50 |
| 274 | H274Q | 0.84 | 1.47 |
| 274 | H274R | 0.80 | 1.50 |
| 274 | H274S | 0.67 | 1.28 |
| 274 | H274T | 0.69 | 1.38 |
| 274 | H274W | 1.26 | 0.79 |
| 274 | H274Y | 1.05 | 1.07 |
| 275 | N275A | 0.32 | 1.01 |
| 275 | N275C | 0.22 | 0.68 |
| 275 | N275D | 0.08 | 1.03 |
| 275 | N275G | 0.18 | 1.00 |
| 275 | N275H | 0.60 | 1.10 |
| 275 | N275I | 0.15 | 0.87 |
| 275 | N275K | 0.22 | 1.22 |
| 275 | N275L | 0.20 | 1.02 |
| 275 | N275M | 0.20 | 0.96 |
| 275 | N275Q | 0.21 | 0.96 |
| 275 | N275R | 0.28 | 1.04 |
| 275 | N275S | 0.28 | 0.92 |
| 275 | N275T | 0.19 | 0.79 |
| 275 | N275V | 0.19 | 0.76 |
| 275 | N275W | 0.05 | 0.76 |
| 275 | N275Y | 0.89 | 0.93 |
| 283 | T283A | 1.06 | 0.97 |
| 283 | T283C | 1.16 | 0.78 |
| 283 | T283D | 0.92 | 1.03 |
| 283 | T283E | 0.95 | 1.01 |
| 283 | T283G | 0.97 | 1.01 |
| 283 | T283H | 1.09 | 0.84 |
| 283 | T283I | 1.10 | 0.72 |
| 283 | T283K | 1.14 | 1.01 |
| 283 | T283L | 1.07 | 0.76 |
| 283 | T283M | 1.26 | 0.93 |
| 283 | T283N | 1.29 | 0.96 |
| 283 | T283P | 0.46 | 0.56 |
| 283 | T283R | 0.82 | 1.08 |
| 283 | T283S | 1.02 | 1.06 |
| 283 | T283V | 1.23 | 0.81 |
| 283 | T283W | 1.07 | 0.75 |
| 283 | T283Y | 1.01 | 1.04 |
| 285 | S285A | 0.93 | 0.80 |
| 285 | S285C | 0.73 | 0.61 |
| 285 | S285D | 0.91 | 1.09 |
| 285 | S285E | 1.33 | 0.89 |
| 285 | S285F | 1.18 | 1.02 |
| 285 | S285H | 0.98 | 1.10 |
| 285 | S285I | 0.84 | 0.52 |
| 285 | S285K | 1.16 | 0.84 |
| 285 | S285L | 0.85 | 0.54 |
| 285 | S285M | 0.98 | 0.76 |
| 285 | S285Q | 1.38 | 1.22 |
| 285 | S285R | 0.84 | 0.96 |
| 285 | S285T | 0.98 | 0.79 |
| 285 | S285V | 0.70 | 0.63 |
| 285 | S285W | 1.13 | 1.08 |
| 285 | S285Y | 0.97 | 1.49 |
| 293 | N293A | 1.02 | 0.93 |
| 293 | N293C | 0.78 | 0.69 |
| 293 | N293D | 1.08 | 0.89 |
| 293 | N293E | 0.87 | 0.92 |
| 293 | N293F | 0.89 | 0.70 |
| 293 | N293G | 1.31 | 0.92 |
| 293 | N293H | 1.12 | 1.05 |
| 293 | N293I | 0.94 | 0.75 |
| 293 | N293K | 1.42 | 1.41 |
| 293 | N293L | 0.87 | 0.81 |
| 293 | N293M | 0.95 | 1.07 |
| 293 | N293P | 0.97 | 0.40 |
| 293 | N293Q | 1.14 | 1.06 |
| 293 | N293R | 0.86 | 1.37 |
| 293 | N293S | 0.93 | 0.95 |
| 293 | N293T | 1.10 | 1.12 |
| 293 | N293V | 1.04 | 0.82 |
| 293 | N293W | 1.09 | 0.78 |
| 293 | N293Y | 1.19 | 0.74 |
| 294 | K294A | 0.83 | 0.92 |
| 294 | K294C | 0.83 | 0.50 |

TABLE 26-5-continued

Combinable mutations in AmyS

| POS | variant | Stability PI | Activity PI |
|---|---|---|---|
| 294 | K294D | 0.82 | 0.57 |
| 294 | K294E | 0.83 | 0.68 |
| 294 | K294F | 0.69 | 0.59 |
| 294 | K294G | 0.92 | 0.75 |
| 294 | K294H | 0.84 | 0.90 |
| 294 | K294I | 1.08 | 0.71 |
| 294 | K294L | 0.80 | 0.92 |
| 294 | K294M | 1.12 | 0.80 |
| 294 | K294N | 0.97 | 0.83 |
| 294 | K294Q | 0.88 | 0.87 |
| 294 | K294R | 1.18 | 0.90 |
| 294 | K294S | 0.95 | 0.83 |
| 294 | K294T | 0.83 | 0.16 |
| 294 | K294V | 0.89 | 0.73 |
| 294 | K294W | 1.23 | 0.66 |
| 294 | K294Y | 0.76 | 0.82 |
| 297 | T297C | 0.86 | 0.53 |
| 297 | T297D | 0.70 | 0.98 |
| 297 | T297E | 0.93 | 0.84 |
| 297 | T297F | 1.01 | 0.68 |
| 297 | T297G | 1.17 | 0.78 |
| 297 | T297H | 0.80 | 1.01 |
| 297 | T297I | 1.07 | 0.84 |
| 297 | T297K | 0.93 | 1.14 |
| 297 | T297L | 0.89 | 0.97 |
| 297 | T297M | 0.99 | 0.91 |
| 297 | T297N | 0.78 | 1.03 |
| 297 | T297P | 0.97 | 0.48 |
| 297 | T297Q | 1.01 | 0.89 |
| 297 | T297R | 1.03 | 1.14 |
| 297 | T297S | 0.92 | 1.00 |
| 297 | T297V | 1.01 | 0.86 |
| 297 | T297W | 0.98 | 0.60 |
| 297 | T297Y | 0.91 | 0.93 |
| 300 | K300A | 0.99 | 0.79 |
| 300 | K300C | 0.95 | 0.39 |
| 300 | K300D | 0.91 | 0.61 |
| 300 | K300E | 0.86 | 0.78 |
| 300 | K300F | 0.74 | 0.63 |
| 300 | K300G | 0.98 | 0.62 |
| 300 | K300H | 1.04 | 0.83 |
| 300 | K300I | 1.02 | 0.82 |
| 300 | K300L | 0.91 | 0.73 |
| 300 | K300M | 1.17 | 0.80 |
| 300 | K300N | 1.02 | 0.80 |
| 300 | K300Q | 0.90 | 0.86 |
| 300 | K300R | 1.20 | 0.92 |
| 300 | K300S | 0.93 | 0.80 |
| 300 | K300T | 1.16 | 0.87 |
| 300 | K300V | 1.15 | 0.84 |
| 300 | K300W | 0.97 | 0.57 |
| 301 | S301A | 1.10 | 0.89 |
| 301 | S301E | 1.12 | 0.94 |
| 301 | S301F | 1.44 | 0.68 |
| 301 | S301G | 1.02 | 1.05 |
| 301 | S301H | 1.12 | 0.87 |
| 301 | S301I | 1.28 | 0.74 |
| 301 | S301K | 1.08 | 1.05 |
| 301 | S301L | 1.09 | 0.97 |
| 301 | S301M | 1.09 | 0.87 |
| 301 | S301N | 1.16 | 0.64 |
| 301 | S301P | 1.21 | 0.61 |
| 301 | S301Q | 1.18 | 0.95 |
| 301 | S301R | 1.35 | 0.89 |
| 301 | S301T | 1.23 | 0.85 |
| 301 | S301V | 1.18 | 0.81 |
| 301 | S301W | 1.27 | 0.75 |
| 301 | S301Y | 1.10 | 0.80 |
| 306 | D306A | 0.82 | 0.40 |
| 306 | D306C | 0.74 | 0.30 |
| 306 | D306E | 0.80 | 0.71 |
| 306 | D306F | 0.71 | 0.10 |
| 306 | D306G | 0.76 | 0.26 |
| 306 | D306H | 0.84 | 0.35 |
| 306 | D306I | 0.80 | 0.18 |
| 306 | D306K | 0.77 | 0.41 |
| 306 | D306L | 0.78 | 0.18 |
| 306 | D306N | 1.15 | 0.89 |
| 306 | D306P | 0.82 | 0.39 |
| 306 | D306Q | 1.03 | 0.43 |
| 306 | D306R | 0.82 | 0.27 |
| 306 | D306S | 0.81 | 0.50 |
| 306 | D306T | 0.88 | 0.29 |
| 306 | D306V | 0.99 | 0.22 |
| 306 | D306Y | 0.94 | 0.12 |
| 309 | T309C | 1.15 | 0.59 |
| 309 | T309D | 1.27 | 0.89 |
| 309 | T309E | 0.95 | 0.91 |
| 309 | T309F | 1.15 | 0.80 |
| 309 | T309G | 1.17 | 1.00 |
| 309 | T309H | 0.94 | 0.97 |
| 309 | T309I | 1.17 | 0.82 |
| 309 | T309K | 1.18 | 1.08 |
| 309 | T309L | 1.15 | 0.95 |
| 309 | T309M | 1.15 | 0.97 |
| 309 | T309N | 1.20 | 0.99 |
| 309 | T309P | 0.93 | 0.20 |
| 309 | T309Q | 1.19 | 0.98 |
| 309 | T309R | 1.12 | 1.08 |
| 309 | T309S | 1.00 | 1.04 |
| 309 | T309V | 1.38 | 0.95 |
| 309 | T309W | 1.08 | 0.77 |
| 309 | T309Y | 1.11 | 0.94 |
| 312 | T312A | 1.01 | 1.00 |
| 312 | T312C | 0.99 | 0.70 |
| 312 | T312D | 1.03 | 0.96 |
| 312 | T312E | 1.15 | 0.95 |
| 312 | T312F | 1.05 | 0.92 |
| 312 | T312G | 1.18 | 1.07 |
| 312 | T312H | 1.30 | 0.99 |
| 312 | T312K | 0.83 | 0.25 |
| 312 | T312L | 1.08 | 0.95 |
| 312 | T312M | 0.98 | 0.91 |
| 312 | T312N | 1.04 | 0.99 |
| 312 | T312P | 0.74 | 0.85 |
| 312 | T312Q | 1.05 | 0.94 |
| 312 | T312R | 1.13 | 1.00 |
| 312 | T312S | 1.29 | 0.99 |
| 312 | T312V | 1.40 | 0.87 |
| 312 | T312W | 1.14 | 0.83 |
| 312 | T312Y | 1.31 | 0.92 |
| 313 | N313A | 1.01 | 0.93 |
| 313 | N313C | 0.95 | 0.63 |
| 313 | N313D | 0.95 | 0.51 |
| 313 | N313E | 1.05 | 0.90 |
| 313 | N313F | 1.06 | 0.64 |
| 313 | N313G | 1.25 | 0.96 |
| 313 | N313H | 1.25 | 0.94 |
| 313 | N313I | 1.44 | 0.55 |
| 313 | N313K | 1.12 | 0.85 |
| 313 | N313L | 1.21 | 0.85 |
| 313 | N313M | 1.02 | 0.89 |
| 313 | N313P | 1.05 | 0.81 |
| 313 | N313Q | 1.00 | 1.00 |
| 313 | N313R | 1.19 | 1.13 |
| 313 | N313S | 1.25 | 1.05 |
| 313 | N313V | 1.28 | 0.74 |
| 313 | N313W | 1.01 | 0.67 |
| 313 | N313Y | 1.10 | 0.90 |
| 317 | K317A | 0.98 | 0.94 |
| 317 | K317C | 0.83 | 0.54 |
| 317 | K317D | 0.82 | 0.86 |
| 317 | K317E | 0.78 | 0.91 |
| 317 | K317F | 0.92 | 0.84 |
| 317 | K317G | 0.91 | 0.88 |
| 317 | K317L | 1.10 | 0.86 |
| 317 | K317M | 1.02 | 0.95 |
| 317 | K317N | 1.03 | 0.92 |
| 317 | K317P | 0.86 | 0.80 |
| 317 | K317Q | 0.76 | 0.94 |

TABLE 26-5-continued

Combinable mutations in AmyS

| POS | variant | Stability PI | Activity PI |
|---|---|---|---|
| 317 | K317R | 0.78 | 0.89 |
| 317 | K317S | 1.04 | 0.93 |
| 317 | K317T | 0.94 | 0.88 |
| 317 | K317V | 1.00 | 0.93 |
| 317 | K317W | 1.08 | 0.83 |
| 317 | K317Y | 1.05 | 0.93 |
| 318 | D318A | 0.93 | 1.38 |
| 318 | D318E | 0.90 | 1.09 |
| 318 | D318F | 0.78 | 1.22 |
| 318 | D318G | 0.91 | 1.39 |
| 318 | D318H | 1.12 | 1.10 |
| 318 | D318I | 0.75 | 1.40 |
| 318 | D318K | 0.65 | 1.73 |
| 318 | D318L | 1.00 | 1.31 |
| 318 | D318M | 0.90 | 1.26 |
| 318 | D318N | 0.92 | 1.19 |
| 318 | D318P | 0.61 | 0.37 |
| 318 | D318Q | 0.93 | 1.14 |
| 318 | D318R | 0.71 | 1.54 |
| 318 | D318S | 1.11 | 1.37 |
| 318 | D318T | 1.40 | 1.32 |
| 318 | D318V | 0.81 | 1.34 |
| 318 | D318W | 0.90 | 1.07 |
| 318 | D318Y | 1.10 | 1.33 |
| 319 | Q319A | 1.02 | 1.13 |
| 319 | Q319C | 0.73 | 1.38 |
| 319 | Q319D | 0.85 | 1.31 |
| 319 | Q319E | 0.98 | 1.20 |
| 319 | Q319F | 0.87 | 1.11 |
| 319 | Q319G | 1.14 | 1.03 |
| 319 | Q319H | 0.94 | 1.28 |
| 319 | Q319I | 0.94 | 1.32 |
| 319 | Q319K | 1.10 | 1.52 |
| 319 | Q319L | 0.95 | 1.11 |
| 319 | Q319M | 0.90 | 1.09 |
| 319 | Q319N | 0.91 | 1.12 |
| 319 | Q319P | 1.13 | 0.57 |
| 319 | Q319R | 1.18 | 1.44 |
| 319 | Q319S | 0.91 | 1.12 |
| 319 | Q319T | 0.98 | 1.10 |
| 319 | Q319V | 1.07 | 1.08 |
| 319 | Q319W | 1.05 | 1.08 |
| 319 | Q319Y | 1.04 | 1.41 |
| 320 | P320A | 1.02 | 0.96 |
| 320 | P320C | 1.01 | 0.75 |
| 320 | P320D | 0.74 | 0.91 |
| 320 | P320E | 1.04 | 0.85 |
| 320 | P320F | 0.76 | 0.77 |
| 320 | P320G | 1.00 | 1.00 |
| 320 | P320H | 1.00 | 1.18 |
| 320 | P320I | 0.86 | 0.80 |
| 320 | P320K | 0.96 | 1.23 |
| 320 | P320L | 0.87 | 0.83 |
| 320 | P320M | 1.04 | 0.60 |
| 320 | P320Q | 0.95 | 1.08 |
| 320 | P320R | 0.79 | 1.25 |
| 320 | P320S | 1.16 | 1.03 |
| 320 | P320T | 1.11 | 1.28 |
| 320 | P320V | 1.08 | 0.88 |
| 320 | P320W | 0.90 | 1.03 |
| 320 | P320Y | 1.05 | 1.03 |
| 338 | L338A | 1.36 | 1.29 |
| 338 | L338C | 1.24 | 0.67 |
| 338 | L338D | 1.00 | 0.94 |
| 338 | L338E | 0.87 | 0.65 |
| 338 | L338F | 0.90 | 0.17 |
| 338 | L338G | 1.38 | 1.34 |
| 338 | L338H | 0.05 | 0.05 |
| 338 | L338I | 1.12 | 1.32 |
| 338 | L338M | 1.20 | 1.27 |
| 338 | L338P | 1.11 | 1.23 |
| 338 | L338Q | 0.96 | 0.61 |
| 338 | L338S | 1.13 | 1.51 |
| 338 | L338T | 1.42 | 1.05 |
| 338 | L338V | 1.14 | 1.55 |
| 338 | L338W | 0.98 | 0.14 |
| 338 | L338Y | 1.15 | 0.11 |
| 339 | Q339A | 1.08 | 1.13 |
| 339 | Q339C | 0.88 | 0.79 |
| 339 | Q339D | 0.93 | 0.11 |
| 339 | Q339E | 1.07 | 0.84 |
| 339 | Q339F | 0.86 | 0.55 |
| 339 | Q339G | 1.17 | 1.21 |
| 339 | Q339H | 1.03 | 1.04 |
| 339 | Q339K | 1.26 | 1.13 |
| 339 | Q339L | 1.12 | 0.70 |
| 339 | Q339M | 0.93 | 0.81 |
| 339 | Q339P | 1.02 | 1.24 |
| 339 | Q339R | 0.81 | 0.35 |
| 339 | Q339S | 1.02 | 1.02 |
| 339 | Q339T | 1.35 | 1.01 |
| 339 | Q339V | 1.23 | 0.76 |
| 339 | Q339Y | 1.14 | 0.78 |
| 340 | S340A | 1.23 | 1.43 |
| 340 | S340C | 0.74 | 0.75 |
| 340 | S340D | 0.97 | 1.63 |
| 340 | S340E | 0.92 | 1.58 |
| 340 | S340F | 0.83 | 0.82 |
| 340 | S340H | 1.12 | 1.45 |
| 340 | S340I | 1.07 | 1.07 |
| 340 | S340K | 0.99 | 1.76 |
| 340 | S340M | 1.24 | 1.20 |
| 340 | S340N | 1.10 | 1.75 |
| 340 | S340P | 0.69 | 0.81 |
| 340 | S340Q | 1.21 | 1.76 |
| 340 | S340T | 1.21 | 1.14 |
| 340 | S340V | 1.00 | 1.09 |
| 340 | S340Y | 1.02 | 0.97 |
| 343 | D343A | 0.96 | 0.35 |
| 343 | D343C | 1.32 | 0.74 |
| 343 | D343E | 1.00 | 1.07 |
| 343 | D343F | 0.91 | 0.79 |
| 343 | D343H | 0.98 | 1.02 |
| 343 | D343I | 1.27 | 0.88 |
| 343 | D343L | 0.95 | 1.08 |
| 343 | D343M | 0.99 | 1.02 |
| 343 | D343N | 1.05 | 0.88 |
| 343 | D343P | 1.30 | 1.03 |
| 343 | D343Q | 1.14 | 1.01 |
| 343 | D343R | 1.25 | 1.03 |
| 343 | D343T | 1.08 | 0.98 |
| 343 | D343W | 1.00 | 0.64 |
| 343 | D343Y | 1.29 | 0.82 |
| 345 | W345A | 1.05 | 0.90 |
| 345 | W345C | 0.97 | 0.43 |
| 345 | W345D | 1.10 | 1.15 |
| 345 | W345E | 1.06 | 1.24 |
| 345 | W345F | 1.07 | 0.55 |
| 345 | W345H | 1.15 | 1.10 |
| 345 | W345I | 1.28 | 0.90 |
| 345 | W345L | 1.07 | 0.99 |
| 345 | W345M | 1.02 | 1.01 |
| 345 | W345N | 1.07 | 1.10 |
| 345 | W345P | 1.00 | 0.94 |
| 345 | W345Q | 1.26 | 1.10 |
| 345 | W345S | 1.01 | 1.12 |
| 345 | W345T | 1.15 | 1.15 |
| 345 | W345V | 1.16 | 1.02 |
| 363 | C363A | 0.84 | 1.06 |
| 363 | C363D | 0.87 | 1.74 |
| 363 | C363E | 0.99 | 1.34 |
| 363 | C363F | 0.83 | 1.03 |
| 363 | C363G | 0.61 | 0.83 |
| 363 | C363H | 0.78 | 0.76 |
| 363 | C363I | 0.92 | 0.63 |
| 363 | C363L | 0.73 | 0.89 |
| 363 | C363M | 0.97 | 1.36 |
| 363 | C363N | 0.92 | 1.86 |
| 363 | C363Q | 0.88 | 1.78 |
| 363 | C363S | 0.88 | 1.35 |

TABLE 26-5-continued

Combinable mutations in AmyS

| POS | variant | Stability PI | Activity PI |
|---|---|---|---|
| 363 | C363T | 1.15 | 0.18 |
| 363 | C363V | 1.02 | 0.99 |
| 363 | C363W | 0.35 | 0.70 |
| 363 | C363Y | 0.92 | 0.12 |
| 366 | Y366A | 0.96 | 1.14 |
| 366 | Y366D | 0.52 | 1.18 |
| 366 | Y366E | 0.91 | 1.18 |
| 366 | Y366F | 0.91 | 0.87 |
| 366 | Y366G | 0.94 | 1.08 |
| 366 | Y366H | 1.07 | 1.12 |
| 366 | Y366I | 0.85 | 0.87 |
| 366 | Y366K | 0.72 | 0.82 |
| 366 | Y366L | 0.77 | 0.61 |
| 366 | Y366M | 0.92 | 0.79 |
| 366 | Y366N | 1.03 | 0.91 |
| 366 | Y366P | 0.54 | 0.78 |
| 366 | Y366Q | 1.03 | 1.49 |
| 366 | Y366R | 0.96 | 0.96 |
| 366 | Y366S | 1.07 | 1.02 |
| 366 | Y366T | 1.01 | 0.91 |
| 366 | Y366V | 1.04 | 0.94 |
| 366 | Y366W | 1.11 | 0.99 |
| 369 | Y369E | 0.98 | 0.87 |
| 369 | Y369F | 1.03 | 0.79 |
| 369 | Y369G | 0.86 | 0.33 |
| 369 | Y369H | 0.89 | 0.78 |
| 369 | Y369I | 1.33 | 0.91 |
| 369 | Y369K | 1.07 | 0.80 |
| 369 | Y369M | 1.06 | 1.02 |
| 369 | Y369P | 0.49 | 0.20 |
| 369 | Y369Q | 1.07 | 0.79 |
| 369 | Y369R | 1.11 | 0.95 |
| 369 | Y369S | 0.89 | 0.60 |
| 369 | Y369T | 1.28 | 0.68 |
| 369 | Y369V | 1.17 | 0.91 |
| 369 | Y369W | 1.09 | 0.95 |
| 370 | Y370A | 1.03 | 1.21 |
| 370 | Y370D | 0.48 | 1.35 |
| 370 | Y370E | 0.98 | 1.35 |
| 370 | Y370F | 0.90 | 0.73 |
| 370 | Y370G | 1.21 | 1.18 |
| 370 | Y370H | 0.96 | 1.36 |
| 370 | Y370I | 0.99 | 1.00 |
| 370 | Y370K | 0.93 | 1.65 |
| 370 | Y370L | 0.93 | 0.88 |
| 370 | Y370M | 0.91 | 1.04 |
| 370 | Y370N | 1.04 | 1.41 |
| 370 | Y370P | 0.44 | 0.67 |
| 370 | Y370Q | 0.87 | 1.51 |
| 370 | Y370S | 1.06 | 1.50 |
| 370 | Y370T | 1.07 | 1.10 |
| 370 | Y370V | 1.05 | 1.13 |
| 370 | Y370W | 0.94 | 0.91 |
| 375 | Y375A | 1.03 | 1.39 |
| 375 | Y375C | 0.59 | 0.48 |
| 375 | Y375D | 0.96 | 1.52 |
| 375 | Y375E | 0.96 | 1.48 |
| 375 | Y375F | 0.90 | 1.00 |
| 375 | Y375G | 0.90 | 0.98 |
| 375 | Y375H | 0.98 | 1.16 |
| 375 | Y375I | 0.94 | 1.06 |
| 375 | Y375K | 0.96 | 1.43 |
| 375 | Y375L | 1.03 | 1.07 |
| 375 | Y375M | 0.98 | 1.05 |
| 375 | Y375N | 0.92 | 1.48 |
| 375 | Y375P | 0.92 | 0.89 |
| 375 | Y375Q | 0.92 | 1.56 |
| 375 | Y375R | 0.77 | 1.61 |
| 375 | Y375S | 0.92 | 1.29 |
| 375 | Y375T | 1.25 | 1.04 |
| 375 | Y375W | 0.98 | 0.88 |
| 379 | S379A | 1.01 | 1.02 |
| 379 | S379C | 0.60 | 0.44 |
| 379 | S379D | 0.92 | 0.96 |
| 379 | S379E | 0.99 | 1.01 |
| 379 | S379G | 0.90 | 0.91 |
| 379 | S379I | 0.80 | 0.70 |
| 379 | S379K | 1.00 | 1.12 |
| 379 | S379L | 0.84 | 0.56 |
| 379 | S379M | 0.87 | 0.80 |
| 379 | S379N | 1.03 | 0.98 |
| 379 | S379P | 0.61 | 0.39 |
| 379 | S379Q | 0.94 | 0.98 |
| 379 | S379R | 0.96 | 1.01 |
| 379 | S379T | 1.07 | 0.95 |
| 379 | S379V | 0.90 | 0.75 |
| 379 | S379W | 0.70 | 0.35 |
| 379 | S379Y | 0.92 | 0.59 |
| 381 | K381A | 0.85 | 0.78 |
| 381 | K381C | 0.86 | 0.35 |
| 381 | K381D | 0.87 | 0.65 |
| 381 | K381E | 0.93 | 0.81 |
| 381 | K381F | 0.96 | 0.20 |
| 381 | K381G | 0.96 | 0.82 |
| 381 | K381H | 1.13 | 0.73 |
| 381 | K381I | 0.98 | 0.36 |
| 381 | K381L | 0.95 | 0.38 |
| 381 | K381M | 0.93 | 0.56 |
| 381 | K381N | 0.87 | 0.68 |
| 381 | K381P | 1.18 | 0.39 |
| 381 | K381Q | 1.03 | 0.90 |
| 381 | K381R | 1.20 | 0.95 |
| 381 | K381S | 1.18 | 0.89 |
| 381 | K381T | 1.01 | 0.60 |
| 381 | K381V | 1.00 | 0.43 |
| 381 | K381W | 0.90 | 0.22 |
| 381 | K381Y | 0.87 | 0.63 |
| 385 | D385A | 1.01 | 0.88 |
| 385 | D385E | 0.89 | 1.05 |
| 385 | D385F | 0.73 | 0.54 |
| 385 | D385G | 1.05 | 0.88 |
| 385 | D385H | 0.96 | 0.99 |
| 385 | D385K | 1.00 | 1.06 |
| 385 | D385L | 0.96 | 0.47 |
| 385 | D385N | 0.91 | 0.96 |
| 385 | D385Q | 1.02 | 1.01 |
| 385 | D385R | 0.86 | 0.95 |
| 385 | D385S | 1.10 | 1.00 |
| 385 | D385T | 1.22 | 0.92 |
| 385 | D385V | 0.85 | 0.43 |
| 385 | D385W | 0.98 | 0.53 |
| 386 | P386A | 0.90 | 0.80 |
| 386 | P386C | 0.72 | 0.69 |
| 386 | P386D | 0.85 | 0.94 |
| 386 | P386E | 0.94 | 0.87 |
| 386 | P386F | 0.72 | 0.66 |
| 386 | P386G | 1.02 | 0.77 |
| 386 | P386H | 0.89 | 0.93 |
| 386 | P386I | 1.12 | 0.73 |
| 386 | P386K | 1.22 | 0.87 |
| 386 | P386L | 0.96 | 0.73 |
| 386 | P386M | 0.94 | 0.70 |
| 386 | P386N | 0.91 | 0.86 |
| 386 | P386Q | 0.95 | 0.86 |
| 386 | P386S | 0.83 | 0.82 |
| 386 | P386T | 1.00 | 0.54 |
| 386 | P386V | 1.11 | 0.79 |
| 386 | P386W | 0.90 | 0.44 |
| 386 | P386Y | 0.91 | 0.78 |
| 391 | R391A | 0.58 | 0.22 |
| 391 | R391H | 0.59 | 0.29 |
| 391 | R391K | 0.88 | 0.59 |
| 391 | R391N | 0.71 | 0.38 |
| 391 | R391Q | 0.62 | 0.28 |
| 391 | R391T | 0.67 | 0.25 |
| 392 | R392A | 0.89 | 0.73 |
| 392 | R392C | 0.74 | 0.66 |
| 392 | R392E | 0.79 | 0.46 |
| 392 | R392F | 1.03 | 0.43 |
| 392 | R392G | 0.99 | 0.65 |

TABLE 26-5-continued

Combinable mutations in AmyS

| POS | variant | Stability PI | Activity PI |
|---|---|---|---|
| 392 | R392H | 0.86 | 0.96 |
| 392 | R392I | 1.08 | 0.57 |
| 392 | R392K | 1.10 | 1.09 |
| 392 | R392L | 0.91 | 0.63 |
| 392 | R392M | 1.07 | 0.72 |
| 392 | R392N | 0.89 | 0.90 |
| 392 | R392P | 0.67 | 0.31 |
| 392 | R392Q | 1.12 | 0.75 |
| 392 | R392S | 1.00 | 0.73 |
| 392 | R392T | 1.00 | 0.91 |
| 392 | R392V | 0.89 | 0.48 |
| 392 | R392W | 0.68 | 0.23 |
| 392 | R392Y | 1.00 | 0.60 |
| 393 | D393A | 0.98 | 0.77 |
| 393 | D393C | 0.69 | 0.48 |
| 393 | D393E | 0.92 | 0.81 |
| 393 | D393F | 0.84 | 0.61 |
| 393 | D393G | 1.08 | 0.75 |
| 393 | D393H | 0.88 | 0.75 |
| 393 | D393K | 1.09 | 0.80 |
| 393 | D393L | 1.04 | 0.70 |
| 393 | D393Q | 1.00 | 0.82 |
| 393 | D393R | 0.88 | 0.64 |
| 393 | D393S | 0.92 | 0.91 |
| 393 | D393T | 1.12 | 0.90 |
| 393 | D393V | 1.04 | 0.63 |
| 393 | D393W | 0.95 | 0.66 |
| 393 | D393Y | 1.01 | 0.66 |
| 394 | Y394A | 0.91 | 0.86 |
| 394 | Y394D | 0.98 | 0.84 |
| 394 | Y394E | 0.92 | 1.03 |
| 394 | Y394F | 1.07 | 0.98 |
| 394 | Y394G | 1.13 | 0.85 |
| 394 | Y394H | 1.04 | 0.99 |
| 394 | Y394I | 1.11 | 0.95 |
| 394 | Y394K | 1.09 | 1.07 |
| 394 | Y394L | 1.22 | 1.11 |
| 394 | Y394M | 0.74 | 0.23 |
| 394 | Y394N | 1.00 | 1.01 |
| 394 | Y394Q | 1.09 | 1.13 |
| 394 | Y394S | 1.11 | 1.15 |
| 394 | Y394V | 3.00 | 0.75 |
| 394 | Y394W | 1.11 | 1.16 |
| 400 | H400A | 1.24 | 0.89 |
| 400 | H400C | 1.16 | 0.73 |
| 400 | H400D | 1.05 | 0.82 |
| 400 | H400E | 0.99 | 0.95 |
| 400 | H400F | 1.01 | 0.94 |
| 400 | H400G | 0.90 | 0.83 |
| 400 | H400I | 1.04 | 0.91 |
| 400 | H400K | 0.92 | 1.03 |
| 400 | H400L | 0.90 | 0.88 |
| 400 | H400M | 1.01 | 0.91 |
| 400 | H400N | 1.26 | 0.92 |
| 400 | H400Q | 0.96 | 0.94 |
| 400 | H400R | 1.03 | 0.87 |
| 400 | H400S | 0.94 | 0.92 |
| 400 | H400T | 0.95 | 0.88 |
| 400 | H400V | 1.28 | 0.91 |
| 400 | H400W | 1.17 | 0.80 |
| 400 | H400Y | 1.15 | 0.92 |
| 402 | Y402A | 1.07 | 0.97 |
| 402 | Y402C | 0.92 | 0.76 |
| 402 | Y402D | 0.90 | 0.80 |
| 402 | Y402E | 1.09 | 0.77 |
| 402 | Y402F | 0.89 | 0.82 |
| 402 | Y402G | 0.92 | 0.81 |
| 402 | Y402H | 1.21 | 0.91 |
| 402 | Y402I | 1.36 | 0.75 |
| 402 | Y402K | 0.95 | 0.84 |
| 402 | Y402L | 1.09 | 0.49 |
| 402 | Y402M | 1.14 | 0.88 |
| 402 | Y402N | 1.06 | 0.86 |
| 402 | Y402P | 1.03 | 0.28 |
| 402 | Y402Q | 0.98 | 0.83 |
| 402 | Y402R | 1.16 | 0.75 |
| 402 | Y402T | 1.32 | 1.02 |
| 402 | Y402V | 1.40 | 0.95 |
| 402 | Y402W | 1.24 | 0.89 |
| 403 | L403A | 1.20 | 0.89 |
| 403 | L403C | 1.10 | 0.98 |
| 403 | L403D | 1.03 | 0.95 |
| 403 | L403E | 1.26 | 0.93 |
| 403 | L403F | 1.03 | 0.74 |
| 403 | L403G | 1.22 | 0.96 |
| 403 | L403H | 1.10 | 0.90 |
| 403 | L403M | 1.11 | 0.99 |
| 403 | L403N | 0.98 | 0.95 |
| 403 | L403P | 0.78 | 0.47 |
| 403 | L403Q | 1.24 | 0.98 |
| 403 | L403R | 1.36 | 1.01 |
| 403 | L403S | 1.17 | 1.00 |
| 403 | L403T | 1.53 | 0.99 |
| 403 | L403V | 1.34 | 1.00 |
| 403 | L403W | 1.15 | 0.85 |
| 403 | L403Y | 1.16 | 0.97 |
| 404 | D404A | 1.12 | 0.73 |
| 404 | D404C | 1.28 | 0.61 |
| 404 | D404E | 1.38 | 0.78 |
| 404 | D404G | 1.25 | 0.77 |
| 404 | D404I | 1.20 | 0.84 |
| 404 | D404K | 1.10 | 0.83 |
| 404 | D404L | 1.09 | 0.91 |
| 404 | D404M | 1.13 | 0.76 |
| 404 | D404N | 1.13 | 0.98 |
| 404 | D404P | 1.05 | 0.56 |
| 404 | D404Q | 1.17 | 0.91 |
| 404 | D404R | 1.15 | 0.77 |
| 404 | D404S | 1.19 | 0.99 |
| 404 | D404V | 1.28 | 0.79 |
| 404 | D404W | 1.05 | 0.76 |
| 404 | D404Y | 1.08 | 0.81 |
| 406 | S406A | 0.99 | 0.99 |
| 406 | S406C | 1.11 | 0.85 |
| 406 | S406D | 0.93 | 1.02 |
| 406 | S406E | 0.95 | 0.91 |
| 406 | S406F | 0.86 | 0.88 |
| 406 | S406G | 0.93 | 0.86 |
| 406 | S406H | 0.88 | 0.98 |
| 406 | S406I | 0.92 | 0.91 |
| 406 | S406K | 0.95 | 0.82 |
| 406 | S406L | 0.94 | 0.98 |
| 406 | S406M | 0.89 | 0.90 |
| 406 | S406N | 1.09 | 0.94 |
| 406 | S406P | 0.91 | 0.93 |
| 406 | S406T | 1.18 | 0.97 |
| 406 | S406V | 1.14 | 0.87 |
| 406 | S406Y | 0.99 | 0.80 |
| 407 | D407C | 1.14 | 0.41 |
| 407 | D407E | 0.82 | 0.59 |
| 407 | D407F | 0.88 | 0.35 |
| 407 | D407G | 1.10 | 0.38 |
| 407 | D407H | 0.85 | 0.63 |
| 407 | D407I | 1.05 | 0.22 |
| 407 | D407K | 1.00 | 0.44 |
| 407 | D407L | 0.91 | 0.18 |
| 407 | D407M | 1.05 | 0.37 |
| 407 | D407N | 1.11 | 0.96 |
| 407 | D407Q | 0.94 | 0.53 |
| 407 | D407R | 0.78 | 0.36 |
| 407 | D407S | 0.93 | 0.65 |
| 407 | D407T | 1.06 | 0.49 |
| 407 | D407V | 0.93 | 0.29 |
| 407 | D407W | 1.06 | 0.20 |
| 407 | D407Y | 0.85 | 0.38 |
| 410 | G410A | 0.90 | 1.00 |
| 410 | G410C | 1.04 | 0.81 |
| 410 | G410F | 0.96 | 0.22 |
| 410 | G410H | 0.93 | 0.34 |
| 410 | G410M | 1.13 | 0.35 |

TABLE 26-5-continued

Combinable mutations in AmyS

| POS | variant | Stability PI | Activity PI |
|---|---|---|---|
| 410 | G410N | 0.99 | 0.27 |
| 410 | G410Q | 1.05 | 0.14 |
| 410 | G410R | 0.98 | 0.27 |
| 410 | G410T | 1.08 | 0.70 |
| 410 | G410V | 1.10 | 0.42 |
| 410 | G410Y | 0.92 | 0.49 |
| 413 | R413A | 1.02 | 1.06 |
| 413 | R413D | 0.71 | 0.40 |
| 413 | R413E | 0.86 | 0.67 |
| 413 | R413G | 1.19 | 0.33 |
| 413 | R413H | 1.06 | 0.95 |
| 413 | R413I | 0.96 | 0.75 |
| 413 | R413K | 1.08 | 0.95 |
| 413 | R413L | 1.02 | 0.96 |
| 413 | R413M | 0.81 | 0.81 |
| 413 | R413N | 0.93 | 0.72 |
| 413 | R413Q | 0.81 | 0.35 |
| 413 | R413S | 0.85 | 0.87 |
| 413 | R413V | 0.93 | 0.73 |
| 413 | R413W | 0.92 | 0.41 |
| 413 | R413Y | 0.73 | 0.49 |
| 414 | E414A | 1.06 | 0.70 |
| 414 | E414C | 1.05 | 0.55 |
| 414 | E414D | 1.13 | 0.75 |
| 414 | E414F | 0.81 | 0.59 |
| 414 | E414G | 0.82 | 0.68 |
| 414 | E414H | 0.89 | 0.65 |
| 414 | E414I | 0.98 | 0.60 |
| 414 | E414K | 0.96 | 0.65 |
| 414 | E414L | 1.16 | 0.71 |
| 414 | E414M | 0.88 | 0.72 |
| 414 | E414N | 0.99 | 0.57 |
| 414 | E414P | 0.85 | 0.60 |
| 414 | E414Q | 0.85 | 0.70 |
| 414 | E414R | 1.00 | 0.65 |
| 414 | E414S | 0.91 | 0.63 |
| 414 | E414T | 0.79 | 0.67 |
| 414 | E414W | 1.03 | 0.25 |
| 414 | E414Y | 0.78 | 0.58 |
| 416 | V416A | 0.93 | 0.67 |
| 416 | V416C | 0.94 | 0.61 |
| 416 | V416D | 1.05 | 0.71 |
| 416 | V416H | 0.92 | 0.78 |
| 416 | V416I | 0.83 | 0.74 |
| 416 | V416K | 0.71 | 0.65 |
| 416 | V416L | 0.96 | 0.81 |
| 416 | V416M | 1.06 | 0.78 |
| 416 | V416N | 0.92 | 0.66 |
| 416 | V416P | 1.18 | 0.53 |
| 416 | V416Q | 1.02 | 0.74 |
| 416 | V416R | 1.02 | 0.29 |
| 416 | V416S | 1.15 | 0.46 |
| 416 | V416T | 1.01 | 0.65 |
| 416 | V416W | 0.83 | 0.55 |
| 416 | V416Y | 0.89 | 0.69 |
| 419 | K419A | 1.36 | 1.29 |
| 419 | K419C | 1.24 | 0.67 |
| 419 | K419D | 1.00 | 0.94 |
| 419 | K419E | 0.87 | 0.65 |
| 419 | K419F | 0.90 | 0.17 |
| 419 | K419H | 0.05 | 0.05 |
| 419 | K419I | 1.12 | 1.32 |
| 419 | K419M | 1.20 | 1.27 |
| 419 | K419P | 1.11 | 1.23 |
| 419 | K419Q | 0.96 | 0.61 |
| 419 | K419S | 1.13 | 1.51 |
| 419 | K419T | 1.42 | 1.05 |
| 419 | K419V | 1.14 | 1.55 |
| 419 | K419W | 0.98 | 0.14 |
| 419 | K419Y | 1.15 | 0.11 |
| 422 | S422A | 0.64 | 0.97 |
| 422 | S422C | 0.96 | 0.71 |
| 422 | S422D | 0.97 | 0.96 |
| 422 | S422E | 1.31 | 0.78 |
| 422 | S422F | 0.96 | 0.71 |
| 422 | S422G | 1.20 | 0.99 |
| 422 | S422H | 1.06 | 0.66 |
| 422 | S422I | 1.11 | 0.85 |
| 422 | S422K | 1.16 | 0.96 |
| 422 | S422L | 0.99 | 0.74 |
| 422 | S422M | 1.04 | 0.94 |
| 422 | S422N | 1.12 | 1.03 |
| 422 | S422P | 0.84 | 0.70 |
| 422 | S422Q | 0.15 | 0.82 |
| 422 | S422R | 1.02 | 0.94 |
| 422 | S422T | 0.97 | 0.92 |
| 422 | S422V | 1.17 | 0.88 |
| 422 | S422W | 0.96 | 0.70 |
| 422 | S422Y | 1.09 | 0.92 |
| 427 | L427A | 0.93 | 0.66 |
| 427 | L427C | 1.02 | 0.68 |
| 427 | L427E | 0.86 | 0.27 |
| 427 | L427F | 0.89 | 0.30 |
| 427 | L427G | 0.63 | 0.26 |
| 427 | L427I | 1.08 | 0.64 |
| 427 | L427M | 0.86 | 0.79 |
| 427 | L427N | 0.76 | 0.31 |
| 427 | L427P | 1.13 | 0.06 |
| 427 | L427Q | 0.95 | 0.53 |
| 427 | L427S | 0.78 | 0.27 |
| 427 | L427T | 0.80 | 0.70 |
| 427 | L427V | 0.82 | 0.72 |
| 433 | G433A | 1.27 | 1.08 |
| 433 | G433C | 1.15 | 0.69 |
| 433 | G433D | 1.05 | 0.96 |
| 433 | G433E | 0.92 | 0.99 |
| 433 | G433F | 1.04 | 0.92 |
| 433 | G433H | 1.27 | 0.99 |
| 433 | G433I | 1.37 | 0.86 |
| 433 | G433K | 1.27 | 1.05 |
| 433 | G433L | 1.30 | 0.90 |
| 433 | G433M | 1.23 | 1.01 |
| 433 | G433N | 1.07 | 0.75 |
| 433 | G433P | 1.13 | 0.95 |
| 433 | G433Q | 0.78 | 0.99 |
| 433 | G433R | 1.00 | 0.91 |
| 433 | G433S | 1.17 | 0.96 |
| 433 | G433T | 1.17 | 0.90 |
| 433 | G433V | 1.27 | 0.95 |
| 433 | G433Y | 1.26 | 1.01 |
| 436 | K436A | 0.92 | 0.94 |
| 436 | K436C | 0.90 | 0.84 |
| 436 | K436D | 0.86 | 0.93 |
| 436 | K436E | 0.70 | 0.87 |
| 436 | K436F | 0.81 | 0.64 |
| 436 | K436G | 0.84 | 0.77 |
| 436 | K436H | 1.09 | 0.89 |
| 436 | K436I | 1.08 | 0.81 |
| 436 | K436L | 1.01 | 0.78 |
| 436 | K436M | 0.76 | 0.85 |
| 436 | K436N | 0.98 | 0.92 |
| 436 | K436P | 0.88 | 0.71 |
| 436 | K436Q | 1.01 | 0.96 |
| 436 | K436R | 1.06 | 0.79 |
| 436 | K436S | 0.75 | 0.92 |
| 436 | K436T | 0.95 | 0.90 |
| 436 | K436V | 0.98 | 0.87 |
| 436 | K436W | 1.07 | 0.71 |
| 436 | K436Y | 0.99 | 0.80 |
| 439 | Y439A | 1.02 | 0.78 |
| 439 | Y439D | 1.01 | 0.85 |
| 439 | Y439F | 0.77 | 0.78 |
| 439 | Y439G | 1.01 | 0.77 |
| 439 | Y439H | 0.96 | 0.73 |
| 439 | Y439K | 0.96 | 0.74 |
| 439 | Y439M | 1.04 | 0.77 |
| 439 | Y439N | 0.96 | 0.83 |
| 439 | Y439P | 0.87 | 0.85 |
| 439 | Y439Q | 0.90 | 0.88 |
| 439 | Y439R | 0.75 | 0.80 |

TABLE 26-5-continued

Combinable mutations in AmyS

| POS | variant | Stability PI | Activity PI |
|---|---|---|---|
| 439 | Y439S | 0.94 | 0.82 |
| 439 | Y439T | 0.84 | 0.79 |
| 439 | Y439V | 1.04 | 0.70 |
| 439 | Y439W | 0.86 | 0.72 |
| 442 | K442A | 1.38 | 0.98 |
| 442 | K442F | 1.04 | 0.97 |
| 442 | K442G | 1.23 | 1.02 |
| 442 | K442H | 1.07 | 1.04 |
| 442 | K442I | 1.13 | 0.93 |
| 442 | K442N | 1.39 | 1.03 |
| 442 | K442P | 1.11 | 1.03 |
| 442 | K442Q | 1.11 | 1.05 |
| 442 | K442R | 1.33 | 1.01 |
| 442 | K442S | 1.24 | 1.07 |
| 442 | K442T | 1.34 | 1.06 |
| 442 | K442V | 1.20 | 0.99 |
| 442 | K442W | 1.32 | 0.98 |
| 442 | K442Y | 1.24 | 1.08 |
| 445 | A445C | 0.98 | 0.83 |
| 445 | A445D | 1.04 | 0.87 |
| 445 | A445G | 1.21 | 1.01 |
| 445 | A445H | 0.90 | 0.93 |
| 445 | A445I | 1.25 | 0.84 |
| 445 | A445K | 1.20 | 0.11 |
| 445 | A445L | 1.17 | 0.92 |
| 445 | A445N | 1.20 | 0.91 |
| 445 | A445P | 0.91 | 0.77 |
| 445 | A445R | 0.91 | 0.89 |
| 445 | A445S | 1.16 | 0.94 |
| 445 | A445T | 1.29 | 0.88 |
| 445 | A445V | 1.27 | 0.93 |
| 445 | A445W | 1.25 | 0.80 |
| 447 | K447A | 1.09 | 1.06 |
| 447 | K447C | 1.11 | 0.87 |
| 447 | K447D | 1.00 | 0.99 |
| 447 | K447F | 1.09 | 0.84 |
| 447 | K447G | 1.06 | 0.94 |
| 447 | K447H | 1.13 | 0.92 |
| 447 | K447I | 1.22 | 0.91 |
| 447 | K447L | 1.06 | 1.01 |
| 447 | K447M | 1.07 | 0.96 |
| 447 | K447N | 1.43 | 0.97 |
| 447 | K447Q | 1.34 | 1.00 |
| 447 | K447R | 1.10 | 0.96 |
| 447 | K447S | 0.90 | 0.92 |
| 447 | K447T | 1.21 | 0.37 |
| 447 | K447V | 0.69 | 0.86 |
| 447 | K447W | 1.31 | 0.89 |
| 447 | K447Y | 1.21 | 0.96 |
| 448 | V448A | 0.98 | 0.96 |
| 448 | V448C | 1.36 | 0.98 |
| 448 | V448D | 1.15 | 1.02 |
| 448 | V448F | 1.48 | 1.01 |
| 448 | V448G | 1.26 | 1.05 |
| 448 | V448H | 1.37 | 1.03 |
| 448 | V448I | 1.44 | 0.97 |
| 448 | V448K | 1.20 | 1.07 |
| 448 | V448L | 1.04 | 1.08 |
| 448 | V448M | 1.13 | 0.97 |
| 448 | V448N | 1.24 | 0.70 |
| 448 | V448P | 0.84 | 1.19 |
| 448 | V448Q | 1.18 | 1.16 |
| 448 | V448S | 1.20 | 1.10 |
| 448 | V448W | 1.08 | 0.89 |
| 448 | V448Y | 1.33 | 1.27 |
| 450 | Y450A | 0.95 | 0.94 |
| 450 | Y450C | 1.22 | 0.84 |
| 450 | Y450D | 1.19 | 0.95 |
| 450 | Y450E | 1.01 | 0.92 |
| 450 | Y450G | 1.02 | 0.93 |
| 450 | Y450H | 1.23 | 0.90 |
| 450 | Y450K | 1.18 | 0.94 |
| 450 | Y450L | 0.93 | 0.69 |
| 450 | Y450M | 1.29 | 0.89 |
| 450 | Y450N | 1.23 | 0.96 |
| 450 | Y450P | 0.75 | 0.30 |
| 450 | Y450Q | 1.00 | 0.95 |
| 450 | Y450R | 1.22 | 1.02 |
| 450 | Y450S | 1.22 | 1.01 |
| 450 | Y450T | 1.32 | 0.96 |
| 450 | Y450W | 1.21 | 0.95 |
| 452 | L452A | 1.08 | 1.06 |
| 452 | L452C | 1.00 | 1.01 |
| 452 | L452D | 0.98 | 1.08 |
| 452 | L452E | 0.75 | 0.55 |
| 452 | L452F | 0.79 | 0.93 |
| 452 | L452G | 1.07 | 1.00 |
| 452 | L452H | 1.05 | 0.99 |
| 452 | L452K | 1.11 | 1.08 |
| 452 | L452M | 1.13 | 1.09 |
| 452 | L452N | 1.06 | 1.28 |
| 452 | L452P | 1.02 | 0.78 |
| 452 | L452Q | 0.92 | 1.22 |
| 452 | L452R | 0.93 | 1.26 |
| 452 | L452S | 0.86 | 1.21 |
| 452 | L452T | 1.02 | 1.18 |
| 452 | L452V | 1.14 | 1.14 |
| 452 | L452Y | 1.17 | 1.07 |
| 455 | N455A | 1.07 | 1.04 |
| 455 | N455C | 0.85 | 0.89 |
| 455 | N455D | 1.07 | 0.97 |
| 455 | N455E | 1.14 | 0.94 |
| 455 | N455G | 1.23 | 1.00 |
| 455 | N455H | 1.05 | 1.01 |
| 455 | N455I | 1.23 | 0.95 |
| 455 | N455K | 1.10 | 1.08 |
| 455 | N455L | 1.06 | 0.97 |
| 455 | N455M | 0.95 | 0.96 |
| 455 | N455P | 1.36 | 0.93 |
| 455 | N455Q | 0.96 | 0.91 |
| 455 | N455R | 1.13 | 1.02 |
| 455 | N455S | 1.04 | 0.91 |
| 455 | N455T | 1.16 | 0.90 |
| 455 | N455V | 1.26 | 0.89 |
| 455 | N455W | 1.12 | 0.76 |
| 455 | N455Y | 1.08 | 0.15 |
| 463 | N463A | 1.25 | 1.06 |
| 463 | N463D | 0.97 | 1.02 |
| 463 | N463F | 1.04 | 0.87 |
| 463 | N463G | 1.04 | 1.00 |
| 463 | N463H | 1.12 | 0.99 |
| 463 | N463K | 1.07 | 1.00 |
| 463 | N463L | 1.16 | 1.01 |
| 463 | N463M | 1.24 | 1.08 |
| 463 | N463P | 0.93 | 1.05 |
| 463 | N463Q | 0.98 | 1.04 |
| 463 | N463R | 0.95 | 0.93 |
| 463 | N463S | 1.27 | 0.96 |
| 463 | N463T | 1.38 | 0.91 |
| 463 | N463V | 1.32 | 0.86 |
| 463 | N463W | 1.45 | 0.74 |
| 463 | N463Y | 1.20 | 0.90 |
| 465 | D465A | 0.76 | 1.06 |
| 465 | D465C | 0.84 | 0.74 |
| 465 | D465E | 0.95 | 0.93 |
| 465 | D465F | 0.78 | 0.89 |
| 465 | D465G | 1.35 | 0.92 |
| 465 | D465H | 1.06 | 0.92 |
| 465 | D465I | 1.37 | 0.85 |
| 465 | D465K | 1.53 | 0.88 |
| 465 | D465L | 1.14 | 0.95 |
| 465 | D465M | 1.06 | 0.98 |
| 465 | D465N | 1.32 | 0.93 |
| 465 | D465P | 1.13 | 0.71 |
| 465 | D465Q | 0.86 | 0.94 |
| 465 | D465R | 1.18 | 0.90 |
| 465 | D465S | 0.87 | 0.98 |
| 465 | D465T | 1.42 | 0.92 |
| 465 | D465V | 1.24 | 0.93 |
| 465 | D465W | 1.00 | 0.83 |

TABLE 26-5-continued

Combinable mutations in AmyS

| POS | variant | Stability PI | Activity PI |
|---|---|---|---|
| 465 | D465Y | 1.06 | 0.93 |
| 469 | E469A | 1.16 | 1.01 |
| 469 | E469C | 1.03 | 0.86 |
| 469 | E469D | 1.22 | 1.02 |
| 469 | E469F | 1.11 | 1.00 |
| 469 | E469G | 1.19 | 1.00 |
| 469 | E469H | 1.04 | 0.96 |
| 469 | E469K | 1.16 | 0.96 |
| 469 | E469L | 1.10 | 0.98 |
| 469 | E469N | 1.19 | 0.47 |
| 469 | E469P | 0.85 | 1.05 |
| 469 | E469Q | 1.03 | 1.04 |
| 469 | E469R | 1.01 | 0.75 |
| 469 | E469S | 0.91 | 1.08 |
| 469 | E469T | 1.15 | 1.06 |
| 469 | E469V | 1.15 | 1.08 |
| 469 | E469W | 1.24 | 0.97 |
| 469 | E469Y | 1.35 | 1.09 |
| 471 | K471A | 1.09 | 1.09 |
| 471 | K471C | 1.04 | 0.91 |
| 471 | K471D | 1.01 | 1.06 |
| 471 | K471F | 1.10 | 1.05 |
| 471 | K471G | 1.13 | 1.12 |
| 471 | K471H | 1.00 | 1.10 |
| 471 | K471I | 1.22 | 1.02 |
| 471 | K471L | 0.99 | 1.07 |
| 471 | K471M | 0.95 | 1.14 |
| 471 | K471N | 1.04 | 1.12 |
| 471 | K471P | 0.84 | 0.98 |
| 471 | K471Q | 0.90 | 1.08 |
| 471 | K471R | 0.77 | 1.33 |
| 471 | K471S | 0.97 | 1.01 |
| 471 | K471T | 1.11 | 1.09 |
| 471 | K471V | 1.28 | 1.11 |
| 471 | K471Y | 1.15 | 1.36 |
| 473 | N473A | 1.03 | 0.99 |
| 473 | N473C | 1.15 | 0.74 |
| 473 | N473D | 1.14 | 0.98 |
| 473 | N473E | 1.20 | 0.99 |
| 473 | N473F | 1.10 | 0.83 |
| 473 | N473G | 1.35 | 0.99 |
| 473 | N473H | 1.02 | 0.91 |
| 473 | N473I | 0.66 | 0.45 |
| 473 | N473K | 1.02 | 1.02 |
| 473 | N473M | 1.11 | 1.00 |
| 473 | N473P | 1.01 | 0.95 |
| 473 | N473Q | 1.13 | 0.99 |
| 473 | N473R | 1.08 | 1.05 |
| 473 | N473S | 1.15 | 0.98 |
| 473 | N473T | 1.04 | 1.04 |
| 473 | N473W | 0.85 | 0.64 |
| 473 | N473Y | 1.23 | 0.86 |
| 476 | S476A | 1.51 | 1.02 |
| 476 | S476C | 0.91 | 0.89 |
| 476 | S476D | 0.98 | 0.91 |
| 476 | S476E | 1.08 | 0.91 |
| 476 | S476F | 1.09 | 0.87 |
| 476 | S476G | 1.22 | 0.97 |
| 476 | S476H | 1.07 | 0.96 |
| 476 | S476I | 1.03 | 0.78 |
| 476 | S476K | 1.01 | 0.97 |
| 476 | S476L | 1.46 | 0.93 |
| 476 | S476M | 1.58 | 1.08 |
| 476 | S476N | 1.61 | 0.98 |
| 476 | S476P | 1.02 | 0.62 |
| 476 | S476Q | 1.13 | 1.03 |
| 476 | S476R | 1.01 | 1.08 |
| 476 | S476T | 1.78 | 1.01 |
| 476 | S476V | 1.21 | 0.89 |
| 476 | S476W | 1.43 | 0.78 |
| 476 | S476Y | 1.79 | 0.94 |

Example 27

Restrictive Versus Non-Restrictive Positions

Based on the relative performance and stability data for the AmyS positions described in Example 26, AmyS positions were classified as "restrictive" versus "non-restrictive" as follows: Non-restrictive positions have ≧20% neutral mutations for at least one property; and restrictive positions have <20% neutral mutations for activity and stability. Non-restrictive positions are good candidates for mutation to design α-amylases having improved function because a large number of mutations are either tolerated (to maintain near wild-type performance) or improved performance. Restrictive positions are not good candidates for mutation because mutations are generally not tolerated. The properties of any amylase can be improved by combining mutations at non-restrictive positions. Table 27-1 shows the two restrictive positions identified in AmyS (%=percent of variants evaluated that meet definition of neutral mutation). Table 27-2 shows the 150 non-restrictive positions identified in AmyS (%=percent of variants evaluated that meet definition of neutral mutation; ≧20% neutral mutations for at least one property). Restrictive and non-restrictive positions are expected to be conserved among different α-amylases.

TABLE 27-1

Restrictive positions in AmyS

| Position | Wild type amino acid | Stability PI % > 0.5 | Activity PI % > 0.5 |
|---|---|---|---|
| 106 | H | 18% | 0% |
| 199 | L | 13% | 0% |

TABLE 27-2

Non-Restrictive positions in AmyS

| Position | Wild type amino acid | Satbility PI % > 0.5 | Activity PI % > 0.5 |
|---|---|---|---|
| 5 | N | 100% | 6% |
| 6 | G | 100% | 100% |
| 13 | E | 11% | 89% |
| 14 | W | 100% | 84% |
| 15 | Y | 100% | 100% |
| 16 | L | 94% | 100% |
| 18 | D | 100% | 100% |
| 20 | G | 95% | 16% |
| 25 | K | 100% | 100% |
| 27 | A | 100% | 89% |
| 29 | E | 100% | 53% |
| 36 | L | 100% | 74% |
| 39 | T | 100% | 80% |
| 50 | T | 95% | 74% |
| 52 | R | 94% | 94% |
| 53 | S | 100% | 100% |
| 54 | D | 11% | 79% |
| 67 | E | 94% | 81% |
| 71 | K | 95% | 100% |
| 73 | T | 83% | 100% |
| 75 | R | 100% | 100% |
| 77 | K | 24% | 94% |
| 80 | T | 100% | 100% |
| 81 | K | 100% | 94% |
| 83 | Q | 100% | 94% |
| 85 | L | 100% | 100% |
| 90 | A | 100% | 95% |
| 92 | H | 94% | 56% |
| 107 | K | 21% | 95% |
| 111 | D | 74% | 95% |

TABLE 27-2-continued

Non-Restrictive positions in AmyS

| Position | Wild type amino acid | Satbility PI % > 0.5 | Activity PI % > 0.5 |
|---|---|---|---|
| 113 | T | 100% | 100% |
| 114 | E | 50% | 94% |
| 120 | E | 17% | 100% |
| 121 | V | 6% | 94% |
| 126 | R | 6% | 88% |
| 128 | Q | 29% | 88% |
| 131 | S | 13% | 94% |
| 133 | T | 53% | 100% |
| 137 | Q | 94% | 94% |
| 138 | A | 39% | 72% |
| 139 | W | 100% | 88% |
| 141 | K | 100% | 100% |
| 143 | D | 93% | 80% |
| 147 | R | 95% | 0% |
| 149 | N | 100% | 93% |
| 150 | T | 100% | 88% |
| 151 | Y | 100% | 100% |
| 152 | S | 94% | 47% |
| 155 | K | 100% | 100% |
| 160 | H | 89% | 78% |
| 165 | D | 47% | 11% |
| 168 | E | 89% | 84% |
| 172 | L | 94% | 100% |
| 173 | S | 100% | 67% |
| 177 | K | 6% | 100% |
| 188 | E | 6% | 100% |
| 191 | T | 24% | 100% |
| 192 | E | 6% | 88% |
| 193 | N | 53% | 100% |
| 196 | Y | 18% | 100% |

Example 28

Viscosity Reduction by AmyS Variants

Figure 32:
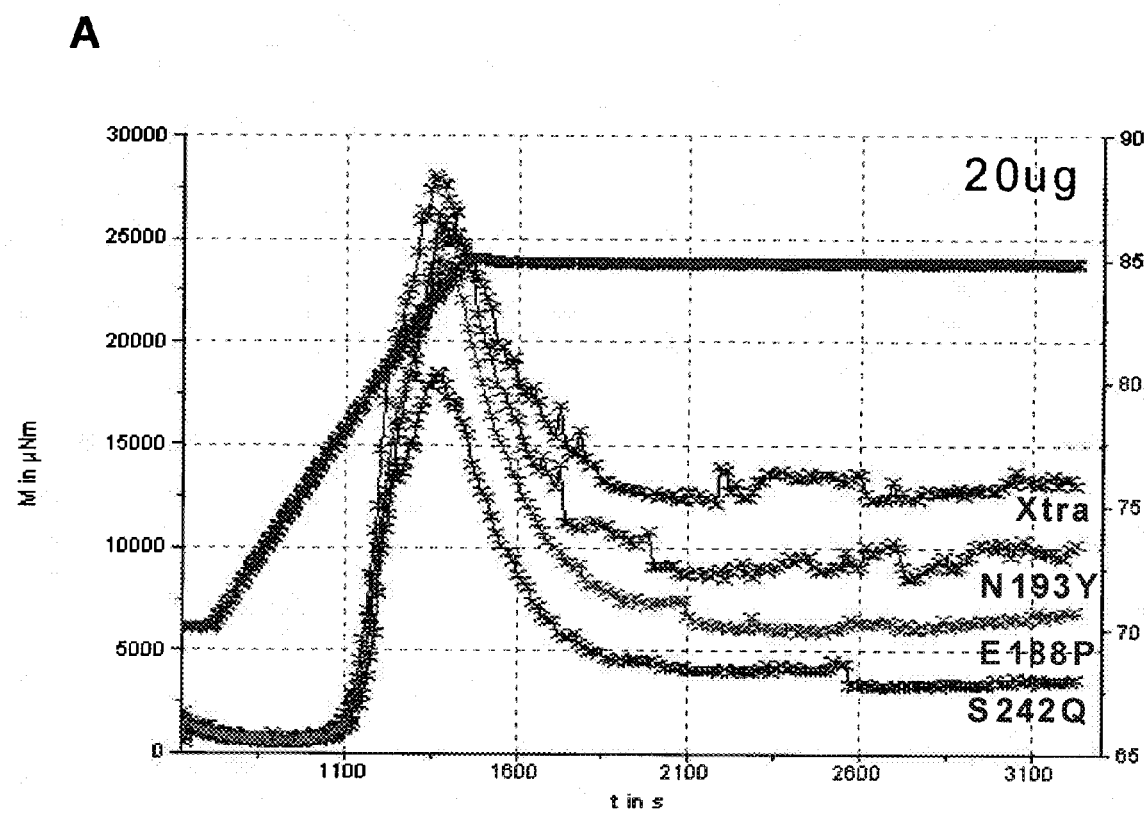
FIG. 32A shows the viscosity reduction of corn flour by AmyS variants compared to SPEZYME® Xtra.
FIG. 32B shows viscosity reduction of corn fluor by AmyS N193Y.
FIG. 32C shows the effect of phytase addition on viscosity reduction by AmyS N193Y.

Viscosity reduction of different batches of corn flour (bag A, C, E, G) by AmyS variants was monitored as described in Example 6 and was compared to viscosity reduction by SPEZYME® Xtra (Genencor). Results are shown in FIG. 32A and Table 28-1. Improved AmyS variants in the viscometer assay can be identified by a number of criteria: decreased peak viscosity, decreased final viscosity, or a decreased enzyme dose required to produce similar peak or final viscosities relative to the dose required for the wildtype enzyme. In Table 28-1, improved properties of AmyS variants are shown in bold type.

TABLE 28-1

Viscosity reduction of corn flour by AmyS variants compared to Xtra

| | | dose (ug) | peak viscosity | final viscosity |
|---|---|---|---|---|
| corn flour bag A | Xtra (UFC) | 30.0 | 20610 | 4850 |
| | I181A | 27.5 | 16930 | 13140 |
| | I181P | 27.5 | 17320 | 13910 |
| corn flour bag C | Xtra | 30.0 | 10870 | 3033 |
| | I181C | 30.0 | 11810 | 1280 |
| | I181E | 30.0 | 10800 | 1200 |
| | I181Y | 30.0 | 8990 | 2495 |
| | S242A | 30.0 | 10770 | 740 |
| | S242Q | 30.0 | 8220 | 440 |
| corn flour bag E | Xtra | 15.0 | 18890 | 2830 |
| | S242A | 15.0 | 17300 | 1165 |
| | S242E | 15.0 | 18640 | 1345 |
| | S242Q | 15.0 | 20490 | 1800 |
| corn flour bag G | Xtra | 20.0 | 26300 | 13100 |
| | S242Q | 20.0 | 20433 | 3660 |
| | G132A | 20.0 | 18400 | 10800 |
| | N193Y | 20.0 | 28900 | 11500 |
| | E188P | 20.0 | 24000 | 6950 |

Example 29

Viscosity Reduction by AmyS Variants in Presence of Phytase

Viscosity reduction of corn fluor by AmyS N193Y was monitored with and without the addition of Phytase BP111 as described in Example 6 with the following modifications. The effect of viscosity reduction was measured at pH 5.2, pH 5.5 and 5.8. Results are shown in FIGS. 32B and C. Addition of Phytase (BP111) to AmyS N193Y makes significant improvements to the variant's ability to reduce viscosity in the Viscometer.

All publications and patents mentioned above are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An isolated variant polypeptide having α-amylase activity and at least one altered characteristic that improves enzyme performance, the variant polypeptide comprising an amino acid sequence at least 99% identical to the parental α-amylase polypeptide of SEQ ID NO: 2, and having an E188P substitution that introduces a proline residue at a position corresponding to position 188 of SEQ ID NO: 1, wherein said variant polypeptide exhibits increased viscosity reduction in a starch liquefaction assay compared to the parental α-amylase polypeptide of SEQ ID NO: 2, and wherein said variant polypeptide does not have the amino acid sequence of amino acids 487-515 of SEQ ID NO: 1.

* * * * *